(12) United States Patent
Moen et al.

(10) Patent No.: US 11,544,843 B2
(45) Date of Patent: Jan. 3, 2023

(54) TRACKING BIOLOGICAL OBJECTS OVER TIME AND SPACE

(71) Applicant: California Institute of Technology, Pasadena, CA (US)

(72) Inventors: Erick K. Moen, El Segundo, CA (US); Enrico Z. Borba, Pasadena, CA (US); David A. Van Valen, Pasadena, CA (US); William H. Graf, Pasadena, CA (US); Barry D. Bannon, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 123 days.

(21) Appl. No.: 16/859,885

(22) Filed: Apr. 27, 2020

(65) Prior Publication Data

US 2020/0364857 A1 Nov. 19, 2020

Related U.S. Application Data

(60) Provisional application No. 62/839,513, filed on Apr. 26, 2019.

(51) Int. Cl.
*G06T 7/00* (2017.01)
*G06T 7/90* (2017.01)
(Continued)

(52) U.S. Cl.
CPC .............. *G06T 7/0012* (2013.01); *G06T 7/20* (2013.01); *G06T 7/90* (2017.01); *G06T 11/001* (2013.01); *G06T 2200/24* (2013.01); *G06T 2207/10024* (2013.01); *G06T 2207/20081* (2013.01); *G06T 2207/30024* (2013.01)

(58) Field of Classification Search
CPC .......... G06T 7/0012; G06T 7/90; G06T 7/20; G06T 11/001; G06T 2200/24; G06T 2207/10024; G06T 2207/20081; G06T 2207/30024
See application file for complete search history.

(56) References Cited

U.S. PATENT DOCUMENTS 9,547,908 B1 * 1/2017 Kim .................... G06V 40/162
10,643,396 B2 * 5/2020 Eastwood ............... G06T 7/194
(Continued)

FOREIGN PATENT DOCUMENTS

CA          2842282 A1 * 1/2013 ......... G01N 21/4795
WO   WO-2018156133 A1 * 8/2018 ......... G01N 33/4833

OTHER PUBLICATIONS

Akram et al., "Cell Tracking via Proposal Generation and Selection," arXiv:1705.03386v1 2017, 1-13.
(Continued)

*Primary Examiner* — Shefali D Goradia
(74) *Attorney, Agent, or Firm* — Sheppard, Mullin, Richter & Hampton LLP

(57) ABSTRACT

Disclosed herein include systems and methods for biological object tracking and lineage construction. Also disclosed herein include cloud-based systems and methods for allocating computational resources for deep learning-enabled image analysis of biological objects. Also disclosed herein include systems and methods for annotating and curating biological object tracking-specific training datasets.

29 Claims, 199 Drawing Sheets

(51) Int. Cl.
G06T 7/20 (2017.01)
G06T 11/00 (2006.01)

(56) References Cited

U.S. PATENT DOCUMENTS

| | | | | |
|---|---|---|---|---|
| 10,657,643 B2* | 5/2020 | Chukka | ............ | G06T 7/0012 |
| 11,170,897 B2* | 11/2021 | Stumpe | ............ | G06T 7/11 |
| 2009/0319291 A1* | 12/2009 | Noordvyk | ............ | G16H 50/20 |
| | | | | 705/2 |
| 2015/0339838 A1* | 11/2015 | Friedman | ............ | G06T 11/60 |
| | | | | 345/641 |

OTHER PUBLICATIONS

Altschul et al., "Gapped BLAST and PSI-BLAST: a new generation of protein database search programs," Nucleic Acids Research 1997, 25(17), 3389-3402.
Bai & Urtasun, "Deep Watershed Transform for Instance Segmentation," arXiv:1611.08303v2 2017, 1-9.
Bannon et al., "DeepCell 2.0: Automated cloud deployment of deep learning models for large-scale cellular image analysis," bioRxiv 2018, in 6 pages. https://doi.org/10 1101/505032.
Bannon et al., "Dynamic allocation of computational resources for deep learning-enabled cellular image analysis with Kubernetes," bioRxiv 2019, in 17 pages, https://doi.org/10.1101/505032.
Belthangandy & Royer, "Applications, promises, and pitfalls of deep learning for fluorescence image reconstruction," Nature Methods 2019, 16, 1215-1225.
Berstein et al., "Containers and Cloud: From LXC to Docker to Kubernetes," IEEE Cloud Computing 2014, 1, 81-84.
Bintu et al., "Dynamics of epigenetic regulation at the single-cell level," Science 2016, 351(6274), 720-724.
Caicedo et al., "Evaluation of Deep Learning Strategies for Nucleus Segmentation in Fluorescence Images," Cytometry Part A 2019, 95A, 952-965.
Christiansen et al., "In silica labeling: Predicting fluorescent labels in unlabeled images," Cell 2018, 173(3), 792-803.
Elowitz et al., "Stochastic Gene Expression in a Single Cell," Science 2002, 297(5584), 1183-1186.
Facchetti et al., "Reprogramming Cdr2-Dependent Geometry-Based Cell Size Control in Fission Yeast," Current Biology 2019, 29, 350-358.
Falk et al., "U-Net—Deep Learning for Cell Counting, Detection, and Morphometry," Nature Methods 2019, 16, 67-70.
Foreman & Wollman, "Mammalian gene expression variability is explained by underlying cell state," bioRxiv 2019, in 30 pages, https://doi.org/10.1101/626424.
Fu et al., "RetinaMask: Learning to predict masks improves state-of-the-art single-shot detection for free," arXiv:1901.03353v1 2019, 1-11.
Girkin & Carvalho, "The light-sheet microscopy revolution," Journal of Optics 2018, 20(053002), 1-20.
Golding et al., "Real-Time Kinetics of Gene Activity in Individual Bacteria," Cell 2005, 123, 1025-1036.
Haberl et al., "*CDeep3M*—Plug-and-Play cloud based deep learning for image segmentation," Nature Methods 2018, 15(9), 677-680.
He et al., "Mask R-CNN," 2017 IEEE International Conference on Computer Vision (ICCV). IEEE 2018, 2961-2969.
Hormoz et al., "Inferring Cell-State Transition Dynamics from Lineage Trees and Endpoint Single-Cell Measurements," Cell Systems 2016, 3, 419-433.
Jaqaman et al., "Robust single particle tracking in live cell time-lapse sequences," Nature Methods 2008, 5(8), 695-702.
Karpathy et al., "Software 2.0," Medium 2017, in 8 pages. https://medium.com/@karpathy/software-2-0-a64152b37c35.
Keren et al, "A Structured Tumor-Immune Microenvironment in Triple Negative Breast Cancer Revealed by Multiplexed Ion Beam Imaging," Cell 2018, 174, 1373-1387.

Kingma & Ba, "Adam: A Method for Stochastic Optimization," arXiv:1412.6980v9 2017, 1-15.
Kirillov et al., "Panoptic Feature Pyramid Networks," arXiv:1901.02446v2 2019, 1-10.
Kraus et al., "Automated analysis of high-content microscopy data with deep learning," Molecular Systems Biology 2017, 13(924), 1-15.
Kudo et al.. "Live-cell measurements of kinase activity in single cell using translocation reporters," Nature Protocols 2018, 13(1), 155-169.
Kuhn, "The Hungarian Method for the Assignment Problem," Naval Research Logistics Quarterly 1955, 2, 83-97.
Lane et al., "Measuring Signaling and RNA-Seq in the Same Cell Links Gene Expression to Dynamic Patterns of NF-kB Activation," Cell Systems 2017, 4(4), 458-469.
Lecun et al., "Deep learning," Nature 2015, 521, 436-444.
Lin et al., "Focal Loss for Dense Object Detection," 2017 IEEE International Conference on Computer Vision (ICCV), IEEE 2018, 2980-2988. doi:10.1109/ICCV.2017.324.
Liu et al., "Visualizing long-term single-molecule dynamics in vivo by stochastic protein labeling," PNAS 2018, 115(2), 343-348.
Lugagne et al., "DeLTA: Automated cell segmentation, tracking, and lineage reconstruction using deep learning," bioRxiv 2019, in 20 pages, https://doi.org/10 1101/720615.
Magnusson et al., "Global Linking of Cell Tracks Using the Viterbi Algorithm," IEEE Transactions on Medical Imaging 2015, 34(4), 911-929.
Maška et al., "A benchmark for comparison of cell tracking algorithms," Bioinformatics 2014, 30(11), 1609-1617.
Matula et al., "Cell Tracking Accuracy Measurement Based on Comparison of Acyclic Oriented Graphs," PLoS One 2015, 10(12), e0144959, in 19 pages.
McDole et al., "In Toto Imaging and Reconstruction of Post-Implantation Mouse Development at the Single-Cell Level," Cell 2018, 175, 859-876.
Moen et al., "Accurate cell tracking and lineage construction in live-cell imaging experiments with deep learning," bioRxiv 2019, in 27 pages. https://doi.org/10.1101/803205.
Moen et al., "Deep learning for cellular image analysis," Nature Methods 2019, 16, 1233-1246.
Morris et al., "Infrastructure as Code: Managing Servers in the Cloud," O'Reilly Media 2016.
Nakamoto, "Bitcoin: A Peer-to-Peer Electronic Cash System," 2008, in 9 pages.
Newby et al., "Convolutional neural networks automate detection for tracking of submicron-scale particles in 2D and 3D," PNAS 2018, 115(36), 9026-9031.
Ni et al., "Live-cell imaging of cell signaling using genetically encoded fluorescent reporters," FEBS Journal 2018, 285(2), 203-219.
Ounkomol et al., "Label-free prediction of three-dimensional fluorescence images from transmitted light microscopy," Nat Methods 2018, 15(11), 917-920.
Payer et al., "Instance Segmentation and Tracking with Cosine Embeddings and Recurrent Hourglass Networks," International Conference on Medical Image Computing and Computer-Assisted Intervention, Medical Image Computing and Computer Assisted Intervention—MICCAI 2018, 1-12.
Purvis et al., "Encoding and Decoding Cellular Information through Signaling Dynamics," Cell 2013, 152(5), 945-956.
Regot et al., "High-sensitivity measurements of multiple kinase activities in live single cells," Cell 2014, 157(7), 1724-1734.
Ren et al., "Faster R-CNN: Towards Real-Time Object Detection with Region Proposal Networks," arXiv:1506.01497v3 2016, 1-14.
Ronneberger et al., "U-Net: Convolutional Networks for Biomedical Image Segmentation," arXiv:1505.04597v1 2015, 1-8.
Sadeghian et al., "Tracking the Untrackable: Learning to Track Multiple Cues with Long-Term Dependencies," arXiv:1701.01909v2 2017, 1-12.
Schindelin et al., "Fiji—an Open Source platform for biological image analysis," Nature Methods 2012, 9(7), 676-682.

(56) References Cited

OTHER PUBLICATIONS

Selimkhanov et al., "Accurate Information Transmission Through Dynamic Biochemical Signaling Networks," Science 2014, 346(6215), 1370-1373.
Shah et al., "In Situ Transcription Profiling of Single Cells Reveals Spatial Organization of Cells in the Mouse Hippocampus," Neuron 2016, 92, 342-357.
Tarkowska et al., "Eleven quick tips to build a usable REST API for life sciences," PLoS Computational Biology 2018, 14(12), e1006542, in 8 pages.
Tsai et al., "Usiigaci: Instance-aware cell tracking in stain-free phase contrast microscopy enabled by machine learning," SoftwareX 2019, 230-237.
Ulman et al., "An Objective Comparison of Cell Tracking Algorithms," Nature Methods 2017, 14(12), 1141-1152.
Van Valen et al., "Deep Learning Automates the Quantitative Analysis of Individual Cells in Live-Cell Imaging Experiments," PLoS Computational Biology 2016, 12(11), e1005177, in 24 pages.
Voigtlaender et al., "MOTS: Multi-Object Tracking and Segmentation," arXiv:1902.03604v2 2019, in 17 pages.
Walt et al., "scikit-image: image processing in Python," PeerJ 2014, 2(e453), in 18 pages.
Wang et al., "Learn to segment single cells with deep distance estimator and deep cell detector," Computers in Biology and Medicine 2019, 108, 133-141.
Weigert et al.. "Content-Aware Image Restoration: Pushing the Limits of Fluorescence Microscopy," bioRxiv 2018, 1-16. https://doi.org/10.1101/236463.
Weinberger et al., "Stochastic Gene Expression in a Lentiviral Positive-Feedback Loop: HIV-1 Tat Fluctuations Drive Phenotypic Diversity," Cell 2005, 122, 169-182.

* cited by examiner

FIG. 11

| Annotation Type: | nuclear |
| --- | --- |
| | cytoplasm |

DeepCell with RetinaMask

| With Small Object Removal (< 100 pixels) | | Correct Detections | Incorrect Detections | Total | | | | | | |
| --- | --- | --- | --- | --- | --- | --- | --- | --- | --- | --- |
| | | | | Splits | Merges | Catastrophes | Recall | Precision | Average Jaccard Index |
| Live-Cell Imaging Datasets | Example 2 | 3T3 | 6180 | 630 | 22 | 4 | 24 | 88.3615 | 90.7489 | 0.7986 |
| | | HEK293 | 11604 | 713 | 76 | 85 | 1 | 82.2512 | 94.2113 | 0.8566 |
| | | HeLa | 5252 | 400 | 14 | 0 | 0 | 90.1631 | 92.9229 | 0.8341 |
| | | RAW264.7 | 4372 | 203 | 10 | 0 | 0 | 91.2164 | 95.5628 | 0.8158 |
| | ISBI | Fluo-N2DL-HeLa | 27025 | 3834 | 60 | 307 | 4 | 85.0672 | 87.5757 | 0.7653 |

Original DeepCell Model

| With Small Object Removal (< 100 pixels) | | Correct Detections | Incorrect Detections | Total | | | | | | |
| --- | --- | --- | --- | --- | --- | --- | --- | --- | --- | --- |
| | | | | Splits | Merges | Catastrophes | Recall | Precision | Average Jaccard Index |
| Live-Cell Imaging Datasets | Example 2 | 3T3 | 6048 | 679 | 41 | 13 | 0 | 86.4741 | 90.9064 | 0.8196 |
| | | HEK293 | 11618 | 679 | 45 | 221 | 9 | 82.3504 | 94.4783 | 0.8484 |
| | | HeLa | 4845 | 592 | 9 | 12 | 0 | 83.1760 | 89.1116 | 0.7322 |
| | | RAW264.7 | 4392 | 167 | 9 | 1 | 0 | 91.6336 | 96.3369 | 0.8341 |
| | ISBI | Fluo-N2DL-HeLa | 28774 | 2053 | 87 | 84 | 4 | 90.5754 | 93.3403 | 0.7780 |

DeepCell Watershed Model

| With Small Object Removal (< 100 pixels) | | Correct Detections | Incorrect Detections | Total | | | | | | |
| --- | --- | --- | --- | --- | --- | --- | --- | --- | --- | --- |
| | | | | Splits | Merges | Catastrophes | Recall | Precision | Average Jaccard Index |
| Live-Cell Imaging Datasets | Example 2 | 3T3 | 5956 | 1593 | 84 | 30 | 0 | 85.1587 | 78.8979 | 0.7857 |
| | | HEK293 | 11136 | 1506 | 116 | 469 | 18 | 78.9339 | 88.0873 | 0.7984 |
| | | HeLa | 5236 | 637 | 1 | 20 | 0 | 89.8884 | 89.1538 | 0.8339 |
| | | RAW264.7 | 4246 | 405 | 0 | 44 | 0 | 88.5875 | 91.2922 | 0.8017 |
| | ISBI | Fluo-N2DL-HeLa | 29941 | 1134 | 21 | 121 | 3 | 94.2489 | 96.3508 | 0.7919 |

DeepCell with RetinaMask

| With Small Object Removal (< 100 pixels) | | Correct Detections | Incorrect Detections | Total | | | | | | |
| --- | --- | --- | --- | --- | --- | --- | --- | --- | --- | --- |
| | | | | Splits | Merges | Catastrophes | Recall | Precision | Average Jaccard Index |
| Live-Cell Imaging Datasets | Composite Cytoplasmic Data (ISBI + Example 2) | 17841 | 2959 | 478 | 318 | 116 | 75.0346974 | 85.7740 | 0.7957 |

| | | |
|---|---|---|
| Roughly color the same cell in all panels using the paintbrush tool. | Click on the background of the image with the magic tool. | Select the eraser tool and click on the colored area that is outside of the cell. This should leave only the cells colored in. Go back and correct the coloring if need be. |

| | Normal Cells | Dividing/Disappearing Cells |
|---|---|---|
| Raw Image | | |
| Correct Annotation | | |
| Description | Accurately color in the entire cell, including the boundary. Work one cell at a time and make sure the same cell has the same color across all frames. Color in all cells in the image. | In this example a cell divides, i.e. it disappears and produces two new cells. The color of the original cell (pink) should not be used again, and the two new cells should be colored with colors that haven't been used before (brown and light blue). If a cell moves out of the frame of an image before returning, color it as the same cell. |

| Different Cell Shapes | | | | | |
|---|---|---|---|---|---|
| Raw image | 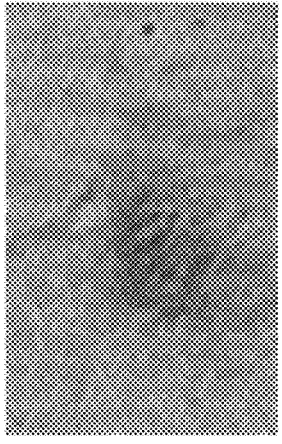 | 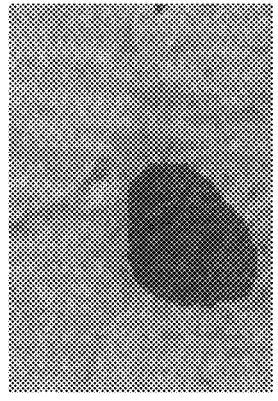 | 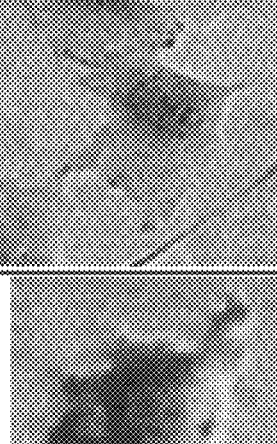 | 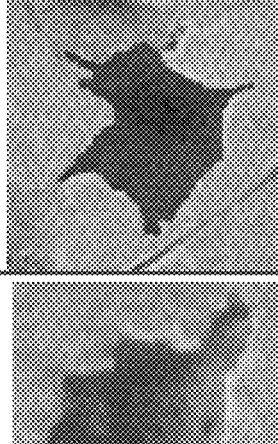 | 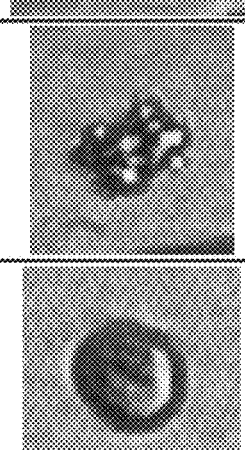 |
| Correct annotation | 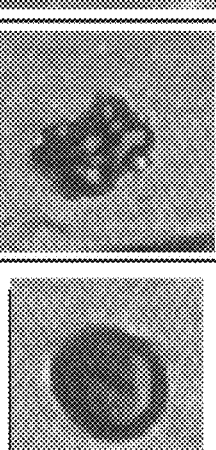 | | | | |
| Description | Some cells are compact and dark. These are still cells, not debris, and SHOULD be annotated. | | Some cells are spread out and can have very different shapes. If the edges of the cells can be clearly made out, they can be annotated. | | Sometimes, the edges of a cell are too hard to see. Color in the part of the cell that you can see clearly. |

FIG. 18

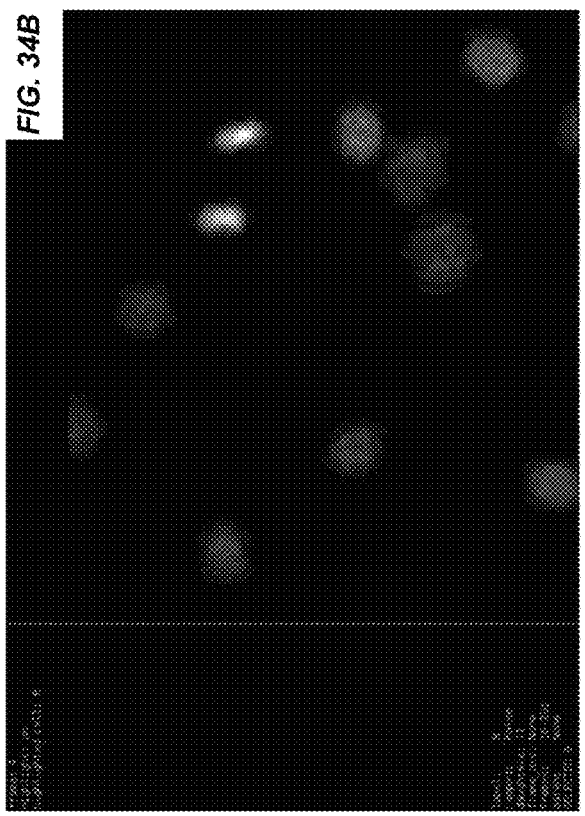

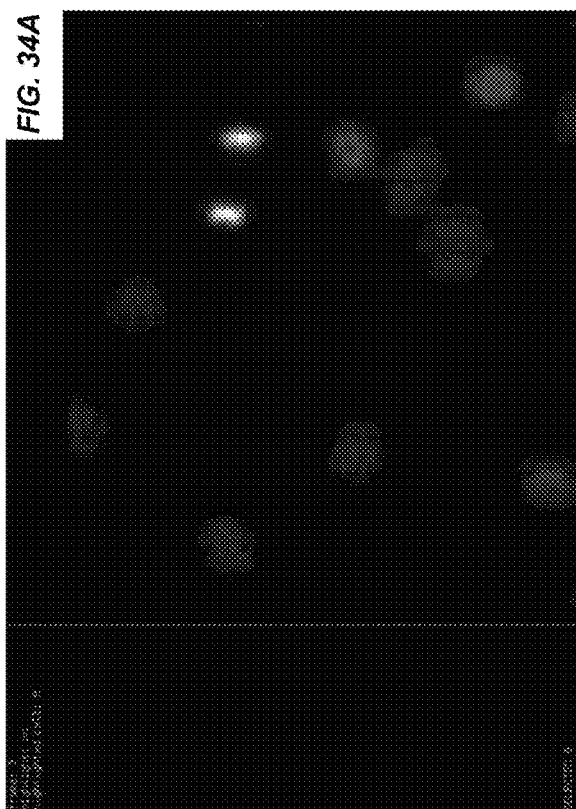

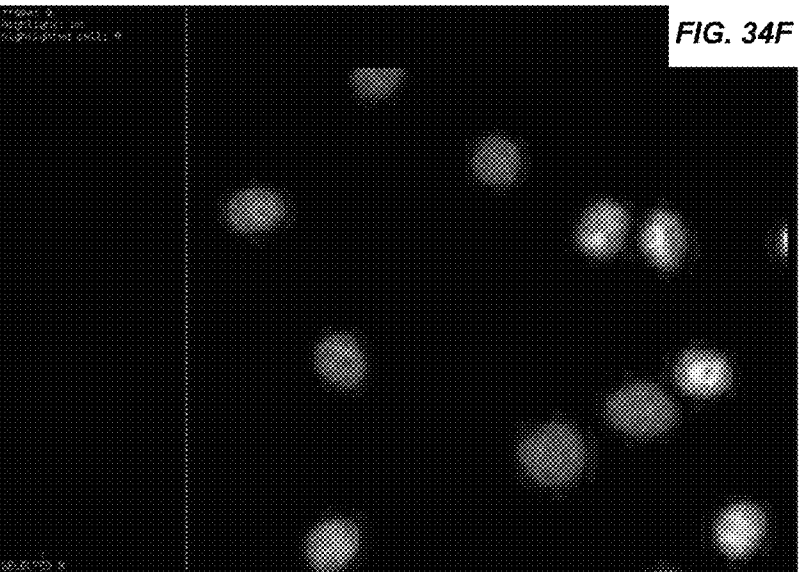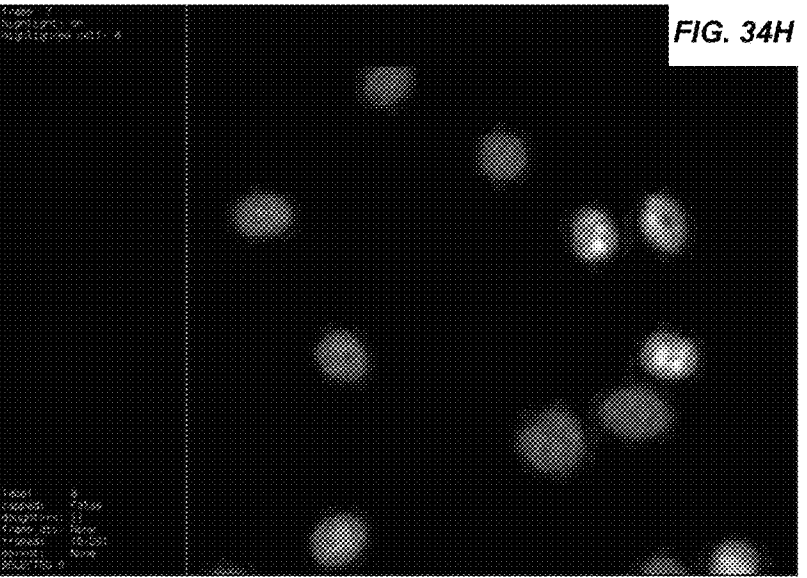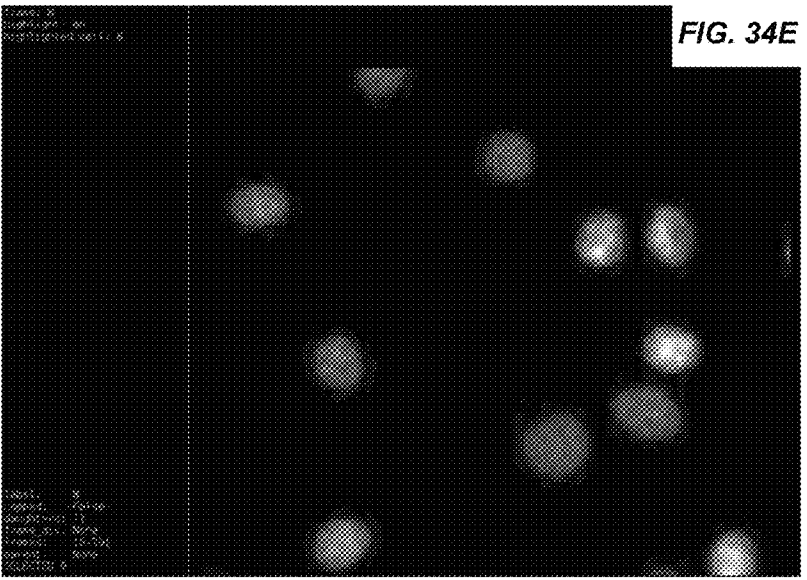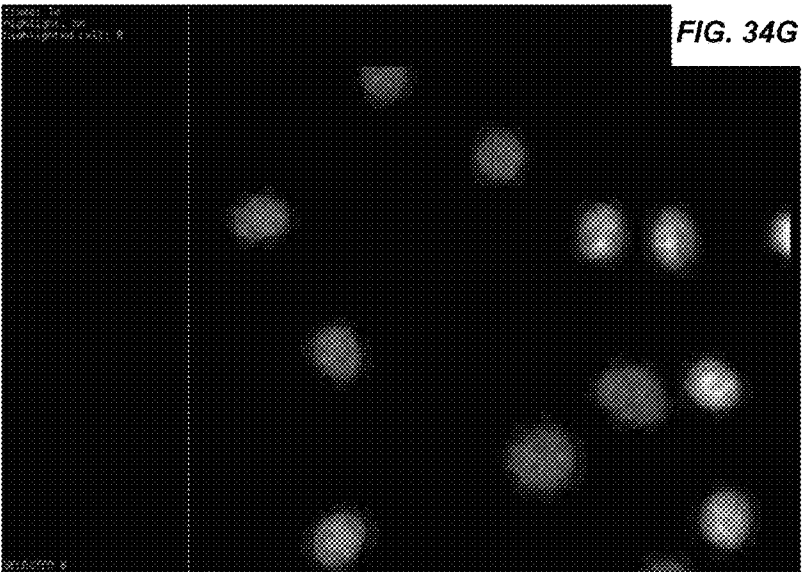

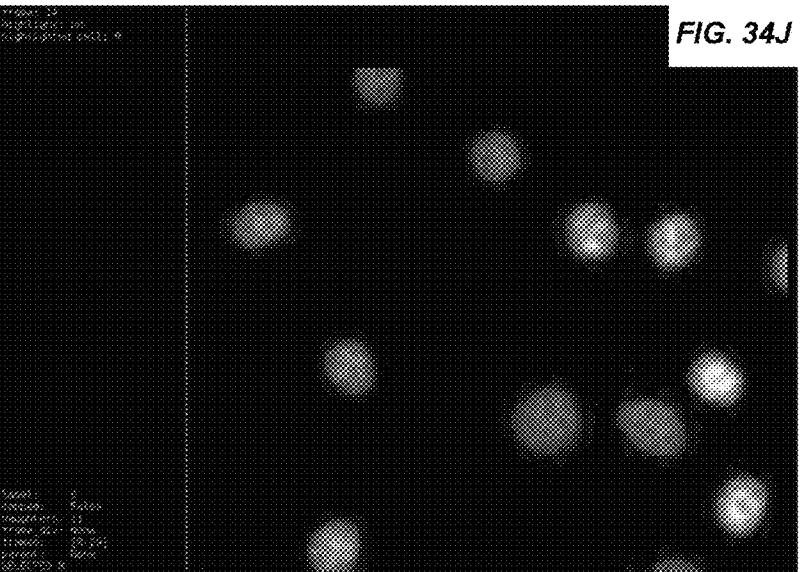
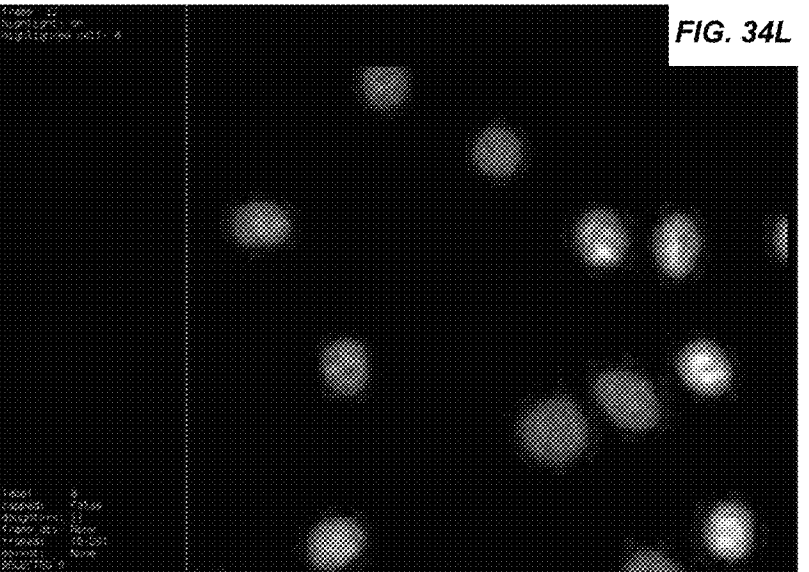
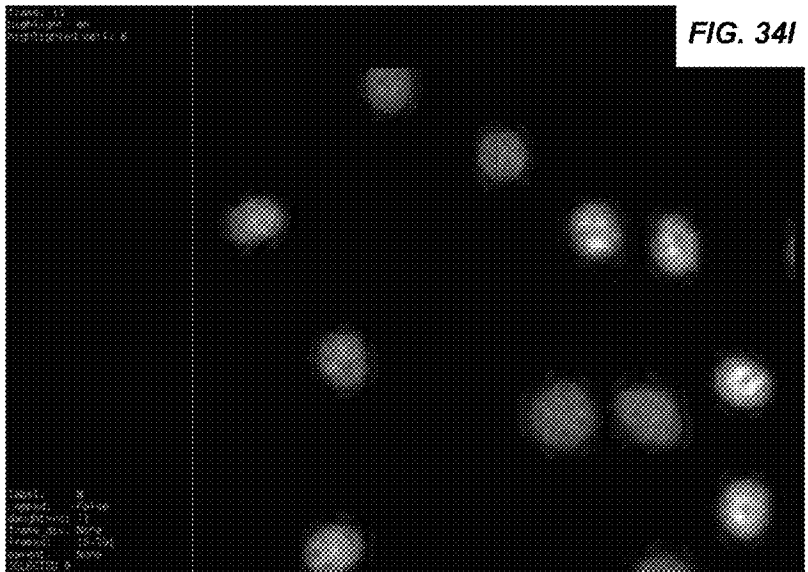
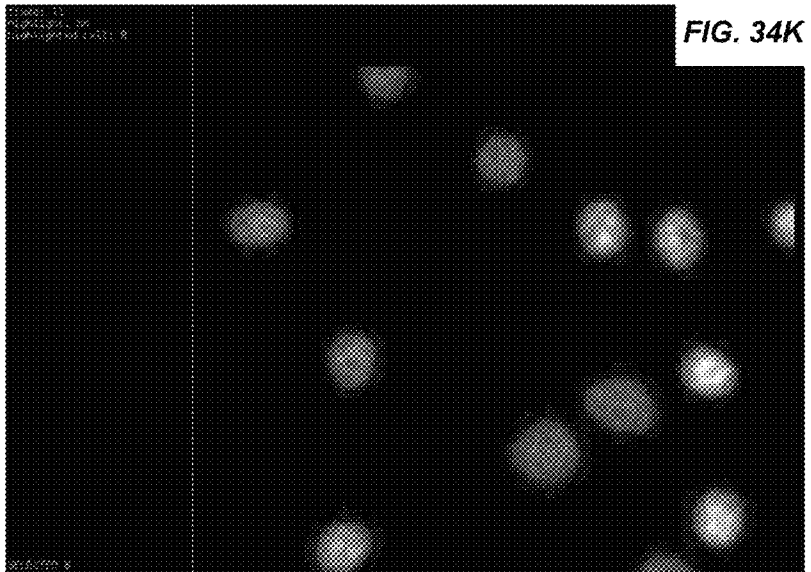

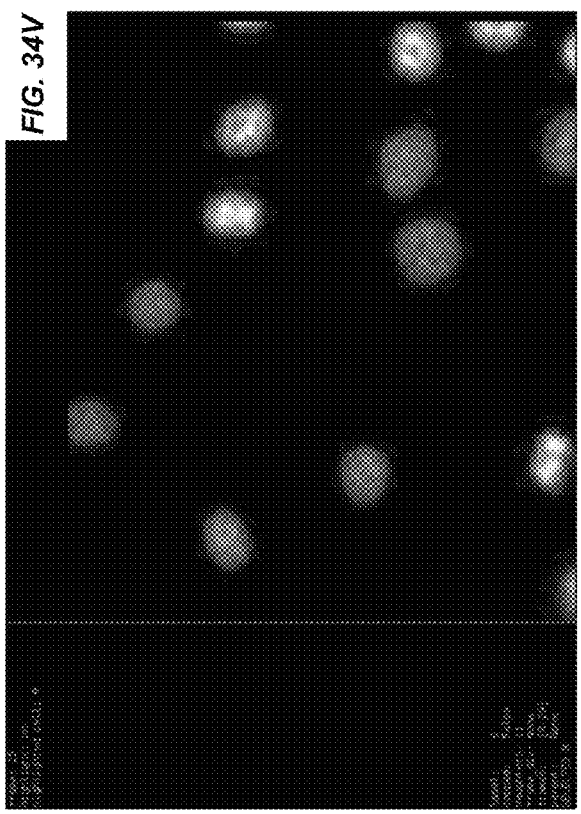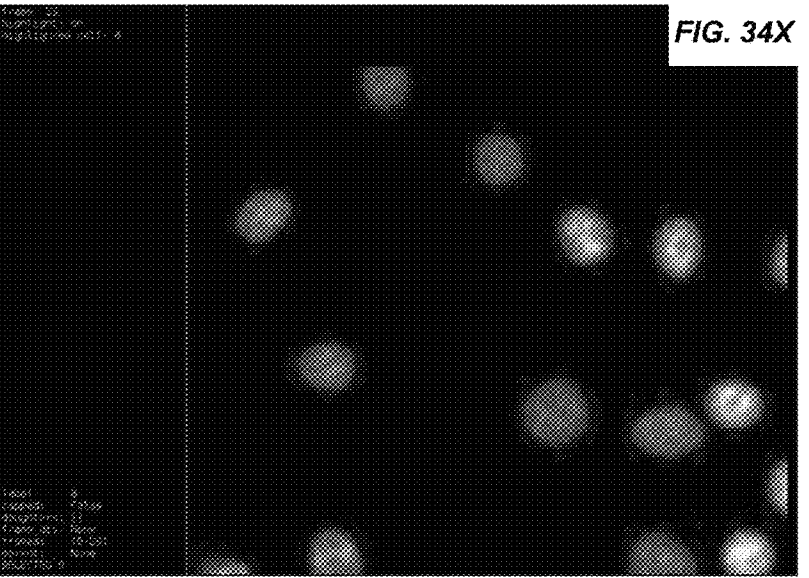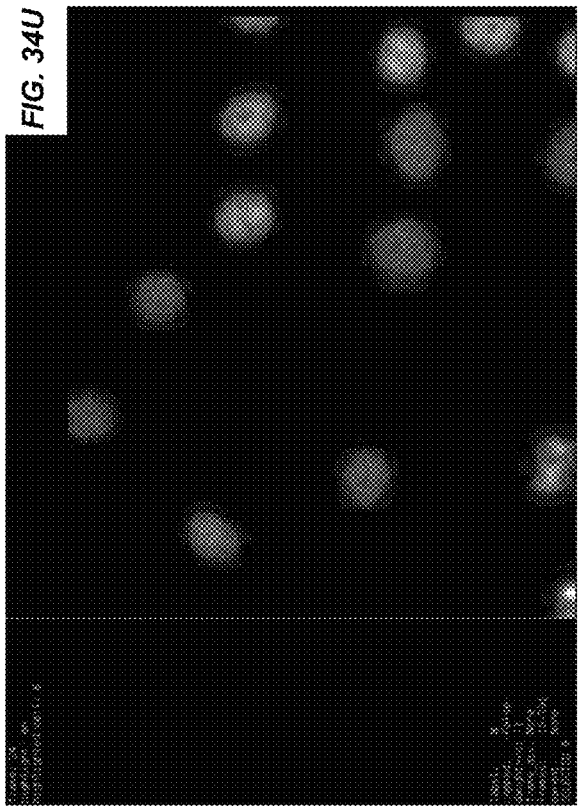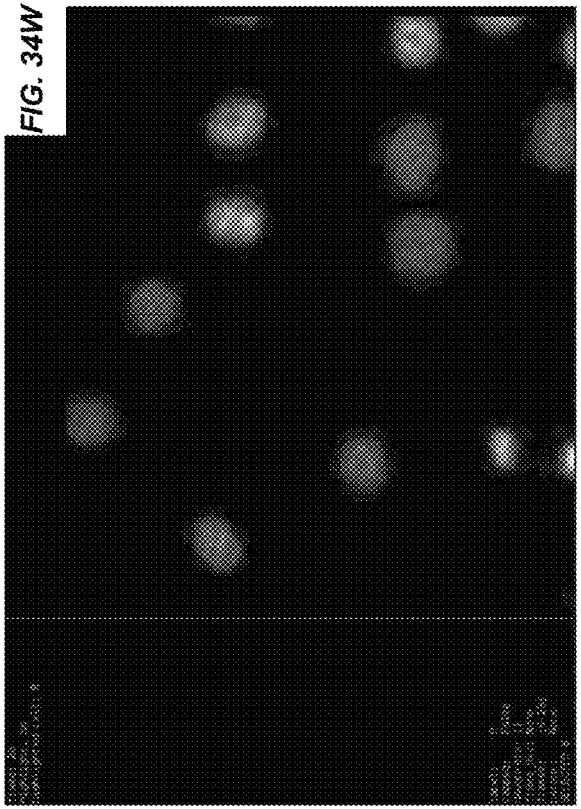

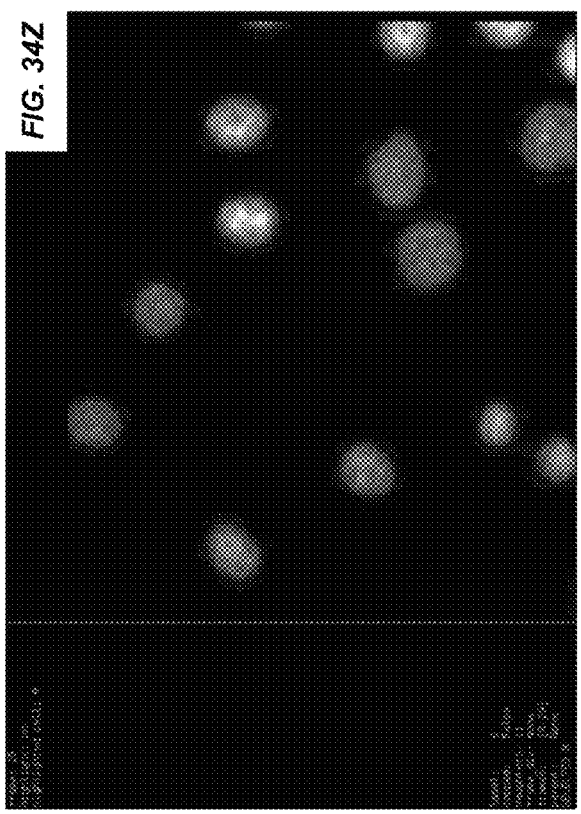
FIG. 34Z
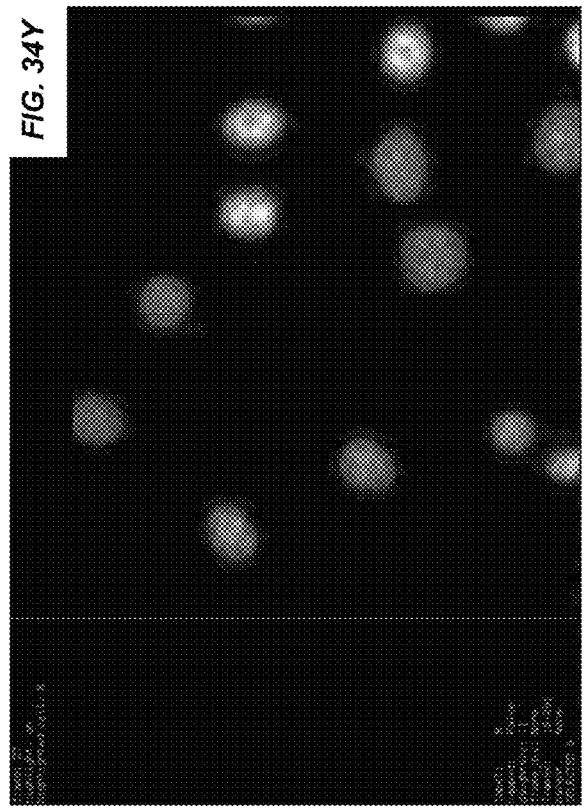
FIG. 34Y
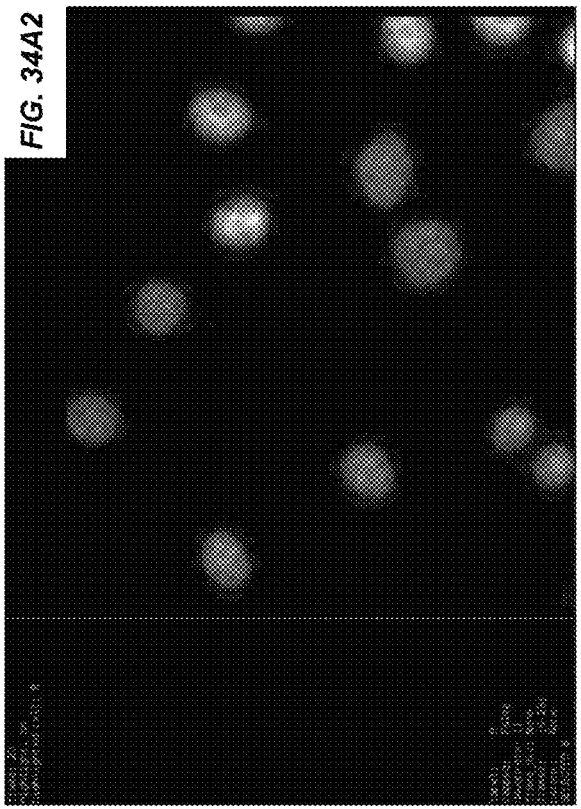
FIG. 34A2

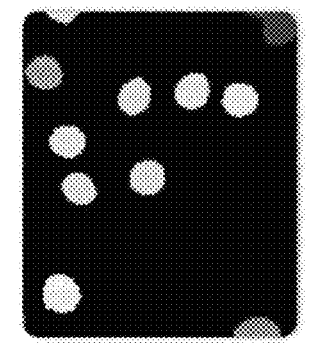
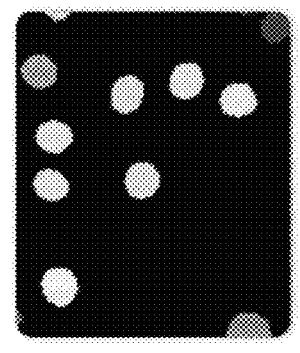
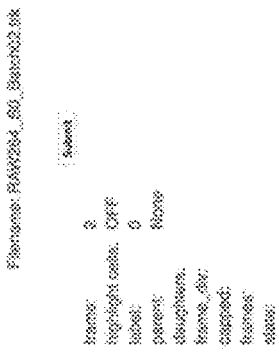
FIG. 35B
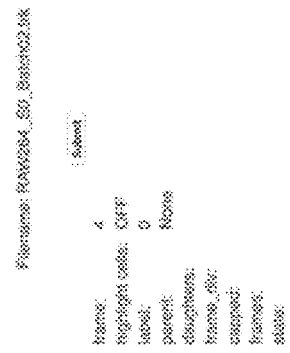
FIG. 35D
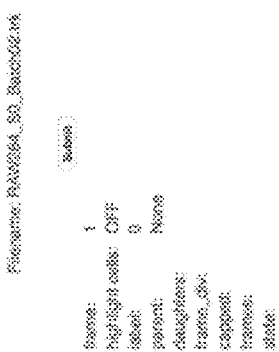
FIG. 35A
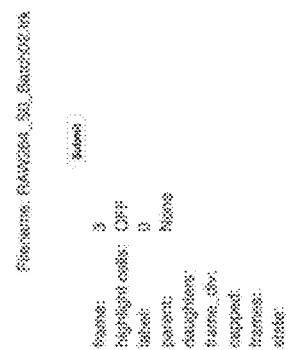
FIG. 35C

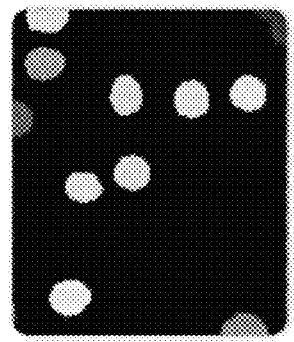
*FIG. 35Y*
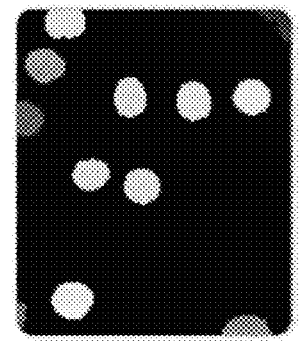
*FIG. 35Z*
*FIG. 35A2*
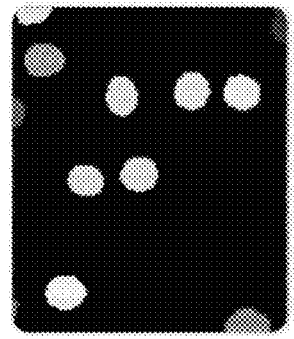
*FIG. 35B2*
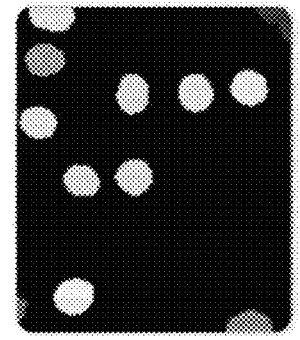

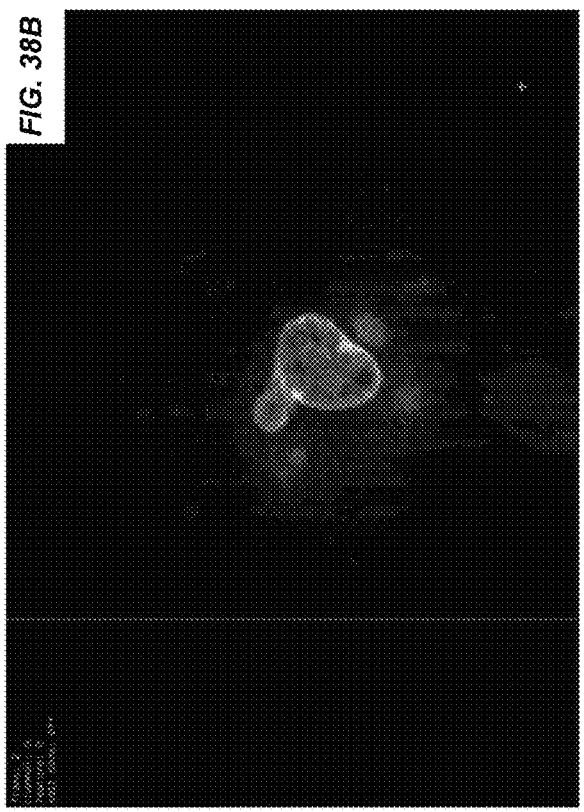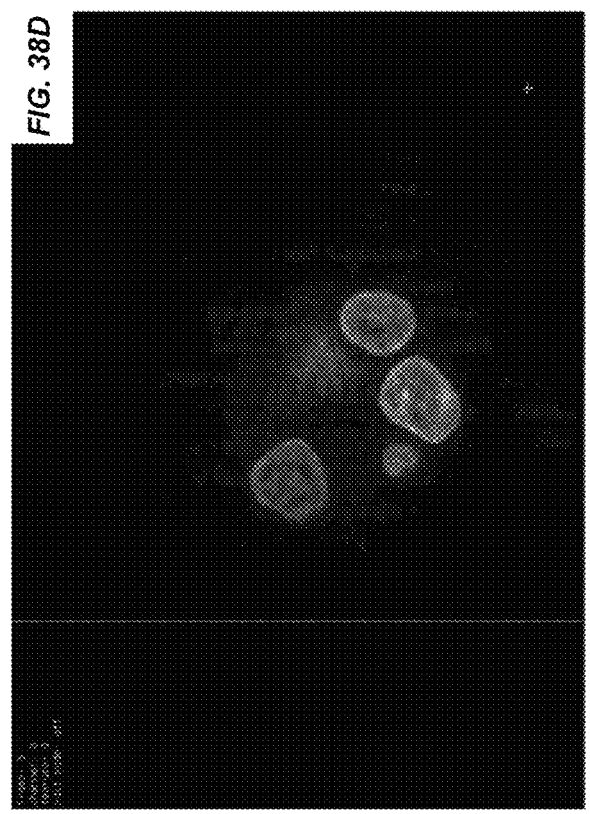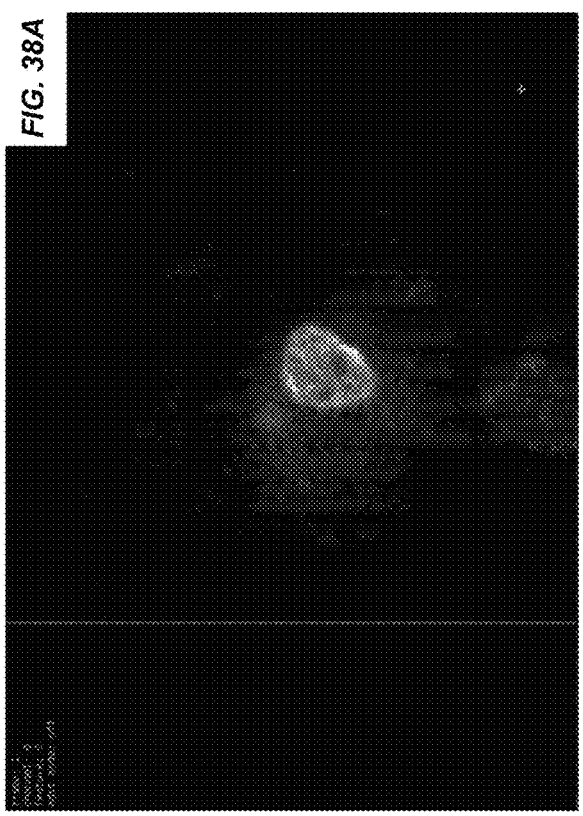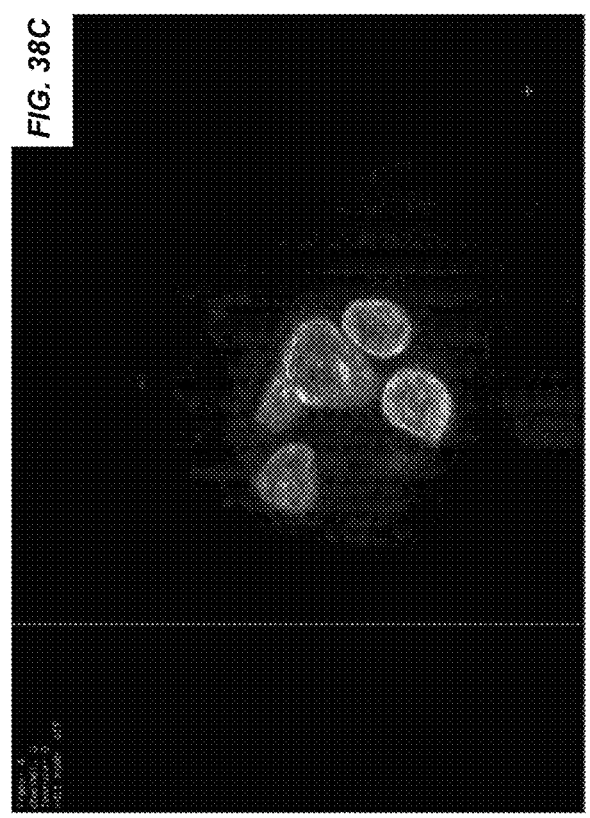

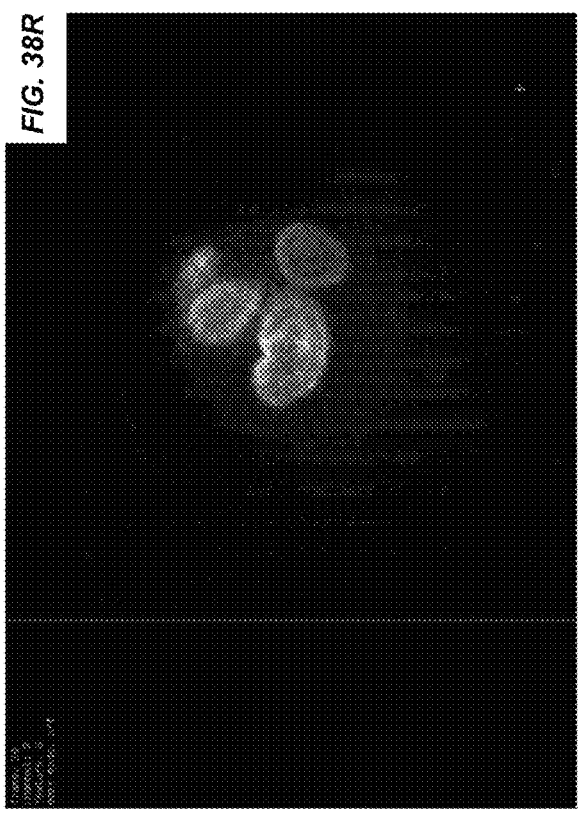
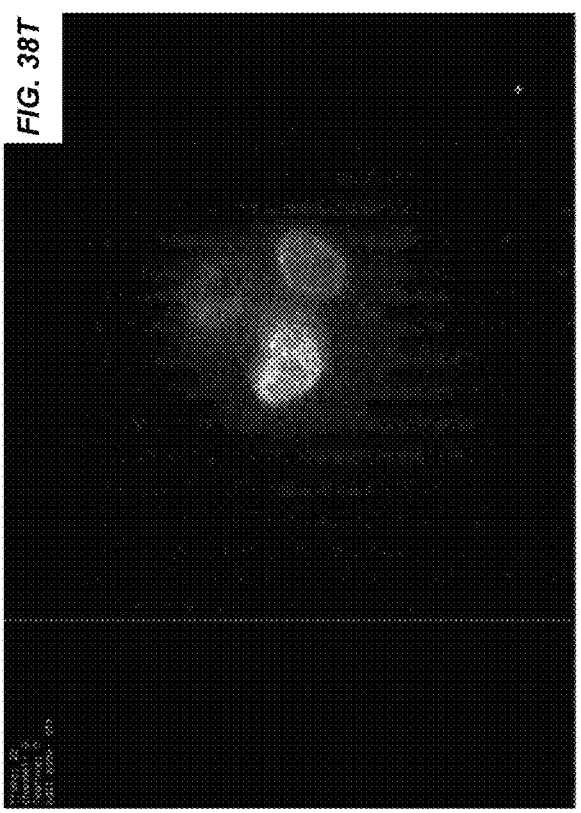
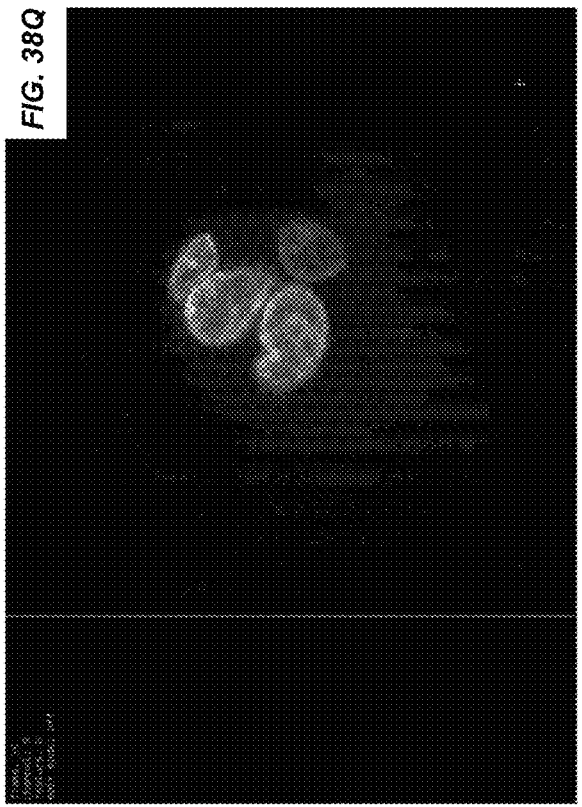
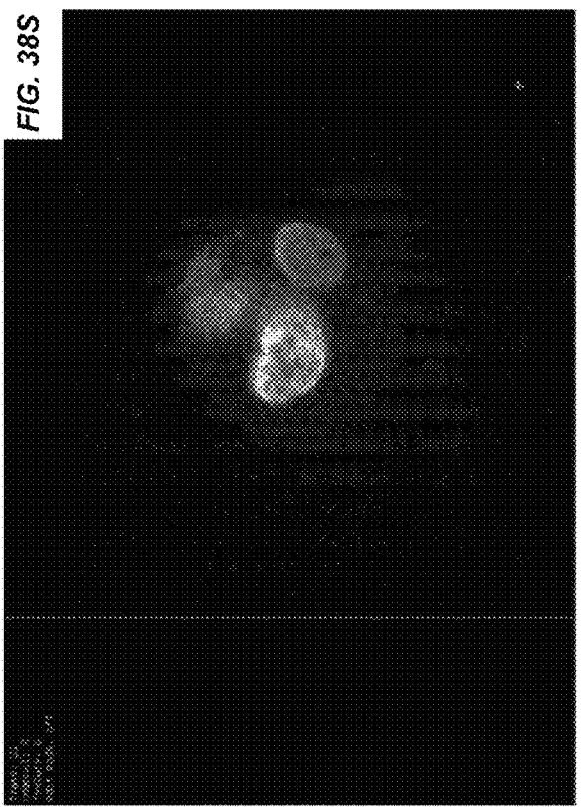

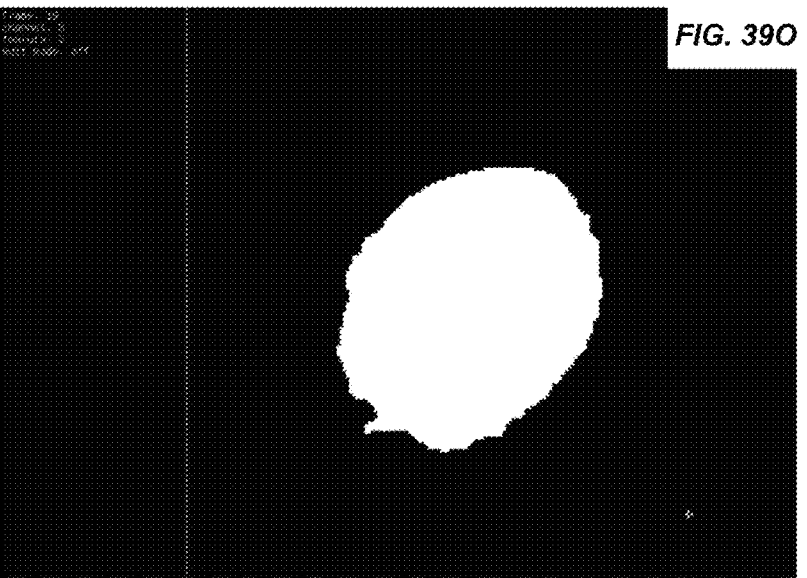

Changing frames will work with any of the display options.

Use the "a" or right arrow key to go backward one frame at a time.

Use the "d" or right arrow key to go forward one frame at a time.

Changing frames will work with any of the display options.

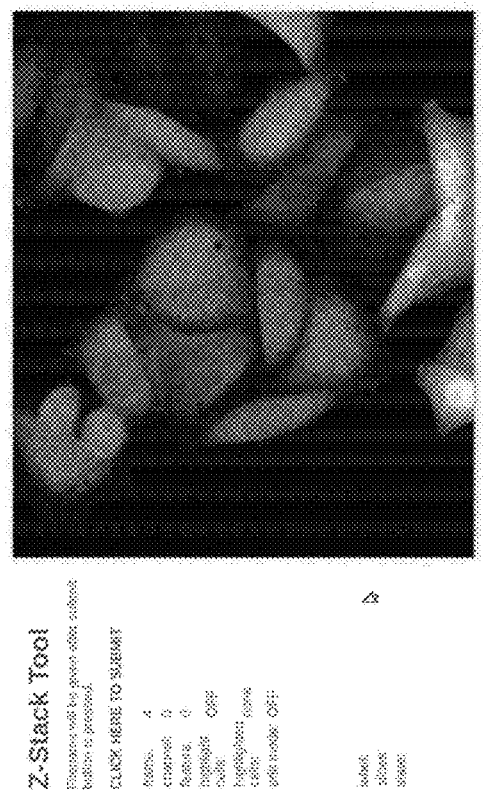
FIG. 40M
Going backward from frame 0 will go to the last frame of the file.
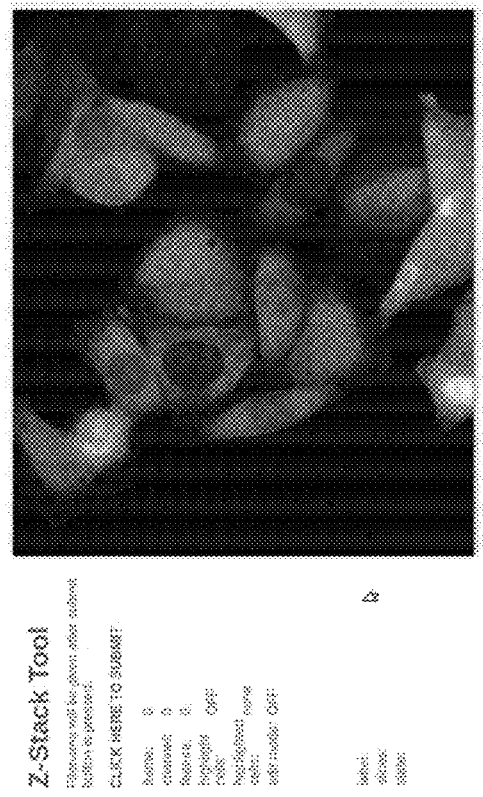
FIG. 40N
Going backward from frame 0 will go to the last frame of the file.
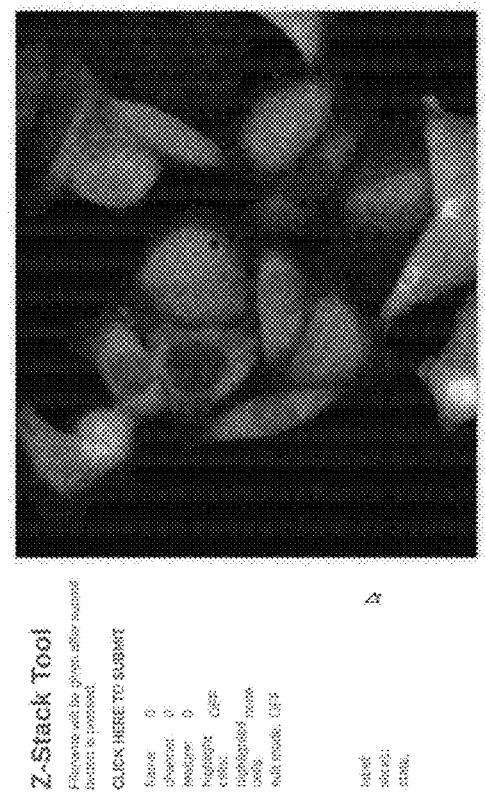
FIG. 40O
Going forward from the last frame of the file will go to frame 0.
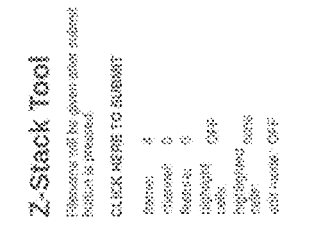
FIG. 40P
Going forward from the last frame of the file will go to frame 0.

Use the mouse scroll wheel to adjust the brightness of the image.

Use the mouse scroll wheel to adjust the brightness of the image.

Use the mouse scroll wheel to adjust the brightness of the image.

Use the mouse scroll wheel to adjust the brightness of the image.

FIG. 41E
Use the mouse scroll wheel to adjust the brightness of the image.

FIG. 41F
Use the mouse scroll wheel to adjust the brightness of the image.

FIG. 41G
Use the mouse scroll wheel to adjust the brightness of the image.

FIG. 41H
Use the mouse scroll wheel to adjust the brightness of the image.

Use the mouse scroll wheel to adjust the brightness of the image.

Press "i" to invert the color of the image.

Use the mouse scroll wheel to adjust the brightness of the image.

Press "i" to invert the color of the image.

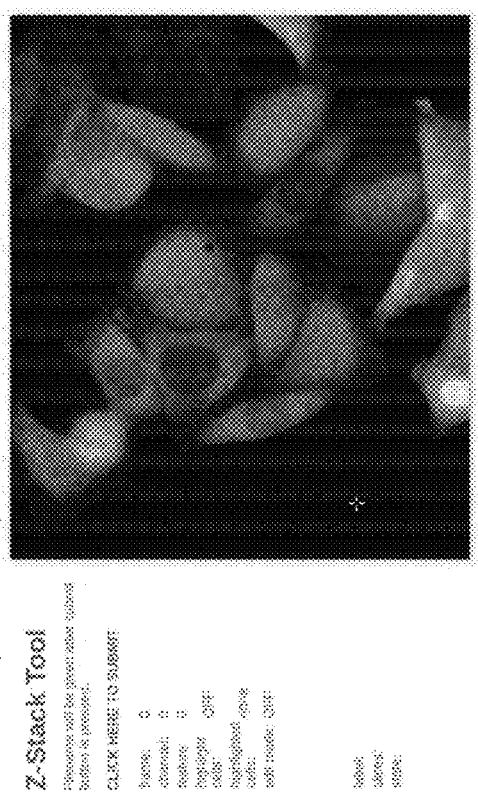
FIG. 42E Press "c" to change the channel of the image.
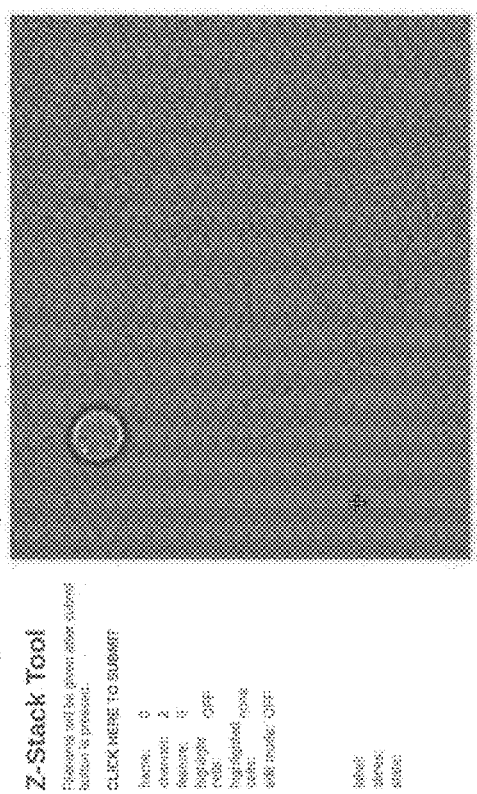
FIG. 42F Hold down the shift key while pressing "c" to cycle through channels in the opposite order.
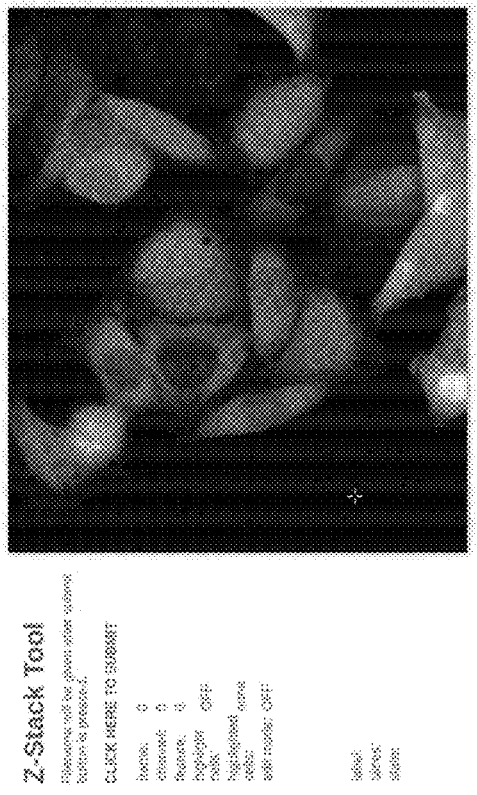
FIG. 42G Hold down the shift key while pressing "c" to cycle through channels in the opposite order.
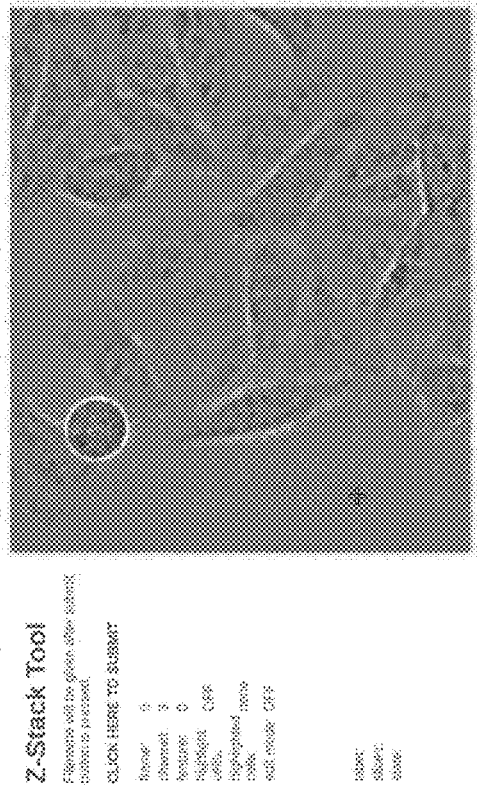
FIG. 42H Hold down the shift key while pressing "c" to cycle through channels in the opposite order.

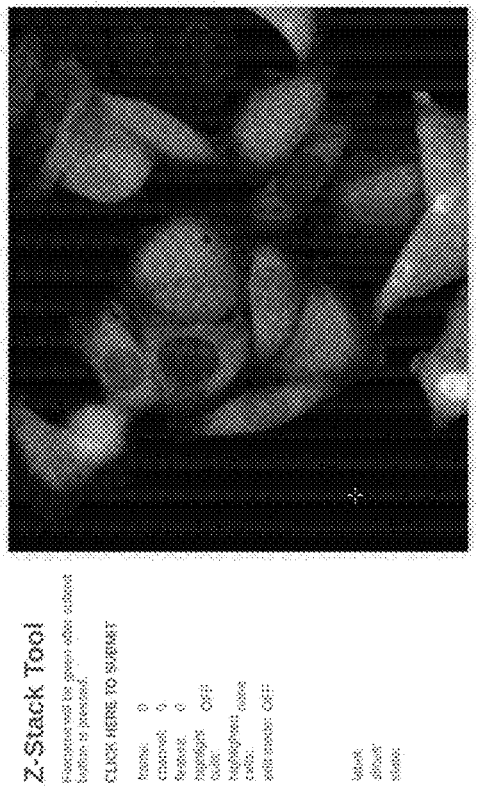
FIG. 42J Hold down the shift key while pressing "c" to cycle through channels in the opposite order.
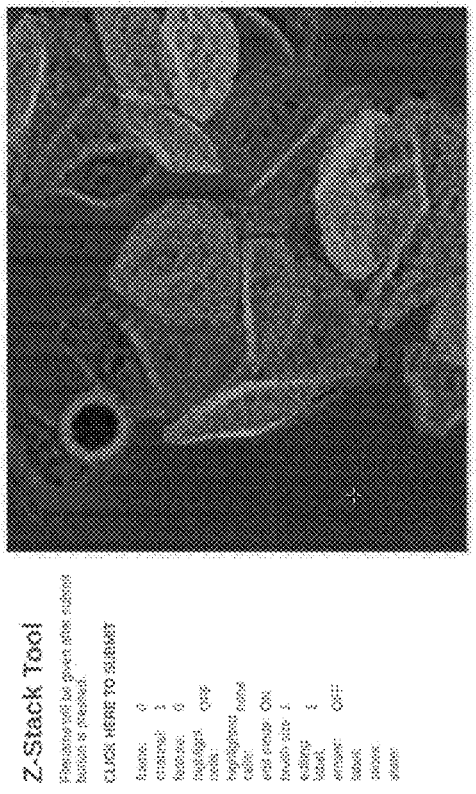
FIG. 42L The channel can be changed in pixel-editing mode.
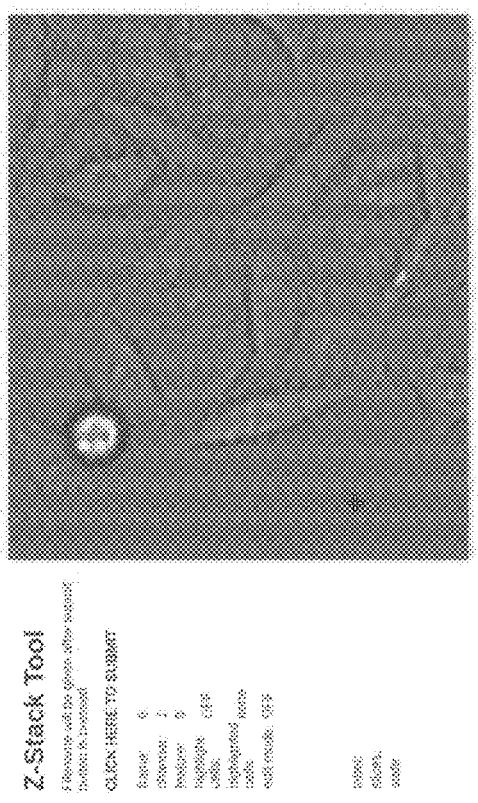
FIG. 42I Hold down the shift key while pressing "c" to cycle through channels in the opposite order.
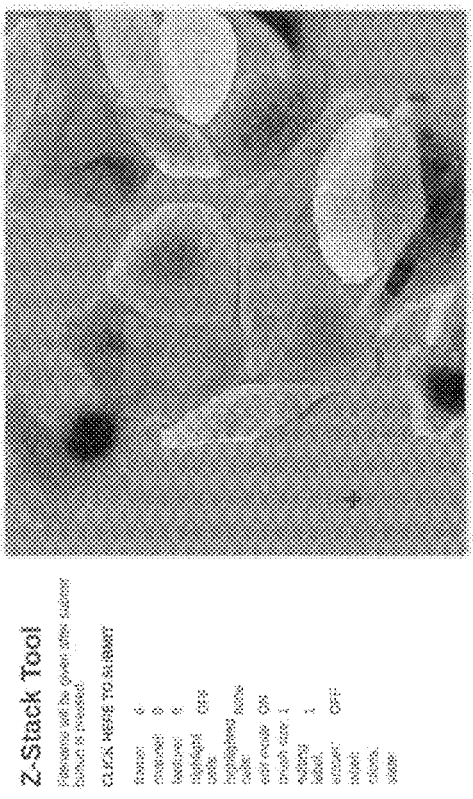
FIG. 42K The channel can be changed in pixel-editing mode.

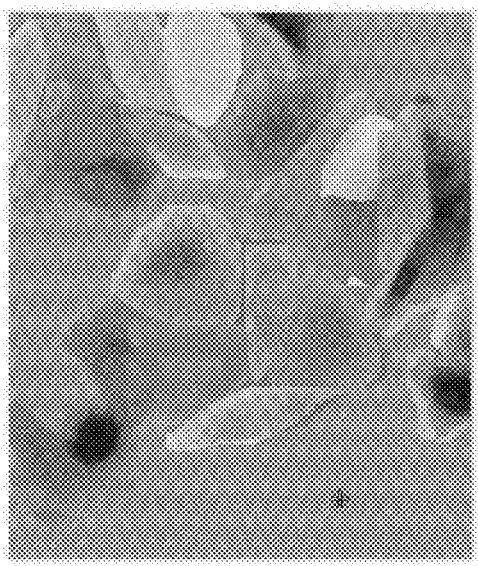
FIG. 43E
FIG. 43F
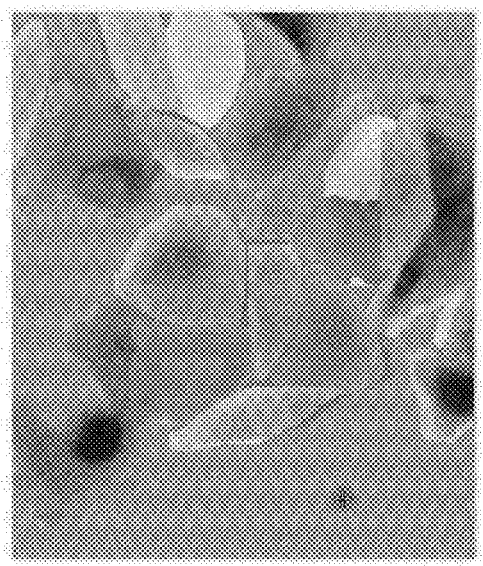
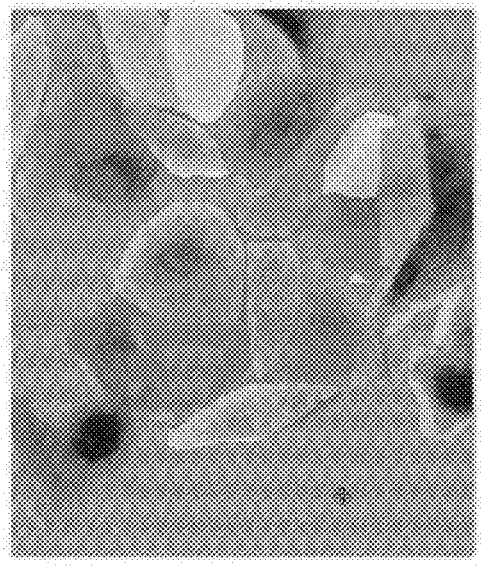
FIG. 43G
FIG. 43H
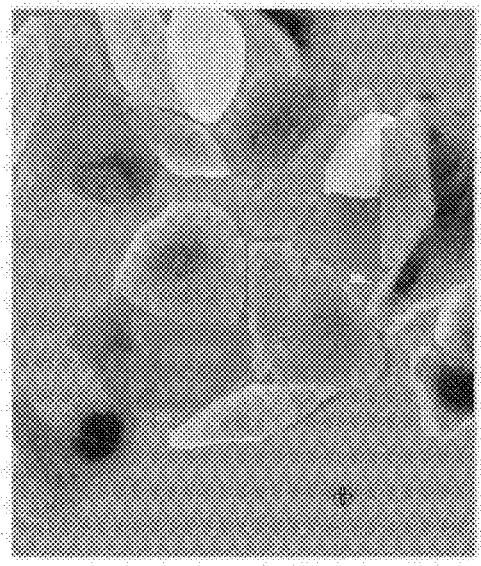

In pixel-editing mode, increase the brush size with the up arrow key.

In pixel-editing mode, decrease the brush size with the down arrow key.

In pixel-editing mode, increase the brush size with the up arrow key.

In pixel-editing mode, decrease the brush size with the down arrow key.

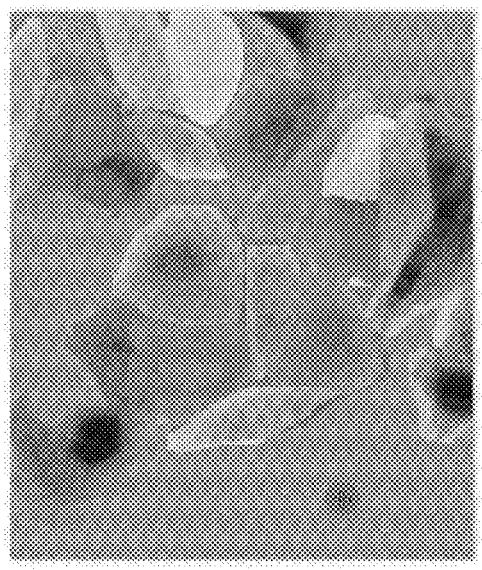
*FIG. 43Y*
In pixel-editing mode, decrease the brush size with the down arrow key.
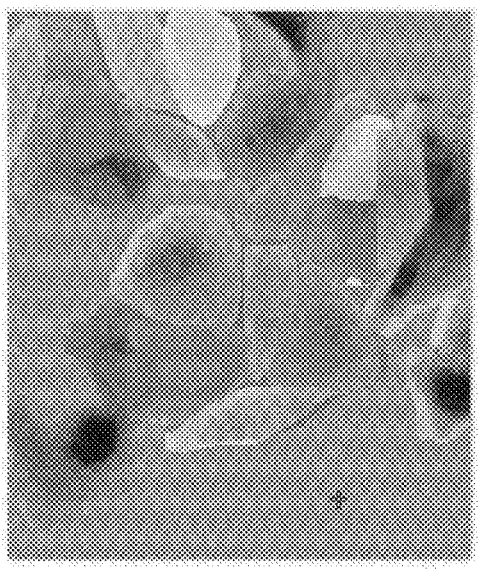
*FIG. 43Z*
In pixel-editing mode, decrease the brush size with the down arrow key.
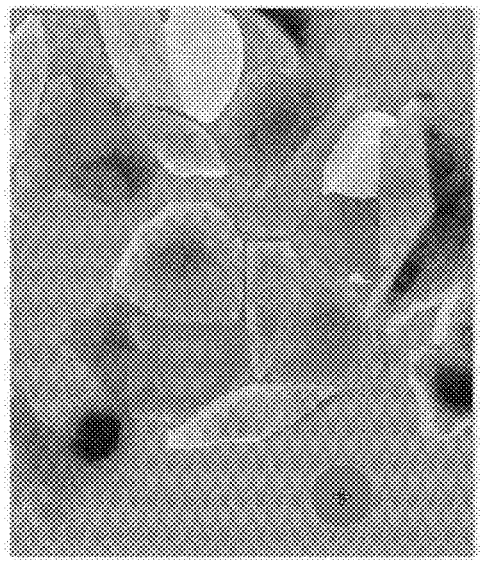
*FIG. 43A2*
In pixel-editing mode, decrease the brush size with the down arrow key.
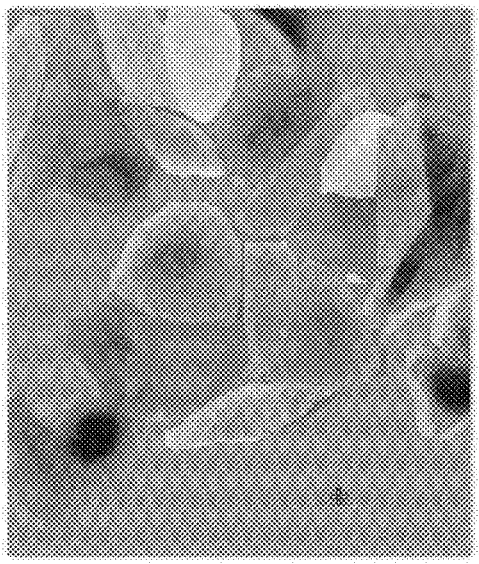
*FIG. 43B2*
In pixel-editing mode, decrease the brush size with the down arrow key.

Turn highlighting on or off with the "h" key.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

In pixel-editing mode, the current value of the brush is highlighted.

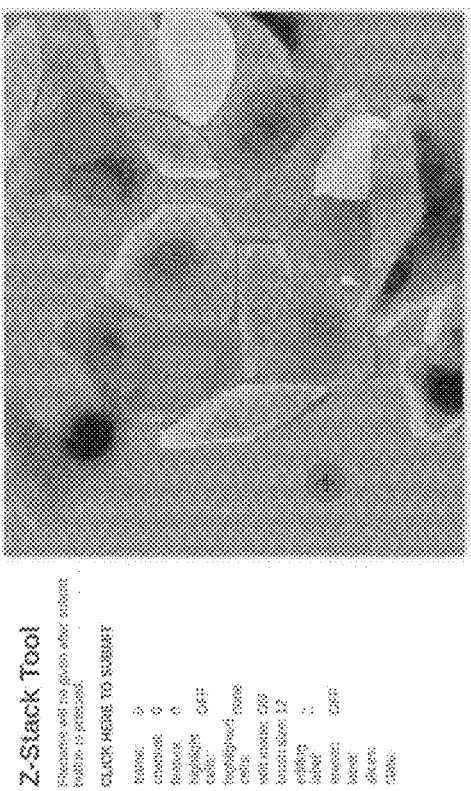
FIG. 45A In pixel-editing mode, increase the value of the brush using the "=" key.
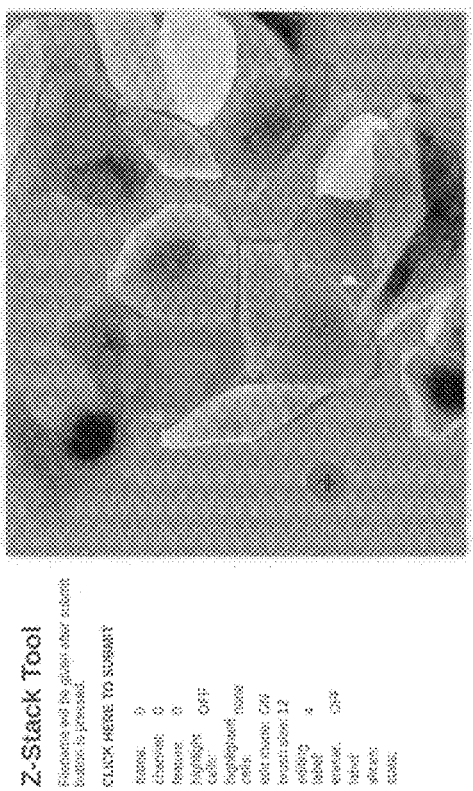
FIG. 45B In pixel-editing mode, increase the value of the brush using the "=" key.
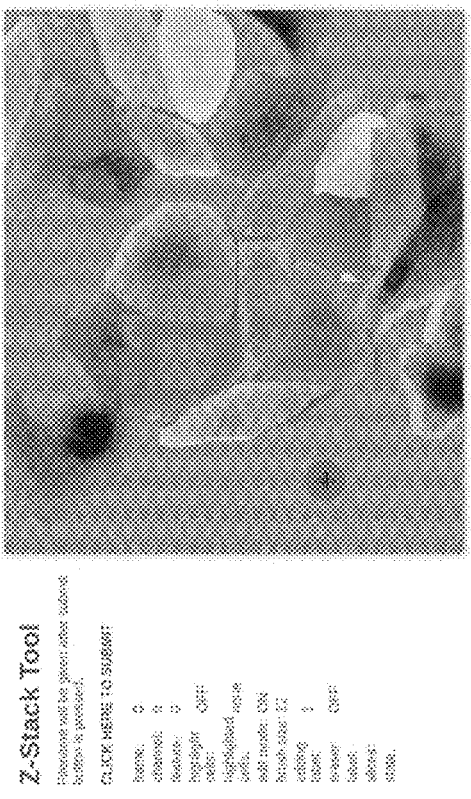
FIG. 45C In pixel-editing mode, increase the value of the brush using the "=" key.
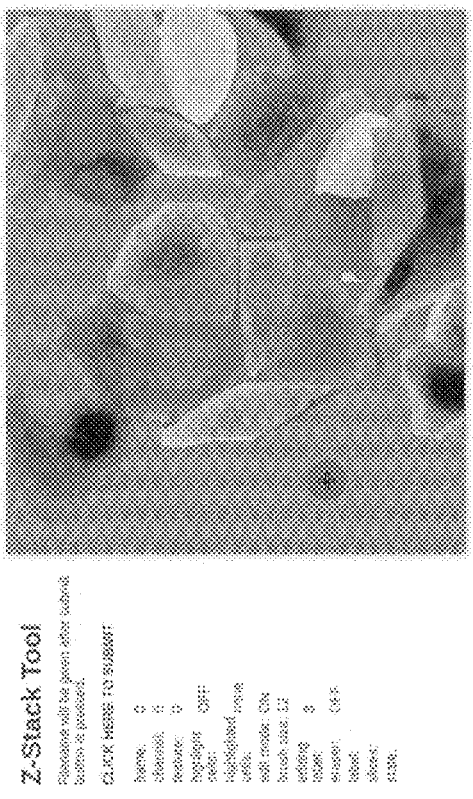
FIG. 45D In pixel-editing mode, increase the value of the brush using the "=" key.

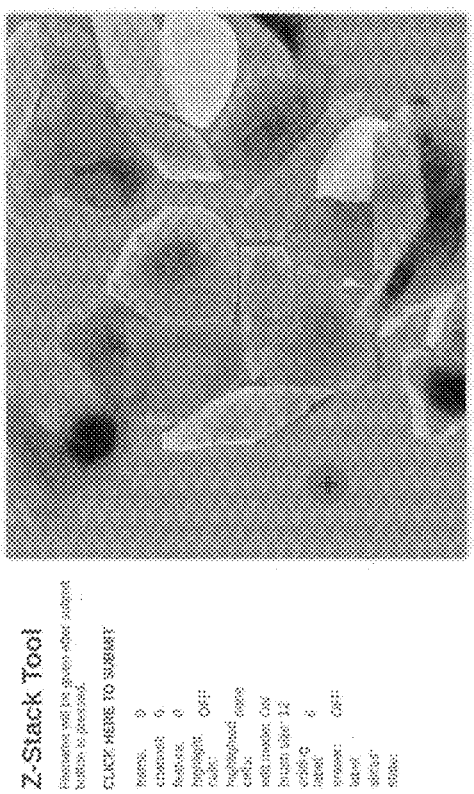
FIG. 45E In pixel-editing mode, increase the value of the brush using the "=" key.
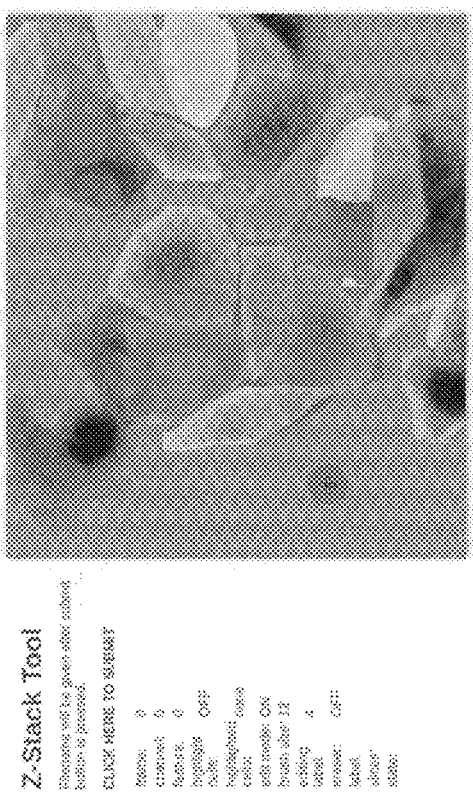
FIG. 45F In pixel-editing mode, increase the value of the brush using the "=" key.
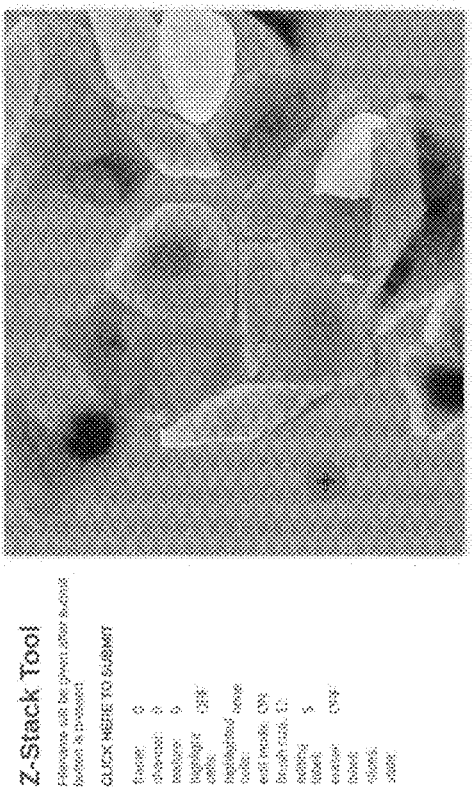
FIG. 45G In pixel-editing mode, decrease the value of the brush using the "-" key.
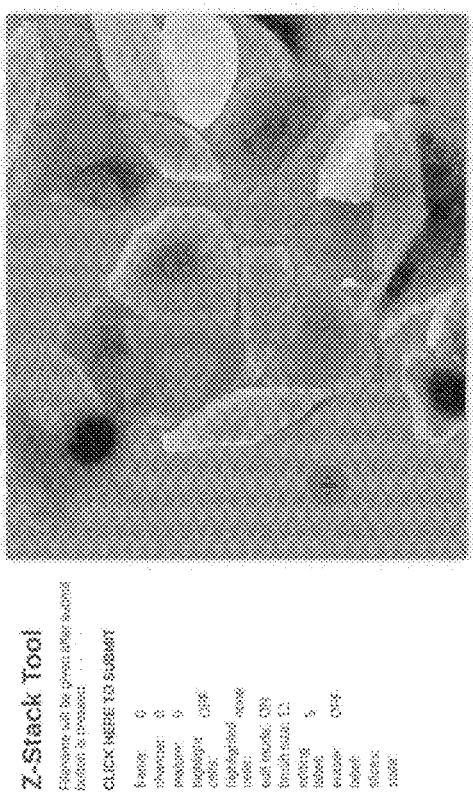
FIG. 45H In pixel-editing mode, decrease the value of the brush using the "-" key.

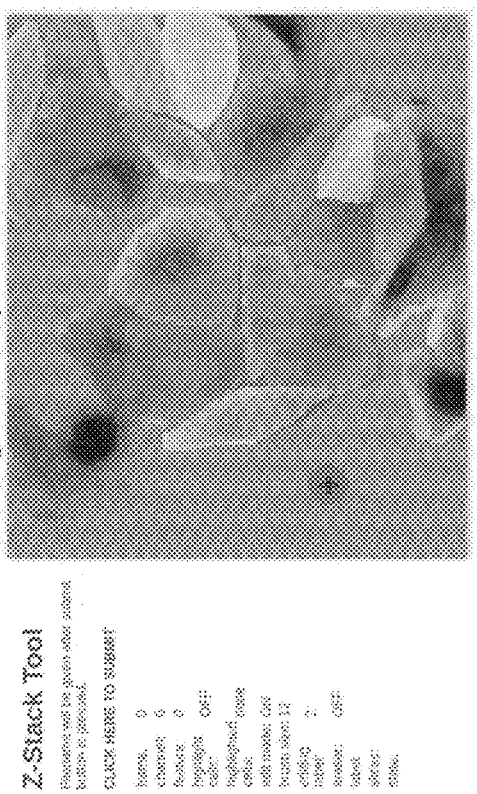
FIG. 45I In pixel-editing mode, decrease the value of the brush using the "-" key.
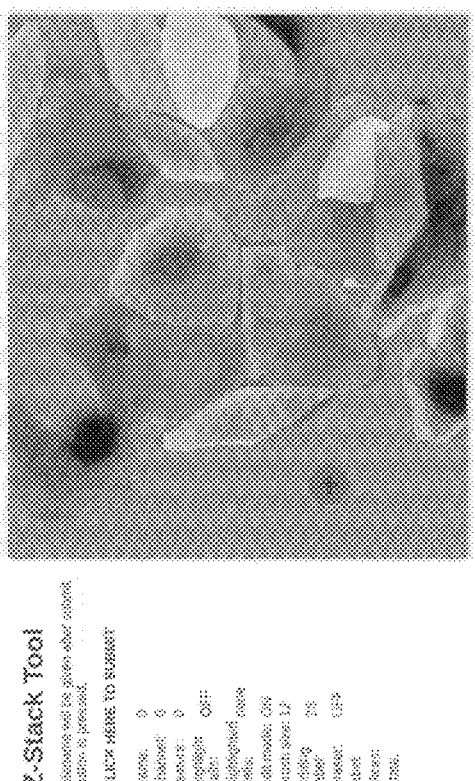
FIG. 45J In pixel-editing mode, decrease the value of the brush using the "-" key.
FIG. 45K In pixel-editing mode, decrease the value of the brush using the "-" key.
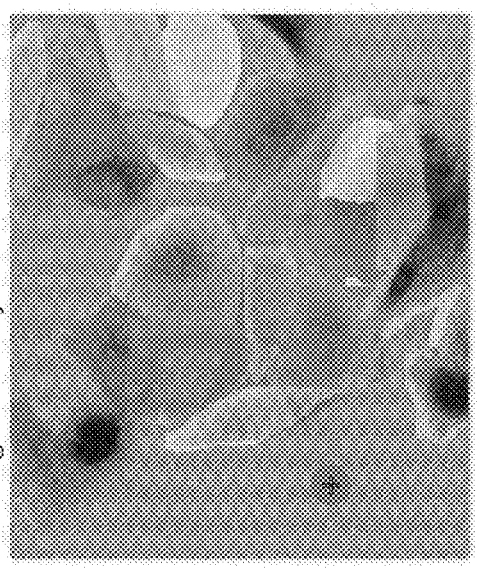
FIG. 45L In pixel-editing mode, set the brush to an unused value using the "n" key.

Turn highlighting on or off with the "h" key.

Turn highlighting on or off with the "h" key.

With highlighting on, selected labels will be red.

Highlighting can be toggled on and off while labels are selected.

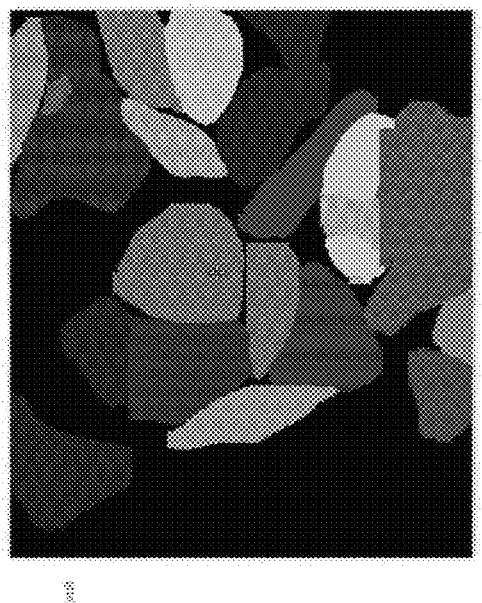
*FIG. 47E* Highlighting can be toggled on and off while labels are selected.
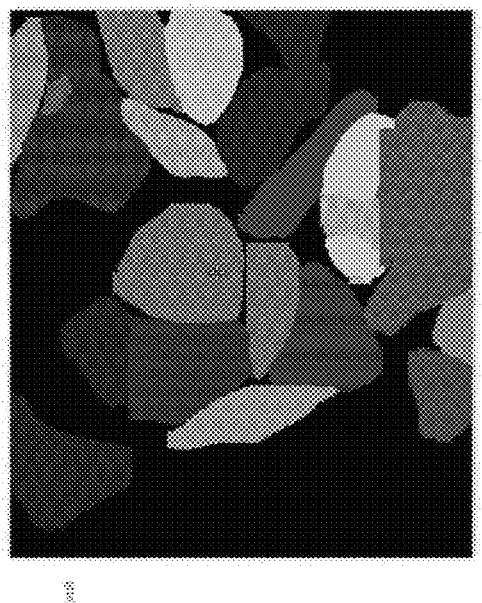
*FIG. 47F* Press the "=" key to highlight the next label.
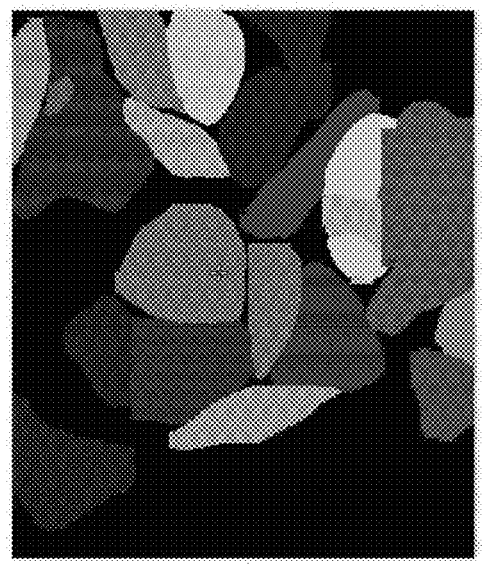
*FIG. 47G* Press the "=" key to highlight the next label.
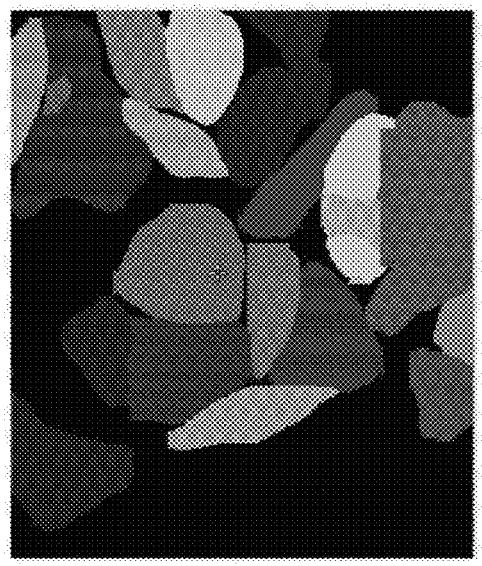
*FIG. 47H* Press the "=" key to highlight the next label.

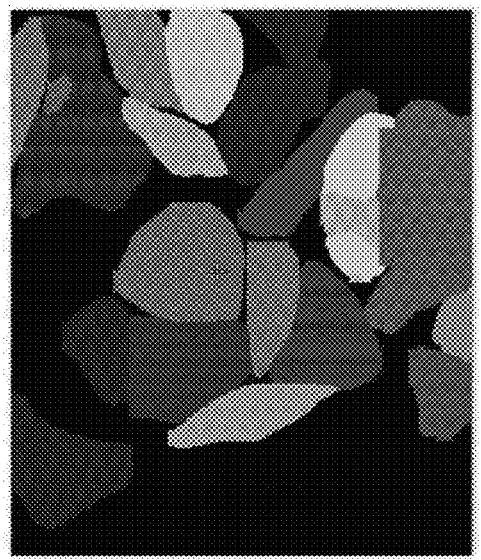
FIG. 47J Press the "=" key to highlight the next label.
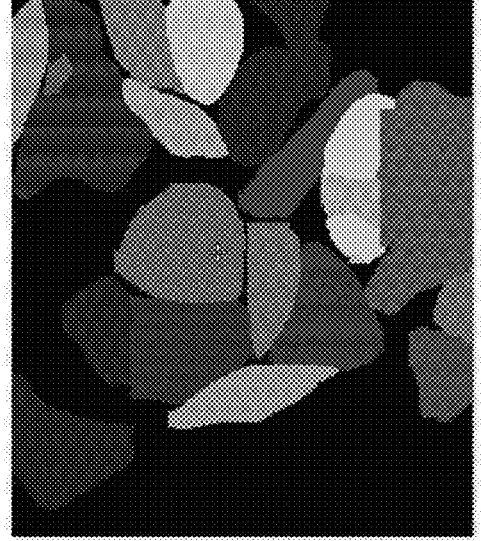
FIG. 47L Press the "-" key to highlight the previous label.
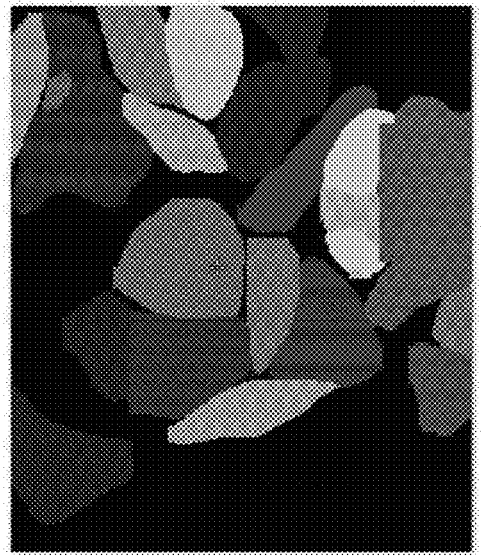
FIG. 47I Press the "=" key to highlight the next label.
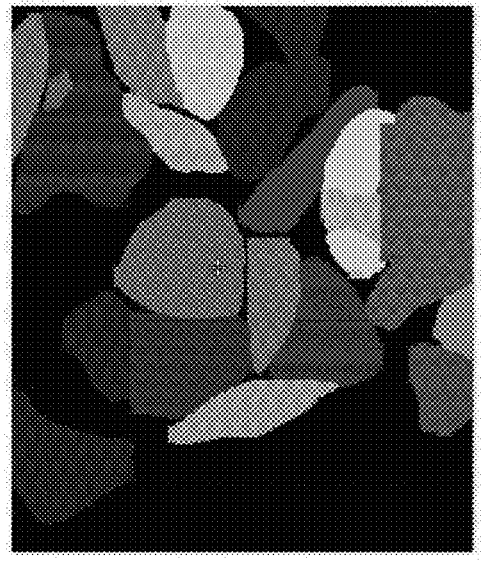
FIG. 47K Press the "-" key to highlight the previous label.

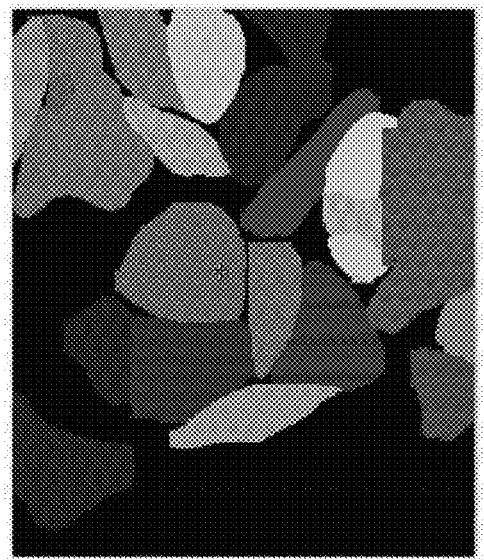
FIG. 47U
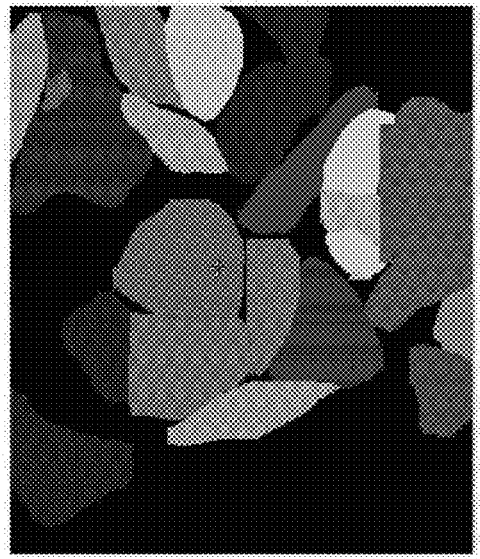
FIG. 47W
FIG. 47V
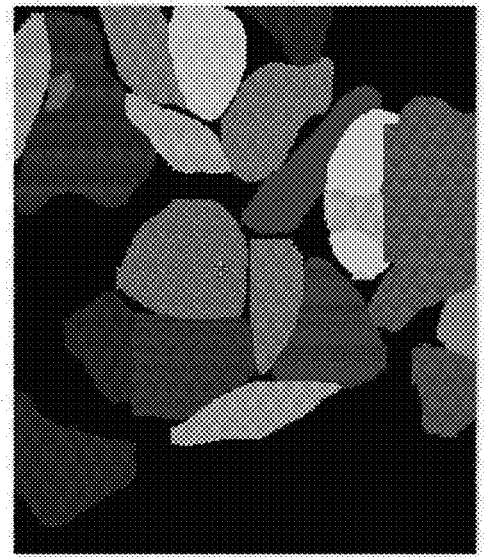
FIG. 47X

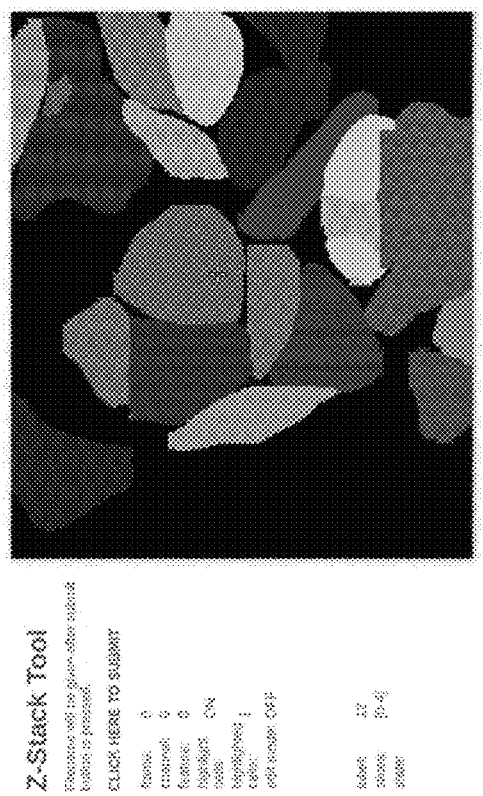
FIG. 47Y
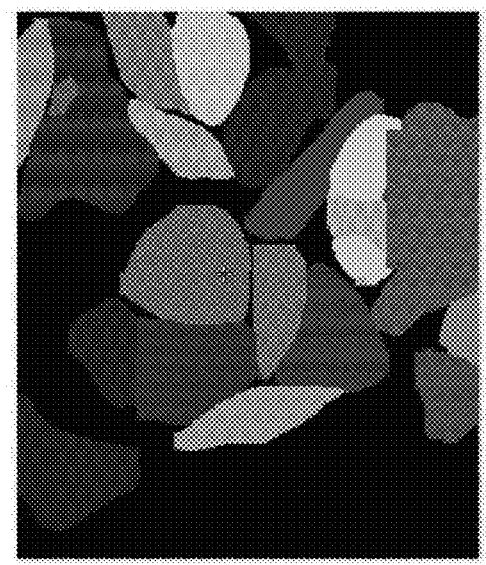
FIG. 47Z
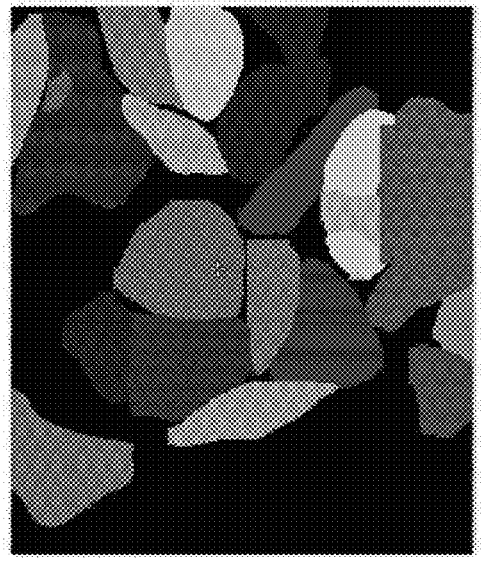
FIG. 47A2
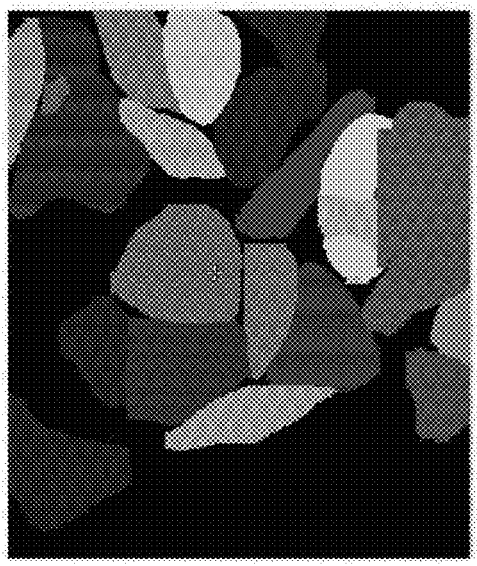
FIG. 47B2

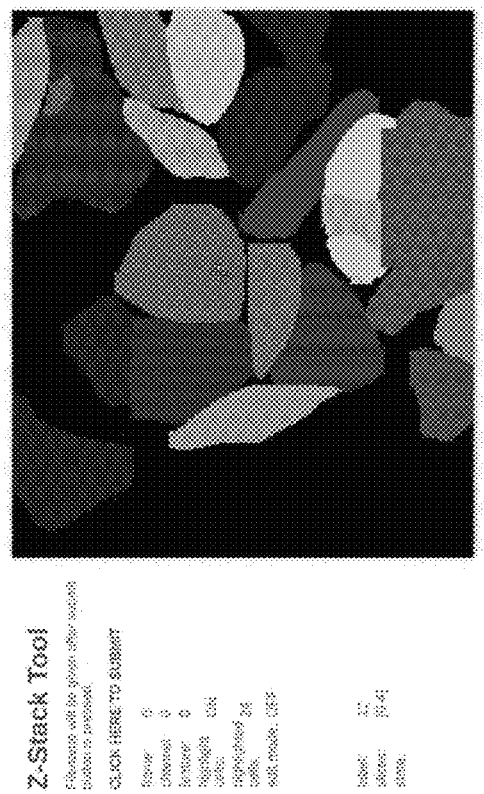
FIG. 47C2
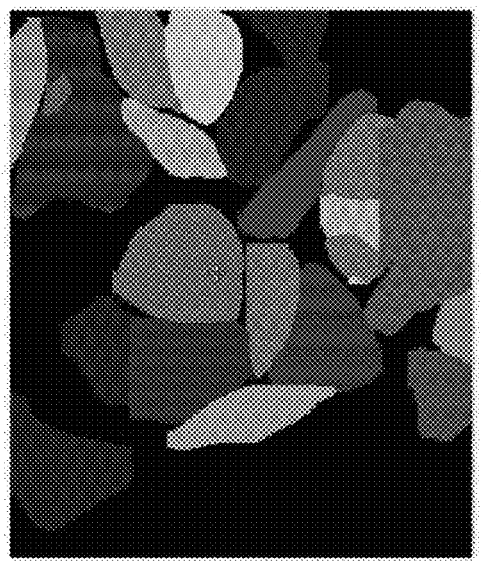
FIG. 47D2
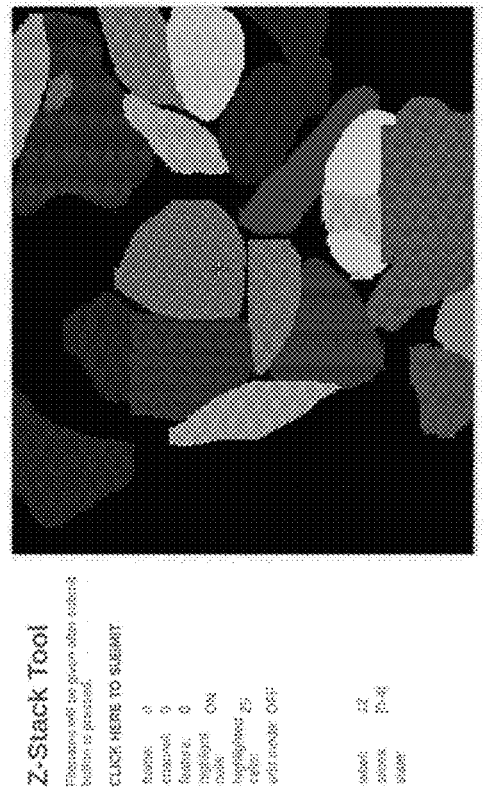
FIG. 47E2
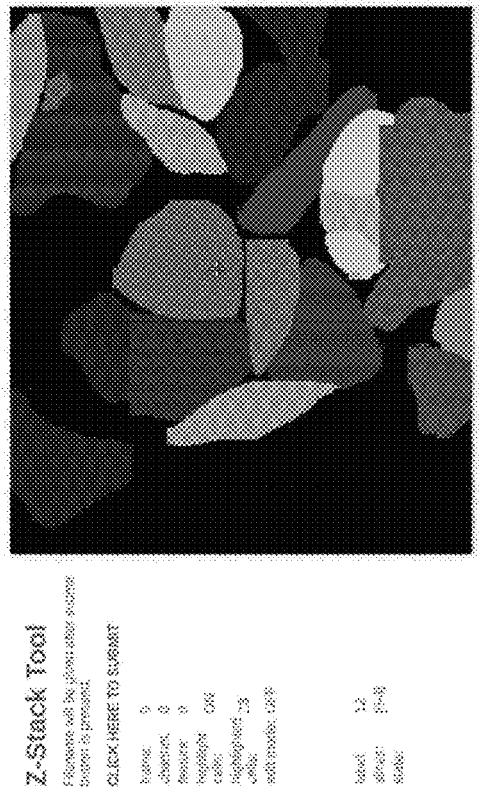
FIG. 47F2

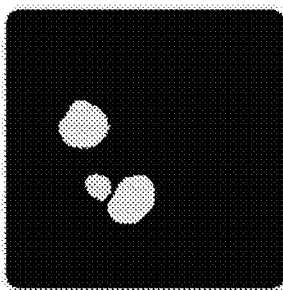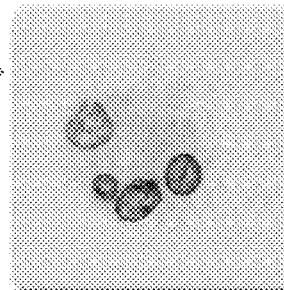
FIG. 48A                FIG. 48B
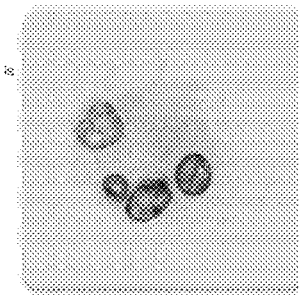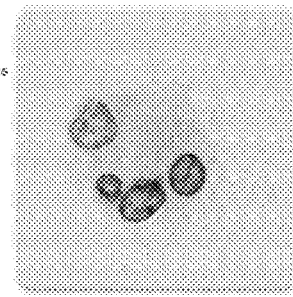
FIG. 48C                FIG. 48D
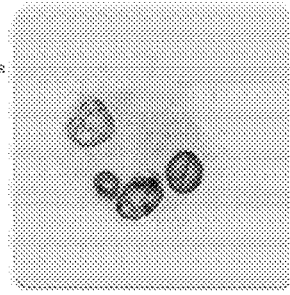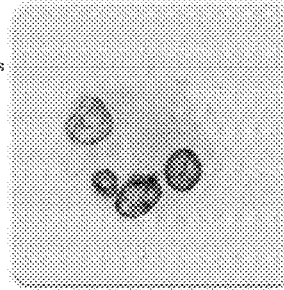
FIG. 48E                FIG. 48F

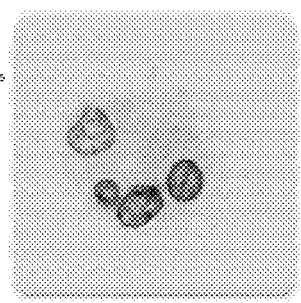
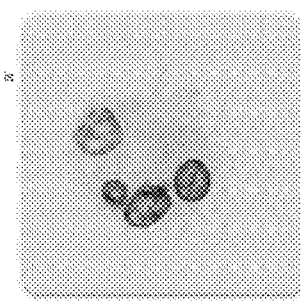
FIG. 48G                    FIG. 48H
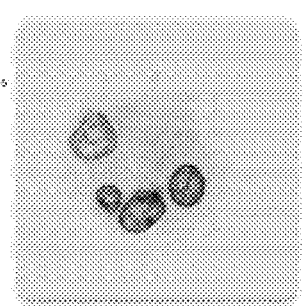
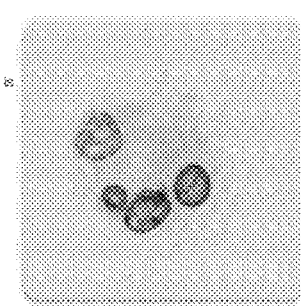
FIG. 48I                    FIG. 48J
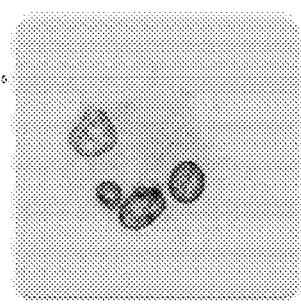
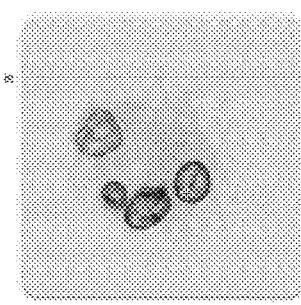
FIG. 48K                    FIG. 48L

Z-Stack Tool

Filename will be given after submit button is pressed.

[Submit]

frame:
6
channel:
0
feature:
0
highlight mode:
OFF
edit mode:
ON
    brush size: 4
    editing label: 4
    eraser mode: OFF

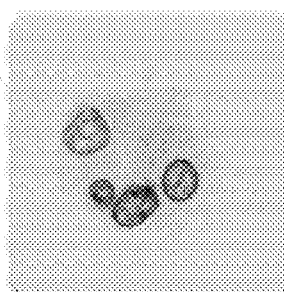

FIG. 48M

Z-Stack Tool

Filename will be given after submit button is pressed.

[Submit]

frame:
6
channel:
0
feature:
0
highlight mode:
OFF
edit mode:
ON
    brush size: 4
    editing label: 4
    eraser mode: OFF

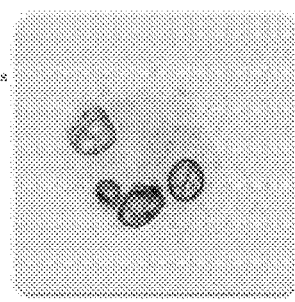

FIG. 48N

Z-Stack Tool

Filename will be given after submit button is pressed.

[Submit]

frame:
6
channel:
0
feature:
0
highlight mode:
OFF
edit mode:
ON
    brush size: 4
    editing label: 4
    eraser mode: OFF

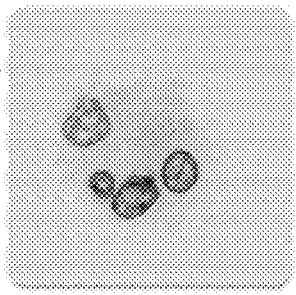

FIG. 48O

Z-Stack Tool

Filename will be given after submit button is pressed.

[Submit]

frame:
6
channel:
0
feature:
0
highlight mode:
OFF
edit mode:
OFF
label:
4

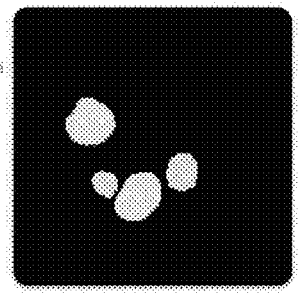

FIG. 48P

Z-Stack Tool

Filename will be given after submit button is pressed.

[Submit]

frame:
6
channel:
0
feature:
0
highlight mode:
OFF
edit mode:
OFF
label:
4

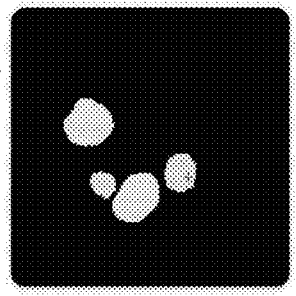

FIG. 48Q

Z-Stack Tool

Filename will be given after submit button is pressed.

[Submit]

frame:
6
channel:
0
feature:
0
highlight mode:
OFF
edit mode:
OFF
label:
slices:

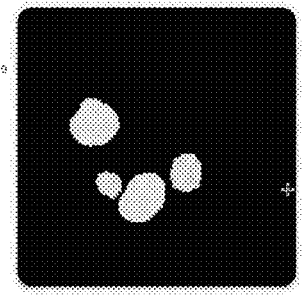

FIG. 48R

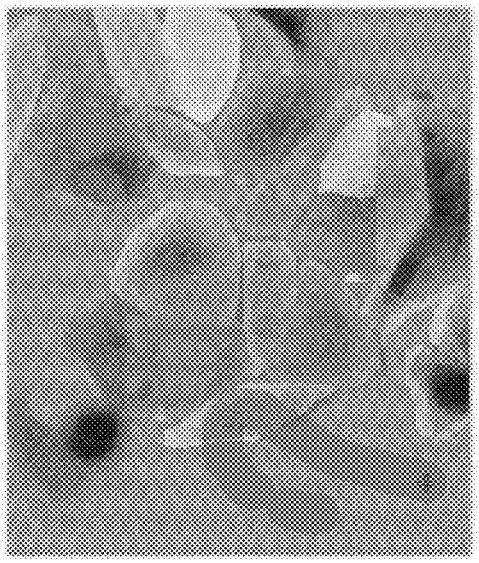
FIG. 49A In pixel-editing mode, click and drag brush to draw.
FIG. 49B The brush will not draw over other labels.
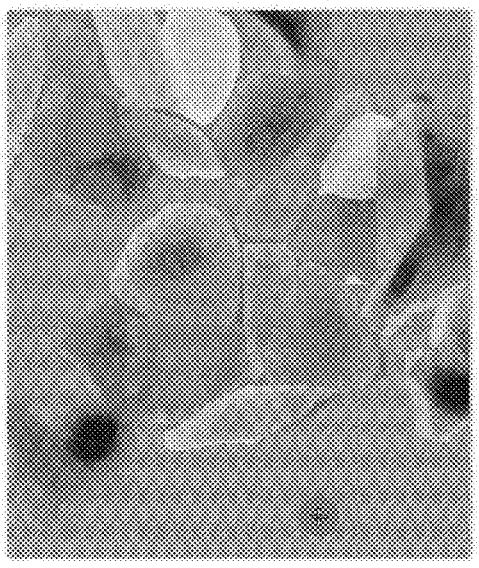
FIG. 49C The brush will not draw over other labels.
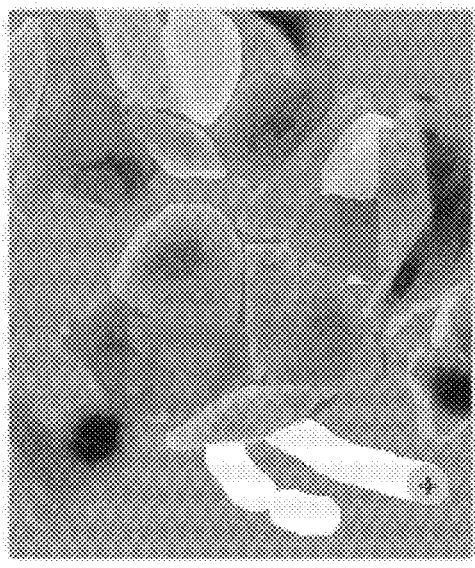
FIG. 49D Turn the eraser on and off with "x".

In pixel-editing mode, turn on the conversion brush with "r".

Follow the prompts to set the brush values.

Follow the prompts to set the brush values.

Follow the prompts to set the brush values.

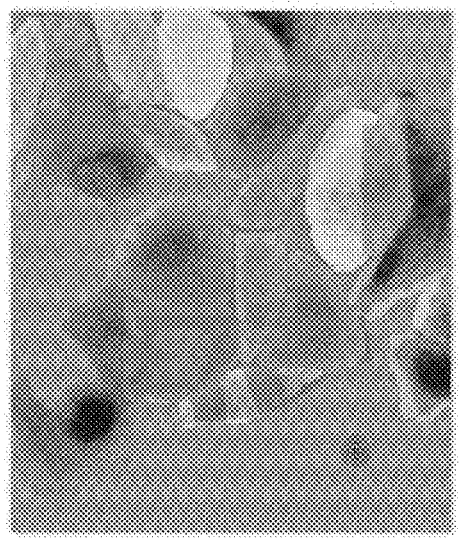
FIG. 50I
Use the escape key to stop using the conversion brush.
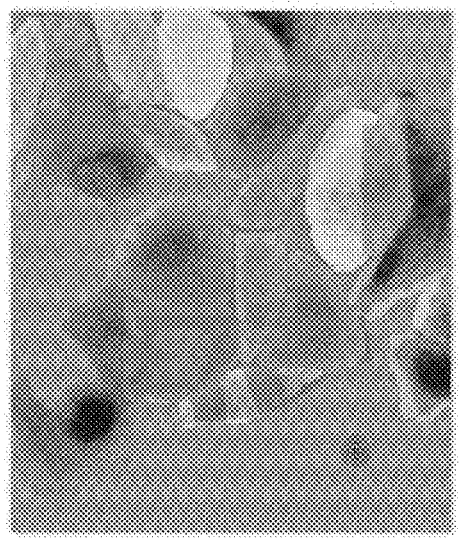
FIG. 50J
Use the escape key to stop using the conversion brush.
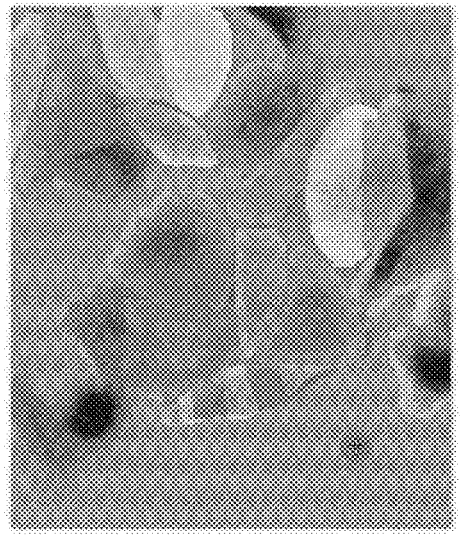
FIG. 50K
Use the escape key to stop using the conversion brush.
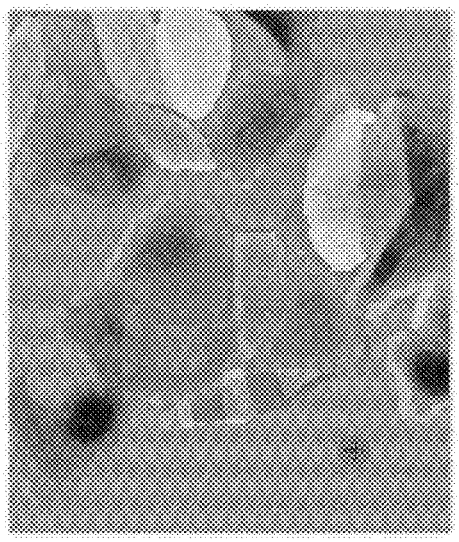

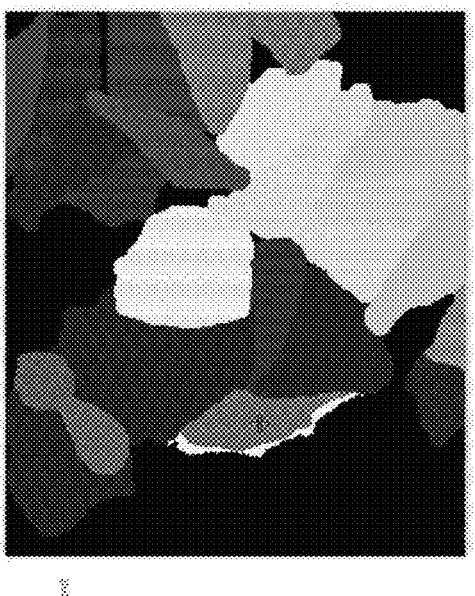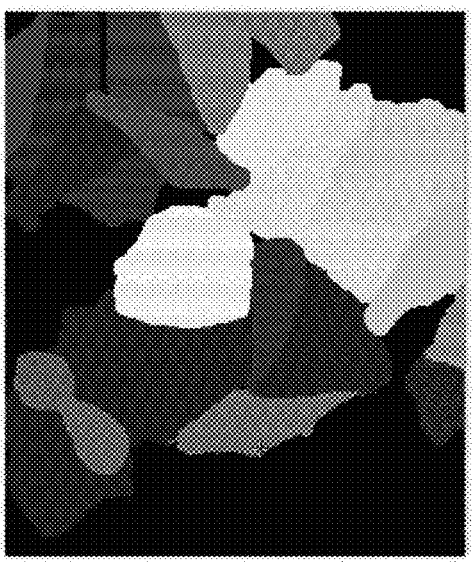

FIG. 51A
Select two labels, then press "r" to use the "replace" action.
The second label will be replaced with the first label.

FIG. 51B
Select two labels, then press "r" to use the "replace" action.
The second label will be replaced with the first label.

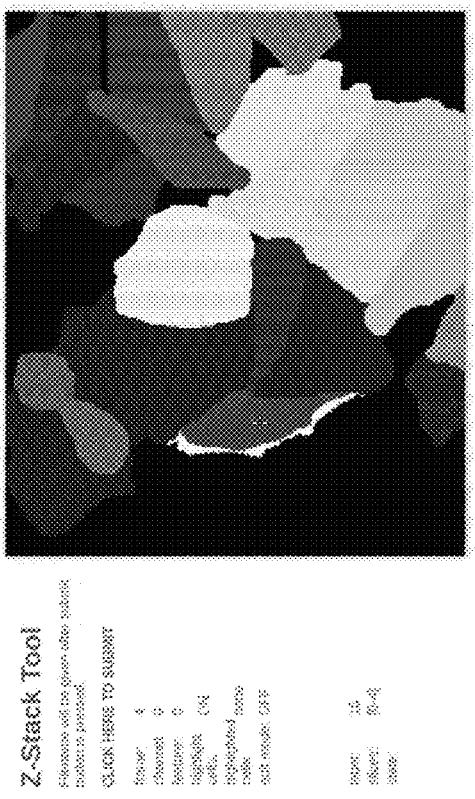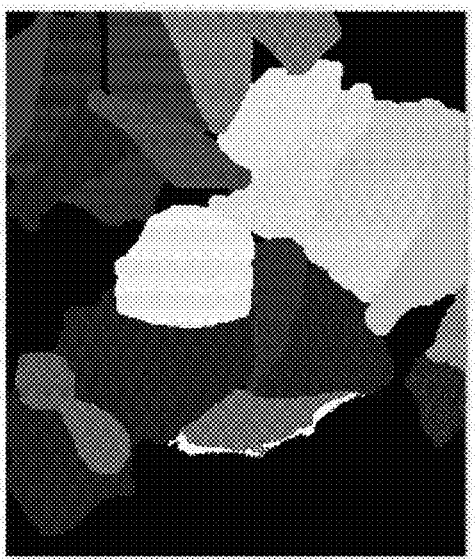

FIG. 51C
Select two labels, then press "r" to use the "replace" action.
The second label will be replaced with the first label.

FIG. 51D
Select two labels, then press "r" to use the "replace" action.
The second label will be replaced with the first label.

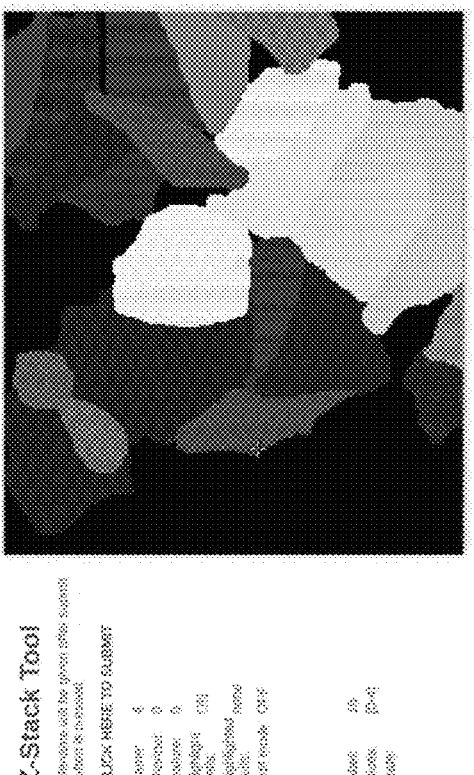

FIG. 51E
Select two labels, then press "r" to use the "replace" action.
The second label will be replaced with the first label.

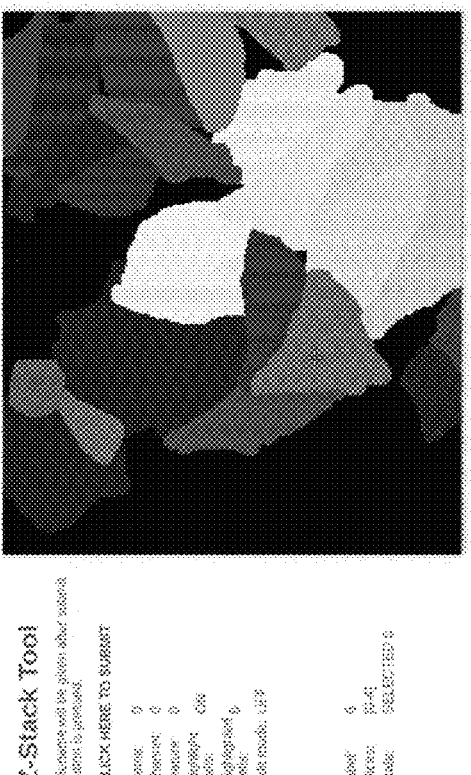

FIG. 51F
Confirm with "s" to affect only one frame.

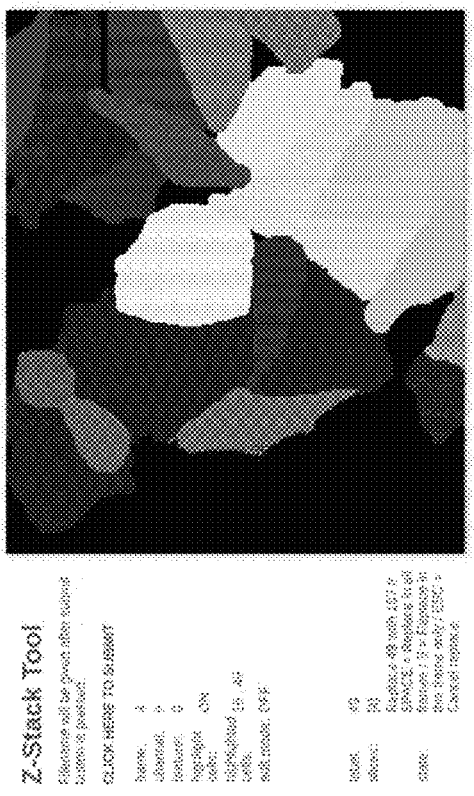

FIG. 51G
Select two labels, then press "r" to use the "replace" action.
The second label will be replaced with the first label.

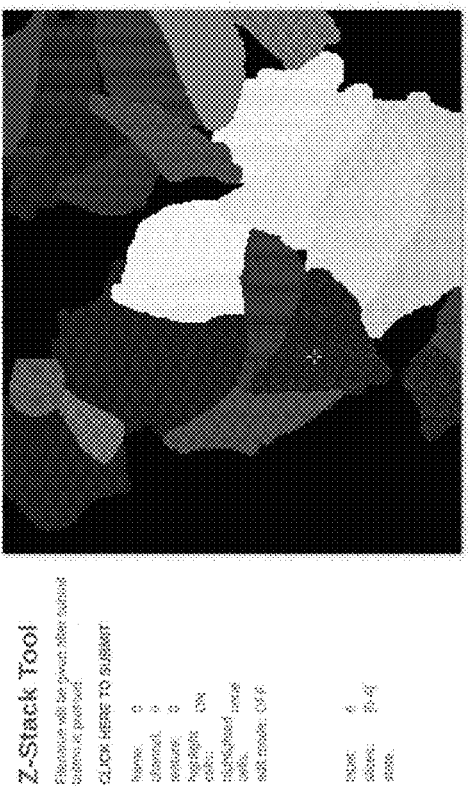

FIG. 51H
Select two labels, then press "r" to use the "replace" action.
The second label will be replaced with the first label.

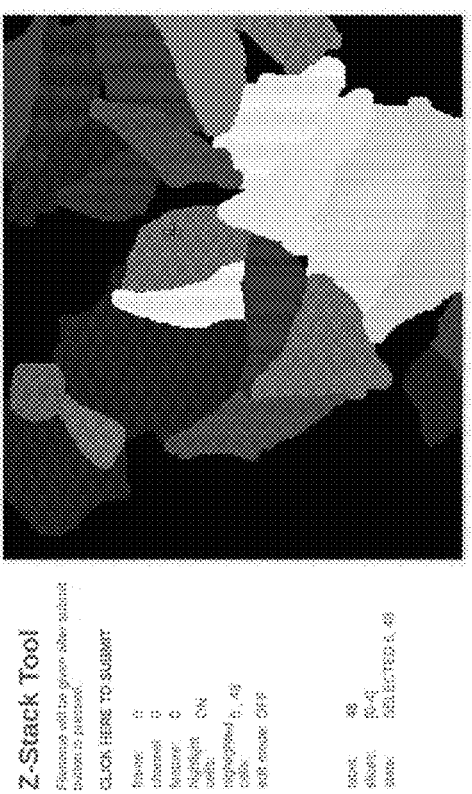

FIG. 51J
Select two labels, then press "r" to use the "replace" action.
The second label will be replaced with the first label.

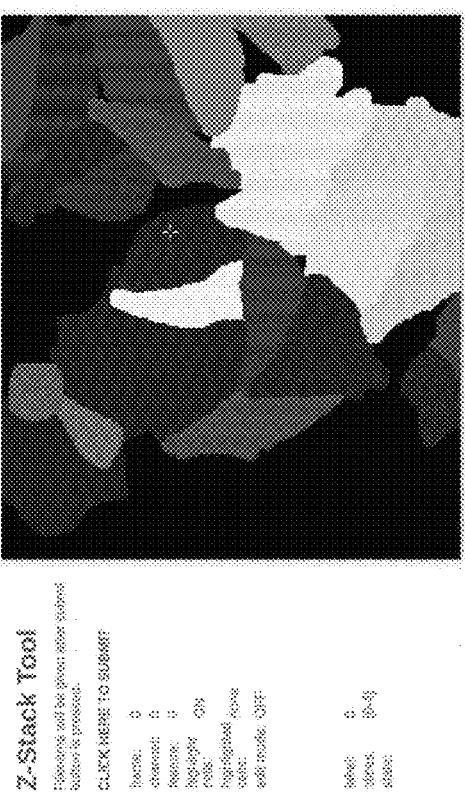

FIG. 51L
Confirm with "space" to affect all frames.

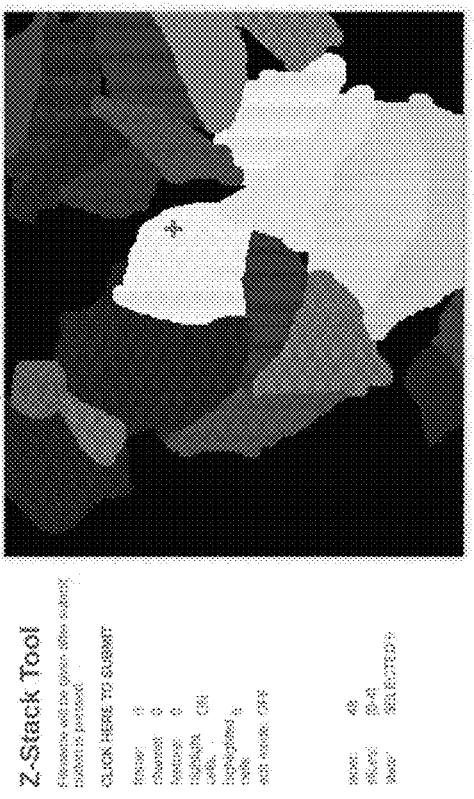

FIG. 51I
Select two labels, then press "r" to use the "replace" action.
The second label will be replaced with the first label.

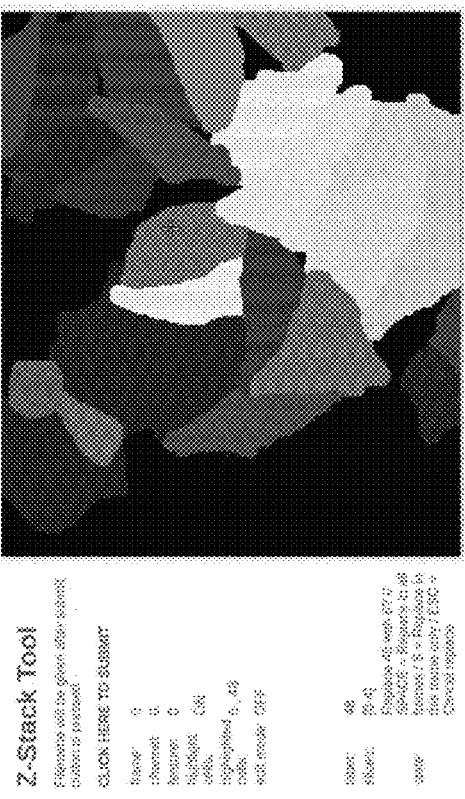

FIG. 51K
Select two labels, then press "r" to use the "replace" action.
The second label will be replaced with the first label.

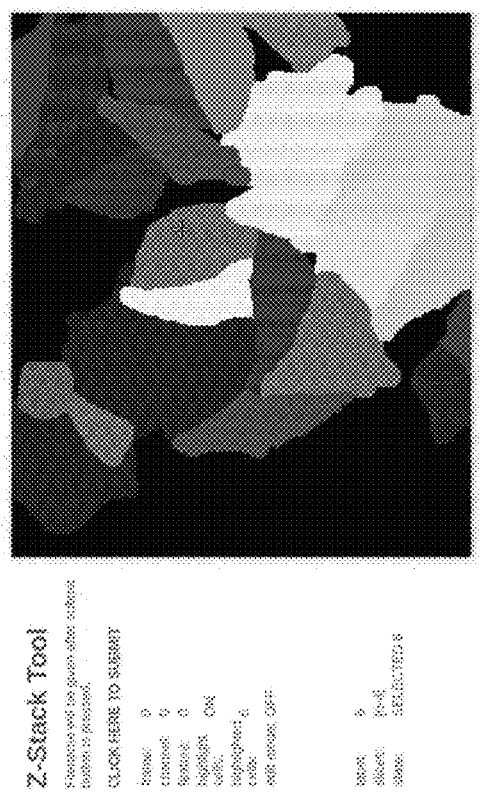
FIG. 51Q
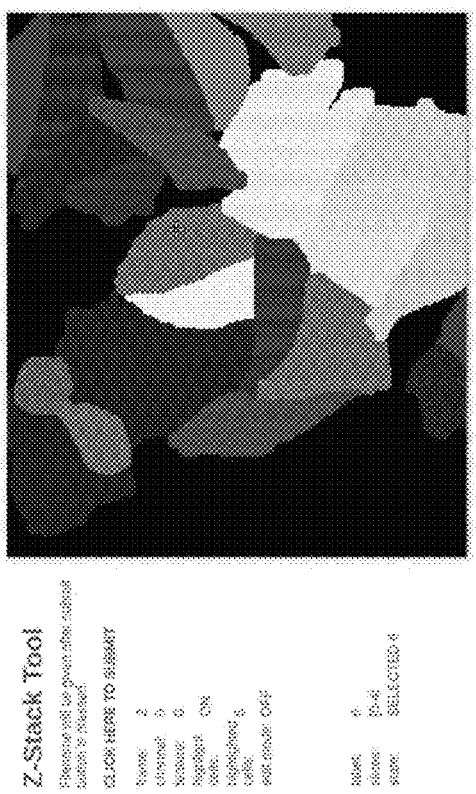
FIG. 51R
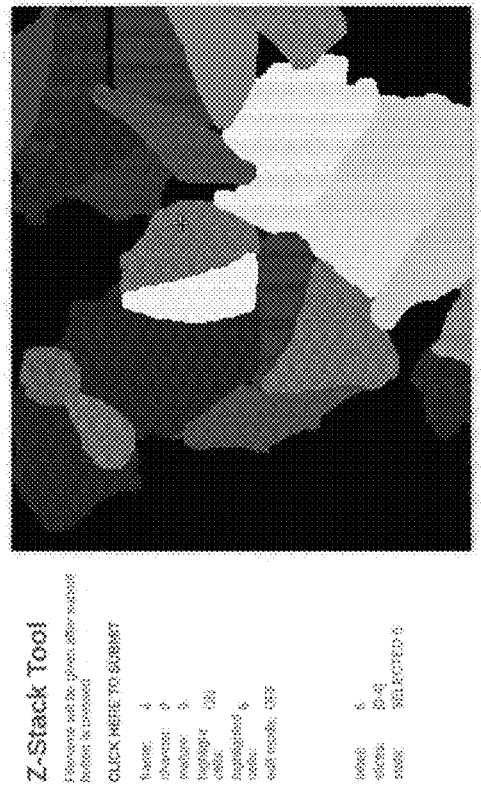
FIG. 51S
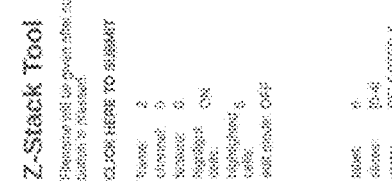
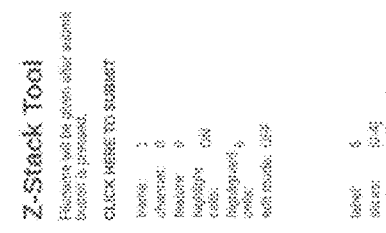
FIG. 51T

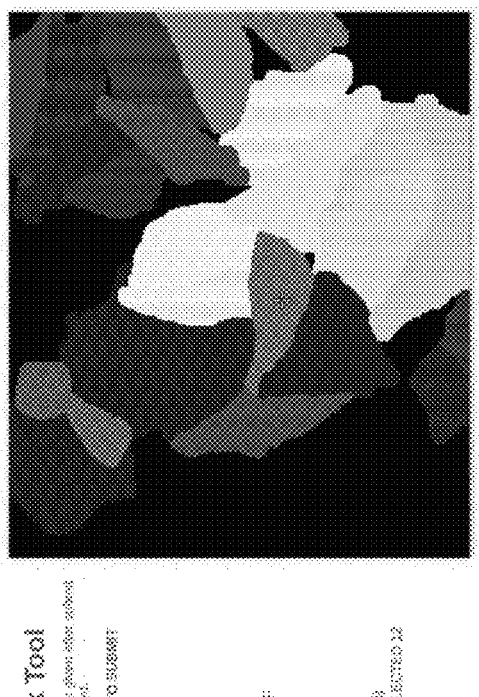
FIG. 52A Select a label and press "x" to use the delete action.
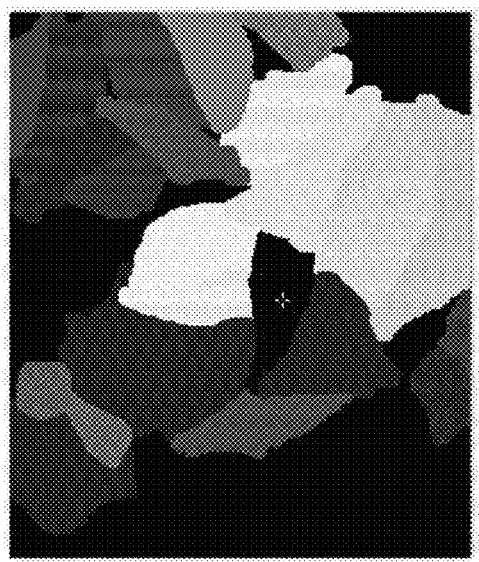
FIG. 52B Select a label and press "x" to use the delete action.
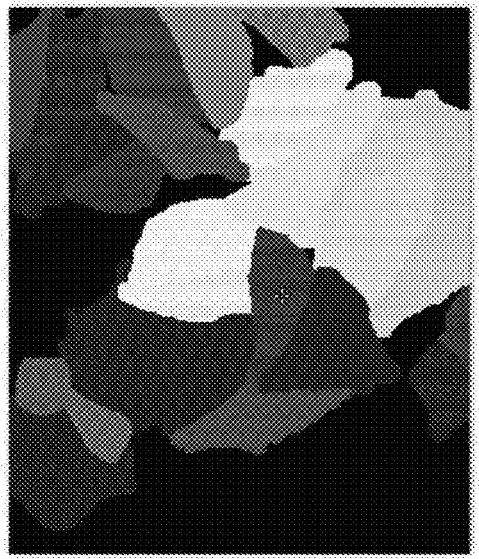
FIG. 52C Confirm with "space" to remove the whole label from that frame only.
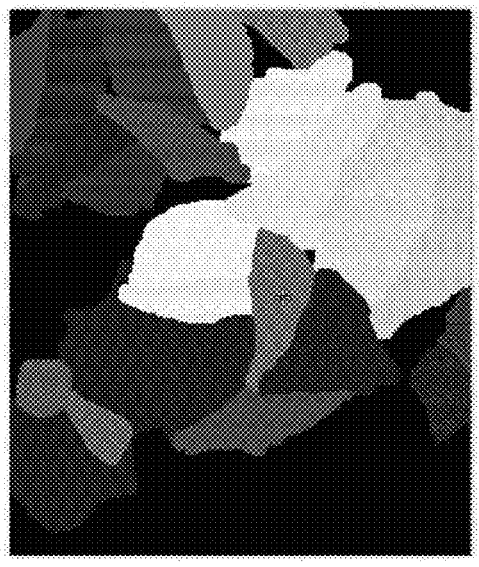
FIG. 52D Confirm with "space" to remove the whole label from that frame only.

Include some of the image background in the box for best results.

In pixel-editing mode, press "t" to threshold.

Follow the prompt to draw a box.

In pixel-editing mode, press "t" to threshold.

Include some of the image background in the box for best results.

The new label will not replace any existing labels.

The new label will not replace any existing labels.

The new label will not replace any existing labels.

Hold down the "alt" key while clicking on a label to use the flood action.

Hold down the "alt" key while clicking on a label to use the flood action.

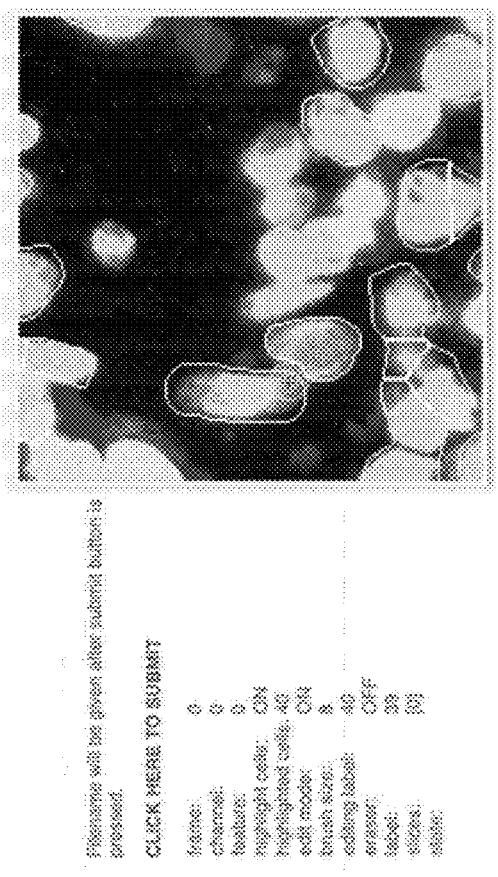
FIG. 65E
FIG. 65F
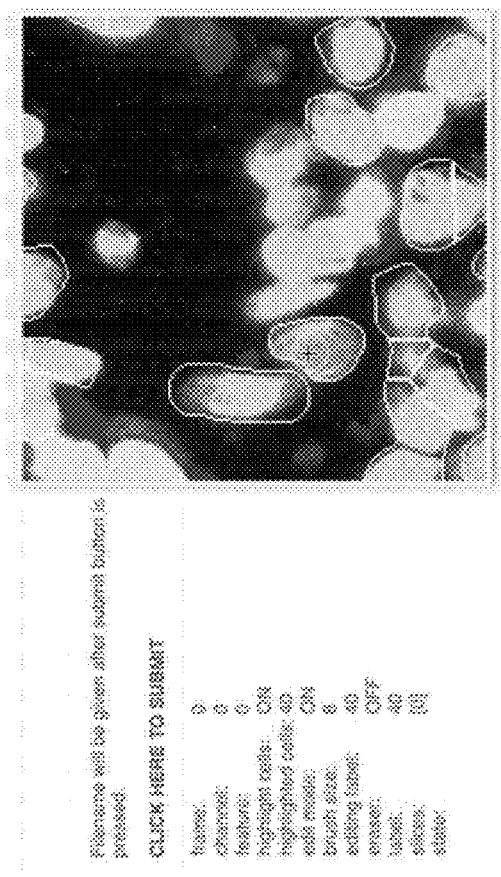
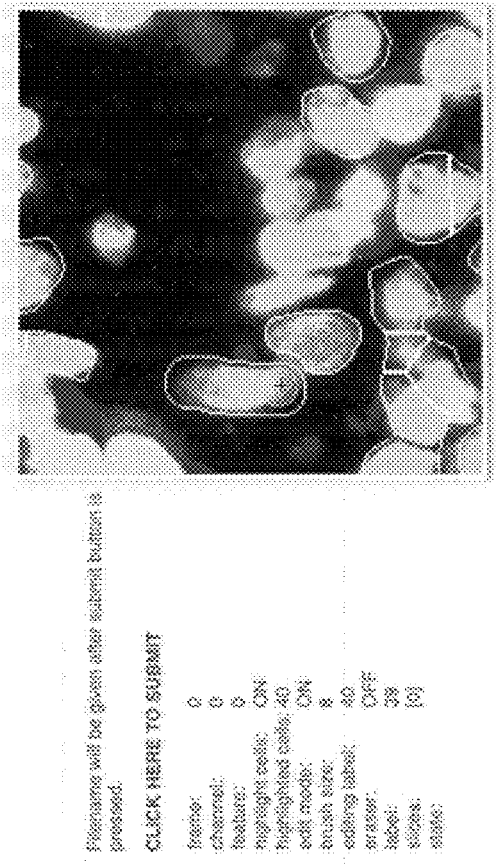
FIG. 65G
FIG. 65H
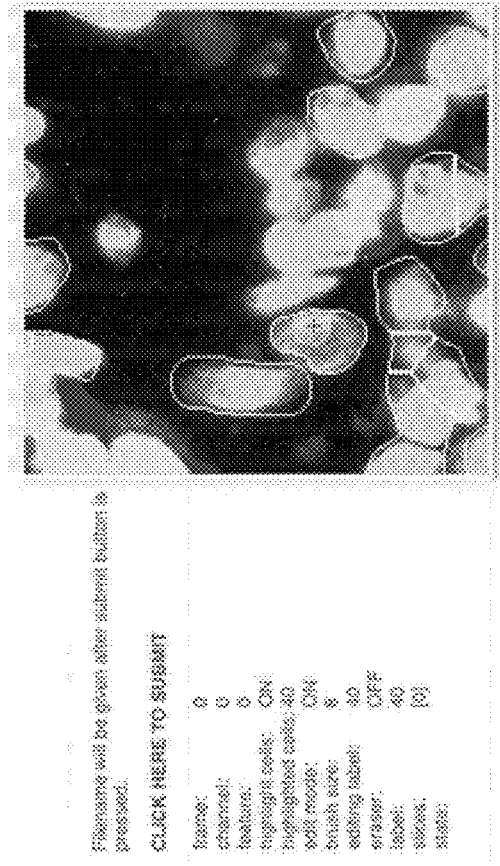

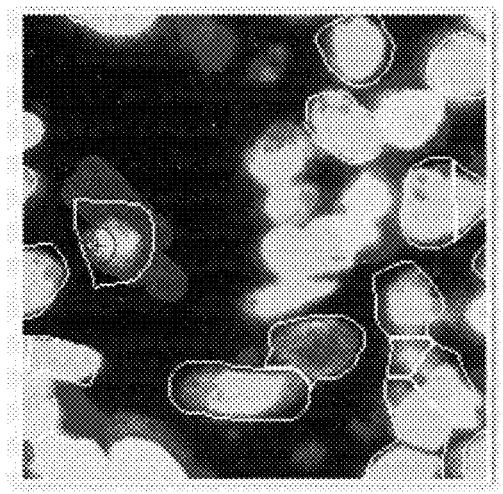
FIG. 69E
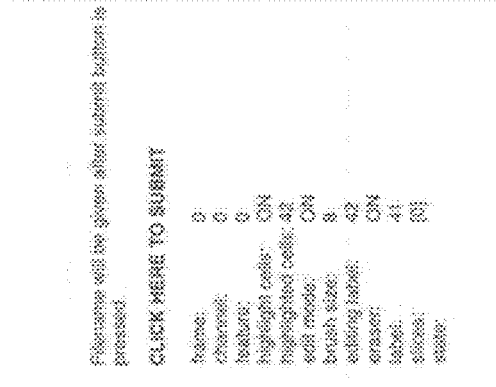
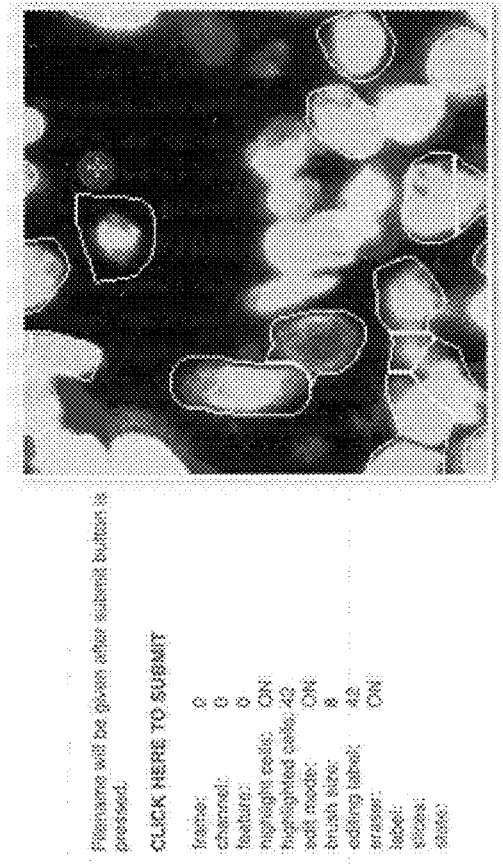
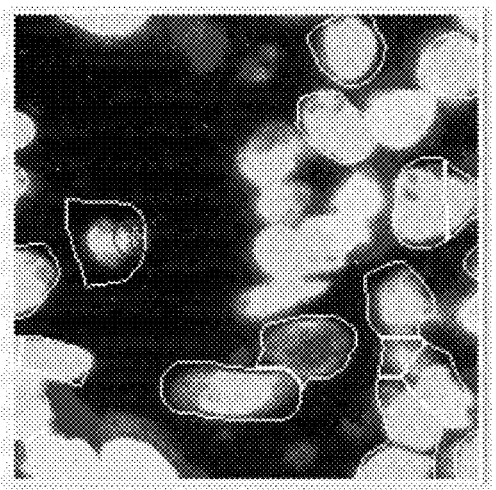
FIG. 69F
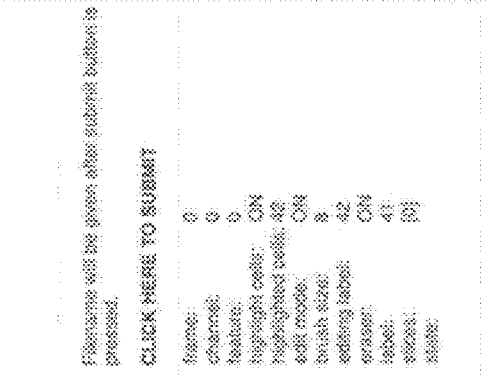
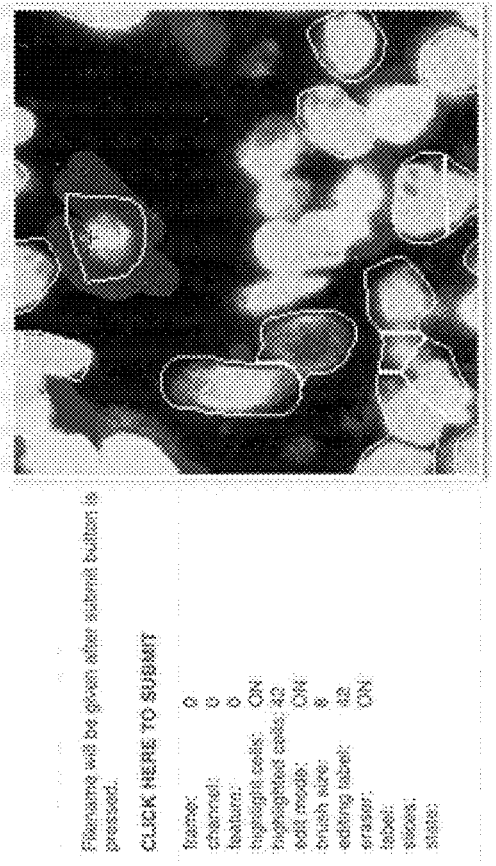
FIG. 69G
FIG. 69H

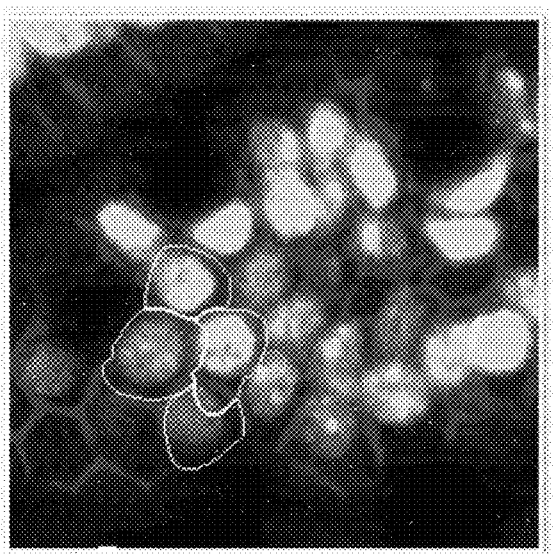
FIG. 72A
FIG. 72B
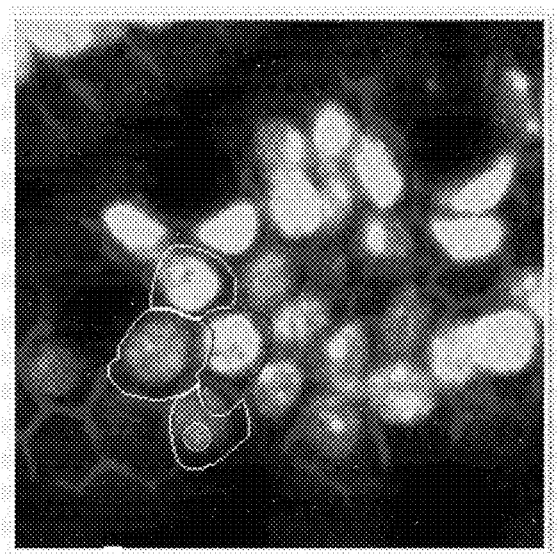
FIG. 72C
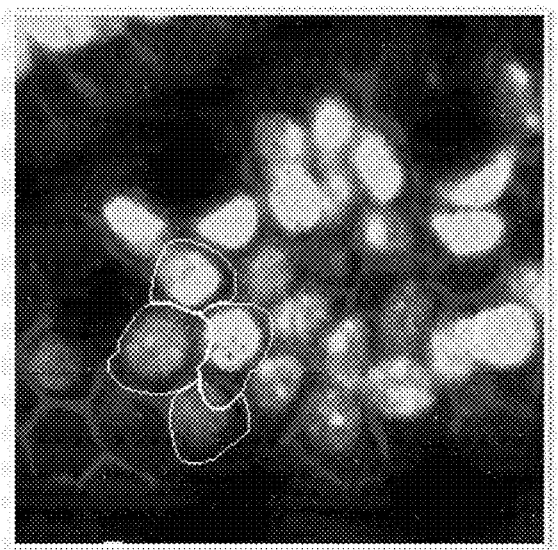
FIG. 72D

FIG. 72N
FIG. 72P

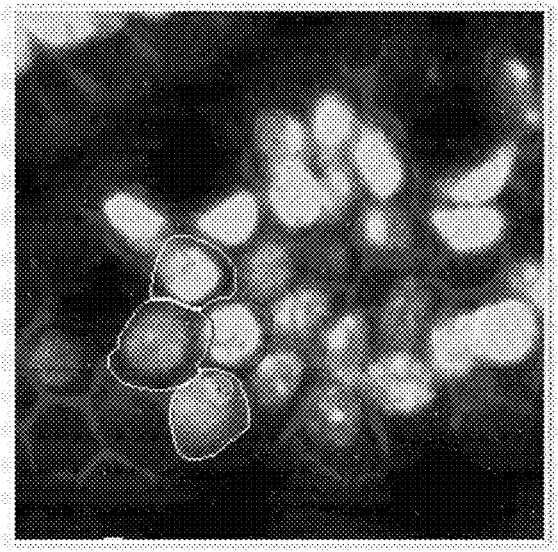
FIG. 72M
FIG. 72O

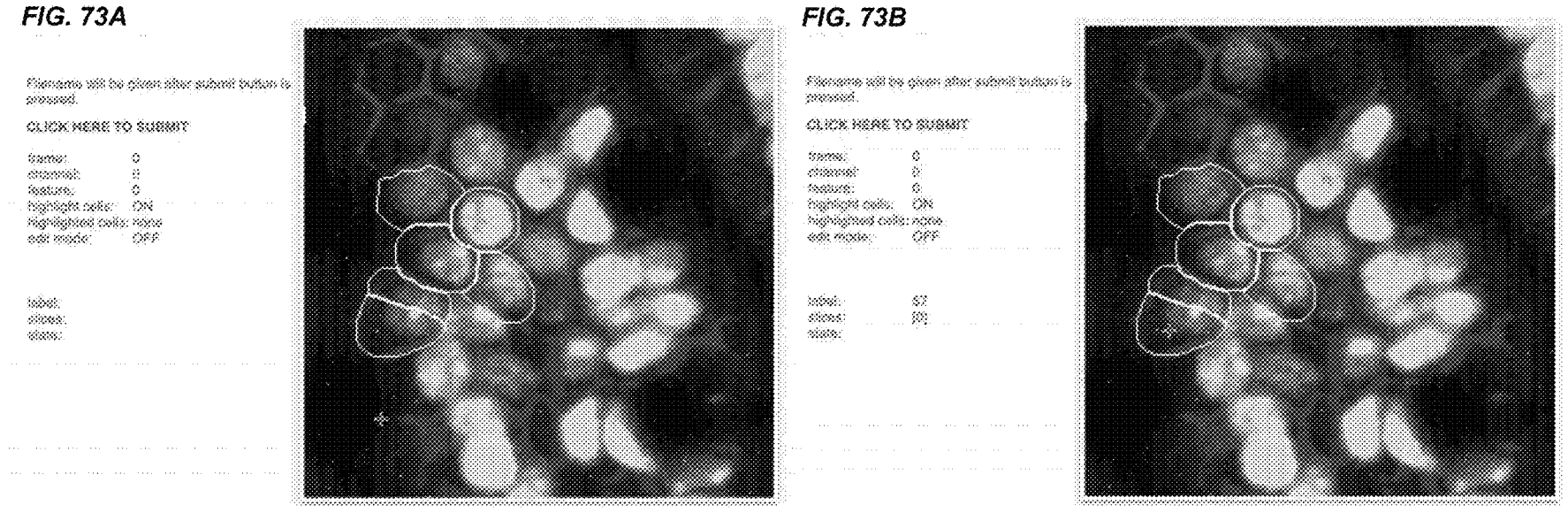
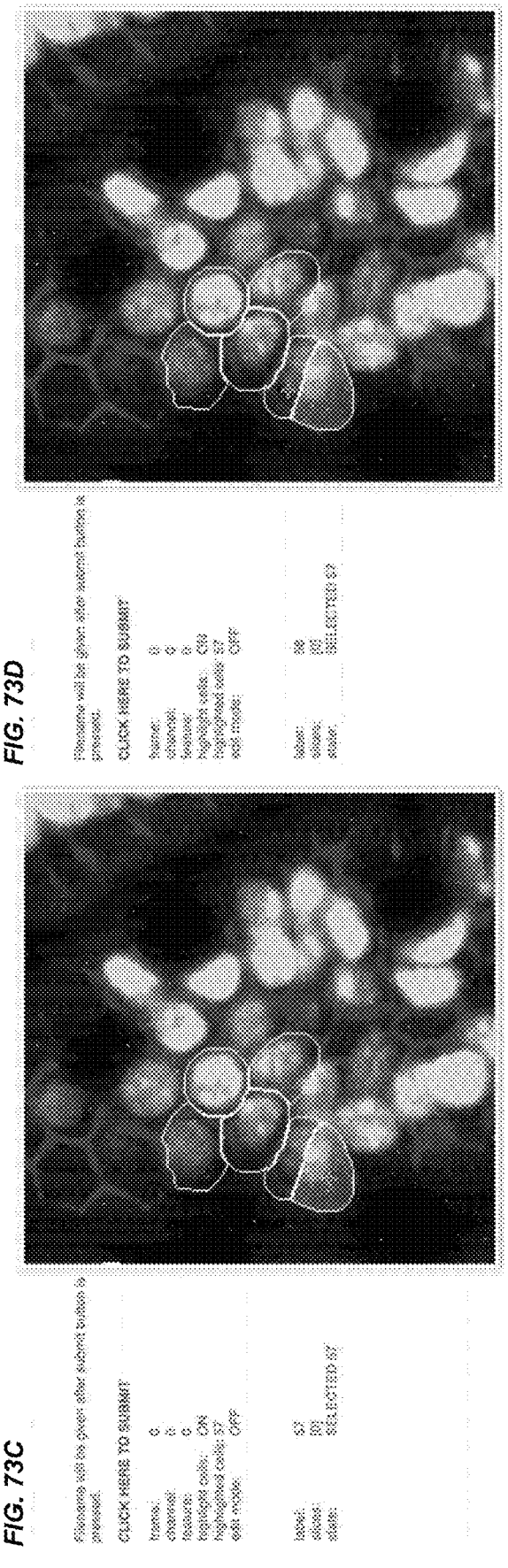
FIG. 73A, FIG. 73B, FIG. 73C, FIG. 73D

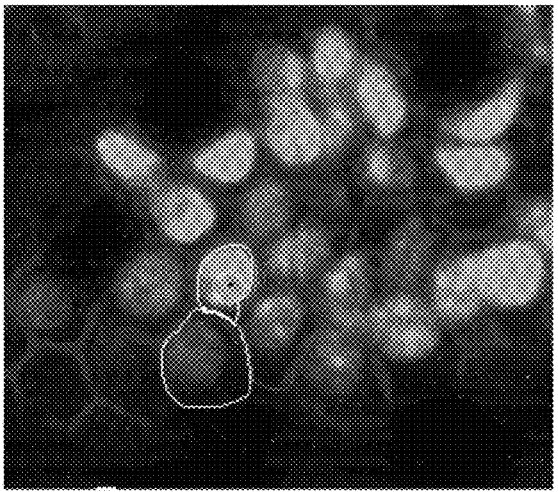
FIG. 75U
FIG. 75V
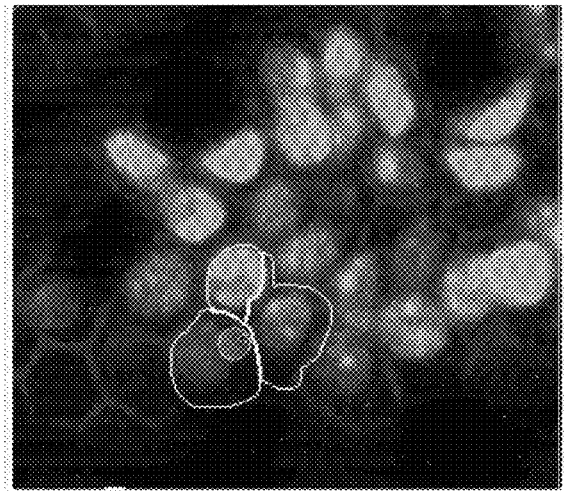
FIG. 75W
FIG. 75X

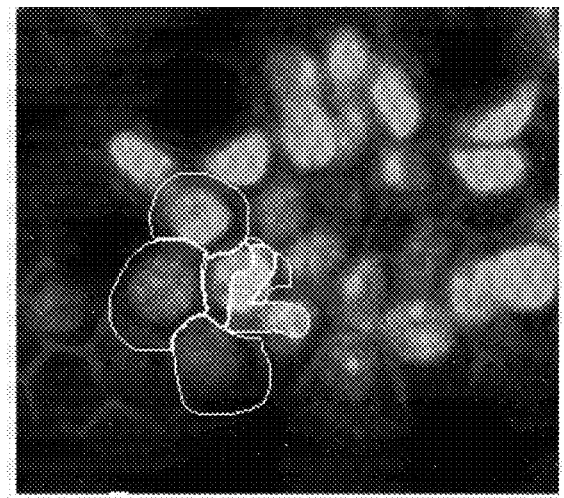
FIG. 77F
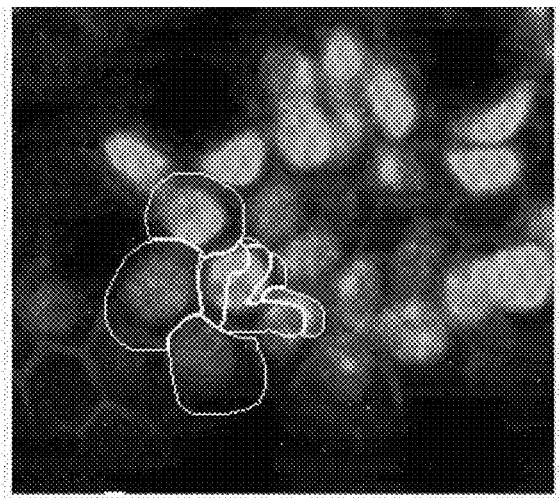
FIG. 77E
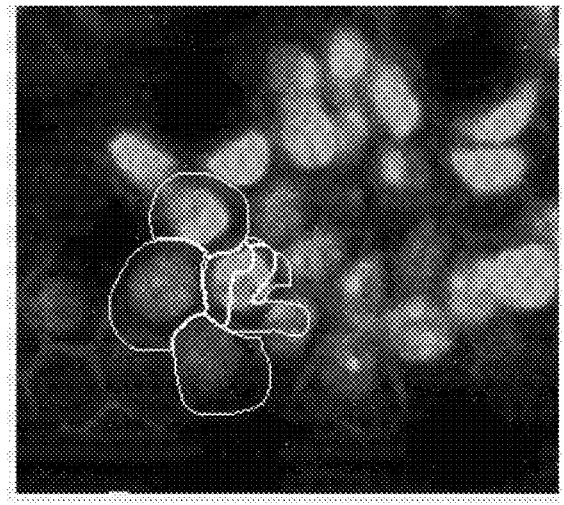
FIG. 77H
FIG. 77G

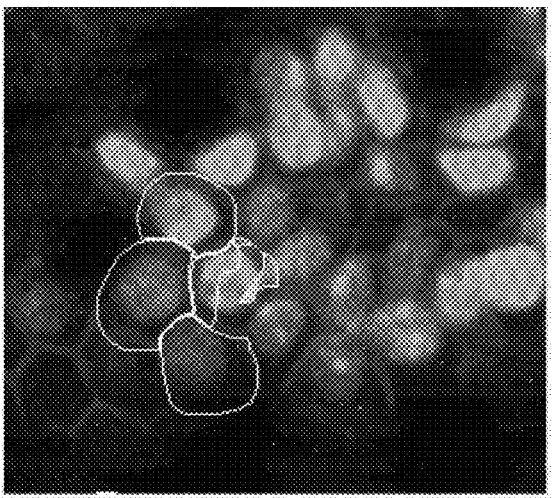
FIG. 77J
FIG. 77I
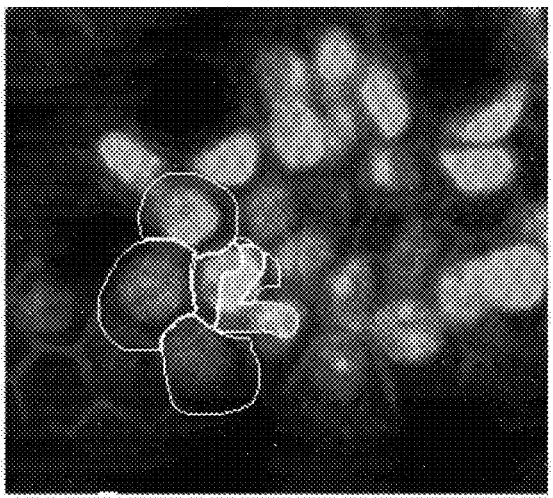
FIG. 77L
FIG. 77K

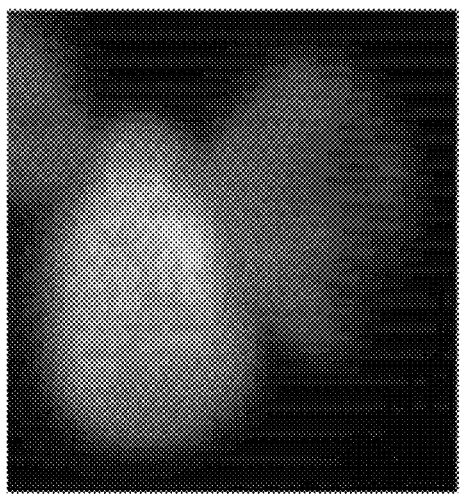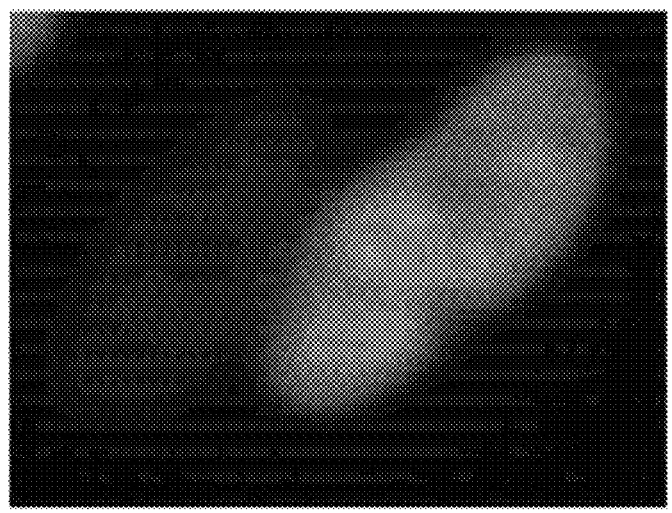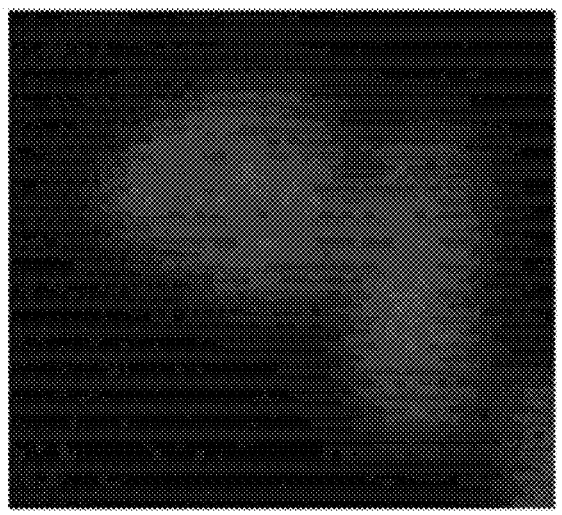
FIG. 81

Frame 22: 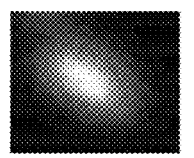 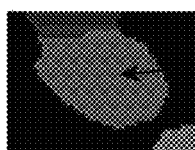

```
label:      12
capped:     False
daughters:  []
frame_div:  None
frames:     [0-29]
parent:     None
```

↓ Cell divides, but division is not detected

Frame 23: 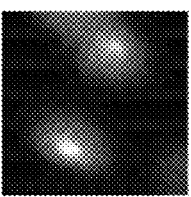 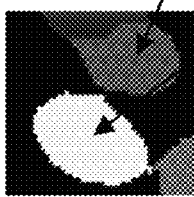

```
label:      31
capped:     False
daughters:  []
frame_div:  None
frames:     [23-29]
parent:     None
```

FIG. 83A

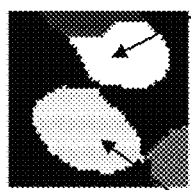

```
label:      34
capped:     False
daughters:  []
frame_div:  None
frames:     [23-29]
parent:     None
```

```
label:      31
capped:     False
daughters:  []
frame_div:  None
frames:     [23-29]
parent:     None
```

FIG. 83B

```
label:      12              label:      31
capped:     True            capped:     False
daughters:  [34, 31]        daughters:  []
frame_div:  23              frame_div:  None
frames:     [0-22]          frames:     [23-29]
parent:     None            parent:     12
```

FIG. 83C

Frame 8:

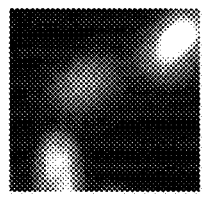 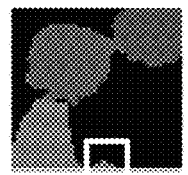

```
label:      18
capped:     True
daughters:  [21, 22]
frame_div:  9
frames:     [0, 7-8]
parent:     None
```

Frame 9:

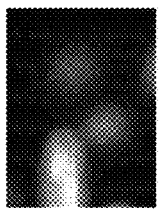 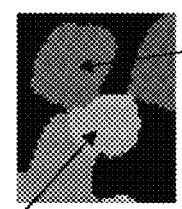

```
label:      13
capped:     False
daughters:  []
frame_div:  None
frames:     [0-19, 22-29]
parent:     None
```

```
label:      21
capped:     False
daughters:  []
frame_div:  None
frames:     [9-29]
parent:     18
```

```
label:      22
capped:     False
daughters:  []
frame_div:  None
frames:     [9-29]
parent:     18
```

*FIG. 84A*

```
label:      22
capped:     False
daughters:  []
frame_div:  None
frames:     [9-29]
parent:     18
replace 22 with 18?
  (SPACE=YES / ESC=NO)
```

*FIG. 84B*

```
label:      21
capped:     False
daughters:  []
frame_div:  None
frames:     [9-29]
parent:     None
```

*FIG. 84C*

TRACKING BIOLOGICAL OBJECTS OVER TIME AND SPACE

CROSS-REFERENCE TO RELATED APPLICATIONS

This application claims the benefit of priority to U.S. Patent Application No. 62/839,513, filed on Apr. 26, 2019, the content of which is incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field

This disclosure relates generally to the field of tracking biological objects, and more particularly to tracking biological objects over time and space.

Background

Deep learning is transforming the ability of life scientists to extract information from images. These techniques have better accuracy than conventional approaches and enable previously impossible analyses. The performance of deep learning can depend on the availability and quality of training data

SUMMARY

Disclosed herein include embodiments of a method for determining biological object associations. In some embodiments, the method is under control of a hardware processor and comprises: receiving raw images, frame numbers associated with the raw images, and associations each comprising a cell mask having pixels and an associated cell label assigned to one biological object in the raw images, if any. The method can comprise: generating and/or causing display a user interface comprising (i) a first panel for displaying a frame of (ia) at least one raw image of the raw images at a time, (ib) a mask image comprising one or more cell masks associated with one or more biological objects in the at least one raw image, if any, and/or (ic) an outline corresponding to boundaries of the one or more cell masks associated with the one or more biological objects in the at least one raw image, and (ii) a second panel for displaying (iia) the frame number of the at least one raw image being displayed, (iib) tracking information associated with one more biological objects, and/or for (iic) cell selection information of one or more cells selected. The method can comprise: receiving a user input to activate a pixel editing mode. The method can comprise: receiving a user input to create a new cell mask. The method can comprise: receiving one or more new pixels of the at least one raw image being displayed. The method can comprise: generating and/or causing display an updated user interface comprising (i) the first panel displaying the frame of the at least one raw image of the raw images and the one or more new pixels highlighted. The method can comprise: generating a new association of (iiia) the new cell mask having the one or more new pixels of the at least one raw image, and (iiib) a new cell label. The method can comprise: storing the new association.

In some embodiments, the method comprises: receiving a user input to modify at least one modified cell mask of the new association or one association of the associations. The method can comprise: receiving modifying pixels of the at least one raw image being displayed. The method can comprise: updating the at least one modified cell mask to comprise one or more modifying pixels of the modifying pixels. Updating the at least one modified cell mask can comprise updating the at least one modified cell mask to comprise the modifying pixels. Cell masks of the new association and the associations other than the at least one modified cell masks can comprise none of the one or more modifying pixels.

In some embodiments, the method comprises: receiving a user input to modify at least one modified cell mask of the new association or one association of the associations. The method can comprise: receiving one or more modifying pixels of the at least one raw image being displayed. The method can comprise: updating the at least one modified cell mask not to comprise the modifying pixels.

In some embodiments, receiving the one or more new pixels of the at least one raw image being displayed comprises: receiving pixels for determining the one or more new pixels; and determining the one or more new pixels of the at least one raw image from the pixels for determining the one or more new pixels using a watershed function. In some embodiments, receiving the one or more new pixels of the at least one raw image being displayed comprises receiving the one or more new pixels of the at least one raw image from a user input device.

In some embodiments, receiving the one or more modifying pixels comprises receiving the one or more modifying pixels selected using a brush tool. The brush tool can be associated with a default brush size. The method can comprise: generating and/or causing display an updated user interface comprising (i) the first panel displaying a visual representation of the default brush size overlaid on the frame. The method can comprise: receiving a user input to modify a modified brush size; and generating and/or causing display an updated user interface comprising (i) the first panel displaying an updated visual representation of the modified brush size overlaid on the frame. The brush tool can be associated with a brush value of a cell label.

In some embodiments, the method comprises: receiving a user display preference input. The method can comprise: generating an updated user interface comprising (i) the first panel displaying, based on the user display preference input, the frame comprising (ia) the at least one raw image of the raw images, (ib) the mask image comprising the one or more cell masks associated with the one or more biological objects in the at least one raw image, if any, or (ic) the outline corresponding to the boundaries of the one or more cell masks associated with the one or more biological objects in the at least one raw image;

In some embodiments, the method comprises: receiving a user display preference input. The method can comprise: generating and/or updating the user interface comprising (i) the first panel displaying the frame of (ia) the at least one raw image with modified brightness and/or an inverse raw image of the at least one raw image.

In some embodiments, the mask image comprises the new cell mask in a light color, optionally wherein the light color is white. The mask image can comprise one or more cell masks each in a different color. The mask image can comprise one or more cell masks each in a different color that is invariant across mask images. The mask image can comprise a dark background, optionally wherein the dark background comprises a black background. In some embodiments, the method comprises: determining a color of a cell mask of the cell masks in the mask image based on a number of the cell masks and/or the cell label associated with the cell mask.

In some embodiments, the method comprises: receiving a user input of a cell mask in the mask image. The method can comprise: generating and/or causing display an updated user interface, wherein the cell mask is highlighted in the mask image. In some embodiments, the method comprises: receiving a user input of a mother-daughter relationship associated with three cell labels of two of the cell labels of the associations and the new cell label. The method can comprise: updating associations comprising the three cell labels to comprise the mother-daughter relationship.

In some embodiments, the user interface comprises (i) the first panel on the right and (ii) the second panel on the left. In some embodiments, the (ii) second panel comprises (iia) the frame number of the at least one raw image being displayed, (iib) tracking information associated with one or more biological objects, and for (iic) cell selection information of one or more cells selected, from top to bottom.

In some embodiments, the raw images comprise two-dimensional spatial images over time. In some embodiments, the raw images comprise a Z-stack of three-dimensional spatial images. In some embodiments, the raw images comprise multi-channel images.

In some embodiments, the method comprises: generating training data form the raw images, the frame numbers associated with the raw images, and the associations and the new association. The method can comprise: training a deep learning model for cell tracking and lineage construction using the training data generated Training the deep learning model n can comprise training the deep learning model for cell tracking and lineage construction using a system that dynamically allocates computational resources for training the deep learning model based on GPU utilization and work demand.

In some embodiments, the method comprises: generating the associations from the raw images and the frame numbers using a deep learning model for cell tracking and lineage construction. The method can comprise: generating the associations from the raw images and the frame numbers using a system that dynamically allocates computational resources for training the deep learning model based on GPU utilization and work demand. The system can comprise pods. The system can dynamically allocate the computational resources using horizontal pod scaling.

In some embodiments, the deep learning model comprises a hybrid convolutional/recurrent deep learning model. Inputs of the deep learning model can comprise an appearance of a cell, a neighborhood of the cell, a morphology of the cell, and a motion of the cell in a first raw image and an appearance of a cell, a neighborhood of the cell, a morphology of the cell, and a motion of the cell in a second raw image. The appearance of the cell, the neighborhood of the cell, the morphology of the cell, and the motion of the cell in the first raw image comprises appearance vectors, neighborhood vectors, morphology vectors, and motion vectors can be determined from a plurality of raw images comprising the first raw image, and optionally wherein the appearance of the cell, the neighborhood of the cell, the morphology of the cell. The motion of the cell in the second raw image can be determined from the first raw image and the second raw image.

Disclosed herein includes embodiments of a system for determining biological object associations. In some embodiments, the system comprises: non-transitory memory configured to store executable instructions; and a hardware processor in communication with the non-transitory memory, the hardware processor programmed by the executable instructions to: determine biological object associations using any method of the present disclosure.

Disclosed herein include embodiments of method of live-cell imaging analysis. In some embodiments, the method comprises performing a live-cell imaging analysis using a deep learning model for cell tracking and lineage construction of the present disclosure. Disclosed herein includes system for biological object tracking and lineage construction. In some embodiments, the system comprises: non-transitory memory configured to store executable instructions; and a hardware processor in communication with the non-transitory memory, the hardware processor programmed by the executable instructions to: perform biological object tracking and lineage construction using a deep learning model for cell tracking and lineage construction of the present disclosure.

Disclosed herein include embodiments of a system for analyzing images of biological objects. In some embodiments, the system comprises: non-transitory memory configured to store executable instructions; and a hardware processor in communication with the non-transitory memory, the hardware processor programmed by the executable instructions to: analyze images of biological objects using a deep learning model for cell tracking and lineage construction of the present disclosure.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 3A illustrates the selection a target object and its comparison to other similar objects in the subsequent image. FIG. 3B demonstrates the use of model outputs in building a cost matrix for object linking.

FIG. 11. Segmentation benchmarks for deep learning segmentation models for fluorescent nuclear images.

FIGS. 12A-12C. Optimization and benchmarking of a deep learning-based cell tracker.

FIG. 14. Example using the eraser tool to correct mistakes.

FIG. 16. Example nuclear annotations of normal cells and dividing/disappearing cells.

FIG. 18. Example cell annotations of cells of different shapes.

FIGS. 34A-34A2. Desktop Caliban showing raw images of frames from a trk file.

FIGS. 35A-35B2. Browser Caliban showing images comprising cell masks of frames from a trk file.

FIGS. 42A-42L. Changing the channels of a raw image (the channels combined and individually) when displaying the raw image or in pixel-editing mode using Browser Caliban.

FIGS. 43A-43B2. Increasing brush size from size 1 to size 22 and decreasing brush size from 22 to 1 in the pixel-editing mode of Caliban.

FIGS. 45A-45L. Increasing and decreasing the value of the brush (the value of the label) and setting the brush to an unused value of the brush (an unused label value) in the pixel-editing mode of Caliban.

FIGS. 47A-47F2. Turning/toggling on and off highlighting and selecting labels with the selected labels highlighted.

FIGS. 48A-48R. Increasing the brush size in the annotation mode and using the brush to annotate (or color or select) pixels of a label with Browser Caliban.

FIGS. 49A-49H. Drawing and erasing with a brush only affect pixels associated with (or assigned to) the label the brush is set to.

FIGS. 50A-50K. Using the conversion brush to change some or all pixels associated with (or assigned to) one label to be associated with (or assigned to) another label without affecting the pixels of the background or the pixels associated with (or assigned to) other labels.

FIGS. 52A-52G. Delete a label from a single frame.

FIGS. 65A-65L. Using the brush tool to draw (e.g., select) pixels associated with (or assigned to) a cell label in a three-step process, where pixels associated (or assigned to) with another cell label and drawn by the brush tool are not associated with (or assigned to) the cell label.

FIGS. 69A-69H. Using the brush tool to erase (e.g., remove) some pixels associated with a cell label (cell label 42 shown in the figures). When the brush tool erase pixels associated with another cell label (cell label 41 shown in the figures), the pixels are not erased (i.e., the pixels are still assigned to, or associated with, the other cell label).

FIGS. 73A-73G. Merging two cells by associating pixels of one cell label (cell label 56 shown in the figures) with the other cell label (cell label 57 shown in the figures).

FIGS. 75A-75B2. Fixing errors two cells assigned three cell labels (cell labels 51, 52, and 53 shown in the figures) and a third cell assigned another cell label (cell label 54 shown in the figures). Cell labels 51 and 53 were first merged as cell label 51. The conversion brush was used to assign some pixels associated with cell label 51 to be associated with cell label 52. The conversion brush was used to assign some pixels associated with cell label 54 to be associated with cell label 51.

FIG. 81. Other examples of cells that are difficult to separate with the watershed tool.

FIGS. 83A-83C. Division not detected.

FIGS. 84A-84C. Incorrect division detected.

DETAILED DESCRIPTION

Figure 1:
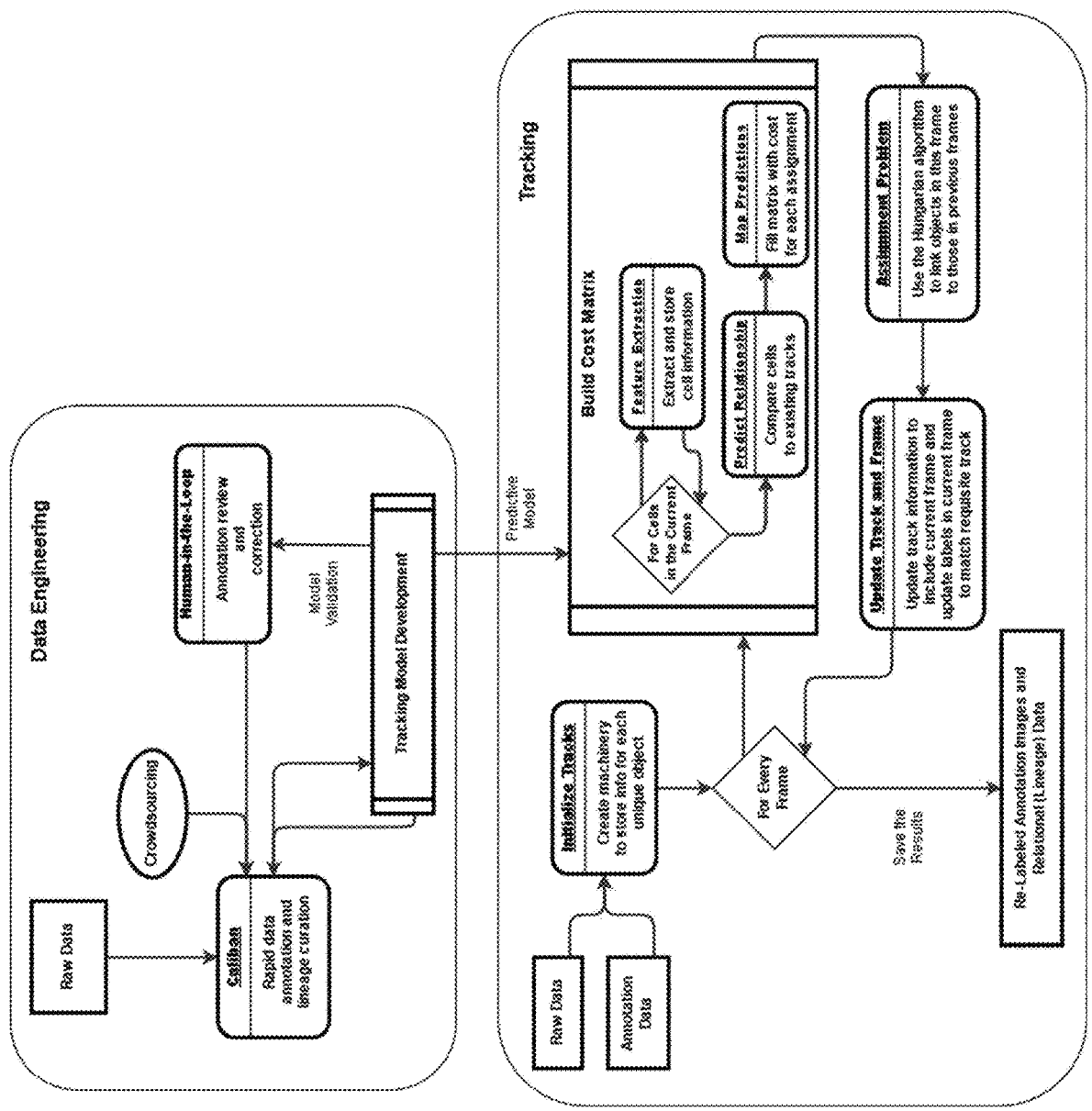
FIG. 1 shows a non-limiting exemplary workflow diagram outlining data engineering and tracking aspects of tracking biological materials.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Disclosed herein include systems and methods for biological object tracking and lineage construction. Also disclosed herein include cloud-based systems and methods for allocating computational resources for deep learning-enabled image analysis of biological objects. Also disclosed herein include systems and methods for annotating and curating biological object tracking-specific training datasets.

Disclosed herein include embodiments of a method for determining biological object associations. In some embodiments, the method is under control of a hardware processor and comprises: receiving raw images, frame numbers associated with the raw images, and associations each comprising a cell mask having pixels and an associated cell label assigned to one biological object in the raw images, if any. The method can comprise: generating and/or causing display a user interface comprising (i) a first panel for displaying a frame of (ia) at least one raw image of the raw images at a time, (ib) a mask image comprising one or more cell masks associated with one or more biological objects in the at least one raw image, if any, and/or (ic) an outline corresponding to boundaries of the one or more cell masks associated with the one or more biological objects in the at least one raw image, and (ii) a second panel for displaying (iia) the frame number of the at least one raw image being displayed, (iib) tracking information associated with one more biological objects, and/or (iic) cell selection information of one or more cells selected. The method can comprise: receiving a user input to activate a pixel editing mode. The method can comprise: receiving a user input to create a new cell mask. The method can comprise: receiving one or more new pixels of the at least one raw image being displayed. The method can comprise: generating and/or causing display an updated user interface comprising (i) the first panel displaying the frame of the at least one raw image of the raw images and the one or more new pixels highlighted. The method can comprise: generating a new association of (iiia) the new cell mask having the one or more new pixels of the at least one raw image, and (iiib) a new cell label. The method can comprise: storing the new association.

Disclosed herein includes embodiments of a system for determining biological object associations. In some embodiments, the system comprises: non-transitory memory configured to store executable instructions; and a hardware processor in communication with the non-transitory memory, the hardware processor programmed by the executable instructions to: determine biological object associations using any method of the present disclosure.

Disclosed herein include embodiments of method of live-cell imaging analysis. In some embodiments, the method comprises performing a live-cell imaging analysis using a deep learning model for cell tracking and lineage construction of the present disclosure. Disclosed herein includes system for biological object tracking and lineage construction. In some embodiments, the system comprises: non-transitory memory configured to store executable instructions; and a hardware processor in communication with the non-transitory memory, the hardware processor programmed by the executable instructions to: perform biological object tracking and lineage construction using a deep learning model for cell tracking and lineage construction of the present disclosure.

Disclosed herein include embodiments of a system for analyzing images of biological objects. In some embodiments, the system comprises: non-transitory memory configured to store executable instructions; and a hardware processor in communication with the non-transitory memory, the hardware processor programmed by the executable instructions to: analyze images of biological objects using a deep learning model for cell tracking and lineage construction of the present disclosure.

Throughout the drawings, reference numbers may be re-used to indicate correspondence between referenced elements. The drawings are provided to illustrate example embodiments described herein and are not intended to limit the scope of the disclosure.

Tracking Biological Objects Over Time and Space in Microscopic Images

A method for identifying and tracking biological material over time and through space is disclosed herein. The method can enable high-throughput, multiplexed, object-level analysis of populations of biological objects. The method can include recognizing objects, and subsets of related objects, from one image in a subsequent image. Also disclosed herein is a tool for curating and storing recognized objects, and subsets of related subjects, referred to herein as Caliban.

Live imaging experiments, where biological matter is imaged over time with fluorescence or brightfield microscopy, have provided crucial insights into the inner workings of biological systems. To date, these experiments have shed light on numerous problems, including information processing in signaling networks and the response of biological material to pharmaceutical compounds. One key strength of these experiments is the ability to obtain dynamic data with single-object resolution. The meaning of a "biological object" can vary from single organisms all the way down to single cells. Being able to understand the behavior of individual cells is particularly important, as it is now well appreciated that individual cells can vary considerably in their behavior. The ability to capture the temporal evolution of cell-to-cell differences has proven essential to understanding this form of cellular heterogeneity. While these live imaging experiments produce rich data, the computational analysis is challenging, as object-level analysis requires that objects be accurately identified in each image and subsequently tracked over time.

The conventional approach to object-level analysis of live imaging data is to combine a segmentation algorithm with a tracking algorithm. While these two components are increasingly being empowered by deep learning, an effective end-to-end deep learning-based solution to object-level analysis of dynamic biological imaging data has yet to be realized. This may be due to three technical challenges. First, successful deep learning solutions are data hungry. While unsupervised deep learning can be a useful tool, most applications of deep learning to imaging data are supervised and require significant amounts of specialized training data. This task is especially difficult because of the additional temporal dimension—objects are segmented and tracked through every frame of a training dataset. Second, the unique features of live imaging data confound tracking methods as well as deep learning-based object trackers. This is particularly true for live-cell imaging data, as accurate detection of cell divisions is difficult. Third, deploying deep learning models is a non-trivial task. The unique hardware requirements of deep learning present a barrier for training models and performing large inference tasks. On premise computing has limited throughput, while cloud computing raises additional software engineering challenges.

Disclosed herein is a method that addresses the current challenges to developing and deploying a deep-learning-based method for tracking multiple biological objects in microscope images. The method can comprise creating low dimensional summaries of elements within these images and extracting a similarity value between each element in each frame. These values can be used to link related elements across collections of images. Also disclosed herein include a method of rapidly annotating and curating tracking-specific training datasets. A turnkey solution to deploy the entire method within a distributed computing framework is also disclosed herein.

A biological object tracking method can operate on a series of digitized raw images of biological material to generate a corresponding series of segmented digital images where the pixels in each image are grouped into regions of interest, corresponding to an object. Each region of interest or object in the segmented image can be given one unique value or label. The method can compare every object in every frame to identify and link the appearances of each object across all frames. There are two outputs that result from this method: (1) a series of sequential segmented images—corresponding to the original raw image series—where each unique object is identified and tracked across all frames that it is present in, and (2) a file containing a record for each object. Because this method is primarily concerned with tracking biological materials, such as cells and nucleus, over time in microscope images, the object record, or track, can contain specific information relevant to cellular activity, such as the frame a cell divides, lineage information, the frame of cell death, etc.

Tracking biological materials across multiple raw images can be a multistep process. As shown in FIG. 1, the first aspect tracking biological materials can be data engineering. Disclosed herein include a portable data engineering tool, referred to herein as Caliban. Caliban is a data annotation tool that allows users to rapidly provide pixel-level annotations for biological data while simultaneously curating lineage information. Caliban can relate objects that result from a division event to its "parent"—this type of information is referred to as relational data. Caliban can be hosted on a local network, to keep data private and annotations in-house, or on crowdsourcing platforms to accelerate data curation. Several crowdsourcing-based solutions like Amazon's Mechanical Turk platform connect users to crowds of both skilled and unskilled workers capable of providing various types of annotation services. Deep learning is critically dependent on well annotated data. Caliban can be used to generate well annotated data. Pixel-level annotations can be important for interpreting biological images but are difficult to create—Caliban significantly reduces the difficulty of annotating live imaging data. The workflow diagram for Caliban is sown in FIG. 2.

Figure 2:
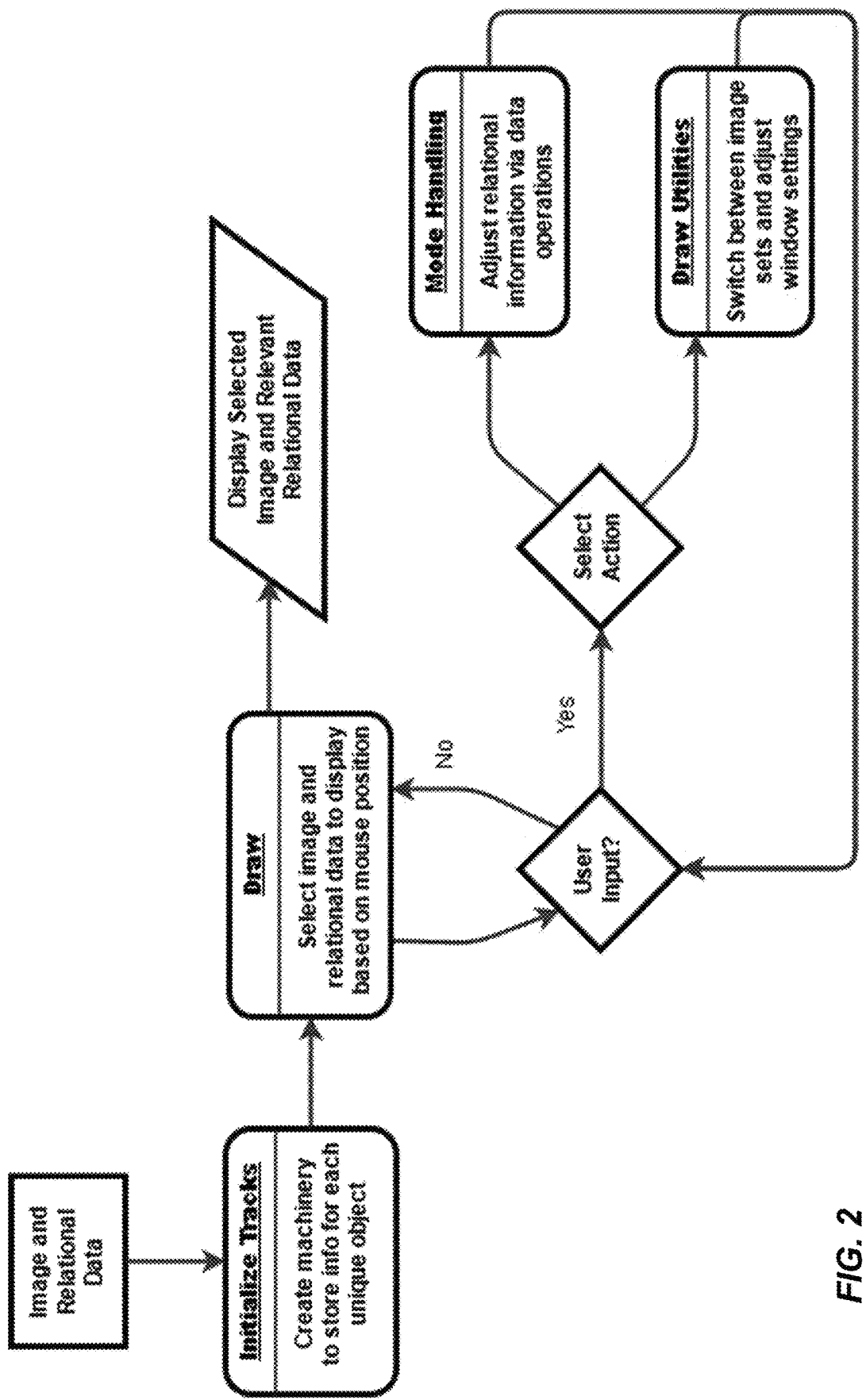
FIG. 2 shows a non-limiting exemplary flowchart describing the data engineering aspects of tracking biological materials.

As shown in FIG. 2, Caliban can display images and relational data while providing options for curating segmentations and relational data. Caliban can associate raw images with the appropriate segmentation or annotation, display the image, and allow users to switch between the two. Caliban can include an additional information pane that provides a full accounting of object information when a mouse hovers over it. Caliban can wait for user input, either via mouse clicks or the keyboard, and selects the appropriate action. Caliban can have two available classes of actions, those that affect display settings and those that adjust segmentations and relational data. Display settings can include window size, contrast, brightness, etc. Segmentations can be adjusted by using the mouse to click areas of interest and using subroutines to automate edits. Relational data can also be adjusted via mouse clicks and keyboard input. For example, segmentations can be added to an existing track or entries can be identified as the result of division. Once curation is complete, the resulting data, both image and relational, can be saved as a track file as a new dataset for training.

Figure 3:
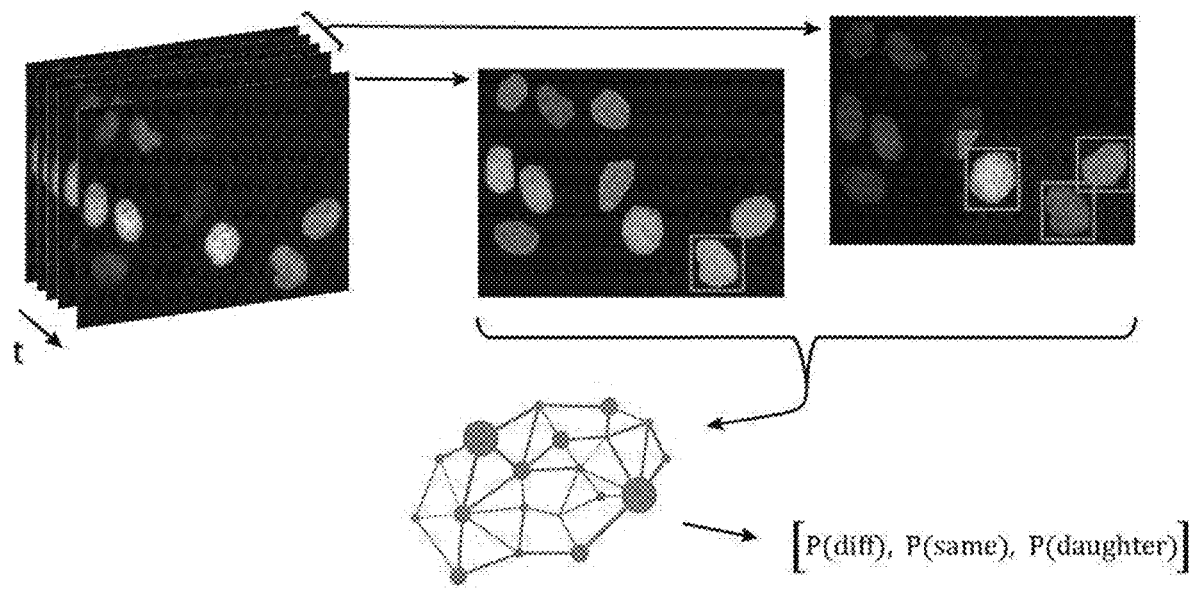
FIGS. 3A-3B show graphical depictions of non-limiting exemplary embodiments of tracking biological materials.

Object tracking can be achieved by using a linear programming framework. In this framework, $N_i$ objects in frame i are assigned to $N_{i+1}$ objects in frame i+1. To solve this assignment problem, a cost function can be constructed for all possible pairing across frames based on each object's location and appearance. The Hungarian algorithm can be used to find the one assignment out of the set of all possible assignments that minimizes the cost function. One complicating factor of biological object tracking is that objects can appear and disappear—this often leads to $N_i$ and $N_{i+1}$ being unequal. This problem can be solved by introducing a "shadow object" for each object in the two frames to be compared—$N_{i+1}$ shadow objects in frame i and $N_i$ shadow objects in frame i+1. These shadow objects represent an opportunity for objects to "disappear" or to be "born." This feature can be important, as objects can leave the field of view and events like cell division will lead to objects being "born." The end result is a cost matrix describing the cost of every possible assignment that is size $N_i+N_{i+1} \times N_i+N_{i+1}$. FIG. 3B demonstrates the use of model outputs in building a cost matrix for object linking. Whole movies can be tracked by sequentially tracking every pair of frames. Optimization of the linear assignment approach comes about through cost function engineering.

As opposed to manual engineering, a cost function can be learned through a supervised deep learning approach. An overview is shown in FIGS. 1 and 3A-3B. The data engineering tool Caliban can be used to generate the annotated training data necessary. To construct the learned cost function, the problem can be considered as a classification task. Given two objects—object 1 in frame i and object 2 in frame i+1—a classifier that takes in information about each object and produces a probability that these two objects are either the same, are different, or have a mother-daughter relationship can be constructed. The scores produced by this classifier can be the desired cost function.

The classifier for performing this task can be a custom deep learning model. This deep learning model can take in 4 pieces of information about each object using 4 separate branches. Each branch can use a deep learning model to summarize a type of information with a vector. To incorporate temporal information, multiple frames of information of object 1 can be used as an input to this classifier. Each frame can be summarized as a vector using convolutional and dense neural networks. This sequence of vectors can be then fed into a recurrent neural network to model the temporal dependencies in the information about object one. The recurrent neural network can allow the access to the temporal information beyond the two frames presently being compared. The first branch can take in the appearance, such as a cropped and resized image, of each object and uses a deep convolutional neural network to summarize the cropped and resized image as a vector. The appearance can provide access to information on what the two objects look like; but the resizing operation can remove any notions of a size scale. To mitigate this, a second branch can take in a vector of morphological information for each object and use a densely connected neural network to summarize the morphologies into a vector. The third branch can acquire information about object motion over time. For object 1, a vector of all the centroid displacements can be collected. For object 2, a single vector that is the displacement between object 1 and object 2's centroid can be created. This branch can give a history of object 1's motion and allow the invention to determine whether a potential positive assignment of object 2 would be inconsistent from the point of view of cell motion. The last branch can incorporate neighborhood information, which can be an image cropped out around the region surrounding object 1. Using the vector of centroid motions, where this neighborhood will be in frame i+1 can be predicted and that neighborhood can be extracted as the neighborhood for object 2. Using neighborhoods in this fashion can be important for detection events like cell divisions. Just as with appearances, a deep convolutional neural network is used to summarize the neighborhoods as a vector. The result of these branches can be a sequence of features that have been extracted from the original image. This sequence can then be fed into fully-connected network to provide the likelihood that two cells are the same cell, different cells, or whether the two cells are related through a mother-daughter relationship.

Figure 4:
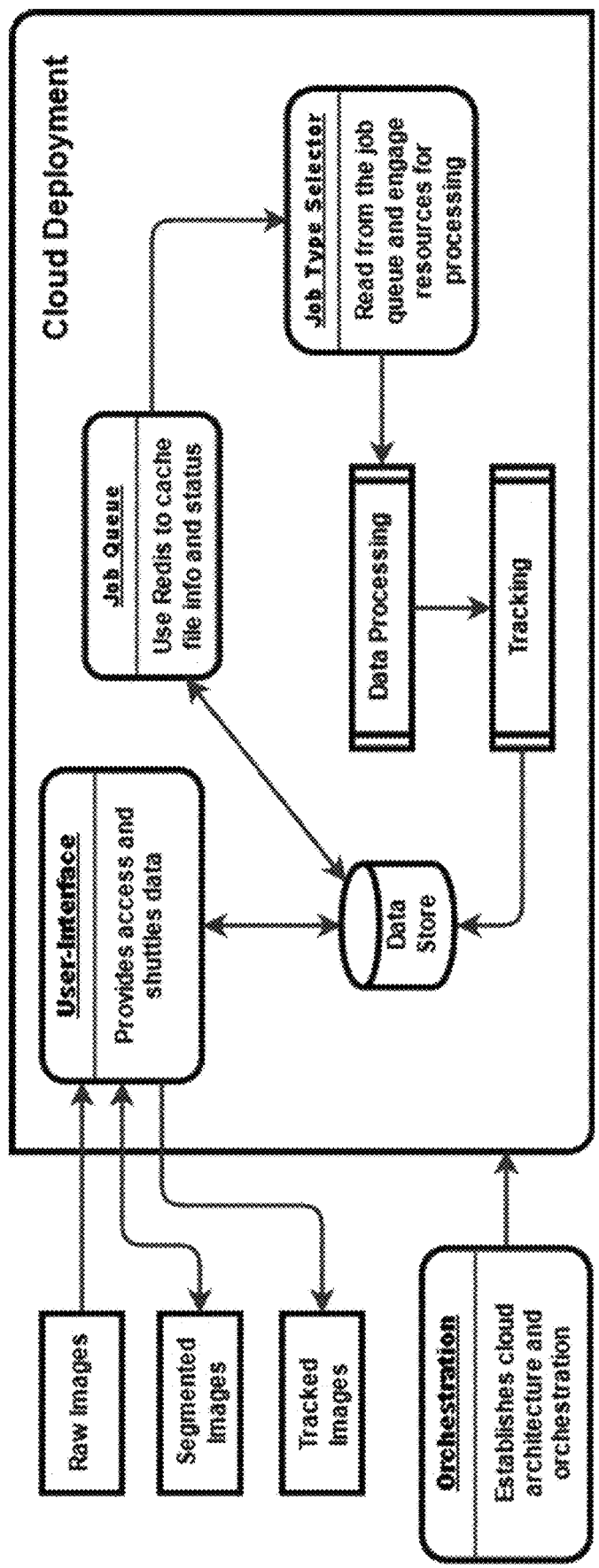
FIG. 4 shows a non-limiting exemplary workflow diagram describing the deployment aspects of tracking biological materials.

The tracking method can be deployed on a cloud-based system for processing large amounts of imaging data. For example, the tracking method can be deployed as a turnkey solution for a persistent cloud deployment. As shown in FIG. 4, the input can be associated raw and/or segmented images and the output can be segmented images and/or tracked segmentations with relational information. The cloud deployment can include a user interface with web portal, data store that can be accessed by stateless APIs, a job queue that maintains records of each image's status, a job type selector that choses the requested process, and pods that perform various processing tasks—one of which is the tracking methodology. The entire deployment architecture can be established and orchestrated by an exterior process. Each element within the cloud deployment represented in FIG. 4, except the data store, can be a containerized process. For example, Kubernetes to deploy and scale these containers. The job queue database container can be Redis.

Disclosed herein include embodiments of a method for determining biological object associations. In some embodiments, the method is under control of a hardware processor and comprises: receiving raw images, frame numbers associated with the raw images, and associations each comprising a cell mask having pixels and an associated cell label assigned to one biological object in the raw images, if any. The method can comprise: generating and/or causing display a user interface comprising (i) a first panel for displaying a frame of (ia) at least one raw image of the raw images at a time, (ib) a mask image comprising one or more cell masks associated with one or more biological objects in the at least one raw image, if any, and/or (ic) an outline corresponding to boundaries of the one or more cell masks associated with the one or more biological objects in the at least one raw image, and (ii) a second panel for displaying (iia) the frame number of the at least one raw image being displayed, (iib) tracking information associated with one or more biological objects, and/or for (iic) cell selection information of one or more cells selected. The method can comprise: receiving a user input to activate a pixel editing mode. The method can comprise: receiving a user input to create a new cell mask. The method can comprise: receiving one or more new pixels of the at least one raw image being displayed. The method can comprise: generating and/or causing display an updated user interface comprising (i) the first panel displaying the frame of the at least one raw image of the raw images and the one or more new pixels highlighted. The method can comprise: generating a new association of (iiia) the new cell mask having the one or more new pixels of the at least one raw image, and (iiib) a new cell label. The method can comprise: storing the new association.

In some embodiments, the method comprises: receiving a user input to modify at least one modified cell mask of the new association or one association of the associations. The method can comprise: receiving modifying pixels of the at least one raw image being displayed. The method can comprise: updating the at least one modified cell mask to comprise one or more modifying pixels of the modifying pixels. Updating the at least one modified cell mask can comprise updating the at least one modified cell mask to comprise the modifying pixels. Cell masks of the new association and the associations other than the at least one modified cell masks can comprise none of the one or more modifying pixels.

In some embodiments, the method comprises: receiving a user input to modify at least one modified cell mask of the new association or one association of the associations. The method can comprise: receiving one or more modifying pixels of the at least one raw image being displayed. The method can comprise: updating the at least one modified cell mask not to comprise the modifying pixels.

In some embodiments, receiving the one or more new pixels of the at least one raw image being displayed comprises: receiving pixels for determining the one or more new pixels; and determining the one or more new pixels of the at least one raw image from the pixels for determining the one or more new pixels using a watershed function. In some embodiments, receiving the one or more new pixels of the at least one raw image being displayed comprises receiving the one or more new pixels of the at least one raw image from a user input device.

In some embodiments, receiving the one or more modifying pixels comprises receiving the one or more modifying pixels selected using a brush tool. The brush tool can be associated with a default brush size. The method can comprise: generating and/or causing display an updated user interface comprising (i) the first panel displaying a visual representation of the default brush size overlaid on the frame. The method can comprise: receiving a user input to modify a modified brush size; and generating and/or causing display an updated user interface comprising (i) the first panel displaying an updated visual representation of the modified brush size overlaid on the frame. The brush tool can be associated with a brush value of a cell label.

In some embodiments, the method comprises: receiving a user display preference input. The method can comprise: generating an updated user interface comprising (i) the first panel displaying, based on the user display preference input, the frame comprising (ia) the at least one raw image of the raw images, (ib) the mask image comprising the one or more cell masks associated with the one or more biological objects in the at least one raw image, if any, or (ic) the outline corresponding to the boundaries of the one or more cell masks associated with the one or more biological objects in the at least one raw image;

In some embodiments, the method comprises: receiving a user display preference input. The method can comprise: generating and/or updating the user interface comprising (i) the first panel displaying the frame of (ia) the at least one raw image with modified brightness and/or an inverse raw image of the at least one raw image.

In some embodiments, the mask image comprises the new cell mask in a light color, optionally wherein the light color is white. The mask image can comprise one or more cell masks each in a different color. The mask image can comprise one or more cell masks each in a different color that is invariant across mask images. The mask image can comprise a dark background, optionally wherein the dark background comprises a black background. In some embodiments, the method comprises: determining a color of a cell mask of the cell masks in the mask image based on a number of the cell masks and/or the cell label associated with the cell mask.

In some embodiments, the method comprises: receiving a user input of a cell mask in the mask image. The method can comprise: generating and/or causing display an updated user interface, wherein the cell mask is highlighted in the mask image. In some embodiments, the method comprises: receiving a user input of a mother-daughter relationship associated with three cell labels of two of the cell labels of the associations and the new cell label. The method can comprise: updating associations comprising the three cell labels to comprise the mother-daughter relationship.

In some embodiments, the user interface comprises (i) the first panel on the right and (ii) the second panel on the left. In some embodiments, the (ii) second panel comprises (iia) the frame number of the at least one raw image being displayed, (iib) tracking information associated with one or more biological objects, and for (iic) cell selection information of one or more cells selected, from top to bottom.

In some embodiments, the raw images comprise two-dimensional spatial images over time. In some embodiments, the raw images comprise a Z-stack of three-dimensional spatial images. In some embodiments, the raw images comprise multi-channel images. The raw images can comprise brightfield images. The raw images can comprise fluorescent images. The raw images can be consecutive raw images taken at intervals such as 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, or more.

In some embodiments, the method comprises: generating training data form the raw images, the frame numbers associated with the raw images, and the associations and the new association. The method can comprise: training a deep learning model for cell tracking and lineage construction using the training data generated Training the deep learning model n can comprise training the deep learning model for cell tracking and lineage construction using a system that dynamically allocates computational resources for training the deep learning model based on GPU utilization and work demand.

In some embodiments, the method comprises: generating the associations from the raw images and the frame numbers using a deep learning model for cell tracking and lineage construction. The method can comprise: generating the associations from the raw images and the frame numbers using a system that dynamically allocates computational resources for training the deep learning model based on GPU utilization and work demand. The system can comprise pods. The system can dynamically allocate the computational resources using horizontal pod scaling.

In some embodiments, the deep learning model comprises a hybrid convolutional/recurrent deep learning model. Inputs of the deep learning model can comprise an appearance of a cell, a neighborhood of the cell, a morphology of the cell, and a motion of the cell in a first raw image and an appearance of a cell, a neighborhood of the cell, a morphology of the cell, and a motion of the cell in a second raw image. The appearance of the cell, the neighborhood of the cell, the morphology of the cell, and the motion of the cell in the first raw image comprises appearance vectors, neighborhood vectors, morphology vectors, and motion vectors can be determined from a plurality of raw images (such as 2, 3, 4, 5, 6, 7, 8, 9, 10, 20, 30, 40, 50, 60, 70, 80, 90, 100, or more images) comprising the first raw image, and optionally wherein the appearance of the cell, the neighborhood of the cell, the morphology of the cell. The motion of the cell in the second raw image can be determined from the first raw image and the second raw image.

Disclosed herein includes embodiments of a system for determining biological object associations. In some embodiments, the system comprises: non-transitory memory configured to store executable instructions; and a hardware processor in communication with the non-transitory memory, the hardware processor programmed by the executable instructions to: determine biological object associations using any method of the present disclosure.

Disclosed herein include embodiments of method of live-cell imaging analysis. In some embodiments, the method comprises performing a live-cell imaging analysis using a deep learning model for cell tracking and lineage construction of the present disclosure. Disclosed herein includes system for biological object tracking and lineage construction. In some embodiments, the system comprises: non-transitory memory configured to store executable instructions; and a hardware processor in communication with the non-transitory memory, the hardware processor programmed by the executable instructions to: perform biological object tracking and lineage construction using a deep learning model for cell tracking and lineage construction of the present disclosure.

Disclosed herein include embodiments of a system for analyzing images of biological objects. In some embodiments, the system comprises: non-transitory memory configured to store executable instructions; and a hardware processor in communication with the non-transitory memory, the hardware processor programmed by the executable instructions to: analyze images of biological objects using a deep learning model for cell tracking and lineage construction of the present disclosure.

Execution Environment

Figure 5:
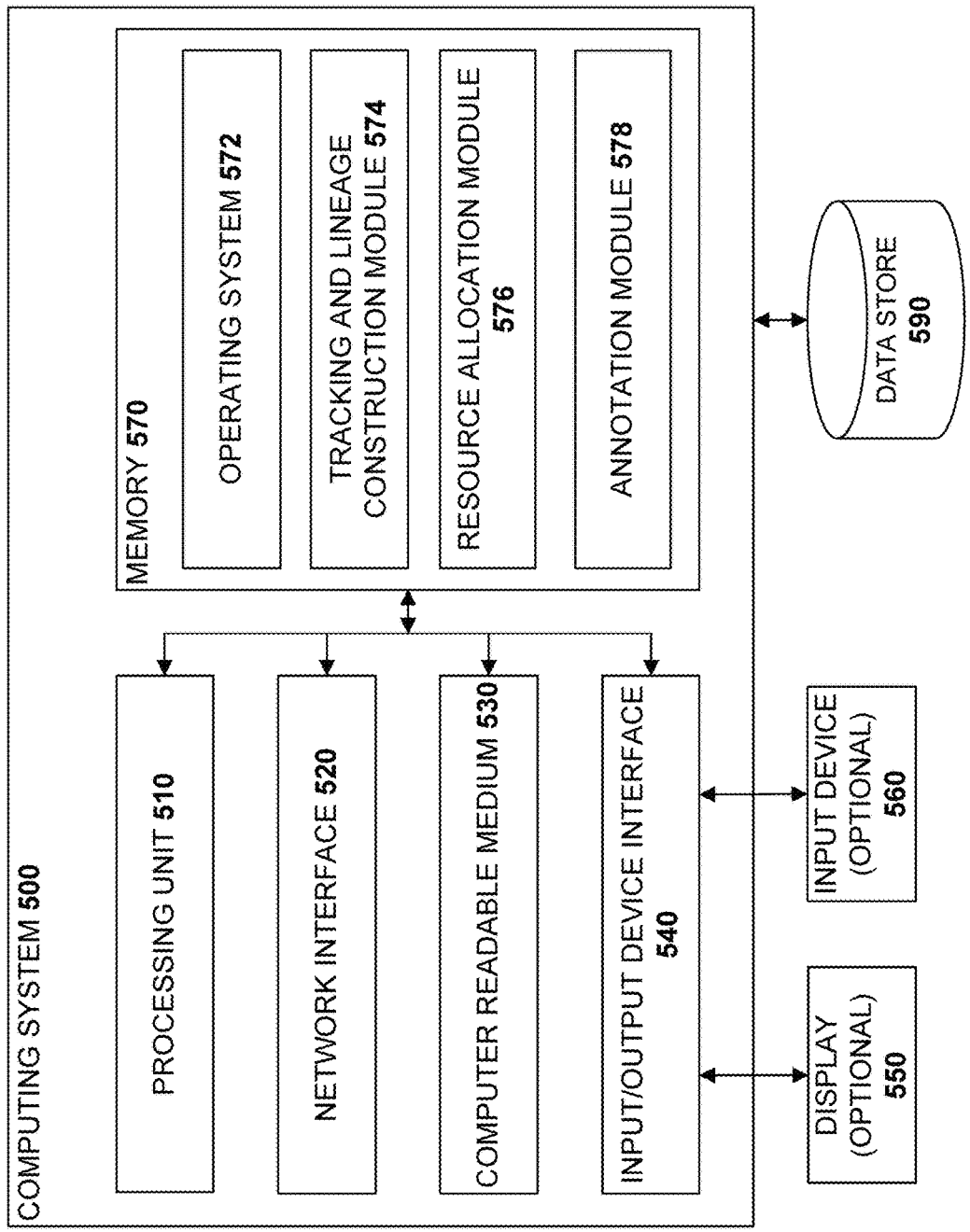
FIG. 5 is a block diagram of an illustrative computing system configured to implement any method or system of the present disclosure.

In FIG. 5 depicts a general architecture of an example computing device 500 configured to implement any method or system disclosed herein. The general architecture of the computing device 500 depicted in FIG. 5 includes an arrangement of computer hardware and software components. The computing device 500 may include many more (or fewer) elements than those shown in FIG. 5. It is not necessary, however, that all of these generally conventional elements be shown in order to provide an enabling disclosure. As illustrated, the computing device 500 includes a processing unit 510, a network interface 520, a computer readable medium drive 530, an input/output device interface 540, a display 550, and an input device 560, all of which may communicate with one another by way of a communication bus. The network interface 520 may provide connectivity to one or more networks or computing systems. The processing unit 510 may thus receive information and instructions from other computing systems or services via a network. The processing unit 510 may also communicate to and from memory 570 and further provide output information for an optional display 550 via the input/output device interface 540. The input/output device interface 540 may also accept input from the optional input device 560, such as a keyboard, mouse, digital pen, microphone, touch screen, gesture recognition system, voice recognition system, gamepad, accelerometer, gyroscope, or other input device.

The memory 570 may contain computer program instructions (grouped as modules or components in some embodiments) that the processing unit 510 executes in order to implement one or more embodiments. The memory 570 generally includes RAM, ROM and/or other persistent, auxiliary or non-transitory computer-readable media. The memory 570 may store an operating system 572 that provides computer program instructions for use by the processing unit 510 in the general administration and operation of the computing device 500. The memory 570 may further include computer program instructions and other information for implementing aspects of the present disclosure.

For example, in one embodiment, the memory 570 includes a tracking and lineage construction module 574 for tracking biological objects (e.g., cells and nuclei) and constructing lineages of tracked biological objects. The memory 570 may additionally or alternatively include a resource allocation module 576 for allocating computational resources for deep learning-enabled biological (e.g., cellular) image analysis. The memory 570 may additionally or alternatively include an annotation module 578 for annotating and curating biological object (e.g., cell and nucleus) tracking-specific training datasets. In addition, memory 570 may include or communicate with the data store 590 and/or one or more other data stores that any data processed or generated using any method or system of the present disclosure, such as raw images, annotations of the images, training datasets, and trained models.

EXAMPLES

Some aspects of the embodiments discussed above are disclosed in further detail in the following examples, which are not in any way intended to limit the scope of the present disclosure.

Example 1

Accurate Cell Tracking and Lineage Construction in Live-Cell Imaging Experiments with Deep Learning Summary Live-cell imaging experiments have opened an exciting window into the behavior of living systems. While these experiments can produce rich data, the computational analysis of these datasets is challenging. Single-cell analysis requires that cells be accurately identified in each image and subsequently tracked over time. Increasingly, deep learning is being used to interpret microscopy image with single cell resolution. In this example, deep learning was applied to the problem of tracking single cells in live-cell imaging data. Using crowdsourcing and a human-in-the-loop approach to data annotation, a dataset of over 11,000 trajectories of cell nuclei that includes lineage information was constructed. Using this dataset, a deep learning model was successfully trained to perform biological object tracking (such as nucleus tracking and cell tracking) within a linear programming framework. Benchmarking tests demonstrate that the method achieves state-of-the-art performance on the task of cell tracking with respect to multiple accuracy metrics. Further, the deep learning-based method was generalized to perform cell tracking for both fluorescent and brightfield images of the cell cytoplasm, despite having never been trained on those data types. This enables analysis of live-cell imaging data collected across imaging modalities.

Introduction

Live-cell imaging experiments, where living cells are imaged over time with fluorescence or brightfield microscopy, has provided crucial insights into the inner workings of biological systems. These experiments have shed light on numerous problems, including information processing in signaling networks and quantifying stochastic gene expression. One key strength of live-cell imaging experiments is the ability to obtain dynamic data with single-cell resolution. Individual cells can vary considerably in their behavior, and the ability to capture the temporal evolution of cell-to-cell differences can aid understanding cellular heterogeneity. These dynamic data can be integrated with end-point genomic assays to uncover even more insights into cellular behavior.

Figure 6B:
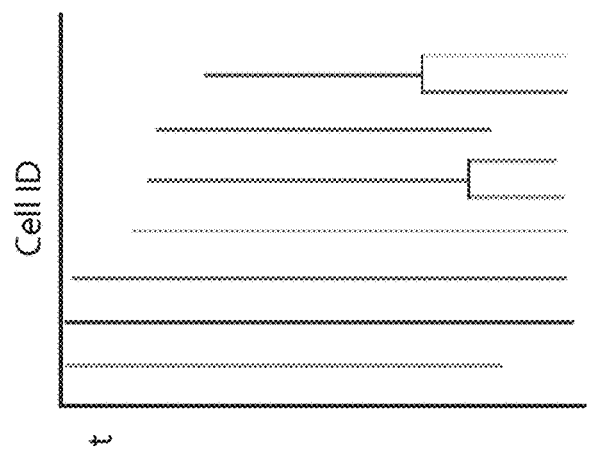
FIGS. 6A-6C. Tracking single cells with deep learning and linear programming.
Figure 6A:
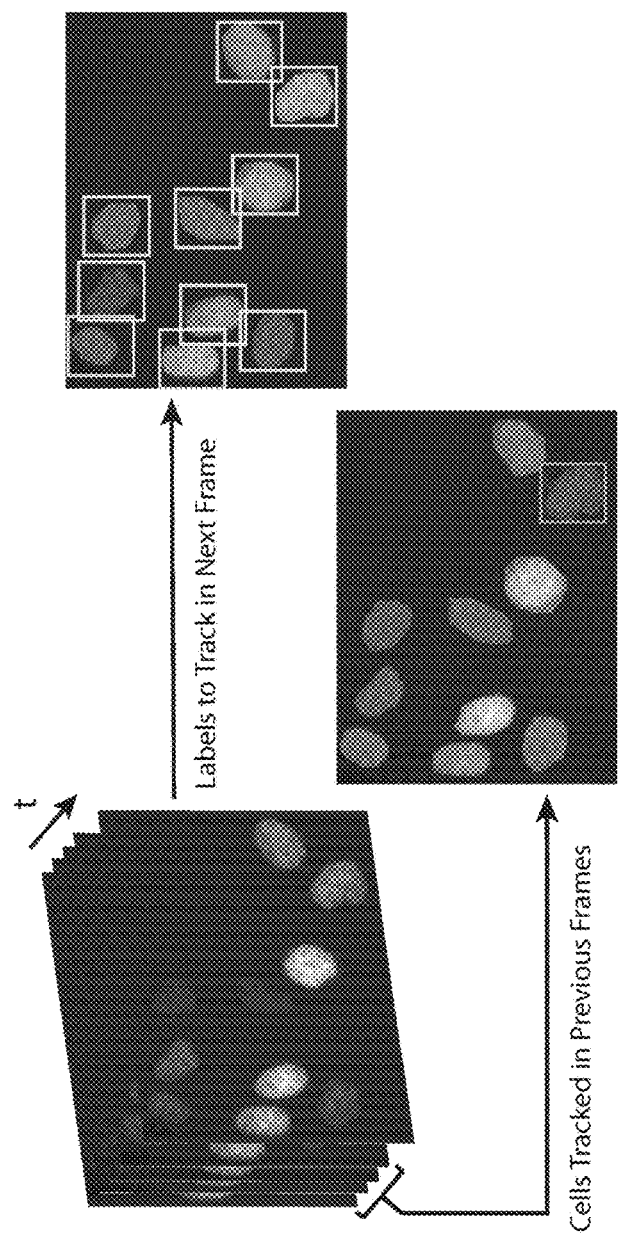

Central to the interpretation of these experiments is image analysis. The analysis of these data can occur in three phases. First, images are cleaned with steps that include background subtraction and drift correction. Next, the image can be segmented to identify each individual cell in every frame. This segmentation step can capture the whole cell or one or more cellular compartments like the nucleus. Lastly, all the detections for an individual cell can be linked together in time to form a temporally cohesive record for each cell; a schematic of this step is shown in FIGS. 6A and 6B. With a suitable algorithm and data structure, these records can contain lineage information such as parent-child relationships for each cell. The output of this analysis pipeline can include a record for each cell of which pixels are associated with the cell in each frame of the dataset as well as lineage information. This record can then be used to obtain quantitative information—ranging from metrics of cellular morphology to fluorescence intensity—over time.

Figure 6C:
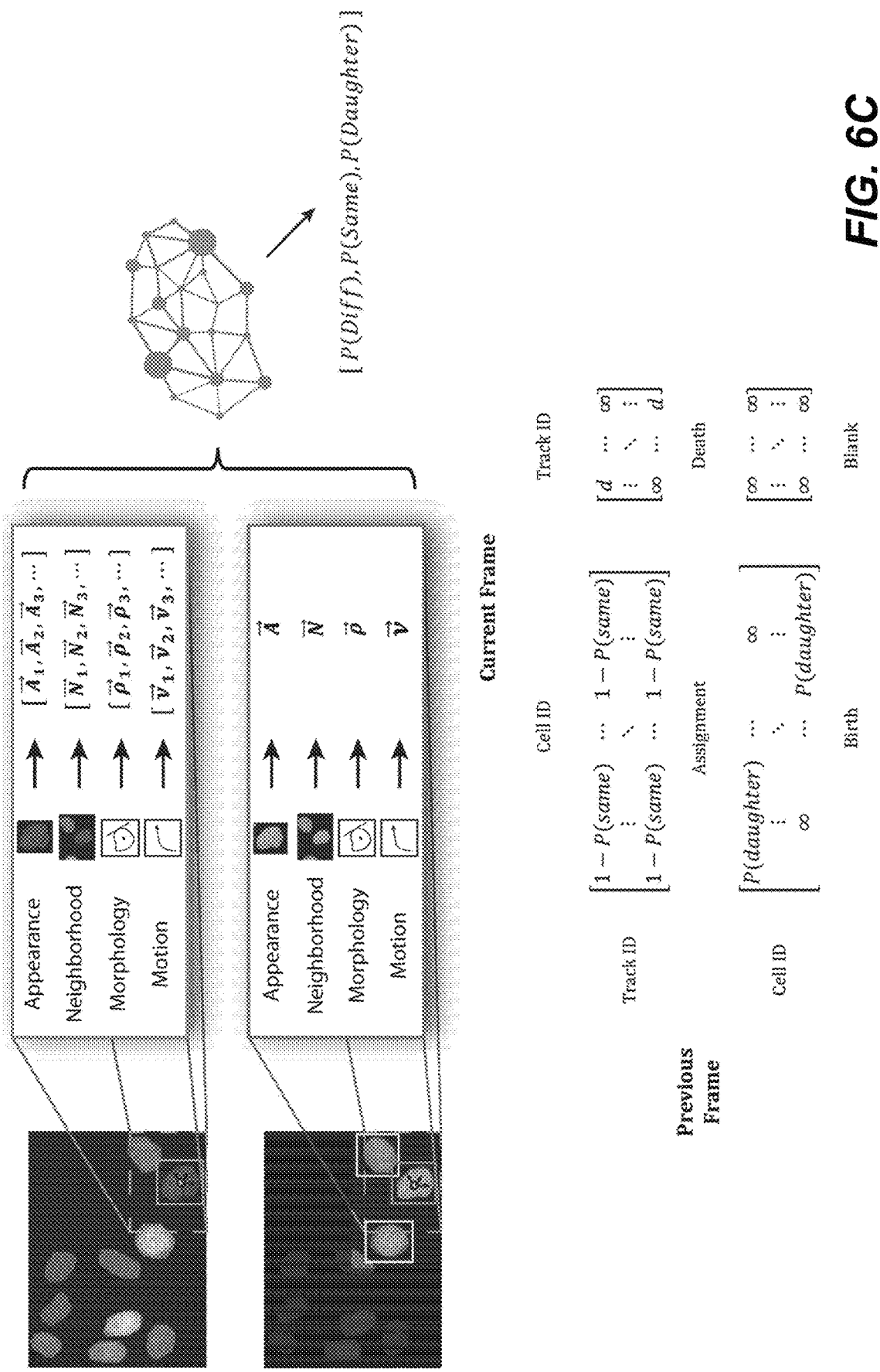

FIGS. 6A-6C. Tracking single cells with deep learning and linear programming. FIGS. 6A-6B. Computational analysis is a significant barrier for extracting single cell information from movies of living cells. Cells can be identified in every frame, and then these detections can be linked together over time to form a temporal record for each cell. FIG. 6C. Cell tracking can be framed as a linear assignment problem in which $N_i$ objects in frame i are matched up with $N_{i+1}$ objects in frame i+1. Shadow objects can be introduced to account for births (e.g., from cell division events) or deaths (e.g., cells leaving the field of view). Solving the linear assignment problem can require first creating a cost matrix, or a cost function that scores each possible assignment. For example, the Hungarian algorithm can be used to find the optimal assignment that minimizes the cost matrix. Instead of manually engineering this cost matrix or function, a deep learning model was used to learn the cost matrix from annotated data. As described herein, $p_{same}$ is the probability that two cells being compared are the same, b is the cost associated with cell "births" (e.g., a cell in frame i+1 being assigned to a shadow cell), and d is the cost associate with a cell death (e.g., a cell in frame i being assigned to a shadow cell). A deep learning model can take information from two cells and compute the probability these are the same cell, different cells, or have a parent-child relationship. This model can take information on each cell's appearance, local neighborhood, morphology, and motion and summarizes as a vector using a deep learning sub-model. A fully connected layer can read these summaries and determine the scores for the three classes.

Advances in imaging technologies—both in microscopes and fluorescent reporters—have significantly reduced the difficulty of acquiring live-cell imaging data, while at the same time increasing the throughput and the number of systems amenable to image analysis. Increasingly, image analysis is a bottleneck for discovery as there is a gap between our ability to collect and analyze data. This gap can be traced to the limited accuracy and generality of cell segmentation and tracking algorithms. These limitations lead to a significant curation time, recently estimated to be more than 100 hours for one manuscript worth of data. Advances in computer vision, specifically deep learning, can close this gap. In this example, deep learning refers to a set of machine learning methods capable of learning effective representations from data in a supervised or unsupervised fashion. Deep learning can have a remarkable ability to extract information from images, and deep learning can be a natural fit for the image analysis needs of the life sciences. Deep learning can be applied to biological imaging data—applications include using classification to determine cellular phenotypes, enhancing image resolution, and extracting latent information from brightfield microscope images. Of interest to those who use live-cell imaging has been the application of this technology to single-cell segmentation. The deep learning model architecture U-Net targeted cell segmentation as its first use case. Deep learning can perform single-cell segmentation for organisms spanning the domains of life as well as in images of tissues. Deep learning can be applied to 3D datasets. The improved accuracy of single-cell segmentations for live-cell imaging can be important, as a single segmentation error in a single frame can impair subsequent attempts at cell tracking and render a cell unsuitable for analysis.

While deep learning has been successfully applied to single-cell segmentation, a robust deep learning-based cell tracker for mammalian cells has been elusive. Integration of deep learning into live-cell imaging analysis pipelines can achieve performance boosts by combining the improved segmentation accuracy of deep learning with conventional object tracking algorithms. These algorithms include linear programming and the Viterbi algorithm; both can be used on live-cell imaging data. While useful, these object tracking algorithms have limitations. Common events that lead to tracking errors include cell division and cells entering and leaving the field of view. Furthermore, their use often necessitates tuning numerous parameters to optimize performance for specific datasets, which leads to fragility on unseen data. Deep learning can be used to track cells; however the performance can be limited by a lack of training data and fine-tuned conventional methods may achieve superior performance.

Three technical challenges have impeded the creation of a readily available, deep learning-based cell tracker. First, the unique features of live-cell imaging data (e.g., cell divisions) can confound traditional tracking methods as well as deep learning-based object trackers. Second, successful deep learning solutions can be data hungry. While unsupervised deep learning can be a useful tool, most applications of deep learning to imaging data can be supervised and require significant amounts of specialized training data. Aggregating and curating training data for tracking can be especially difficult because of the additional temporal dimension—objects are segmented and tracked through every frame of a training dataset. Third, deep learning's requirement for hardware acceleration presents a barrier for performing large inference tasks. On premise computing has limited throughput, while cloud computing poses additional software engineering challenges.

In this example, each of these challenges is addressed to construct an effective deep learning-based solution to cell tracking (or nucleus tracking) in live-cell imaging data (e.g., two dimensional live-cell imaging data). Cell tracking was achieved with deep learning and linear programming. A combination of crowdsourcing and human-in-the-loop data annotation was used to create a live-cell imaging training dataset including over 11,000 single cell trajectories. The resulting tracker was benchmarked using multiple metrics and achieved state-of-the-art performance on several datasets, including data from the ISBI cell tracking challenge. Lastly, the cell tracker was be integrated into a cloud computing single-cell image analysis framework, the Deep-Cell 2.0 single-cell image analysis framework, to enable segmentation and tracking live-cell imaging datasets by users using web browsers.

Tracking Single Cells with Deep Learning and Linear Programming

Object tracking was treated as a linear assignment problem (FIG. 6C). In this framework, $N_i$ objects in frame i can be assigned to $N_{i+1}$ objects in frame i+1. To solve this assignment problem, a cost matrix or a cost function for a possible pairing across frames can be constructed. The cost function can be based on each object's location and appearance features (e.g., brightness, size, etc.). Objects are unlikely to move large distances or have distinct changes in appearance from frame-to-frame if the frame rate is sufficiently high. The problem can be reduced to the selection of one assignment out of the set of all possible assignments that minimizes the cost function, a task that can be accomplished with the Hungarian algorithm. One complicating factor of biological object tracking is that objects can appear and disappear—objects appearing and disappearing can often lead to $N_i$ and $N_{i+1}$ being unequal. This problem can be solved by introducing a "shadow object" for each object in the two frames—$N_{i+1}$ shadow objects in frame i and $N_i$ shadow objects in frame i+1. These shadow objects represent an opportunity for objects to "die" (if an object in frame i is matched with its shadow object in frame i+1) or to be "born" (if an object in frame i+1 is matched with its shadow object in frame i). This framework can lead to a cost matrix describing the cost of every possible assignment that is size $N_i+N_{i+1} \times N_i+N_{i+1}$; the structure of the cost matrix is shown in FIG. 6C.

Assuming error-free image segmentation and an accommodation for dealing with cell divisions, cell tracking can fit neatly into this framework. Whole movies can be tracked by sequentially tracking every pair of frames—this was contrasted with approaches like the Viterbi algorithm that incorporate multiple frames worth of information to determine assignments. One advantage of the approach is that the approach can cope with missing objects—instead of using the objects in frame i for comparison, all objects that have been successfully tracked up to frame i can be used. If objects disappear and reappear, the opportunity to correctly track them still exists. Optimization of the linear assignment approach's performance on real data can come about through cost function engineering. By varying key aspects of the cost function—how sensitive the cost function is to the distance between two cells, how much the cost function weights the importance of cell movement vs cell appearance, etc.—the approach can be tuned to have acceptable performance on live-cell imaging datasets. However, tuning the cost function can have several downsides—the accuracy may be limited, the time required for cost function engineering and curation of results may be prohibitive, and solutions may be tailored to specific datasets which reduces their generality.

In this example, a supervised deep learning approach was used to learn an optimal cost function for the linear assignment framework. The approach included adaptations to deal with the unique features of live-cell imaging data (FIG. 6C). Constructing the learned cost function was considered as a classification task. Suppose there were two cells—cell 1 in frame i and cell 2 in frame i+1. The goal was to construct a classifier that would take in information about each cell and produce a probability that these two cells were either the same, are different, or have a parent-child relationship. If such a classifier worked perfectly, then the classifier can replace a hand engineered cost function, as is shown in FIG. 6C. To incorporate temporal information, multiple frames of information for cell 1 was used as an input to the classifier. This allowed access to the temporal information beyond just the two frames being compared. Seven frames worth of information was used in this example.

The classifier for performing this task was a hybrid recurrent-convolutional deep learning model; the classifier's architecture is shown in FIG. 6C. This deep learning model took in 4 pieces of information about each cell using 4 separate branches. Conceptually, each branch sought to summarize its input information as a vector. These summary vectors was then fed into a fully connected neural network to classify the two cells being compared. The first branch took in the appearance, that was a cropped and resized image, of each cell and used a deep convolutional neural network to generate a summary. This network was applied to every frame for cell 1, creating a sequence of summary vectors. Conversely, cell 2 only had 1 frame of information and hence only had 1 summary vector.

The appearance gave access to information on what the two cells looked like, but the resizing operation removed notions of size scale. To mitigate the lack of notions of size scale from the resizing operation, the classifier included a second branch that took in a vector of morphological information for each cell and used a densely connected neural network to create a summary vector of this information. The morphology information used included the area, perimeter, and eccentricity.

The third branch acquired information about cell motion over time. For cell 1, a vector of all the centroid displacements were collected. For cell 2, a single vector that was the displacement between cell 1 and cell 2's centroid was created. This branch gave a history of cell 1's motion and allowed seeing whether a potential positive assignment of cell 2 would be inconsistent from the point of view of cell motion.

The last branch incorporated neighborhoods, which was an image cropped out around the region surrounding cell 1. Because neighborhoods can contain information about cell divisions, neighborhoods could prove useful in performing lineage assignments. Just as with appearances, a deep convolutional neural network was used to summarize the neighborhoods as a vector. The neighborhood around the area cell 1 was predicted to be located given cell 1's velocity vectors was extracted and use the extracted neighborhood as the neighborhood for cell 2.

The result of these 4 branches were sequences of summary vectors for cell 1 and individual summary vectors for cell 2. Long short-term memory (LSTM) layers were then applied to each of cell 1's sequence of summary vectors to merge the temporal information and to create 4 individual vectors that summarized each of the 4 branches. The vectors for cell 1 and cell 2 were then concatenated and fed into fully connected layers. The final layer applied the softmax transform to produce the final classification scores—$p_{same}$, $p_{diff}$, and $p_{parent-child}$. These three scores, which were all positive and sum to 1, can be thought of as probabilities. The three scores were used to construct the cost matrix, as shown in FIG. 6C. If a cell in frame i+1 was assigned to a shadow cell, e.g., it is "born," then whether there was a parent-child relationship was checked. Checking was done by finding the highest $p_{parent-child}$ among all eligible cells (i.e., the cells in frame i that were assigned to "die")—if the highest $p_{parent-child}$ among all eligible cells was above a threshold, then the lineage assignment was made. Full details of the model architecture, training, hyperparameter optimization, and post processing are described in the Additional Information section of this example.

Dataset Annotation and Cell Segmentation

To power the deep learning approach to cell tracking, an annotated dataset specific to live-cell imaging was generated. This dataset included movies of 4 different cell lines—HeLa-S3, RAW 264.7, HEK293, and NIH-3T3. For each cell line, fluorescence images of the cell nucleus were collected. The nucleus is a commonly used landmark for quantitative analysis of live-cell imaging data, and brightfield images can be translated into images of the cell nucleus. The annotations sought to create included label movies—movies in which every pixel that belonged to a cell got a unique integer id in every frame that cell existed—and lineage information which accounted for cell divisions. This latter piece of information, referred to as relational data, took the form of a JSON object that linked the ids of each parent cell with the ids of child cells. In total, the dataset included 11,393 cell trajectories (about 25 frames per trajectory) with 855 cell divisions in total. This dataset and the deep learning code were important. Existing single-cell datasets were not adequate for a deep learning approach, as the existing single-cell datasets were either too small or did not contain temporal information.

Figure 7A:
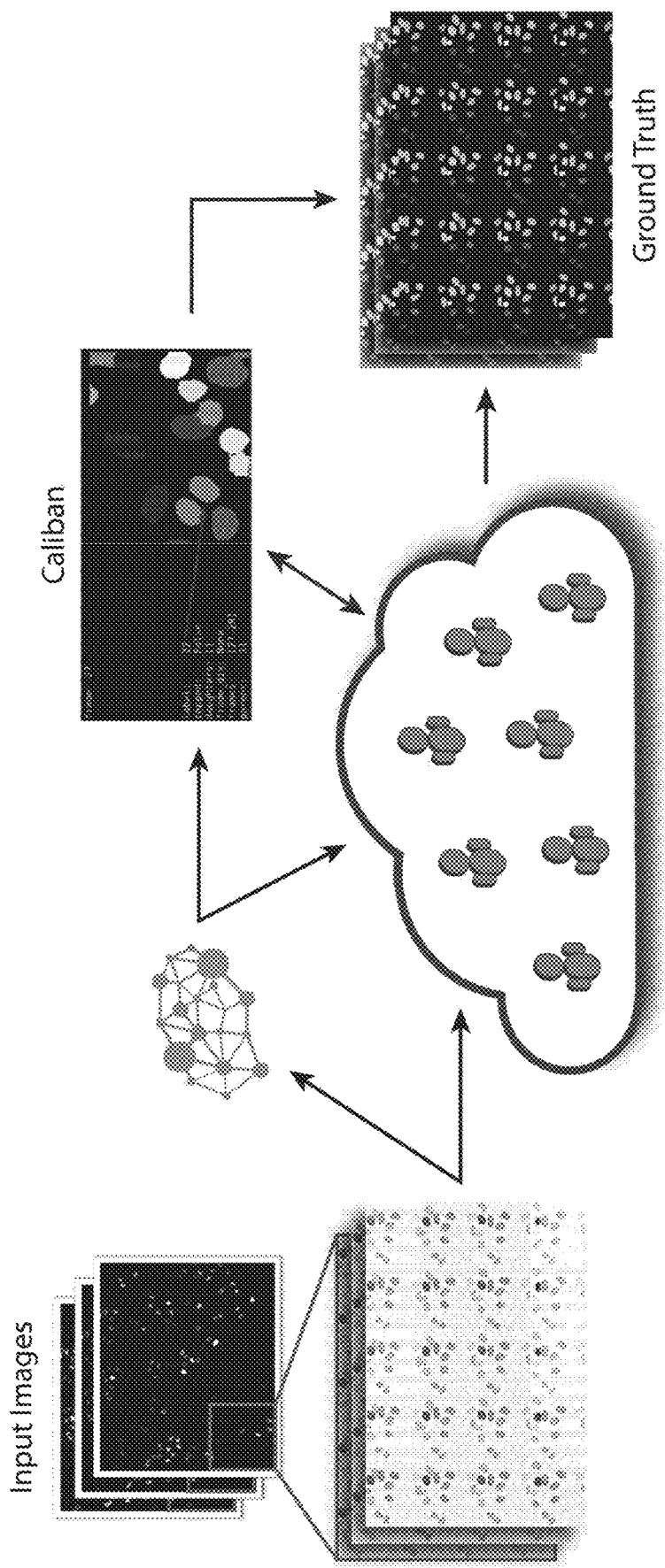
FIGS. 7A-7B. A human-in-the-loop to dataset construction and cloud computing facilitate a scalable solution to live-cell image analysis.

The approach to constructing this dataset is shown in FIG. 7A. Briefly, the dataset annotation included two phases. The first phase relied on crowdsourcing and internal annotators. Using the Figure Eight platform, annotators were given a sequence of frames and instructed to color each cell with a unique color for every frame a cell appeared in. In this fashion, contributors provided both segmentation and tracking annotations simultaneously. Internal annotators took these annotations and manually corrected errors and recorded cell division events in these data. Once enough training data was collected (about 2,000 trajectories), preliminary models for segmentation and cell tracking were trained. These were accurate enough to empower annotators to correct algorithm mistakes as opposed to creating annotations from scratch. To facilitate this human-in-the-loop approach, a software tool called Caliban was developed to specifically curate live-cell imaging data. Caliban, also shown in FIG. 7A, took in segmented and tracked live-cell imaging data and enabled users to quickly correct errors using their keyboard and mouse.

Figure 7B:
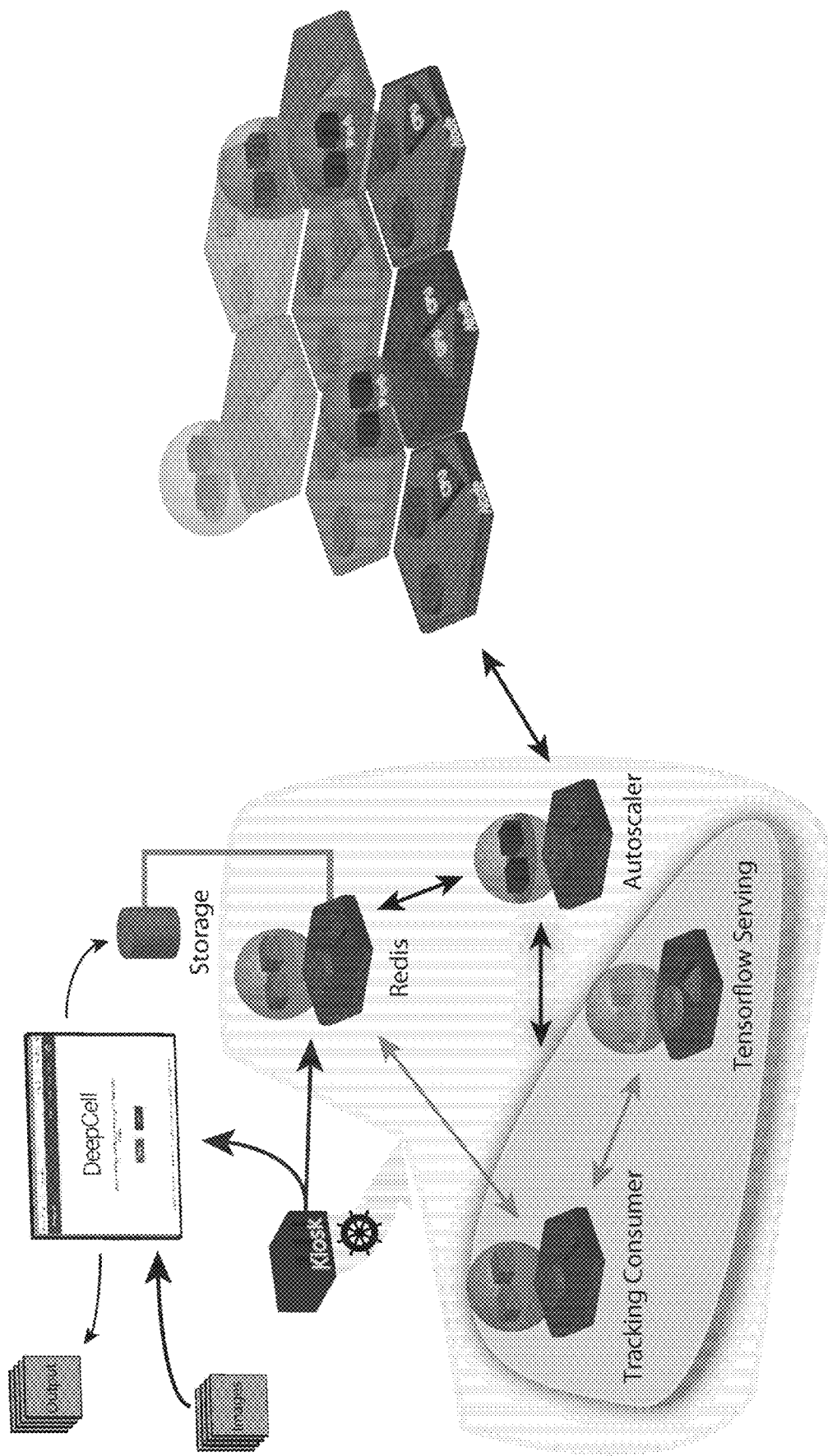

FIGS. 7A-7C. A human-in-the-loop to dataset construction and cloud computing facilitate a scalable solution to live-cell image analysis. FIG. 7A. Combining crowd sourcing and a human-in-the-loop approach to dataset annotation enables the construction of an ImageNet for live-cell imaging. By annotating montages, crowd contributors both segmented and tracked single cells in live-cell imaging data. This data led to models that were used to process additional data; expert annotators use a version of Caliban to correct model errors and identify cell division events. The resulting data was then used to train a final set of deep learning models to perform cell segmentation and tracking. FIG. 7B. Integration of a cell tracking service into DeepCell 2.0. Datasets were uploaded to a cloud bucket; once there, a tracking consumer object facilitated interactions with deep learning models via Tensorflow serving for segmentation and tracking. The implementation within the Kubernetes engine included an autoscaling module that monitored resource utilization and scales the compute resources accordingly.

The resulting dataset was used to train the cell tracking model as well as nuclear segmentation models. A model based on RetinaMask was used for nuclear segmentation, which provided moderate gains to another approach investigated in this example (See FIG. 8). The pipeline for crowdsourcing was used to create single cell annotations of static fluorescent cytoplasm images and brightfield images of 7 different cell lines—MSC (mesenchymal stem cells), NIH-3T3, A549, HeLa, HeLa-S3, CHO, and PC3. This dataset included 63,280 single cell annotations and was used to train models for single cell segmentation of fluorescent cytoplasm and brightfield images, allowing the benchmarking of the cell tracking algorithm (or method, model, approach, framework, or pipeline) on cytoplasmic images. Full details of the annotation methods, model architectures, and model training can be found in the Additional Information section of this example.

Deployment

The need for hardware acceleration and software infrastructure can pose a significant barrier to entry for new adopters of deep learning methods. The barrier is particularly problematic for large inference tasks, as is often the case in the life sciences. To solve the barrier issue, a platform for performing large-scale cellular image analysis in the cloud using deep learning-enabled models was developed. This platform is based on a micro-service architecture. The platform can allow sequences of image analysis steps—some enabled by deep learning and some not—to be applied to an image before returning the result to the user. The platform also can scale resources requested from cloud computing providers to meet demand. This scaling ability can allow large analysis tasks to be finished quickly, making data transfer the sole bottleneck. Further, the platform can allow analysis to be performed through a web portal.

The deep learning-enabled cell segmentation and tracking software was integrated into this platform (FIG. 7B), allowing users to interface with this algorithm through a web portal. Data in the form of a tiff stack (or a zip file with directories that contain multiple tiff stacks) was uploaded into a cloud bucket. Once there, the images were segmented, cells were tracked, and the end result was returned to the user in the form of ".trk" files. The ".trk" file format stored the raw movie, the label movie, and a JSON object with the mother-daughter information. The results can be curated with Caliban to correct errors and then queried for single cell analysis using user generated scripts. While the deep learning-enabled cell segmentation and tracking method was accessible in the form of Jupyter notebooks for both training and inference, incorporating this algorithm into a cloud deployment made the method more accessible because analysis can be performed through a web portal. Further, the cloud deployment can make performing large inference tasks significantly easier.

Benchmarking

Figure 8A:
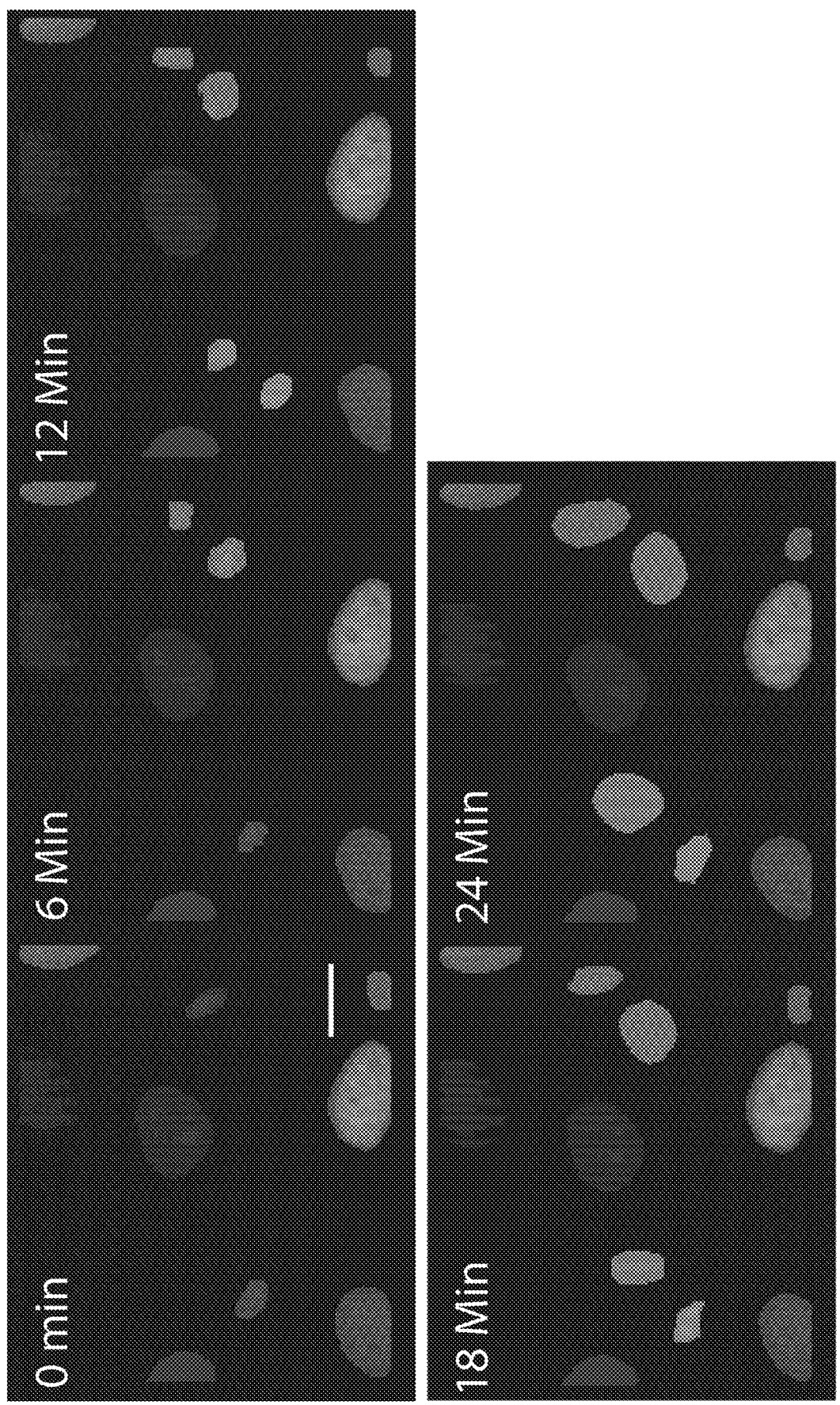
FIGS. 8A-8C. Benchmarking demonstrates that deep learning achieves state-of-the-art performance on cell tracking tasks for a variety of cell types.

A visual montage of the algorithm's output is shown in FIG. 8A. To benchmark the method, 10% of the annotated data was reserved solely for testing. The ISBI cell tracking dataset was also used; where necessary, the pipeline was used to create label movies of these data. As a baseline for the current state-of-the-art, an existing implementation of the Viterbi algorithm was used. The challenge of benchmarking tracking methods was that errors can arise from both segmentation and tracking. Three different tracking metrics were used. The first was confusion matrices for the deep learning model, which provided a sense of which linkage errors were most likely. The second was a graph-based metric that treated cell lineage as a directed acyclic graph (DAG). The number of graph operations (split/delete/add a node and delete/add/change an edge) needed to map the DAGs generated by an algorithm to the ground truth DAGs was used to generate a score from 0 to 1. Last, the true positive, false positive, and false negative rates for detecting cell divisions, one of the most challenging tasks of cell tracking, were quantified.

Figure 8C:
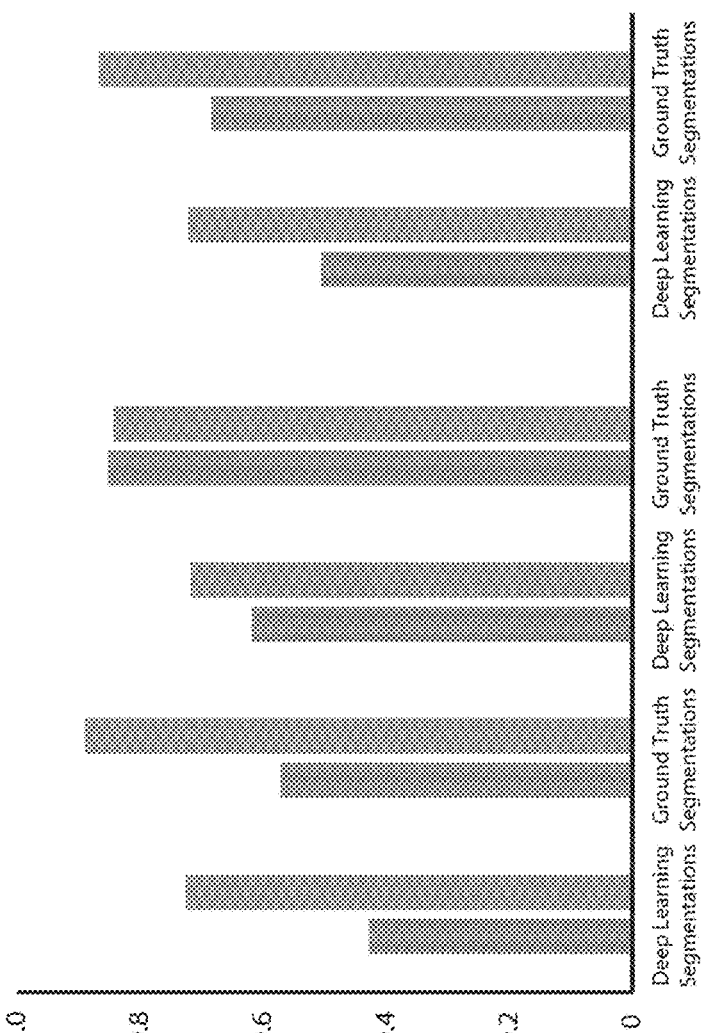
Figure 8B:
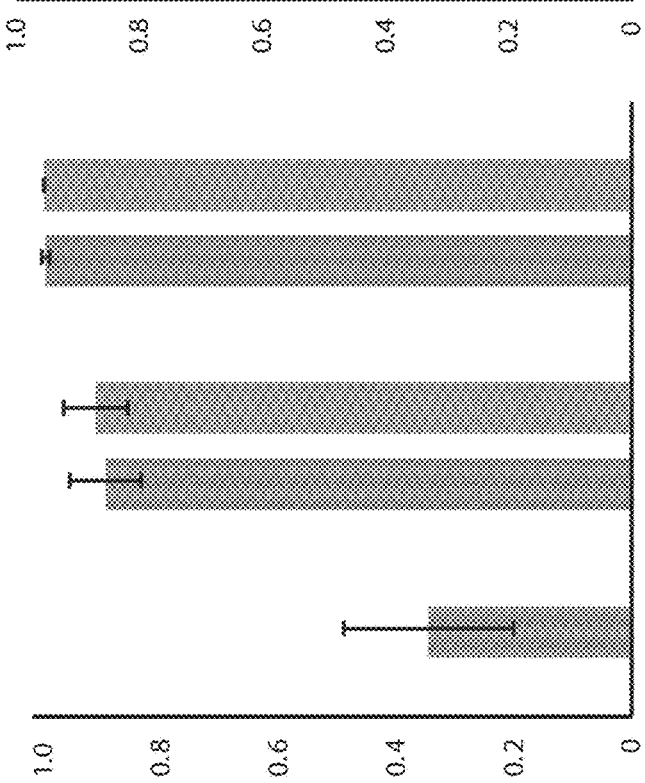

FIGS. 8A-8C. Benchmarking demonstrates that deep learning can achieved state-of-the-art performance on cell tracking tasks for a variety of cell types. FIG. 8A. A montage of tracking results for fluorescent images of cell nuclei and brightfield images of cells. FIG. 8B. ISBI graph metric performance of a Viterbi-based algorithm (KTH-SE) and the deep learning approach of the example on nuclear data. The graph-based metric for cell tracking demonstrates that deep learning can enable state-of-the-art performance, with the bulk of this performance boost coming from improved segmentations with respect to the testing dataset used for benchmarking. Error bars represent the standard deviation. FIG. 8C. Analysis of performance in cell division detection reveals that the performance boost offered by deep learning comes from more accurate detection of cell divisions.

Confusion matrices for the method on the testing dataset was computed; these are shown in the Additional Information section of this example. These demonstrate that the most common error made by our method is confusing linkages between the same cell with linkages between mother and daughter cells. The confusion can lead to false division events, where the mother cell only has one daughter, and missed cell divisions. The former can be mitigated with appropriate post-processing. Next, the graph-based metric was used to compare the performance of the method to a Viterbi-based method that has produced state-of-the-art performance in the ISBI cell tracking challenge; the results are shown in FIG. 8B. To separate cell segmentation performance from cell tracking performance, this metric was applied in three settings. First, a classical computer vision method was used to segment cells and the Viterbi cell tracking algorithm was used to generate a baseline score. Next, to measure the improvement provided by deep learning-enabled cell segmentation, deep learning was used to generate cell segmentations and both the Viterbi and the deep learning-enabled tracking method of this example were used to link cells together over time. Last, to measure the improvement provided by deep learning-enabled cell tracking, the ground truth segmentations were used as the input to both cell trackers. This comparison (FIG. 8B) reveals that the bulk of the performance boost offered by deep learning comes from improved cell segmentations with respect to the test dataset. This comparison also shows that the deep learning-enabled cell tracker outperforms the Viterbi algorithm on these data with respect to the graph-based metric.

While the graph-based metric provides a global measure of performance, the graph-based metric is less informative for rare but important events like cell divisions. To complete the analysis, the recall, precision, and F1 score for cell division detection were quantified on the held-out datasets. This was done for both deep learning generated and ground truth segmentations for the deep learning-enabled method and the Viterbi algorithm. As seen in FIG. 8C, deep learning provided a marked improvement in cell division detection, and hence lineage construction. With ground truth segmentations, the approach of the example achieved a recall and precision of 89% and 84%; the Viterbi algorithm achieves 57% and 85% respectively on these measures. The performance of the method fell to a recall of 72% and a precision of 71% when deep learning generated segmentations are used. These results are consistent with the minor differences seen in the graph-based metric because divisions are rare events, and hence require only a few graph operations to fix if the division events are misidentified. This analysis highlights the strength of the deep learning-enabled approach; live-cell imaging experiments that require correct lineage construction stand to benefit the most.

Last, because the deep learning model was trained in the same fashion as Siamese neural networks (i.e. same vs. different), whether the deep learning model would generalize beyond just nuclear data was of interest. To test this, the crowdsourcing pipeline was used to generate label movies of brightfield and fluorescent cytoplasmic data from the ISBI cell tracking challenge. The segmentations from these label movies were used as the input into the cell tracker. Surprisingly, the cell tracker performed markedly well on this challenge, despite never having seen cytoplasmic data. This finding suggests that single model can be used to track cells irrespective of the imaging modality. This raises the possibility of a pipeline that can process live-cell imaging data while being agnostic to image type or acquisition parameters. As a proof of principle, a pipeline that used deep learning models to find the relative scale of input images to our training data and identify the imaging modality was constructed. Using this information, images were rescaled, direct them to the appropriate segmentation model, and then the results were sent to the deep learning-based cell tracker for lineage construction. While the proof of principle demonstrates the feasibility of analyzing diverse datasets with a single pipeline, additional training data may be needed to produce cytoplasmic segmentations accurate enough for automated analysis.

Additional Information

Cell Line Acquisition and Culture Methods.

The mammalian cell lines NIH-3T3, HeLa-S3, HEK 293, and RAW 264.7 were used to collect training data for nuclear segmentation, and the cell lines NIH-3T3 and RAW 264.7 were used to collect training data for augmented microscopy. All cell lines were acquired from ATCC. The cells had not been authenticated and were not tested for *Mycoplasma* contamination.

Mammalian cells were cultured in Dulbecco's modified Eagle's medium (DMEM, Invitrogen or Caisson) supplemented with 2 mM L-Glutamine (Gibco), 100 U/ml penicillin, 100 µg/ml streptomycin (Gibco or Caisson), and either 10% fetal bovine serum (Omega Scientific or Thermo Fisher) for HeLa-S3 cells, or 10% calf serum (Colorado Serum Company) for NIH-3T3 cells. Cells were incubated at 37° C. in a humidified 5% CO2 atmosphere. When 70-80% confluent, cells were passaged and seeded onto fibronectin coated glass bottom 96-well plates (Thermo Fisher) at 10,000-20,000 cells/well. The seeded cells were then incubated for 1-2 hours to allow for cell adhesion to the bottom of the well plate before imaging.

Collection of Live-Cell Imaging Data.

For fluorescent nuclear imaging, mammalian cells were seeded onto fibronectin (Sigma, 10 ug/ml) coated glass bottom 96-well plates (Nunc) and allowed to attach overnight. Media was removed and replaced with imaging media (FluoroBrite DMEM (Invitrogen) supplemented with 10 mM Hepes, 1% FBS, 2 mM L-Glutamine) at least 1 hour prior to imaging. For nuclear imaging, cells without a genetically encoded nuclear marker were incubated with 50 ng/ml Hoechst (Sigma) prior to imaging. For cytoplasm imaging, cells were incubated with 2 µM CellTracker CMFDA prior to imaging. Cells were imaged with either a Nikon Ti-E or Nikon Ti2 fluorescence microscope with environmental control (37° C., 5% $CO_2$) and controlled by Micro-Manager or Nikon Elements. Images were acquired with a 20× objective (40× for RAW 264.7 cells) and either an Andor Neo 5.5 CMOS camera with 2×2 binning or a Photometrics Prime 95B CMOS camera with 2×2 binning. All data was scaled to so that pixels had the same physical dimension prior to training. Fluorescence images were taken for nuclear data, while both brightfield and fluorescence images were taken for cytoplasmic data. For time-lapse experiments, images were acquired at 6-minute intervals.

Deep Learning Architecture for Single-Cell Segmentation.

Figure 9:
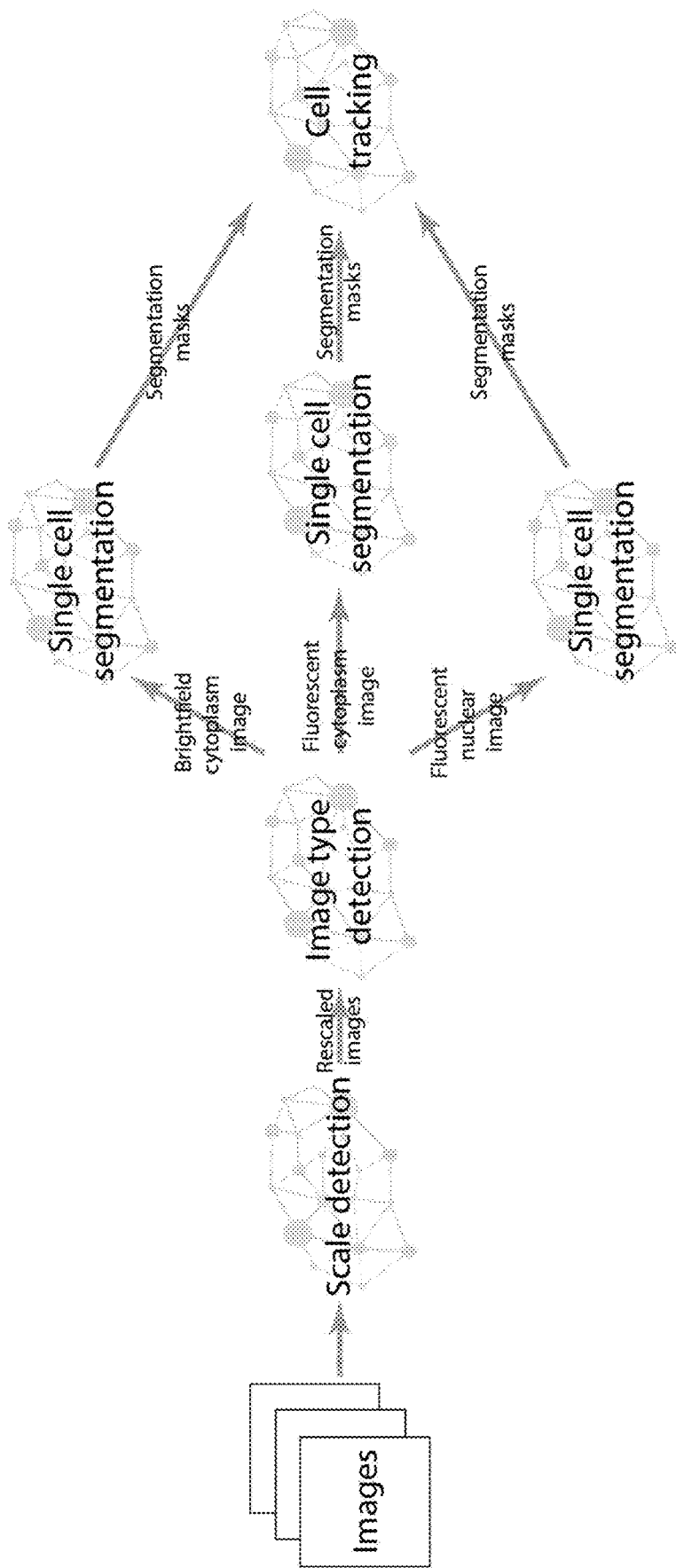
FIG. 9. Computational pipeline for single cell segmentation.

The pipeline for single cell segmentation is shown in FIG. 9. This pipeline used deep learning models to rescale images and direct them to the appropriate segmentation. Modified RetinaMask models were used for single cell segmentation of fluorescent nuclear, fluorescent cytoplasm, and brightfield images. RetinaMask generates instance masks in a fashion similar to Mask-RCNN, but uses single shot detection like RetinaNet rather than feature proposals to identify objects. Each model used a ResNet50 backbone pre-trained on ImageNet. For nuclear segmentation, the P3 and P4 feature pyramid layers were used for object detection with an anchor size of 16 and 32 pixels respectively. For the fluorescent cytoplasmic and brightfield segmentation, the P3, P4, P5, and P6 layers with anchor sizes of 32, 64, 128, and 256 pixels were used. For all three models, two semantic segmentation heads were used to predict pixelwise and deep watershed segmentations. The architecture of two sematic segmentation heads encouraged the backbone and feature pyramid network to learn more general image features. A weighted softmax loss was used for both heads that was weighted by 0.1. All three models were trained on their respective datasets in the same fashion. The Adam optimization algorithm was used with a learning rate of $10^{-5}$ and clip norm of 0.001, batch size of 4, and L2 regularization strength of $10^{-5}$ for 16 epochs on a NVIDIA V100 graphics card. For the nuclear data, the training/validation split was the same as was used for training the cell tracking model. The post processing included removing segmentation masks that had high overlap with more than 2 other masks. Masks that only overlapped with 1 other mask were resolved using a marker based random walker segmentation step. All masks smaller than 100 pixels were also removed during post processing. For nuclear segmentation, the output of the watershed semantic segmentation mask was used to add cells that were missed by the RetinaMask object detection.

Deep Learning Models for Scale and Image Type Detection.

To develop a live-cell imaging analysis workflow that is agnostic to imaging modality and acquisition parameters, two deep learning models for detecting scale and image type were trained. The scale detection model sought to identify the relative scale of between an input image and our training data; affine transformations were applied to the training data to create images of different scales. The model included of a MobileNetV2 backbone connected to an average pooling layer and followed by two dense layers. The model was trained for 20 epochs on a combined dataset (nuclear, fluorescent cytoplasmic, and brightfield images) using a mean squared error (MSE) loss. The Adam optimization algorithm was used with a learning rate of $10^{-5}$ and clip norm of 0.001, batch size of 64, and L2 regularization strength of $10^{-5}$ on an NVIDIA V100 graphics card. The image type detection model included a MobileNetV2 backbone connected to an average pooling layer followed by two dense layers and a softmax layer. The model was trained for 20 epochs on a combined dataset using a weighted categorical cross-entropy loss. The Adam optimization algorithm was used with a learning rate of $10^{-5}$ and clip norm of 0.001, batch size of 64, and L2 regularization strength of $10^{-5}$ on an NVIDIA V100 graphics card. The scale detection model achieved a mean absolute percentage error of 0.85% on validation data, while the image type detection achieved a classification accuracy of 98% on validation data. Using the MobileNetV2 backbone was found provided similar performance to larger networks while offering a higher inference speed and lower memory footprint.

FIG. 9. Computational pipeline for single cell segmentation. The pipeline used a scale detection deep learning model to rescale input images to the same physical pixel dimensions of our training data. Another deep learning model detected whether the rescaled images were fluorescent nuclear images, fluorescent cytoplasm images, or brightfield images. Once the image type was determined, the images were sent to a RetinaMask based deep learning model for single cell segmentation. The segmentation masks were then sent to the cell tracking deep learning model to construct cell lineages.

Segmentation Benchmarking.

Because segmentation performance can be important to cell tracking performance, rigorous benchmarking was performed during model optimization. In addition to pixel-based metrics, an object-based approach was used to segmentation benchmarking. This approach compared ground truth and prediction segmentations to identify segmentation errors. The first step was to link prediction and ground truth segmentations based on object overlap—this can be thought of as constructing of a DeBruijn graph where objects rather than sequences were used. This problem was solved using a linear assignment framework in a manner akin to how cells are linked during cell tracking in this example. A cost matrix was constructed where the cost of linking two cells is 1—iou, where iou is the intersection over union of those two cells. Leaving a ground truth cell unassigned (missed detection) or a prediction cell unassigned (gained detection) had a cost of 0.4. Thus, for a ground truth and predicted cell to be linked, the ground truth and predicted cell had an iou of at least 0.6.

Figure 10:
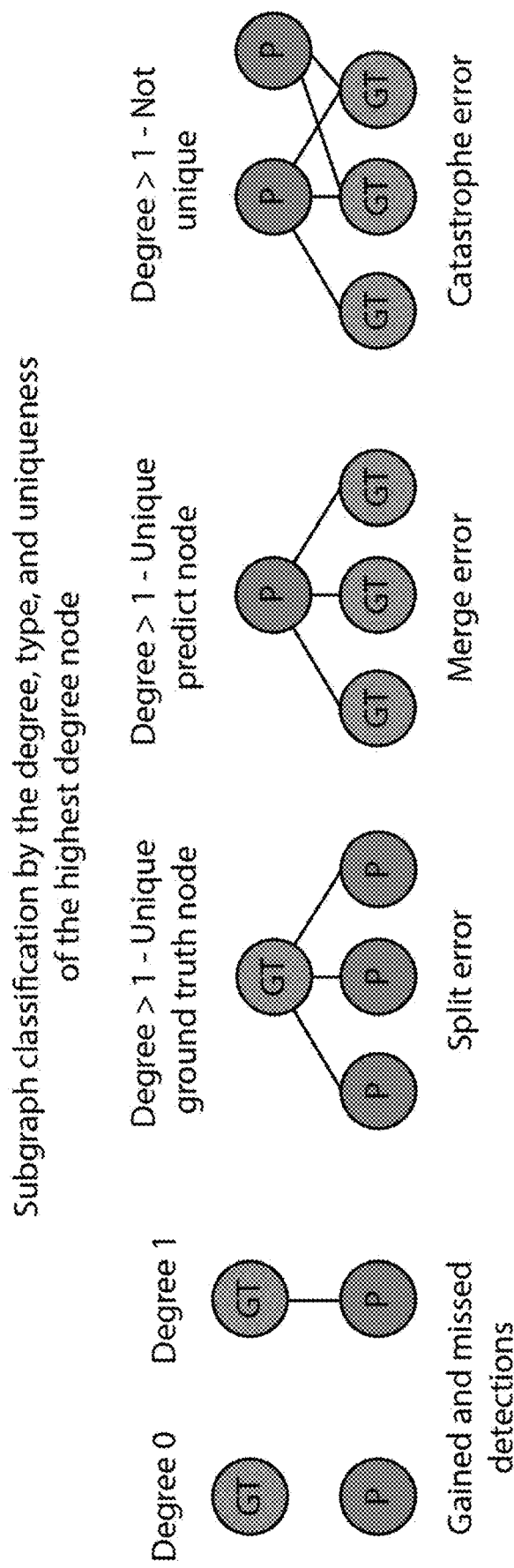
FIG. 10. Subgraph classification enabled the identification of merge, split, and catastrophe errors in cell segmentations.

All the unassigned cells were then gathered for a second round of graph construction to classify error types. This is shown in FIG. 10. Each cell was viewed as a node, and all pairs of unassigned ground truth cells and unassigned predicted cells were examined; two cells were linked if they had an iou greater than 0.1. Then all the subgraphs of this graph were extracted and categorized into three groups. The first group included all subgraphs that had a single node (i.e. the highest degree of any node is 0). If the node was a ground truth cell, this corresponded to a missed detection (i.e. a false negative); if the node was a predicted cell, this corresponded to a gained detection (i.e. a false positive). The next group included all subgraphs where the highest degree node had degree 1. Each subgraph in this group had one node that corresponded to a ground truth cell and one node that corresponded to a prediction cell. Because these cells were not assigned in the first round of graph construction, these cells corresponded to a missed detection and a gained detection. The third group included all subgraphs with a node that has degree >1. This group can be further divided into three subgroups based on the type and uniqueness of the highest degree node. If the highest degree node was a ground truth cell and was unique, then subgraph corresponded to a splitting error. If the highest degree node was a predicted cell and was unique, the subgraph corresponded to a merge error. If the highest degree node was not unique, then the subgraph fell into a third class called catastrophes. Catastrophe's involved both splitting and merging mistakes, but decoupling the two from the subgraphs was not possible. Catastrophes were found to become increasingly common in dense datasets, and that their inclusion was important to accurately categorize segmentation errors. One limitation of this approach was that the approach relied on accurate ground truth datasets. Segmentation "errors" often reflected errors in training data.

FIG. 10. Subgraph classification enabled the identification of merge, split, and catastrophe errors in cell segmentations.

The segmentation benchmarks for the segmentation model are given in tables in FIG. 11. For nuclear segmentation, feature-nets that were trained in a pixel-wise and deep watershed fashion were included for comparison. For all benchmarks, objects smaller than 100 pixels were removed from the ground truth and prediction masks prior to benchmarking.

FIG. 11. Segmentation benchmarks for deep learning segmentation models for fluorescent nuclear images. The RetinaMask approach provided a mild improvement over pixel-wise and deep watershed approaches to segmentation with feature-nets. This improvement allowed for more accurate cell lineage construction. Benchmarking of cytoplasm segmentation models was performed on brightfield images.

Model Training and Post Processing for the Cell Tracking Deep Learning Model.

A hybrid convolutional/recurrent deep learning model was used for identifying whether an existing track of cells and a candidate cell were the same, different, or had a mother daughter relationship. The architecture is described above in the example. The cell tracking deep learning model was trained using stochastic gradient descent with momentum. The following parameters were used for training: a batch size of 128, learning rate of 0.01, momentum of 0.9, and learning rate decay of 0.99; the model was trained for 10 epochs, with each epoch including about 800,000 examples. For post processing, the lineage graphs were examined to identify and remove false division events. A false division event was classified as divisions in a lineage with only one mother-daughter pair and within 9 frames of another division.

Grid Search for Hyperparameter Optimization.

The cell tracking framework contained several hyperparameters including the birth parameter (b), the death parameter (d), division threshold (div), and the number of frames (f) extracted for each track. A grid search to find the optimal values for these hyperparameters. Candidate values for each hyperparameter (b—0.9, 0.95, 0.99, d—0.9, 0.95, 0.99, div—0.9, 0.95, 0.99, f—3, 5, 7, 9). The grid search was conducted in parallel by submitting Jupyter notebooks as Jobs in a Kubernetes cluster. The grid search revealed the optimal values were b=0.99, d=0.99, div=0.9, and f=7.

Cell Tracking Benchmarking.

In addition to using the ISBI executable to benchmark our cell tracker, a graph-based approach was developed to benchmark cell divisions. This approach treated the ground truth and predicted lineages as a graph, with each cell at each time point being a node. The intersection over union was used to link nodes in the ground truth and predicted graphs as being the same cell. All nodes of degree >2 were identified as cell division events; using this information, the number of true positive, false positive, and false negative detections were detected.

Figure 12A:
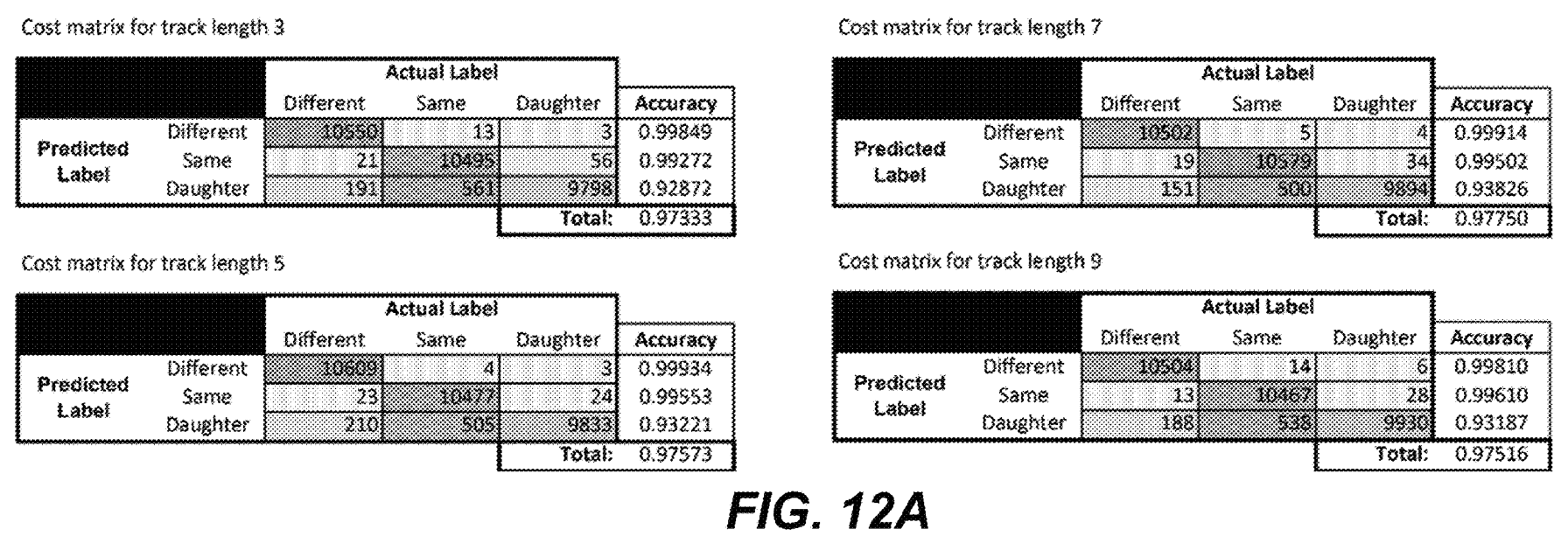
Figures 12B, 12C:
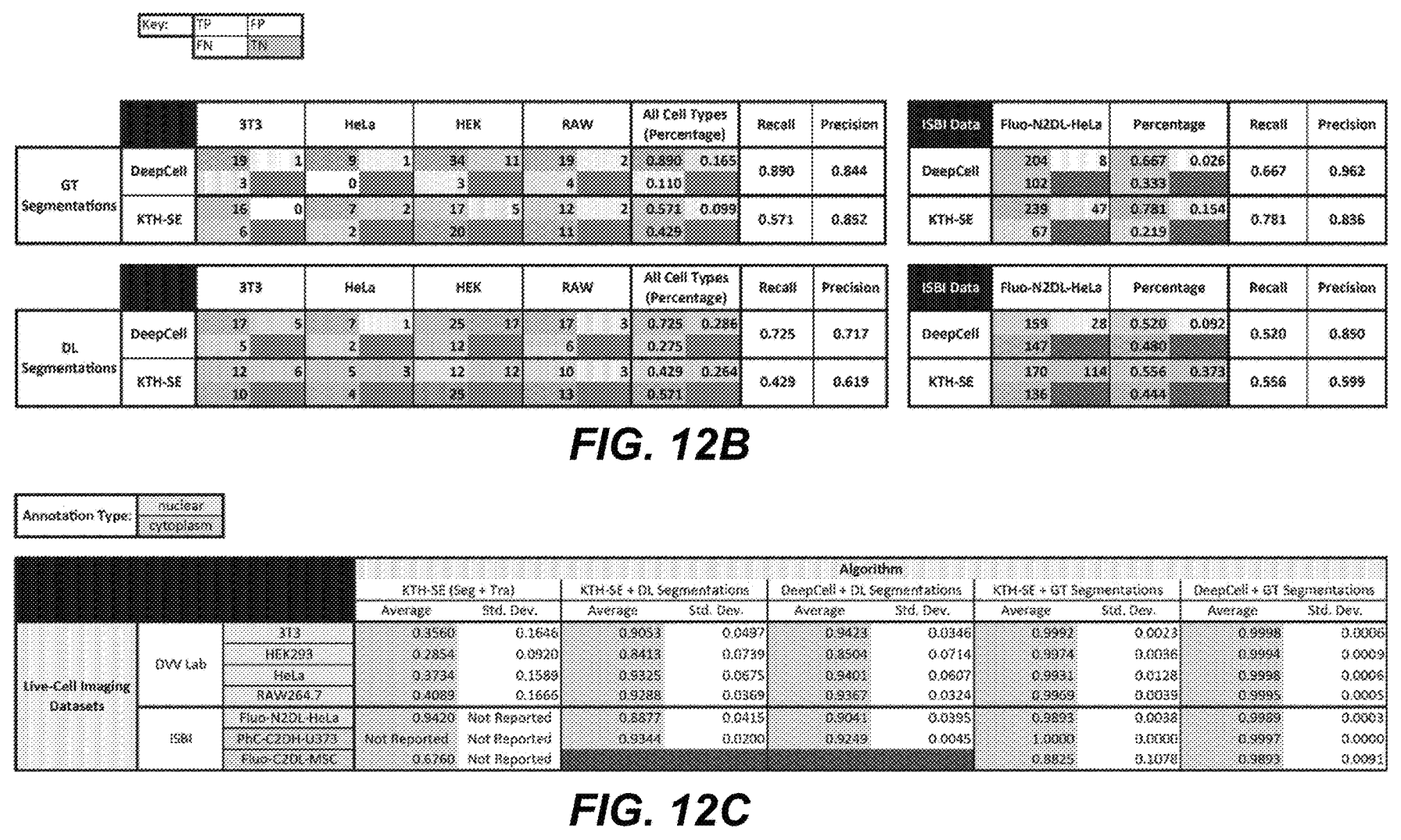

FIGS. 12A-12C. Optimization and benchmarking of a deep learning-based cell tracker. FIG. 12A. A hyperparameter search reveals that a track length of 7 frames provided optimal performance. The most common error type was misclassifying two cells that are the same as having a mother-daughter relationship. FIG. 12B. Recall and precision for cell division detection on our nuclear data as well as nuclear data from the ISBI cell tracking challenge. The performance of a Viterbi-based algorithm (KTH-SE) as well as the performance of the deep learning approach of this example were evaluated. FIG. 12C. ISBI graph metric performance of a Viterbi-based algorithm and the deep learning approach of this example on nuclear and cytoplasmic data. The bulk of the performance boost from deep learning was due to more accurate cell detection with respect to the testing dataset. Fluorescent cytoplasmic data was not benchmarked due to poor segmentations.

Caliban Implementation.

A desktop version of Caliban was implemented in Python and can be run from a Docker container.

Instructions for Crowdsourced Dataset Annotation.

The crowdsourced data annotation was performed on the Figure Eight platform. The instructions given to annotators, which include common error types, are included below.

Annotation Instructions

Nuclear Time-Lapse Cell Annotation

Overview: In this task you will be asked to individually label cells in frames of a microscopy video.

Background: The research group is in the process of writing a computer program to automatically identify and track the movement of individual cells in microscope images. To help us do this, we are asking you to help create annotated datasets where single cells are manually identified. We can then feed this into the computer program to teach it how to accurately identify cells by itself. The program developed using the data you are annotating will be used in other research laboratories to study a range of topics, including viruses and cancer cells. The software we create is only as good as the data used to create it, so accuracy in your annotations is extremely important.

Figure 13:
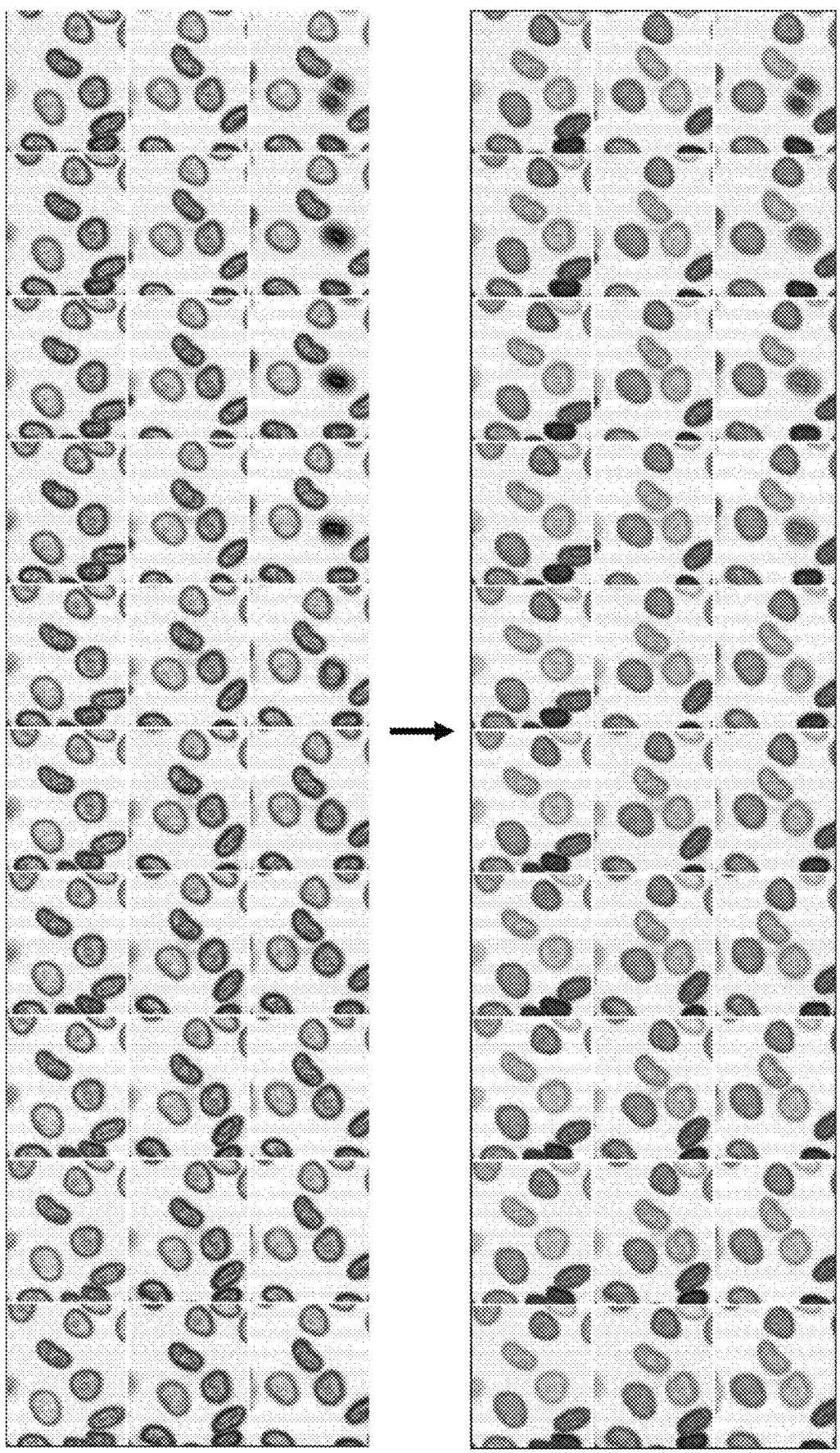
FIG. 13. Example images of nuclear annotation and annotated images.

In this job, each image includes a sequence of snapshots in time, ordered from left to right, top to bottom. Every image in this sequence needs to be annotated. An example of what the image should look like before and after your annotation is shown in FIG. 13.

Annotation Instructions

You should stick to the following rules when labelling cells (further explanations are provided below).

Do.

Label every cell in a frame with a different color

Use the same color for the same cell across different frames

Give new cells new colors, and never reuse the colors of cells that have disappeared Ignore very small objects and cells (or cell-like objects) with unclear boundaries Color to the cell boundary without going outside of the lines Separate touching cells by using different colors When a cell splits in two, label the two new cells with different colors to each other, and different colors to the original cell Remember: Once a cell divides, there will always be two cells (the cell won't recombine) and they should be labelled as such Scroll all the way across an Image to ensure cell are colored in all frames Check for completion before submitting. Only complete judgments will be accepted.

Don't.

Miss cells, leaving them uncolored

Mistake artifacts for cells

Color tiny dots (debris), these are not cells

Continue to use the same color if a cell splits in two

One good strategy to use would be to start from a specific region and follow one cell at a time across all the frames. After the first cell is colored the same across all the frames it is present in, go back and choose a neighboring one. Continue doing this to build up to the entire frame, one cell at a time (never reuse colors for different cells, even if the cell disappears before the end of the frames).

Annotation Technique

Zoom in on a frame and use the brush tool to outline the cell and fill in the middle, changing the brush size using the slider. Use the eraser tool to correct mistakes as shown in FIG.

EXAMPLES

Figure 15:
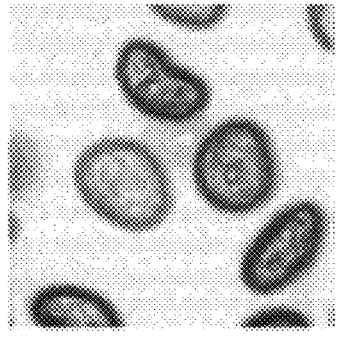
FIG. 15. Example nuclear annotations for edge cells, touching cells, and blurry cells. Artifacts should not be colored.

FIG. 15. Example nuclear annotations for edge cells, touching cells, and blurry cells. Artifacts should not be colored.

FIG. 16. Example nuclear annotations of normal cells and dividing/disappearing cells.

Cytoplasm Time-Lapse Cell Annotation

Overview: In this task you will be asked to individually label cells in frames of a microscopy video.

Background: The research group is in the process of writing a computer program to automatically identify and track the movement of individual cells in microscope images. To help us do this, we are asking you to help create annotated datasets where single cells are manually identified. We can then feed this into the computer program to teach it how to accurately identify cells by itself. The program developed using the data you are annotating will be used in other research laboratories to study a range of topics, including viruses and cancer cells. The software we create is only as good as the data used to create it, so accuracy in your annotations is extremely important.

Figure 17:
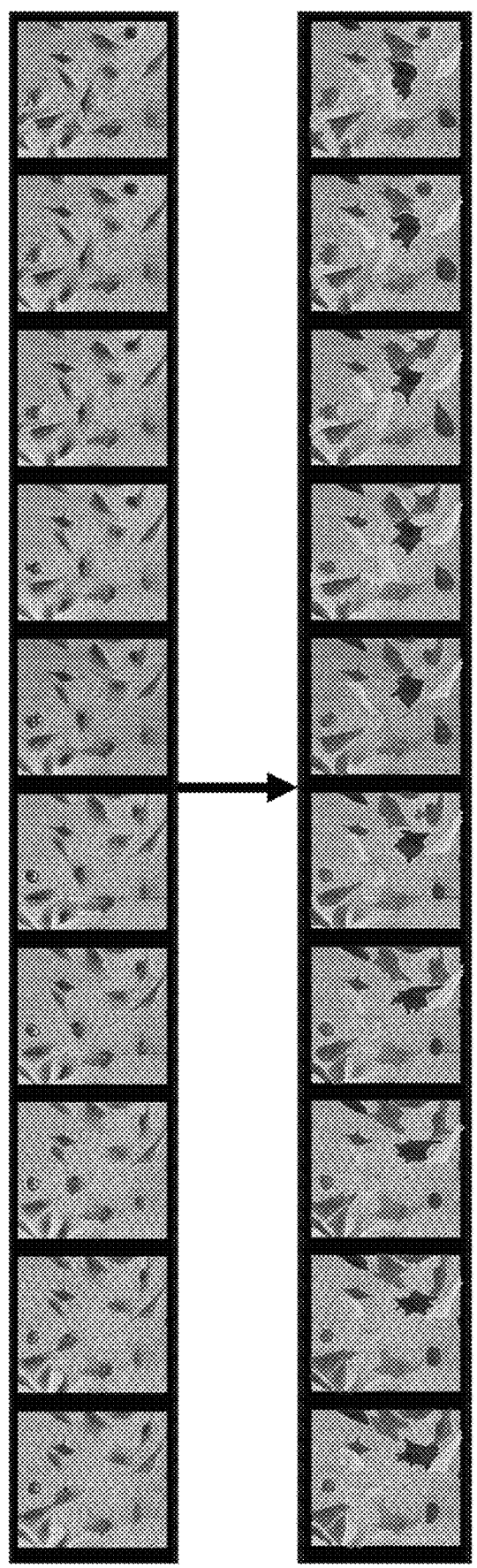
FIG. 17. Example images of cell annotation and annotated images.

In this job, each image includes of a sequence of snapshots in time, ordered from left to right. Every image in this sequence needs to be annotated. An example of what the image should look like before and after your annotation is shown in FIG. 17.

Annotation Instructions

You should stick to the following rules when labelling cells (further explanations are provided below).

Do.

Label every cell in a frame with a different color

Use the same color for the same cell across different frames

Give new cells new colors, and never reuse the colors of cells that have disappeared Ignore very small objects and cells (or cell-like objects) with unclear boundaries Color to the cell boundary without going outside of the lines Separate touching cells by using different colors Scroll all the way across an Image to ensure cell are colored in all frames Check for completion before submitting. Only complete judgments will be accepted.

Don't.

Miss cells, leaving them uncolored

Mistake artifacts for cells

One good strategy to use would be to start from a specific region and follow one cell at a time across all the frames. After the first cell is colored the same across all the frames it is present in, go back and choose a neighboring one. Continue doing this to build up to the entire frame, one cell at a time (never reuse colors, even if the cell disappears before the end of the frames).

Annotation Technique

Zoom in on a frame and use the brush tool to outline the cell and fill in the middle, changing the brush size using the slider. Use the eraser tool to correct mistakes. It is okay if you color in the black edges between images, but NOT if the annotation crosses over into the next image.

EXAMPLES

FIG. 18. Example cell annotations of cells of different shapes.

Figure 19:
FIG. 19. Example cell annotations of overlapping cells.

FIG. 19. Example cell annotations of overlapping cells.

Figure 20:
FIG. 20. Example cell annotations of one cells and separate cells.

FIG. 20. Example cell annotations of one cells and separate cells.

Figure 21:
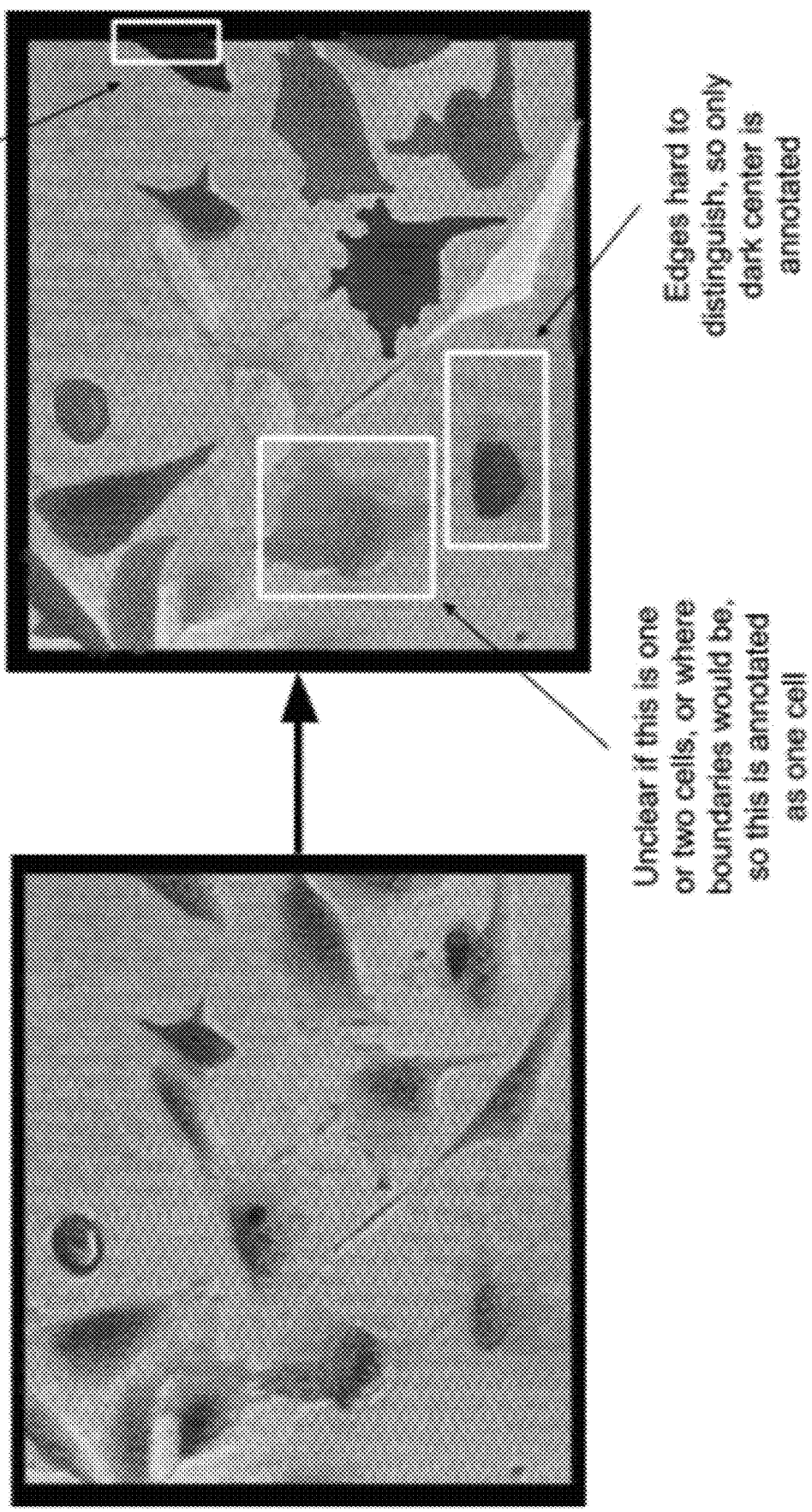
FIG. 21. Example cell annotations where whether there should be one cell or two cells is unclear, wherein the edges of a cell are hard to distinguish, and where a cell is on an edge of the image.

FIG. 21. Example cell annotations where whether there should be one cell or two cells is unclear, wherein the edges of a cell are hard to distinguish, and where a cell is on an edge of the image.

Data Availability

All of the data used in this paper and the associated annotations can be accessed at deepcell.org/data or at github.com/vanvalenlab through the datasets module; the content of each of which is incorporated herein by reference in its entirety.

Code Availability

A persistent deployment of the software described here can be accessed at deepcell.org, the content of which is incorporated herein by reference in its entirety. All source code for cell tracking is available in the DeepCell repository at github.com/vanvalenlab/deepcell-tf, the content of which is incorporated herein by reference in its entirety. Detailed instructions are available at deepcell.readthedocs.io/, the content of which is incorporated herein by reference in its entirety.

Discussion

Live-cell imaging is a transformative technology. Live-cell imaging has led to numerous insights into the behavior of single cells and will continue to do so for many years to come as imaging and reporter technologies evolve. While the adoption of this method has typically been limited to labs with the computational expertise single cell analysis of these data demands, the arrival of deep learning can change this landscape. With suitable architectures and deployment tools, deep learning can turn single cell image segmentation into a data annotation problem. With the work present here, the same can be said for cell tracking. The applications of this technology are numerous, as it enables high throughput studies of cell signaling, cell lineage experiments, and potentially dynamic live-cell imaging-based screens of pharmaceutical compounds.

While deep learning methods are powerful, deep learning methods are not without limitations. Accurate detection is still needed to cell tracking performance, and deep learning-based segmentation methods still make impactful errors as cells become more crowded. This issue may be mitigated as more expansive sets of data are annotated, and as segmentation methods that use spatiotemporal information to inform segmentation decisions come online. This method, and all supervised machine learning methods, is limited by the training data that empower it. The training dataset generated and used in this example contained less than 1000 cell divisions; division detection can become more accurate with additional annotated data. The deep learning-enabled cell tracker can be trained with training data that includes images of cells having markedly change cell phenotypes or fates (e.g., apoptosis or differentiation). The model disclosed in this example can be combined with a human-in-the-loop approach to enhance future annotation efforts. The dataset used in this example included 2D images collected with widefield imaging. The model can be trained with 3D data over time periods (e.g., long time periods) collected using modern confocal and light sheet microscopes. For example, the approach can be adapted to these data by using 3D deep learning sub-models with appropriate annotation task.

Lastly, the example has centered on live-cell imaging of mammalian cell lines. While these are important model systems for understanding human biology, and the potential of deep learning applications to these systems has for improving human health is substantial, they vastly under sample the diversity of life. Much of the understanding of living systems comes from basic science explorations of bacteria, yeast, and archaea. Live-cell imaging and single cell analysis are powerful methods for these systems; the approach of this example can be applied to these systems.

Example 2

Dynamic Allocation of Computational Resources for Deep Learning-Enabled Cellular Image Analysis with Kubernetes Abstract Deep learning is transforming the ability of life scientists to extract information from images. These techniques have better accuracy than conventional approaches and enable previously impossible analyses. As the capability of deep learning methods expands, they are increasingly being applied to large imaging datasets. The computational demands of deep learning present a significant barrier to large-scale image analysis. To meet this challenge, this example describes DeepCell 2.0, a platform/software developed for deploying deep learning models on large imaging datasets (e.g., greater than $10^5$-megapixel images) in the cloud. This software enables the turnkey deployment of a Kubernetes cluster on all commonly used operating systems. By using a microservice architecture, the platform matches computational operations with their hardware requirements to reduce operating costs. Further, the platform scales computational resources to meet demand, drastically reducing the time necessary for analysis of large datasets. A thorough analysis of costs demonstrates that cloud computing is economically competitive for this application. By treating hardware infrastructure as software, this example foreshadows a new generation of software packages for biology in which computational resources are a dynamically allocated resource.

Introduction

Recent advances in imaging—both in optics and in fluorescent probes—are transforming the study of living matter. It is now possible to study cellular function on length scales that span from single molecules to whole organisms with imaging. Concurrent with these advances have come drastic improvements in our ability to computationally extract information from images. Chief among these new tools is deep learning, a set of machine learning tools that can learn effective representation from data in a supervised or unsupervised manner. These methods can be more accurate than prior approaches and can automate the image classification and image segmentation tasks that have formed the bedrock of single-cell analysis. Their ability to extract latent information from images has also enabled previously unforeseen analyses of cellular function and behavior. Applications include interpreting imaging-based screens (image classification), quantifying the behavior of individual immune cells in the tumor microenvironment (image segmentation), improving the resolution of images (extracting latent information), and predicting fluorescence images directly from bright field images (extracting latent information).

As the capabilities of deep learning grow, these models are increasingly being used throughout the life sciences on imaging datasets both small and large. This new reality presents several challenges. Deep learning is a data- and compute-intensive method; new applications often require new training datasets, while developing new deep learning models requires specialized hardware. As these challenges are being met, the remaining challenges increasingly revolve around deployment and scale. Timely inference of deep learning models requires hardware acceleration via graphical processing units (GPUs). However, complete analysis pipelines can require both deep learning and conventional computer-vision operations. This constraint means that the single-workstation model for analysis is inefficient. Further, modern imaging experiments can produce large (e.g., $10^5$-megapixel images) datasets; the turnaround time for analysis is increasingly becoming a bottleneck for imaging-based discovery.

To meet this challenge, DeepCell 2.0, a cloud computing platform for deploying deep learning models on imaging datasets was developed. While the target application of this software is single-cell analysis of large live-cell imaging and cell atlas datasets, DeepCell 2.0 represents a fundamental shift from how software for biological data analysis is traditionally written. Rather than viewing hardware as a fixed resource, hardware is instead viewed as a resource that can be allocated dynamically. In this paradigm, the computational resources requested can scale with the dataset size so that the analysis time remains small even for large datasets. The tradeoff for this feature is that the marginal cost of compute resources is no longer fixed, as is the case for on-premise computing. Scaling computing power with demand while minimizing cost is a new constraint for scientific software. An equivalence between web traffic and units of data was drawn for scalable and accelerated data analysis.

While some advances described in this example parallel recent trends in cloud-native software development, adaptations were necessary to tailor the software to the needs of life scientists. One important adaptation was decentralization. Control of the underlying hardware for most cloud-native software is centralized; one organization manages software deployment while users interact with the software through web browsers. While this model can significantly enhance the user experience when applied to data analysis, as has been the case with BLAST and similar bioinformatics software, there are limitations. For example, analysis of large datasets by single users can impair responsiveness for other users. Further, this model requires users to share their data with the managing organization, raising issues of data ownership and privacy. These concerns become even more pressing in a world where data are becoming increasingly intertwined with software. DeepCell 2.0 can circumvent these issues by enabling decentralized control. On-premise computing is the classic model for decentralized control of hardware, but it lacks the scalability of cloud computing. DeepCell 2.0 can have the best of both worlds by treating the hardware configuration itself as software. This abstraction, which can be enabled by the Kubernetes engine, can allow users to configure and manage their own software deployments and retain control of their data. The tradeoff for this feature is that users pay their own hardware costs. As described below, this cost is manageable.

Software Architecture

Figure 22A:
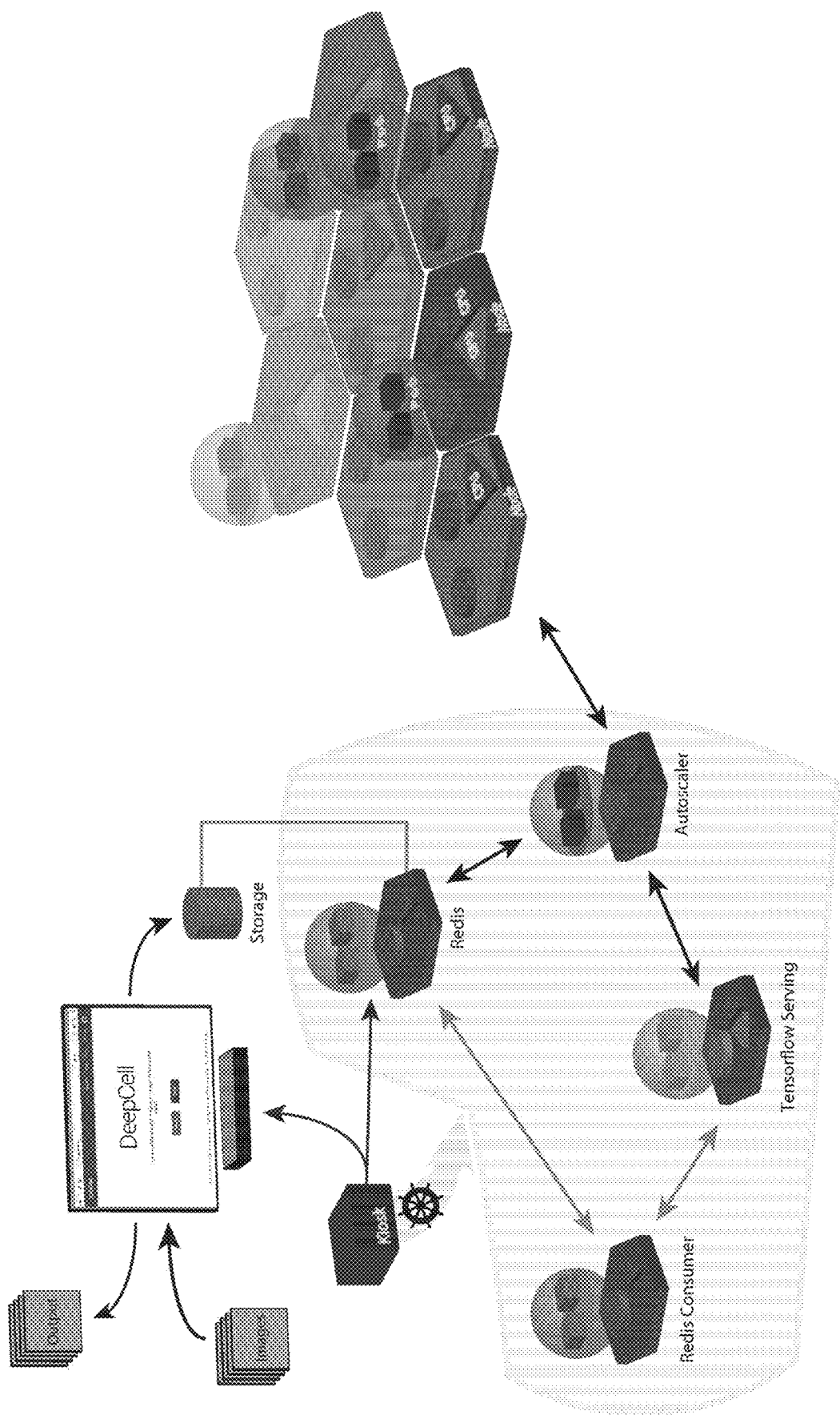
FIGS. 22A-22B. Cloud computing enables large-scale cellular image analysis with deep learning.

DeepCell 2.0 was developed to operate on Google Cloud using the Google Kubernetes Engine (GKE); a full description of the software architecture is shown in FIG. 22A. Some of the features highlighted are enabled by or are unique to deep learning and cloud computing.

Figure 22B:
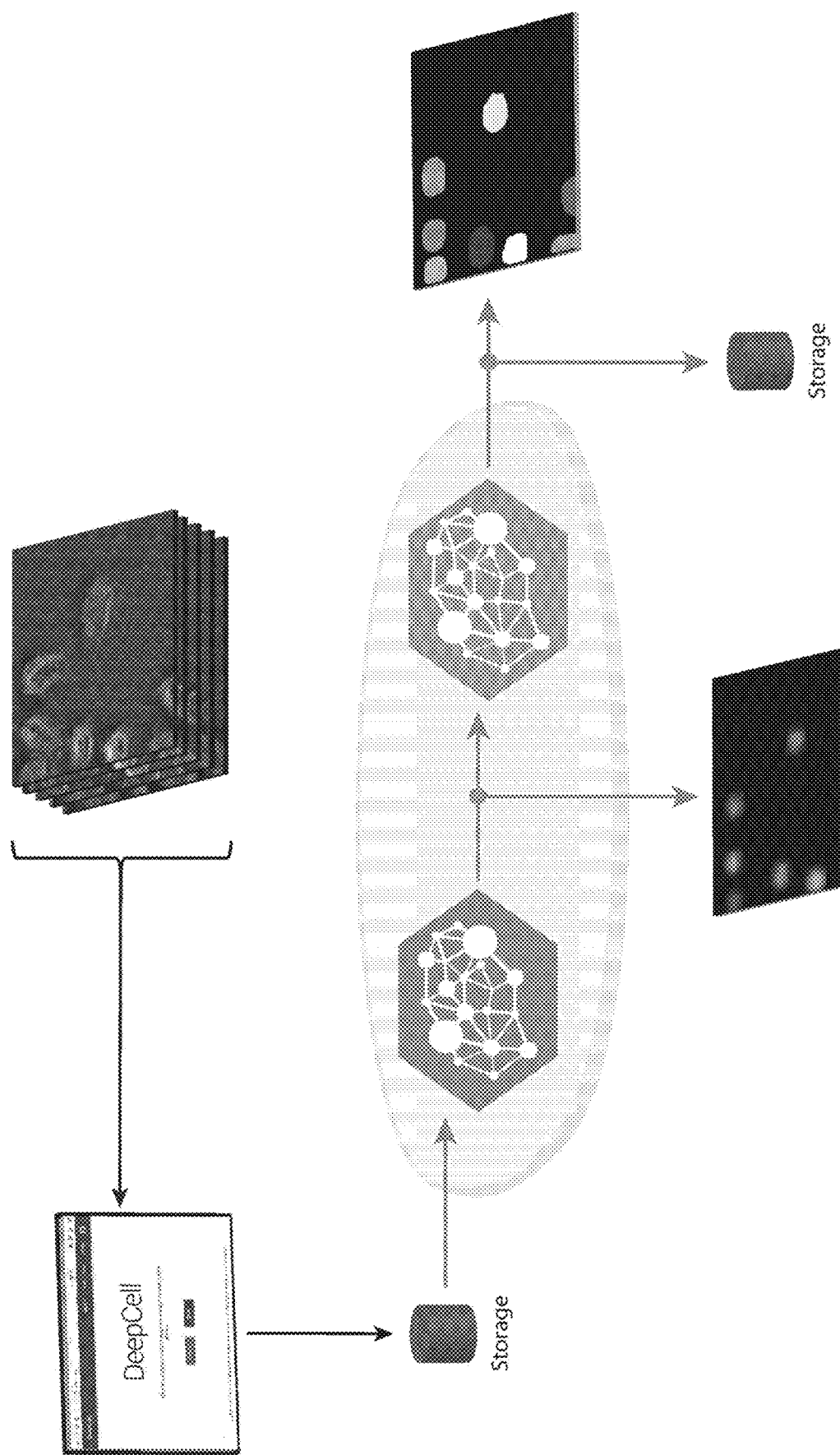

FIGS. 22A-22B. Cloud computing enables large-scale cellular image analysis with deep learning. FIG. 22A. The software architecture of DeepCell 2.0. Blue lines signify flow of data while black lines signify flow of compute resources. Users begin by starting the kiosk container and specifying the parameters (user credentials, GPU type, etc.) of the cloud deployment. These parameters are used by Kubernetes to construct the cloud deployment and to assign pods (collections of containers) to their appropriate node. Some nodes can host multiple pods if appropriate. Trained models are stored in a cloud bucket and are available for inference. Uploaded data are placed in a cloud bucket, triggering the creation of an entry into a Redis queue. A data consumer communicates with the database and manages the analysis of a single data item. This communication includes submitting data to a deep learning model server and applying conventional computer-vision operations. Distinct data consumers can be written for specific workflows. Processed data are downloaded for further analysis. A custom 0 module monitors the Redis database to trigger 0-to-1 scaling of GPU nodes and TensorFlow serving. Once active, Kubernetes' innate horizontal pod autoscaling capability monitors GPU utilization and dynamically adjusts the number of compute nodes and active pods to meet the data-analysis demand. FIG. 22B. By hosting models on a centralized model server, DeepCell 2.0 allows for novel analysis workflows that require chaining multiple models. Here, DeepCell 2.0 used a model that predicts images of cell nuclei from brightfield images and fed the output to a model that performs nuclear segmentation. This workflow removes the need for a fluorescent nuclear marker in live-cell imaging experiments, while the software infrastructure allows for scalable deployment on large imaging datasets.

Containerization.

To create stability and scalability, the software was separated into separate modules: the kiosk configures and initiates the cloud deployment, the autoscaler scales compute resources, the front end is the web-based user interface, Redis is a database that manages incoming data, the Redis consumer shuttles data to the appropriate task and performs conventional data-processing operations, the training module trains new models with training data, and TensorFlow-serving processes data with deep learning models. Each of these modules lives within a Docker container. The design principle of one process per container was used to enhance security and resilience while accelerating the development lifecycle.

Cluster and Container Orchestration Through Kubernetes.

DeepCell 2.0 uses the Kubernetes engine and its associated package manager, Helm, to manage both compute resources and deployment of the containers that comprise DeepCell 2.0. There are several key functions: organizing containers into functional units called pods (in the DeepCell 2.0 architecture, most pods include one container), requisitioning compute nodes (both with and without GPUs) from the cloud, assigning the appropriate pods to each node, scaling the number of nodes to meet demand, and allowing for internal communication between containers within the deployment. Kubernetes can perform some or all of the key functions This architecture marshals significantly more compute resources for large analysis tasks than is possible from a single machine image.

Infrastructure as Code.

Cloud computing requires users to specify the configuration of the compute resources requested from the cloud. Details of this configuration for each compute node include CPU type, memory size, and the presence of a hardware accelerator. The ability to simultaneously requisition different types of nodes provides the opportunity to efficiently match hardware resources with the compute task. While cloud-computing platforms provide a user interface for configuring and managing a deployment, DeepCell 2.0 uses an infrastructure as code paradigm for dynamically configuring the compute resources requisitioned from the cloud. In this paradigm, the configurations of each type of compute node are stored in yaml files. Users can change details about the deployment (e.g. what GPU type to use) through a graphical user interface; these changes are reflected in the updated yaml files. The yaml files are read by the Kubernetes engine to determine the types of compute nodes that are available for the cloud deployment. Infrastructure as code also allows sharing all aspects of DeepCell 2.0—both the source code and the requisite hardware—with end users.

Pre-Emptible Instances.

To decrease the cost of analyzing large datasets, DeepCell 2.0 can be configured to request pre-emptible GPU instances. While pre-emptible instances can be interrupted, they are 4 times cheaper than regular instances and are suitable for large inference tasks.

Resource Allocation.

Complete computer-vision solutions for cellular image analysis can require a hybrid of conventional and deep learning methods to achieve a production-ready solution. In DeepCell 2.0, the conventional and deep learning operations were separated so that they run on different nodes, which allows using hardware acceleration for deep learning while ensuring conventional operations are only run on less expensive hardware.

Horizontal Pod Autoscaling.

DeepCell 2.0 utilizes horizontal pod autoscaling to scale the Kubernetes cluster to meet analysis demand. The scaling policy is based on the utilization of our most expensive resource, GPU nodes. This policy requisitions additional GPU nodes to decrease their collective utilization while, at the same time, increasing the number of consumers to drive the utilization of existing GPU nodes. The full policy is described in the Additional Information section of this example.

Logging and Monitoring.

DeepCell 2.0 can use Prometheus to monitor cluster performance metrics and the ELK stack (Elasticsearch, Logstash, and Kibana) to enable logging throughout the Kubernetes cluster. Robust logging facilitates development, while metric collection provides the real-time data needed for horizontal pod autoscaling. Additionally, these metrics enable extensive benchmarking of cluster performance and cost.

Inter-Service Communication with gRPC.

Because large amounts of imaging data are shuttled between services during analysis tasks, communication between services needs to be efficient. While REST APIs are common communication mechanisms that present data in a human readable format, the need for interpretability can reduce the efficiency of data transfer. Because DeepCell 2.0 has been designed to maximize data throughput, gRPC can be used as an alternative means of communicating between services.

Continuous Integration/Continuous Deployment.

Travis CI can be used to implement continuous integration/continuous deployment. This tool allows changes to the code base to be reflected in a deployment provided that the modifications pass existing unit tests. This strategy enables developers to rapidly implement new features and to deploy novel workflows in DeepCell 2.0.

Algorithmic Modularization.

One advantage of deep learning is the ability to package algorithmic functionality into deployable units. Deep learning models with distinct functionalities, such as extracting latent information or performing image segmentation, can be treated as distinct computational modules. The presence of these models within the same ecosystem allows for novel analysis workflows that involve chaining different models together (FIG. 22B). New algorithms can be added to the ecosystem by exporting the underlying deep learning model to a cloud bucket. The scalability inherent in DeepCell 2.0 allows for deployment of these workflows on large imaging datasets.

User Interface.

A simple drag-and-drop user interface was created from React, Babel, and Webpack, which enables users to process data through a web browser. Trained models are stored in a cloud bucket where they can be accessed for inference. Processed data can be downloaded for further analysis in programs like Fiji or interacted with in Jupyter notebooks. Alternatively, users can submit data to the Kubernetes cluster directly using Python code.

Benchmarking

The three factors that predominantly control analysis speed are data transfer rates, model inference speed, and cluster size. With infinite compute resources, the analysis speed will be bottlenecked by how quickly data can be moved into the cloud; a 100 Gbps (12,500 MB/s) ethernet connection translates up to 12,500 images per second (assuming each image contains 1 million pixels and has 8-bit precision). This rate decreases for slower connections but is markedly faster than the inference speed offered by a single GPU (around 6 megapixel-scale images per second on NVIDIA V100 GPUs). The large image sizes (e.g., greater than 1 megapixel) common in biology preclude extensive batching during inference due to memory constraints. Model inference speed can be effectively increased by increasing the number of GPUs performing inference. The relationship between data transfer, model inference, and cluster size is described further in the Additional Information section of this example.

To test DeepCell 2.0's performance, an extensive set of benchmarking studies were carried out (FIGS. 23A-23C); the full dataset is included in the Additional Information section of this example. To perform benchmarking, a benchmarking pod that generated zip files containing 100 images and submitted them for processing at a set rate was created. By changing this rate, different upload speeds were simulated. Our image-analysis routine can include performing single-cell segmentation using a deep watershed approach, which requires both deep learning and conventional processing steps and reveals the relative impact of different computational operations on inference speed and cost. While scalability was benchmarked using the deep watershed approach, this software can and has been adapted to deploy a variety of deep learning methods, including RetinaNet and Mask-RCNN, on biological imaging data. During benchmarking, the maximum number of images processed (10K, 100K, 1M) and the maximum number of GPUs (1, 4, and 8) were varied. The amount and type of each computational resource in service, the amount of time required to perform each step, and the total cost incurred during deployment were tracked.

Figure 23A:
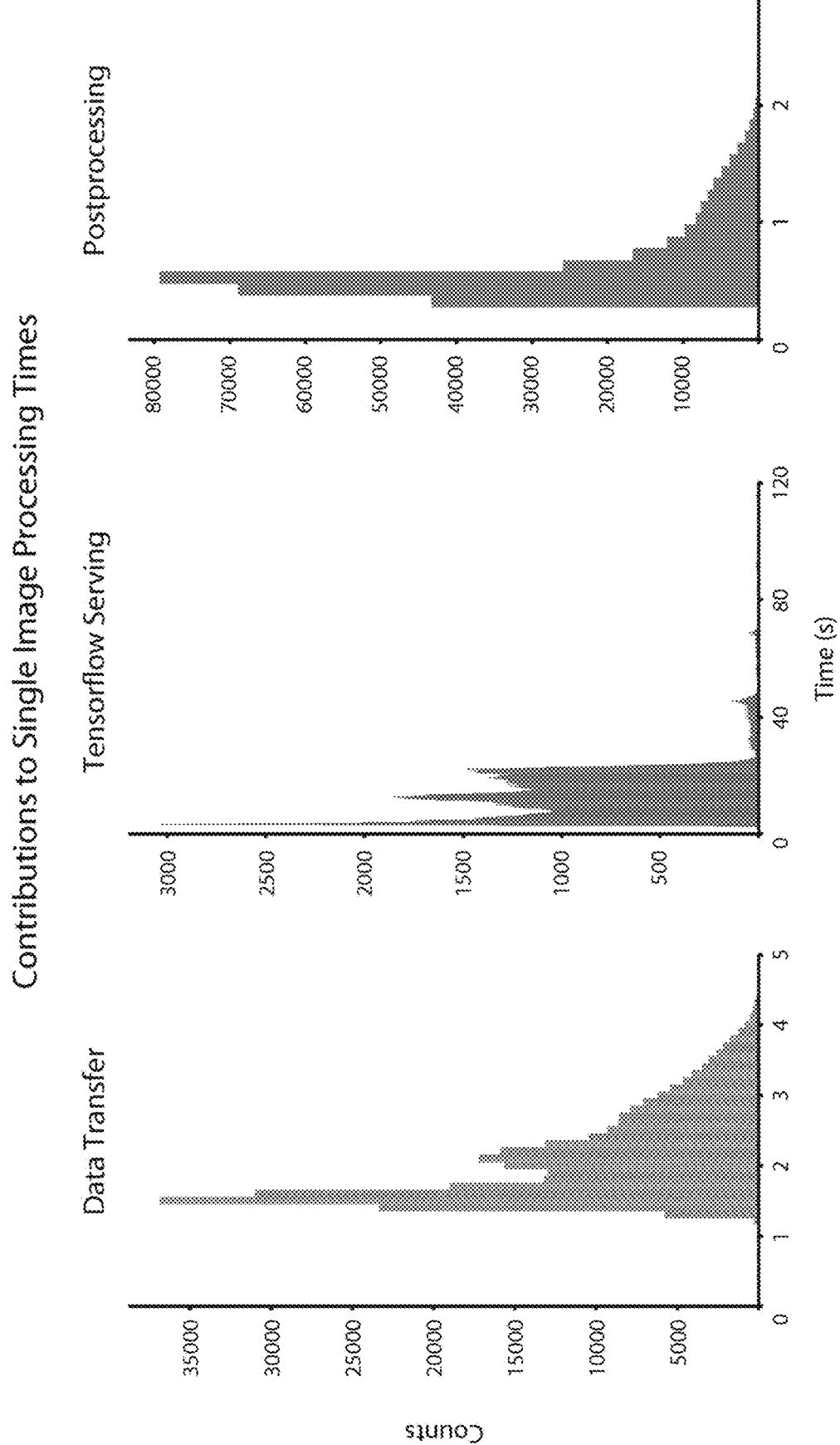
FIGS. 23A-23C. Benchmarking of DeepCell 2.0.
Figure 23C:
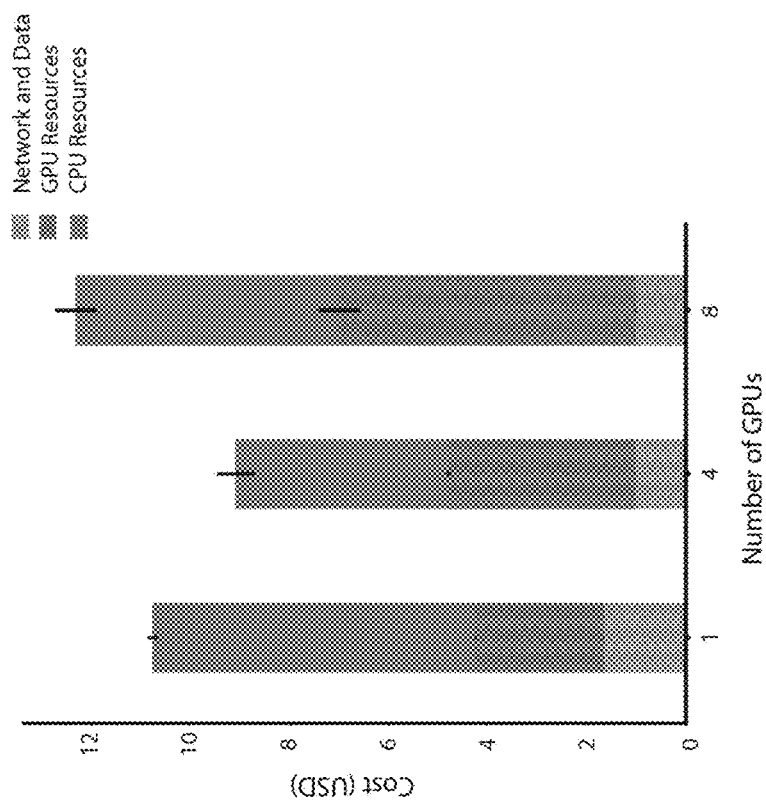
Figure 23B:
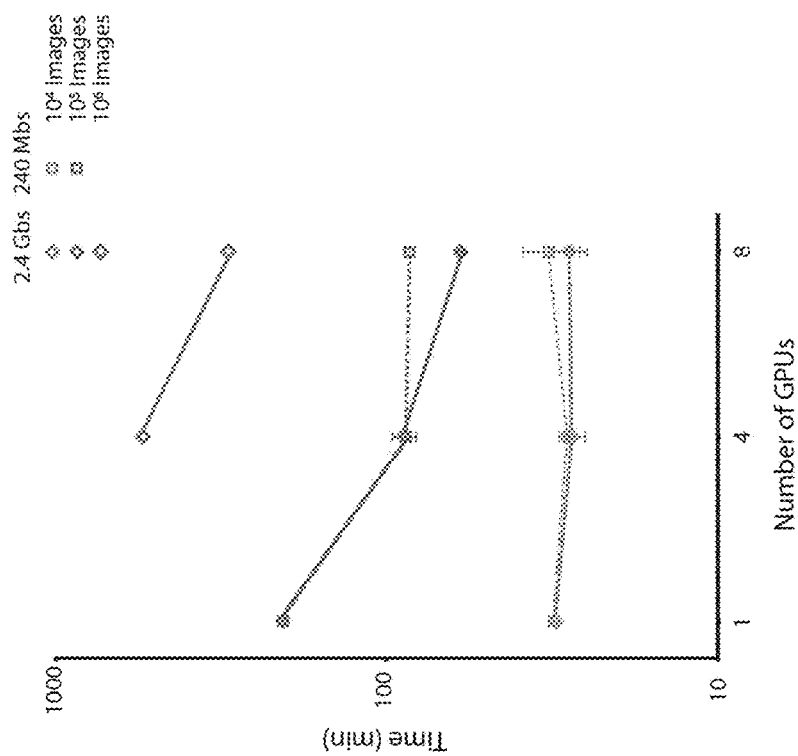

FIGS. 23A-23C. Benchmarking of DeepCell 2.0. FIG. 23A. Contributions of data transfer, TensorFlow-serving latency, and post processing to the total runtime for individual images. These histograms denote the time required for each process during benchmarking for a 4 GPU cluster with a 240 Mbps upload speed. For the tested model, latency from TensorFlow serving dominates the total processing time. Oscillations with a period of about 20 seconds arise from restarts. Despite considerable response time per-image, the high throughput of TensorFlow serving enables large-scale image analysis. FIG. 23B. Total processing time for large imaging datasets. By scaling the cluster size dynamically to meet the data analysis demand, DeepCell 2.0 significantly reduces the time necessary to process large imaging datasets. Datasets with $10^6$ megapixel-scale images can be processed in several hours. An analysis of the tradeoff between cluster size and upload speed appears in the Additional Information section of this example. Error bars in FIGS. 23B and 23C represent the standard deviation. FIG. 23C. Cost as a function of cluster size. While the cost of GPU nodes is considerable, the cost can be mitigated by using pre-emptible instances for GPU inference. Negligible differences in cost between small and large clusters to analyze large imaging datasets were seen. Details of the benchmarking calculations appear in the Additional Information section of this example.

Overall, this benchmarking demonstrated that cloud computing can enable rapid and cost-effective large-scale cellular image analysis with deep learning (FIGS. 23A-23C). For upload speeds common at academic institutions (about 250 Mbps), datasets including $10^5$ 1-megapixel images can be analyzed with a typical deep learning model in about 90 min for about $10 with a 4-GPU cluster. This cost is dominated by the price of GPU computing, which is anticipated to decrease with time as specialized inference hardware becomes available in the cloud. Surprisingly, a financial advantage for recruiting several GPUs to work on large tasks was found; this advantage may arise because increased speed may decrease the time that non-GPU resources are online. With larger clusters (>8 GPUs), one can analyze datasets of greater than $10^6$ megapixel-scale images on the timescale of hours.

Additional Information

Cell Lines and Culturing.

The mammalian cell lines NIH-3T3, HeLa-S3, HEK 293, and RAW 264.7 were used to collect training data for nuclear segmentation, and the cell lines NIH-3T3 and RAW 264.7 were used to collect training data for augmented microscopy. All cell lines were acquired from ATCC. The cells had not been authenticated and were not tested for *mycoplasma* contamination.

Mammalian cells were cultured in Dulbecco's modified Eagle's medium (DMEM, Invitrogen or Caisson) supplemented with 2 mM L-glutamine (Gibco), 100 U/mL penicillin, 100 µg/mL streptomycin (Gibco or Caisson), and either 10% fetal bovine serum (Omega Scientific or Thermo Fisher; HeLa-S3 cells) or 10% calf serum (Colorado Serum Company; NIH-3T3 cells). Cells were incubated at 37° C. in a humidified 5% $CO_2$ atmosphere. When 70-80% confluent, cells were passaged and seeded onto fibronectin-coated, glass-bottom, 96-well plates (Thermo Fisher) at 10,000-20,000 cells/well. Seeded cells were incubated for 1-2 hour to allow cells to adhere to the bottom of the well before imaging.

Collection of Training Data.

For fluorescence nuclear imaging, mammalian cells were seeded onto fibronectin (Sigma, 10 mg/mL) coated glass bottom 96-well plates (Nunc) and allowed to attach overnight. Medium was removed and replaced with imaging medium (FluoroBrite DMEM (Invitrogen) supplemented with 10 mM Hepes pH 7.4, 1% fetal bovine serum, 2 mM L-glutamine) at least 1 hour before imaging. Cells without a genetically encoded nuclear marker were incubated with 50 ng/mL Hoechst 33342 (Sigma) before imaging. Cells were imaged with either a Nikon Ti-E or Nikon Ti2 fluorescence microscope with environmental control (37° C., 5% $CO_2$) and controlled by Micro-Manager or Nikon Elements. Images were acquired with a 20× objective (40× for RAW 264.7 cells) and either an Andor Neo 5.5 CMOS camera with 2×2 binning or a Photometrics Prime 95B CMOS camera with 2×2 binning. All data were scaled so that pixels had the same physical dimension prior to training.

For the augmented microscopy training dataset, which included brightfield and fluorescence nuclear images, cells were imaged on a Nikon Eclipse Ti-2 fluorescence microscope with environmental control (37° C., 5% $CO_2$) at 20× and 40× for NIH-3T3 and RAW264.7 cells, respectively. Nuclei were labeled with Hoescht 33342. Each dataset was generated by collecting a fluorescence image in the focal plane as well as a z-stack of phase images (0.25 µm slices, ±7.5 µm from focal center). Images were collected on a Photometrics Prime 95B CMOS camera with no binning.

Autoscaling Policy.

Novel scaling policies for the Redis consumer and TensorFlow (TF)-serving pods were developed. The TF-serving pod processes images with deep learning models, while the data-consumer pod feeds data into TF serving. The scaling of these two pods is linked, as the data-consumer pods drive utilization of the TF-serving pods. The following was observed: while data-consumer pods can bottleneck inference speed, having too many data-consumer pods present at once results in an effective "denial of service" attack on the TF-serving pods.

To optimally scale both pods, autoscaling policies used were based on GPU utilization and work demand. Because of the distributed nature of the task, horizontal pod autoscaling (more nodes) were used to scale the cluster as opposed to vertical pod autoscaling (bigger nodes). The metrics, available through Prometheus, provide the information necessary for scaling. Horizontal pod autoscaling in Kubernetes works by defining a metric and a target for a given pod. If the metric, measured over a given time period, is larger than the target, then the pod is scaled up; if it is smaller, then it is scaled down. The target number of pods is given by $$N_{pods} = N_{current\ pods} \frac{\text{metric}}{\text{target}}.$$

Typical metrics are based on resource utilization: if utilization is too high (metric greater than target), then the pod needs to be larger. If it is too low (metric smaller target), then the pod needs to smaller. For the TF-serving pod, the metric was set to be GPU utilization, which ranges from 0% to 100%, and the target to be 70%. For the data-consumer pod, the metric was as the follows.

$$\text{metric} = \begin{cases} 0 \text{ if } TF \text{ serving pods} = 0 \\ \min\left(\frac{100 - GPU \text{ utilization}}{100}, \frac{\# \text{predict keys}}{\# \text{redis consumer pods}}\right) & \text{if } \frac{\# \text{redis consumer pods}}{\# TF \text{ serving pods}} < 150. \\ \text{else } 0.135 \end{cases}$$

The target for this metric was set to be 0.15 for several reasons. First, the goal of this scaling policy is to create enough data consumers to efficiently drive the TF-serving pod; tying scaling criteria to the GPU utilization effectively achieves this goal. Second, because there are consumers of different types, care should be taken to ensure that scaling is also sensitive to the amount of work, in order to ensure that new processing tasks are assigned consumers. The work metric measures how much work has built up in the queue; if the amount of work to do is high, then the scaling policy overrides the GPU utilization-based metric to scale up the pod.

Model Architecture and Training.

The code for every model is available at github.com/deepcell-tf under the deepcell.model_zoo module, the content of which is incorporated herein by reference in its entirety. Feature-nets were used extensively in this example for benchmarking. Feature-nets are a deep learning model architecture for general-purpose image segmentation. Various feature-nets can be used for nuclear segmentation in 2D cell culture images, 3D confocal images of brain tissue, and 2D multiplexed ion beam imaging datasets. This architecture can be applied to single-cell segmentation of bacteria and yeast. One important feature of this architecture is its ability to treat the deep learning model's receptive field—the length scale over which it pays attention—as a tunable variable. Deep learning models can work best when the receptive field size is matched to the feature size of a given dataset. This intuition has been valid for both feature-nets and object detection-based approaches like Mask-RCNN (data not shown). Given the diversity in cellular morphologies across the domains of life, feature-nets can be a good starting point for cell biologists seeking to apply deep learning to new datasets.

Three models were trained for this example. The first model was a feature-net for 2D image segmentation using a deep watershed approach with a 41-pixel receptive field for benchmarking. This model was trained in a fully convolutional fashion using stochastic gradient descent with momentum of 0.9, a learning rate of 0.01, weight decay of $10^{-6}$, and an L2 regularization strength of $10^{-5}$ for 5 epochs on a NVIDIA V100 graphics card. A dataset including about 300,000 cell nuclei annotations was used for training.

For nuclear segmentation of brightfield images, two models were trained. The first of these models transforms brightfield images into nuclear images. The first model was a modified 3D feature-net with a 41-pixel receptive field where dilated max pooling layers are replaced with 2D convolutional layers with kernel size 2 and an equivalent dilation rate. This model was trained in a fully convolutional fashion for using stochastic gradient descent with momentum with a learning rate of 0.01, momentum of 0.9, weight decay of $10^{-6}$, and an L2 regularization strength of $10^{-5}$ for 5 epochs on a NVIDIA V100 graphics card. A dataset including matched brightfield image stacks and fluorescent nuclear images was used for training.

The second model for brightfield images was a modified RetinaMask model for nuclear segmentation. RetinaMask generates instance masks in a fashion similar to Mask-RCNN but uses single-shot detection like RetinaNet rather than feature proposals to identify objects. A ResNet50 backbone with the P2, P3, and P4 feature pyramid layers for object detection was used. Custom anchor sizes of 8, 16, and 32 pixels for each of these layers were used. This model was trained using the Adam optimization algorithm with a learning rate of $10^{-5}$, clip norm of 0.001, batch size of 4, and L2 regularization strength of $10^{-5}$ for 16 epochs on a NVIDIA V100 graphics card. A dataset including about 300,000 cell nuclei annotations was used for training.

Relationship Between Data Transfer Rates, Inference Speeds, and Cluster Size.

Data transfer poses a fundamental limit to how quickly data can be analyzed. A cluster that is operating efficiently processes data at the same rate that the data enter. Given a data transfer speed d and a single model with an inference speed of s, this leads to the equation $$d = N_{GPU} s,$$

where $N_{GPU}$, the number of GPUs in the cluster, is effectively the cluster size. A plot of this optimal cluster size as a function of model inference speed for various upload speeds is shown below.

Figure 24:
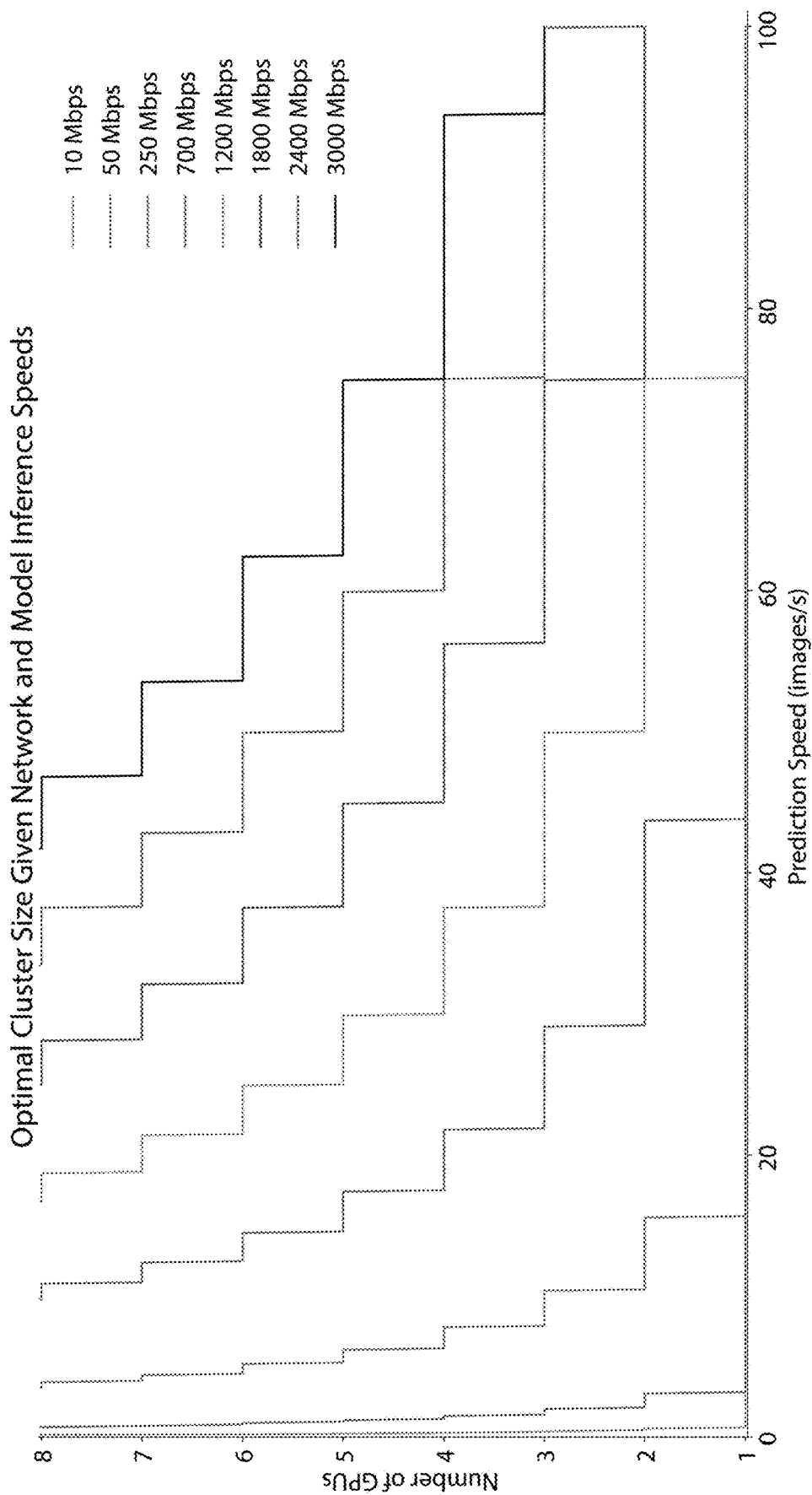
FIG. 24. Optimal cluster size as a function of model inference speed and data upload speeds.

FIG. 24. Optimal cluster size as a function of model inference speed and data upload speeds.

Benchmarking Details.

For benchmarking, data were gathered using the kiosk-benchmarking repo (github.com/vanvalenlab/kiosk-benchmarking, the content of which is incorporated herein by reference in its entirety). All runs of 10,000 or 100,000 images were done in triplicate. Runs of 1,000,000 images were run a single time. All data in FIG. 23A of the main text were derived from timestamps taken from Redis-consumer pods within the cluster. Data Transfer Times from FIG. 23A were calculated by doubling the sum of the time it took a Redis-consumer pod to download a raw image from the storage bucket and then upload the resulting image to the storage bucket. This calculation may mildly underestimate the total time a given image spends in transit in the cluster, because the image would go through several transfer steps.

1) Upload to storage bucket as part of a zip file.
2) Download of zip file from storage bucket by zip-consumer pod.
3) Upload of individual raw image to storage bucket from zip-consumer pod.
4) Download of individual raw image from storage bucket by Redis-consumer pod.
5) Upload of individual predicted image to storage bucket from Redis-consumer pod.
6) Download of individual predicted image from storage bucket to zip-consumer pod.
7) Upload of zipped batch of predicted images to storage bucket from zip-consumer pod.
8) Download of zipped batch of predicted images from storage bucket by client.

The methodology of this example accounts reasonably for steps 3-6, but not steps 1-2 and 7-8. TF Serving Response Times in FIG. 23A were the amount of time Redis-consumer pods had to wait for a response from TF-serving pods. Postprocessing Times in FIG. 23A were the amount of time that a Redis-consumer pod was occupied carrying out postprocessing computations on the results received from TF-serving pods. In FIG. 23B, Number of GPUs refers to the maximum number of GPUs available to a cluster, whether the cluster ever scaled up to the point where that number of GPUs was being utilized simultaneously. NVIDIA Tesla-V100 GPUs were used in all benchmarking runs. In FIG. 23C, costs were computed following methodology documented in the vanvalenlab/kiosk-benchmarking repository, the content of which is incorporated herein by reference in its entirety.

Benchmarking Data.

All data from the benchmarking are shown in FIGS. 25A-25C and FIGS. 26A-26B. Each run was performed in triplicate, except for the 1M image runs, which were performed once.

Figure 25A:
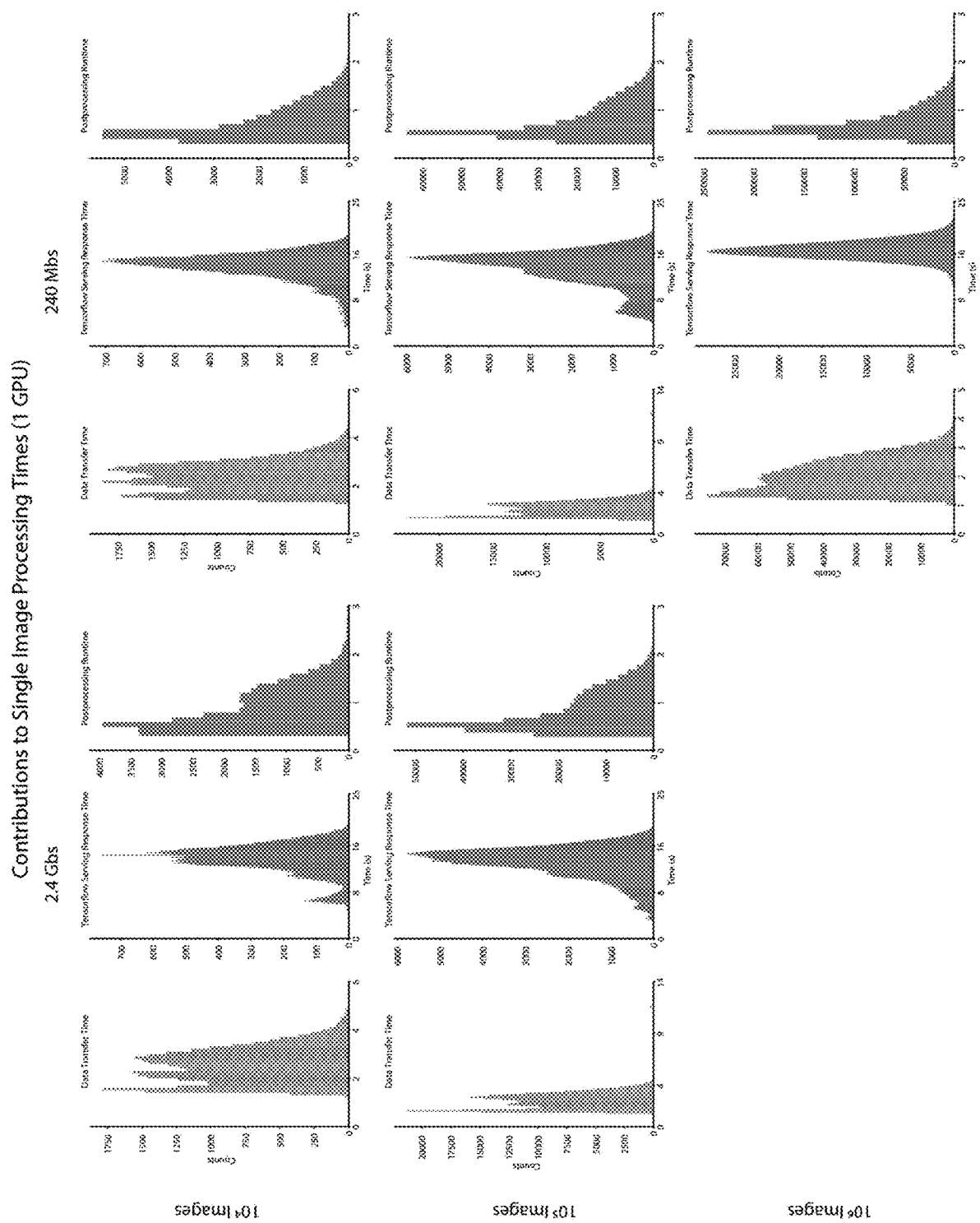
FIGS. 25A-25C. Contributions of data transfer time, Tensorflow serving response time, and post processing time to the time required to process a single image. Data for clusters with 1 GPU (FIG. 25A), 4 GPUs (FIG. 25B), and 8 GPUs (FIG. 25C) are shown.
Figure 25B:
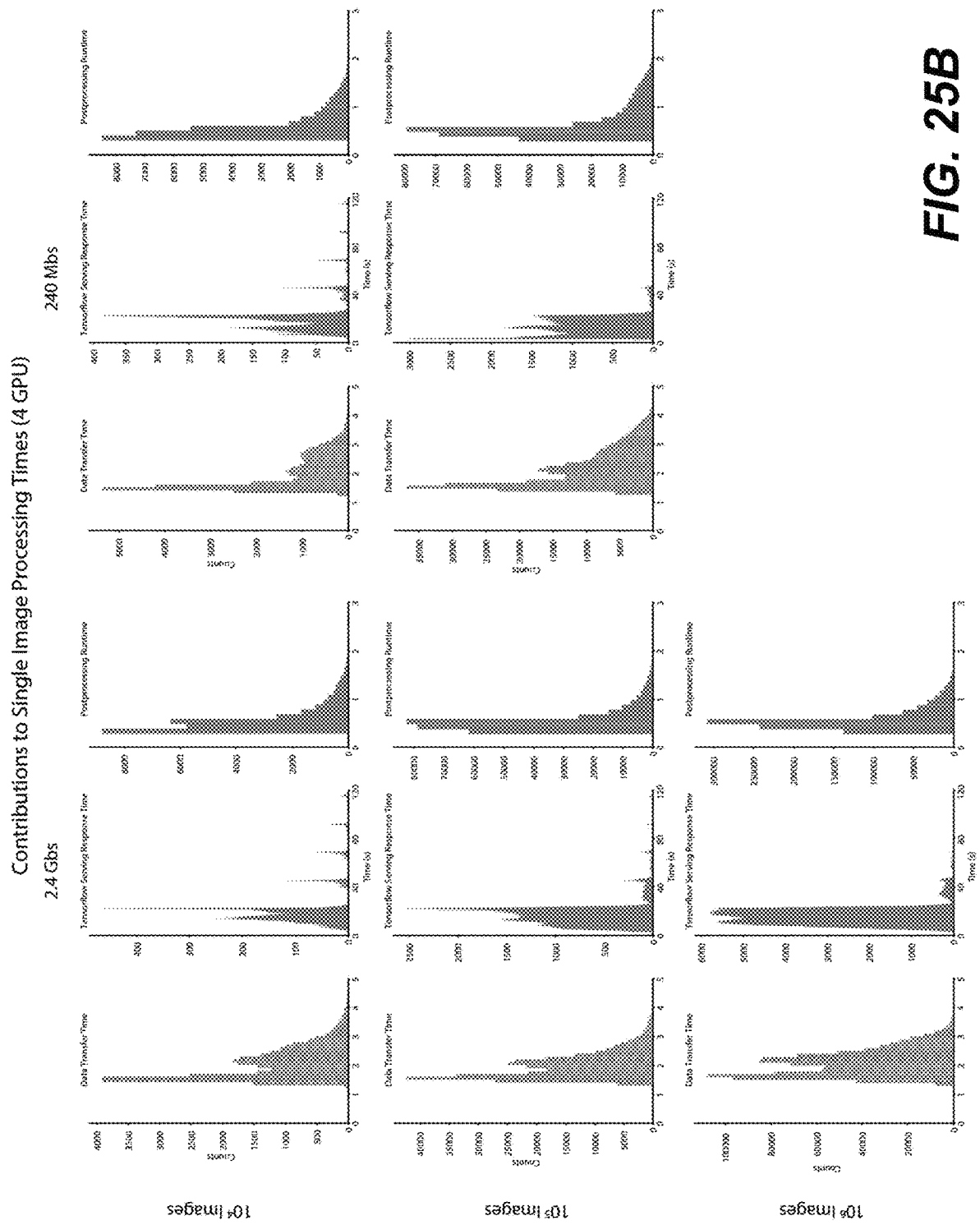
Figure 25C:
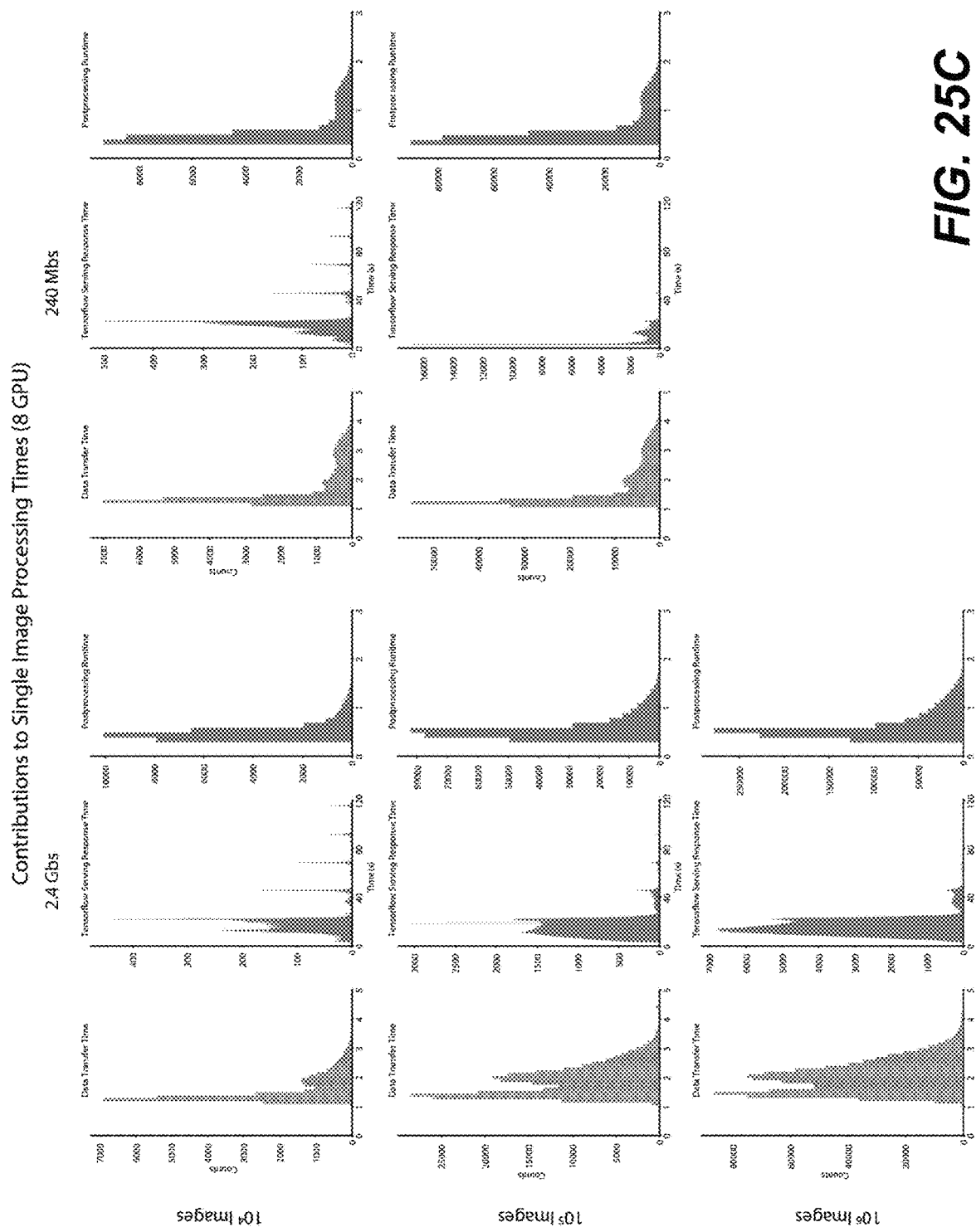

FIG. 25A. Contributions of data transfer time, Tensorflow serving response time, and post processing time to the time required to process a single image. Data for clusters with 1 GPU are shown. FIG. 25B. Contributions of data transfer time, Tensorflow serving response time, and post processing time to the time required to process a single image. Data for clusters with a maximum of 4 GPUs are shown. FIG. 25C. Contributions of data transfer time, Tensorflow serving response time, and post processing time to the time required to process a single image. Data for clusters with a maximum of 8 GPUs are shown.

Figure 26A:
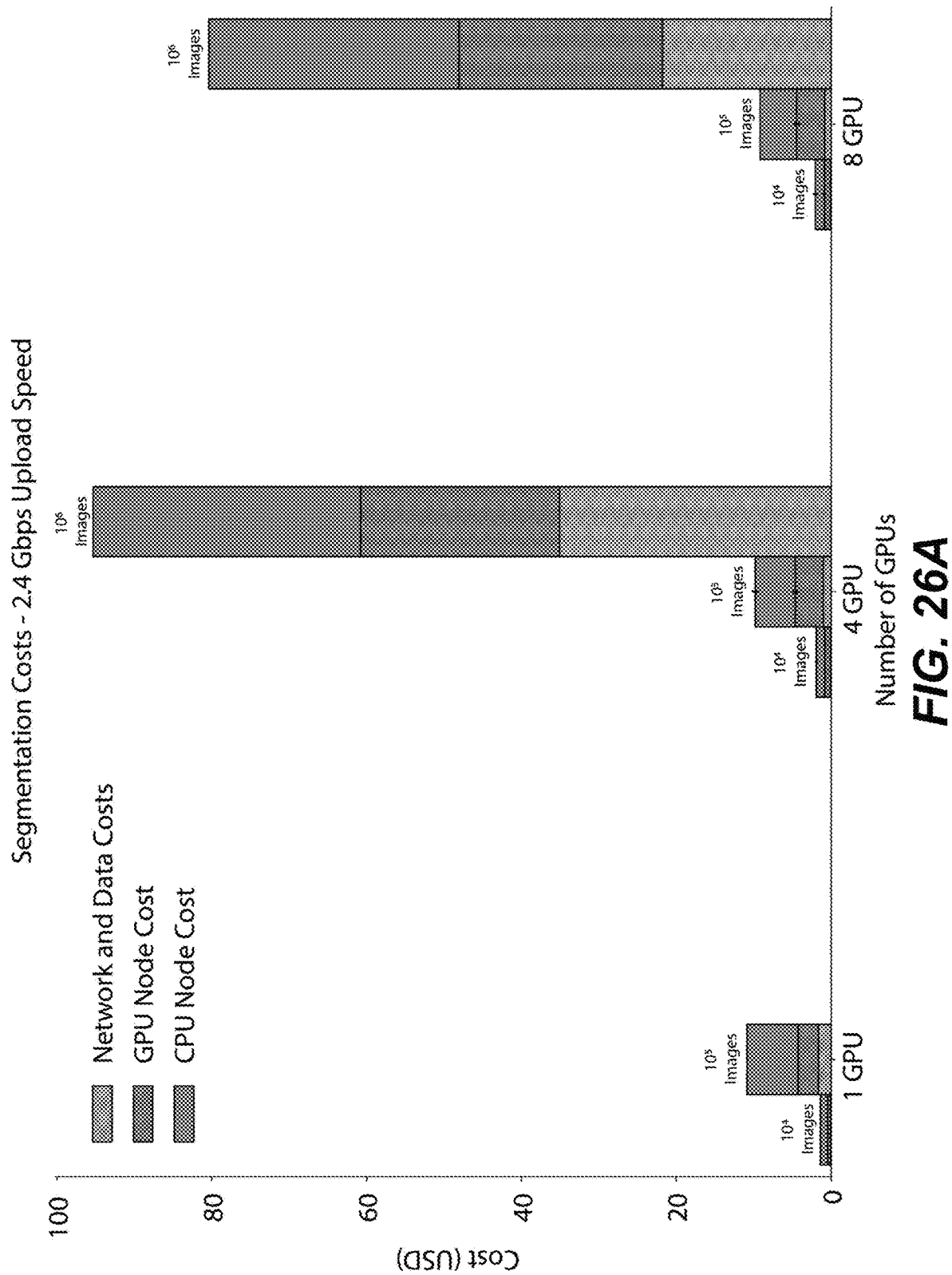
FIGS. 26A-26B. Cloud computation cost across all benchmarking runs with 2.4 Gbps upload speed (FIG. 26A) and 240 Gbps upload speed (FIG. 26B).
Figure 26B:
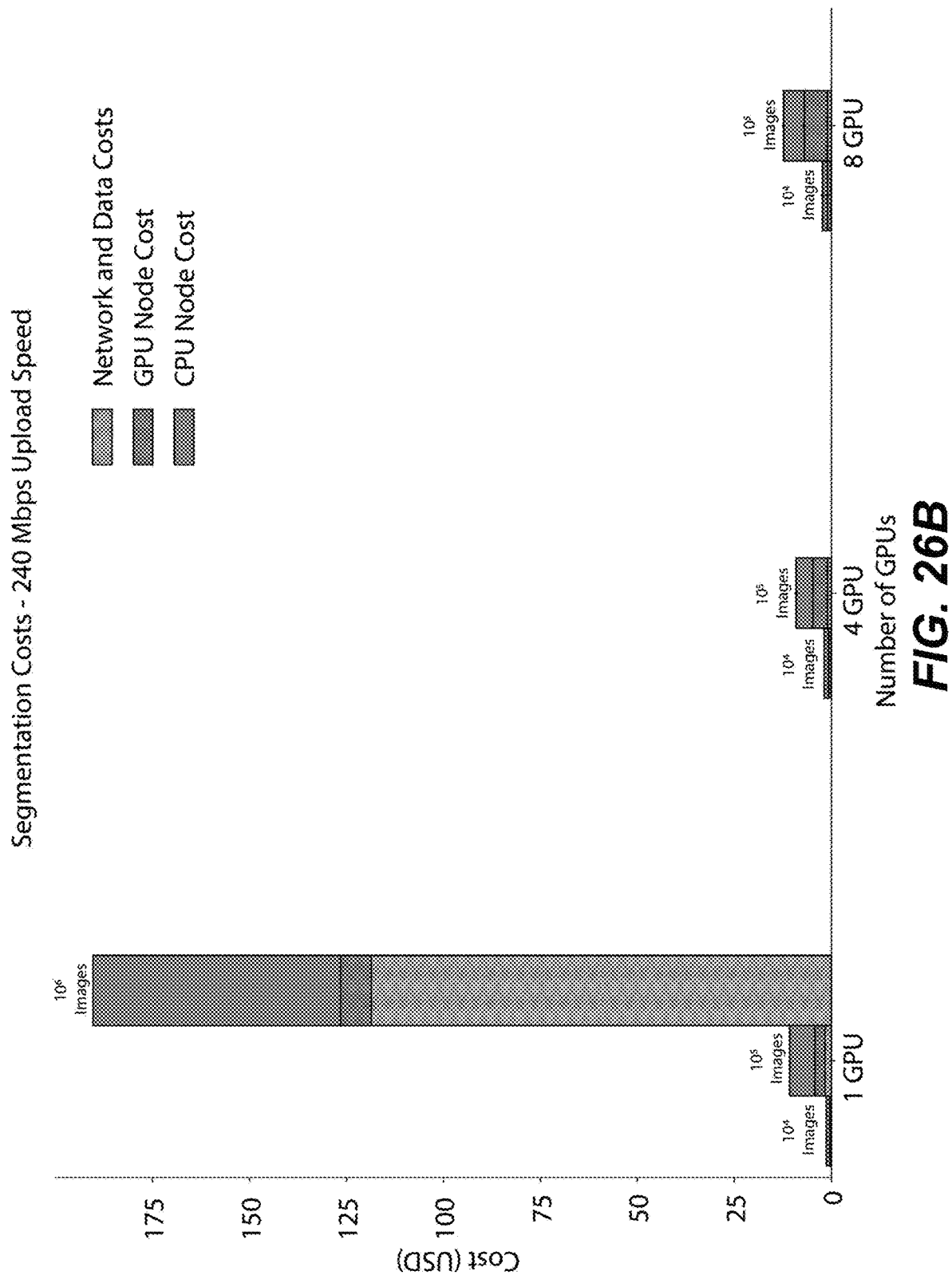

FIG. 26A. Cloud computation cost across all benchmarking runs with 2.4 Gbps upload speed. FIG. 26B. Cloud computation cost across all benchmarking runs with 240 Mbps upload speed.

Data Availability

All data that were used to generate the figures in this paper are available at deepcell.org/data and at github.com/vanvalenlab/deepcell-tf under the deepcell.datasets module; the content of each of which is incorporated herein by reference in its entirety.

Code Availability

A persistent deployment of the software described here can be accessed at deepcell.org, the content of which is incorporated herein by reference in its entirety. All source code is under a modified Apache license and is available at github.com/vanvalenlab, the content of which is incorporated herein by reference in its entirety. Detailed instructions are available at deepcell.readthedocs.io/, the content of which is incorporated herein by reference in its entirety.

Discussion

Just as deep learning is transforming the analysis of biological data, advances in methods for cloud-native software development have the potential to transform the relationship between compute and software in biological data analysis. The degree of abstraction enabled by these advances is changing not just what software can do, but what scientists consider to be software. The rise of deep learning has meant that developing training data and machine learning code can both be essential components of software development. Similarly, Kubernetes can enable one to treat computational infrastructure as software. Here, this abstraction was exploited to dynamically allocate computational resources, thereby scale compute resources to the size of the data analysis task. This strategy controls costs while driving rapid analysis of large datasets. Further, by treating compute as software, the entire software stack—both software and hardware—can be shared with end users, leading to decentralized control of compute while ensuring access to state-of-the-art deep learning models. Critically, training data should remain open, not siloed. Overall, DeepCell 2.0 establishes that any novel deep learning method can be deployed on large imaging datasets in a scalable fashion. The framework of DeepCell 2.0 can significantly empower large-scale image analysis, and the paradigm of treating compute as both a dynamic resource and as software can have widespread use throughout the life and physical sciences.

Example 3

Rapidly Annotating and Curating Tracking-Specific Training Datasets

Overview
Introduction

How living systems and their respective viruses process information are stupied. To do so, the latest advances in imaging and genomics are combined to make novel measurements. A number of machine learning tools are described herein to accelerate and enhance the analysis of these multiplexed biological images. Collectively, these tools are known as DeepCell. One example of DeepCell's capabilities is the models to segment and track cells across time-lapse movies of experiments. Another example is the models to combine several channels of data to identify and segment cell compartments in dense tissue arrays. These models reduce the manual labor previously required to analyze such experiments and makes ambitious, high-throughput studies possible. These models, as well as deep learning in general, are critically dependent on large quantities of high-quality, annotated data.

For the pioneering work on deep learning-based approach to cell segmentation and analysis, data needs to be created and annotated. Several tools to facilitate and expedite this data processing pipeline have been created. The foundation of this pipeline is the annotation engine, Caliban. This example explains the means and methods used to transform raw data into a format suitable for annotation and how to use Caliban to create annotated data in a ready-to-train format for use in the DeepCell ecosystem.

Caliban: An Annotation Engine

Caliban is a segmentation and tracking tool used for human-in-the-loop data curation, the heart of our data annotation pipeline. Caliban displays key information (e.g. lineage data) alongside multiple image channels and annotations. The output files package all of this information (including selected image channels) as training data, for example, for DeepCell (and DeepCell 2.0). The program has been designed as a multi-platform solution to be run within a docker container. Caliban is available in two flavors: Desktop and Browser.

Desktop Caliban is intended as a single-user solution for curating individual image files. Desktop Caliban includes multiple annotation modes and brush features specifically tailored to provide accurate pixel-level semantic segmentations of biological images. Each mode enables a unique feature suite that allows users quickly and easily provide curation or ground-up segmentations and annotations for biological images. For example, these modes include Tracking (where users scroll through multiple time points in a movie and adjust lineage information), Z-Stack (where users can predict and adjust which cells appear in multiple images within a spatially-3D, z-stack), and Multi-Channel (where users can toggle between channels of an image to decide where cell boundaries lie).

Browser Caliban, on the other hand, is intended for use in crowdsourcing annotations of larger datasets. Browser Caliban is designed to be used in concert with a crowdsourcing platform (such as Amazon's Mechanical Turk or Appen) to allow multiple users to render annotations on multiple files at the same time. For clarity and ease of use, each mode and feature suite can be disabled individually before launch to limit the number of tools any one contributor needs to learn before annotating data. In this way, each instance of Caliban can be tailored to the specific annotation job at hand.

CellNet Data Pipeline

The data pipeline for annotating DeepCell data begins with collecting raw imaging data and ends with curated annotations being added to CellNet, the a data catalog for single-cell biological image analysis. Caliban plays a significant role in this pipeline and works in concert with other tools, such as the Caliban-Toolbox, to pre- and post-process files. The general workflow, whereby Caliban and these tools are used to generate and curate files, is shown in FIG. 27.

Figure 27:
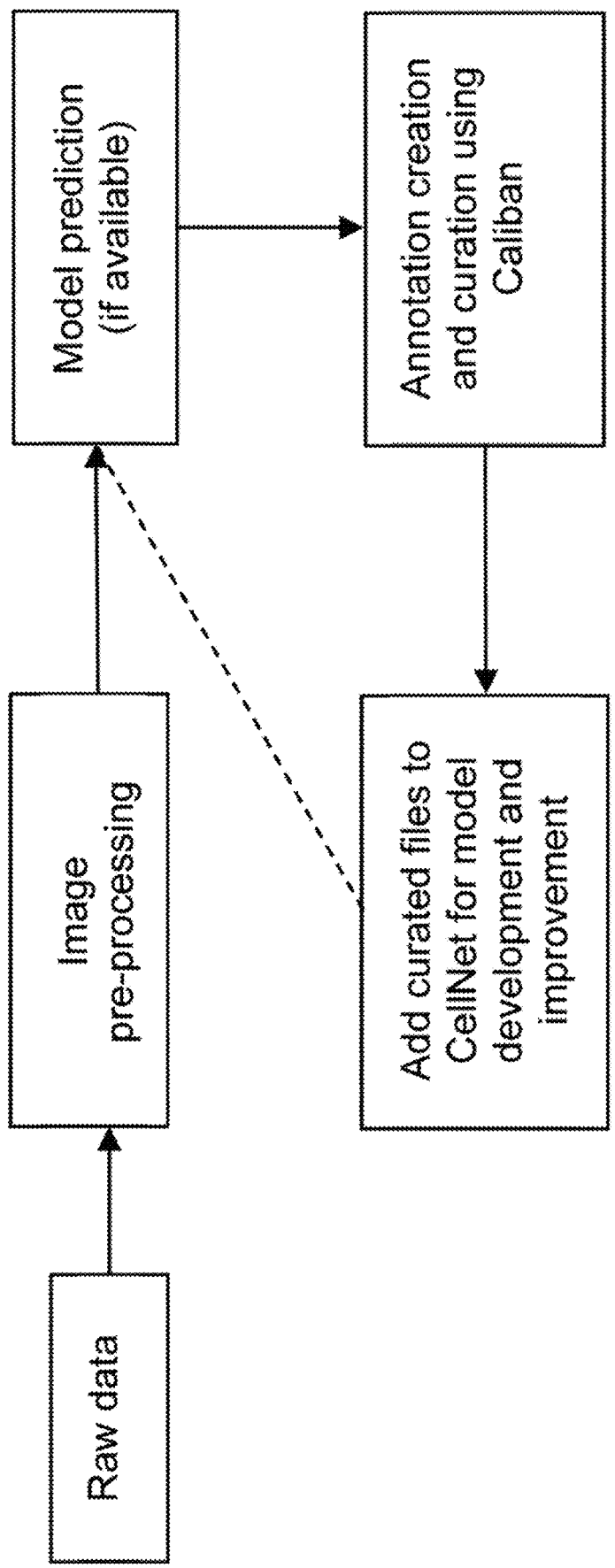
FIG. 27. Flowchart of general steps in the annotation pipeline.

FIG. 27. Flowchart of general steps in the annotation pipeline. Pre-processing allows DeepCell-formatted files to be made and, if available, models can be used to provide an initial prediction on the target of interest. These files can then be manually curated and used to provide a more accurate prediction in the next cycle.

Getting Started
With Desktop Caliban

Figure 28:
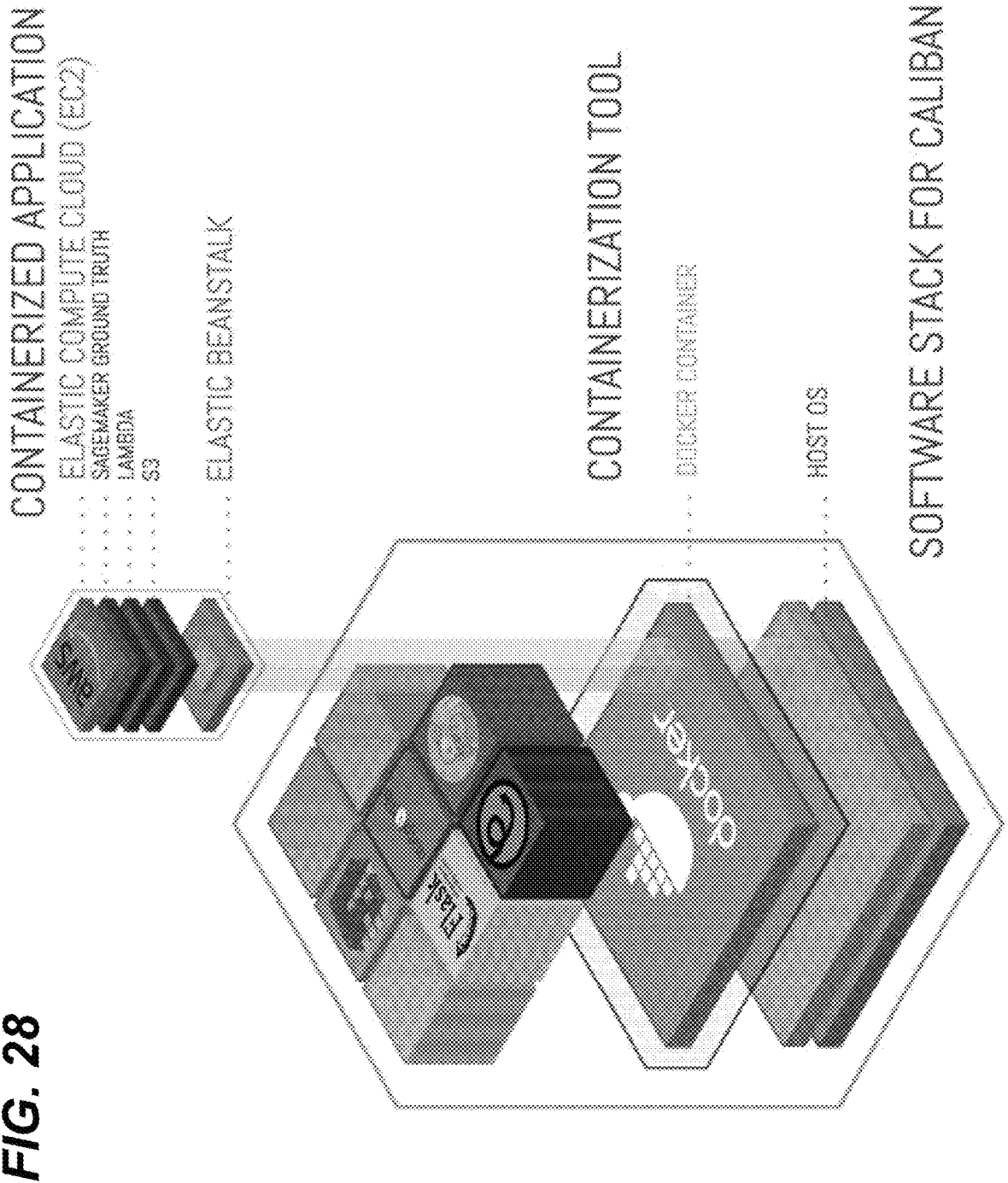
FIG. 28 shows a schematic illustration of a non-limiting exemplar software stack for Caliban.

Desktop Caliban is a lightweight program written in Python and intended as a single-user solution for curating individual image files. FIG. 28 shows software stack for Caliban. The source code is available on github.com/vanvalenlab/Caliban, the content of which is incorporated herein by reference in its entirety. For running on Linux, the code available on GitHub could be used directly with a Python compiler and a virtual environment (docs.python-guide.org/dev/virtualenvs/, the content of which is incorporated herein by reference in its entirety) with the following commands:

git clone https://github.com/vanvalenlab/caliban.git
cd caliban
cd desktop
python3 caliban.py [input file location]

Example files are available in the/example_files directory.

If a user is not using Linux, or prefers not to manage a virtual environment, Caliban has been designed for multi-platform use via Docker. Virtual machines and containers (like Docker) allow for programs to be run within a single managed environment, thereby preventing versioning issues as well as a host of other difficulties. In addition to Docker, this implementation depends on VNC viewer.

Once these two dependencies are installed, follow these steps to build and run Caliban:
Build a Docker Container
git clone https://github.com/vanvalenlab/caliban.git
cd caliban
docker build -t caliban
Run the New Docker Image
docker run \
-p 5900:5900 \
-v $PWD/caliban/desktop:/usr/src/app/desktop \
--privileged \
caliban:latest This will launch a new Docker container and run Xvfb, Fluxbox, and a VNC server. To access the container's display, point a VNC client to 127.0.0.1.

Inside the VNC client, Caliban can be accessed through the terminal emulator. Start the terminal by right-clicking the desktop and selecting:
Applications >Terminal Emulators >XTerm Next, enter the following into the terminal and Caliban will start:
cd desktop
python3 caliban.py [input file location]

As with the Linux only install, the installation can be verified with an example file by running:
cd desktop
python3 caliban.py examples/trackfile1.trk With Browser Caliban Referring to FIG. 28, browser Caliban is an implementation of the Caliban source code for use as part of web server. This solution can be run locally or deployed to a service like Amazon Web Services (AWS) Elastic Beanstalk. Though Browser Caliban can be used by single-users to generate a few annotations, this version of Caliban is meant to be used in concert with a crowdsourcing platform to accelerate data annotation. As a result, in order to deploy Browser Caliban, a user will need the appropriate cloud credentials and services.

Because Browser Caliban is just one specific implementation of the Caliban source code, many of the annotation modes (and their respective key/mouse operations) are similar, if not identical to the Desktop version. Additionally, these features can be selectively disabled to provide a tailored crowdsourcing solution that limits the options a contributor needs to learn before rendering annotations. A stable demo of the browser application can be accessed at caliban.deepcell.org/, the content of which is incorporated herein by reference in its entirety. As with Desktop Caliban, the source code is available on github.com/vanvalenlab/Caliban, the content of which is incorporated herein by reference in its entirety. The following sections walk through the program hierarchy, the install procedure for developers, and how to launch Browser Caliban as a web service.

The Hierarchy of Browser Caliban

Flask provides the web framework for the core Caliban Python library that operates on the raw and annotated files. Flask serves the images as PNGs and metadata as JSON and expects to find these files stored in an AWS bucket. The .js files in the browser/template folder are what makes the requests to the Flask server. The Flask framework also serves as the router that maps the specific URL with the associated function that is intended to perform some task. Specifically, the application.route decorator binds the URL rule to the function below it. Thus, if user performs actions that cause a change in the underlying data, the side-serving .js file will request to visit a specific URL, and the output of the function below the decorator will be rendered in the browser.

The user actions described above depend on Python libraries—including NumPy, Matplotlib, and scikit-image—to change the data within files. After the desired change has been made to the lineage information or mask annotation, the Flask app routing will update the interface to reflect the alterations with support from side-serving JavaScript scripts.

As Caliban is meant to facilitate crowdsourced annotation, the tool utilizes a relational database (caliban.db) to keep track of a unique user id (created on first use) and the Review object users are assigned. Whenever a user makes a change to the Review object, the application will update its state. After the user submits the final datafile, the corresponding id and object will be deleted from the database file. The caliban.db file is created by running application.py. The Python SQL toolkit SQLAlchemy allows Caliban to make use of a wide array of Relational Database Management Systems (RDBMS). Caliban can use SQLite for local deployments of Browser Caliban and MySQL for crowdsourced deployments. The RDBMS of choice can be adjusted in the browser/config.py file.

Deploying Browser Caliban to the Cloud

The Flask application can be optimized for use with the AWS Elastic Beanstalk (EB) environment as a RESTful web service. To deploy this application to AWS EB, an Amazon Relational Database Service (RDS) MySQL database is set up and configured to handle data storage for application use. The database credentials can be added to the .env configuration file. Once a database is appropriately configured, the application can easily be launched by using the AWS EB command line tool or web interface. The .ebextensions folder configures the web service to use the appropriate Flask application.

Browser Caliban for Developers

Given the range of features and deployment options, Browser Caliban has several developer paths. The two considered here are 1) working locally on the core library and 2) troubleshooting crowdsourcing deployments with Docker Compose. In both cases, it will be important to make note of your AWS credentials to inject as necessary (Boto can be used to manage this integration).

1) To Run Browser Caliban Locally:
First, install the dependencies (Recommended: Use a virtual environment to manage the dependencies):
cd browser
pip install -r requirements.txt Then, once the AWS credentials have been added in a .env file, Browser Caliban can be run using the following command:
python3 application.py 2) Docker Compose
Add the AWS credentials to the docker-compose.yaml file.
From the caliban/browser folder, run:
sudo docker-compose up --build -d
Wait a minute for the database to finish setting up before running: sudo docker-compose restart app
Now, navigate to local_host:5000 in a browser window to access the local version of the tool.
To interact with the local MySQL database:
sudo docker exec -it browser_db_1 bash
mysql -p
When finished, a user can take down the container by running: sudo docker-compose down Additionally, removing any stale Docker volumes is a good practice, which can be done by running the following command:

sudo docker system prune -- volumes

Caliban Annotation Modes

In this section, non-limiting exemplary modes available to annotate data using Caliban are highlighted. The modes include: Tracking, Z-Stack, and Multi-Channel.

Tracking

The Tracking mode in Caliban allows for rapid annotation of biological objects in movies. Each frame of the movie can be loaded in sequence and the individual labels created for each object (if any) can be linked according to their relationship. For instance, a two-dimensional (spatial) movie of cell nuclei dividing over time can be segmented and tracked such that each "daughter" cell is linked to its "mother." The frame in which this division occurs as well as the identities of the cell's parents and children can be stored in a lineage file that accompanies the masks generated. The Tracking mode in Caliban can operate on ".trk" files. These files contain a zipped image archive (.npz) and JSON object to store the lineages. This mode is automatically selected when loading a .trk file.

The Layout

Figure 29:
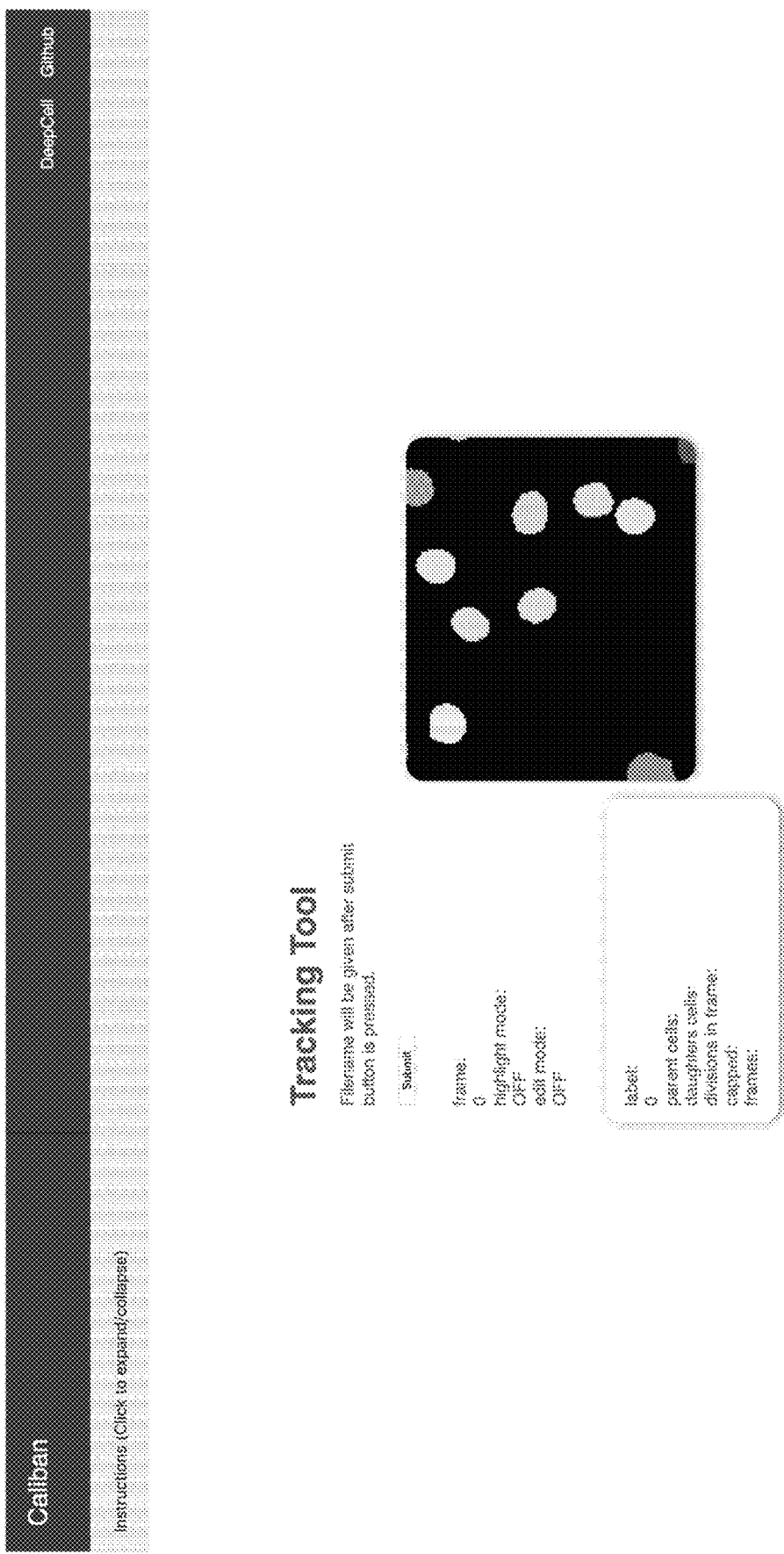
FIG. 29. Browser Caliban in Tracking mode.
Figure 30:
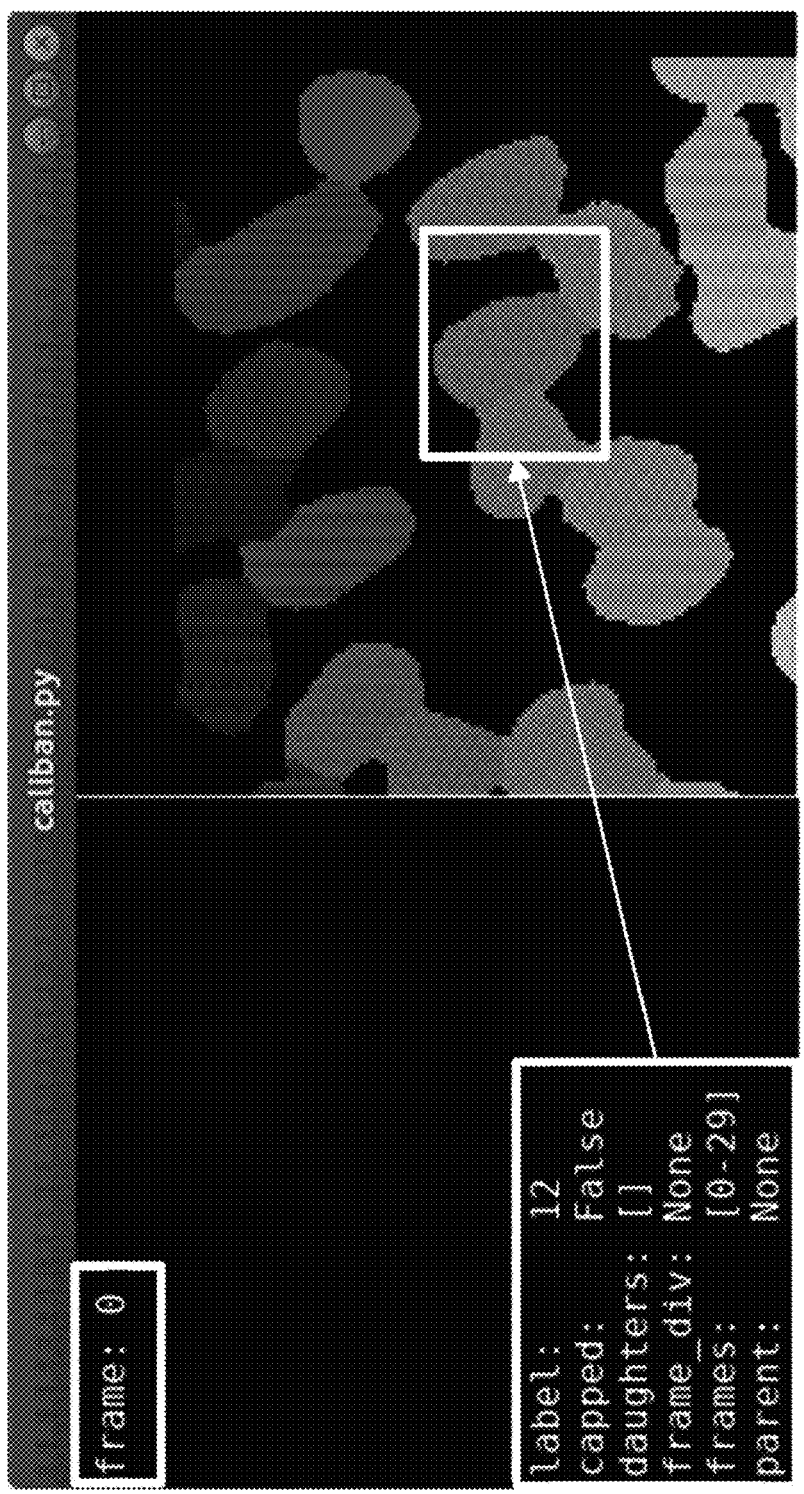
FIG. 30. Desktop Caliban in Tracking mode.

The layout of Broswer Caliban in Tracking mode is shown in FIG. 29. The layout of Desktop Caliban in Tracking mode is shown in FIG. 30. The right panel of Caliban displays an image of cells. This can be toggled between the raw image (not shown) and the cell segmentation masks for that image (shown). Each cell value is represented by a different color. The colors start at dark blue (for cell 1) and continue through a spectrum of green, to brown, to pink, to white. In some embodiments, the color scheme of the masks cannot be changed, but a user can adjust the contrast of the raw images with the scroll wheel of a mouse.

The left pane of Caliban displays information. The frame number being viewed will be displayed in the top left corner. With mouse over a cell in the right pane, the tracking information for that cell will be displayed in the bottom left corner. Cell selections and confirmations can be displayed in the bottom left corner.

FIG. 30. Desktop Caliban in Tracking mode. The Display Box on the right has been toggled to show the current state of the cell masks (also referred to as label masks) in frame 0. The key information, some of which is stored in a JSON object alongside the image and cell mask, is shown highlighted in white boxes in FIG. 30.

The Tools

The annotations on the screen (as well as the underlying files they represent) can be edited using the mouse and keyboard operations.

Navigation Through Frames a or <←—Back one frame d or →—Forward one frame

Edit Operations

Caliban's default setting allows operations to be carried out quickly and easily on existing segmentations. The actions that can modify cell labels and/or lineage information include:

click—click on a cell label to select it. Up to two labels can be selected at one time.

shift+click—trim stray pixels away from selected part of label ctrl+click—flood selected part of label with a new, unused label c—create: relabel selected label with a new, unused label f—fill: select label, press "f", then follow prompt to fill a hole in the selected label r—replace: relabel all instances of a selected cell label with a second selected cell label; replaces lineage data in a trk file r—relabel: sequentially relabel all labels in frame, starting from 1, when no labels are selected (for npz files)

p—parent: assign parent/daughter relationship to pair of selected labels in trk file p—predict: predict zstack relationships in npz when no labels are selected s—swap: swap labels and lineage information between two selected labels x—delete: remove selected cell mask in frame w—watershed: call a watershed transform to split one cell label into two esc—cancel operation space bar—confirm operation s—confirm operation in a single frame, when applicable A user can use esc to return back to a state where no labels are selected.

In Annotation (Pixel Editing) Mode

Keybinds in pixel editing mode are different from those in the label-editing mode.

Annotation mode focuses on using an adjustable brush to modify annotations on a pixel level, rather than using operations that apply to every instance of a label within a frame or set of frames. In some embodiments, the brush tool can only make changes to the currently selected value (e.g. a brush set to edit label 5 will only add or erase "5" to the annotated image).

[(left bracket) /](right bracket)—decrement/increment value that brush is applying ↓ ↑—change size of brush tool x—toggle eraser mode n—change brush label to an unusued label, so that a new label can be created with a unique id. Can be used with conversion brush to overwrite existing label with unused label (follow conversion brush prompt).

p—color picker (click on a label to change the brush value to it)

r—turn on "conversion brush" setting, which changes brush behavior so that one label value is overwritten with another label value. No other labels are affected, and conversion brush will not draw on background. After turning on conversion brush, click on cell labels as prompted to set brush values.

t—threshold to predict annotations based on brightness. After turning this on, click and drag to draw a bounding box around the cell to threshold. Make sure to include some background in the bounding box for accurate threshold predictions. In some embodiments, Caliban will add whatever being thresholded as foreground within the bounding box to the annotation as a new cell with unique label.

Viewing Options

F11—toggle full-screen

-/= or ctrl+scroll wheel—change level of zoom

To pan in image: Hold down the spacebar while clicking and dragging image to pan. Alternatively, the keys home, page up, page down, and end can be used to jump across the screen. Holding the shift key while using these pan buttons will result in a smaller jump; holding the control key will snap to the edge of the image.

h—switch between highlighted mode and non-highlighted mode (highlight exists in label- and pixel-editing modes but is displayed differently; label-editing highlighting recolors solid label with red, pixel-editing highlighting adds white or red outline around label in image). Once highlight mode is on, use [(left bracket) /](right bracket) to decrement/increment selected cell label number.

shift+h—switch between showing and hiding annotation masks in the pixel editor z—switch between annotations and raw images (outside of pixel editor)

i—invert greyscale raw image (viewing raw image or in pixel editor)

k—apply a Sobel filter to raw image (viewing raw image or in pixel editor)

j—apply adaptive histogram equalization to raw image (viewing raw image or in pixel editor)

v—switch between showing and hiding cursor f—cycle between different annotations when no labels are selected (label-editing mode)

c—cycle between different channels when no labels are selected (label-editing mode)

shift+↓/↑—cycle between colormaps for viewing raw images (does not apply to pixel editor)

e—toggle annotation mode between pixel-editing and whole-label-editing (when nothing else selected)

scroll wheel—change image or annotation maximum brightness shift+scroll wheel—change image minimum brightness To Save When a user has completed the work, use the "s" key to save the changed file. The tool will also save the original file in the same folder. In npz mode, a new npz file will be saved with a version number. A npz file can be saved as a trk file (select "t" in response to save prompt). This will bundle together the current channel and feature of the npz along with a generated lineage file, which will contain label and frame information and empty parent/daughter entries for each cell. The new trk file can then be edited in Caliban's trk mode to add relationship information.

Z-Stack

The Z-Stack mode in Caliban is designed to help users annotated three-dimensional (spatial) data, like that produced via confocal microscopy. Each frame of the z-stack can be loaded in sequence and the individual labels created for each object can be linked according to their relationship. The Z-Stack mode in Caliban is designed to operate on a zipped image archive (.npz).

The Layout

Figure 31:
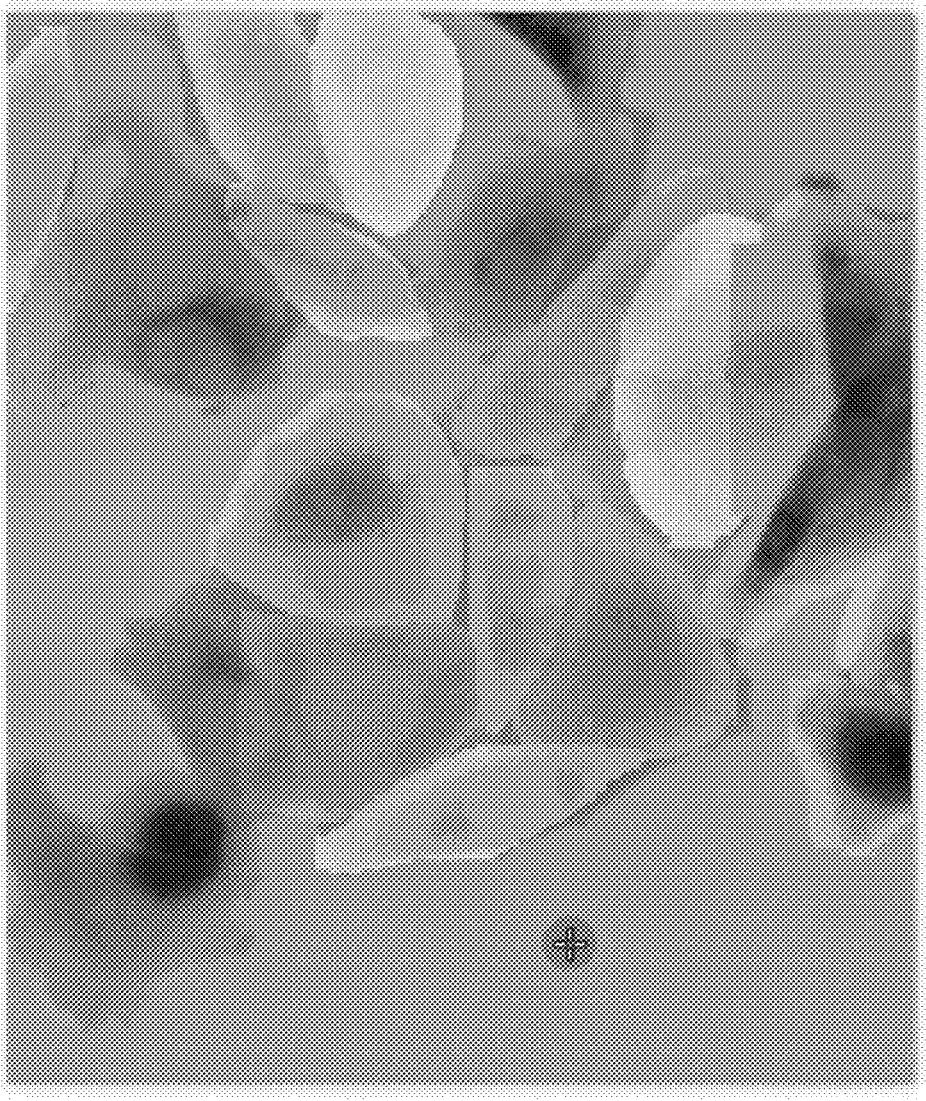
FIG. 31. Browser Caliban in Z-Stack mode.

The layout of Browser Caliban in Z-Stack mode is shown in FIG. 31. FIG. 31. Browser Caliban in Z-Stack mode. The Display Box on the right has been toggled to show the current state of the cell masks (also referred to herein as label masks) in frame 0. These labels exist as an overlay on top of the raw image data. The information panel on the left provides information on the current frame and annotation tools. Label-specific information is displayed on mouse-over events.

The Tools

The annotations on the screen (as well as the underlying files they represent) can be edited using the mouse and keyboard operations.

Navigation Through Frames a or ←—Back one frame d or →—Forward one frame

Edit Operations

Caliban's default setting allows operations to be carried out quickly and easily on existing segmentations. The actions that can modify cell labels and/or lineage information include:

click—click on a cell label to select it. Up to two cells can be selected at one time.

alt key+click—flood connected regions of the selected label with a new value shift key+click—trim away unconnected regions of the selected label c—create: relabel selected cell with an unused label f—fill hole: click on an empty area to flood it with the selected label p—parent: assign parent/daughter relationship to pair of selected cells in trk file p—predict: predict relationships across frames (time or z) in npz when no cells are selected; does not predict cell divisions in time lapse movies r—replace: relabel all instances of a selected cell label with a second selected cell label; replaces lineage data in a trk file s—swap: swap labels and lineage information between two selected cells w—watershed: call a watershed transform to split one cell label into two x—delete: remove selected cell mask in frame esc—cancel operation space bar—confirm operation s—confirm operation in a single frame, when applicable A user can also use esc or click on the black background to return back to a state where no cells are selected.

In Annotation (Pixel Editing) Mode

Keybinds in pixel editing mode are different from those in the label-editing mode.

Annotation mode focuses on using an adjustable brush to modify annotations on a pixel level, rather than using operations that apply to every instance of a label within a frame or set of frames. In some embodiments, the brush tool can only make changes to the currently selected value (e.g. a brush set to edit label 5 will only add or erase "5" to the annotated image).

-/=—increment value that brush is applying

↓ ↑—change size of brush tool i—invert greyscale raw image n—change brush label to an unused label, so that a new cell can be created with a unique id p—color picker (click on a label to change the brush value to it)

r—turn on "conversion brush" setting, which changes brush behavior so that one label value is overwritten with another label value. No other labels are affected, and conversion brush will not draw on background. After turning on conversion brush, click on cell labels as prompted to set brush values. (Eraser mode is automatically turned off when the conversion brush is set.)

t—threshold to predict annotations based on brightness. After turning this on, click and drag to draw a bounding box around the cell to threshold. Make sure to include some background in the bounding box for accurate threshold predictions. In some embodiments, Caliban will add whatever being thresholded as foreground within the bounding box to the annotation as a new cell with unique label.

x—toggle eraser mode

Viewing Options c—cycle between different channels when no cells are selected e—toggle annotation mode (when nothing else selected)

f—cycle between different annotations when no cells are selected h—switch between highlighted mode and non-highlighted mode. When outside of the pixel editor, the selected cell(s) will be highlighted in red and can be cycled through using -/=keys. When in the pixel editor, any pixels with the same label that the brush is set to edit will be highlighted red. (E.g., if the brush is set to an unused value, nothing will be highlighted, but if it is set to the value 5, any pixels with the label 5 will be displayed in red.)

z—switch between annotations and raw images scroll wheel—change image contrast

Multi-Channel

The Multi-Channel (or RGB) mode in Caliban is designed to allow users to create one annotation from the information contain in several channels, like those produced in multiplexed imaging experiments. The Multi-Channel mode in Caliban is designed to operate on a zipped image archive (.npz).

The Layout

Figure 32:
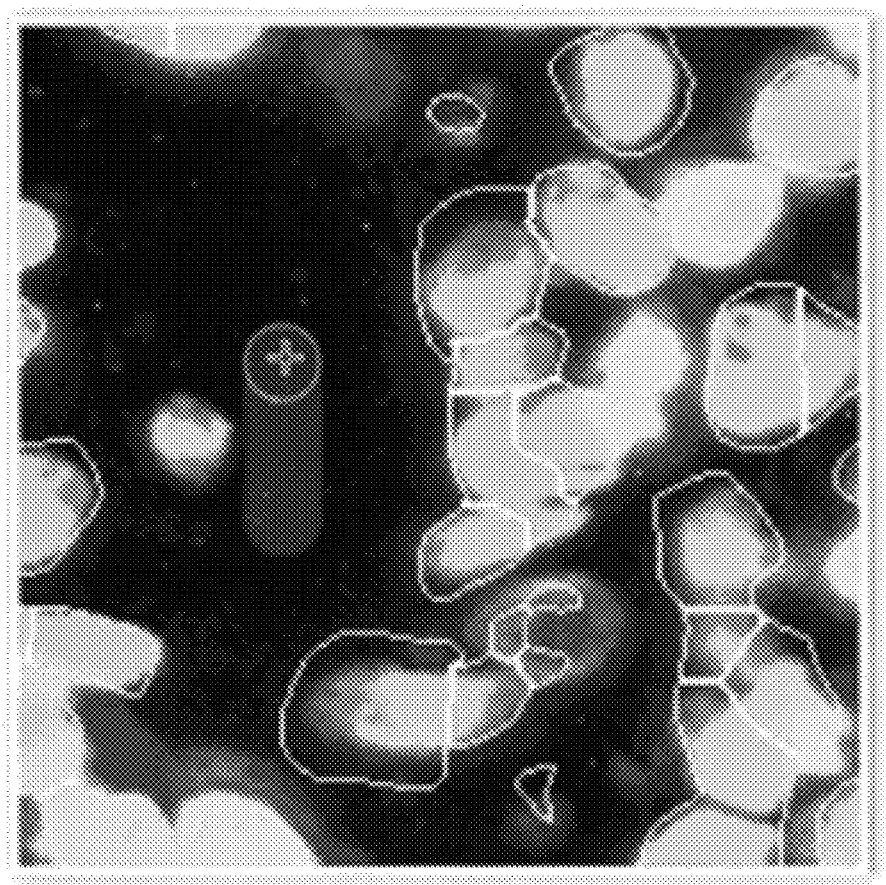
FIG. 32. Browser Caliban in Multi-Channel mode.

The layout of Browser Caliban in Multi-Channel mode is shown in FIG. 32. FIG. 32. Browser Caliban in Multi-Channel mode. The Display Box on the right has been toggled to show the current state of the cell masks (shown as white outlines) in frame 0. These labels exist as an overlay on top of multiple channels of raw image data. The info pane on the left provides information on the current frame and annotation tools. Label-specific information is displayed on mouse-over events.

The Tools

The annotations on the screen (as well as the underlying files they represent) can be edited using the mouse and keyboard operations.

Navigation Through Frames a or ←—Back one frame d or →—Forward one frame

Edit Operations

Caliban's default setting allows operations to be carried out quickly and easily on existing segmentations. The actions that can modify cell labels and/or lineage information are:

click—click on a cell label to select it. Up to two cells can be selected at one time.

alt key+click—flood connected regions of the selected label with a new value shift key+click—trim away unconnected regions of the selected label c—create: relabel selected cell with an unused label f—fill hole: click on an empty area to flood it with the selected label p—parent: assign parent/daughter relationship to pair of selected cells in trk file p—predict: predict relationships across frames (time or z) in npz when no cells are selected; does not predict cell divisions in timelapse movies r—replace: relabel all instances of a selected cell label with a second selected cell label; replaces lineage data in a trk file s—swap: swap labels and lineage information between two selected cells w—watershed: call a watershed transform to split one cell label into two x—delete: remove selected cell mask in frame esc—cancel operation space bar—confirm operation s—confirm operation in a single frame, when applicable A user can also use esc or click on the black background to return back to a state where no cells are selected.

In Annotation (Pixel Editing) Mode

Keybinds in pixel editing mode are different from those in the label-editing mode.

Annotation mode focuses on using an adjustable brush to modify annotations on a pixel level, rather than using operations that apply to every instance of a label within a frame or set of frames. In some embodiments, the brush tool can only make changes to the currently selected value (e.g. a brush set to edit label 5 will only add or erase "5" to the annotated image).

-/=—increment value that brush is applying

↓ ↑—change size of brush tool i—invert greyscale raw image n—change brush label to an unused label, so that a new cell can be created with a unique id p—color picker (click on a label to change the brush value to it)

r—turn on "conversion brush" setting, which changes brush behavior so that one label value is overwritten with another label value. No other labels are affected, and conversion brush will not draw on background. After turning on conversion brush, click on cell labels as prompted to set brush values. (Eraser mode is automatically turned off when the conversion brush is set.)

t—threshold to predict annotations based on brightness. After turning this on, click and drag to draw a bounding box around the cell to threshold. Make sure to include some background in the bounding box for accurate threshold predictions. In some embodiments, Caliban will add whatever being thresholded as foreground within the bounding box to the annotation as a new cell with unique label.

x—toggle eraser mode

Viewing Options c—cycle between different channels when no cells are selected e—toggle annotation mode (when nothing else selected)

f—cycle between different annotations when no cells are selected h—switch between highlighted mode and non-highlighted mode. When outside of the pixel editor, the selected cell(s) will be highlighted in red and can be cycled through using -/=keys. When in the pixel editor, any pixels with the same label that the brush is set to edit will be highlighted red. (E.g., if the brush is set to an unused value, nothing will be highlighted, but if it is set to the value 5, any pixels with the label 5 will be displayed in red.)

z—switch between annotations and raw images scroll wheel—change image contrast

Crowdsourcing Annotations with Browser Caliban

Caliban can be run on a crowdsourcing platform, such as the Figure Eight platform.

Figure 33A:
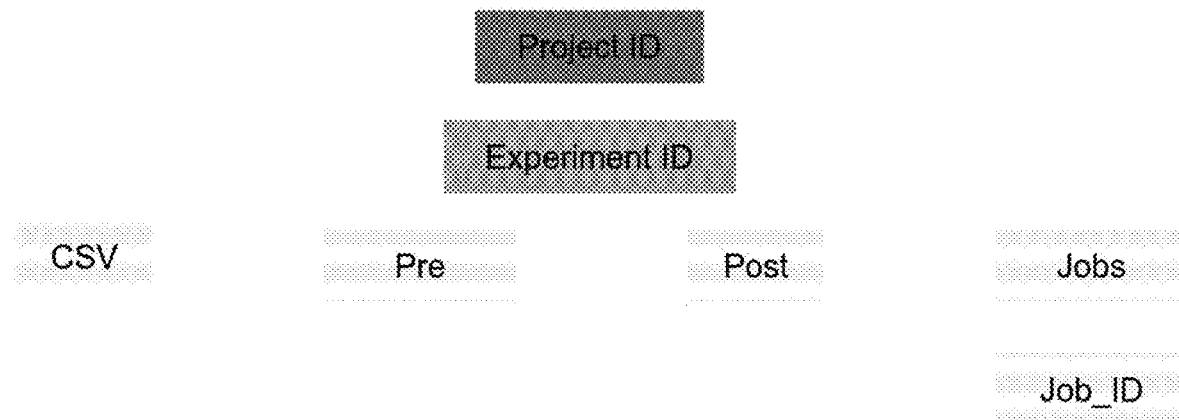
FIGS. 33A-33C. Data ontology for CellNet.
Figure 33B:
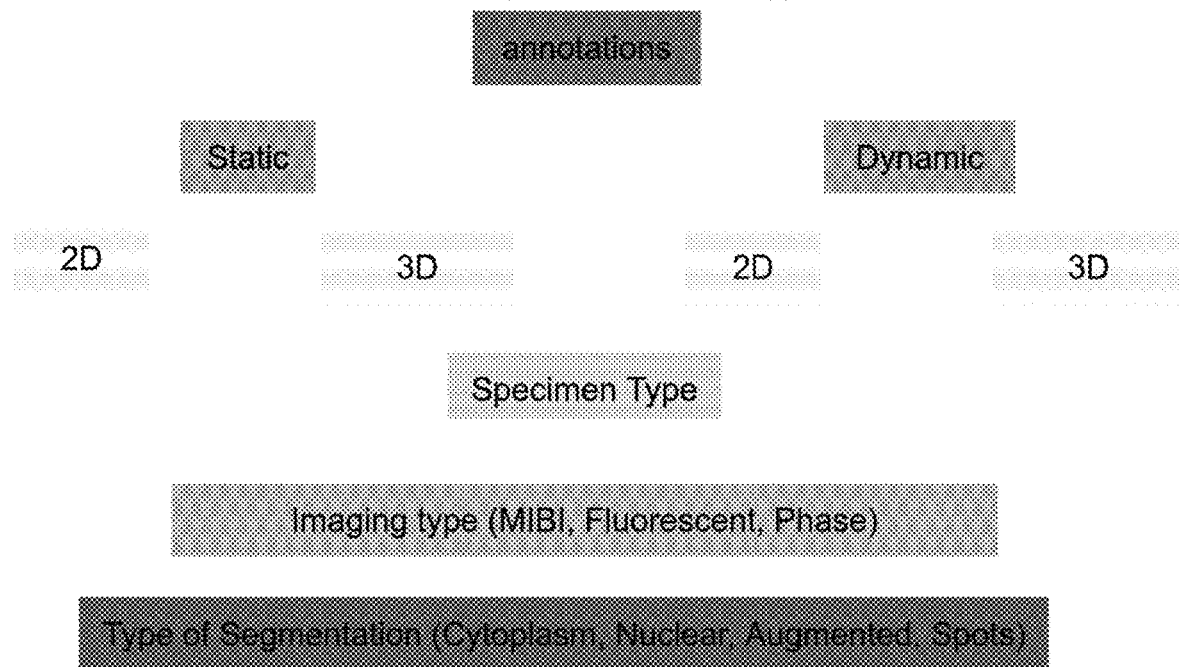
Figure 33C:
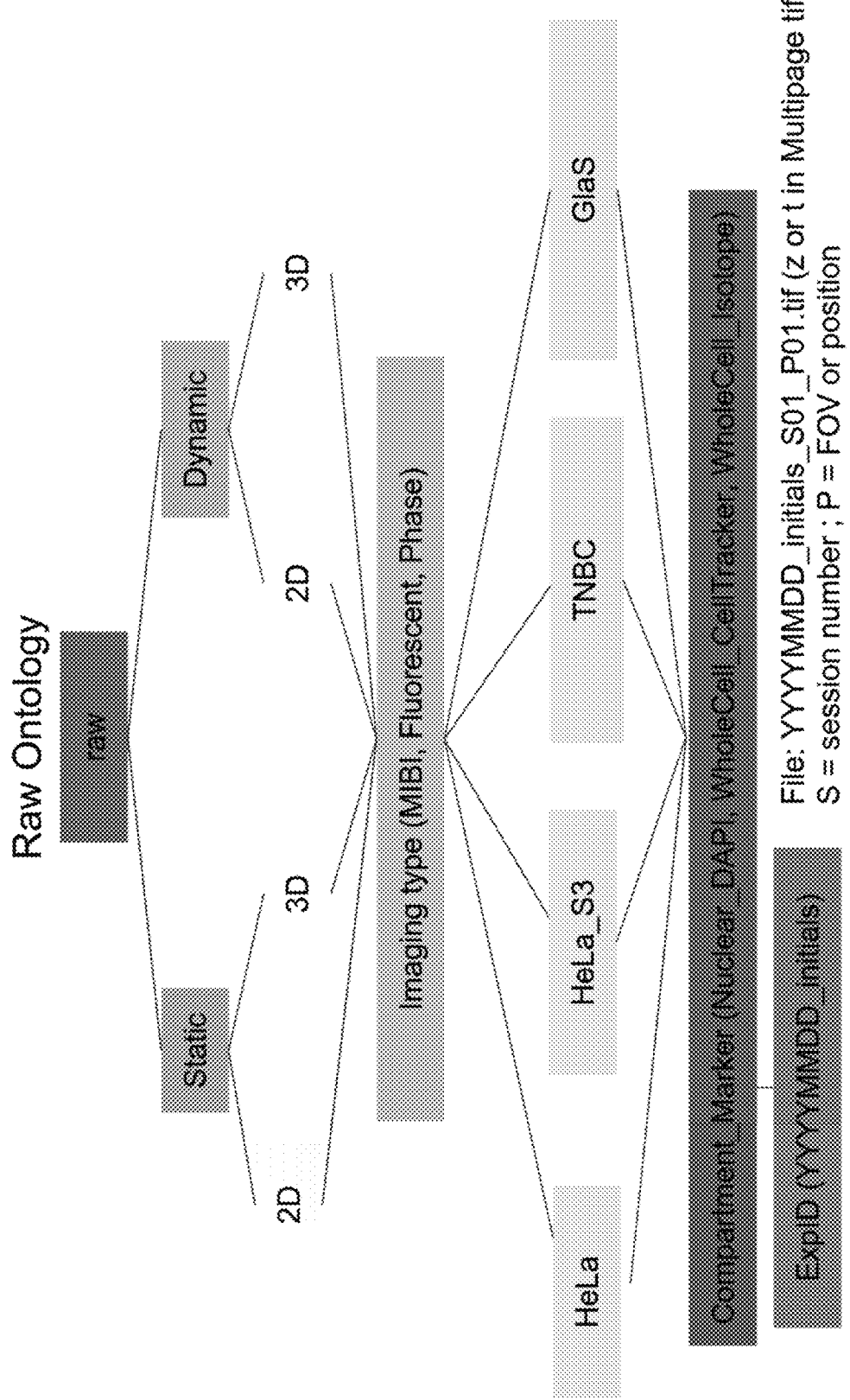

The preferred data ontology for CellNet is as follows in FIGS. 33A-33C.

With the raw data organized according to the CellNet ontology the following can be run to generate crowdsourcing folders. Instructions. Upload.

Examples Caliban Uses

Tracking Mode

Figure 34M:
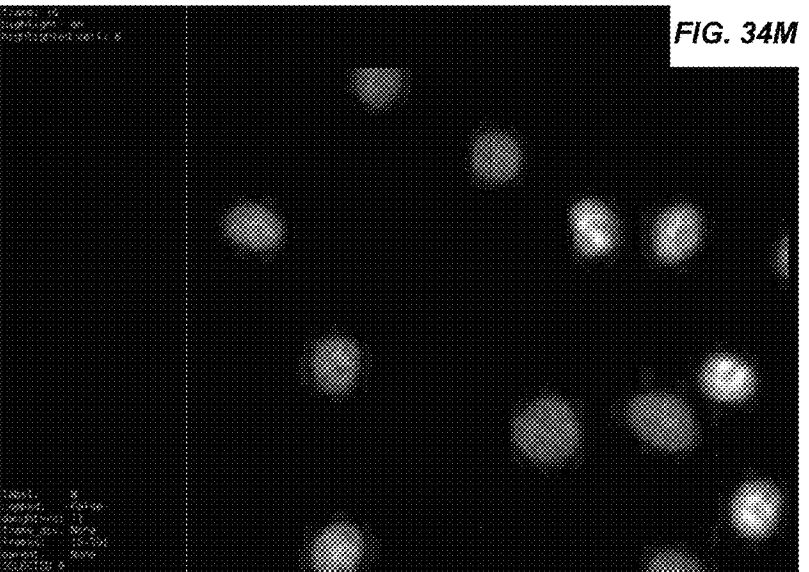
Figure 34N:
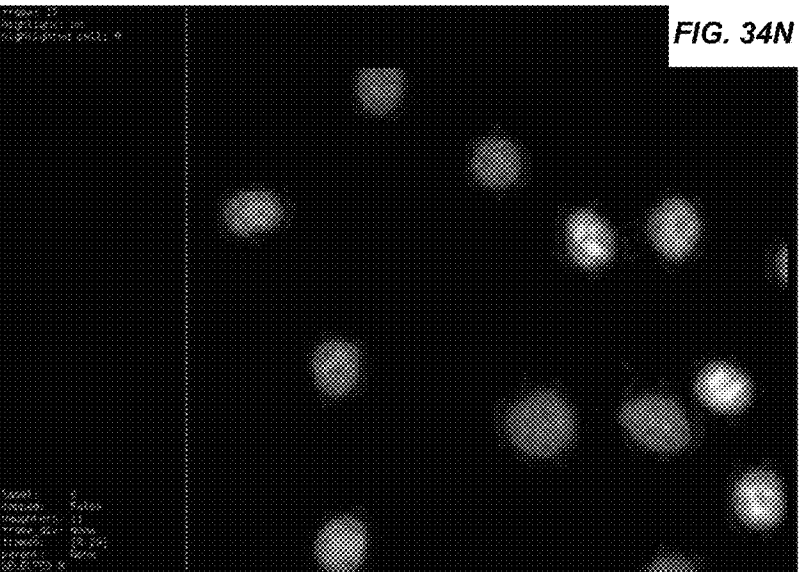
Figure 34O:
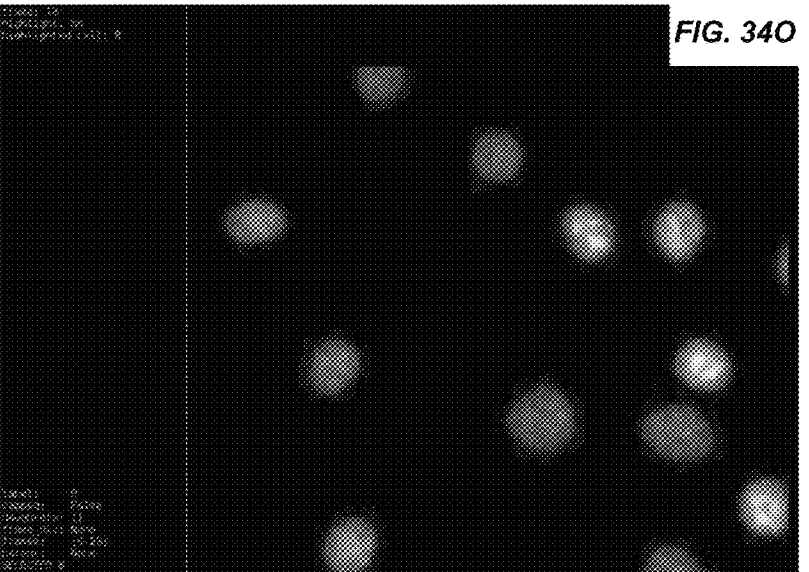
Figure 34P:
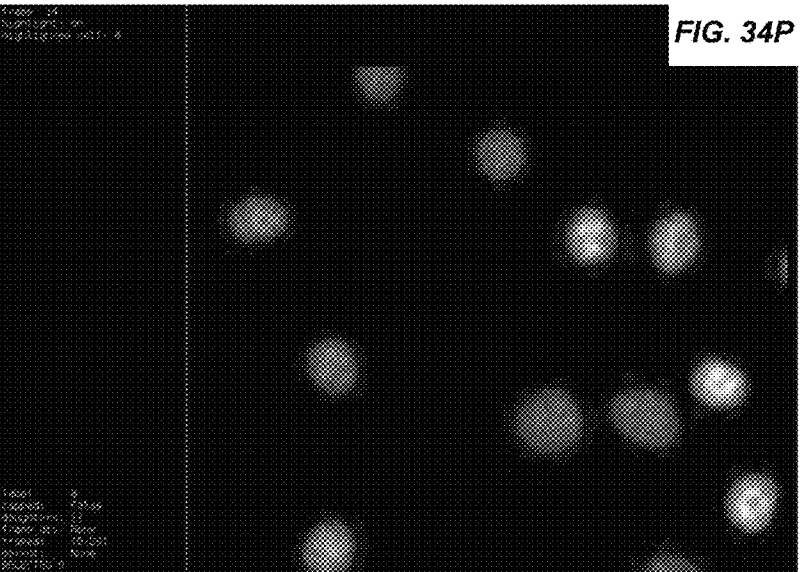
Figure 34R:
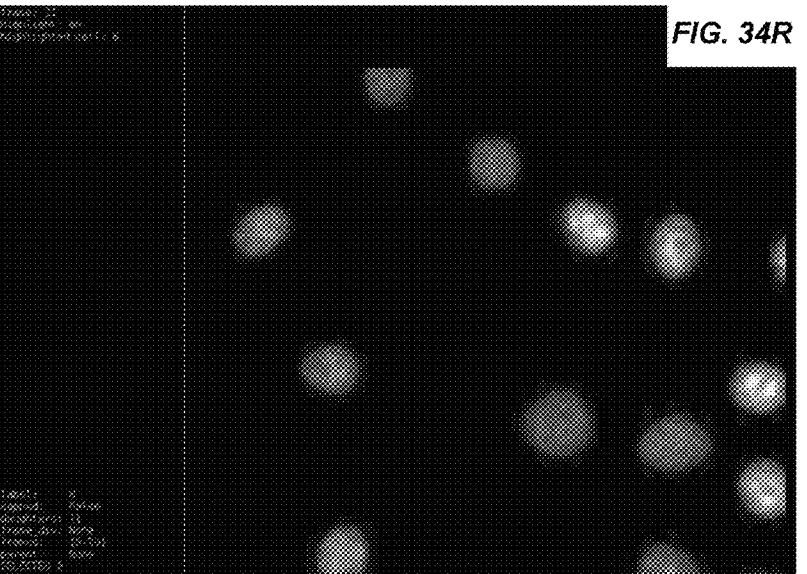
Figure 34T:
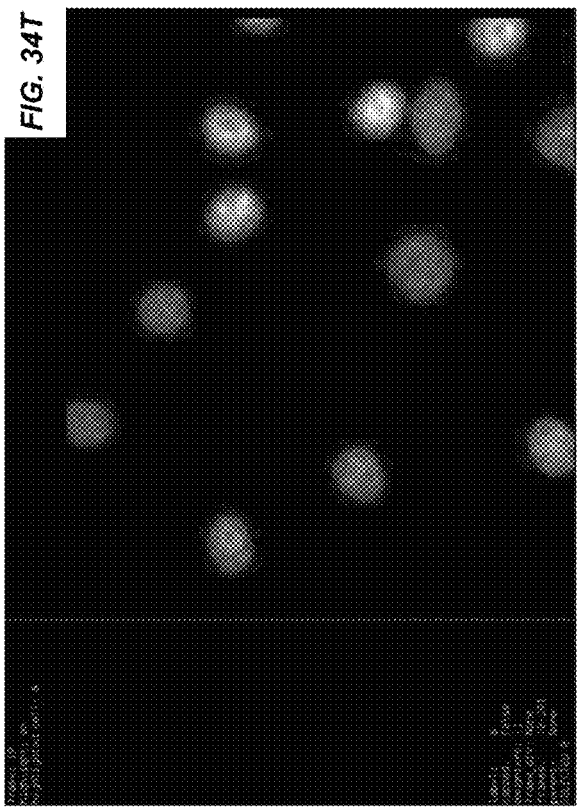
Figure 34Q:
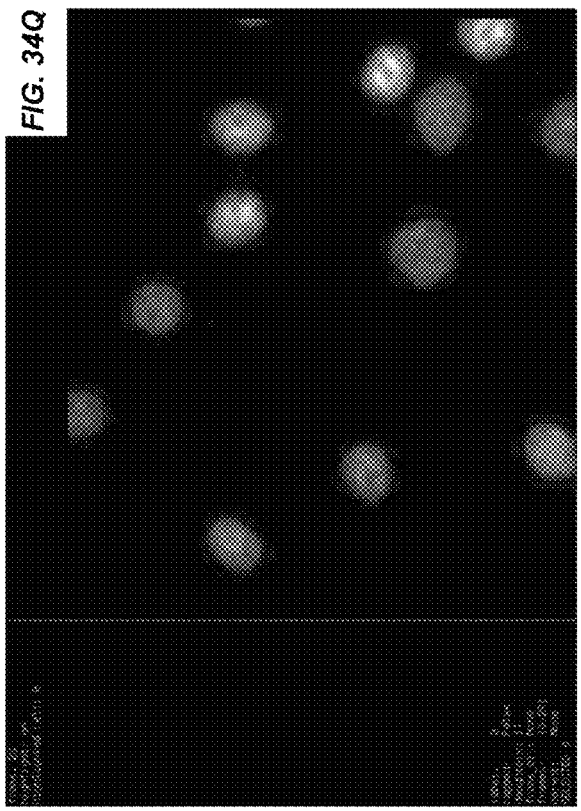
Figure 34S:
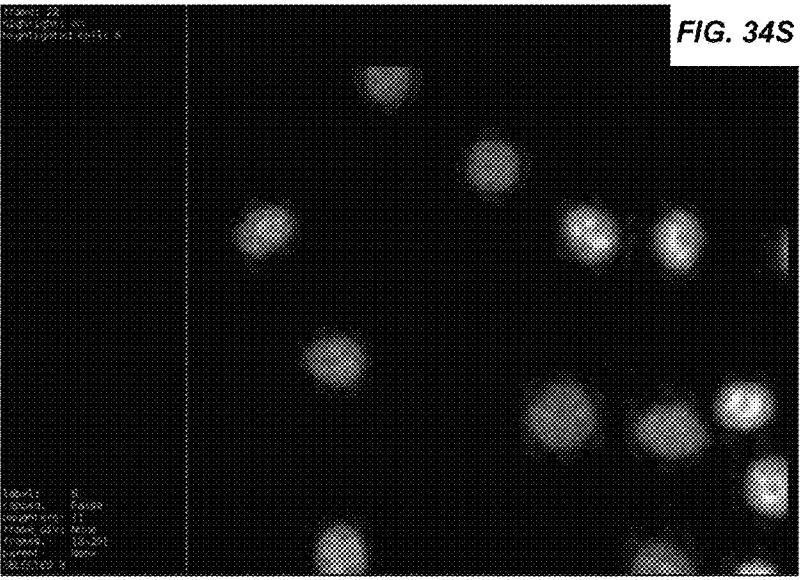

FIGS. 34A-34A2. Desktop Caliban showing raw images of frames from a trk file.

Figure 35E:
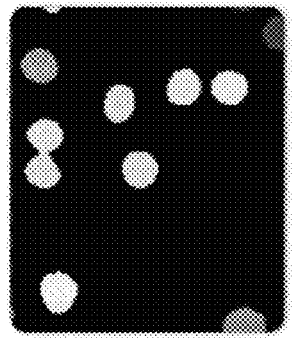
Figure 35F:
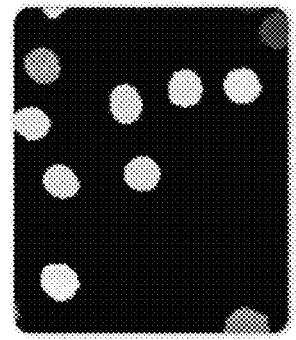
Figure 35G:
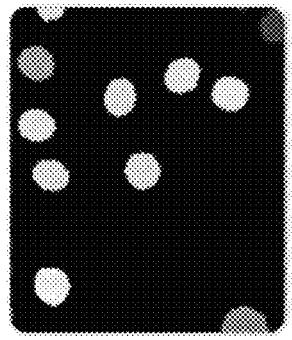
Figure 35H:
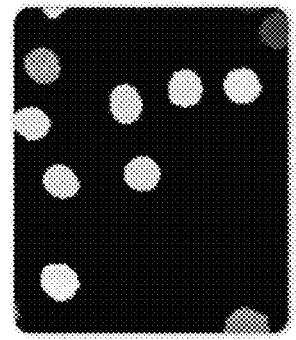
Figure 35J:
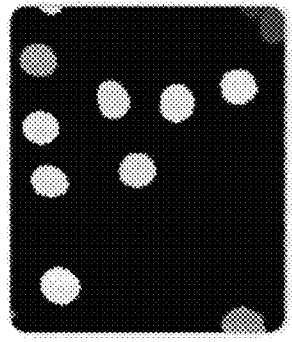
Figure 35L:
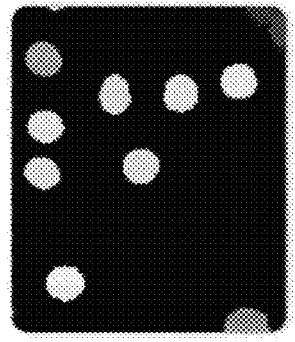
Figure 35I:
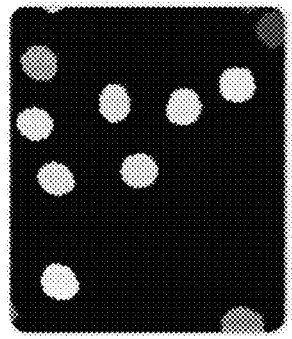
Figure 35K:
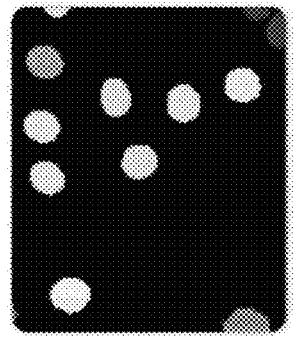
Figure 35N:
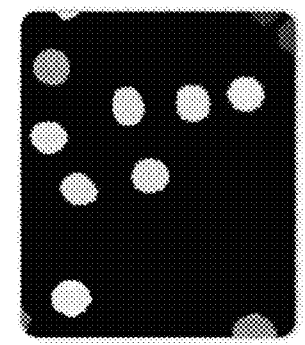
Figure 35M:
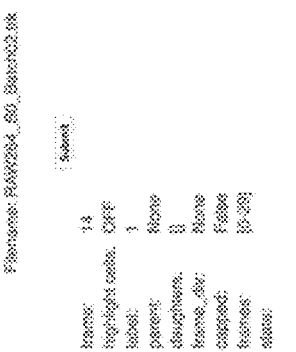
Figure 35P:
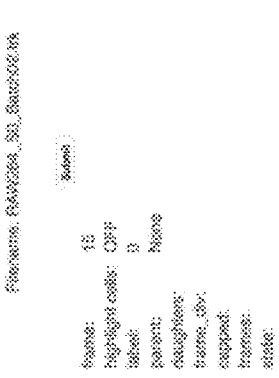
Figure 35O:
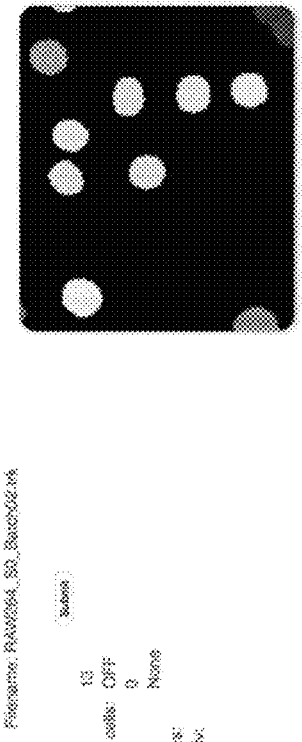
Figure 35R:

Figure 35T:
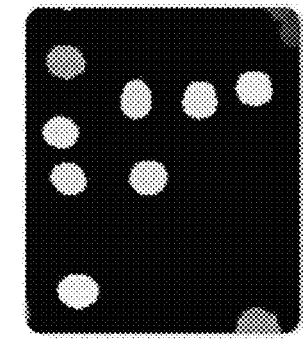
Figure 35Q:
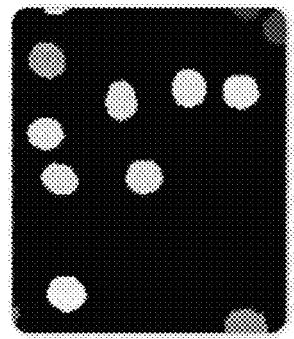
Figure 35S:
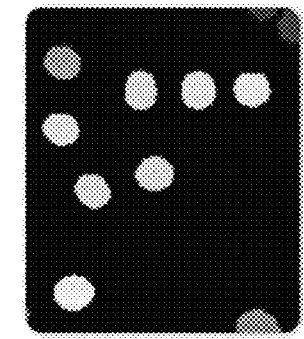
Figure 35U:

Figure 35V:
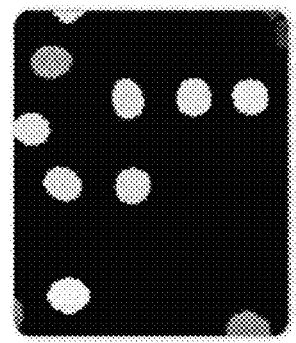
Figure 35W:
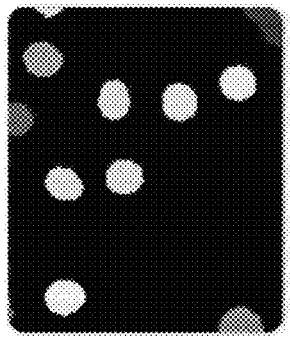
Figure 35X:
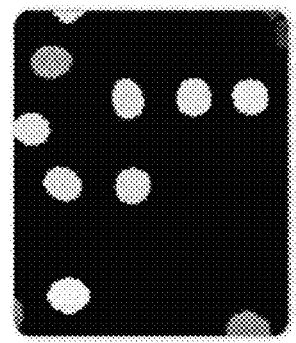
Figure 36A:
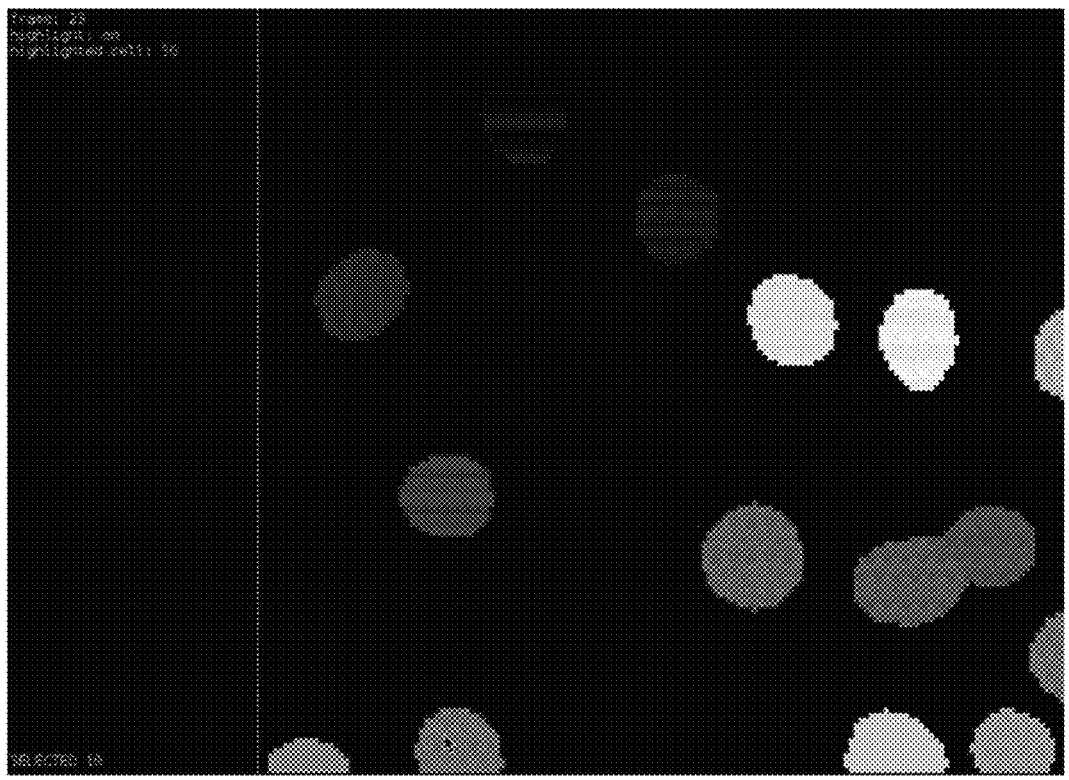
FIGS. 36A-36D. Desktop Caliban showing label selection.
Figure 36B:
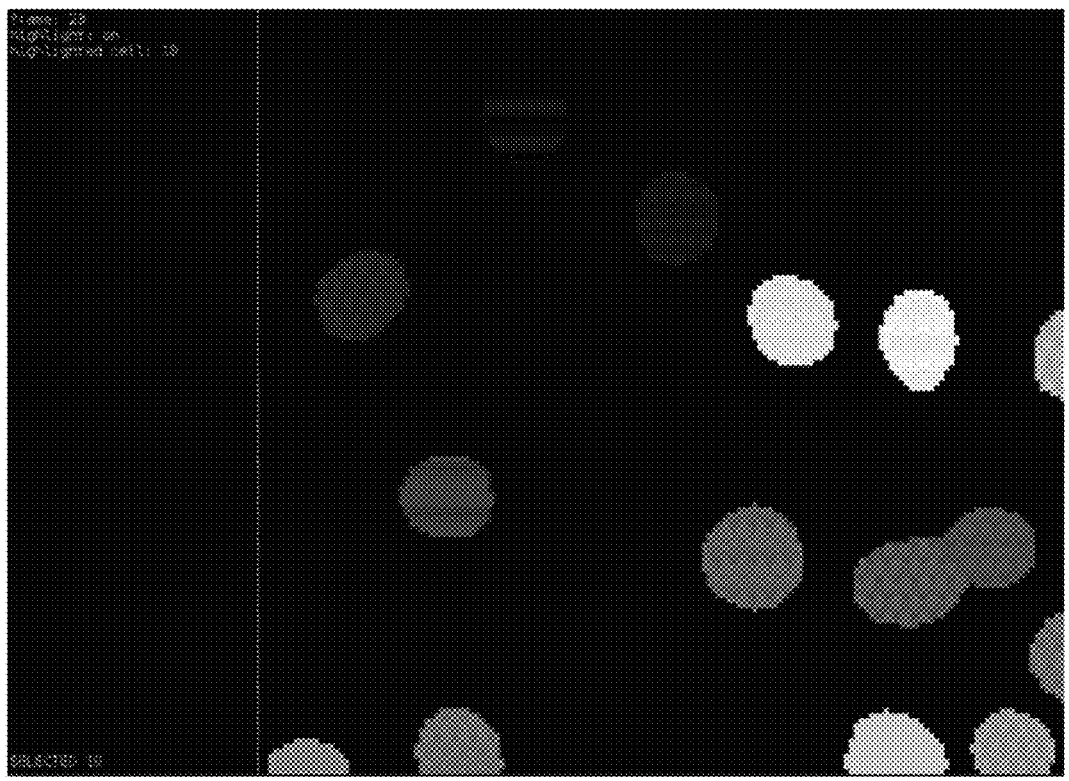
Figure 36C:
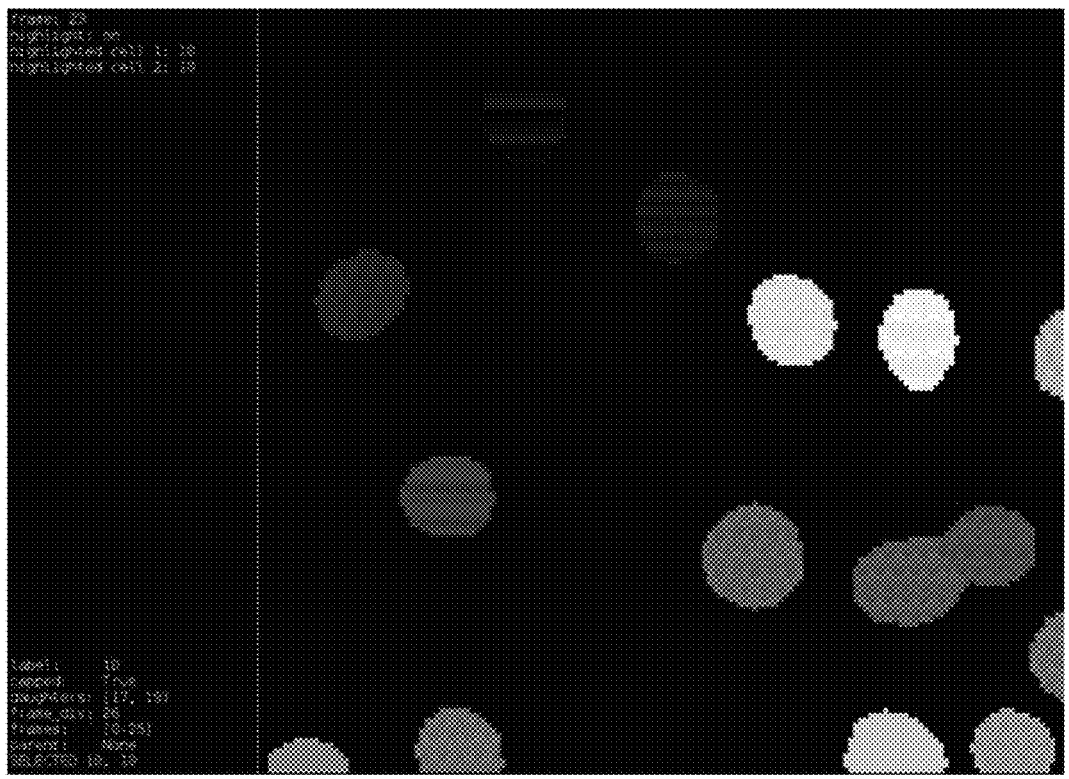
Figure 36D:
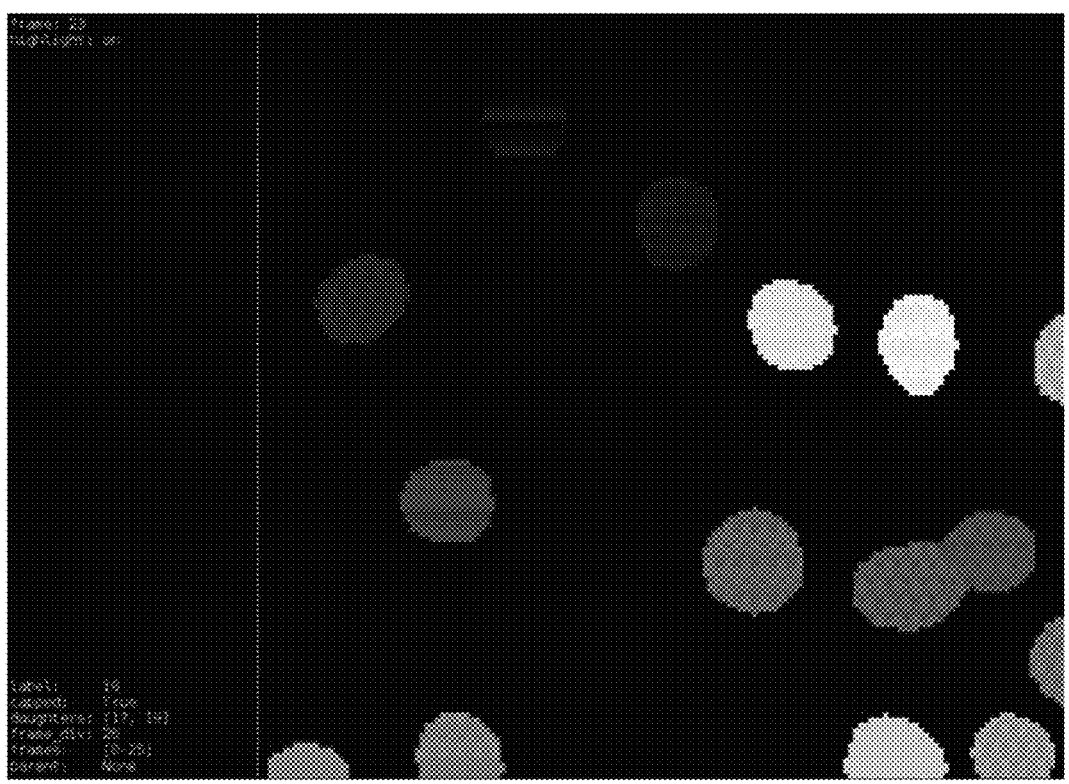
Figure 37A:
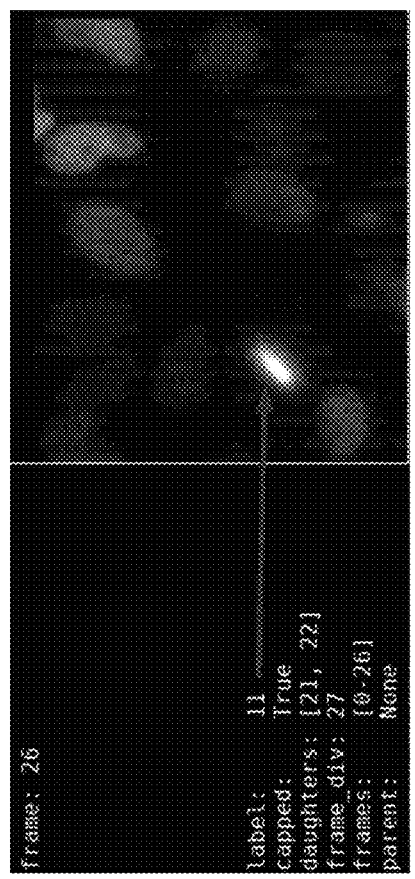
FIGS. 37A-37D. Desktop Caliban displays raw images of two consecutive frames (FIGS. 37A and 37C) and corresponding images comprising cell masks (FIGS. 37B and 37D) showing a cell division event.
Figure 37B:
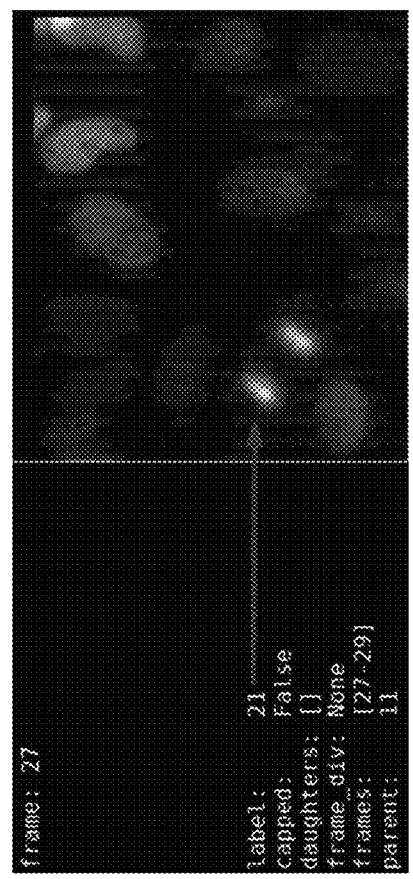
Figure 37C:
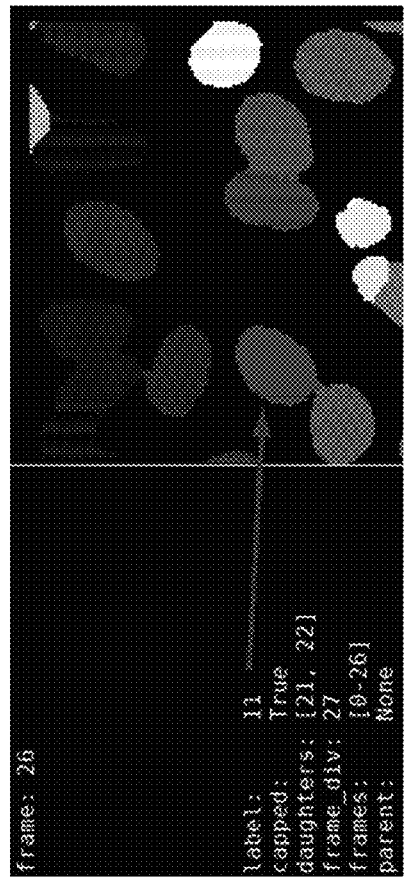
Figure 37D:
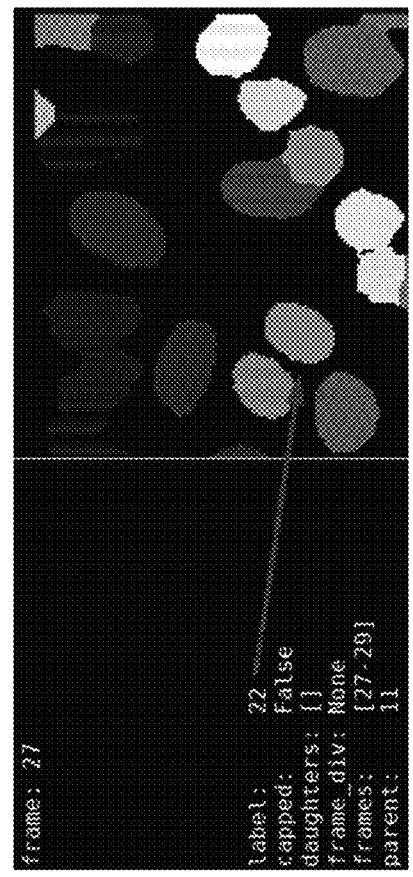

FIGS. 35A-35B2. Browser Caliban showing images comprising cell masks of frames from a trk file.

FIGS. 36A-36D. Desktop Caliban showing label selection.

FIGS. 37A-37D. Desktop Caliban displaying raw images of two consecutive frames (FIGS. 37A and 37C) and corresponding images comprising cell masks (FIGS. 37B and 37D) showing a cell division event.

Z-Stack Mode

Figure 38E:
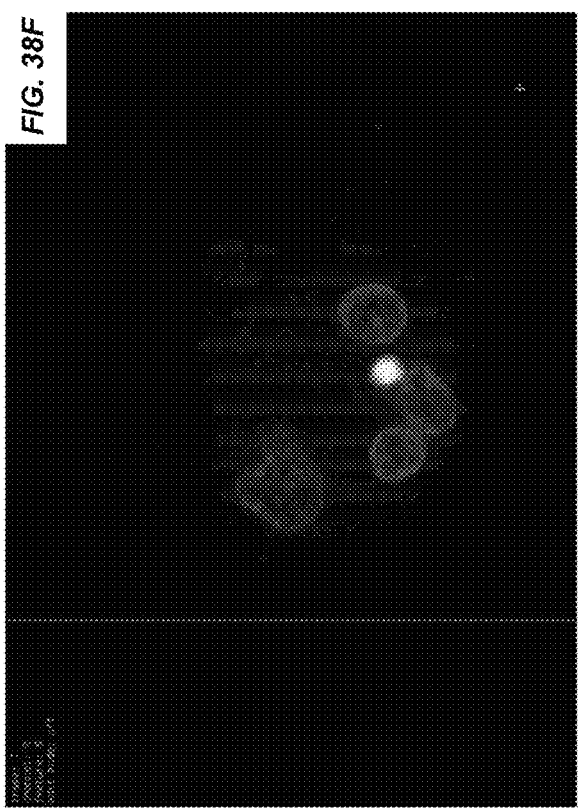
FIGS. 38A-38T. Desktop Caliban showing raw images of frames of a Z-stack from a npz file.
Figure 38F:
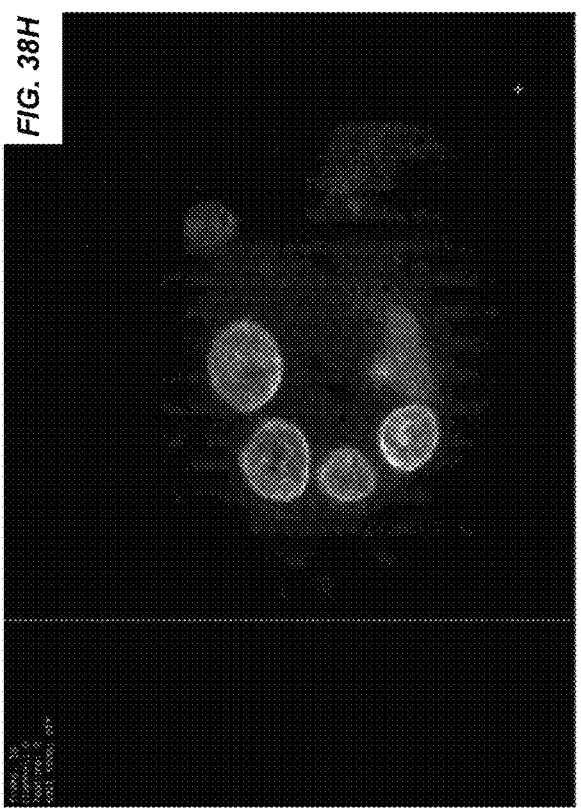
Figure 38G:
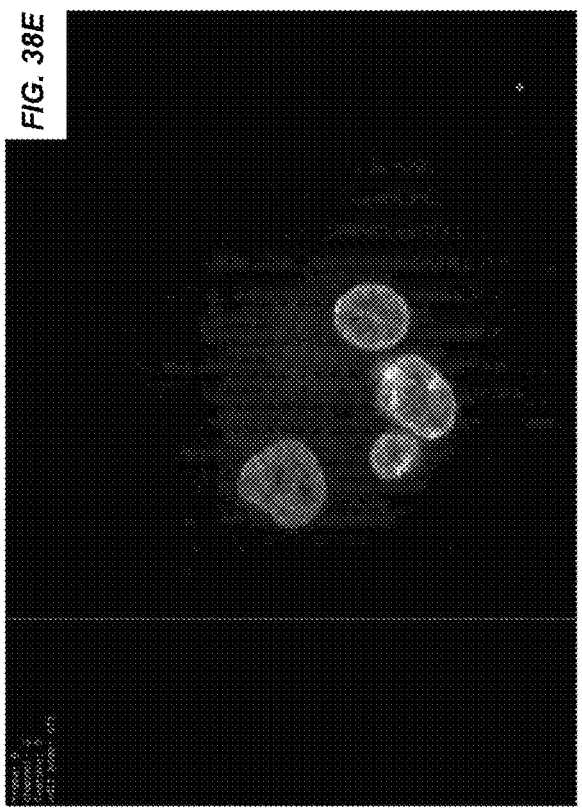
Figure 38H:
Figure 38J:
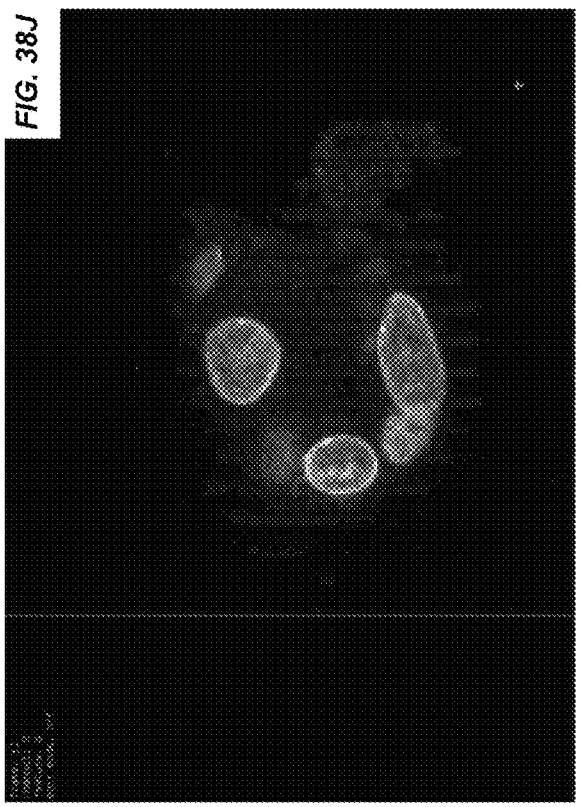
Figure 38L:
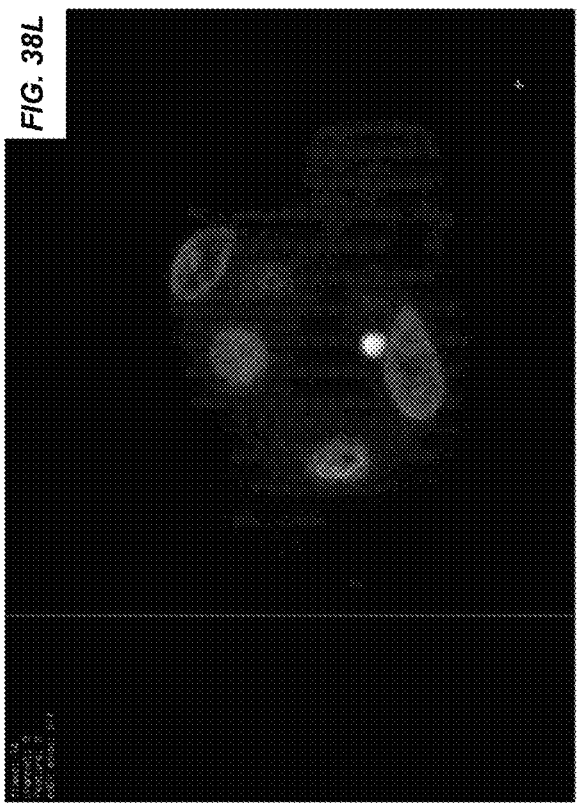
Figure 38I:
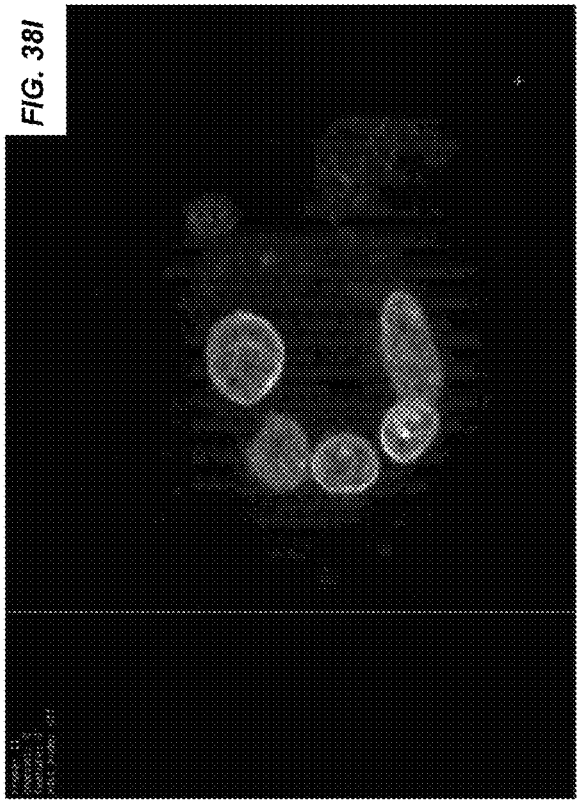
Figure 38K:
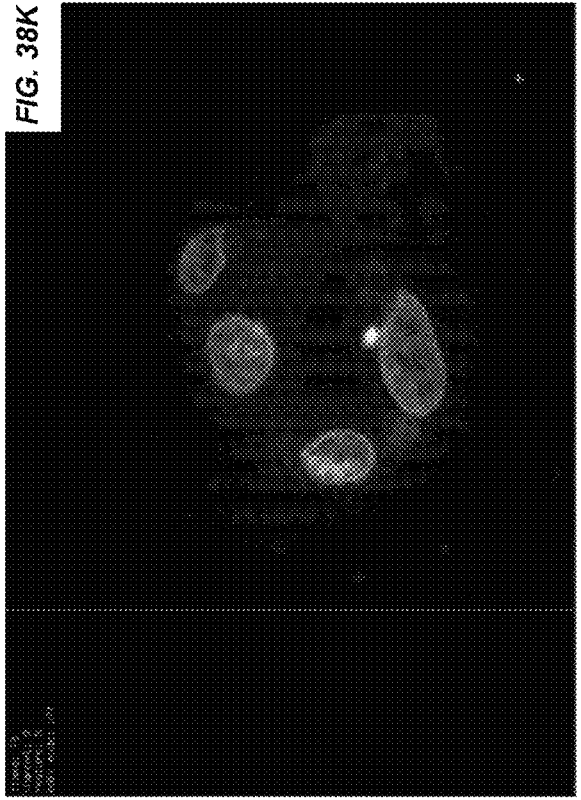
Figure 38N:
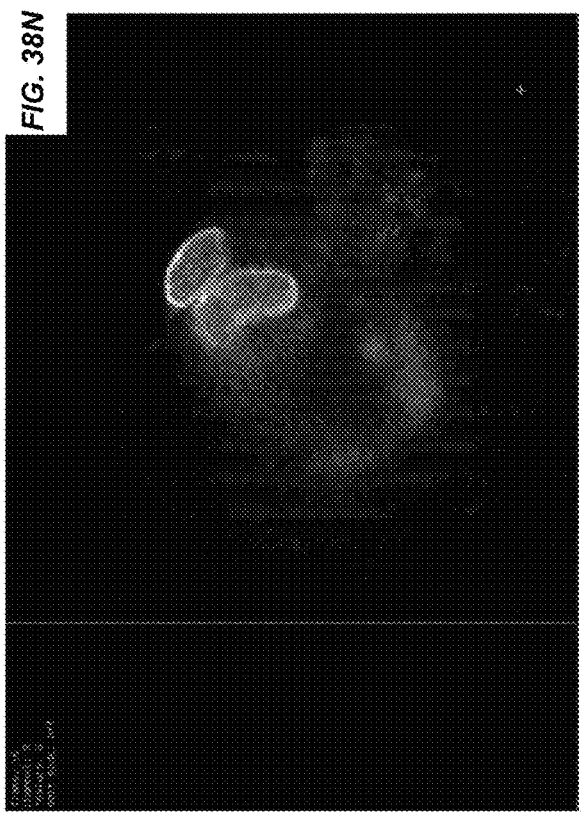
Figure 38P:
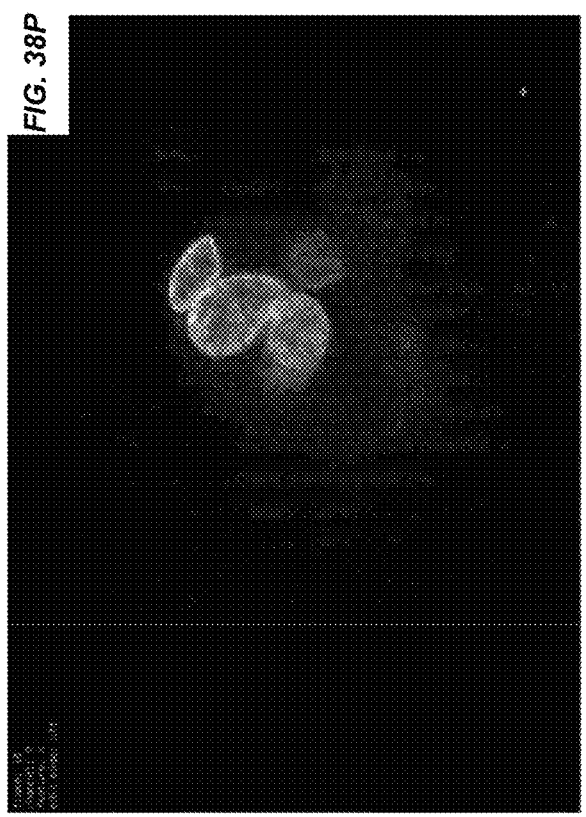
Figure 38M:
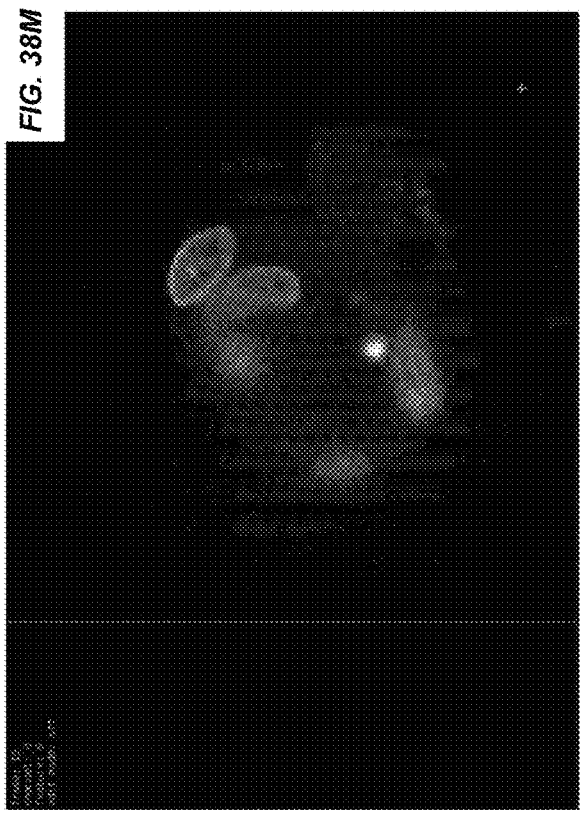
Figure 38O:
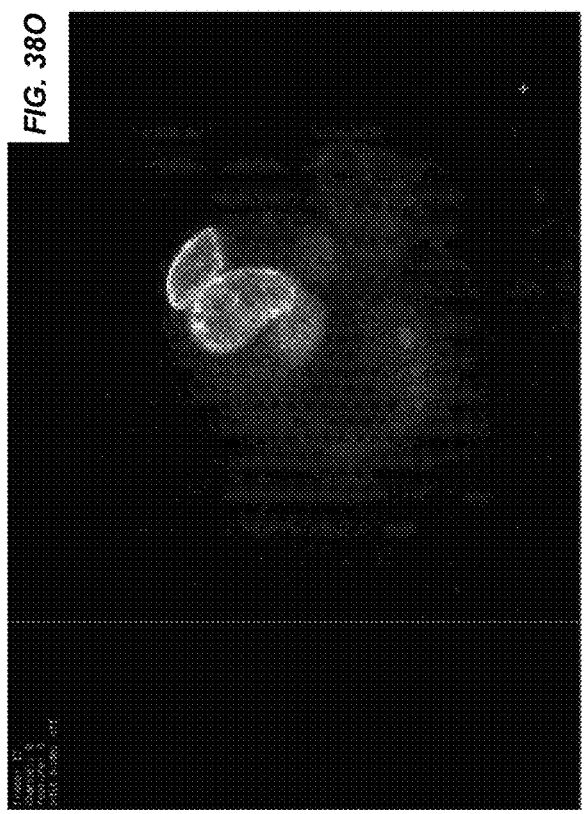
Figure 39A:
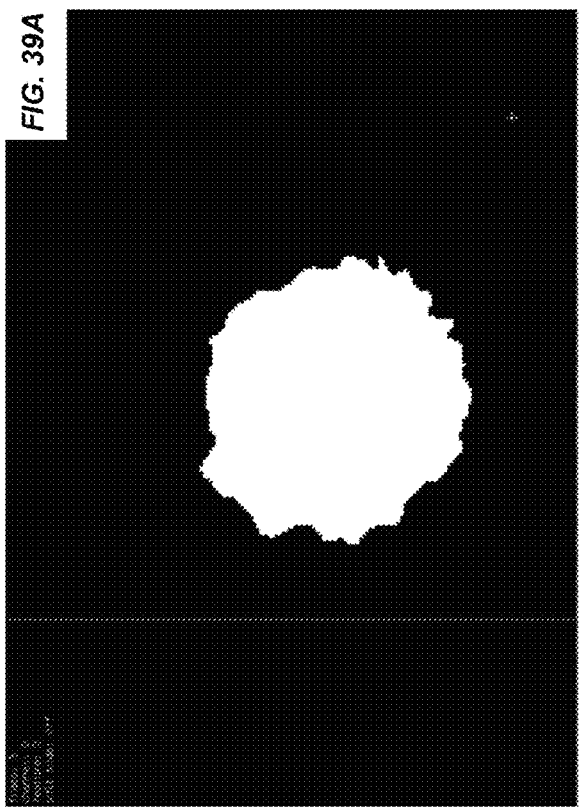
FIGS. 39A-39R. Desktop Caliban showing images comprising cell masks of frames of a Z-stack from a npz file.
Figure 39B:
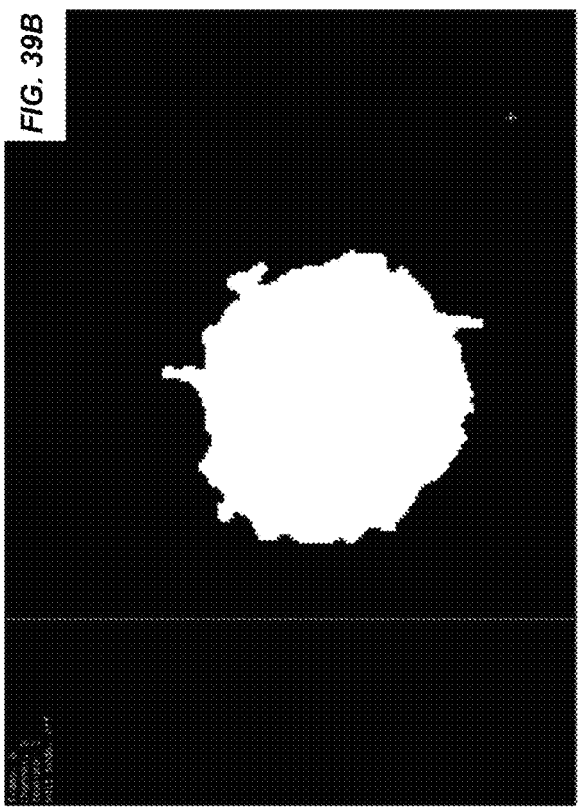
Figure 39C:
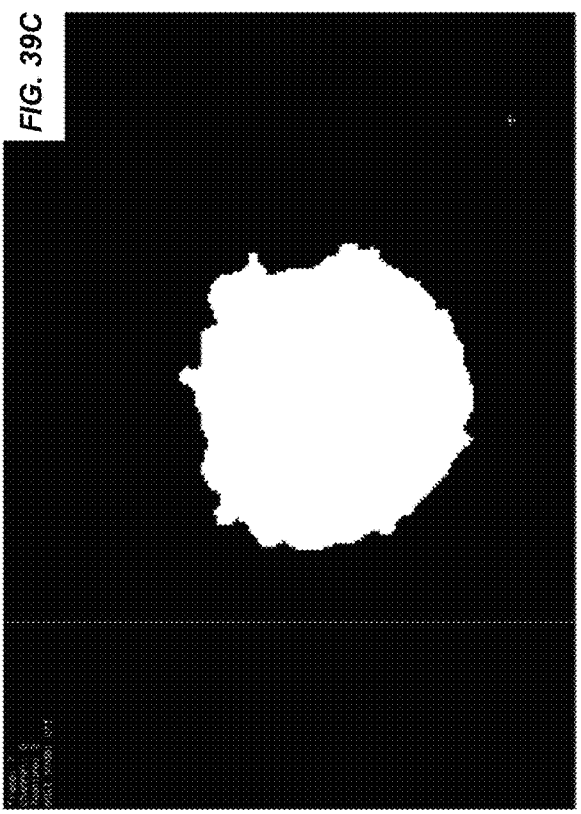
Figure 39D:
Figure 39F:
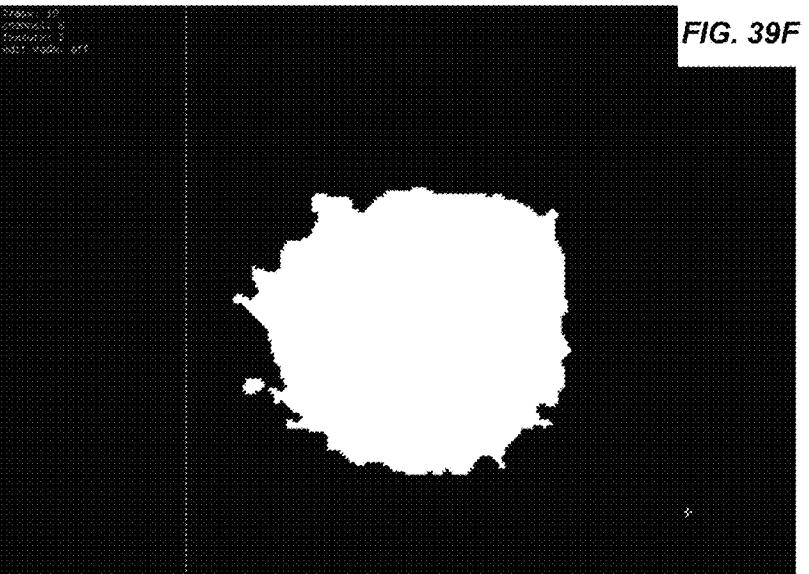
Figure 39H:
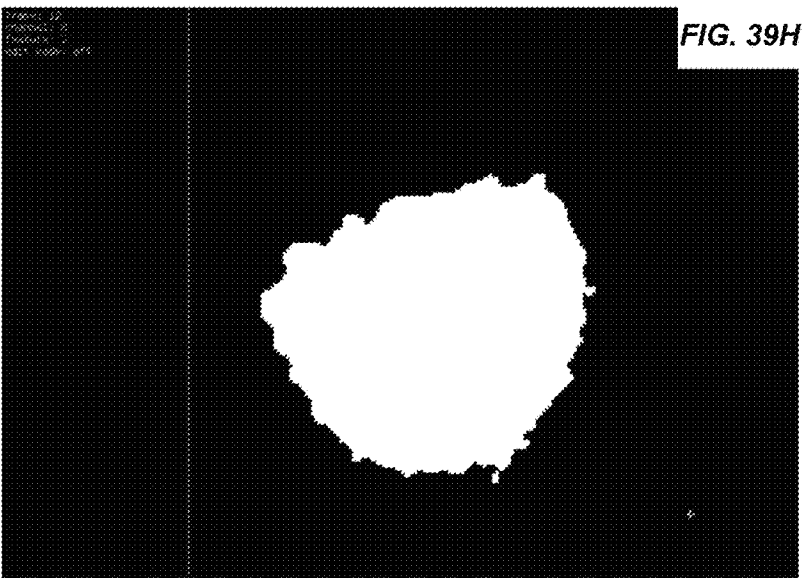
Figure 39E:
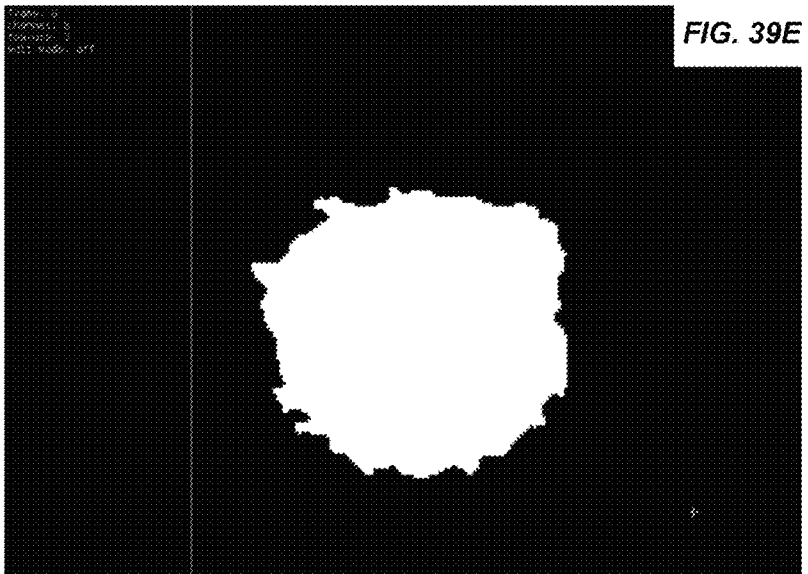
Figure 39G:
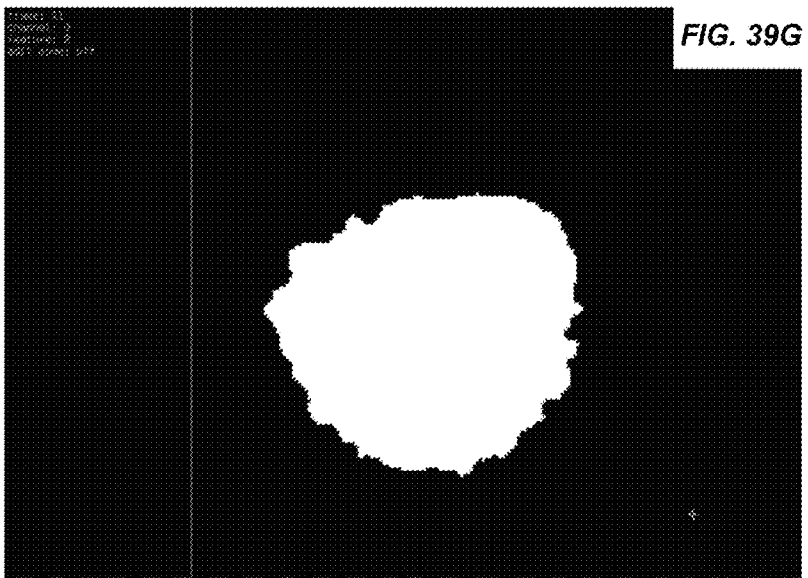
Figure 39J:
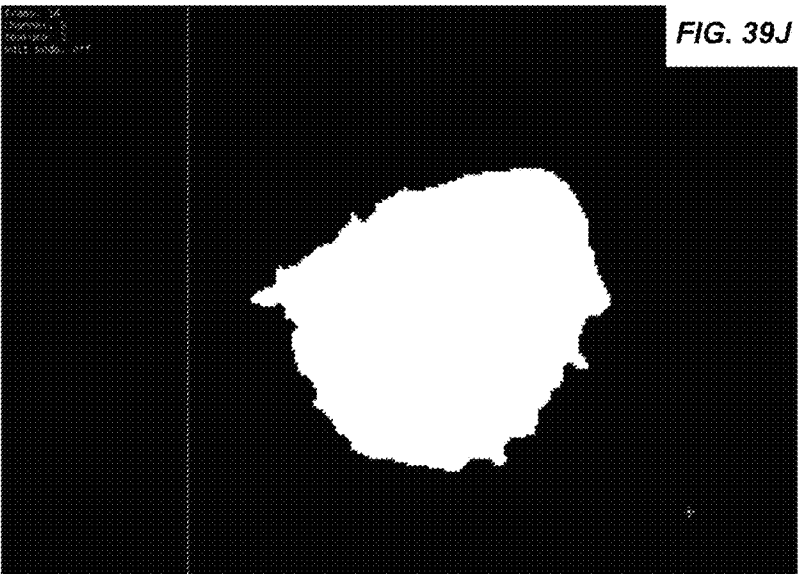
Figure 39L:
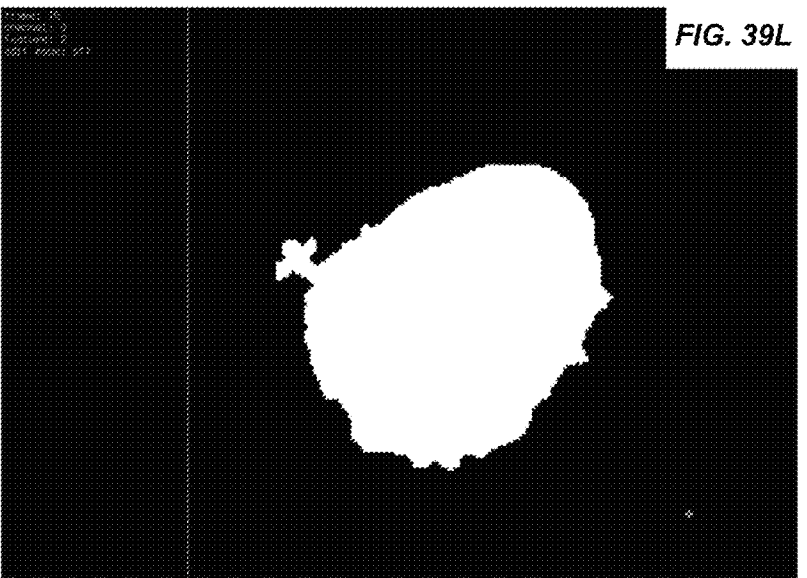
Figure 39I:
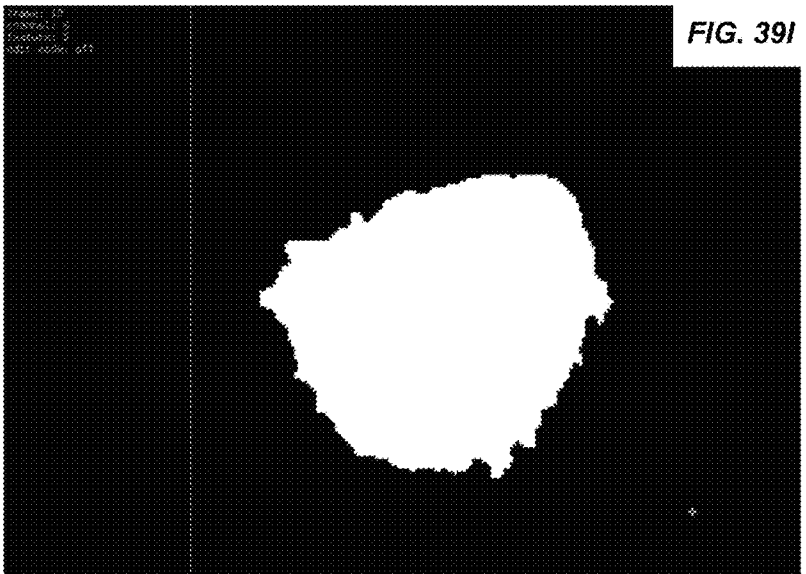
Figure 39K:
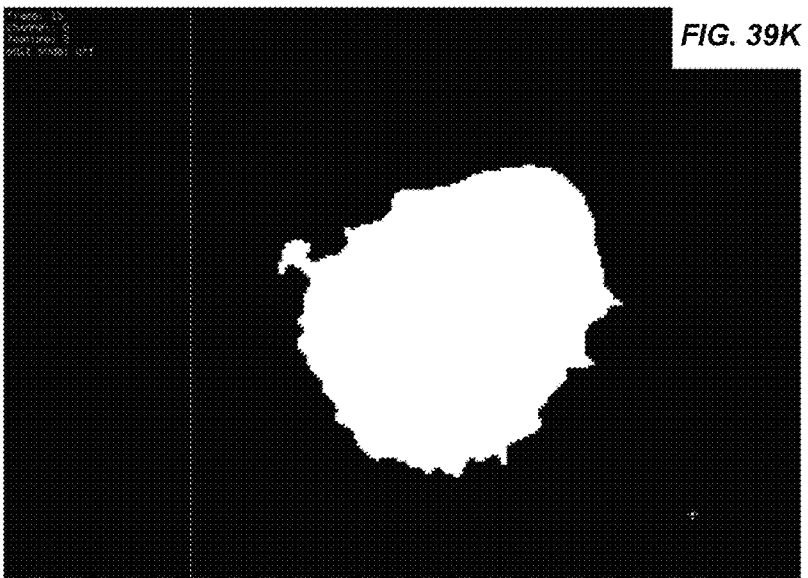
Figure 39R:
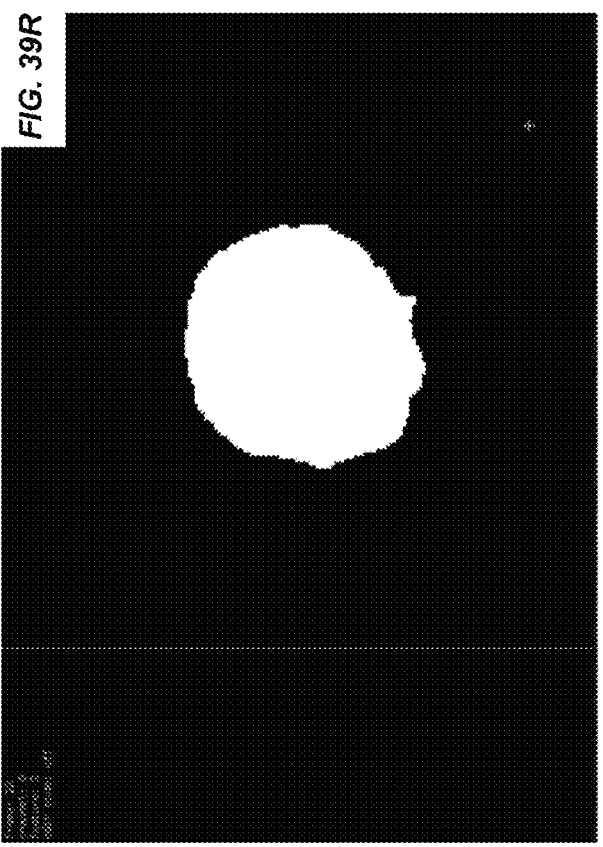
Figure 39Q:
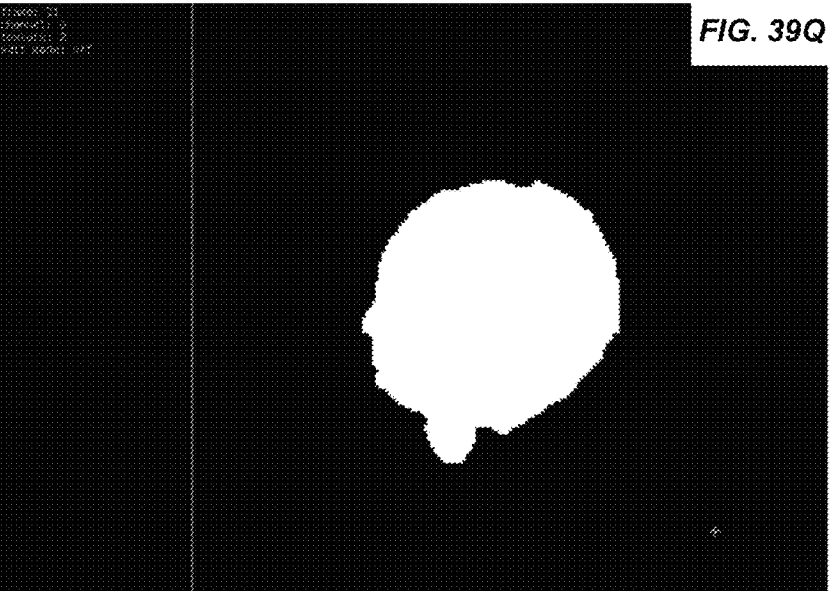

FIGS. 38A-38T. Desktop Caliban showing raw images of frames of a Z-stack from a npz file. FIGS. 39A-39R. Desktop Caliban showing images comprising cell masks of frames of the Z-stack from a npz file.

Figure 40A:
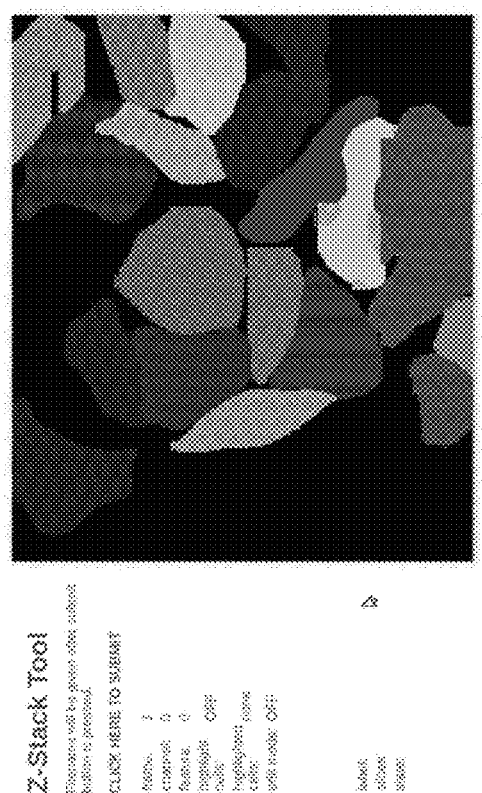
FIGS. 40A-40P. Changing frames forward and backward works with any display options in Caliban.
Figure 40B:
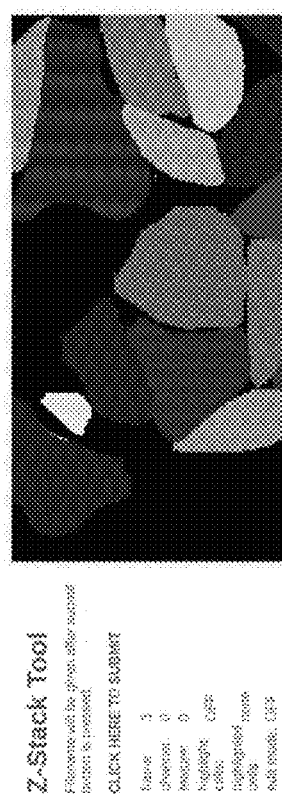
Figure 40C:
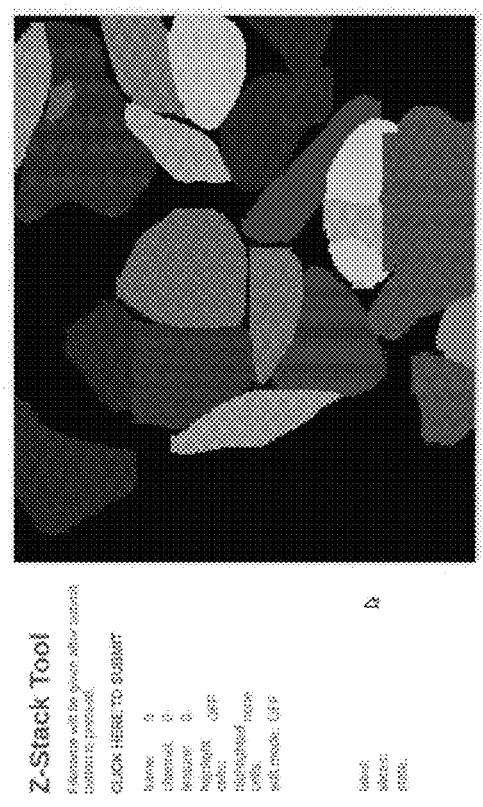
Figure 40D:
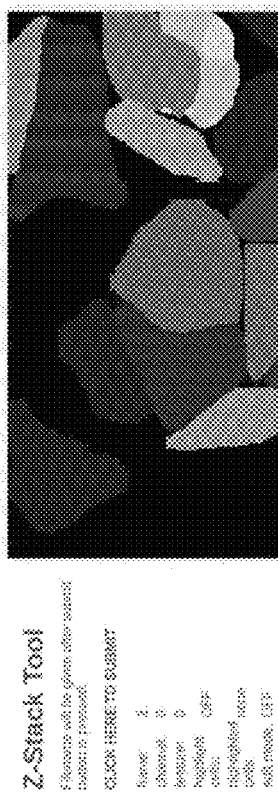
Figure 40F:
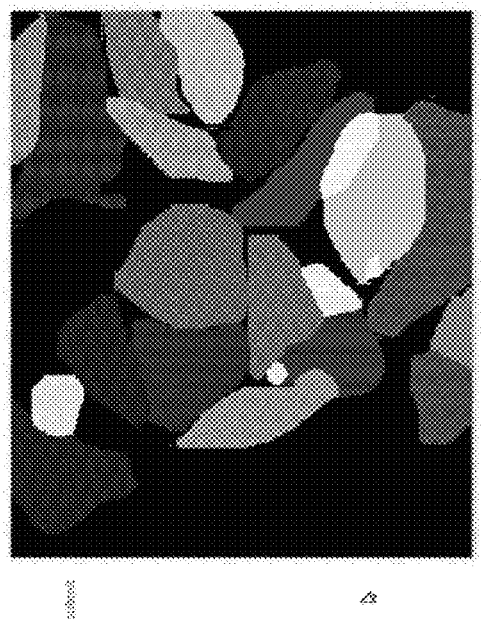
Figure 40H:
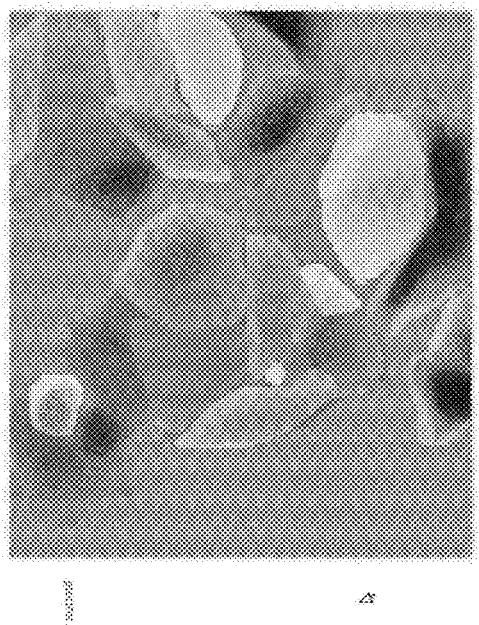
Figure 40E:
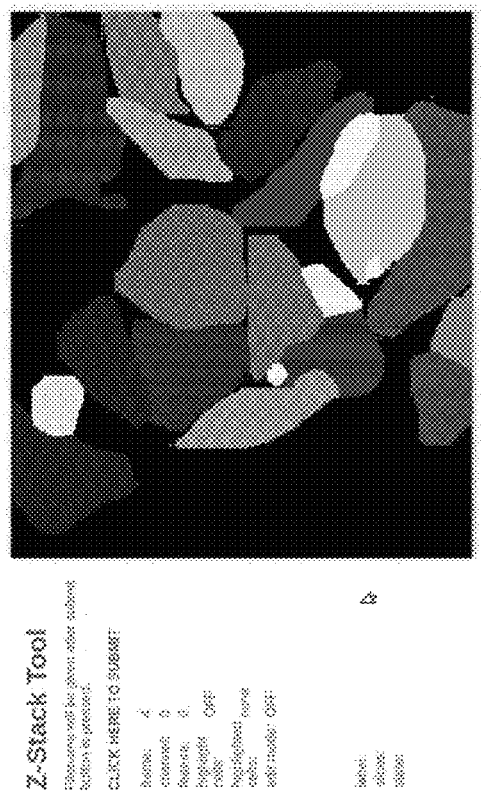
Figure 40G:
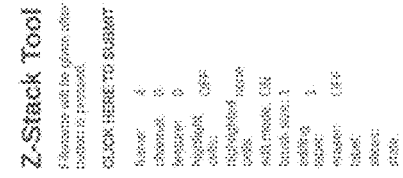
Figure 40J:
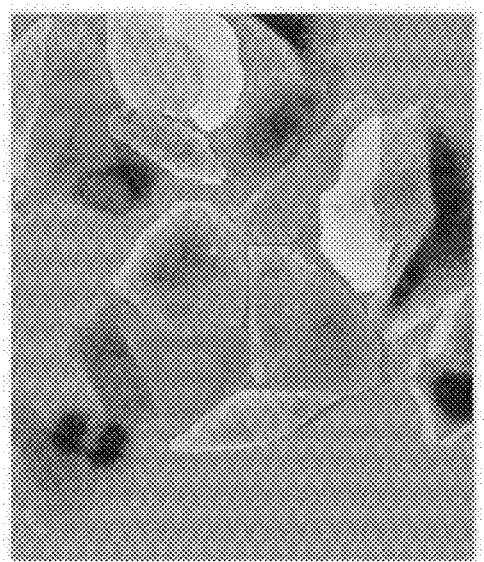
Figure 40L:
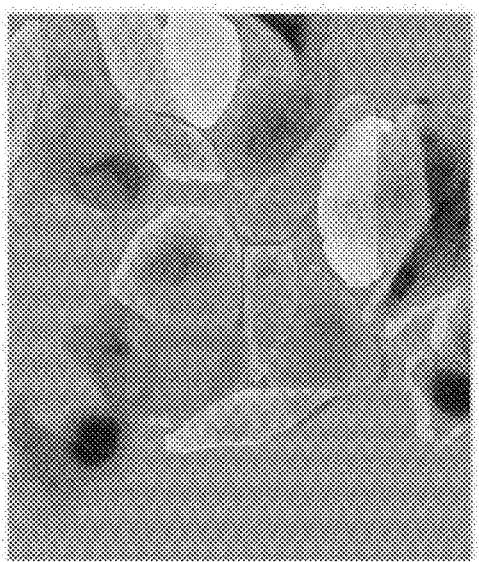
Figure 40I:
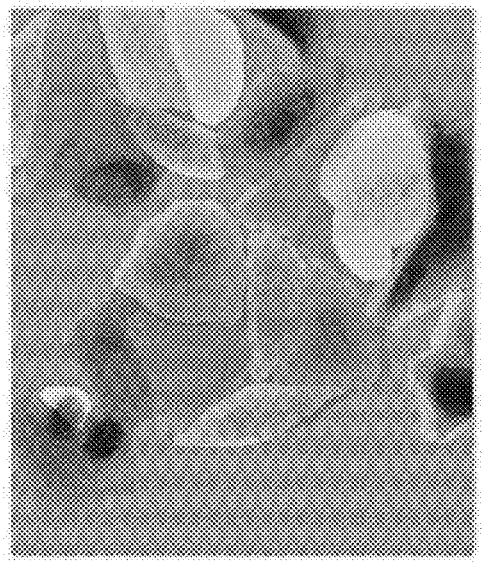
Figure 40K:
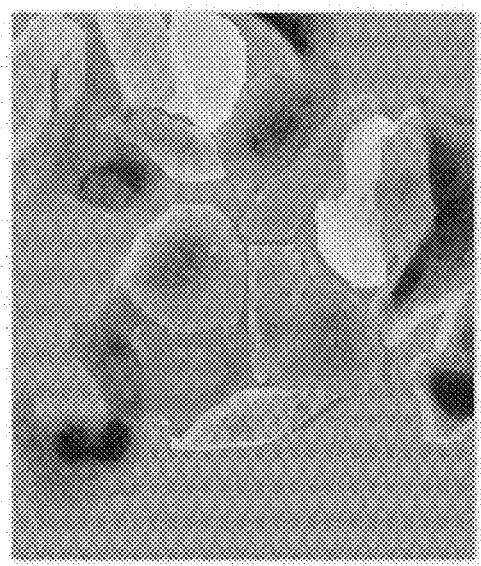
Figure 41A:
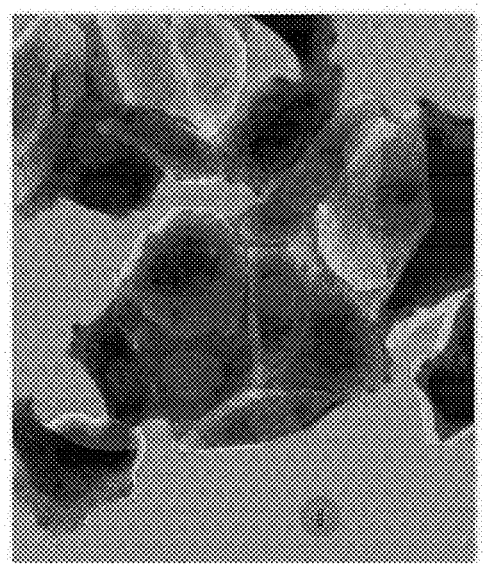
FIGS. 41A-41W. Contrast adjustment and color inversion of raw image.
Figure 41B:
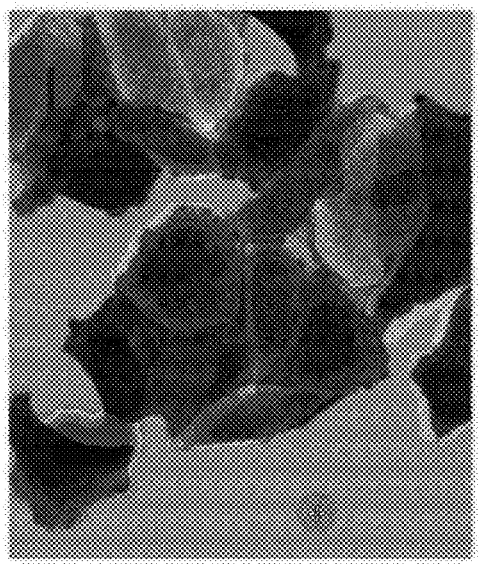
Figure 41C:
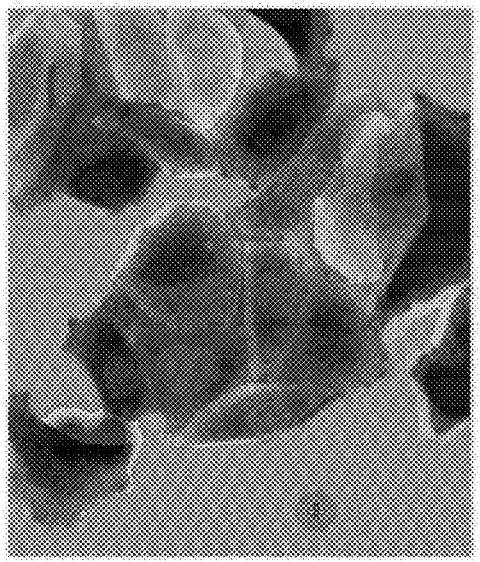
Figure 41D:
Figure 41J:
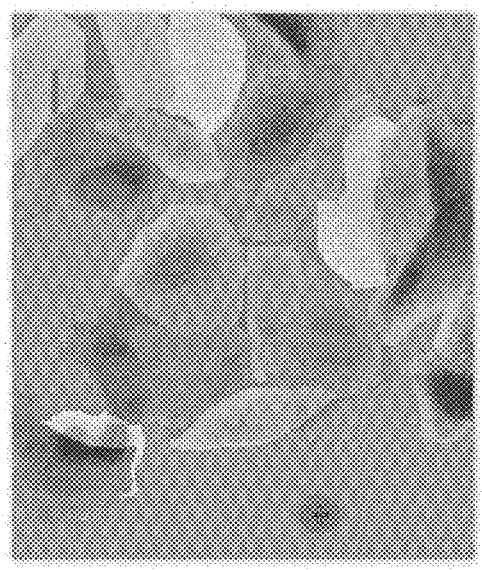
Figure 41L:
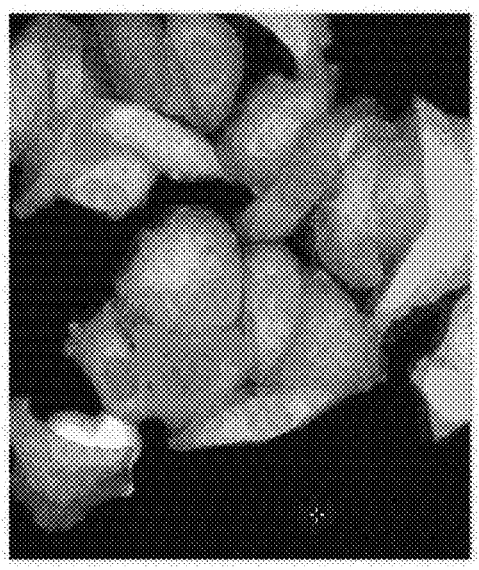
Figure 41I:
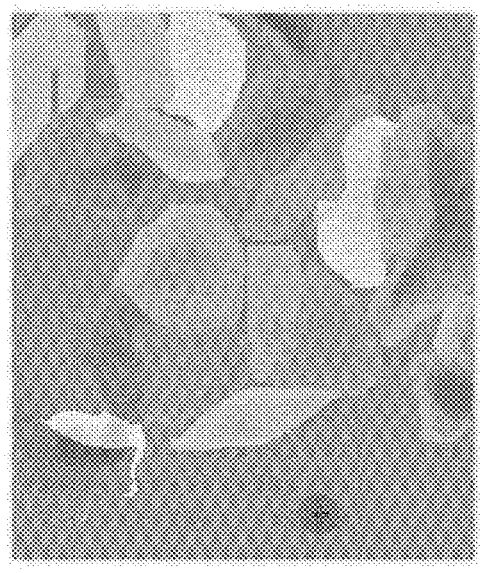
Figure 41K:
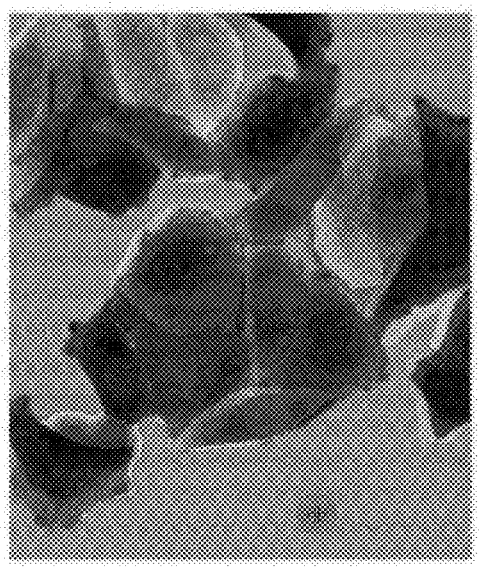
Figure 41M:
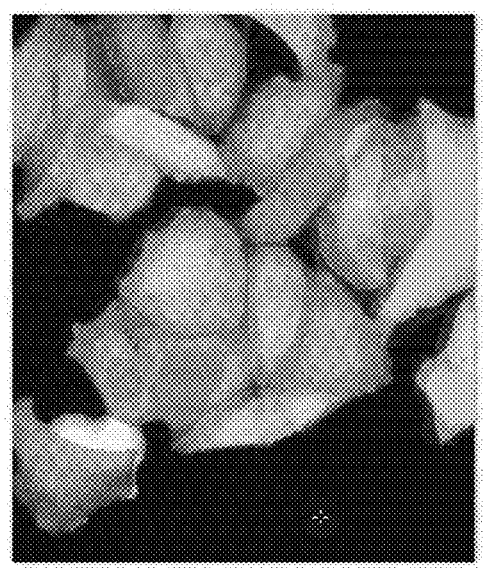
Figure 41N:
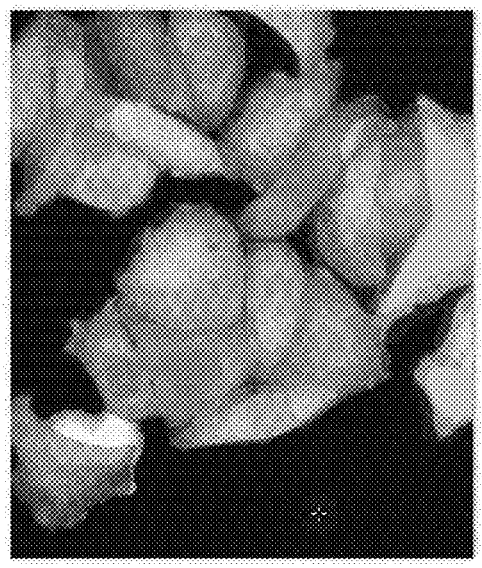
Figure 41O:
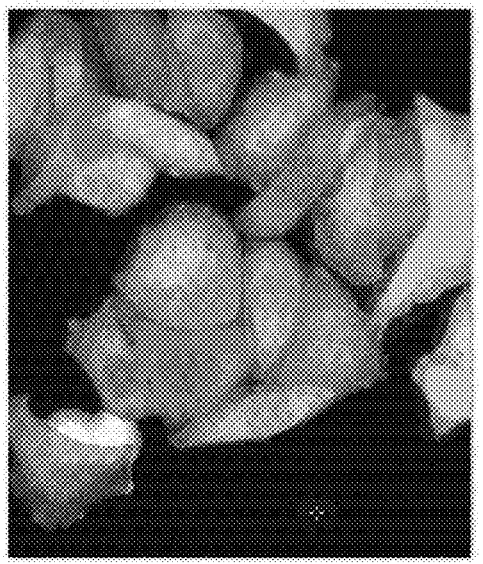
Figure 41P:
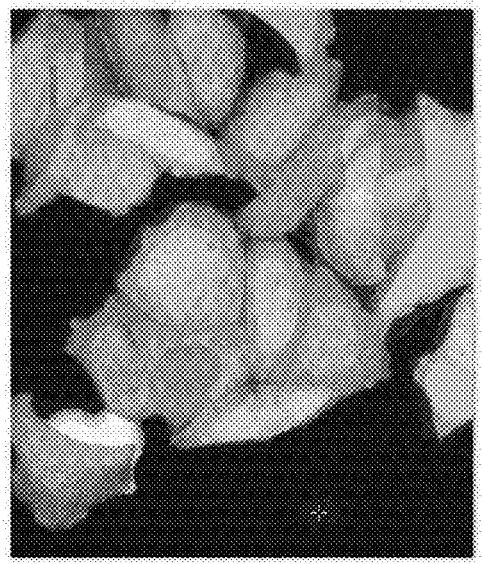
Figure 41Q:
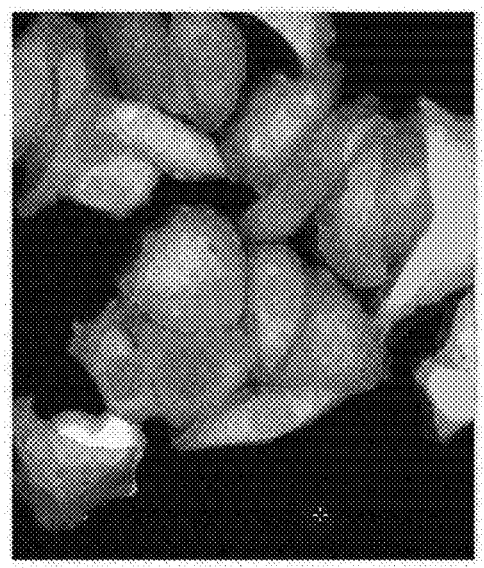
Figure 41R:
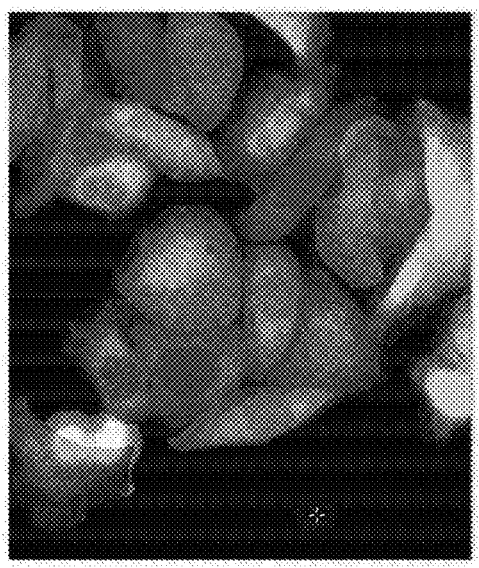
Figure 41S:
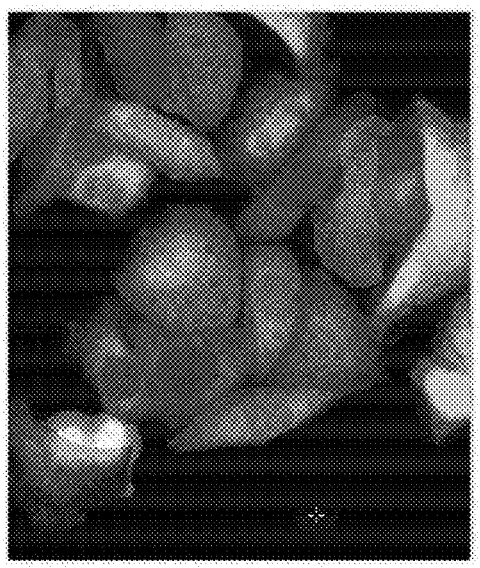
Figure 41T:
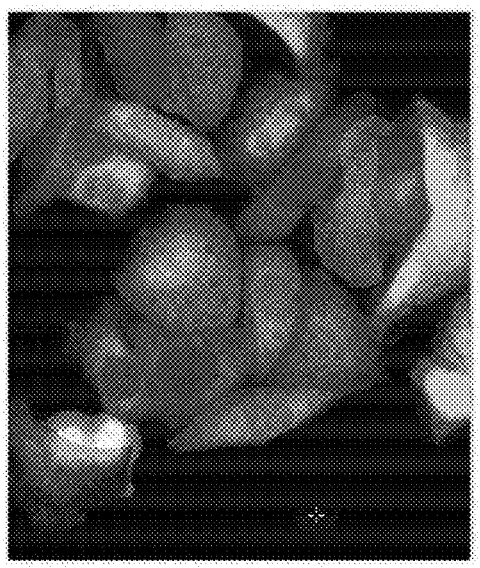
Figure 42A:
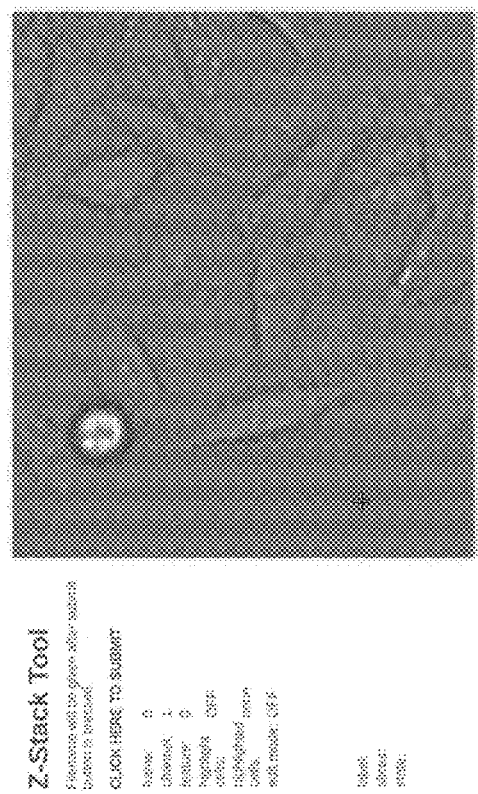
Figure 42B:
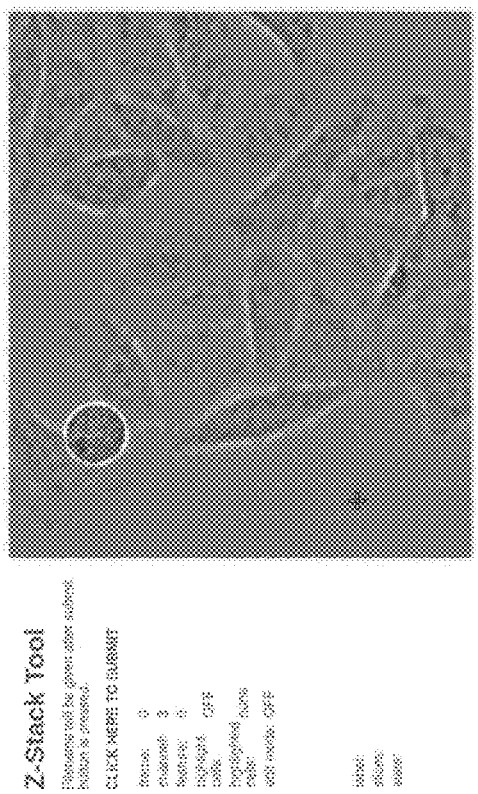
Figure 42C:
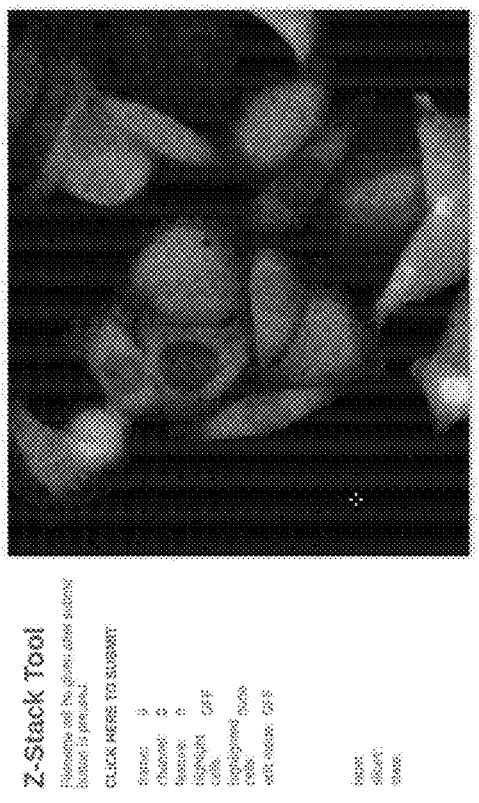
Figure 42D:
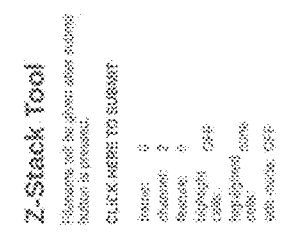

FIGS. 41A-40P. Changing frames forward and backward works with any display options in Caliban.

Figures 41U, 41V, 41W:
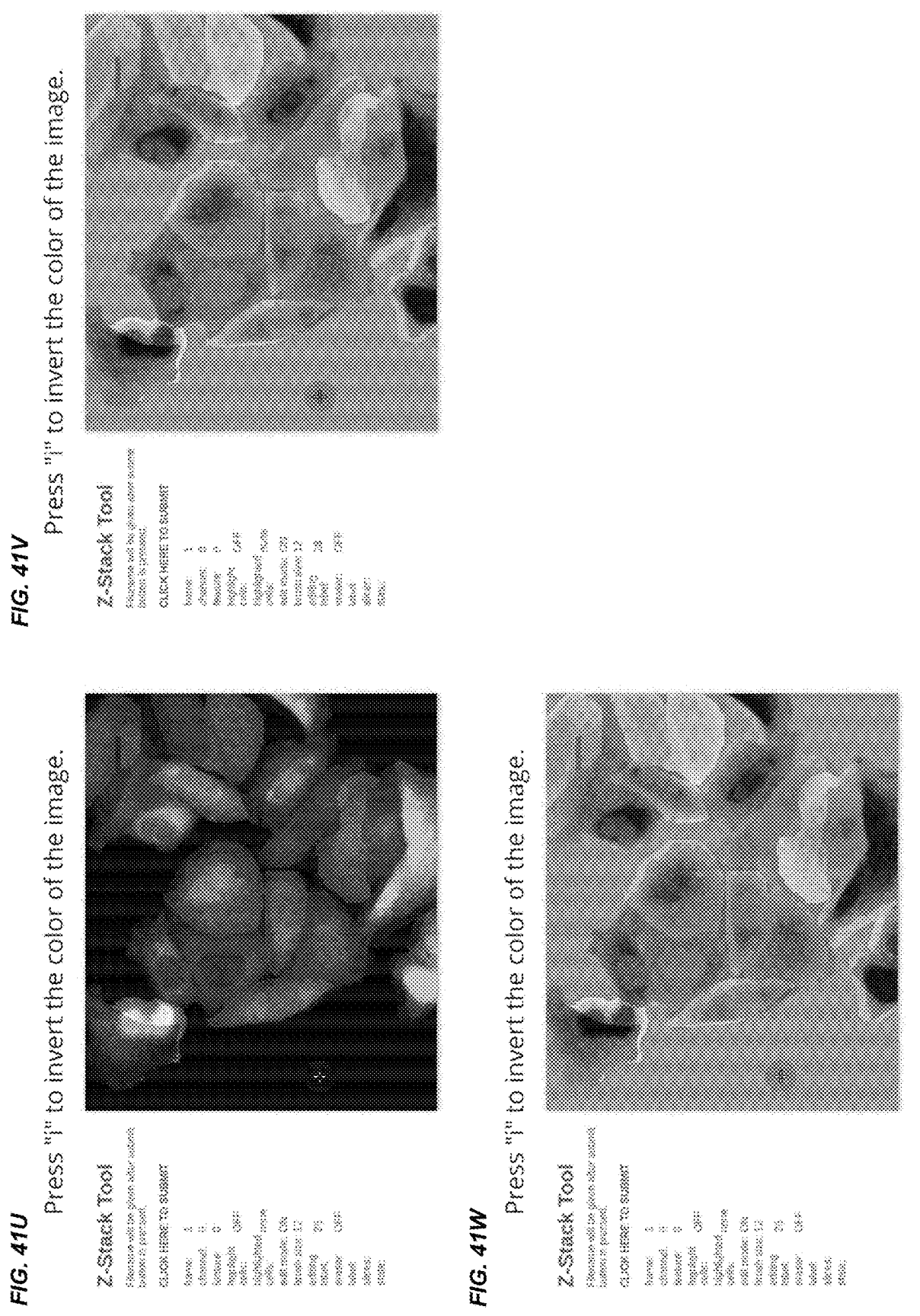

FIGS. 41A-41W. Contrast adjustment and color inversion of raw image.

FIGS. 42A-42L. Changing the channels of a raw image (the channels combined and individually) when displaying the raw image or in pixel-editing mode using Browser Caliban.

Figure 43A:
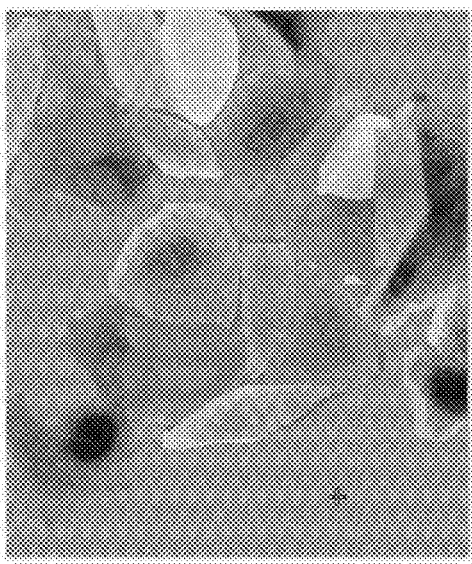
Figure 43B:
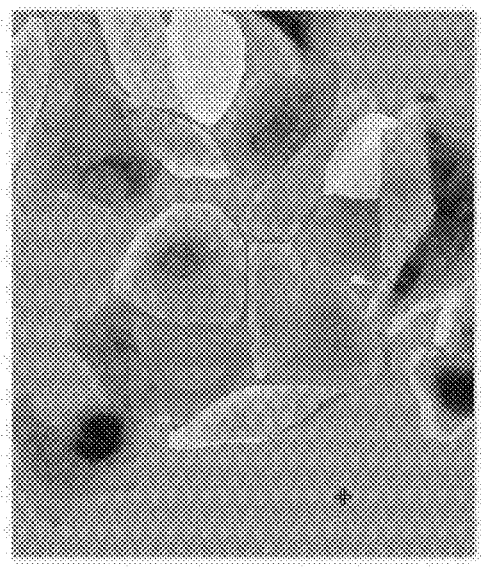
Figure 43C:
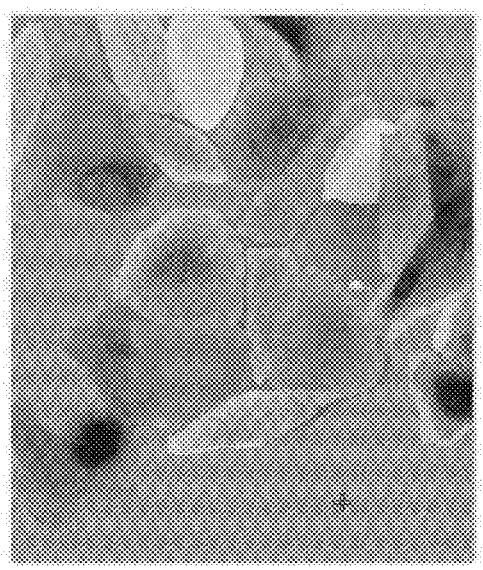
Figure 43D:
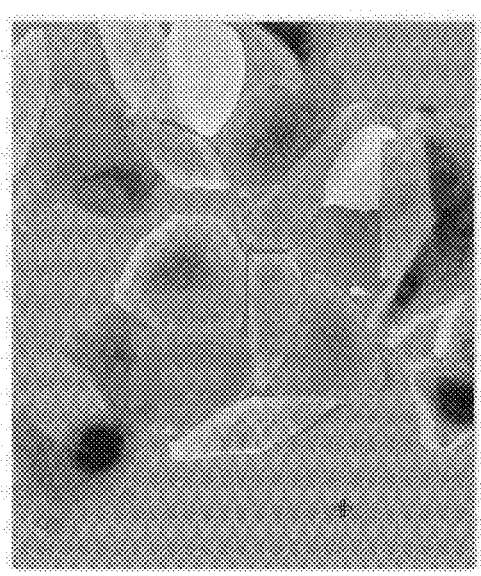
Figure 43J:
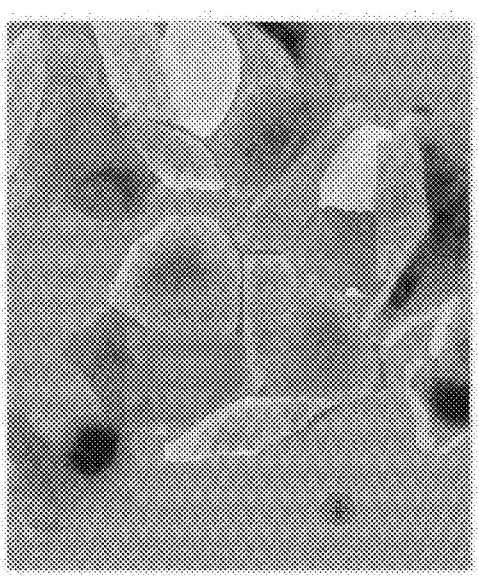
Figure 43L:
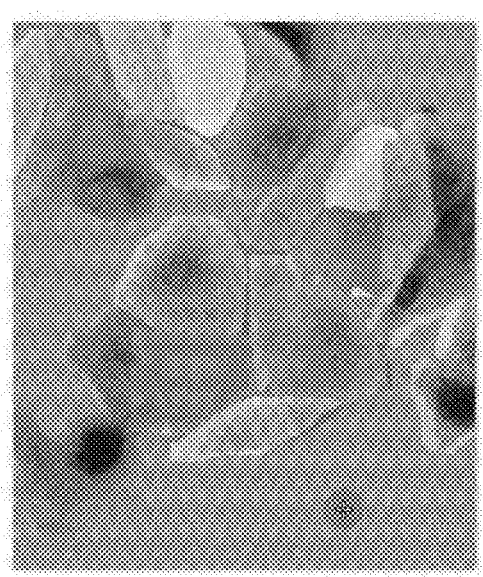
Figure 43I:
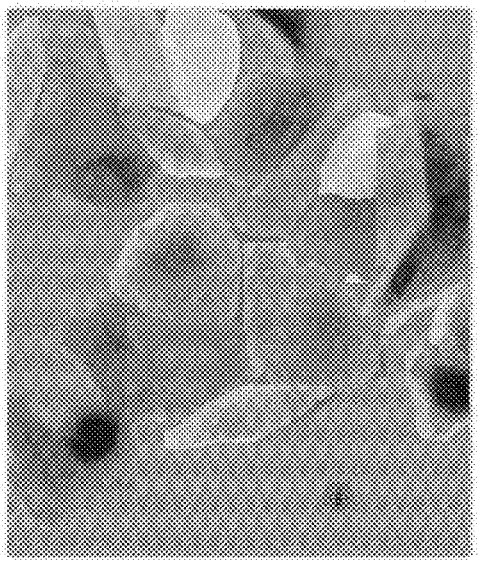
Figure 43K:
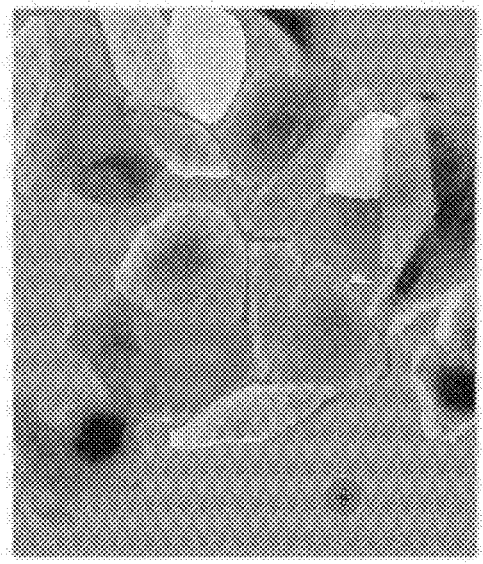
Figure 43M:
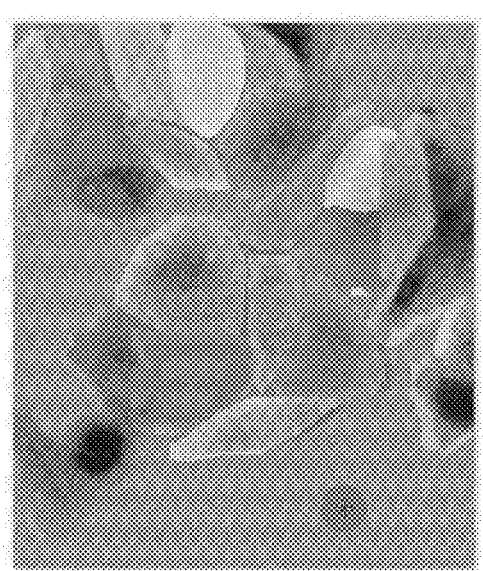
Figure 43N:
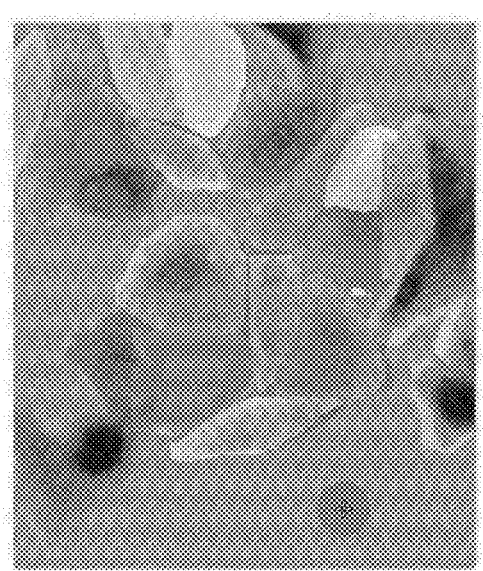
Figure 43O:
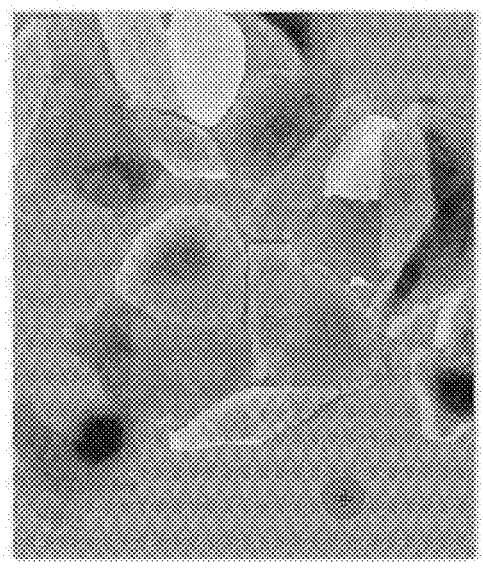
Figure 43P:
Figure 43Q:
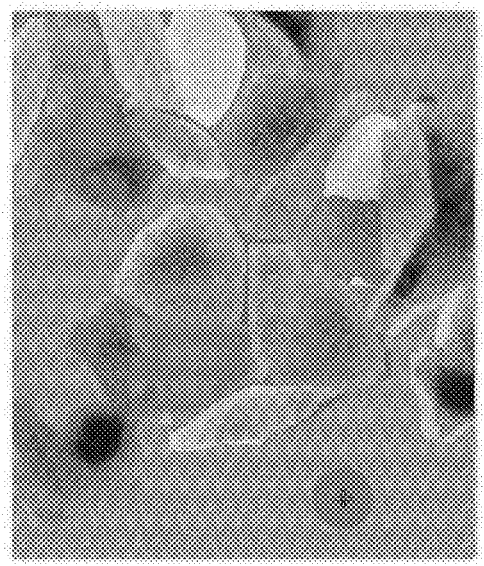
Figure 43R:
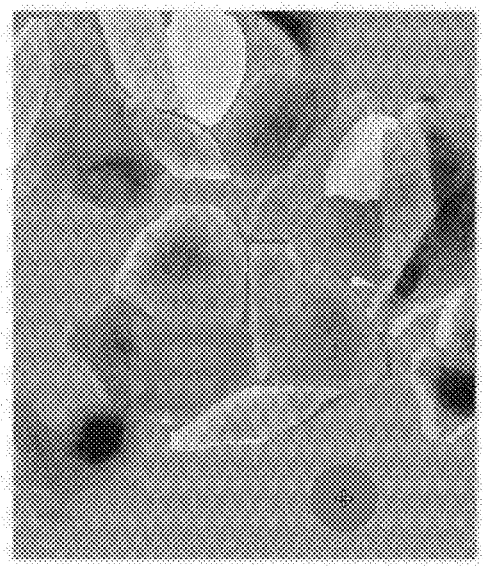
Figure 43S:
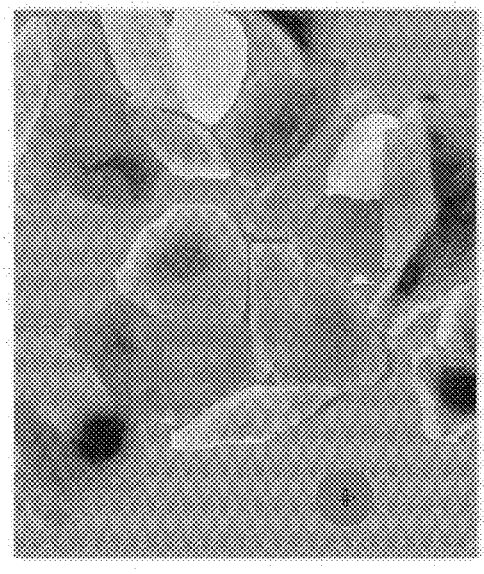
Figure 43T:
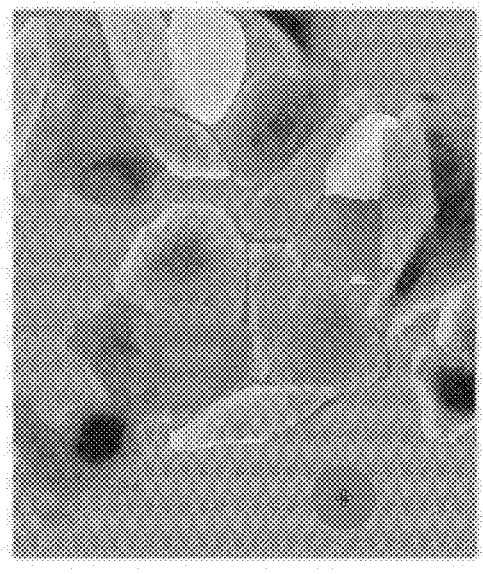
Figure 43V:
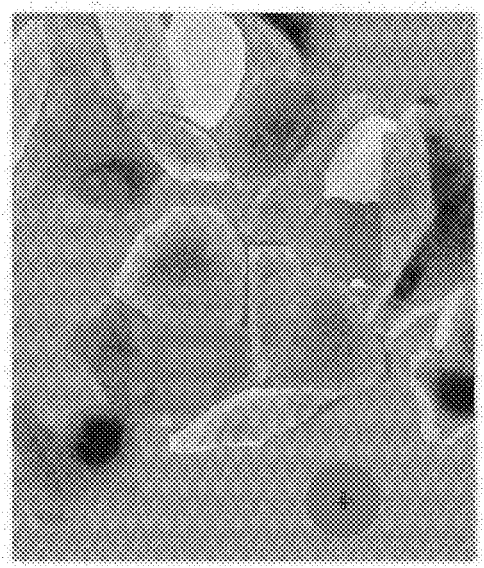
Figure 43X:
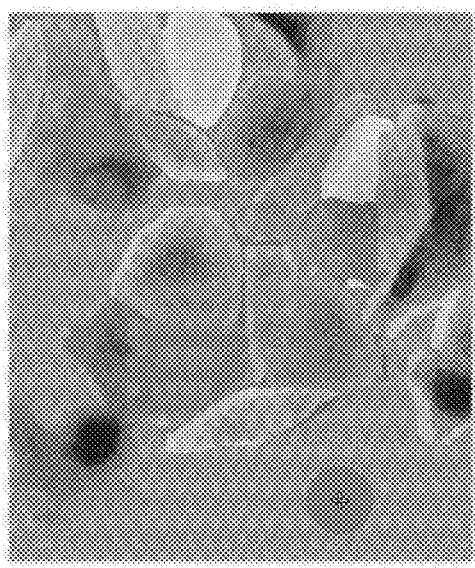
Figure 43U:
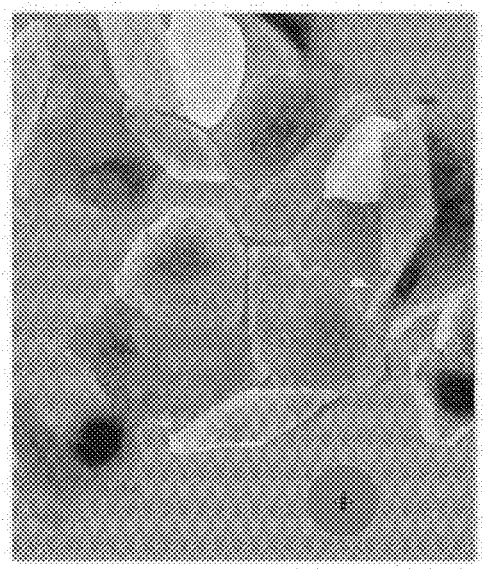
Figure 43W:
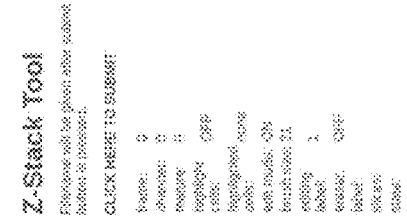
Figure 44A:
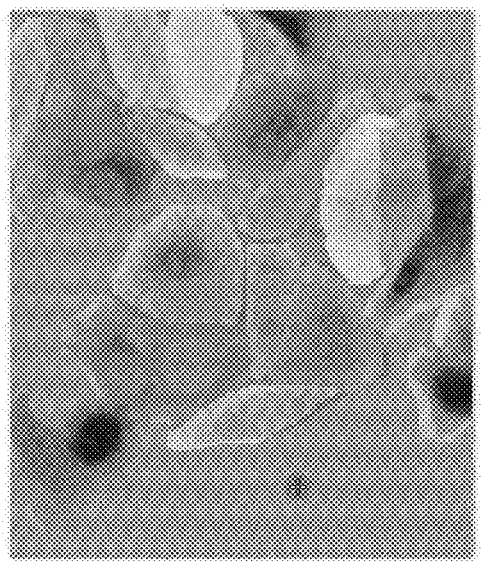
FIGS. 44A-44K. The pixels associated with (or assigned to) the current value of the brush are highlighted.
Figure 44B:
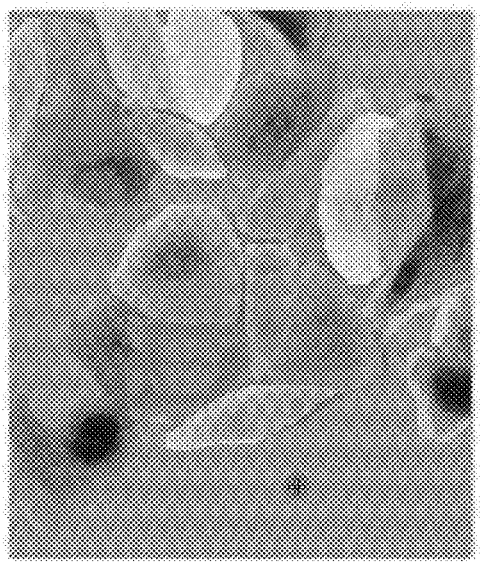
Figure 44C:
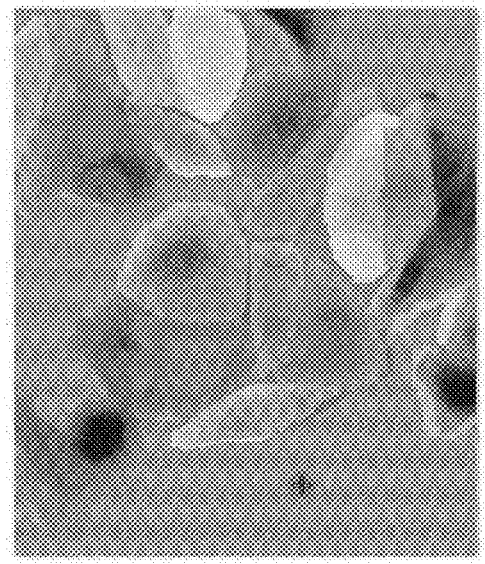
Figure 44D:
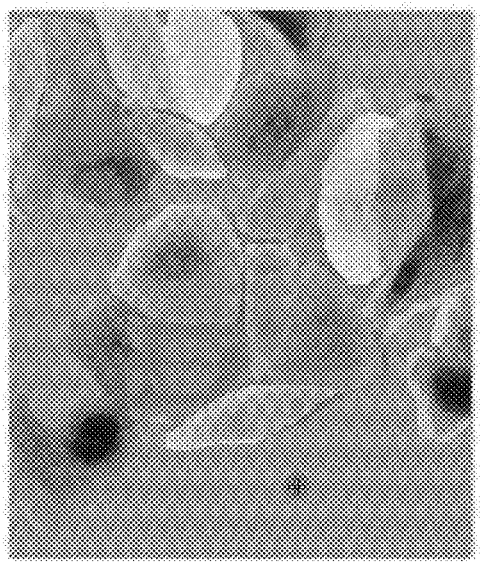
Figure 44E:
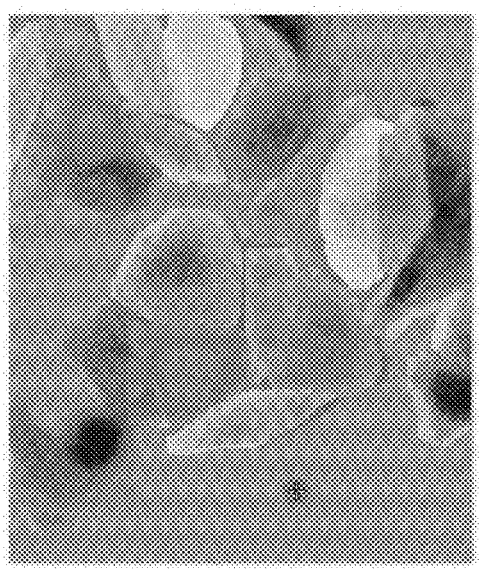
Figure 44F:
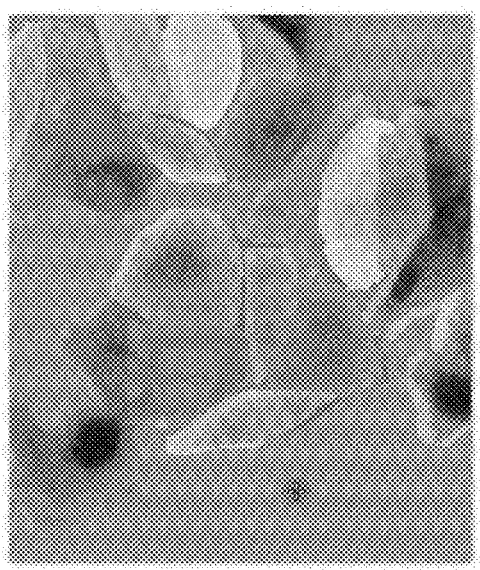
Figure 44G:
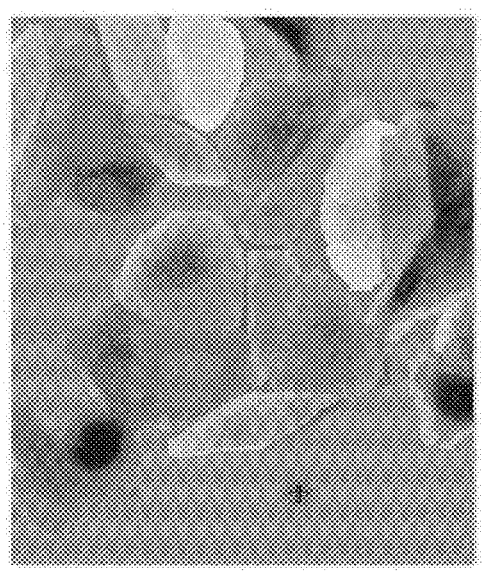
Figure 44H:
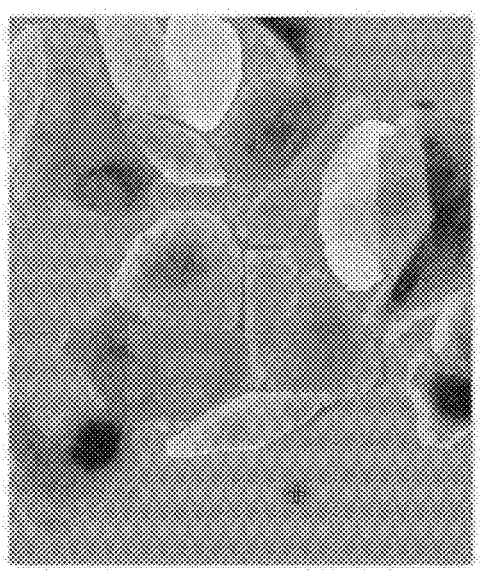
Figure 44J:
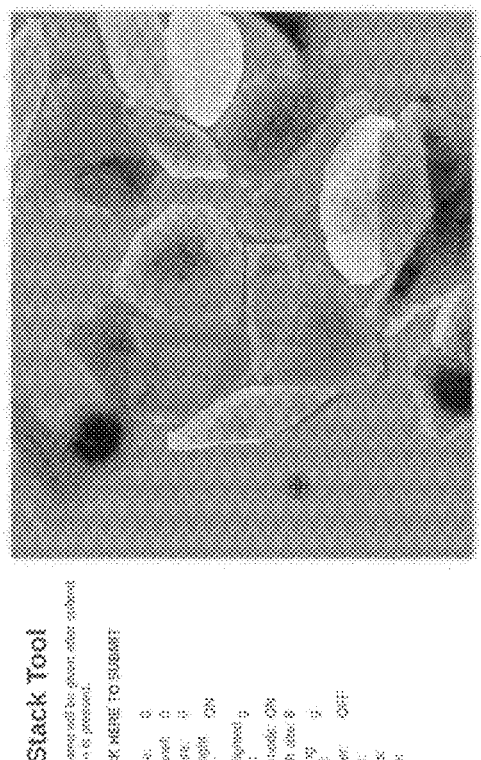
Figure 44I:
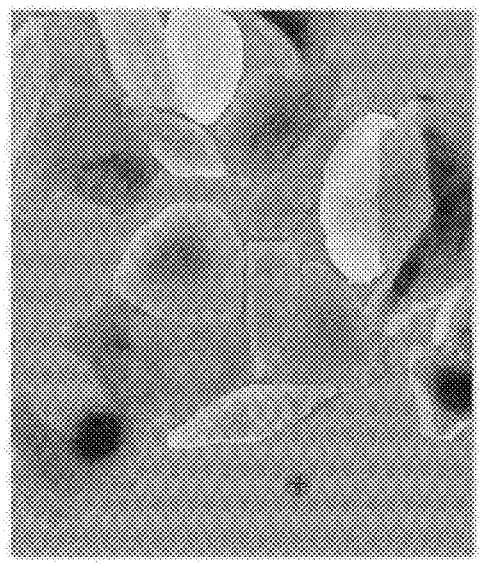
Figure 44K:
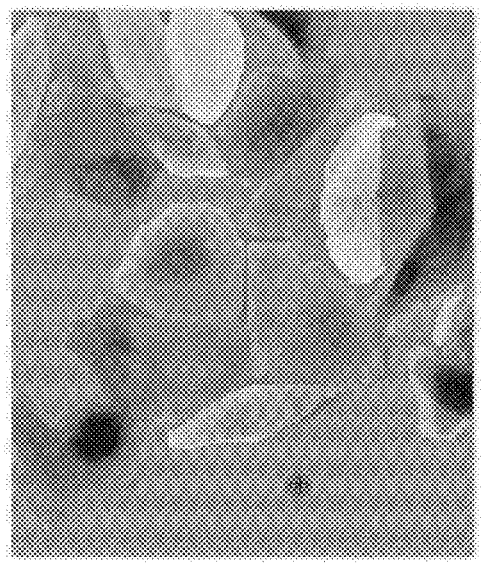
Figure 46A:
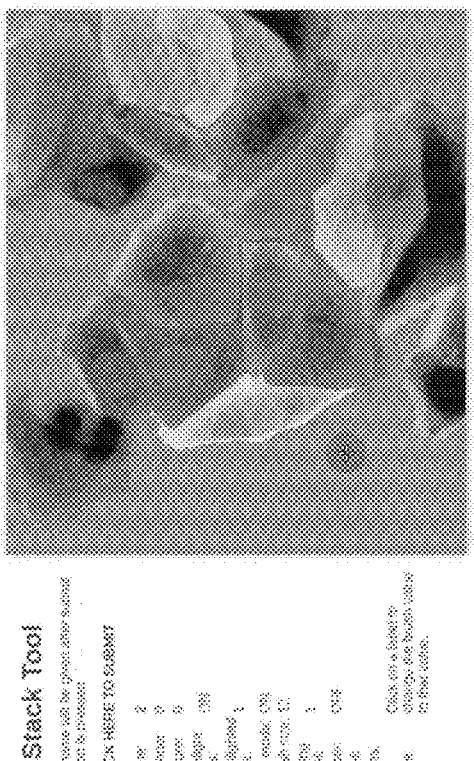
FIGS. 46A-46H. Using the color picker to change the value of the brush in the pixel-editing mode.
Figure 46B:
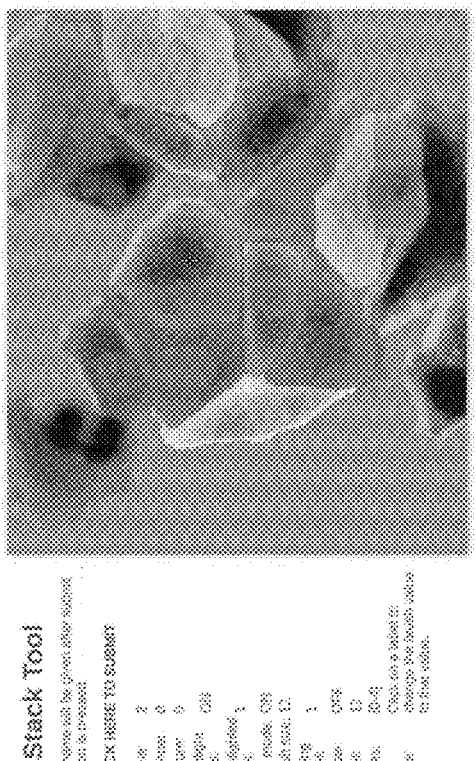
Figure 46C:
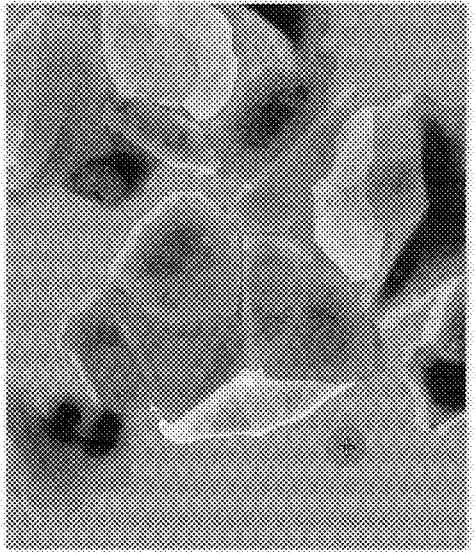
Figure 46D:
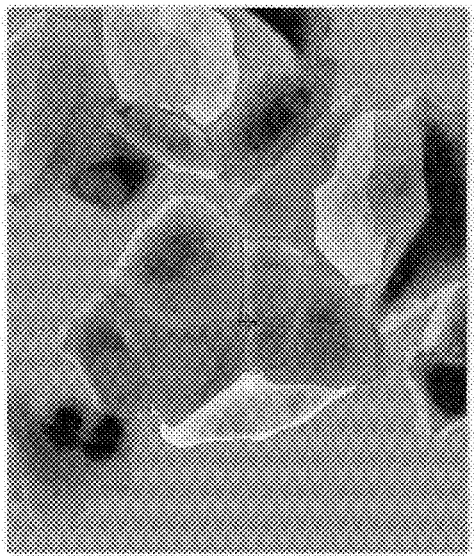
Figure 46E:
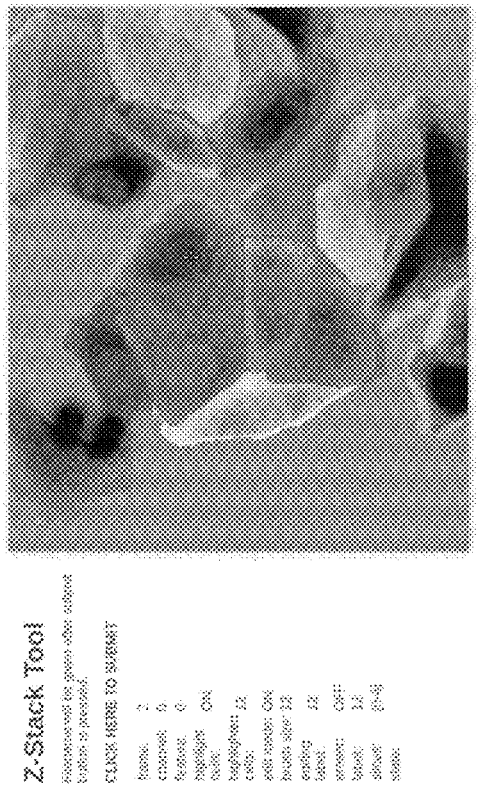
Figure 46F:
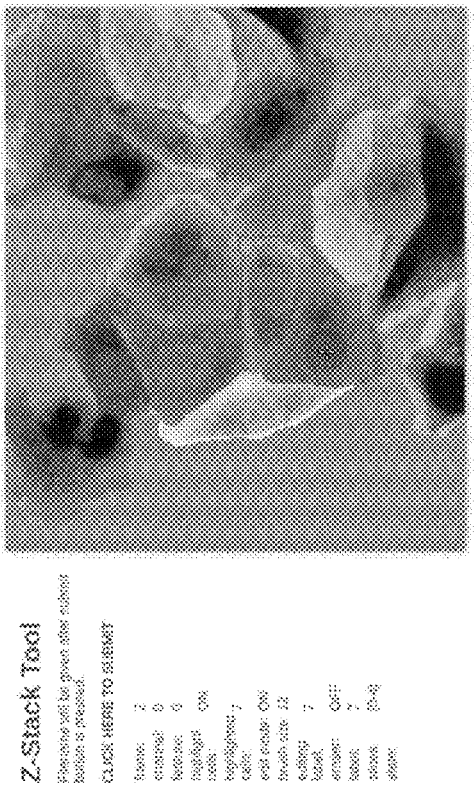
Figure 46G:
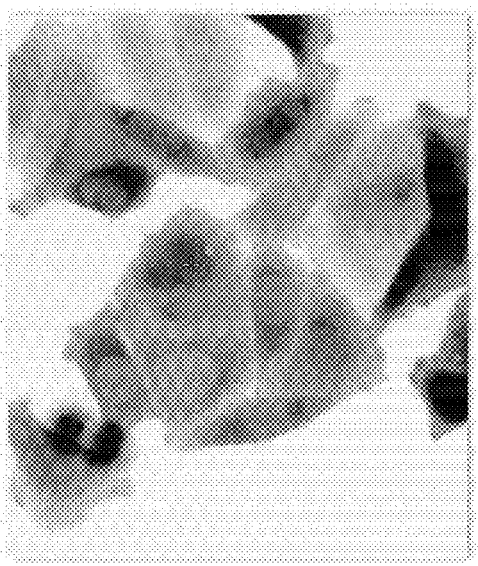
Figure 46H:
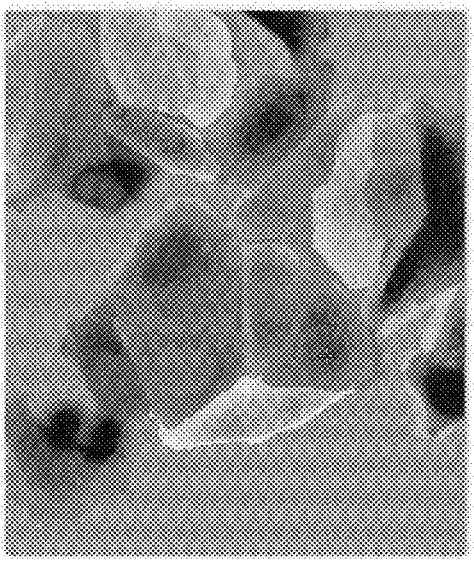

FIGS. 43A-43B2. Increasing brush size from size 1 to size 22 and decreasing brush size from 22 to 1 in the pixel-editing mode of Caliban.

FIGS. 44A-44K. The pixels associated with (or assigned to) the current value of the brush are highlighted.

FIGS. 45A-45L. Increasing and decreasing the value of the brush and setting the brush to an unused value in the pixel-editing mode of Caliban.

FIGS. 46A-46H. Using the color picker to change the value of the brush in the pixel-editing mode.

Figure 47A:
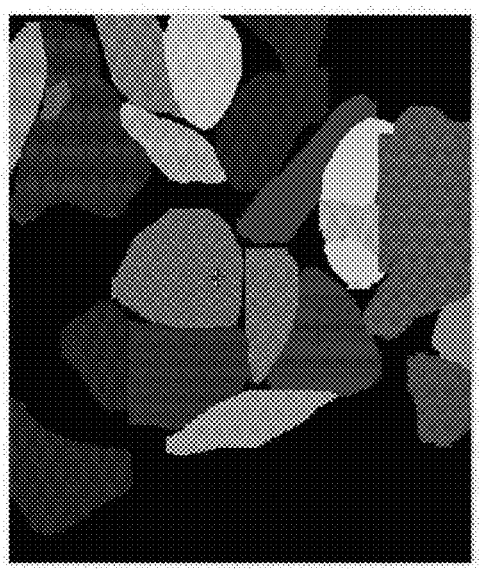
Figure 47B:
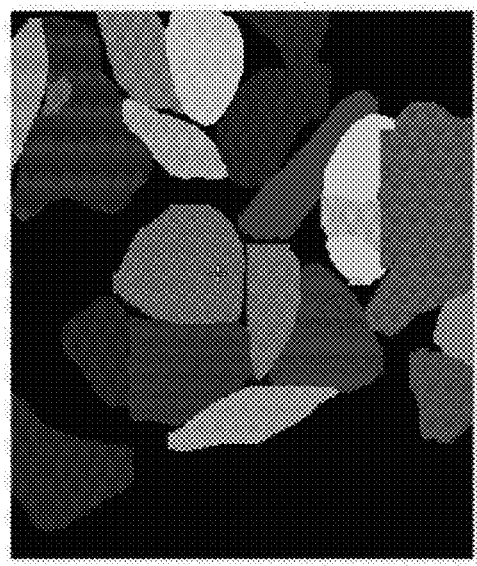
Figure 47C:
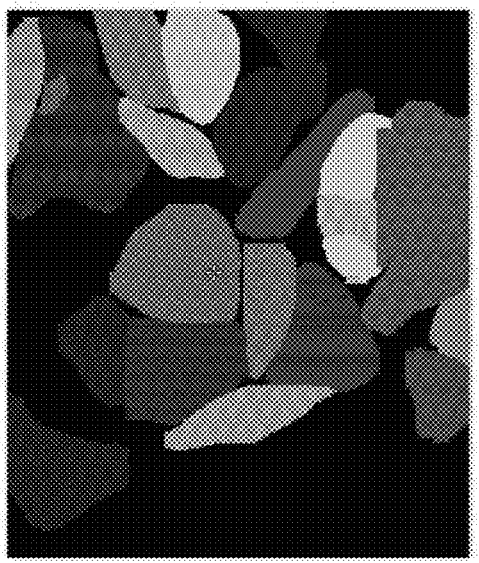
Figure 47D:
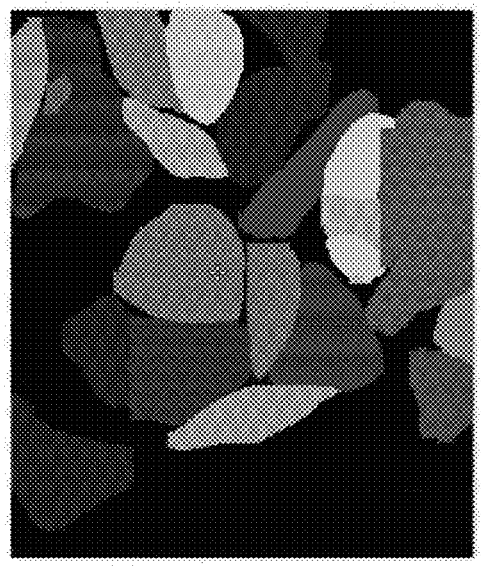
Figure 47M:
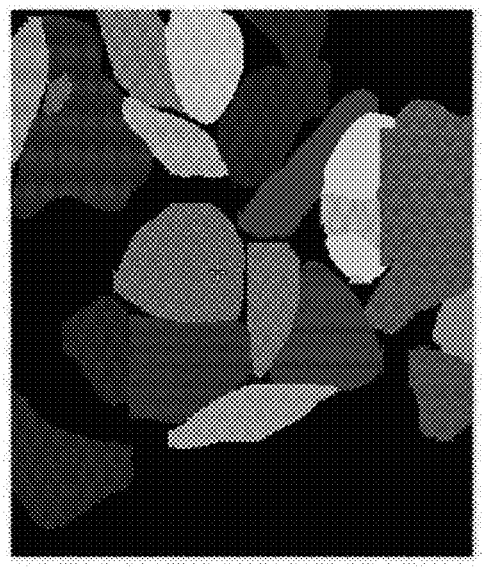
Figure 47N:
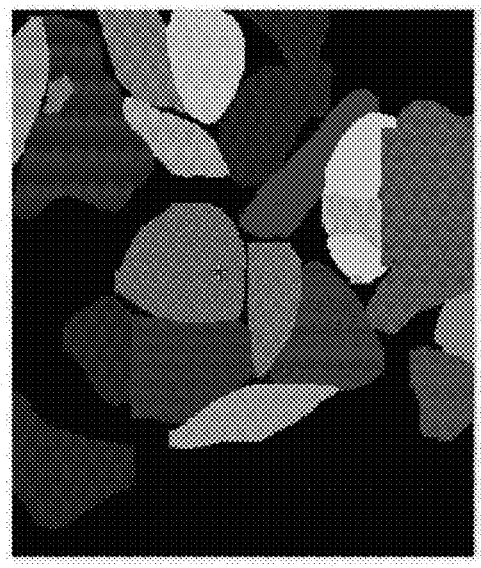
Figure 47O:
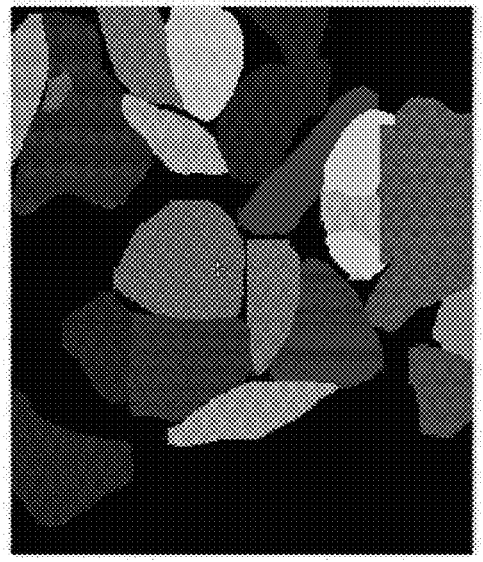
Figure 47P:
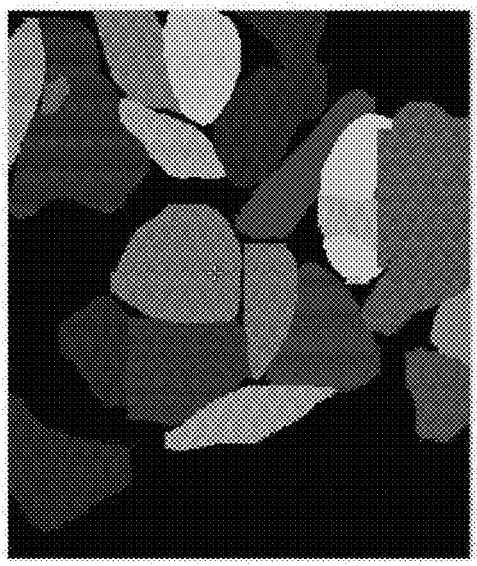
Figure 47Q:
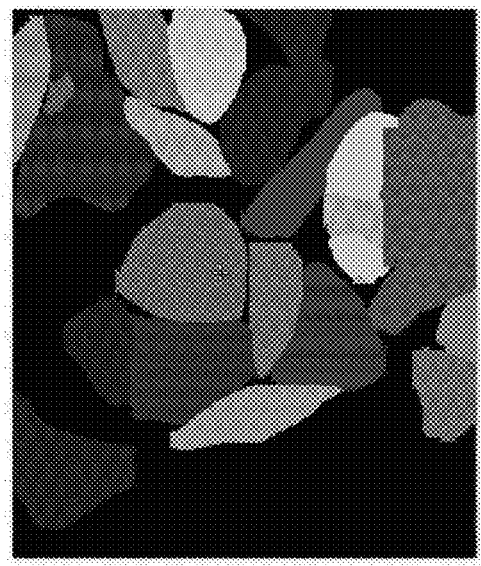
Figure 47R:
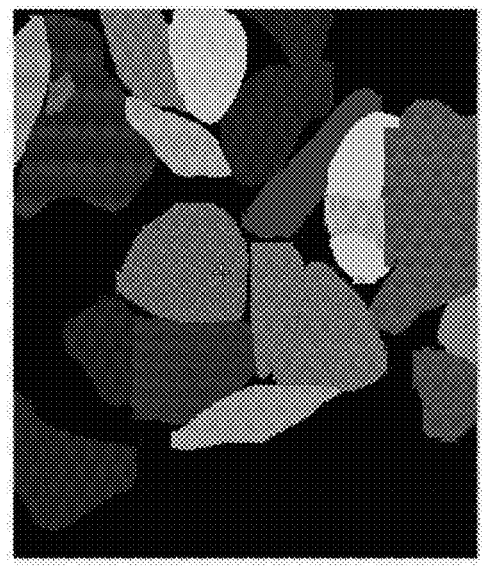
Figure 47S:
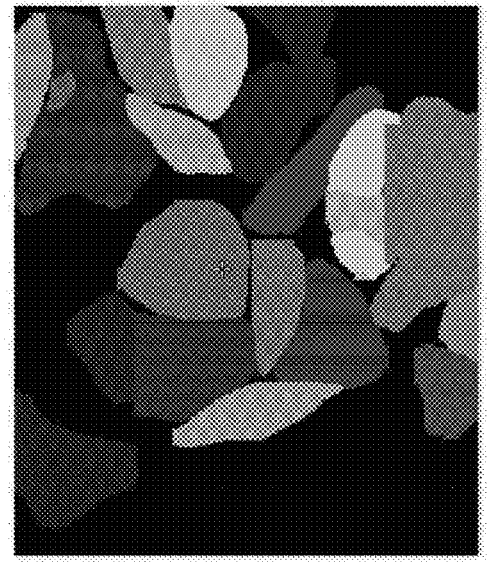
Figure 47T:
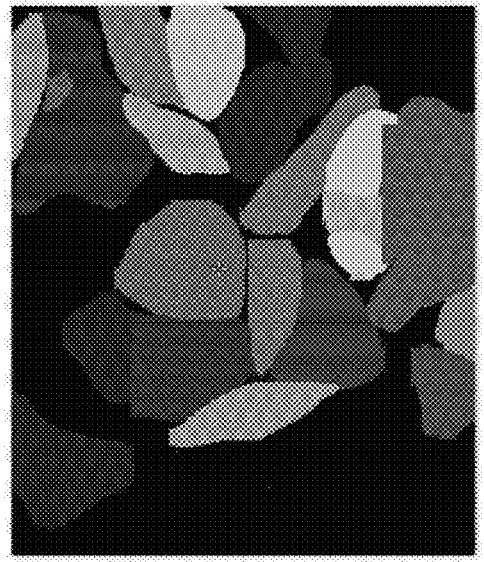
Figure 49E:
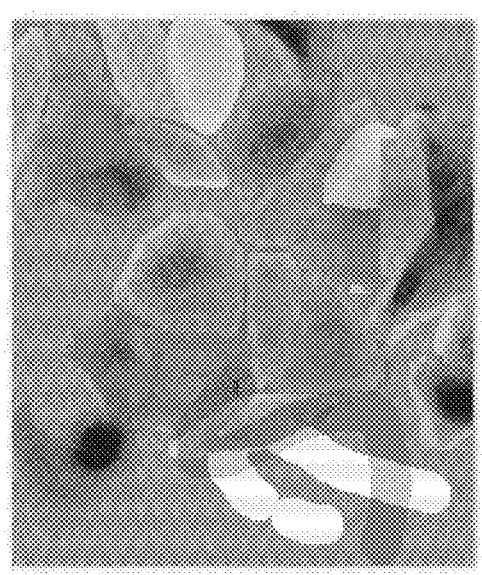
Figure 49F:
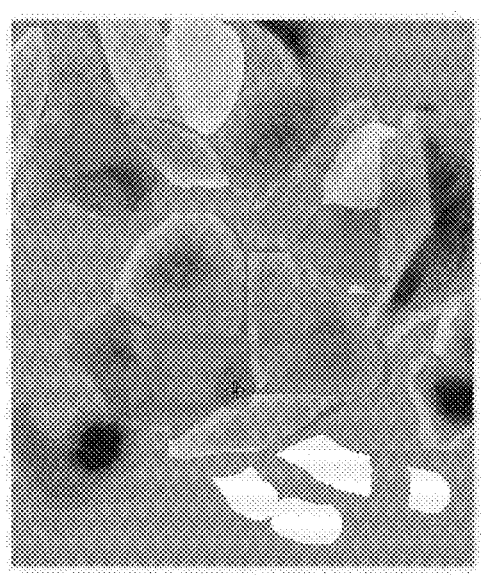
Figure 49G:
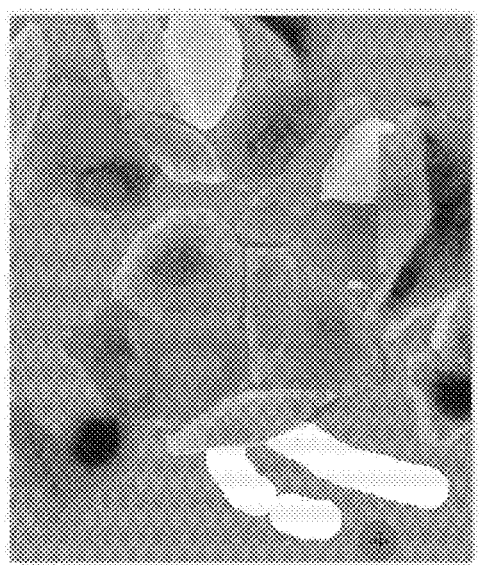
Figure 49H:
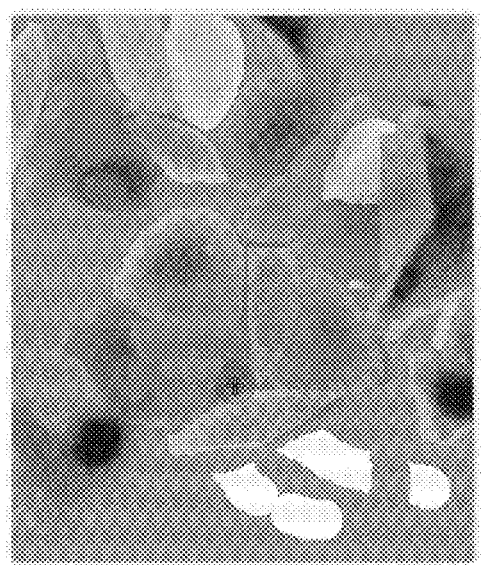
Figure 50A:
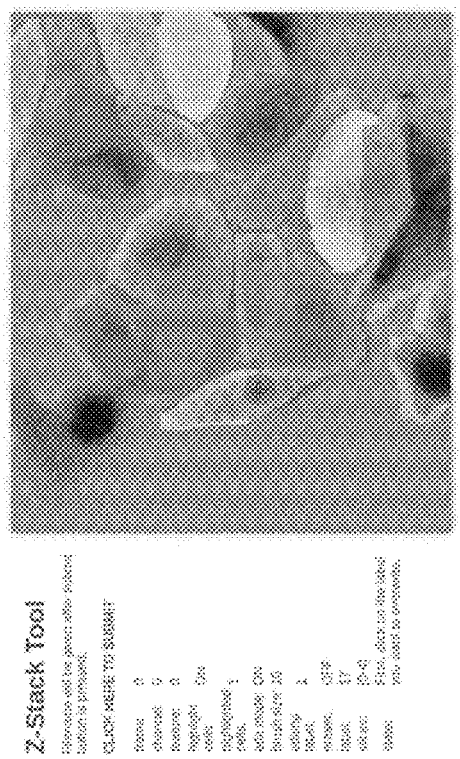
Figure 50B:
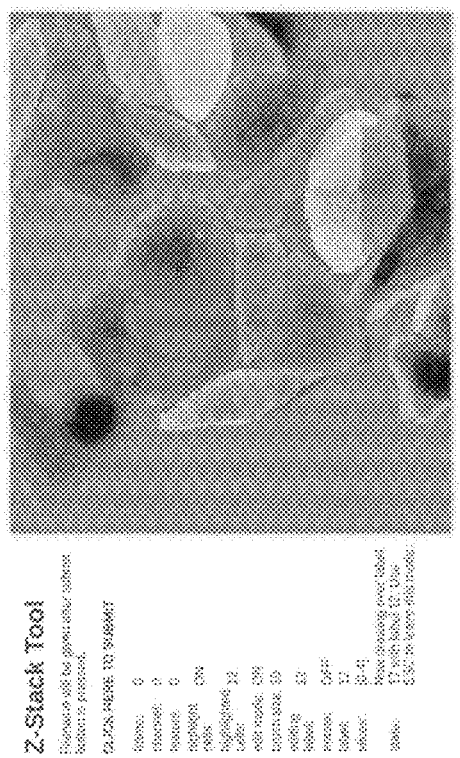
Figure 50C:
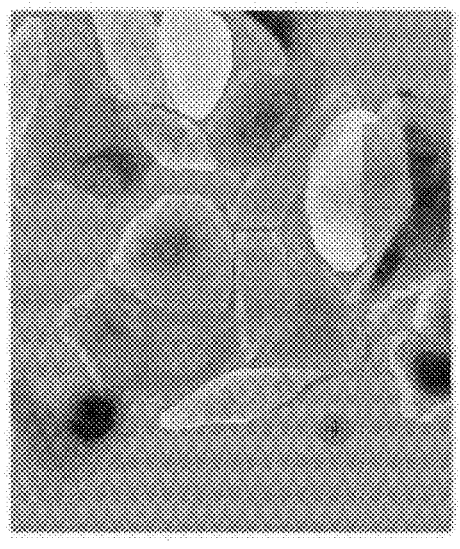
Figure 50D:
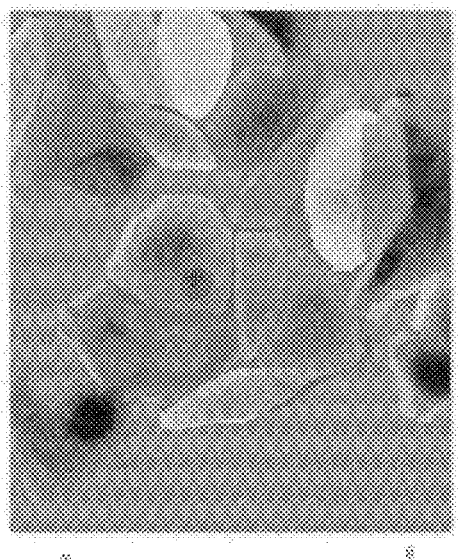
Figure 50E:
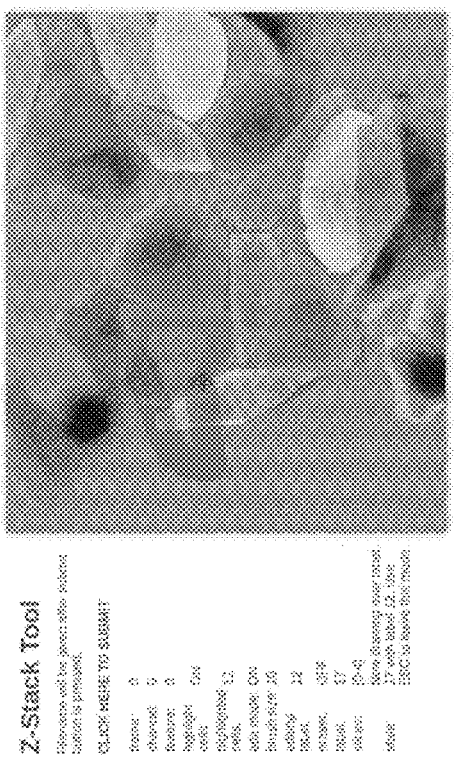
Figure 50F:
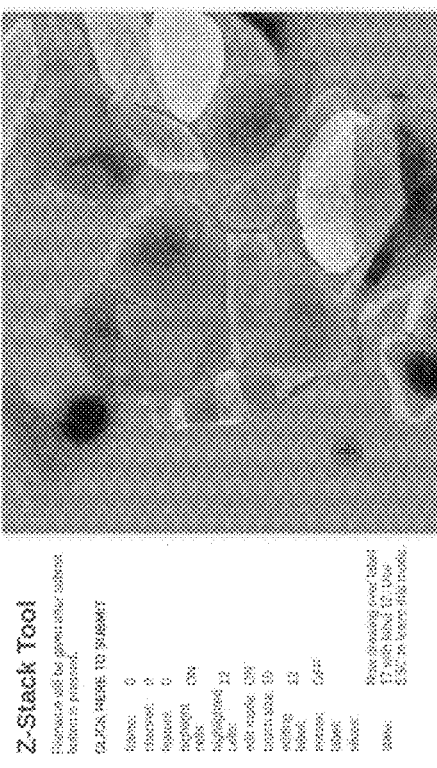
Figure 50G:
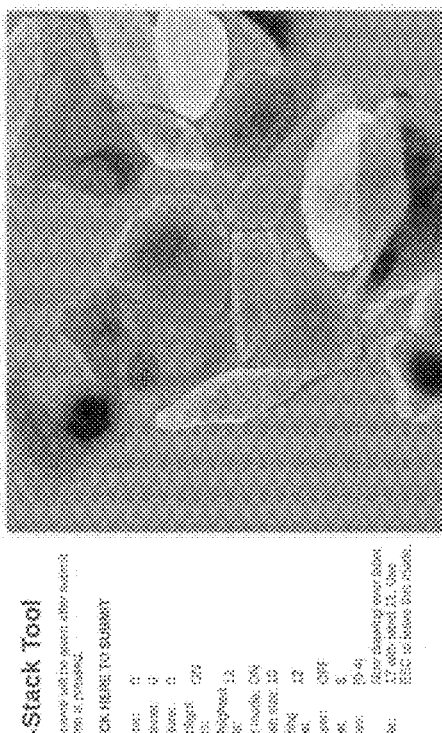
Figure 50H:
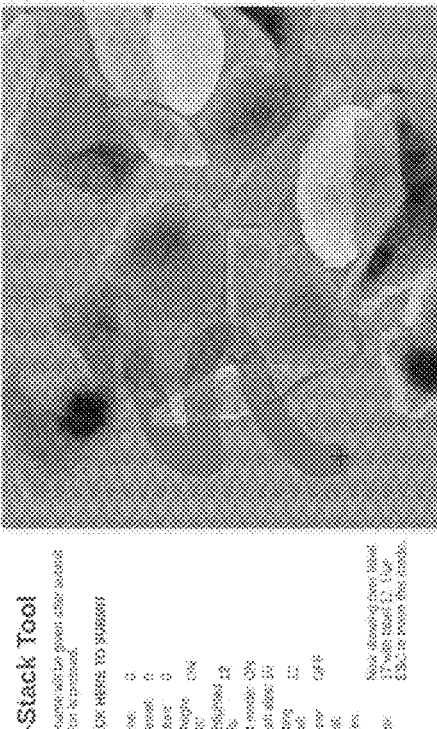

FIGS. 47A-47F2. Turning/toggling on and off highlighting and selecting labels with the selected labels highlighted.

FIGS. 48A-48R. Increasing the brush size in the annotation mode and using the brush to annotate (or color or select) pixels of a label with Browser Caliban.

FIGS. 49A-49H. Drawing and erasing with a brush only affect pixels associated with (or assigned to) the label the brush is set to.

FIGS. 50A-50K. Using the conversion brush to change some or all pixels associated with (or assigned to) one label to be associated with (or assigned to) another label without affecting the pixels of the background or the pixels associated with (or assigned to) other labels.

Figure 51M:
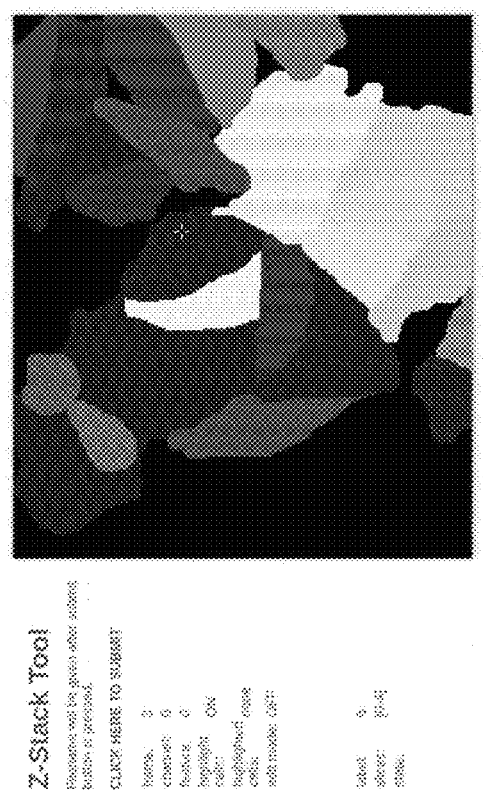
FIGS. 51A-51V. Replacing a second label with a first label in one frame or all frames.
Figure 51N:
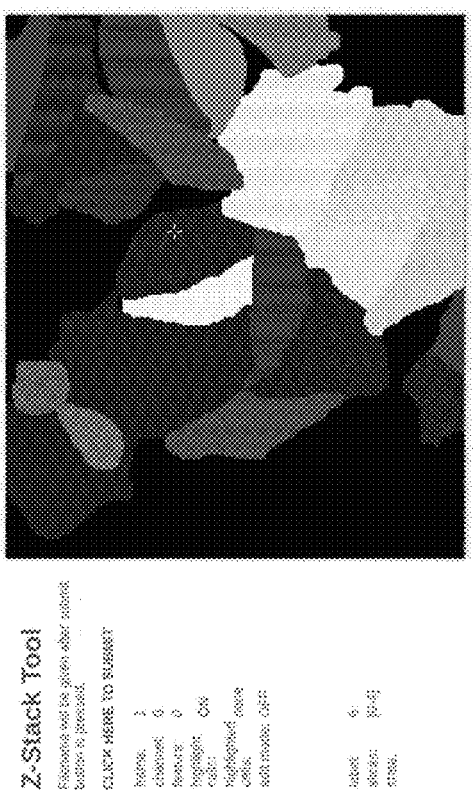
Figure 51O:
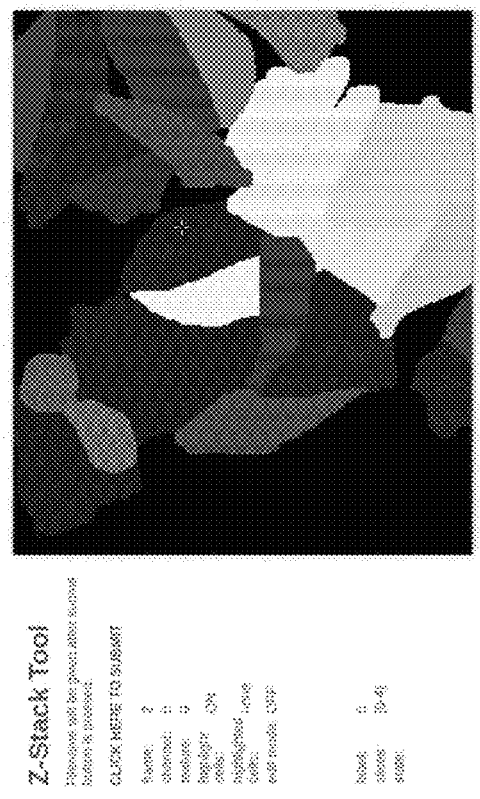
Figure 51P:
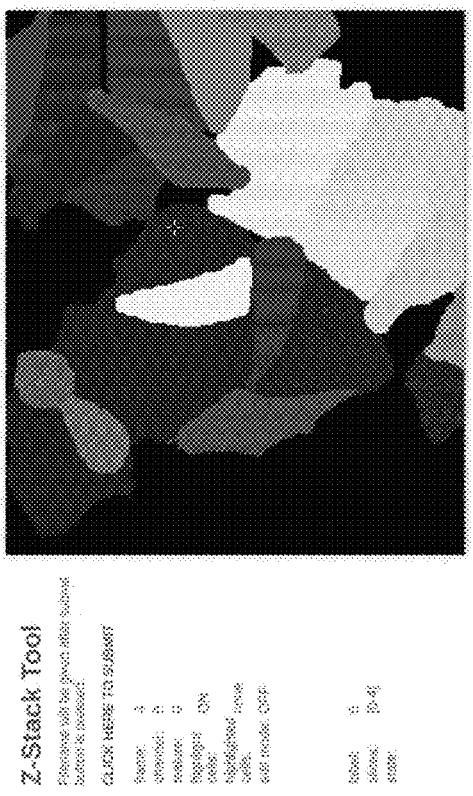
Figure 51V:
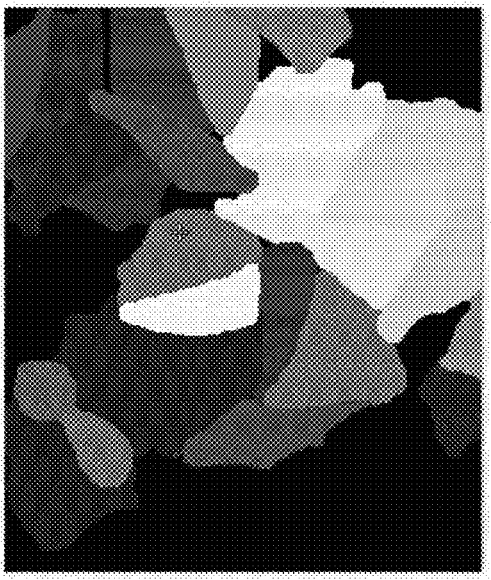
Figure 51U:
Figure 52F:
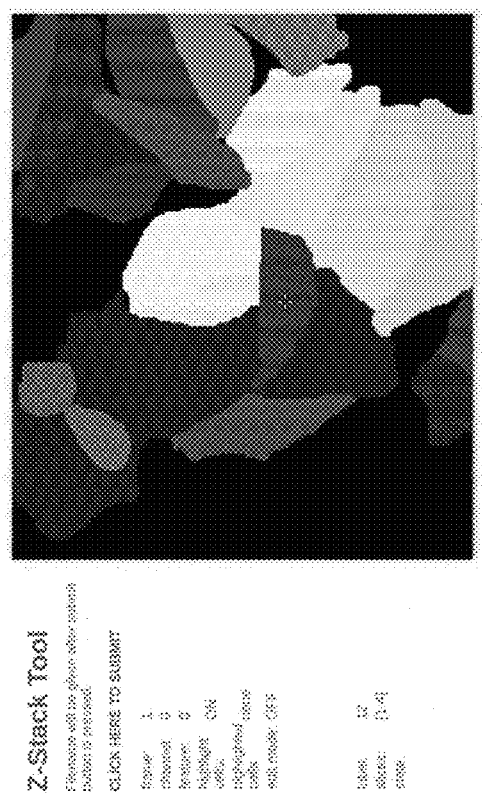
Figure 52E:
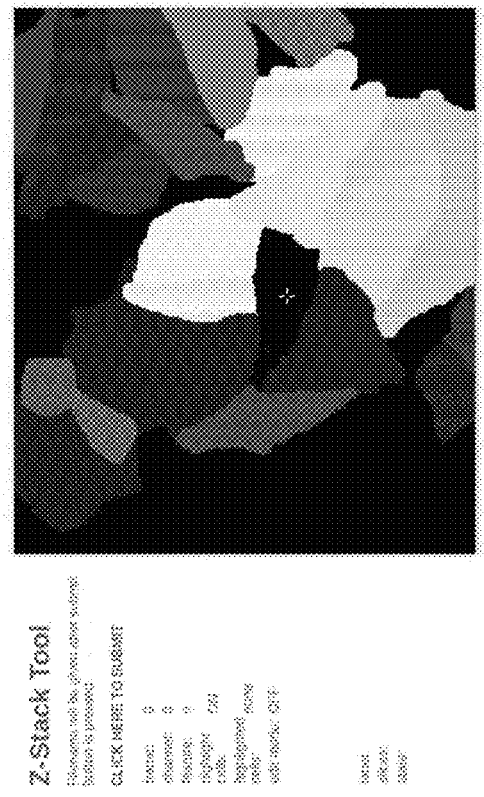
Figure 52G:
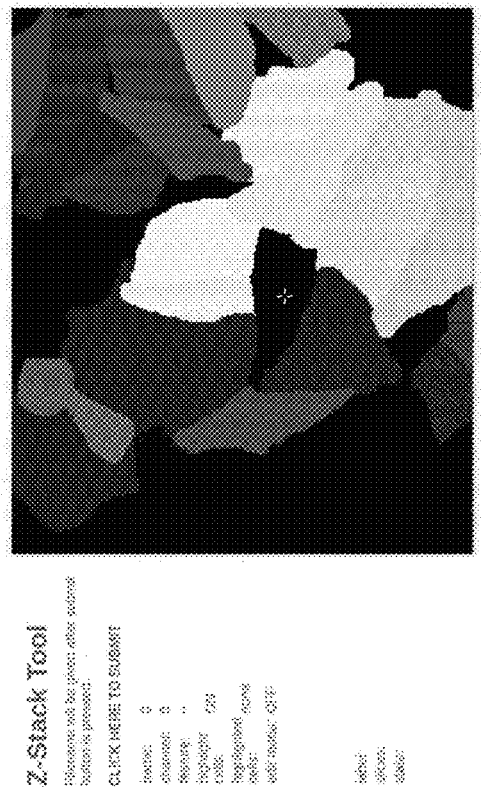
Figure 53B:
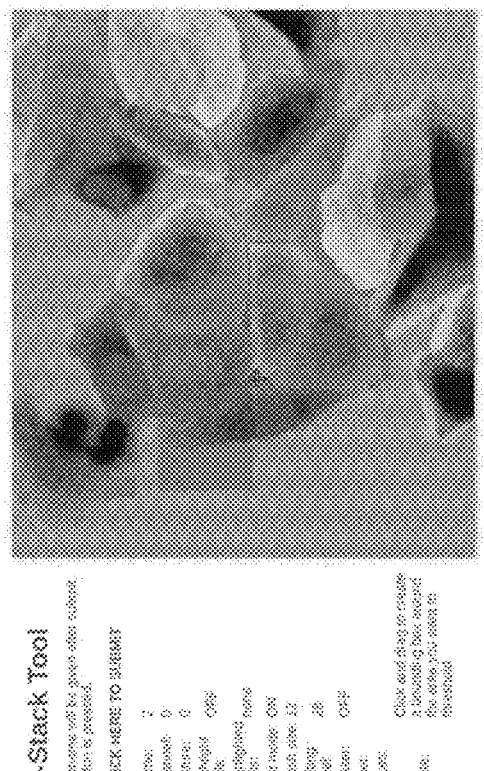
FIGS. 53A-53H. Thresholding in pixel-editing mode.
Figure 53D:
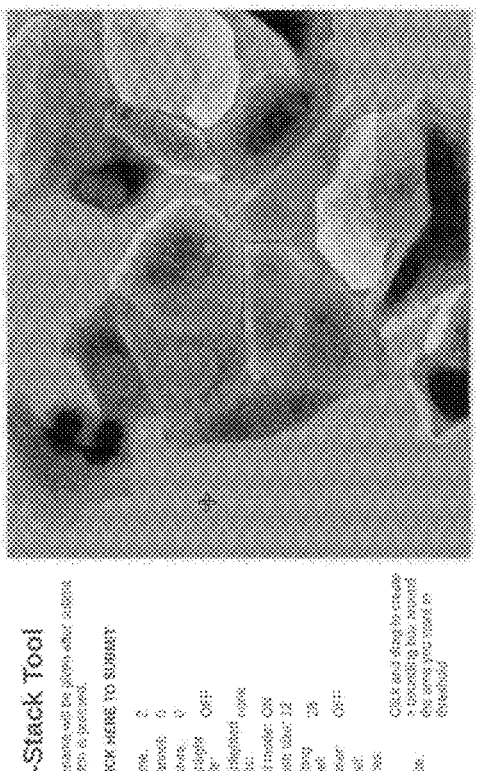
Figure 53A:
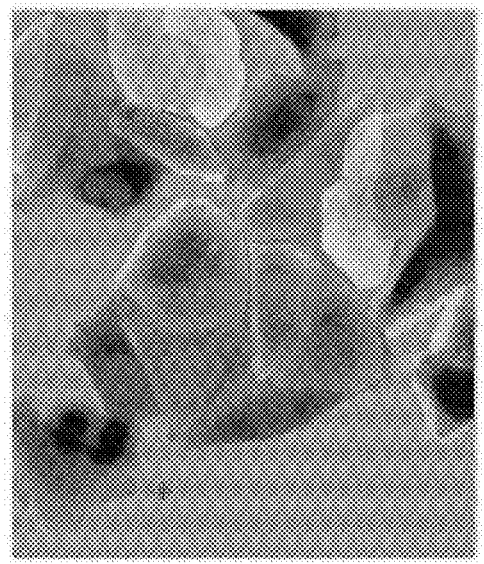
Figure 53C:
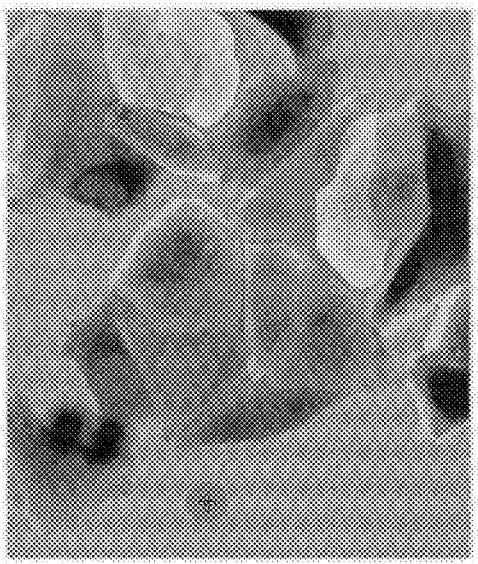
Figure 53E:
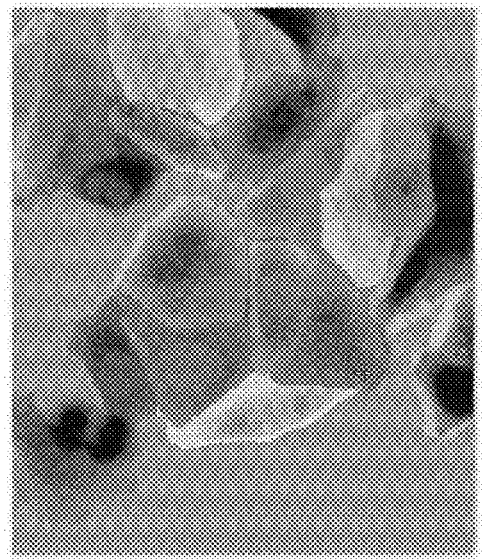
Figure 53F:
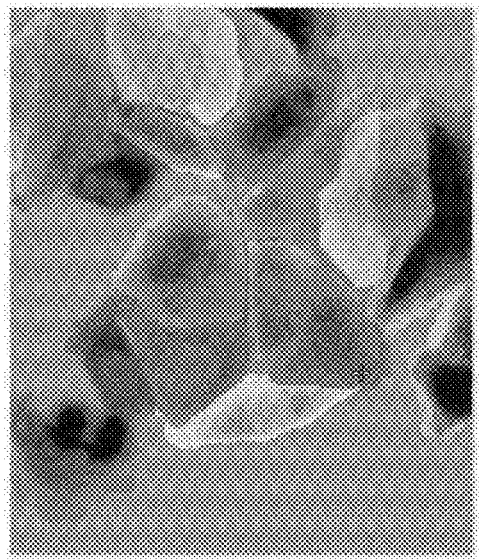
Figure 53G:
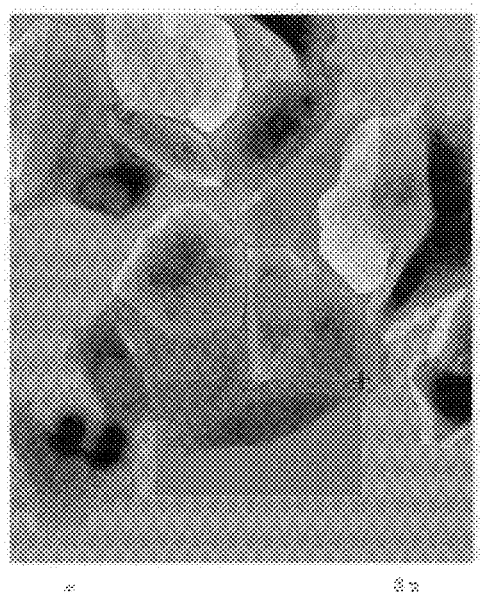
Figure 53H:
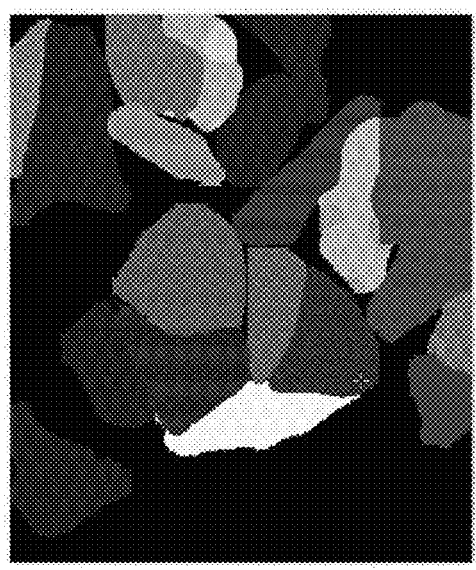
Figure 54A:
FIGS. 54A-54E. Flood action.
Figure 54B:
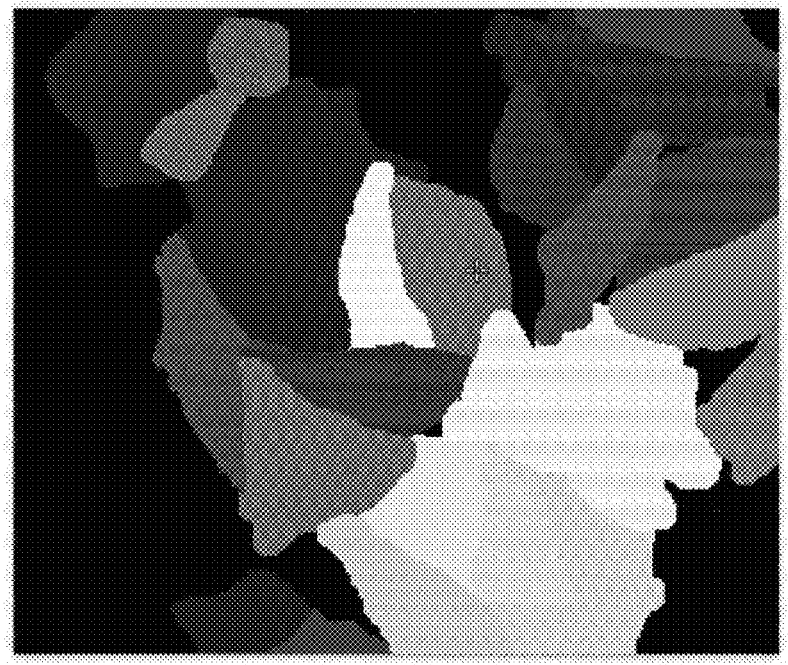
Figure 54C:
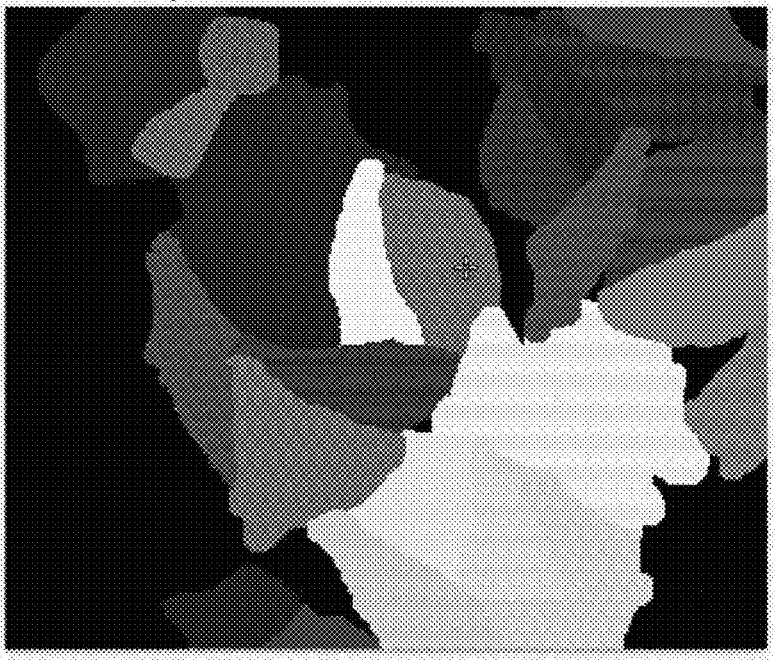
Figure 54D:
Figure 54E:
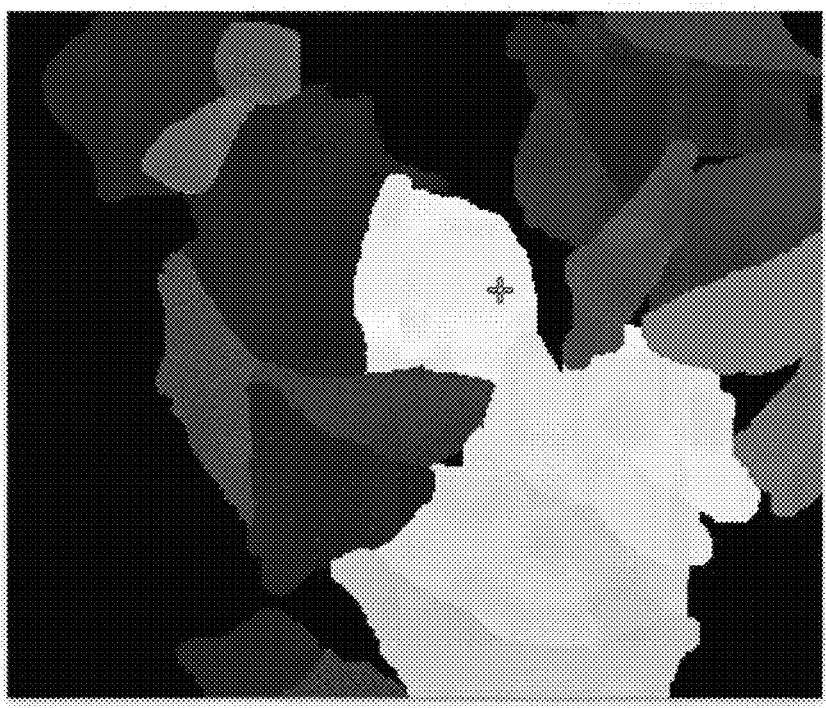
Figure 55A:
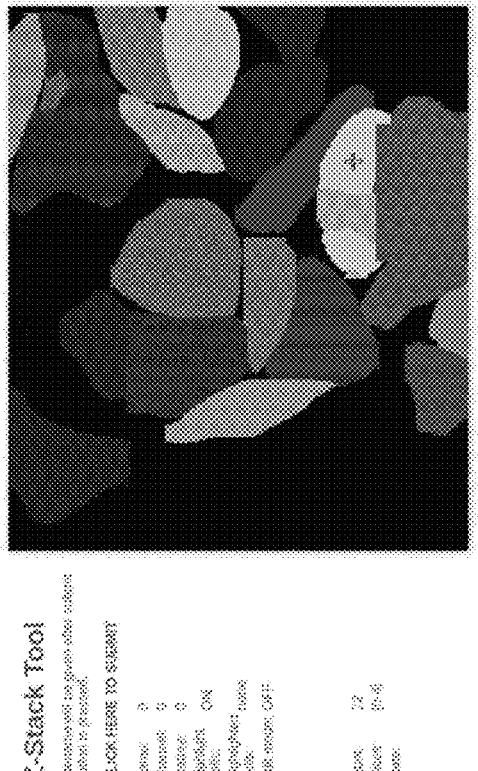
FIGS. 55A-55K. Trimming away unconnected pieces (pixel(s) associated/having with a label unconnected with the remaining pixels associated/having with the label).
Figure 55B:
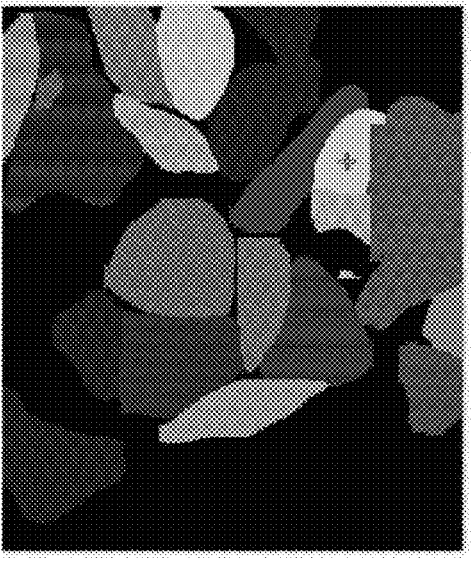
Figure 55C:
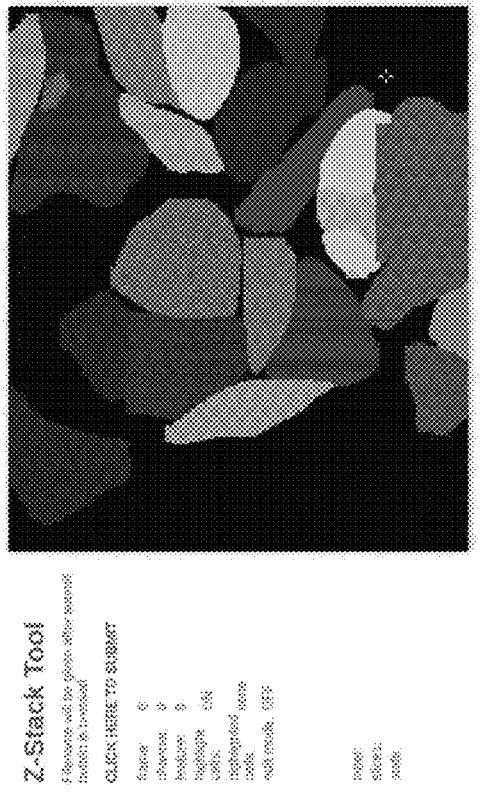
Figure 55D:
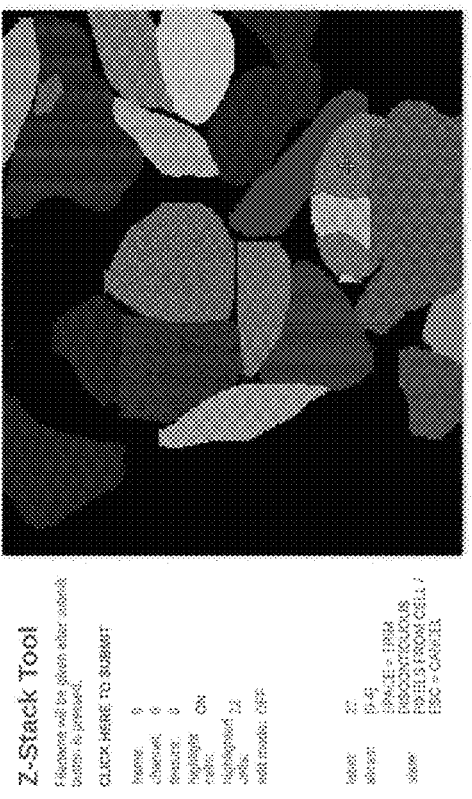
Figure 55E:
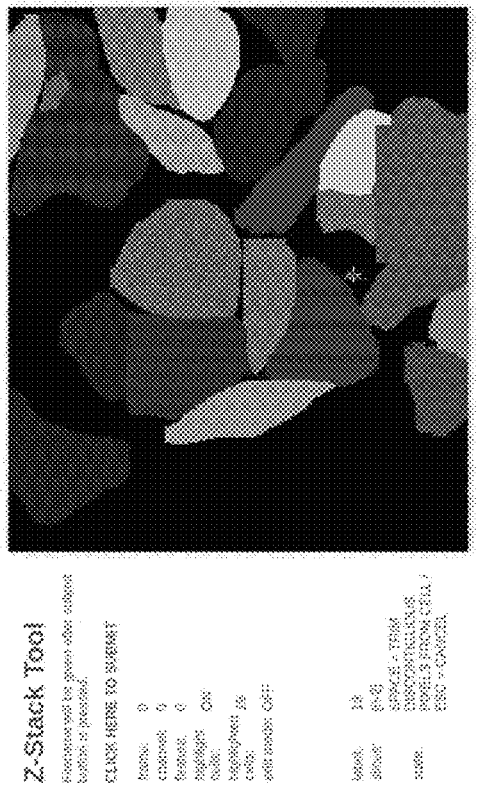
Figure 55F:
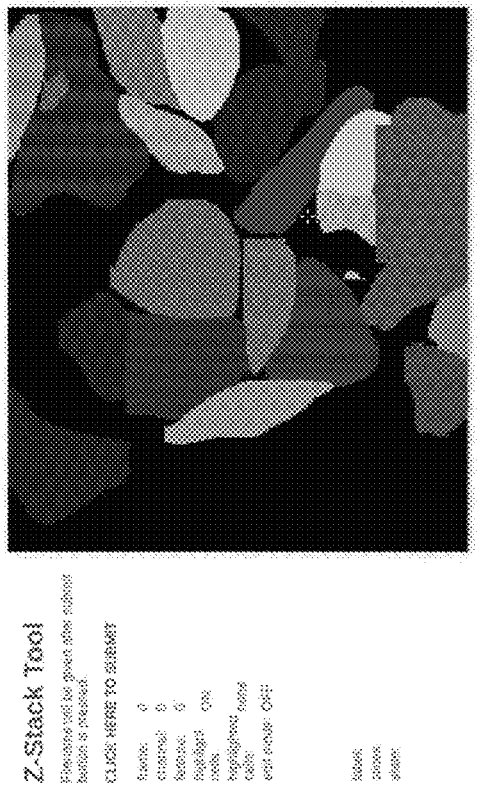
Figure 55G:
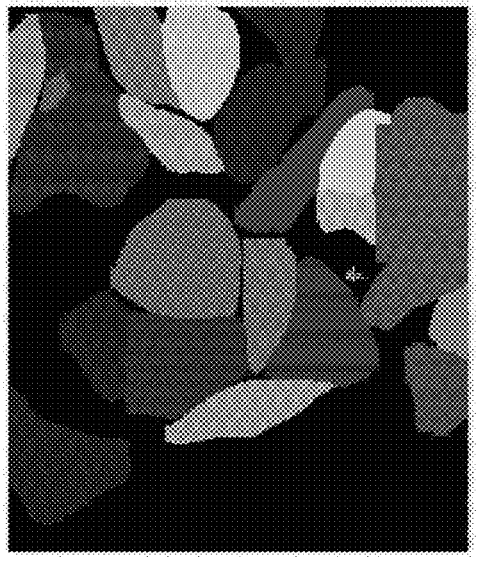
Figure 55H:
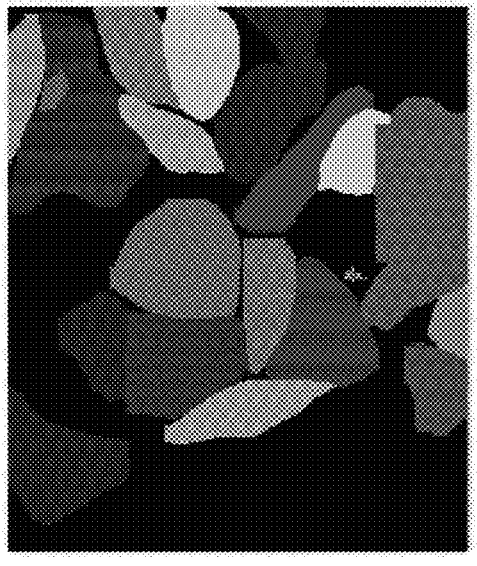
Figure 55J:
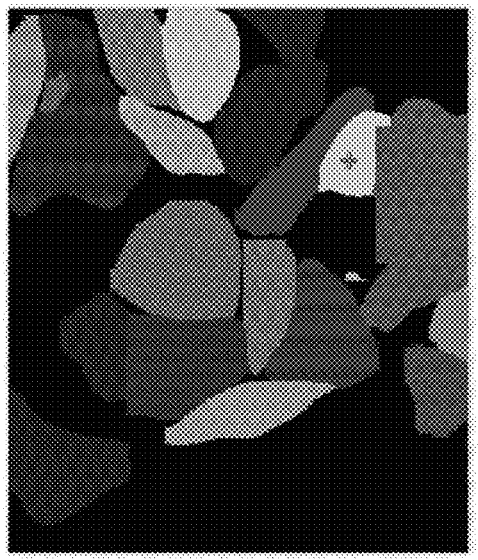
Figure 55I:
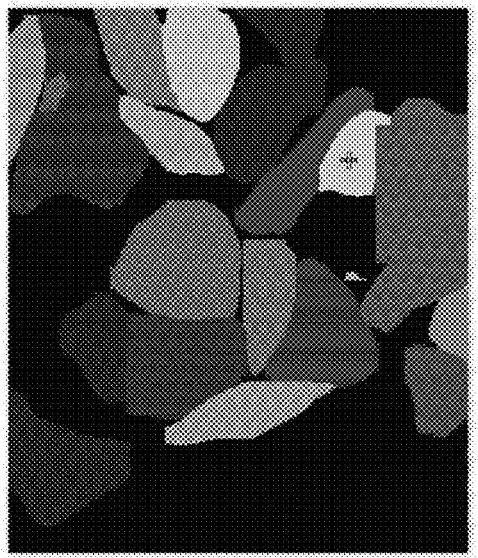
Figure 55K:
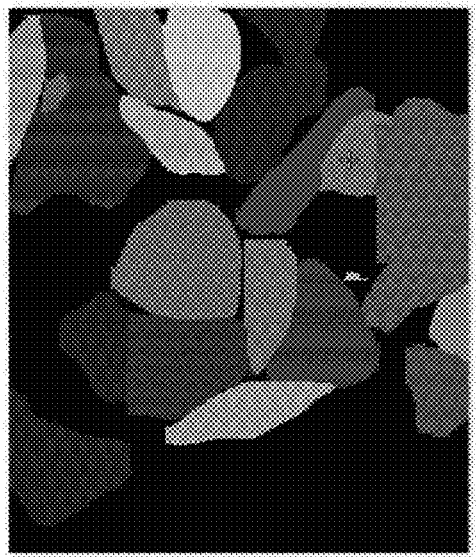
Figure 56A:
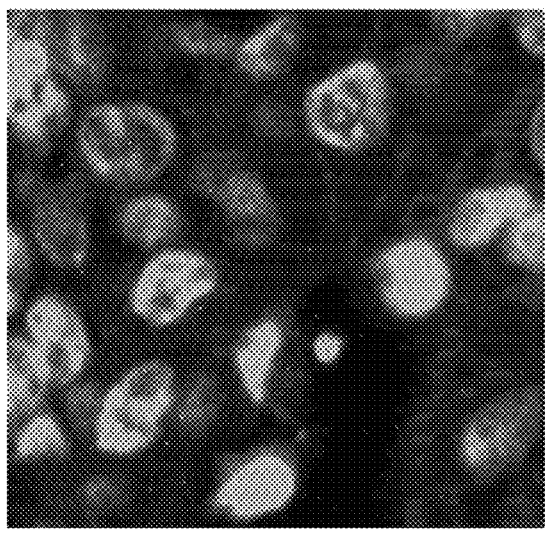
FIGS. 56A-56K. Adjusting the brightness of a raw image displayed by Caliban.
Figure 56B:
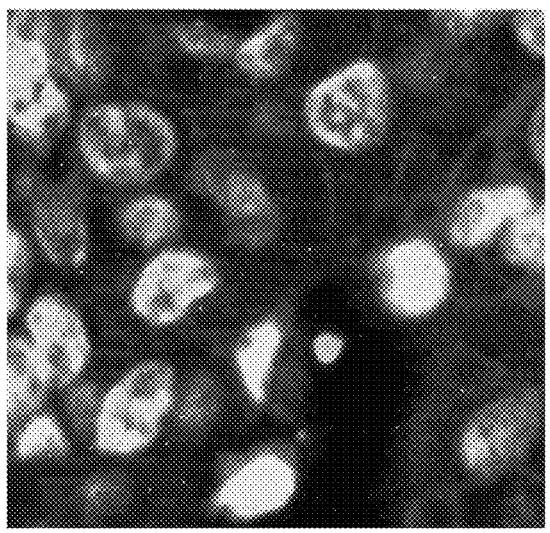
Figure 56C:
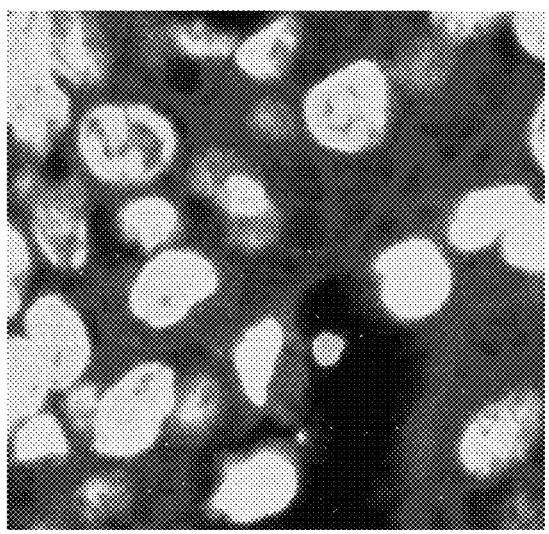
Figure 56D:
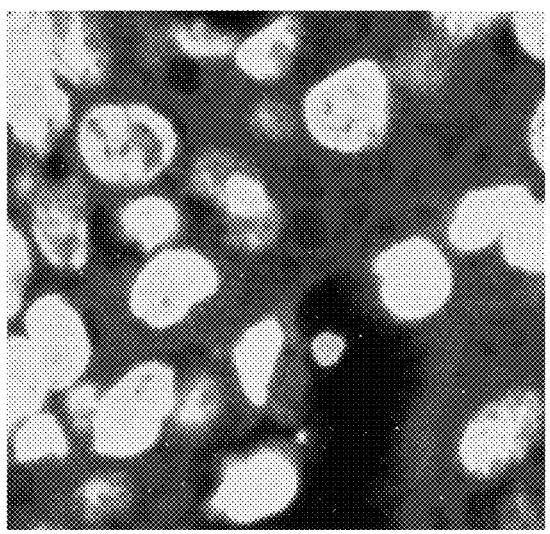
Figure 56E:
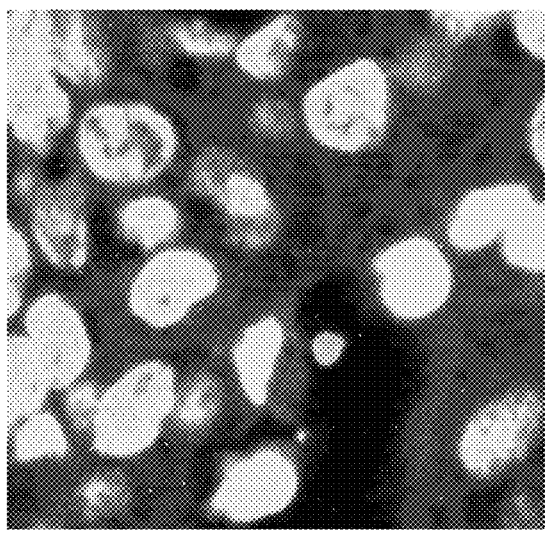
Figure 56F:
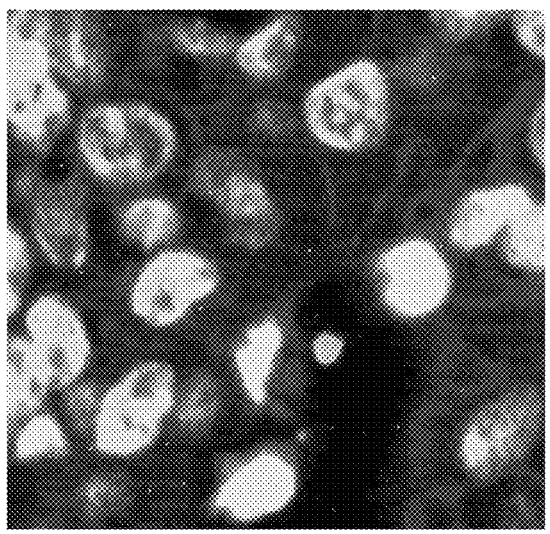
Figure 56G:
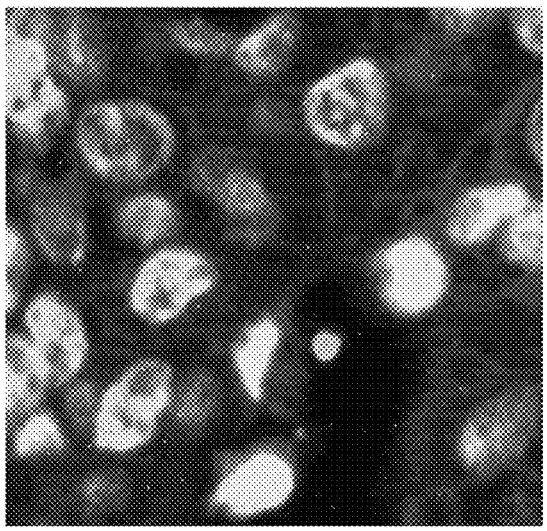
Figure 56H:
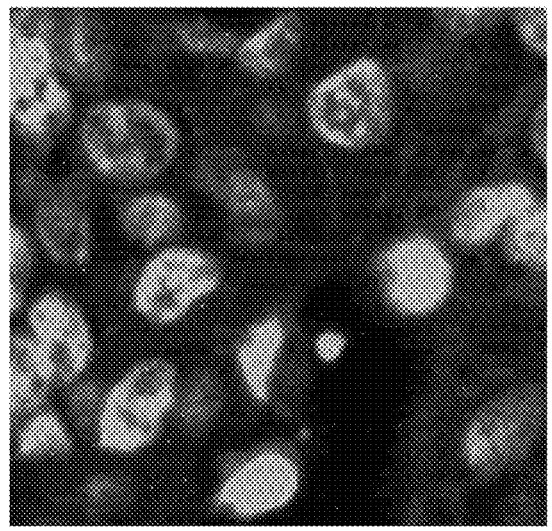
Figure 56I:
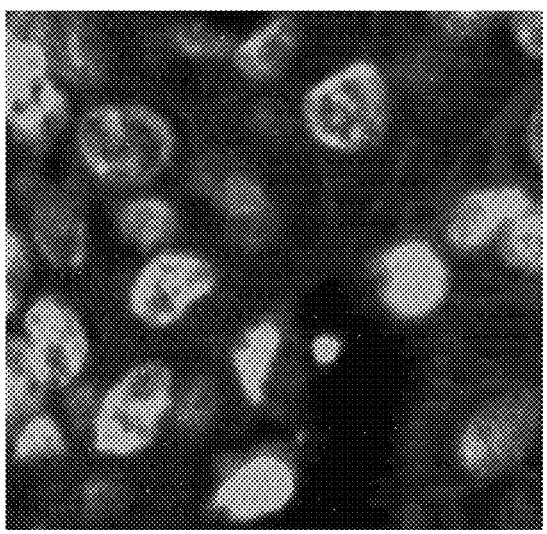
Figure 56J:
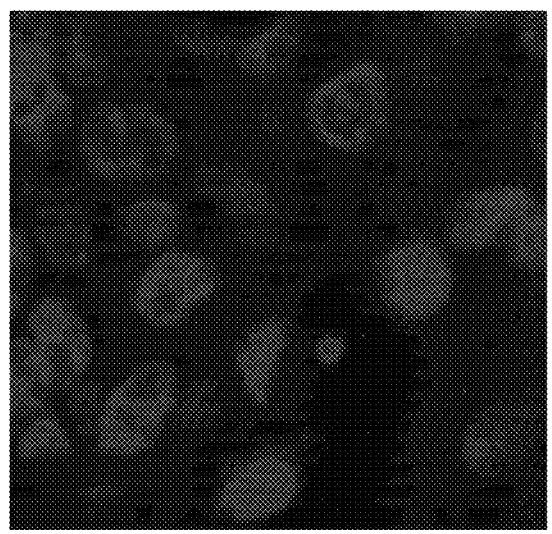
Figure 56K:

FIGS. 51A-51V. Replacing a second label with a first label in one frame or all frames.

FIGS. 52A-52G. Delete a label from a single frame.

FIGS. 53A-53H. Thresholding in pixel-editing mode.

FIGS. 54A-54E. Flood action.

FIGS. 55A-55K. Trimming away unconnected pieces (pixel(s) associated/having with a label unconnected with the remaining pixels associated/having with the label).

Multi-Channel Mode

FIGS. 56A-56K. Adjusting the brightness of a raw image displayed by Caliban.

Figure 57A:
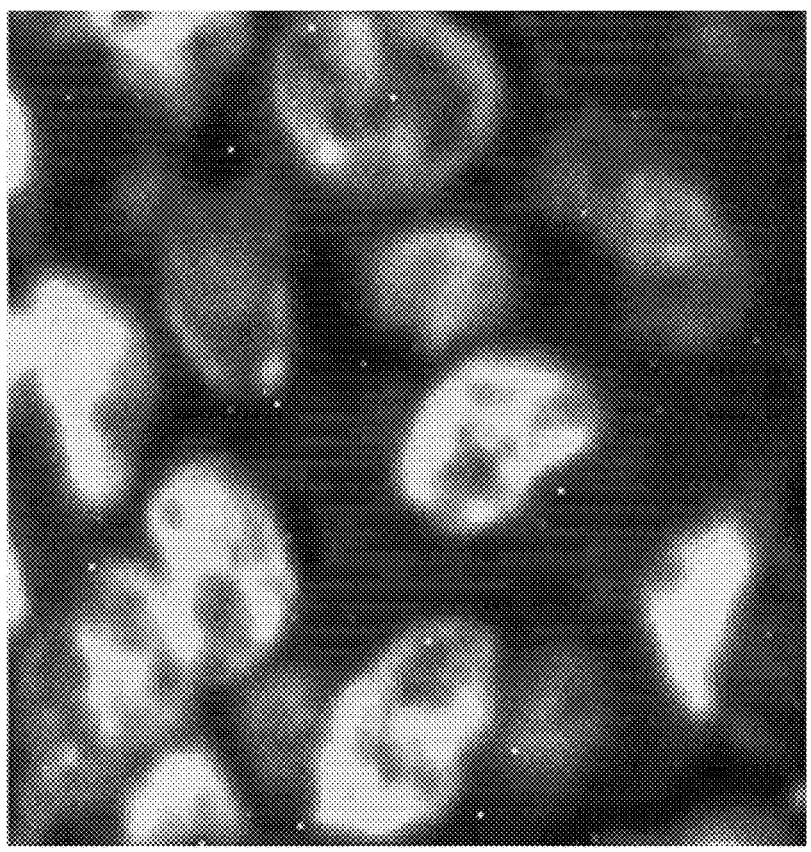
FIGS. 57A-57B. A raw image with the current state of the cell masks (shown as white outlines overlaid on a raw image) toggled off (FIG. 57A) and on (FIG. 57B).
Figure 57B:
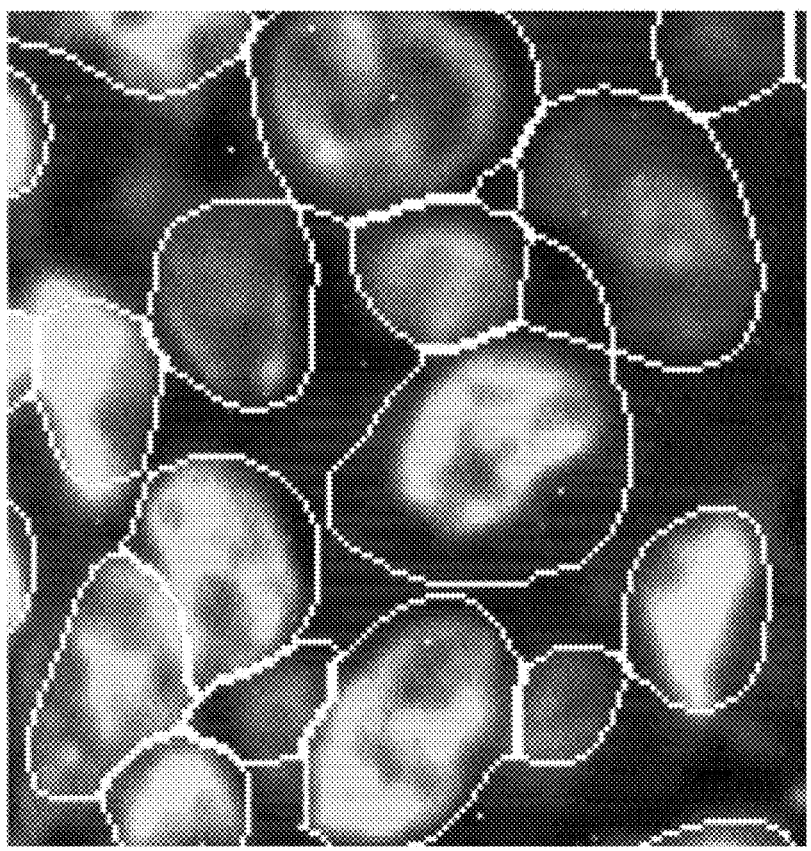

FIGS. high_backgroundA-57B. A raw image with the current state of the cell masks (shown as white outlines overlaid on a raw image) toggled off (FIG. 57A) and on (FIG. 57B).

Figure 58A:
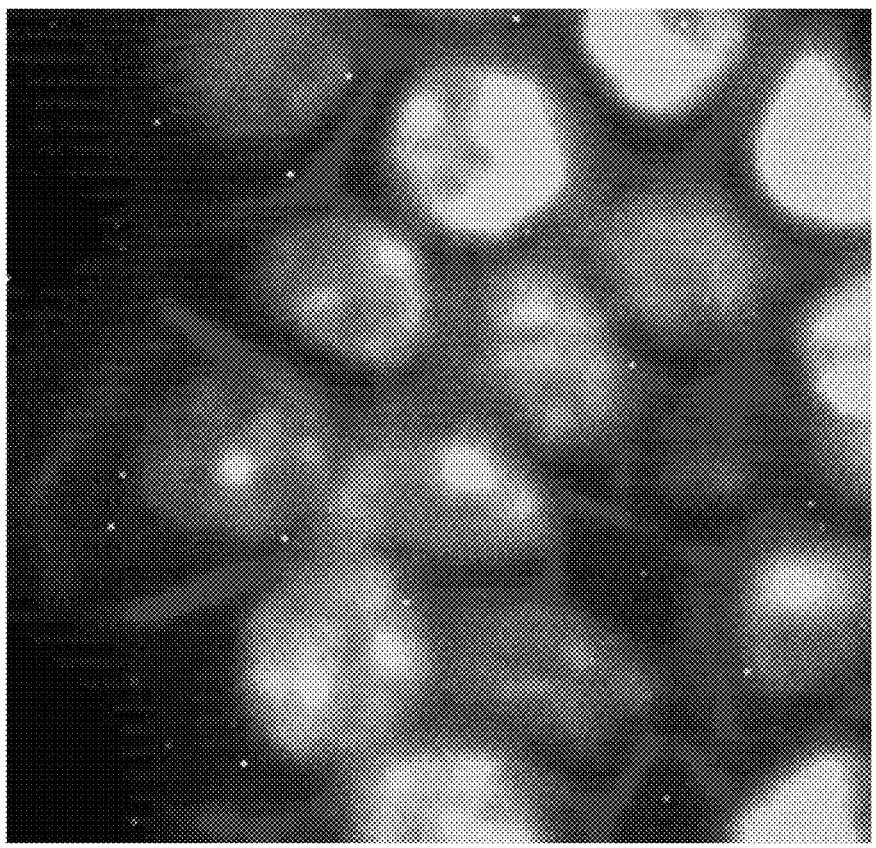
FIGS. 58A-58B. A raw image with the current state of the cell masks (shown as white outlines overlaid on a raw image) toggled off (FIG. 58A) and on (FIG. 58B).
Figure 58B:
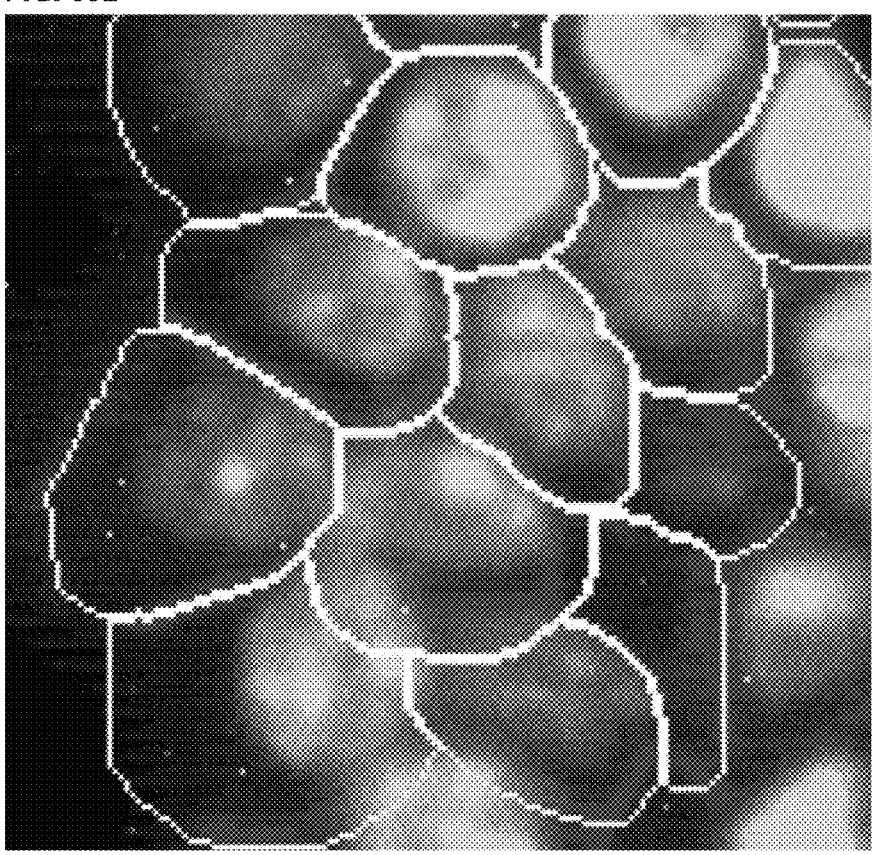

FIGS. toggle_outlinesA-58B. A raw image with the current state of the cell masks (shown as white outlines overlaid on a raw image) toggled off (FIG. 58A) and on (FIG. 58B).

Figure 59A:
FIGS. 59A-59B. Toggle between (1) the current state of the cell masks shown as white outlines overlaid on a raw image and (2) the current state of the cell masks.
Figure 59B:
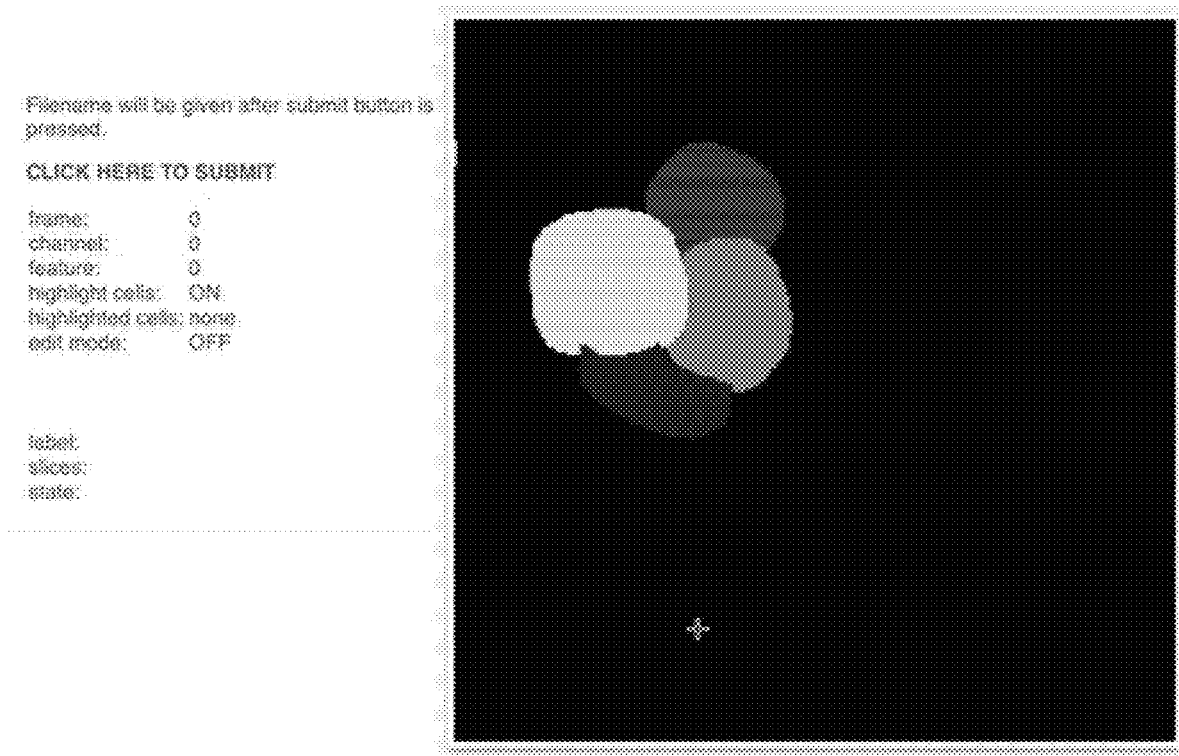

FIGS. 59A-59B. Toggle between (1) the current state of the cell masks shown as white outlines overlaid on a raw image and (2) the current state of the cell masks.

Figure 60A:
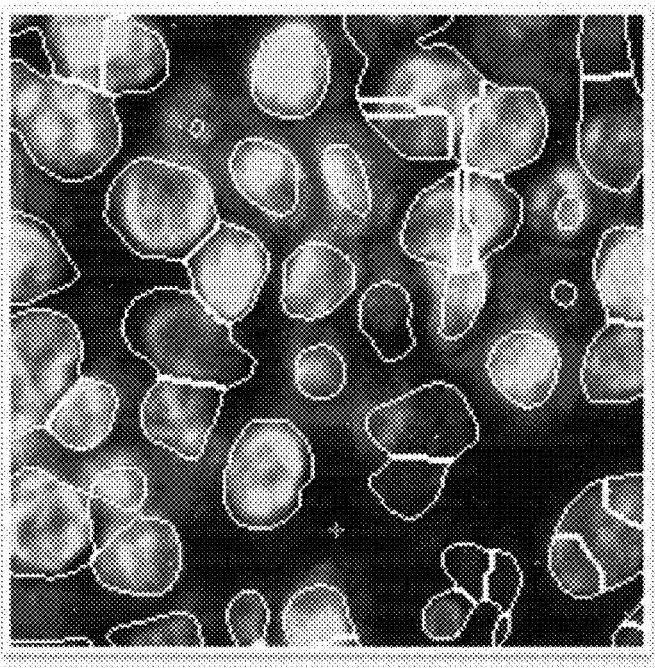
FIGS. 60A-60B. Toggling on and off the edit mode.
Figure 60B:
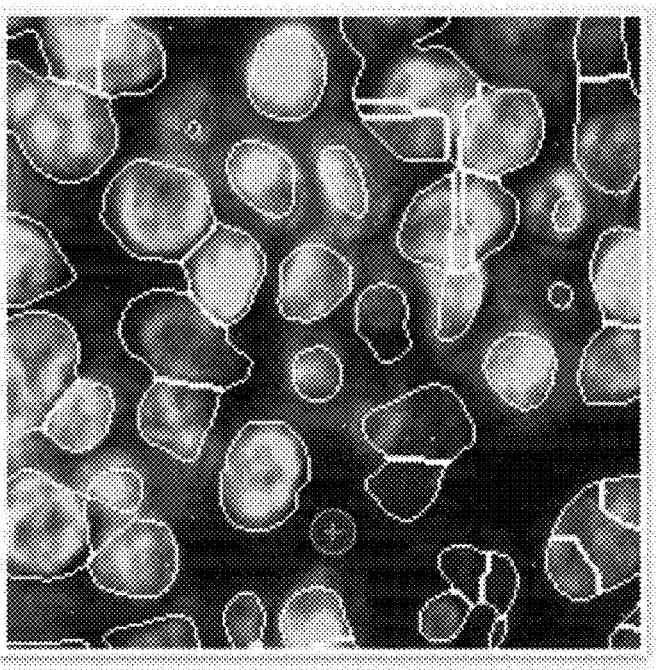
Figure 61A:
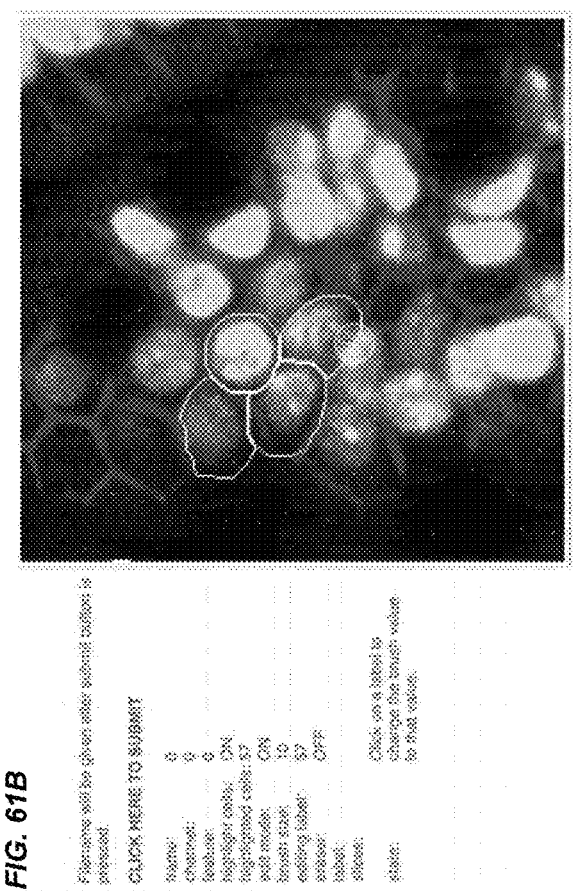
FIGS. 61A-61D. Picking a label with Caliban. The figures show that cell label 57 was first picked, and cell label 53 was subsequently picked.
Figure 61B:
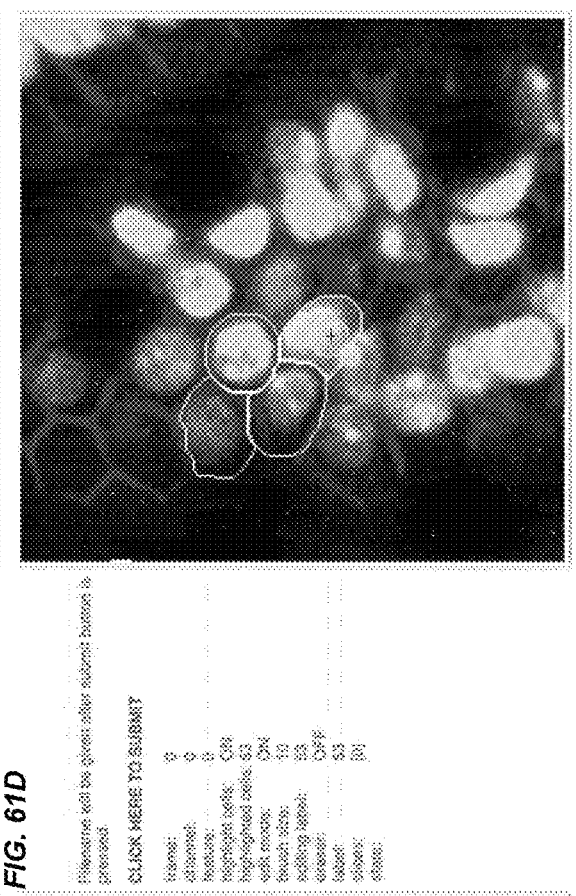
Figure 61C:
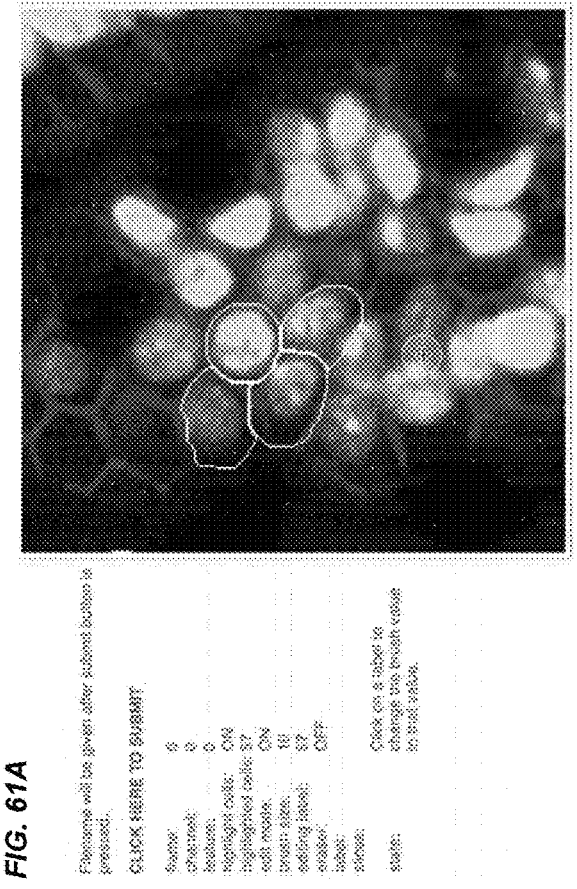
Figure 61D:
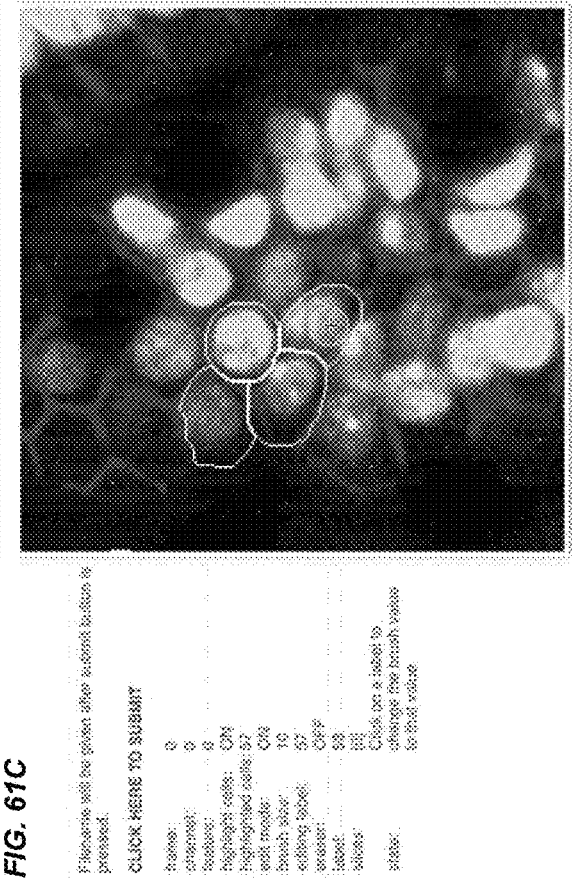
Figure 62B:
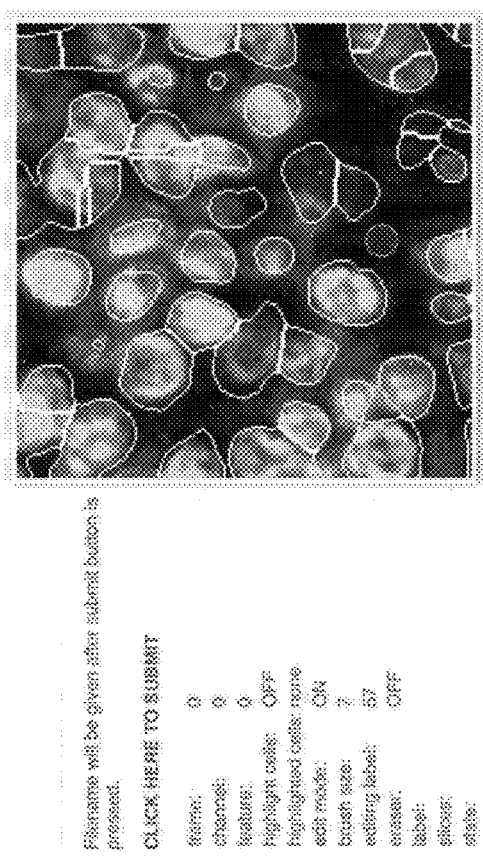
FIGS. 62A-62L. Increasing and increasing the brush size.
Figure 62D:
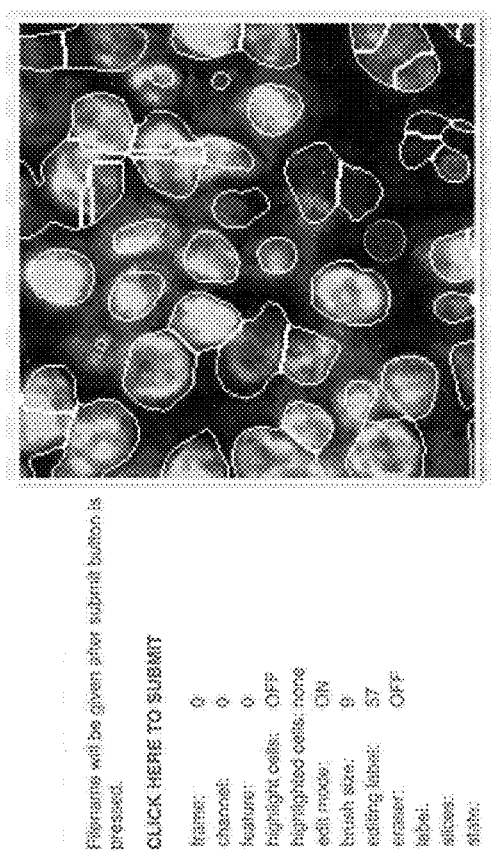
Figure 62A:
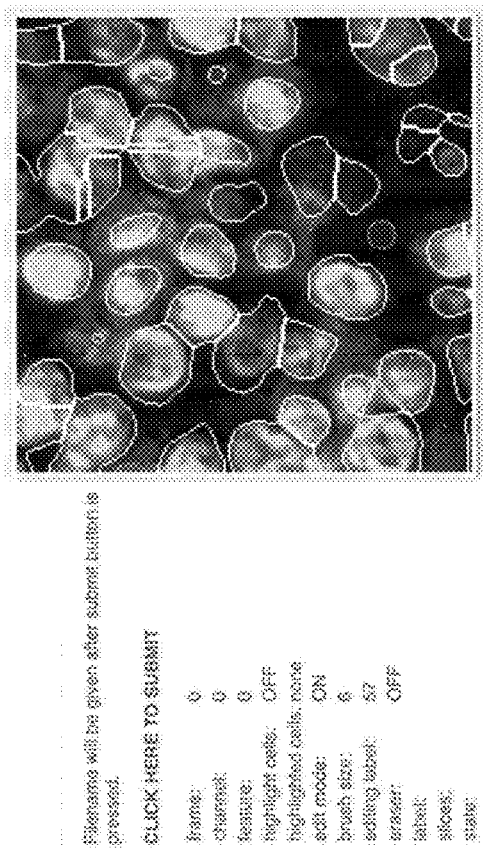
Figure 62C:
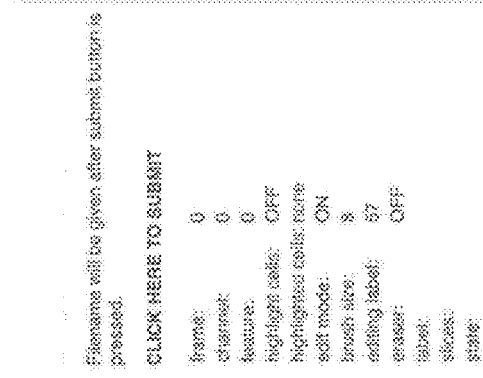
Figure 62F:
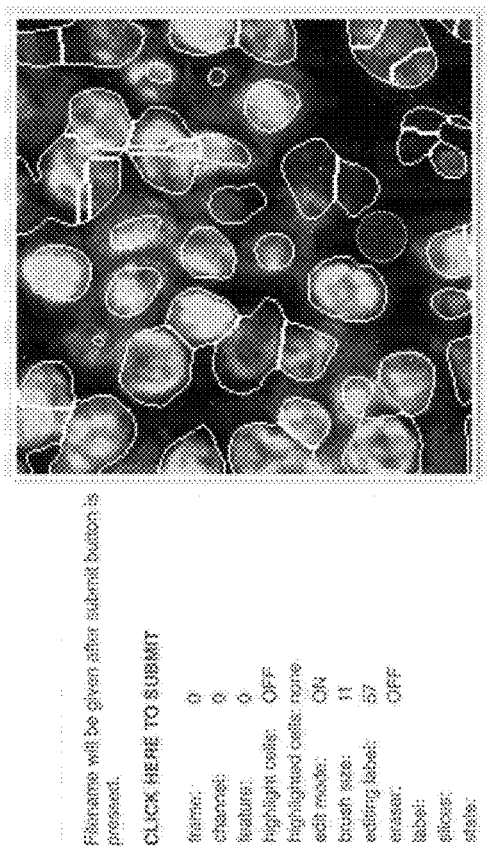
Figure 62H:
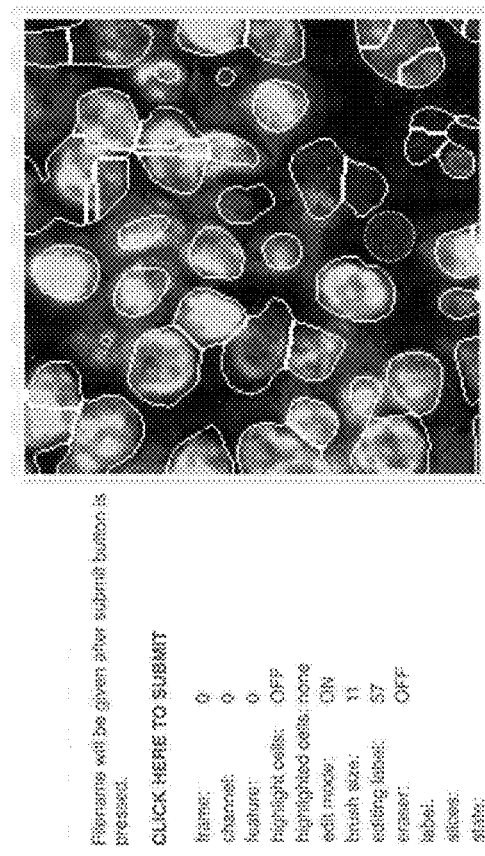
Figure 62E:
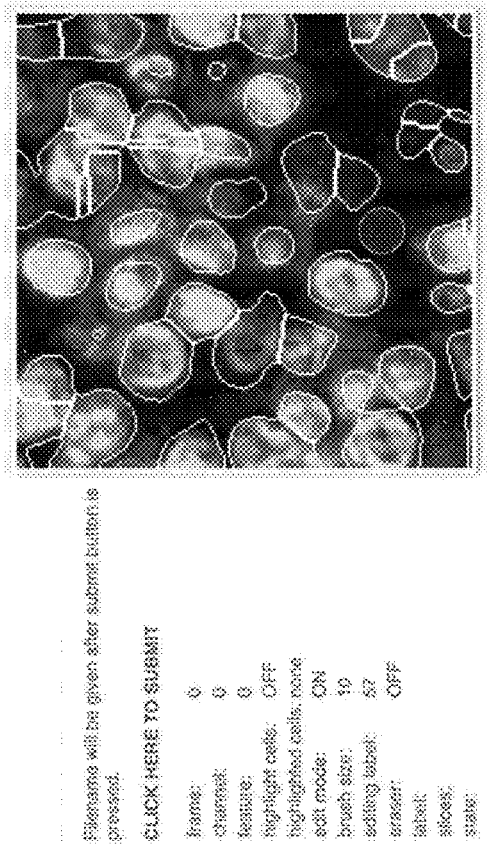
Figure 62G:
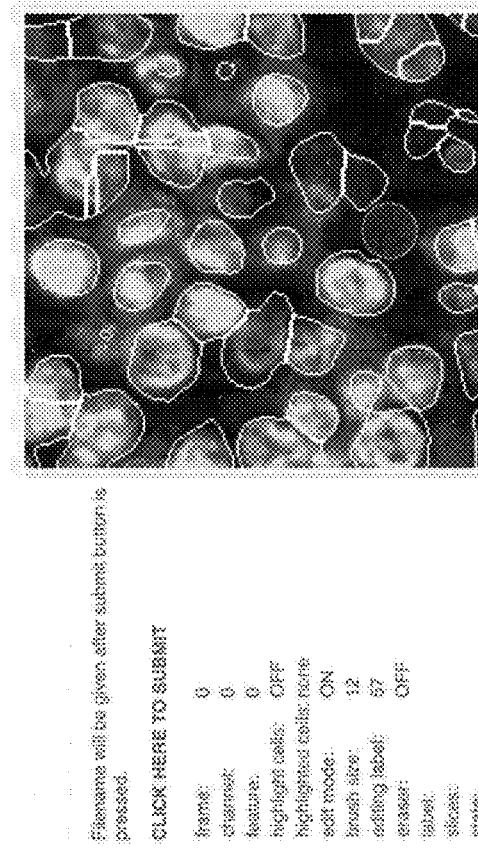
Figure 62J:
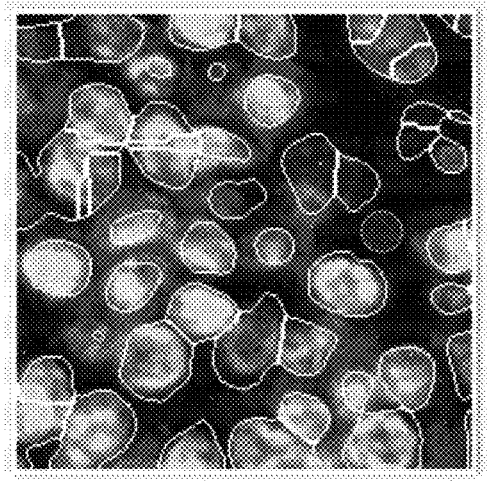
Figure 62L:
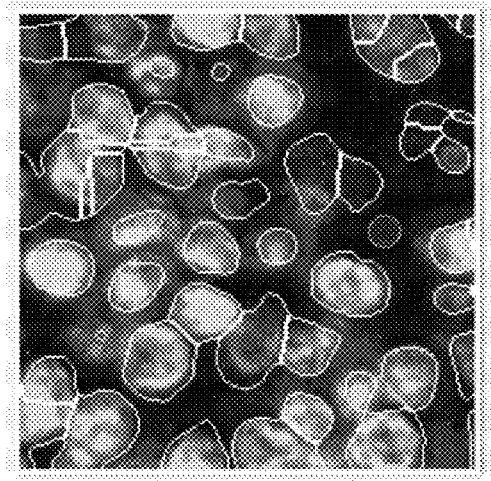
Figure 62I:
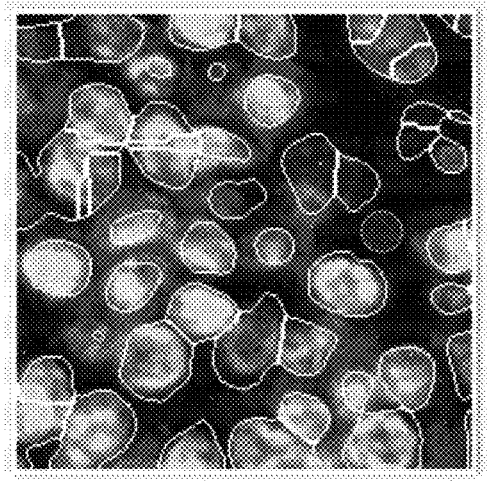
Figure 62K:
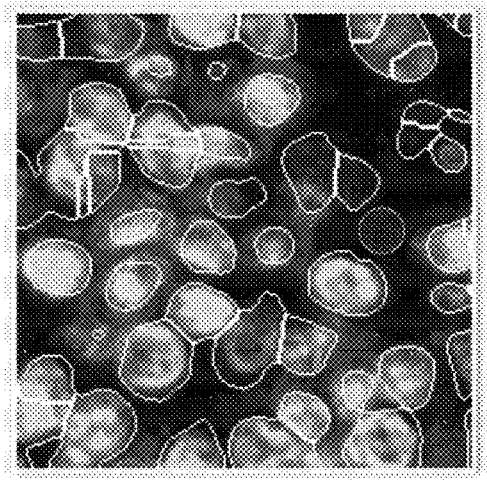
Figure 63A:
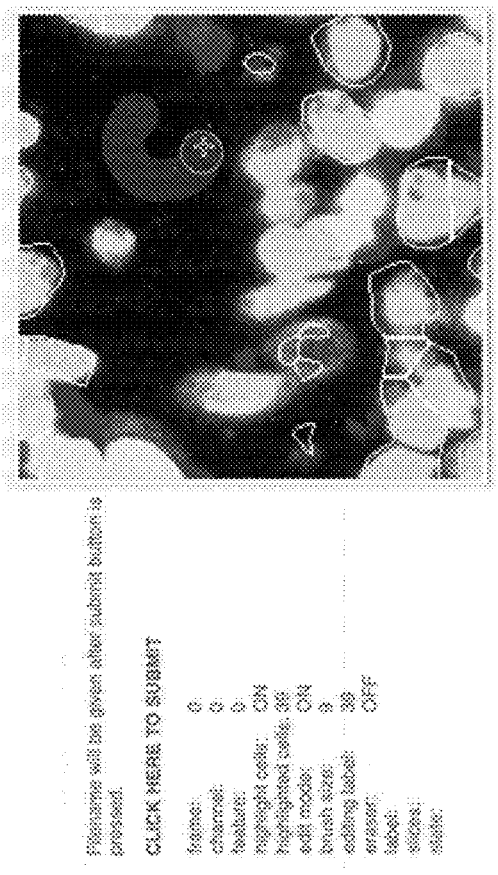
FIGS. 63A-63H. Using the brush tool to draw (e.g., select) pixels associated with (or assigned to) a cell label in a two-step process by drawing the exterior followed by filling the interior. The pixels drawn by the brush are associated with (or assigned to) the cell label.
Figure 63B:
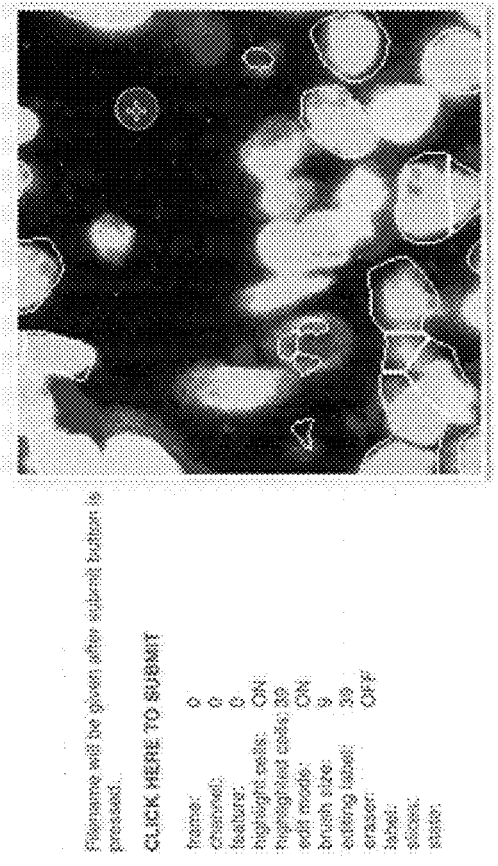
Figure 63C:
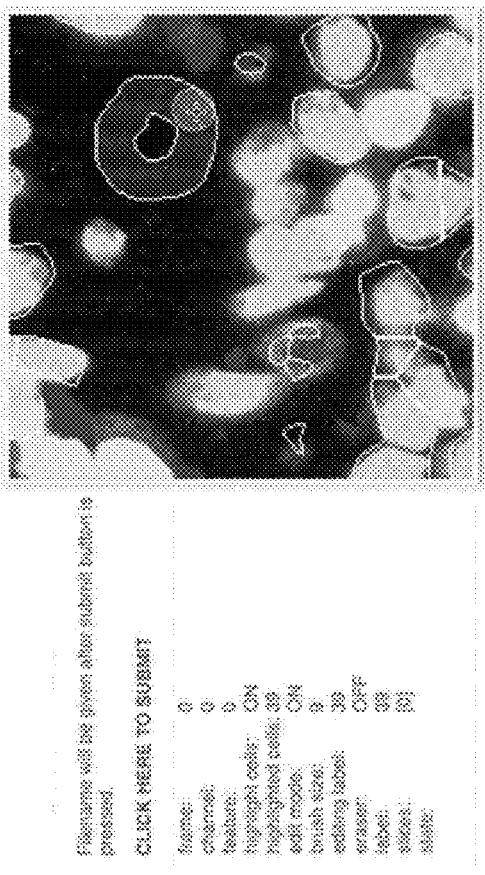
Figure 63D:
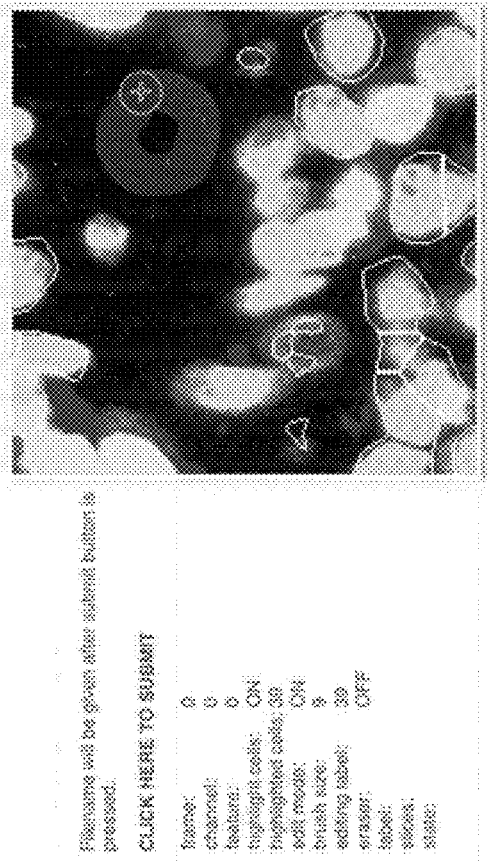
Figure 63F:
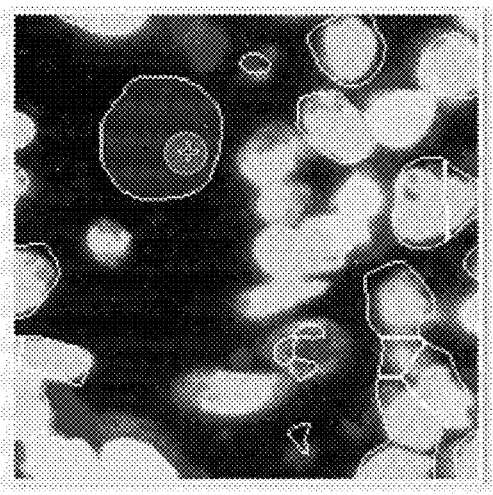
Figure 63H:
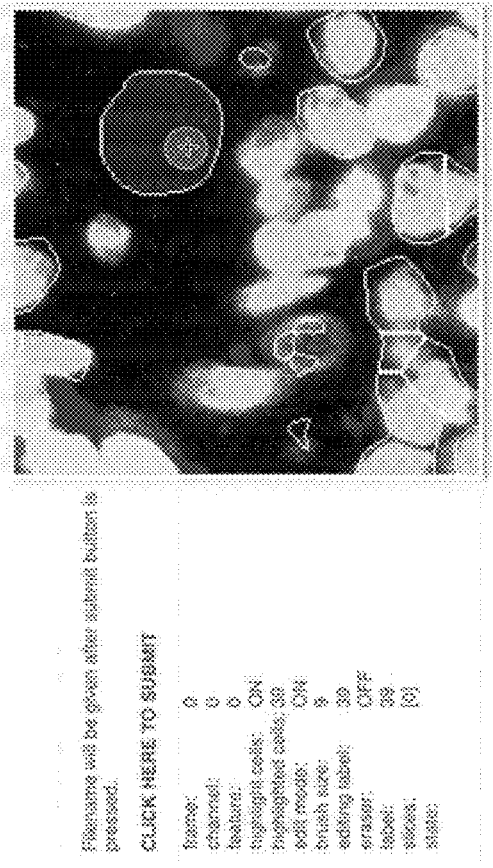
Figure 63E:
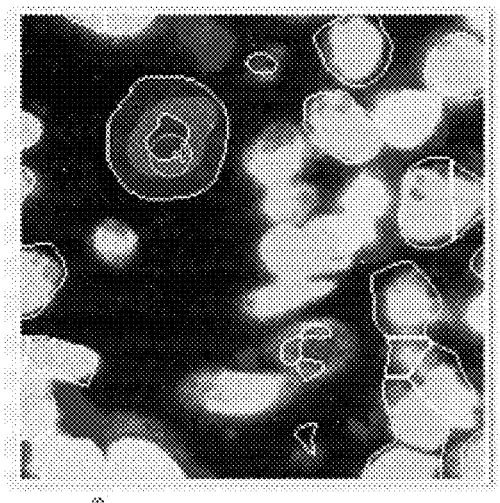
Figure 63G:
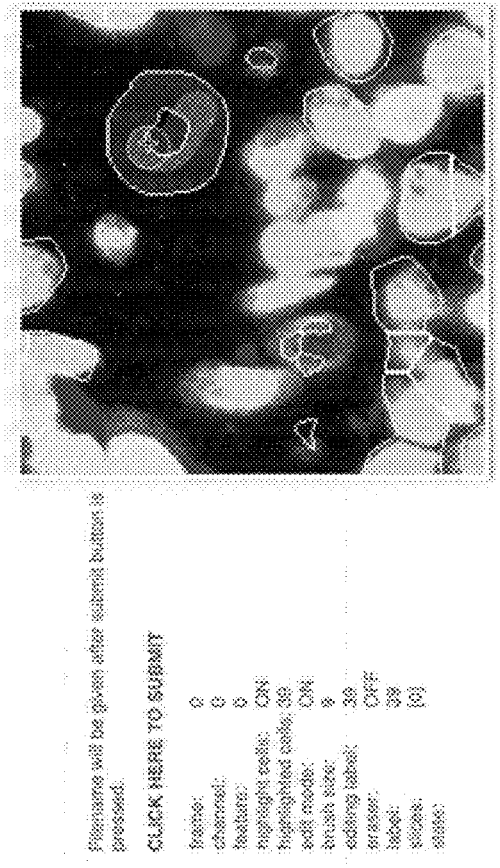
Figure 64B:
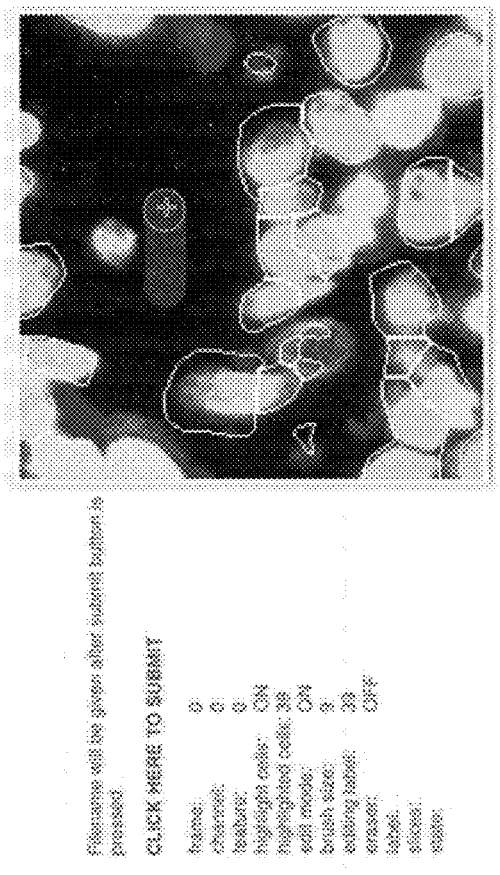
FIGS. 64A-64H. Using the brush tool to draw (e.g., select) pixels associated with (or assigned to) a cell label in a two-step process by drawing the top part followed by drawing the bottom part. The pixels drawn by the brush are associated with (or assigned to) the cell label.
Figure 64D:
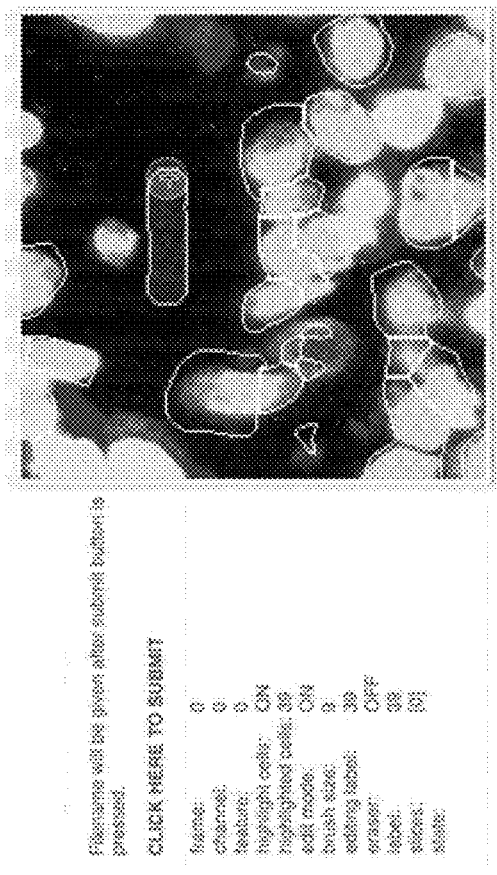
Figure 64A:
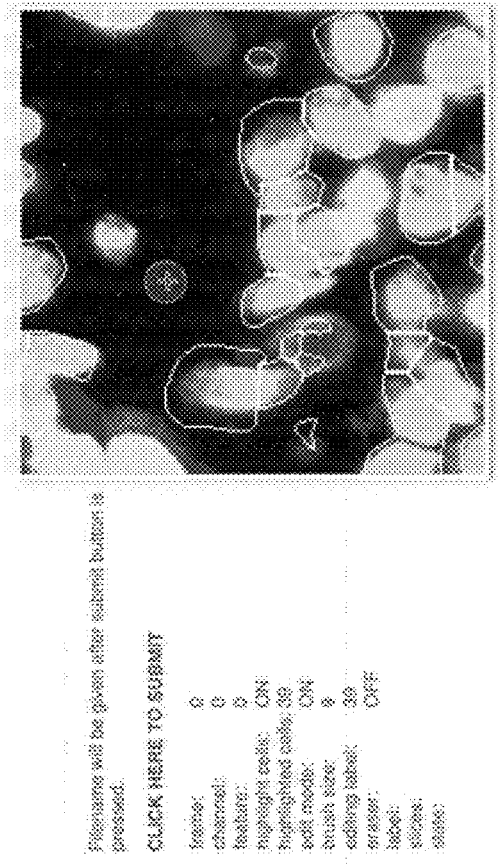
Figure 64C:
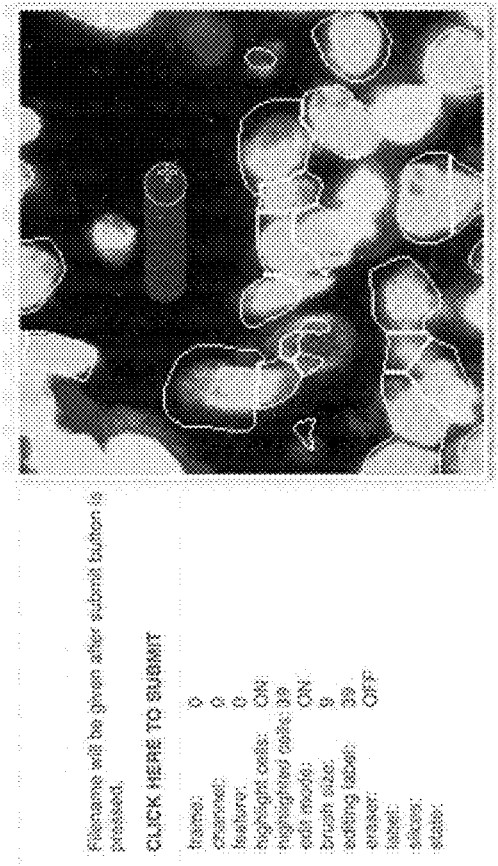
Figure 64E:
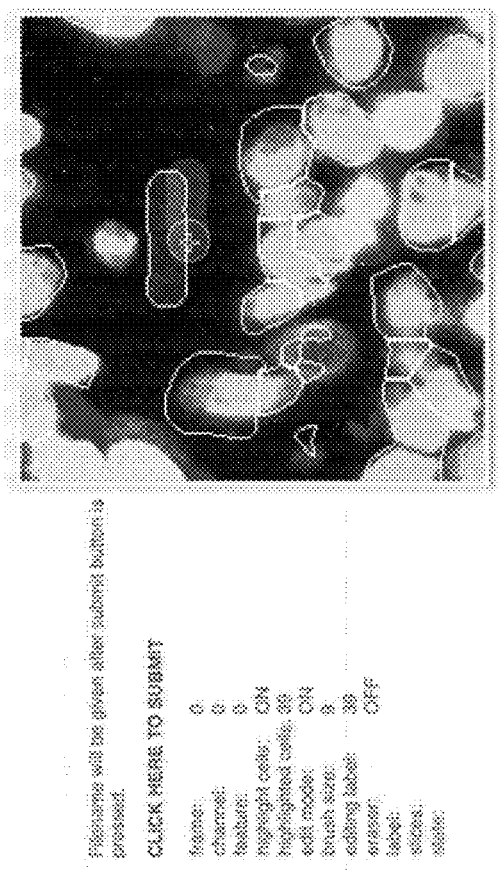
Figure 64F:
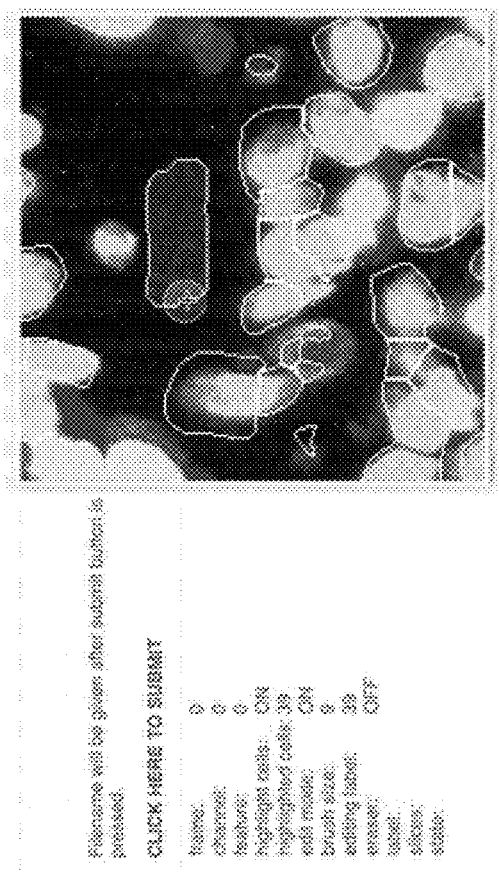
Figure 64G:
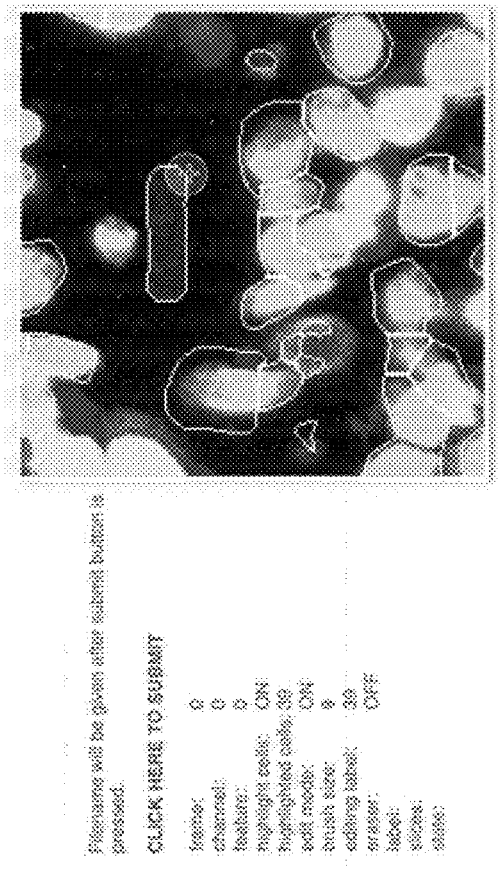
Figure 64H:
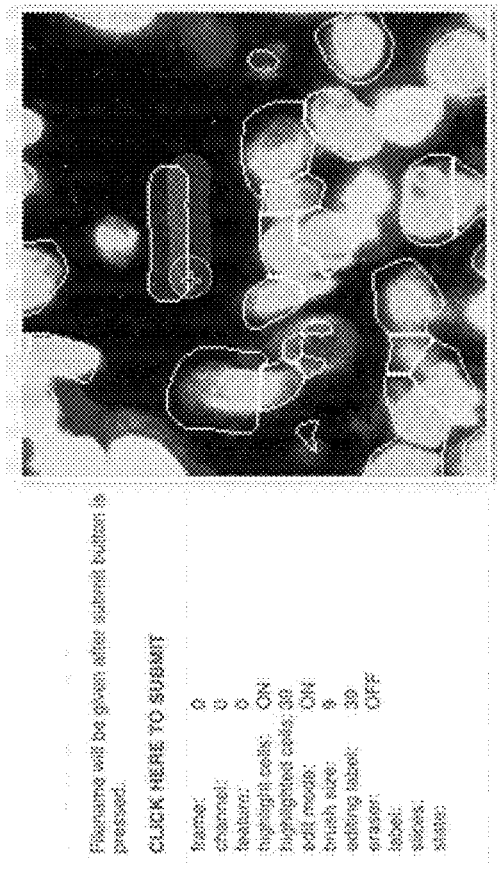
Figure 65A:
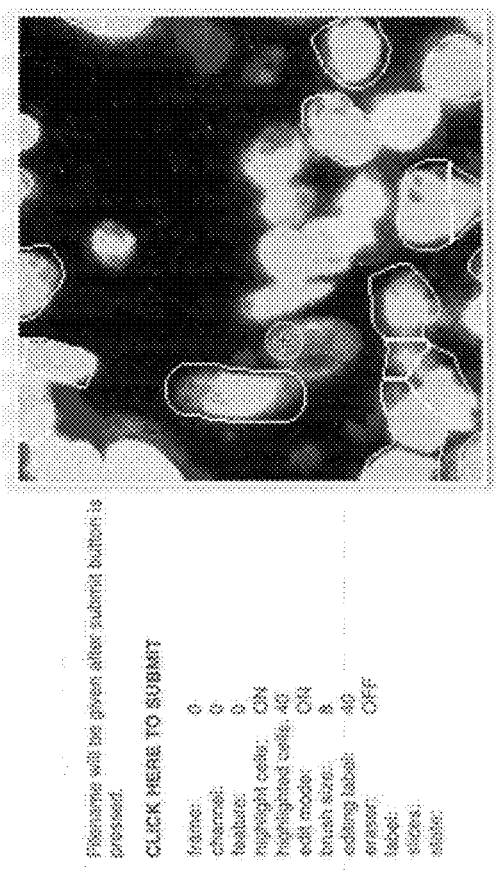
Figure 65B:
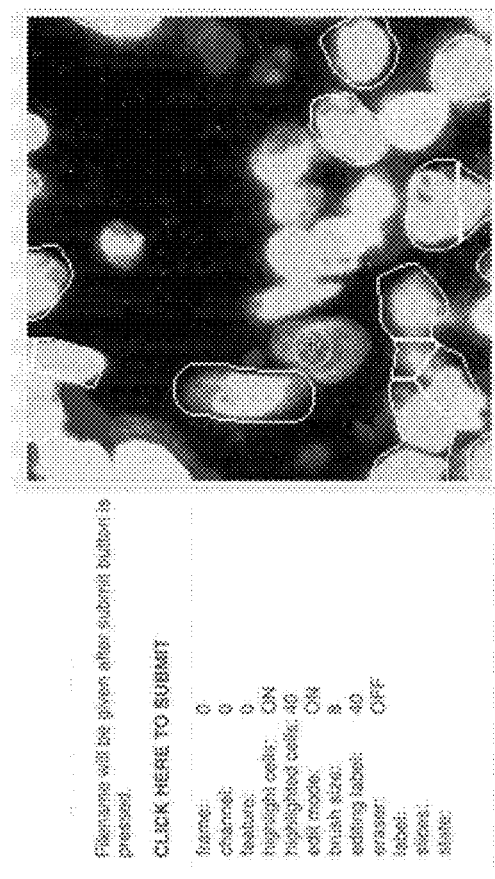
Figure 65C:
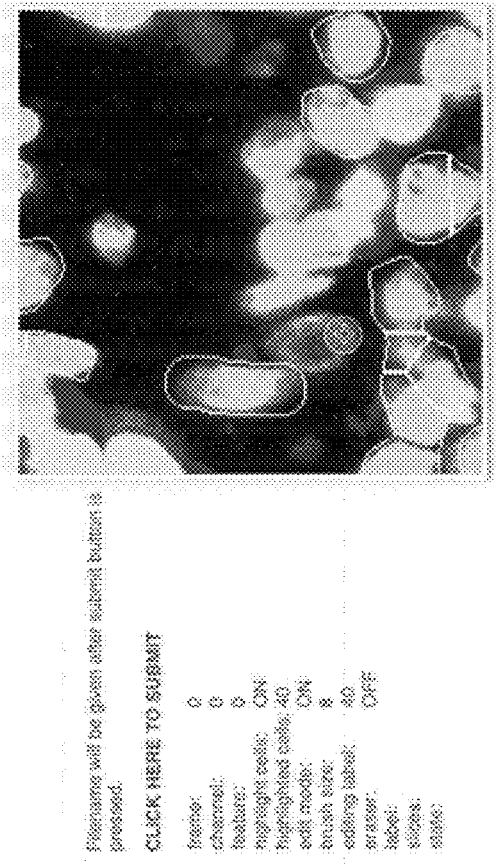
Figure 65D:
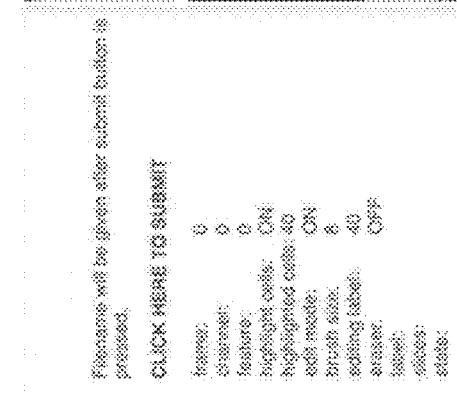
Figure 65I:
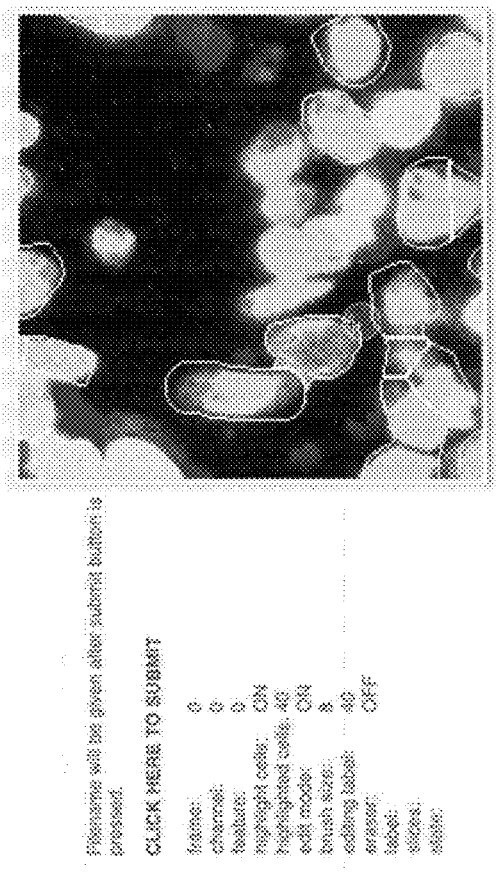
Figure 65J:
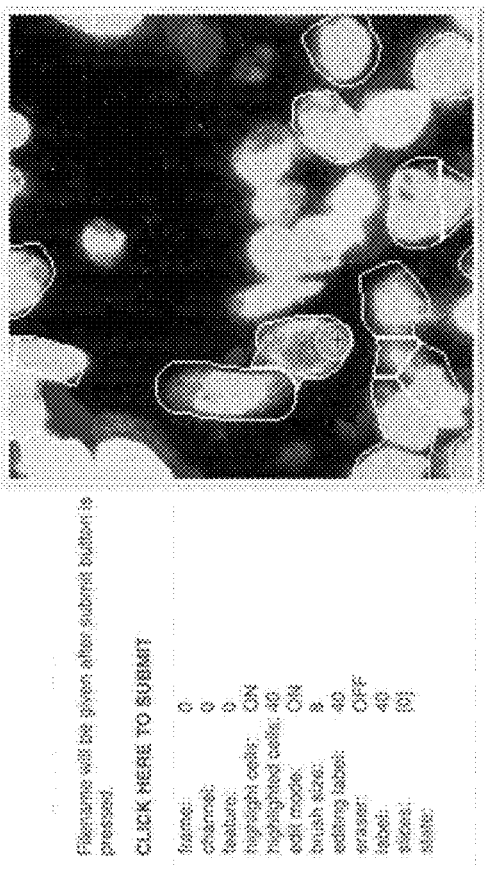
Figure 65K:
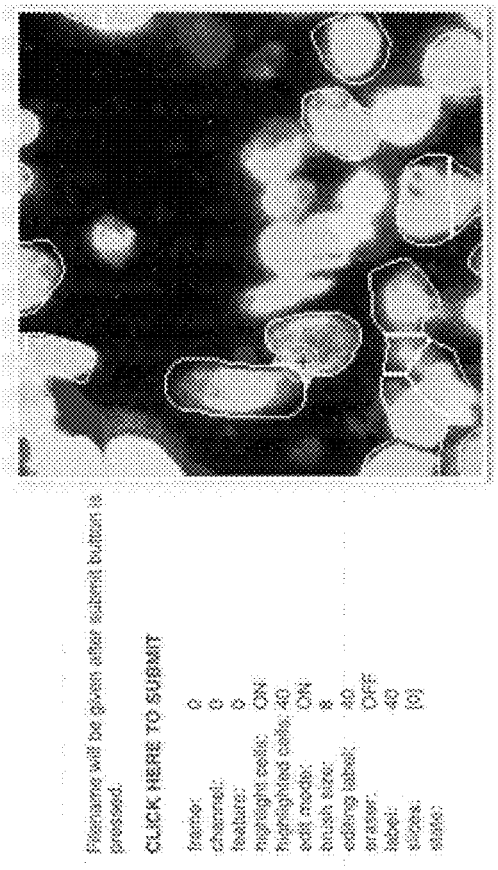
Figure 65L:
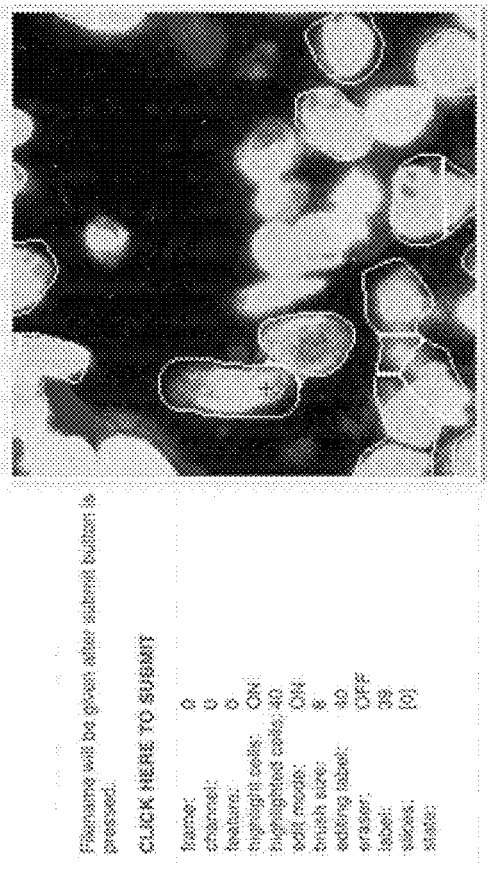
Figure 66B:
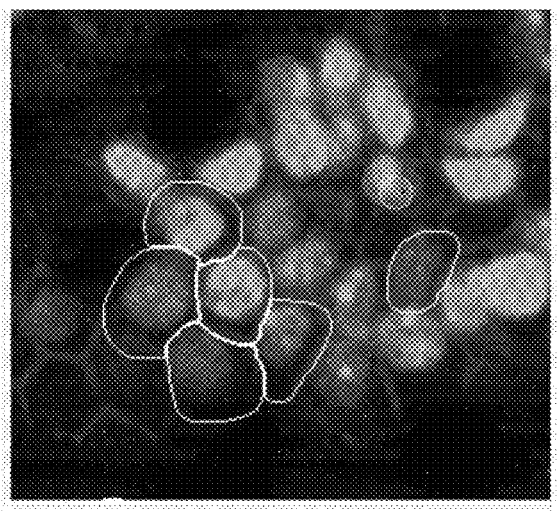
FIGS. 66A-66K. Using the brush tool to draw two new cells. The pixels drawn by the brush are associated with (or assigned to) the cell label of the new cells. The pixels drawn for the first cell and associated with (or assigned to) the first cell label (cell label 58 shown) and also drawn for the second cell were not associated with (or assigned to) the second cell label (cell label 59 shown).
Figure 66D:
Figure 66A:
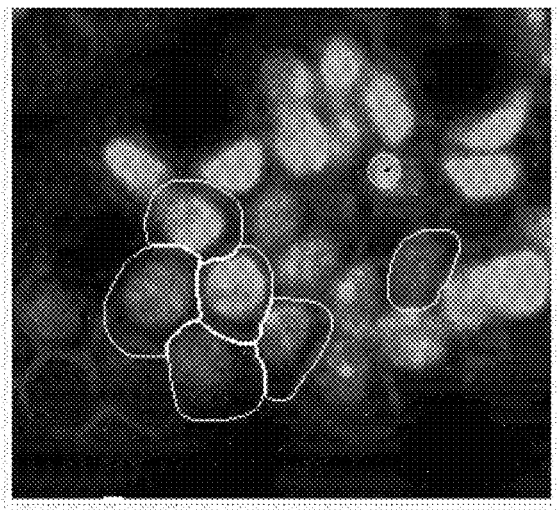
Figure 66C:
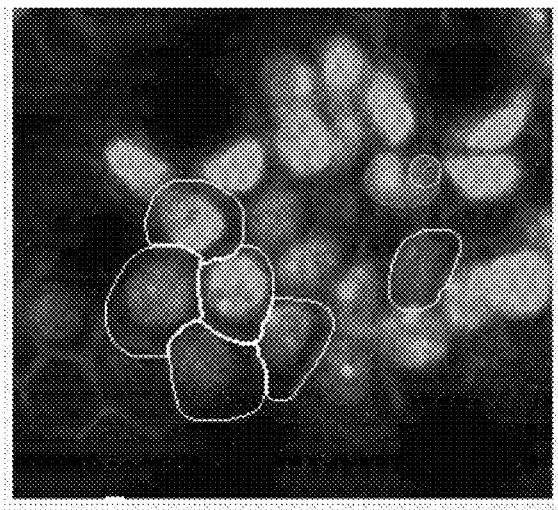
Figure 66E:
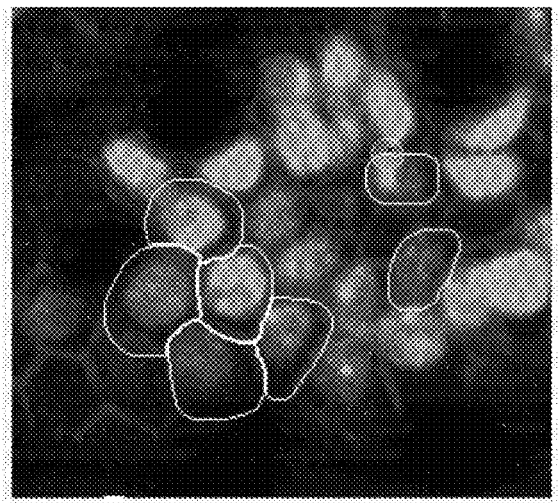
Figure 66F:
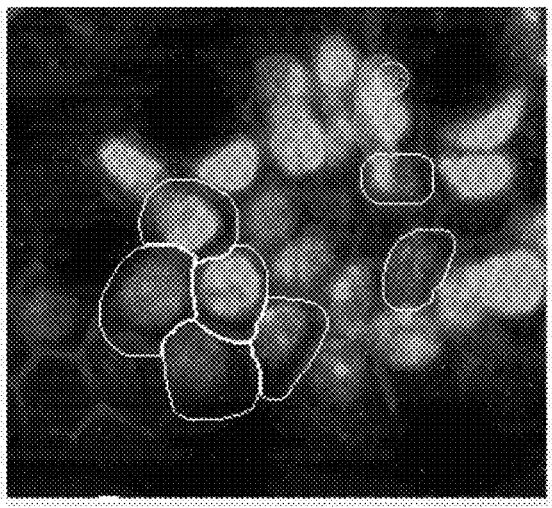
Figure 66G:
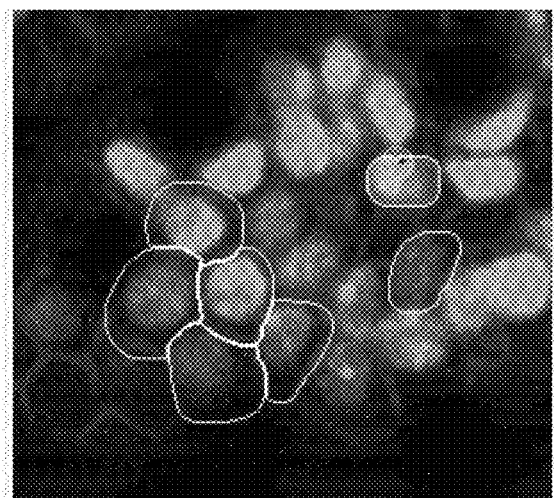
Figure 66H:
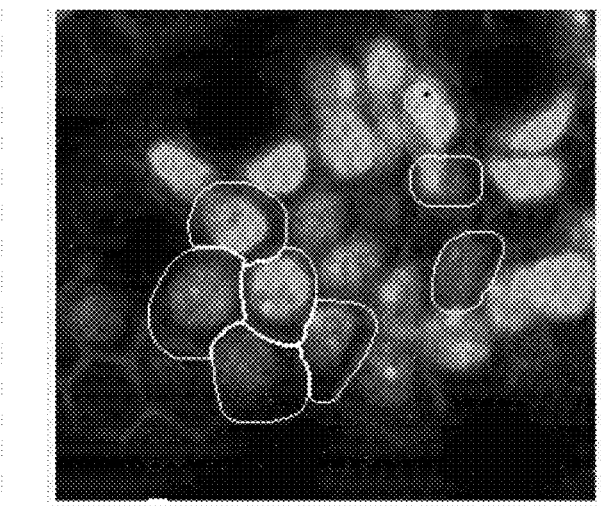
Figure 66J:
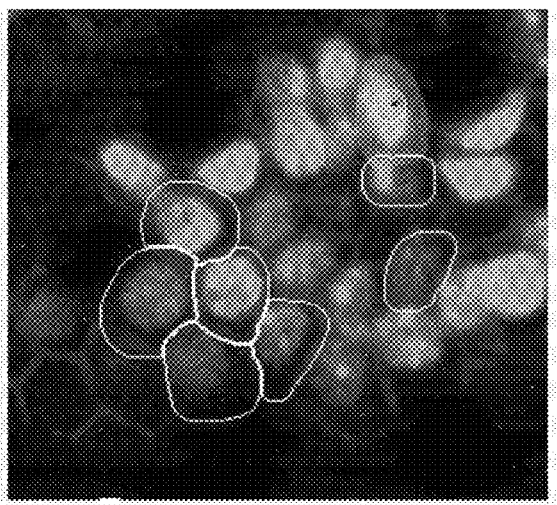
Figure 66I:
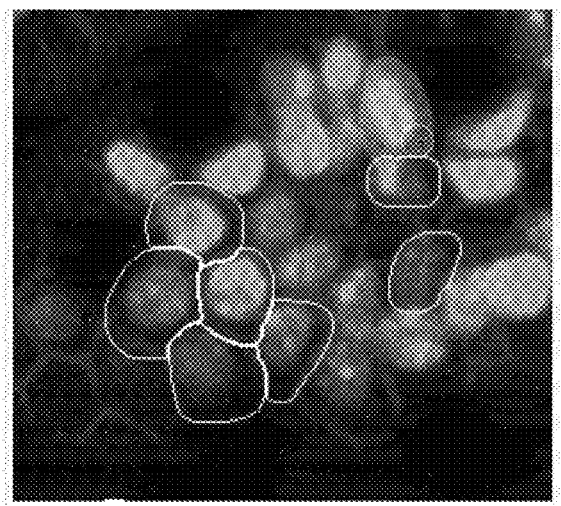
Figure 66K:
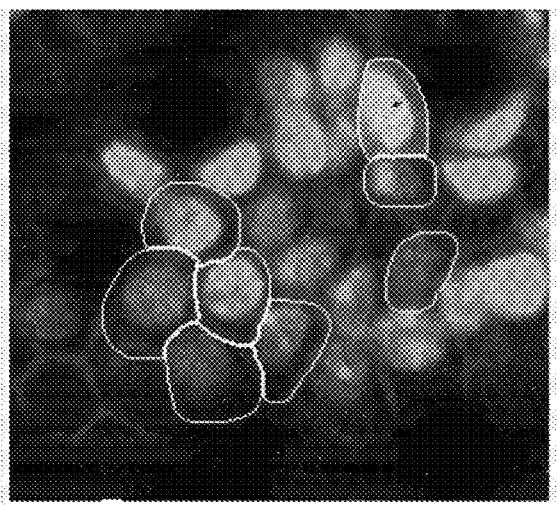
Figure 67B:
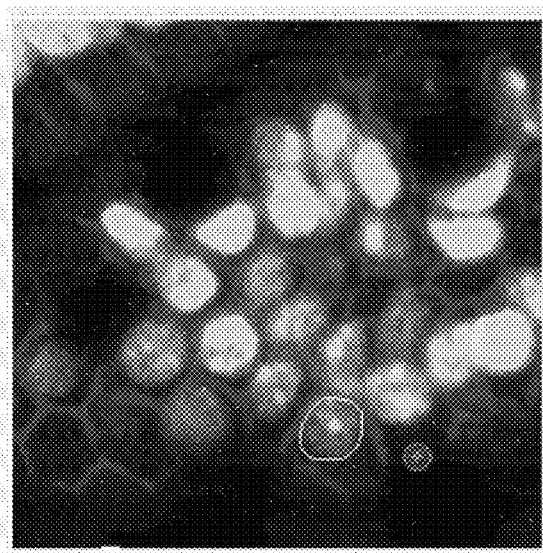
FIGS. 67A-67L. Using the brush tool to add additional pixels to be associated with a label (cell label 51 shown in the figures).
Figure 67D:
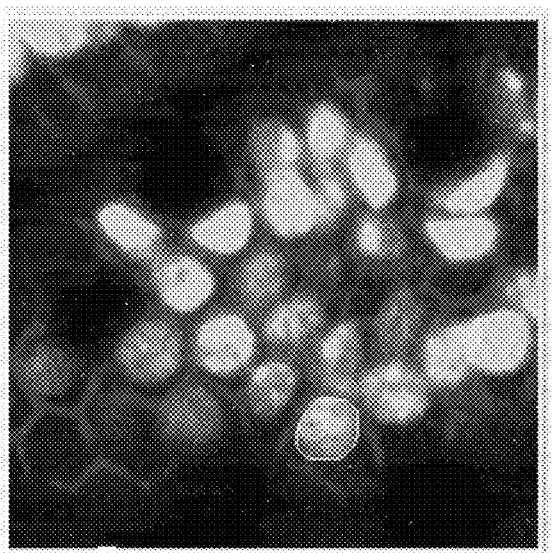
Figure 67A:
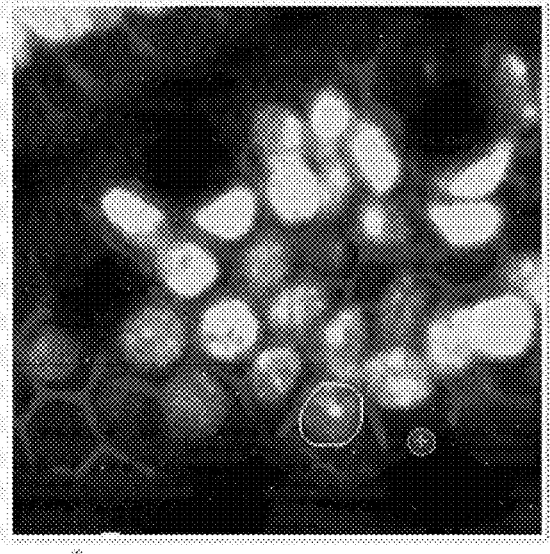
Figure 67C:
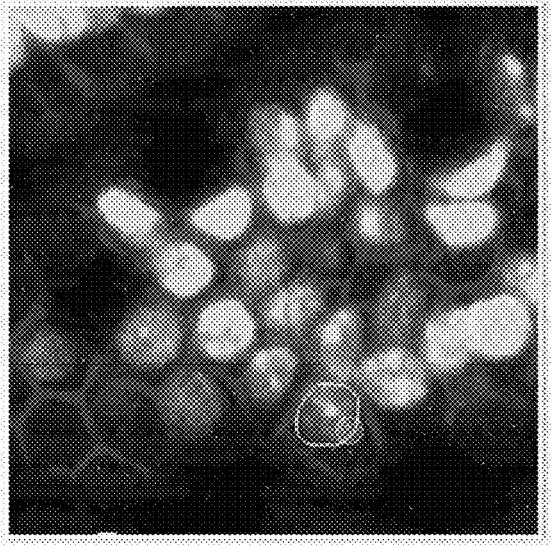
Figure 67F:
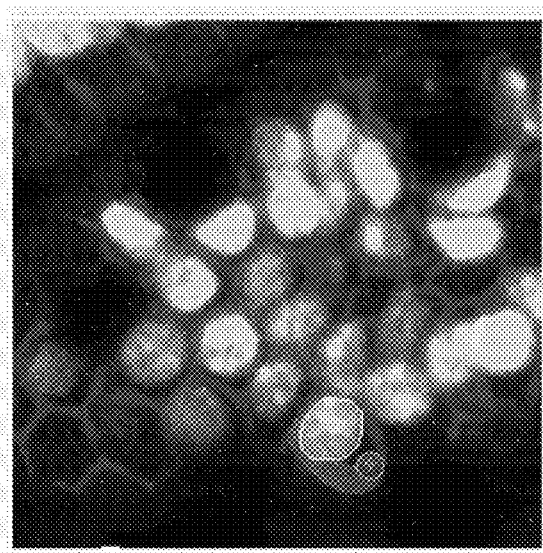
Figure 67H:
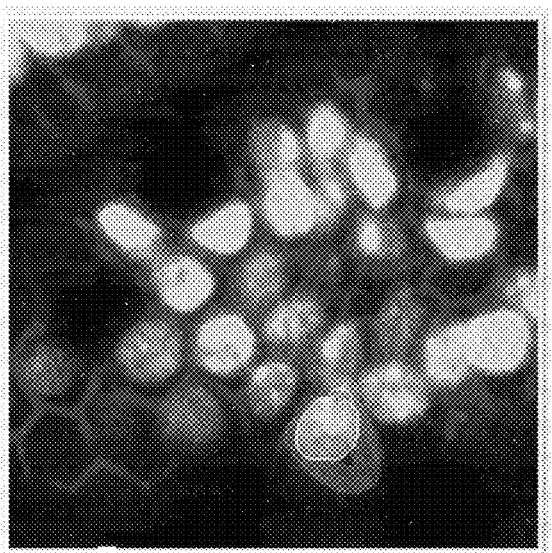
Figure 67E:
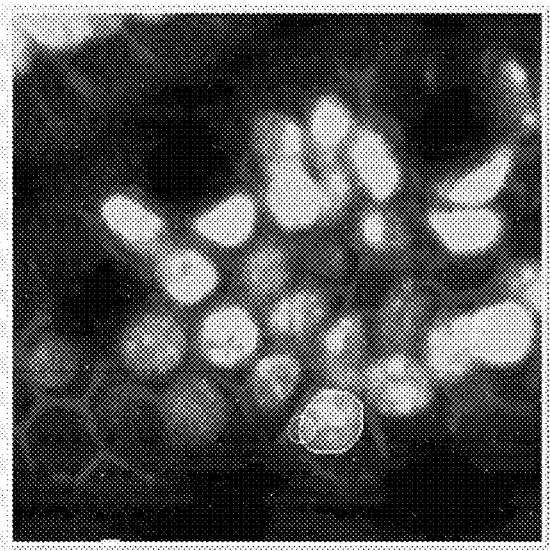
Figure 67G:
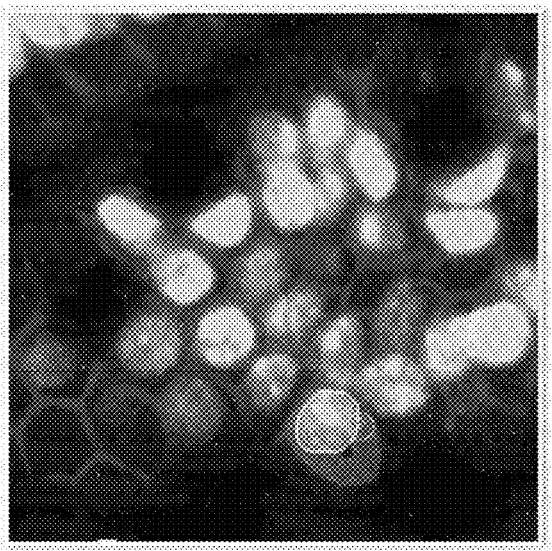
Figure 67J:
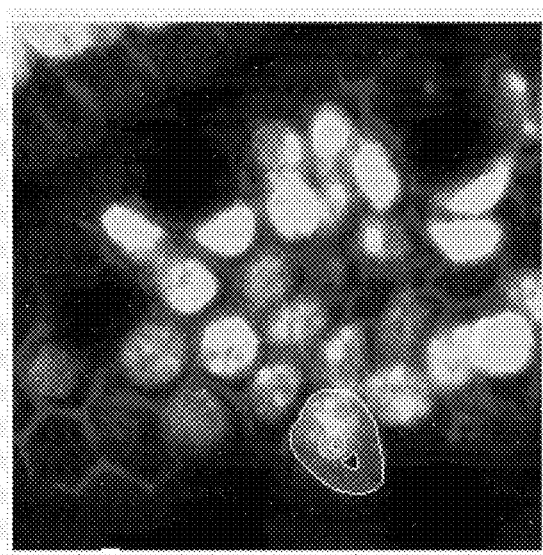
Figure 67L:
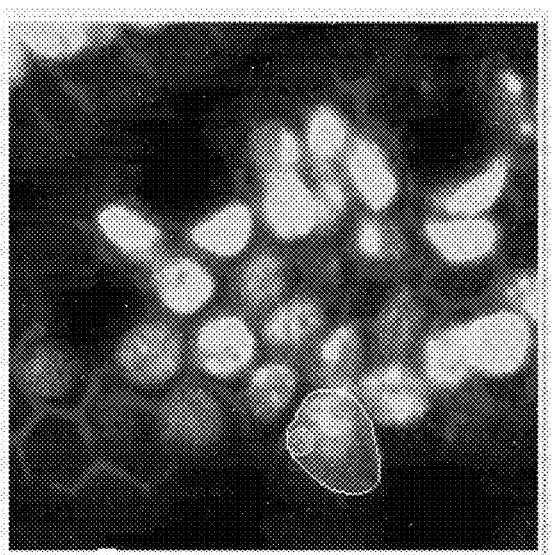
Figure 67I:
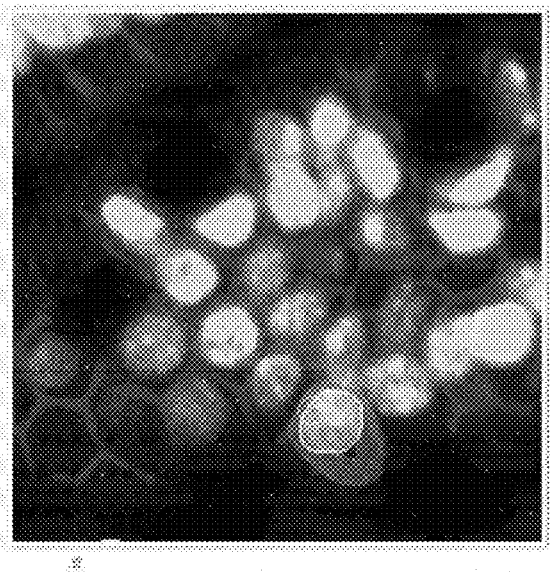
Figure 67K:
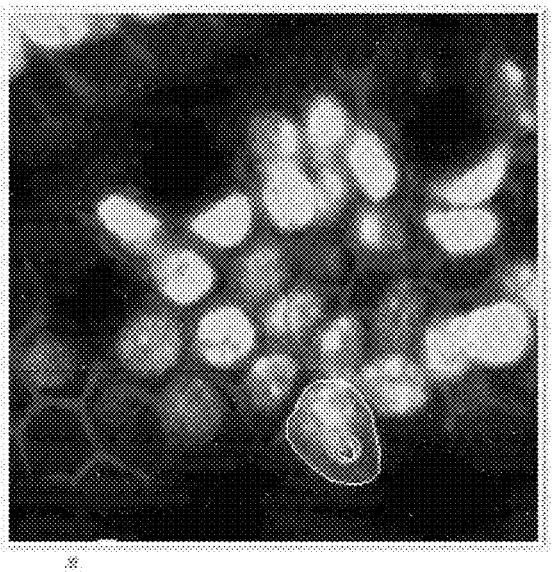
Figure 68A:
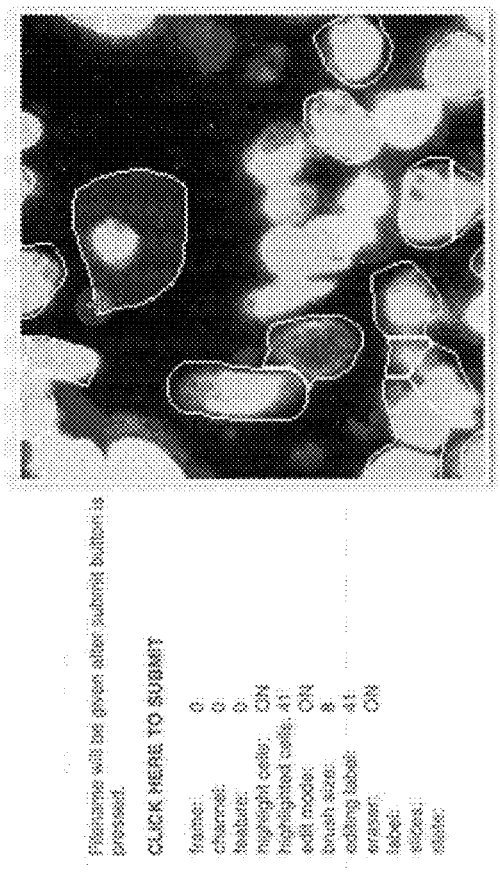
FIGS. 68A-68H. Using the brush tool to erase (e.g., remove) some pixels associated with a cell label (cell label 41 shown in the figures).
Figure 68B:
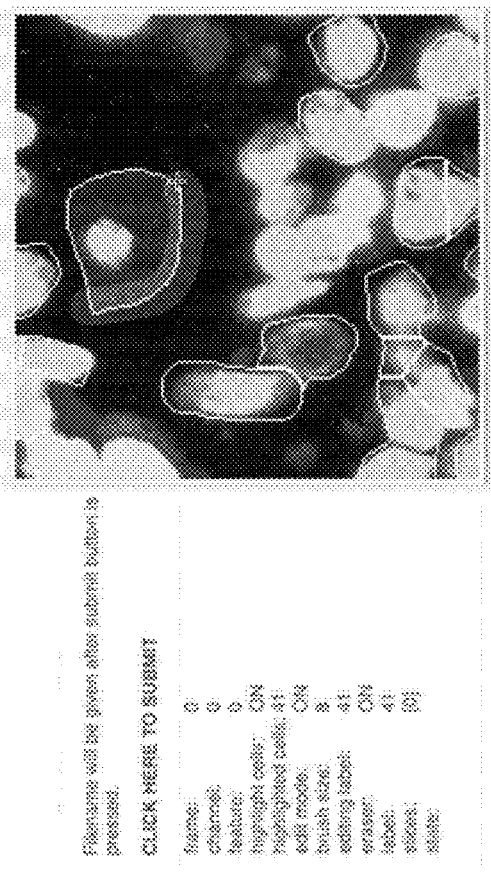
Figure 68C:
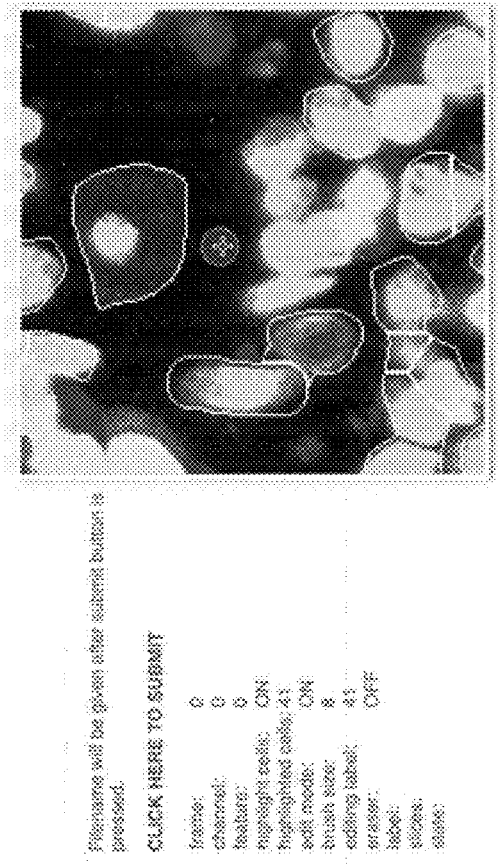
Figure 68D:
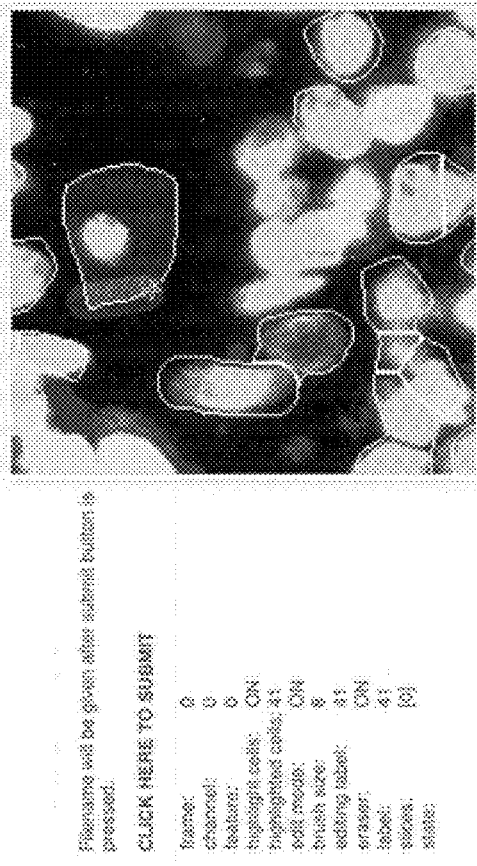
Figure 68E:
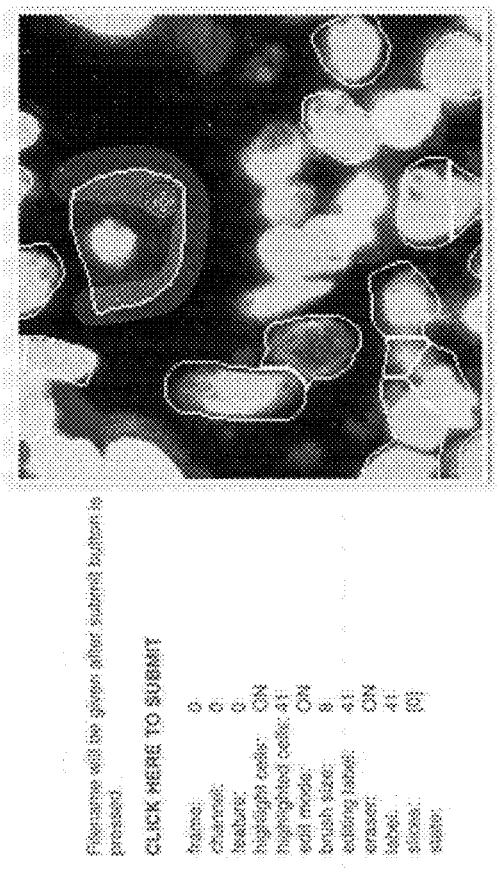
Figure 68F:
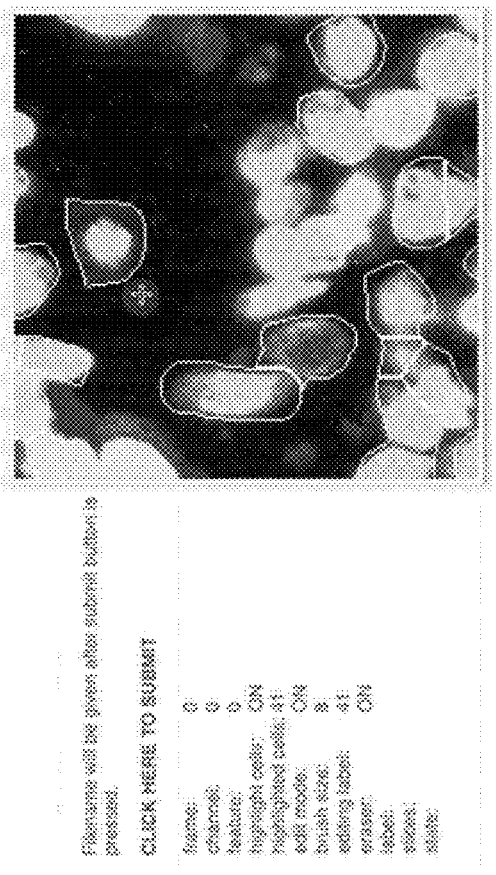
Figure 68G:
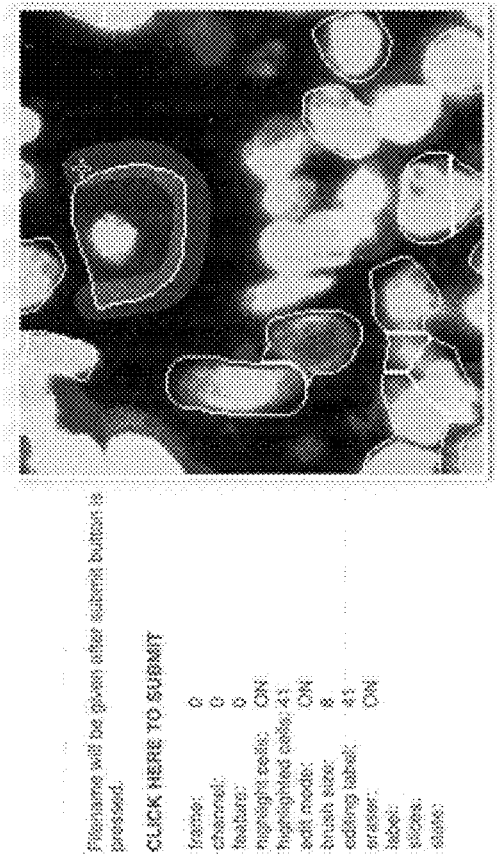
Figure 68H:
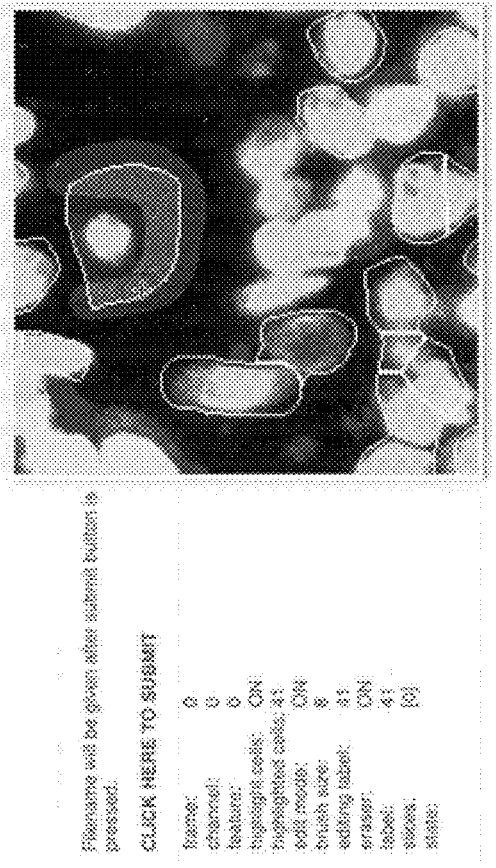
Figure 69B:
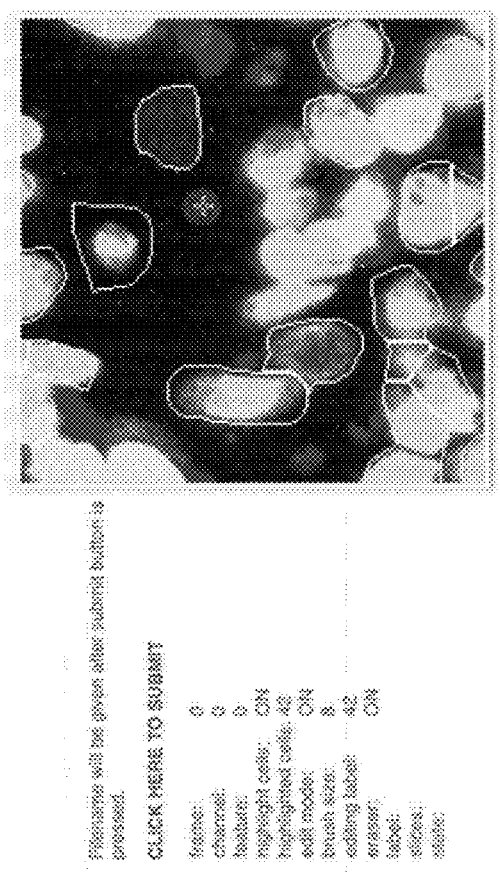
Figure 69D:
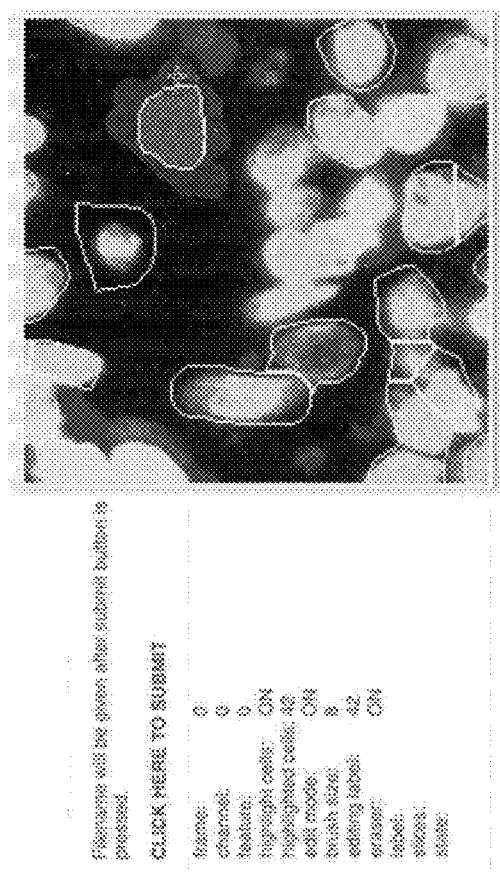
Figure 69A:
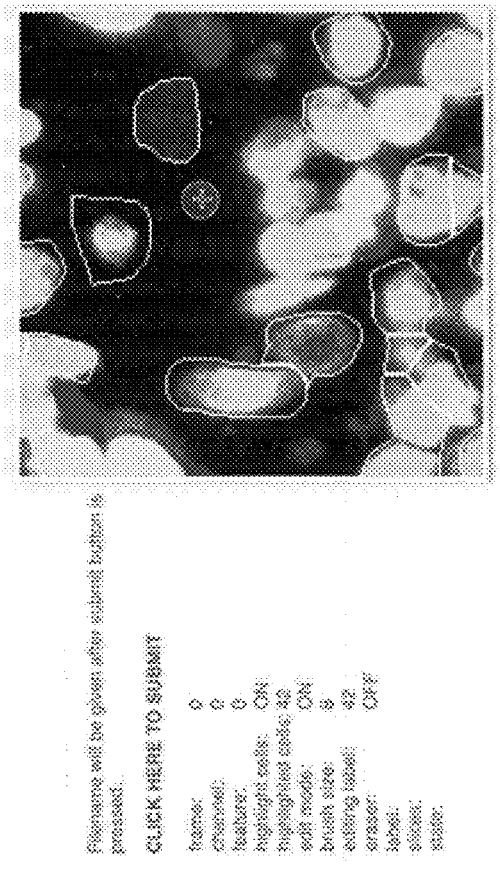
Figure 69C:
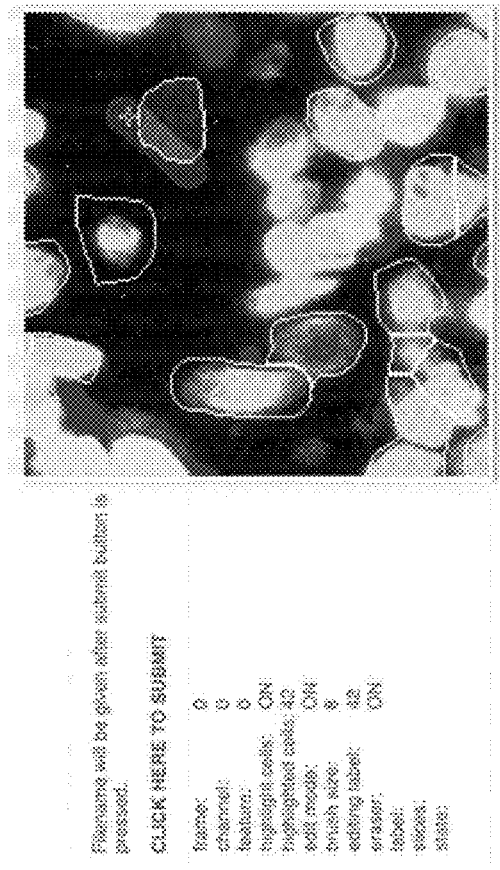

FIGS. 60A-60B. Toggling on and off the edit mode.

FIGS. 61A-61D. Picking a label with Caliban. The figures show that cell label 57 was first picked, and cell label 53 was subsequently picked.

FIGS. 62A-62L. Increasing and increasing the brush size.

FIGS. 63A-63H. Using the brush tool to draw (e.g., select) pixels associated with (or assigned to) a cell label in a two-step process by drawing the exterior followed by filling the interior. The pixels drawn by the brush are associated with (or assigned to) the cell label.

FIGS. 64A-64H. Using the brush tool to draw (e.g., select) pixels associated with (or assigned to) a cell label in a two-step process by drawing the top part followed by drawing the bottom part. The pixels drawn by the brush are associated with (or assigned to) the cell label.

FIGS. 65A-65L. Using the brush tool to draw (e.g., select) pixels associated with a cell label in a three-step process, where pixels associated with another cell label and drawn by the brush tool are not associated with the cell label.

FIGS. 66A-66K. Using the brush tool to draw two new cells. The pixels drawn by the brush are associated with (or assigned to) the cell label of the new cells. The pixels drawn for the first cell and associated with the first cell label (cell label 58 shown) and also drawn for the second cell were not associated with the second cell label (cell label 59 shown).

FIGS. 67A-67L. Using the brush tool to add additional pixels to be associated with a label (cell label 51 shown in the figures).

FIGS. 68A-68H. Using the brush tool to erase (e.g., remove) some pixels associated with a cell label (cell label 41 shown in the figures).

FIGS. 69A-69H. Using the brush tool to erase (e.g., remove) some pixels associated with a cell label (cell label 42 shown in the figures). When the brush tool erase pixels associated with another cell label (cell label 41 shown in the figures), the pixels are not erased (i.e., the pixels are still assigned to, or associated with, the other cell label).

Figure 70A:
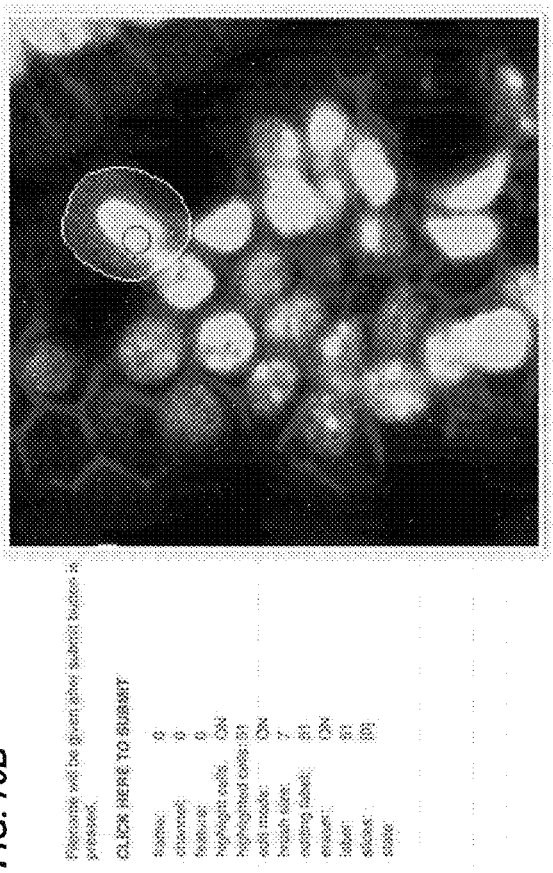
FIGS. 70A-70P. Using the brush tool to remove pixels that should not be associated with a label (cell label 51 shown in the figures).
Figure 70B:
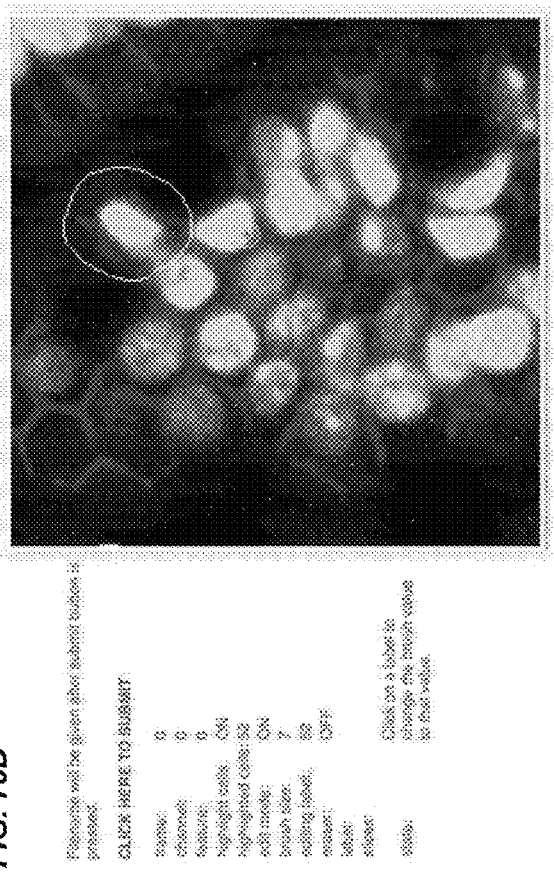
Figure 70C:
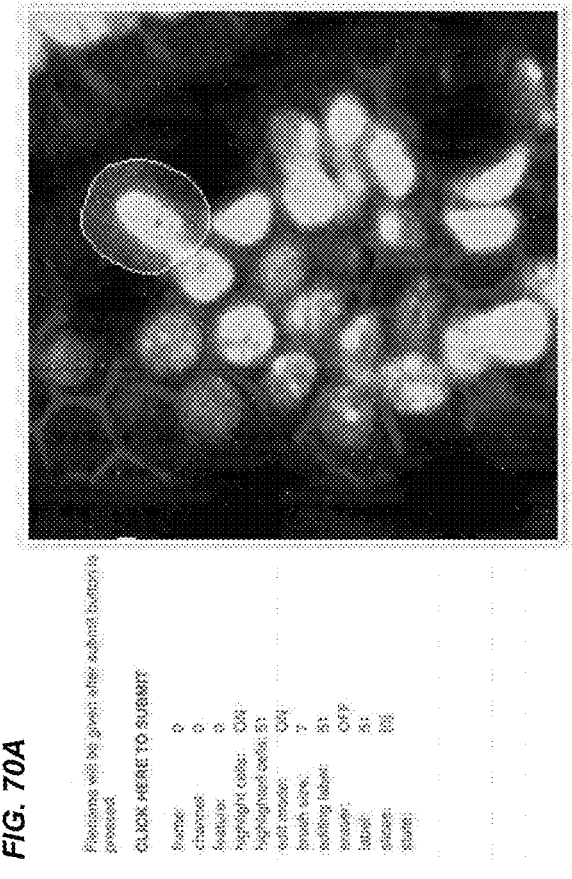
Figure 70D:
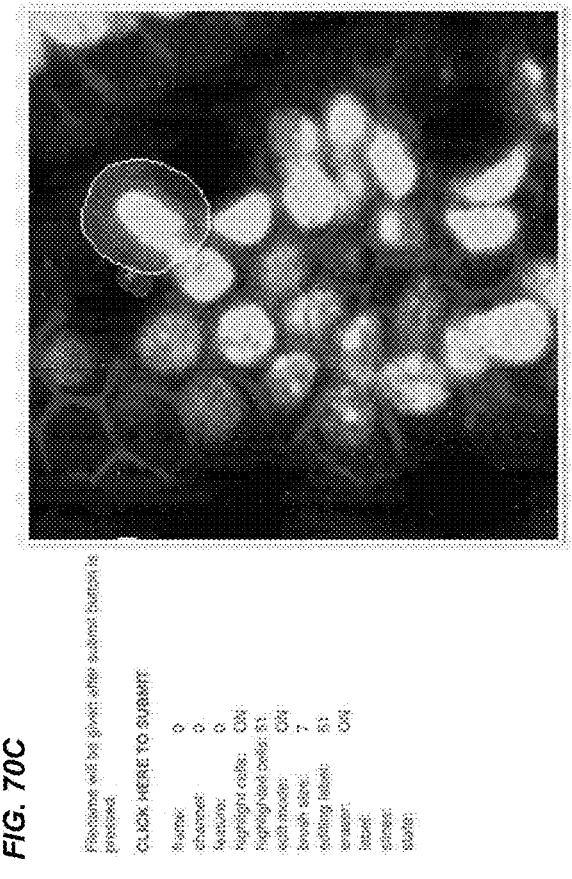
Figure 70F:
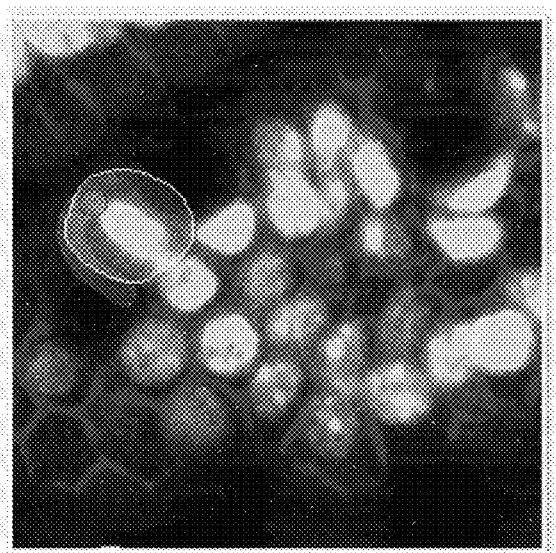
Figure 70H:
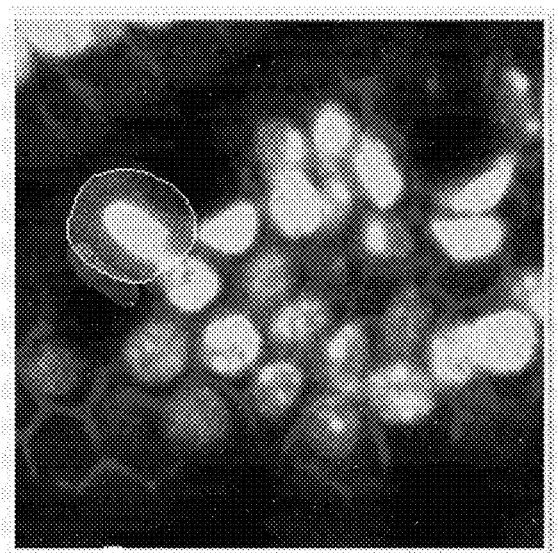
Figure 70E:
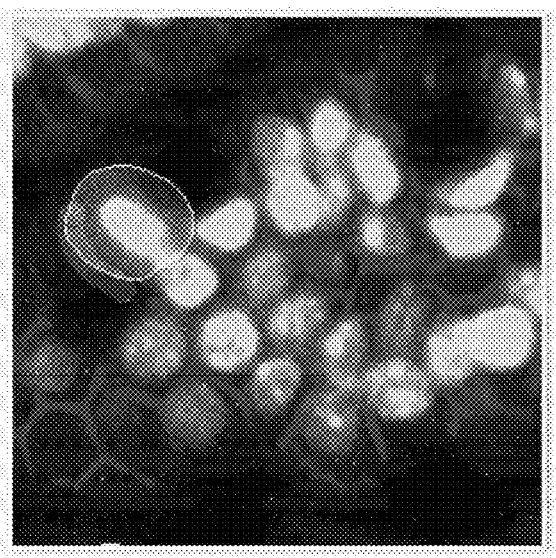
Figure 70G:
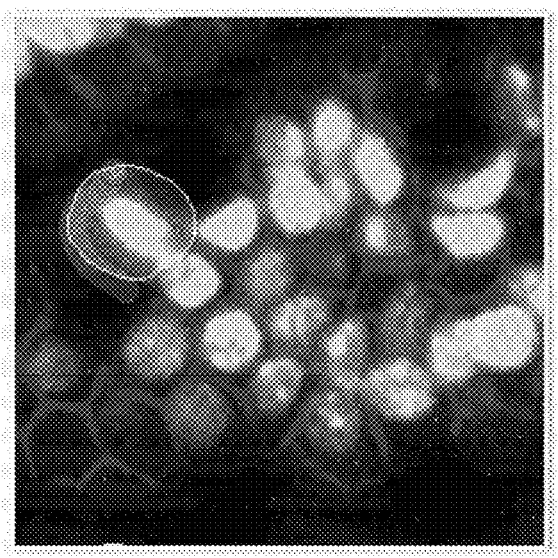
Figure 70I:
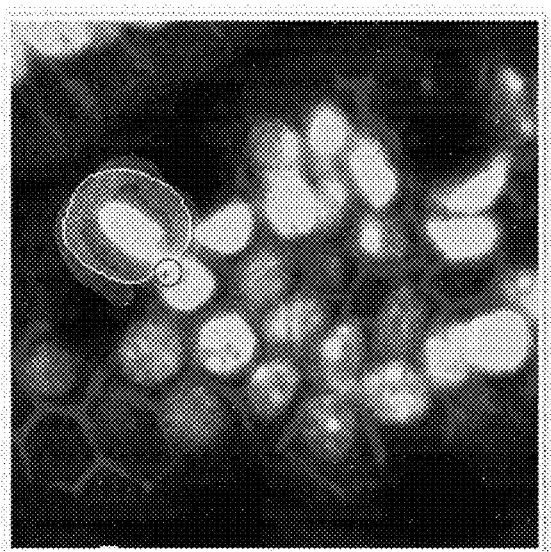
Figure 70J:
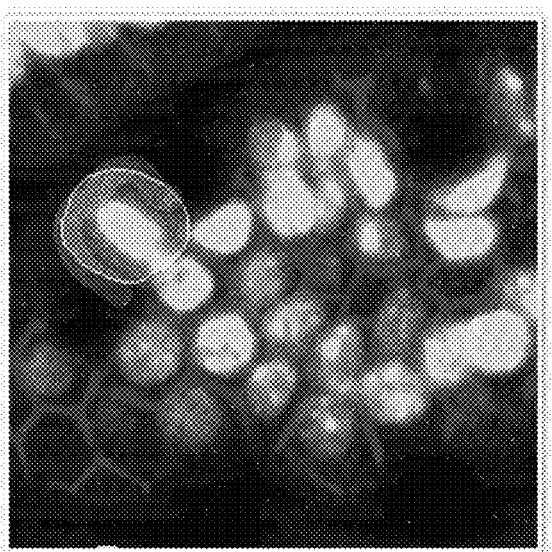
Figure 70K:
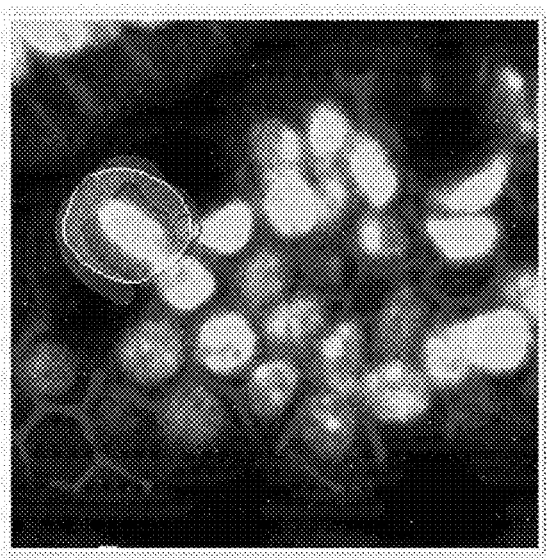
Figure 70L:
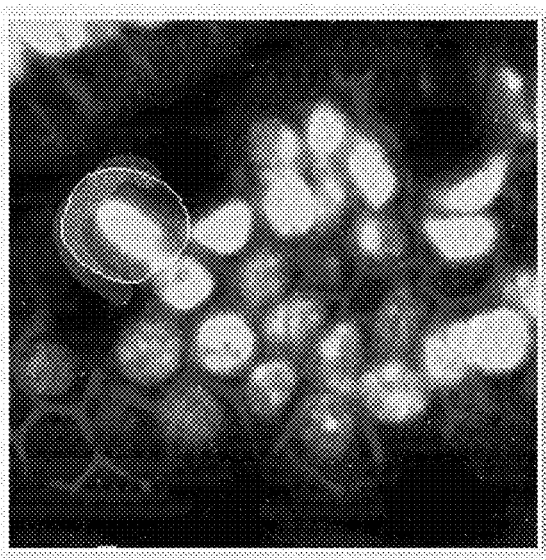
Figure 70N:
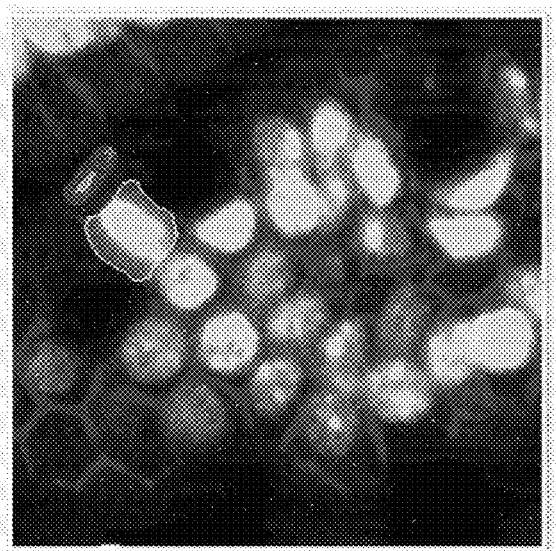
Figure 70P:
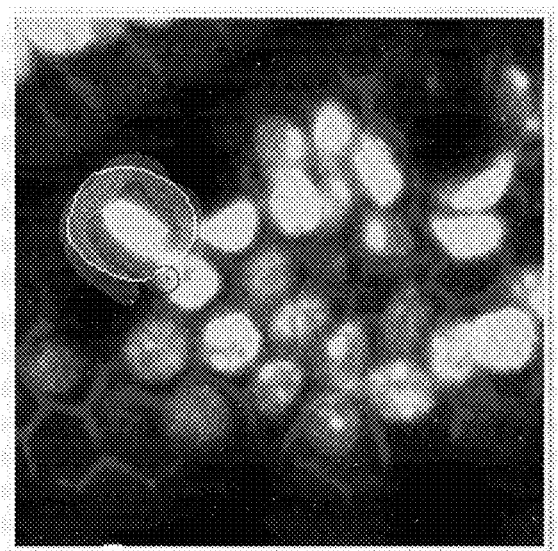
Figure 70M:
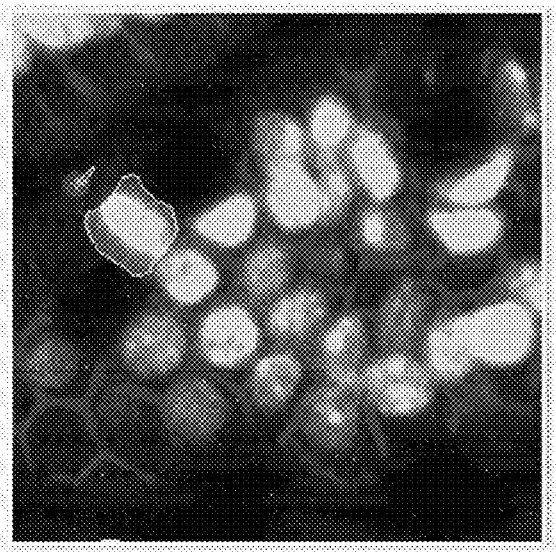
Figure 70O:
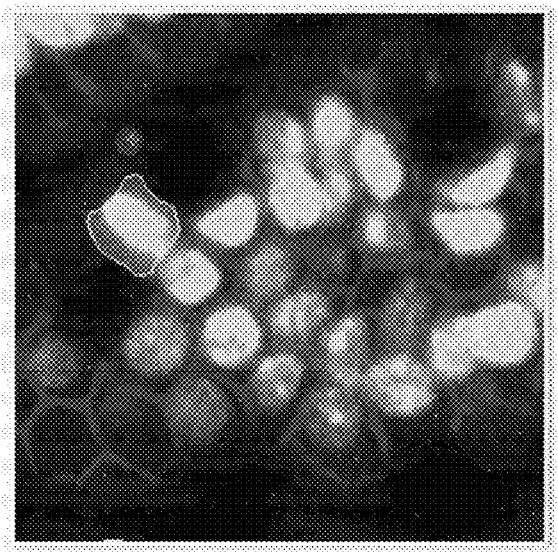
Figure 71B:
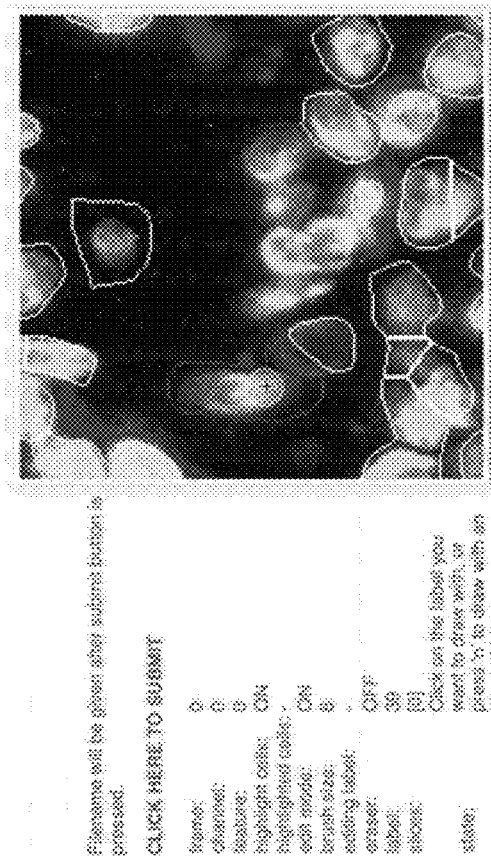
FIGS. 71A-71H. Using the brush tool to convert (e.g., reassign) pixels associated with an incorrect label (e.g., label 39 shown in the figures) by drawing over the pixels with another correct label (e.g., label 42 shown in the figures).
Figure 71D:
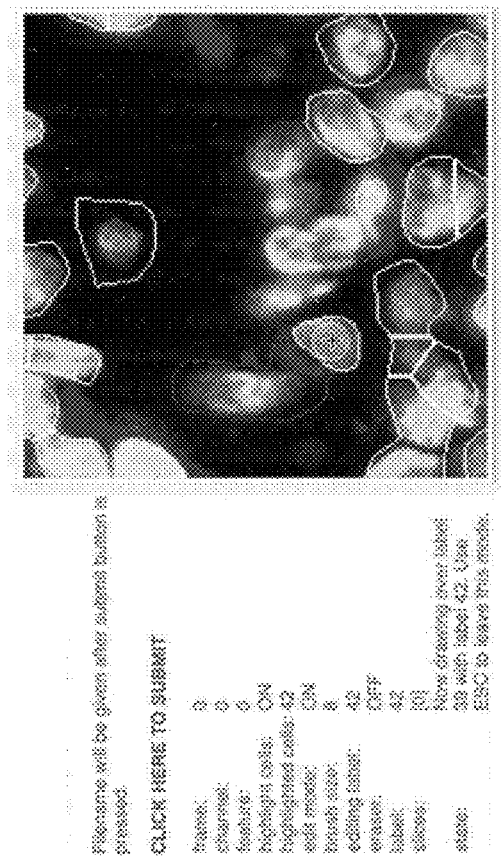
Figure 71A:
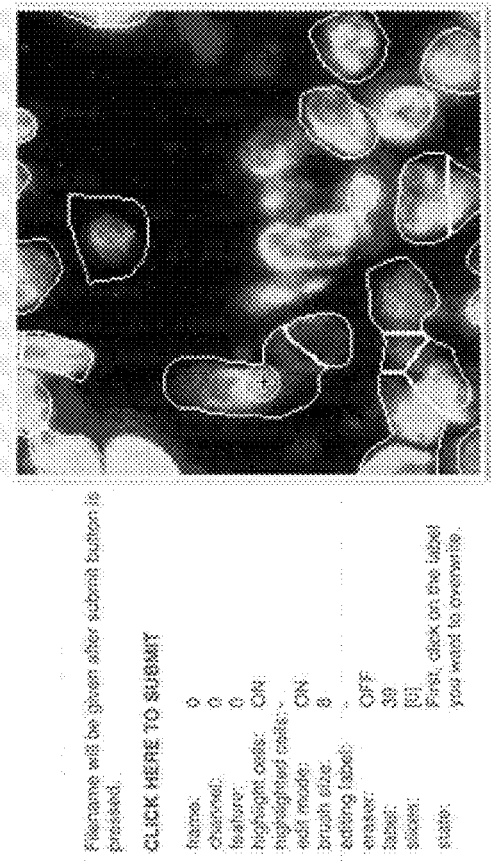
Figure 71C:
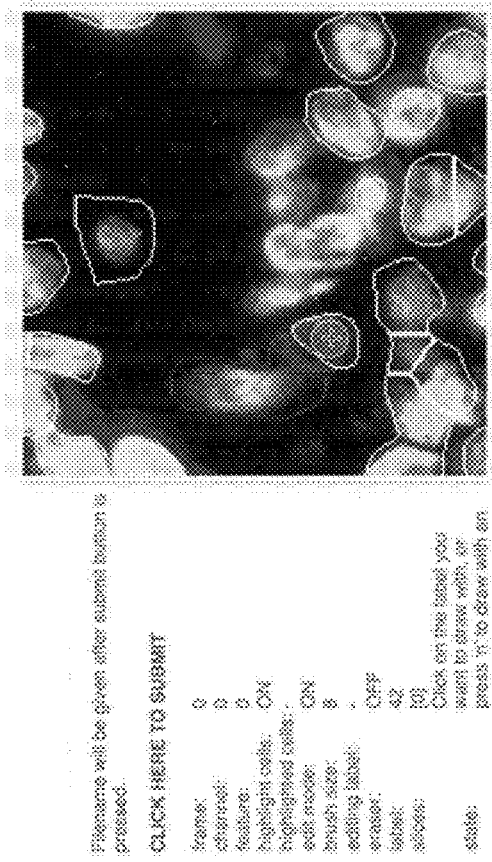
Figure 71E:
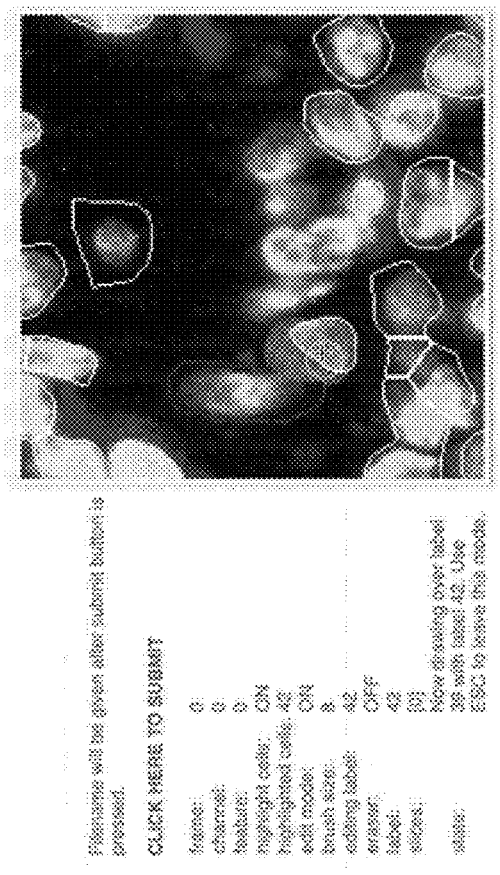
Figure 71F:
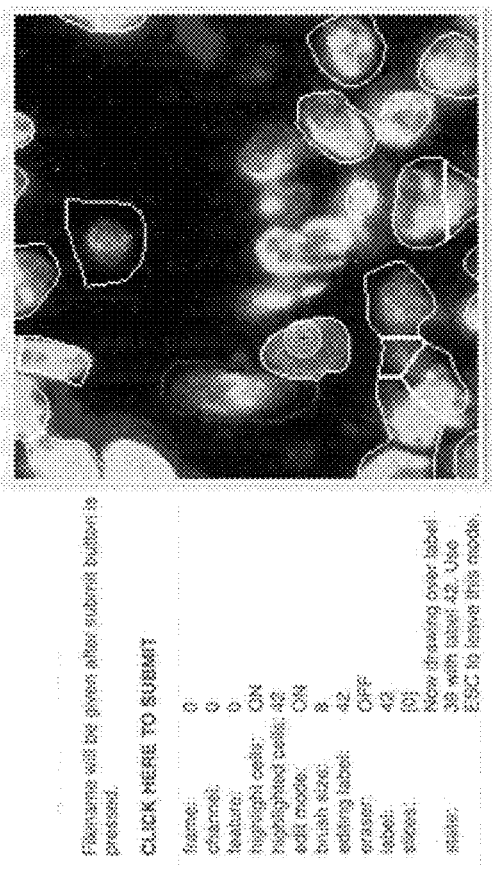
Figure 71G:
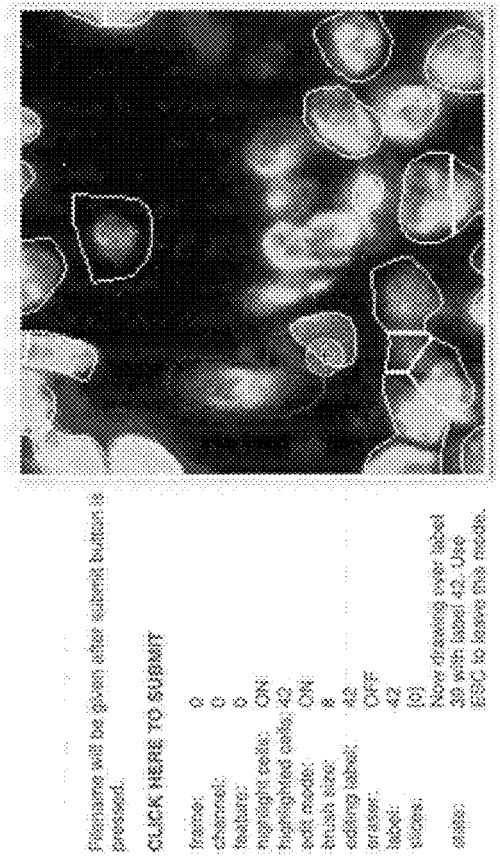
Figure 71H:
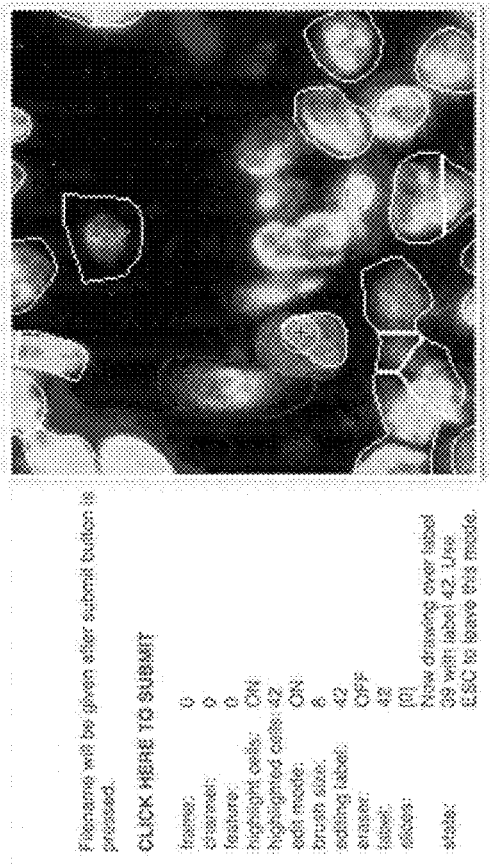

FIGS. 70A-70P. Using the brush tool to remove pixels that should not be associated with a label (cell label 51 shown in the figures).

FIGS. 71A-71H. Using the brush tool to convert (e.g., reassign) pixels associated with an incorrect label (e.g., label 39 shown in the figures) by drawing over the pixels with another correct label (e.g., label 42 shown in the figures).

Figures 72E, 72F, 72G, 72H:
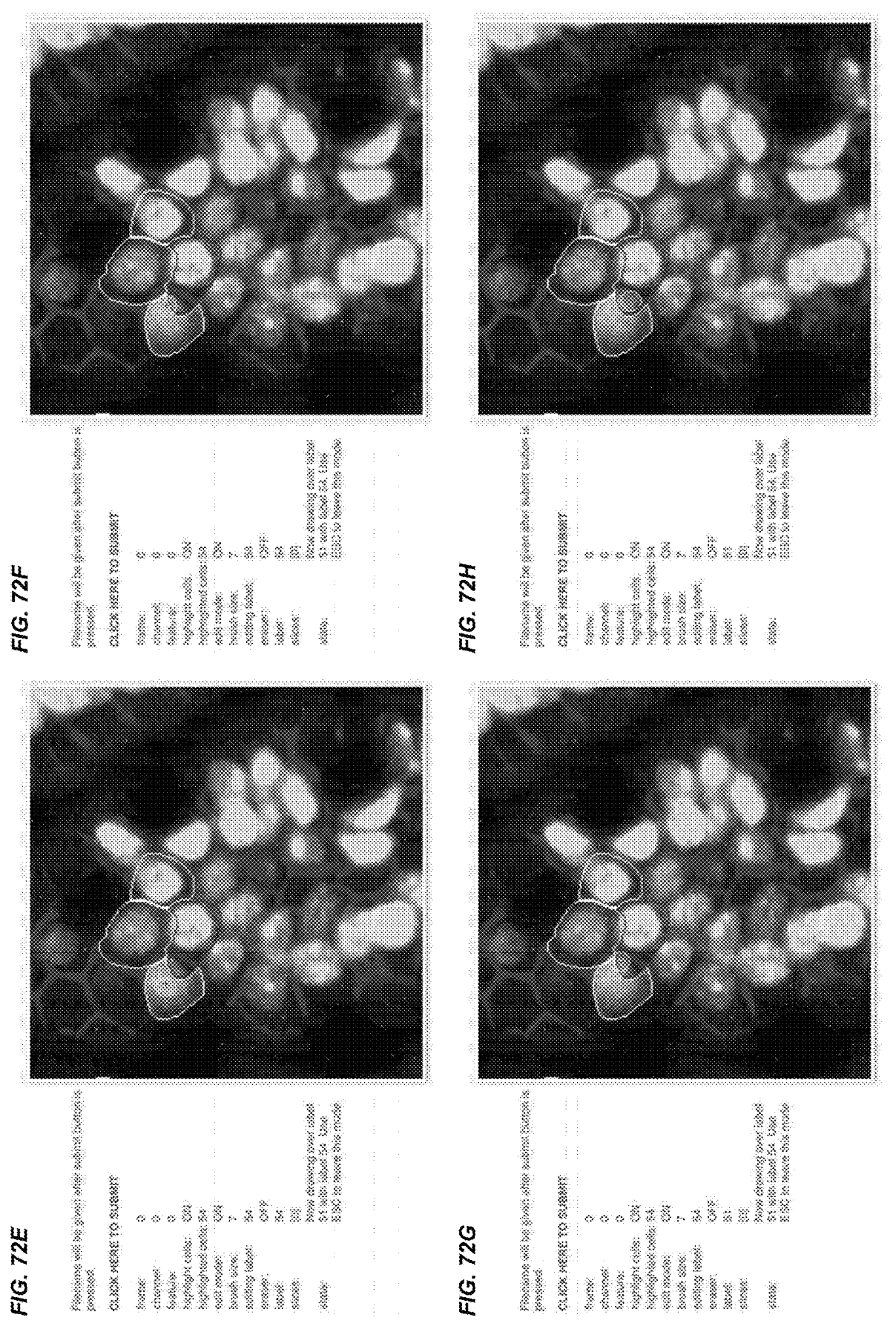
Figure 72J:
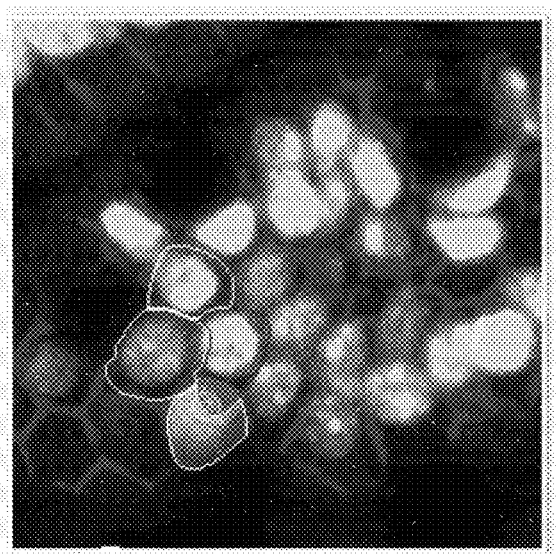
FIGS. 72A-72X. Using the brush tool to convert (e.g., reassign) pixels associated with an incorrect label (e.g., label 51 shown in FIGS. 72B-72L, and label 52 shown in FIGS. 72M-72V) by drawing over the pixels with another correct label (e.g., label 54 shown in FIGS. 72B-72L, and labels 51 shown FIGS. 72M-72V).
Figure 72L:
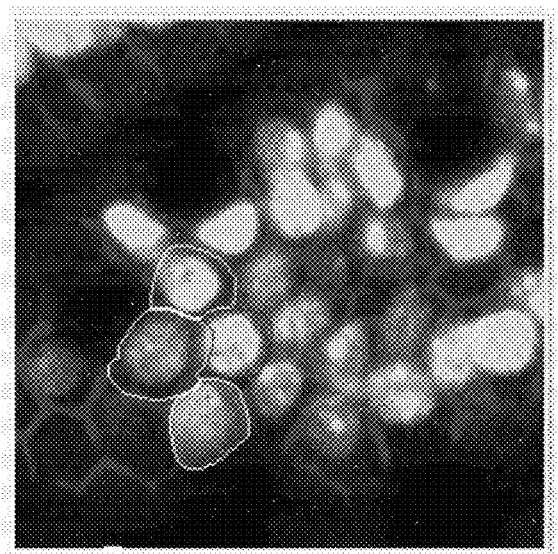
Figure 72I:
Figure 72K:
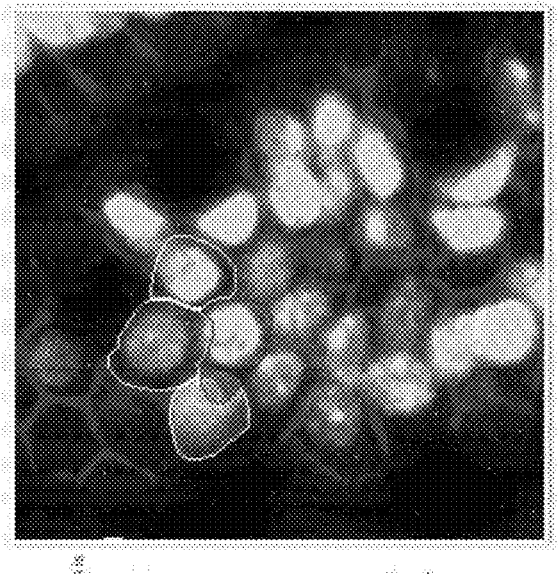
Figure 72R:
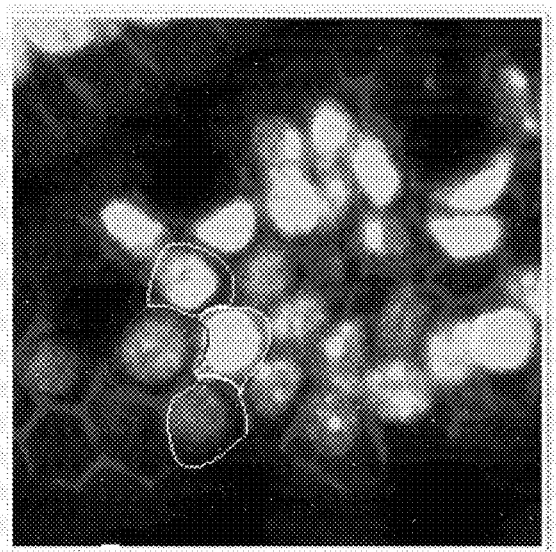
Figure 72T:
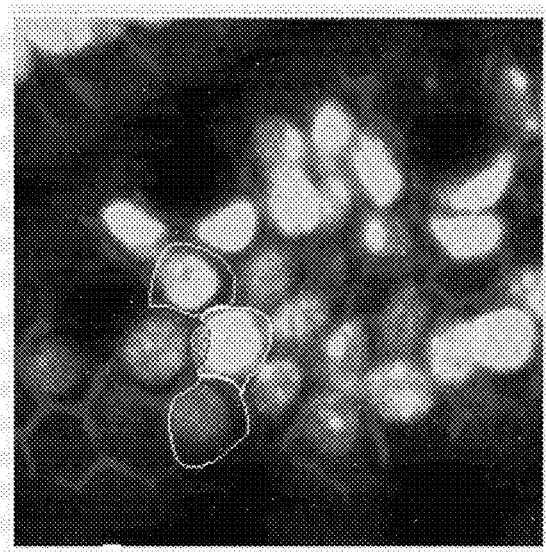
Figure 72Q:
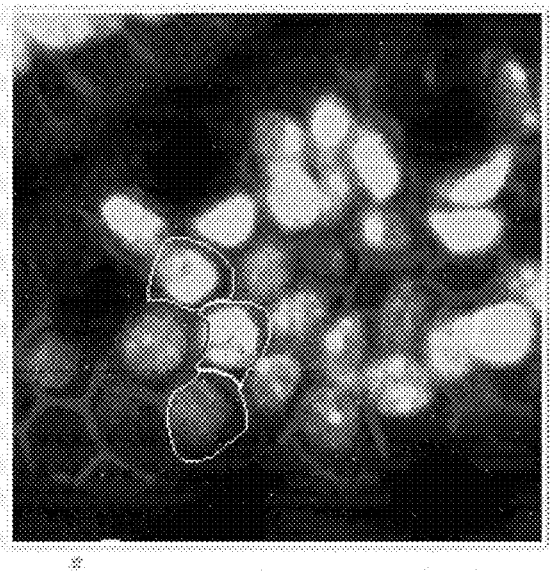
Figure 72S:
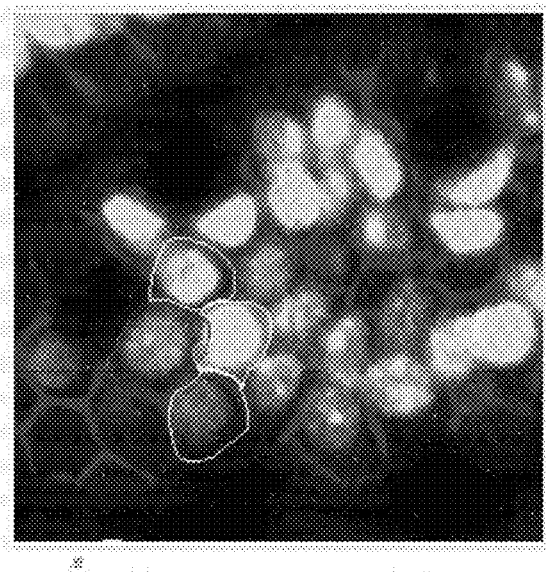
Figure 72V:
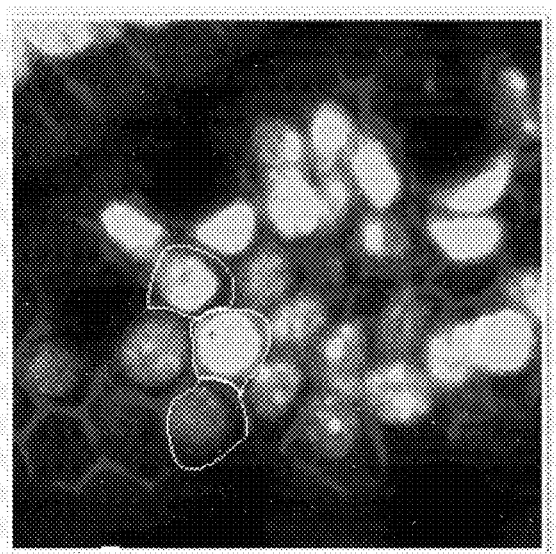
Figure 72X:
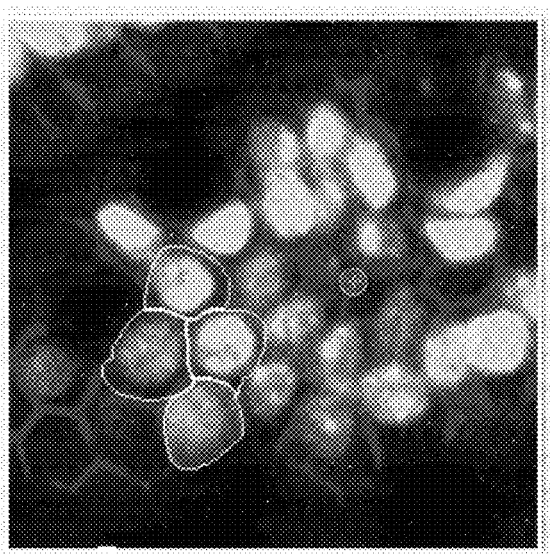
Figure 72U:
Figure 72W:
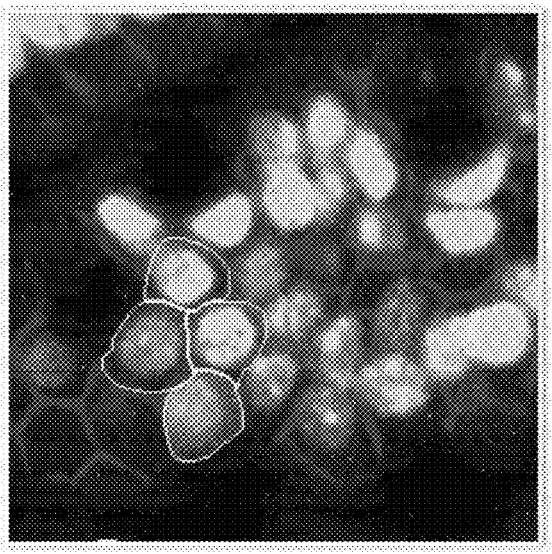
Figure 73F:
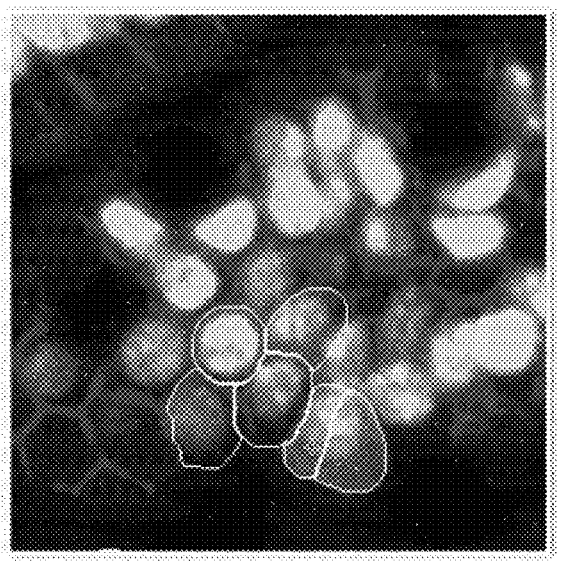
Figure 73E:
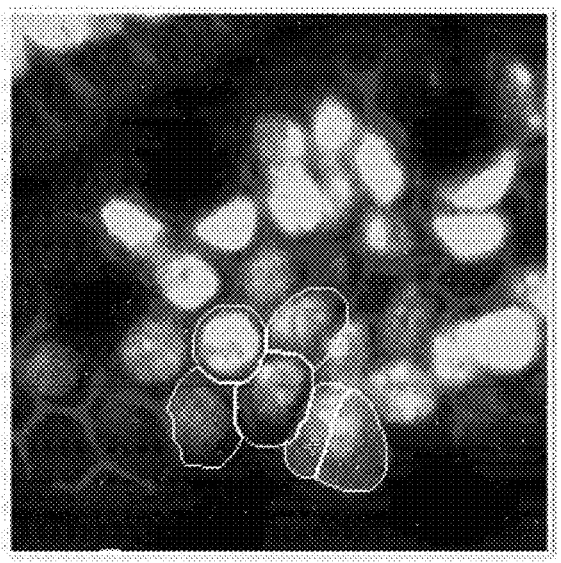
Figure 73G:
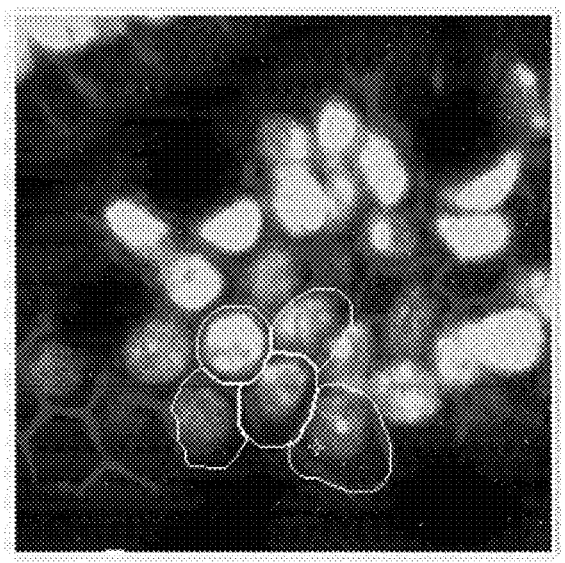
Figure 74B:
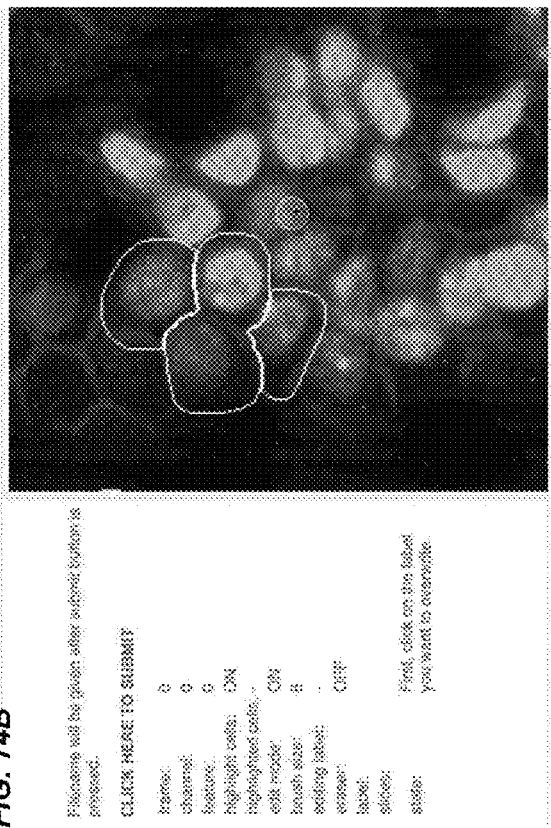
FIGS. 74A-74L. Fixing two cells assigned with one cell label using the conversion brush.
Figure 74D:
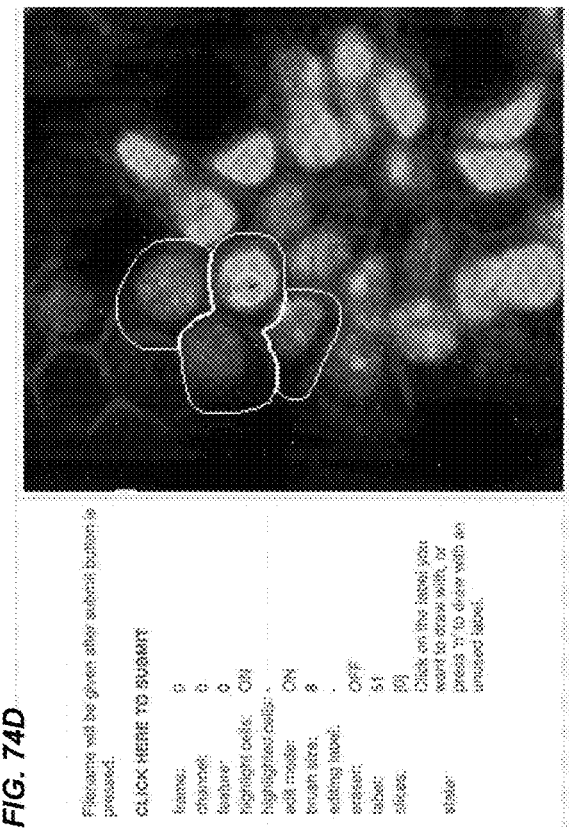
Figure 74A:
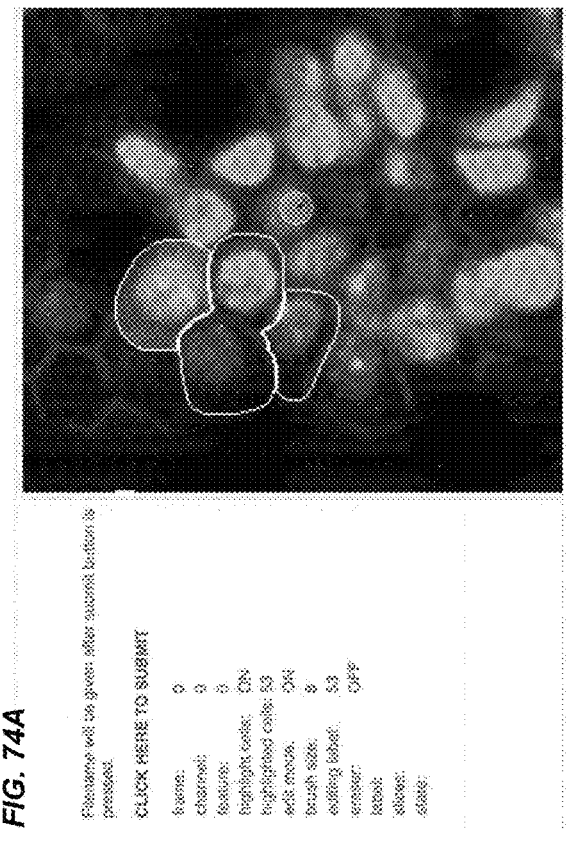
Figure 74C:
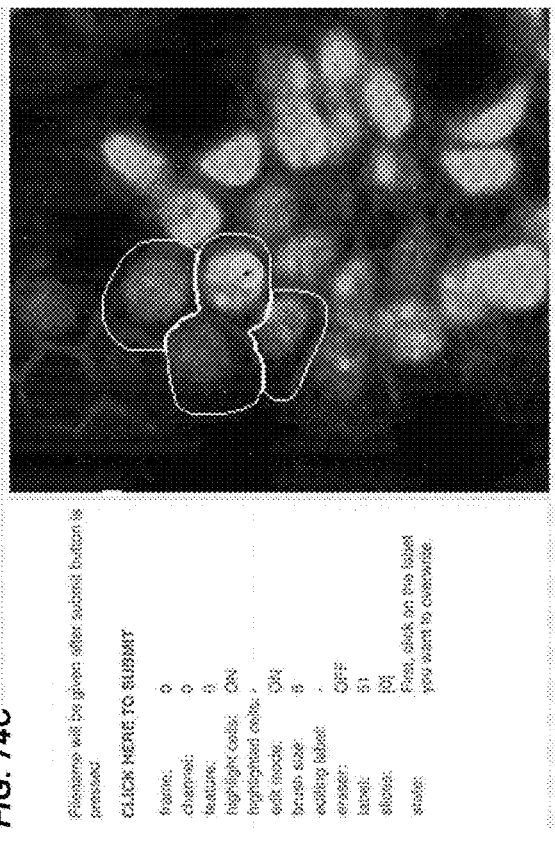
Figure 74E:
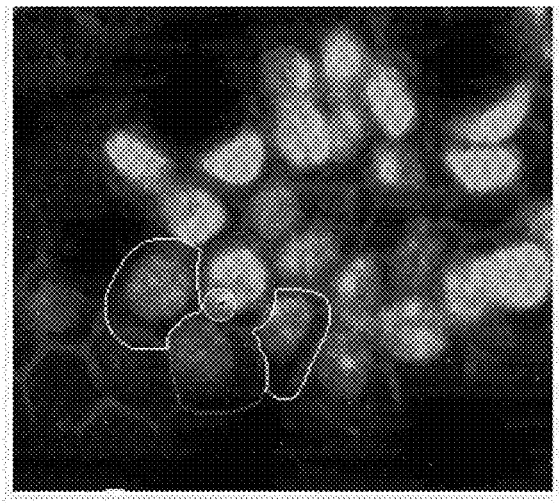
Figure 74F:
Figure 74G:
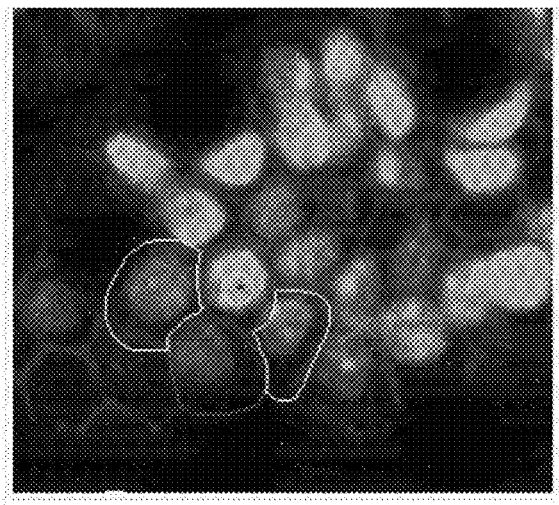
Figure 74H:
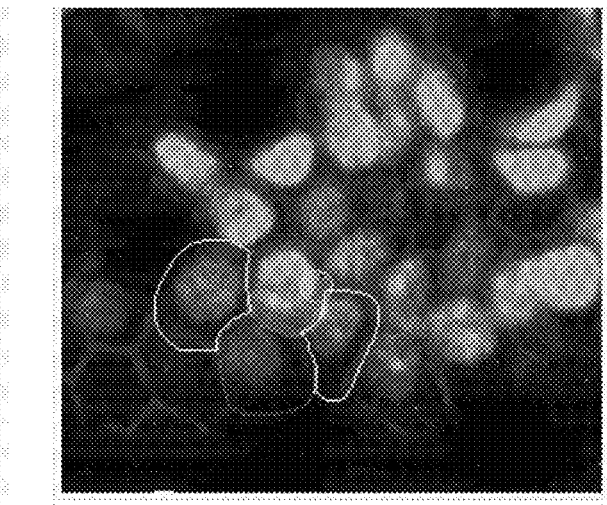
Figure 74J:
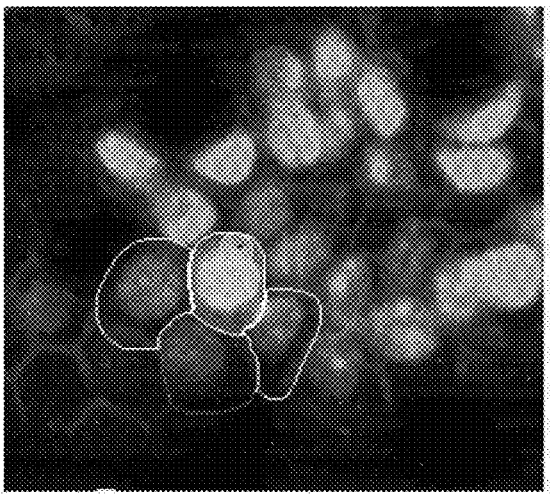
Figure 74L:
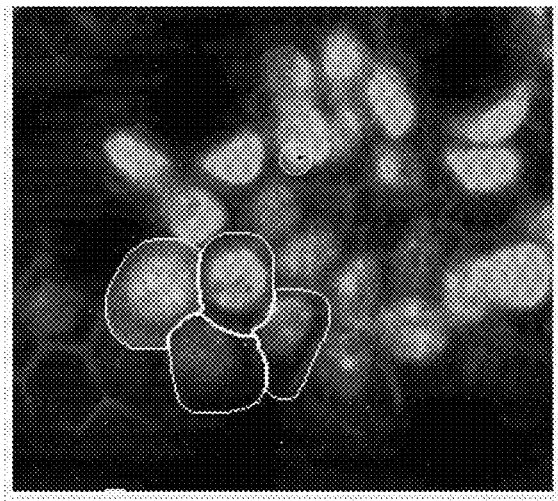
Figure 74I:
Figure 74K:
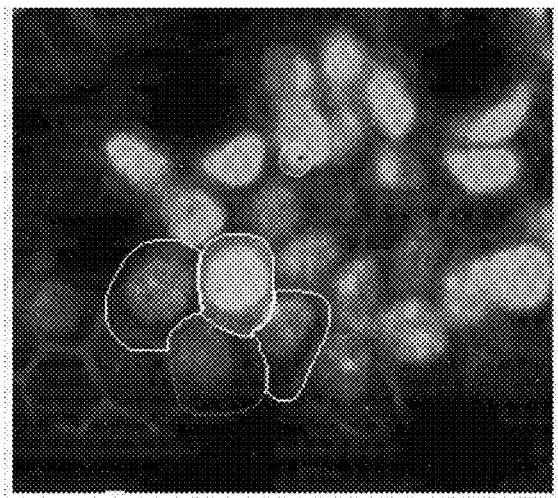

FIGS. 72A-72X. Using the brush tool to convert (e.g., reassign) pixels associated with an incorrect label (e.g., label 51 shown in FIGS. 72B-72L, and label 52 shown in FIGS. 72M-72V) by drawing over the pixels with another correct label (e.g., label 54 shown in FIGS. 72B-72L, and labels 51 shown FIGS. 72M-72V).

FIGS. 73A-73G. Merging two cells by associating pixels of one cell label (cell label 56 shown in the figures) with the other cell label (cell label 57 shown in the figures).

FIGS. 74A-74L. Fixing two cells assigned with one cell label using the conversion brush.

Figure 75A:
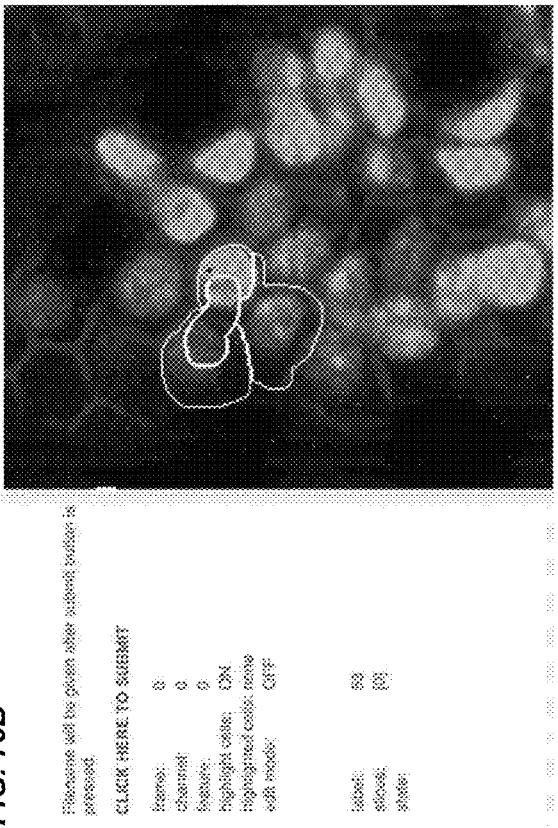
Figure 75B:
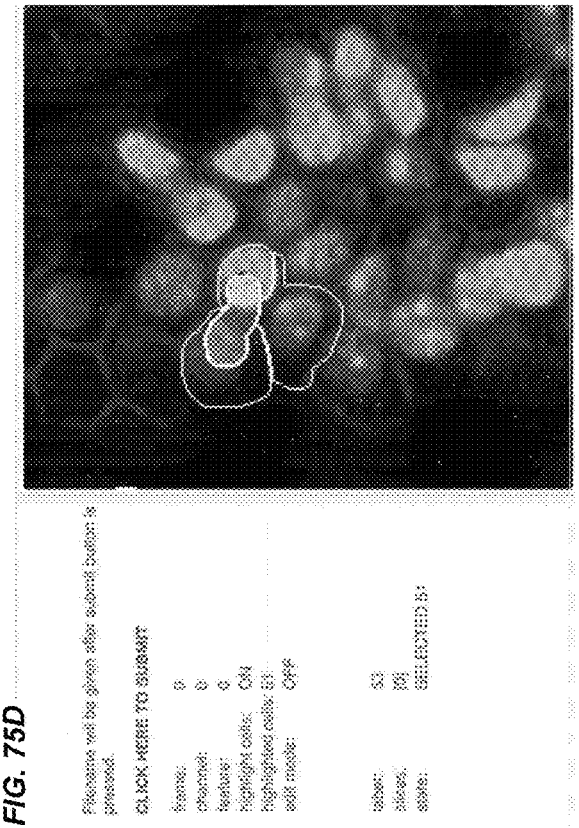
Figure 75C:
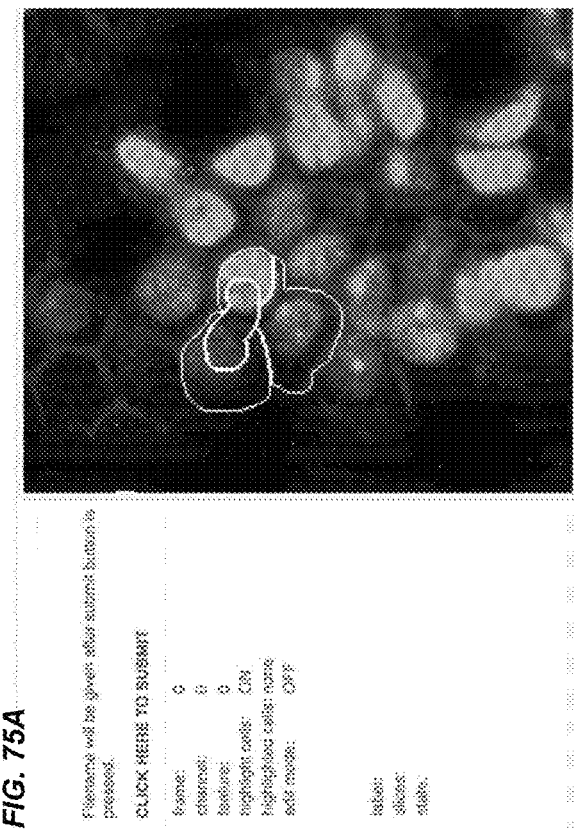
Figure 75D:
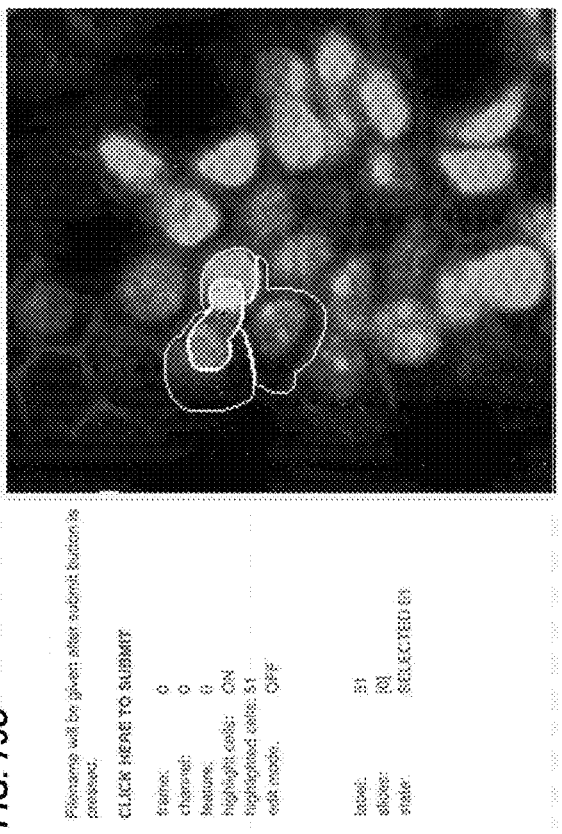
Figure 75E:
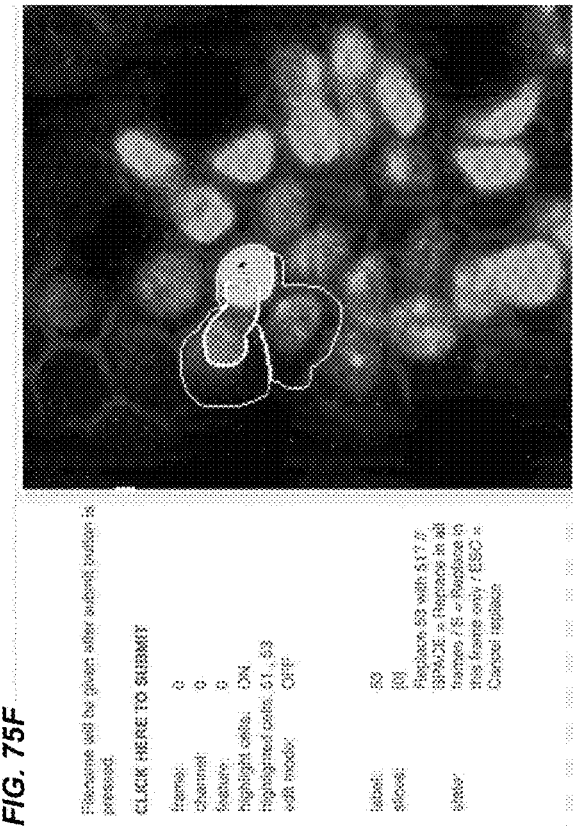
Figure 75F:
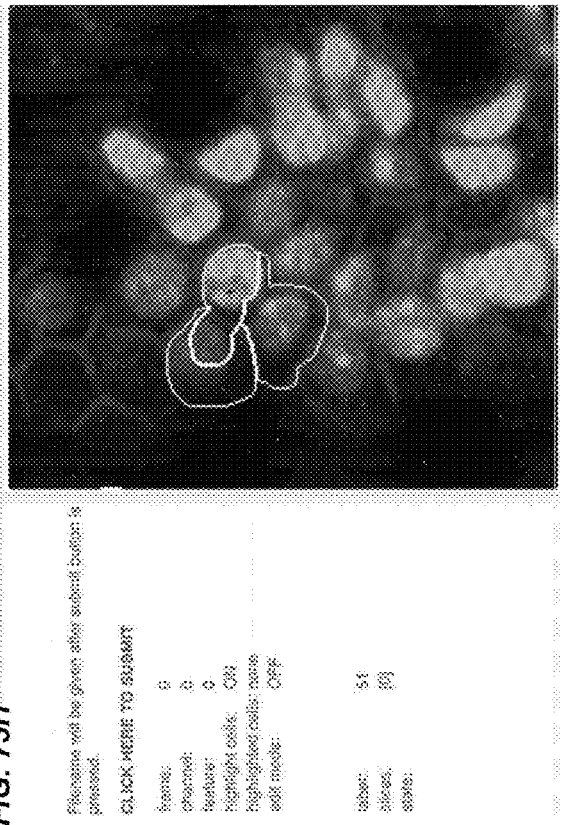
Figure 75G:
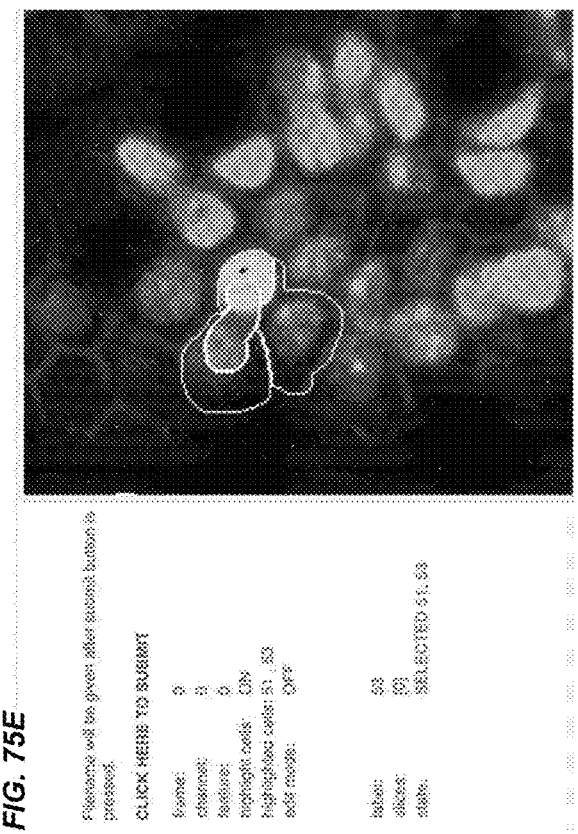
Figure 75H:
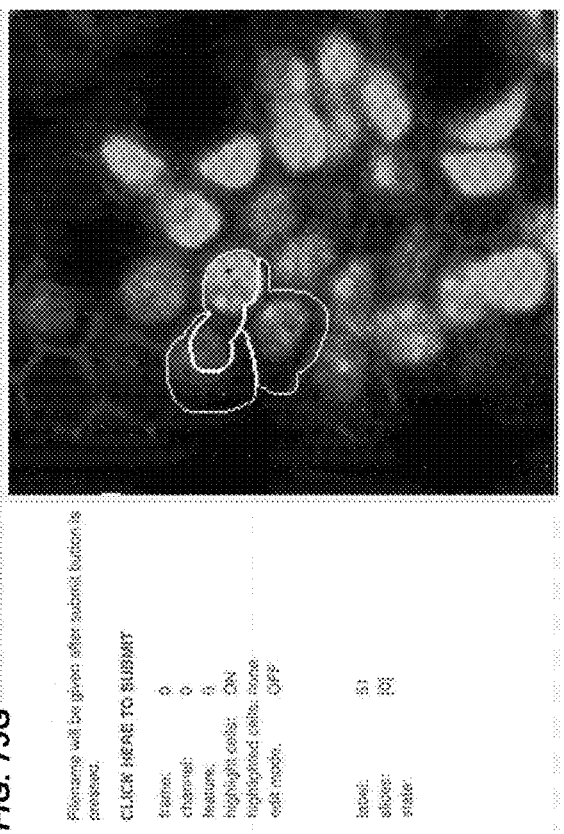
Figures 75I, 75J, 75K, 75L:
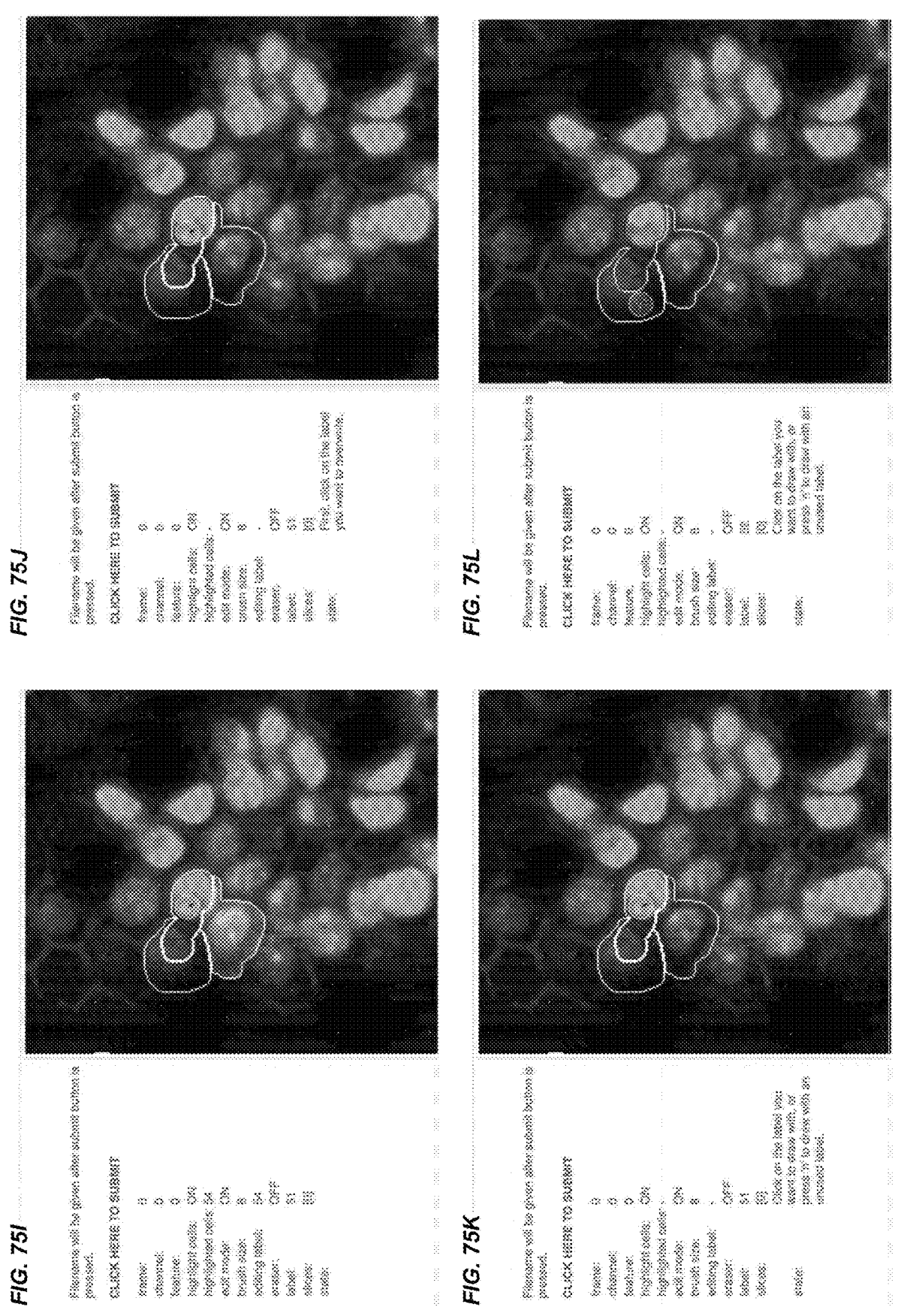
Figures 75M, 75N:
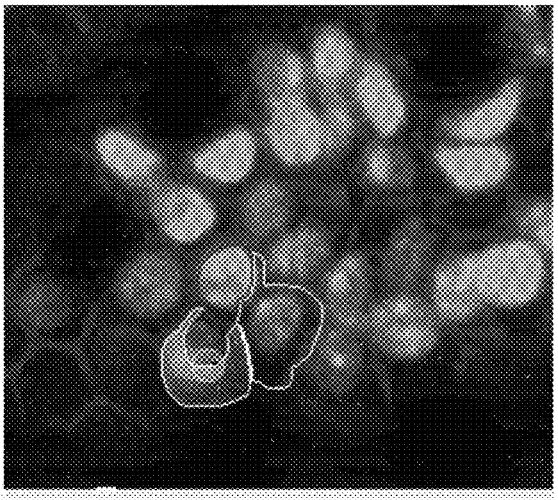
Figures 75O, 75P:
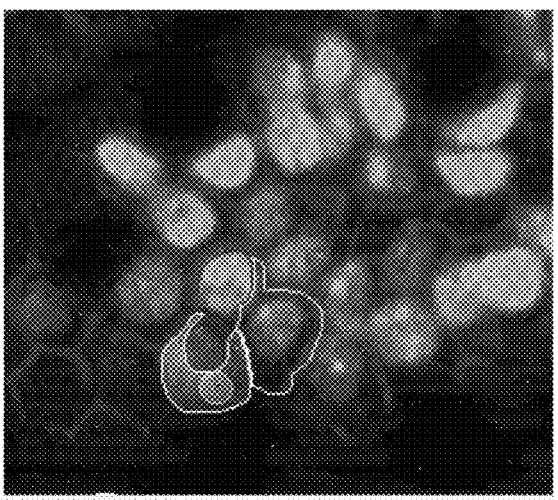
Figure 75Q:
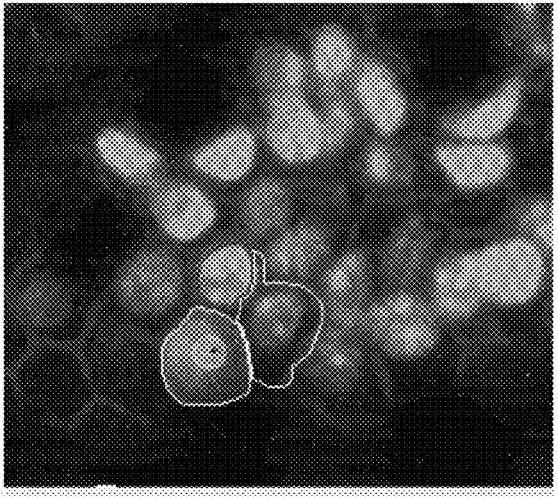
Figure 75R:
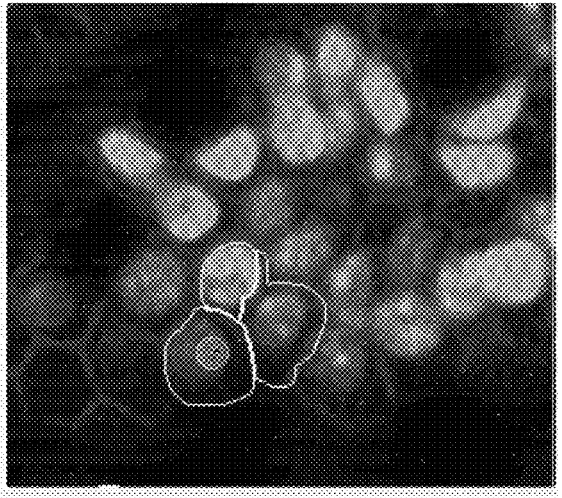
Figure 75S:
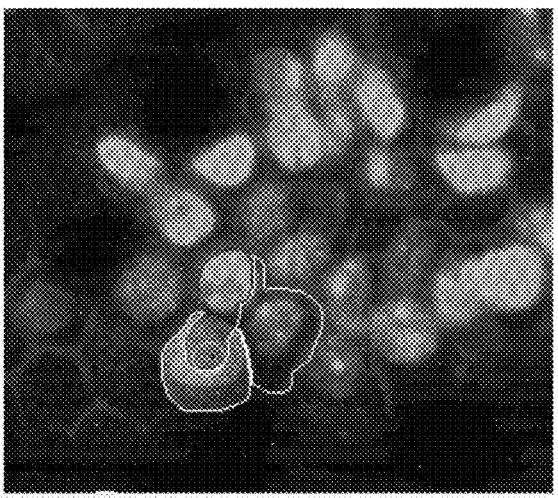
Figure 75T:
Figure 76B:
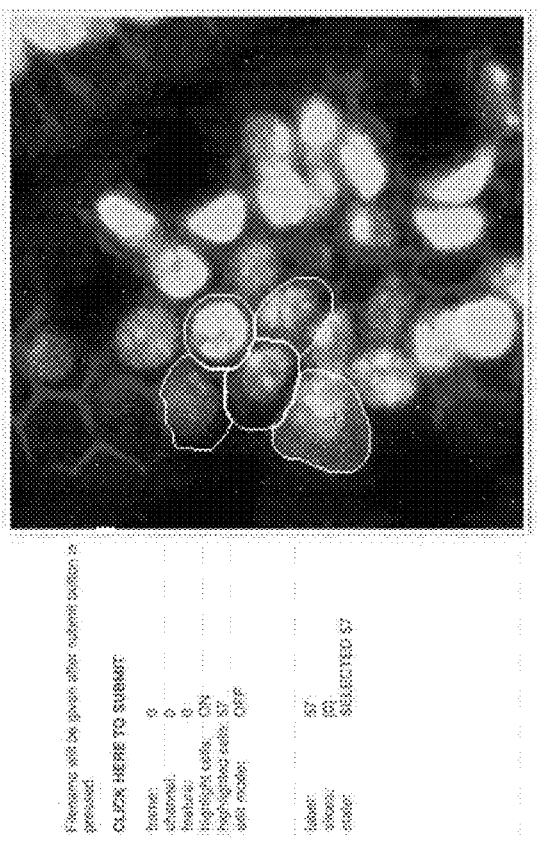
FIGS. 76A-76D. Deleting a cell label (cell label 57 shown in the figures).
Figure 76D:
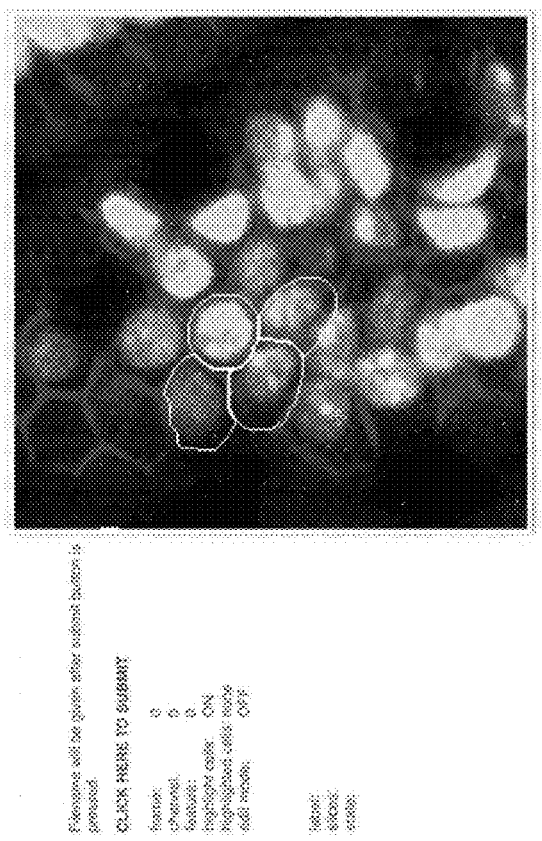
Figure 76A:
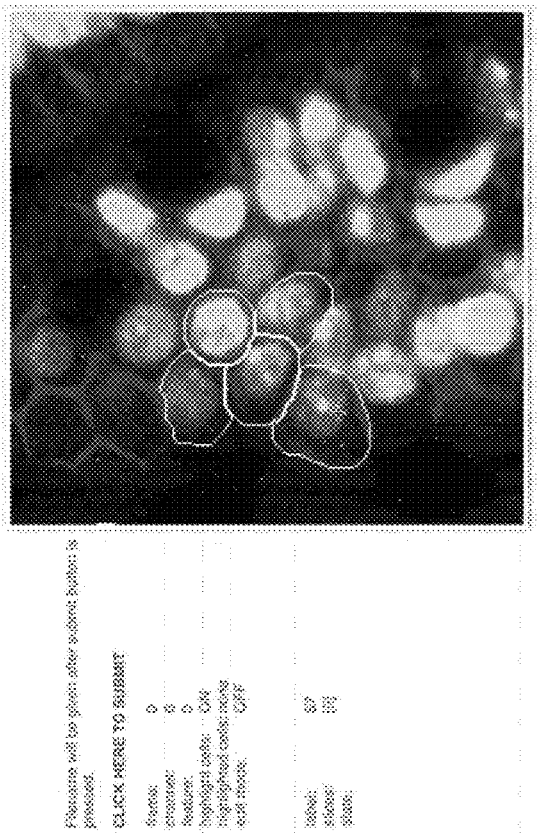
Figure 76C:
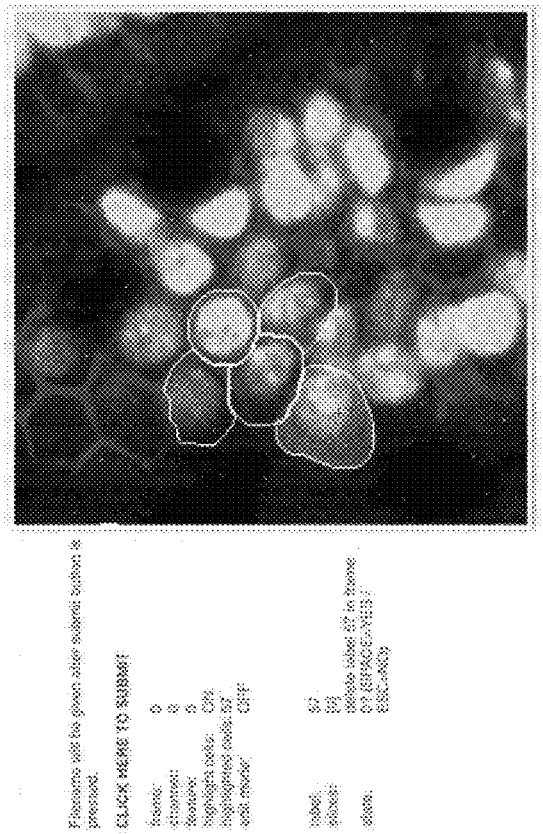

FIGS. 75A-75B2. Fixing errors two cells assigned three cell labels (cell labels 51, 52, and 53 shown in the figures) and a third cell assigned another cell label (cell label 54 shown in the figures). Cell labels 51 and 53 were first merged as cell label 51. The conversion brush was used to assign some pixels associated with cell label 51 to be associated with cell label 52. The conversion brush was used to assign some pixels associated with cell label 54 to be associated with cell label 51.

Figure 77B:
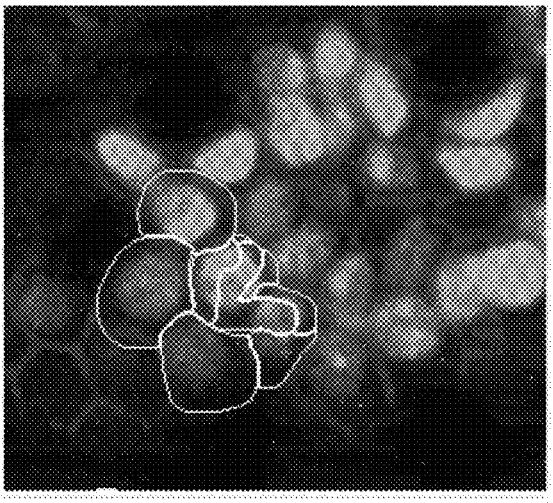
FIGS. 77A-77X. Removing multiple labels assigned to two cells and using the brush tool to draw the two cells.
Figure 77D:
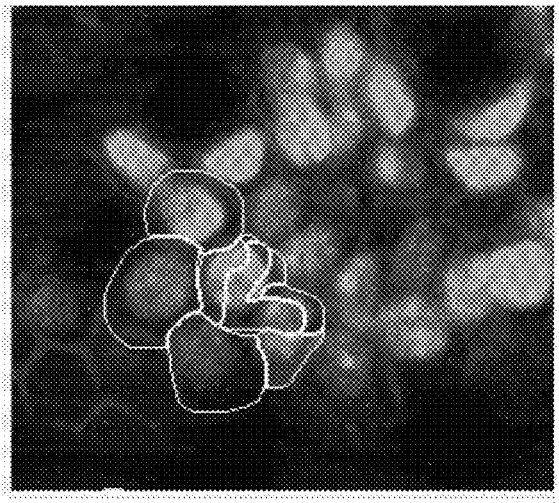
Figure 77A:
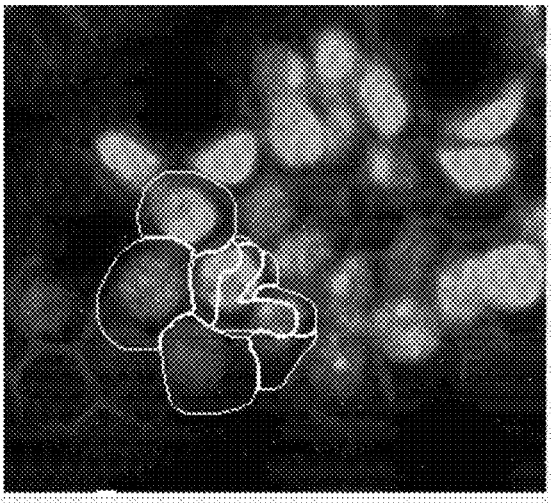
Figure 77C:
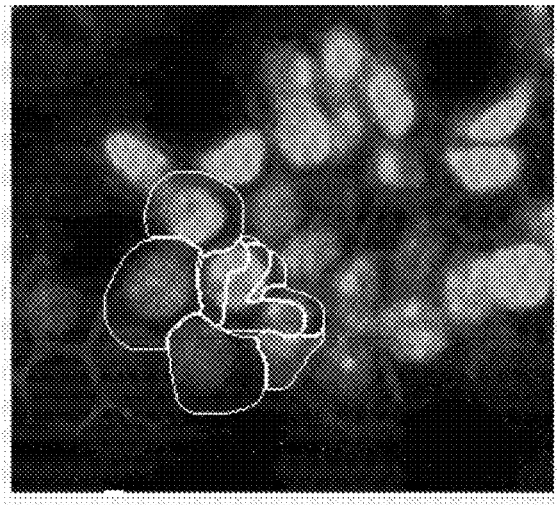
Figure 77N:
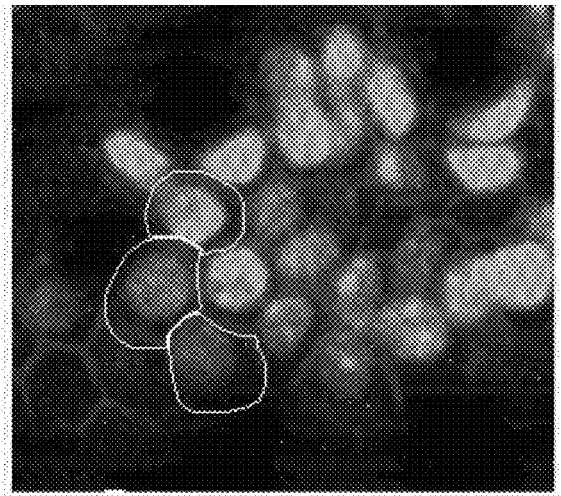
Figure 77P:
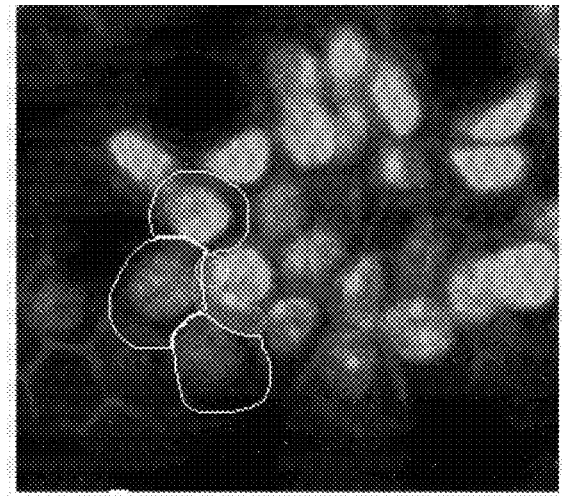
Figure 77M:
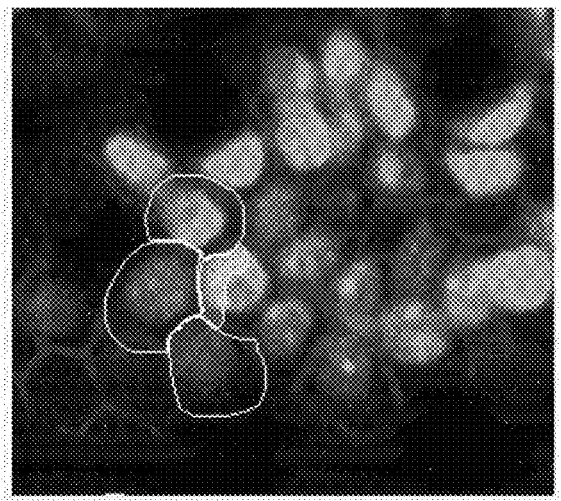
Figure 77O:
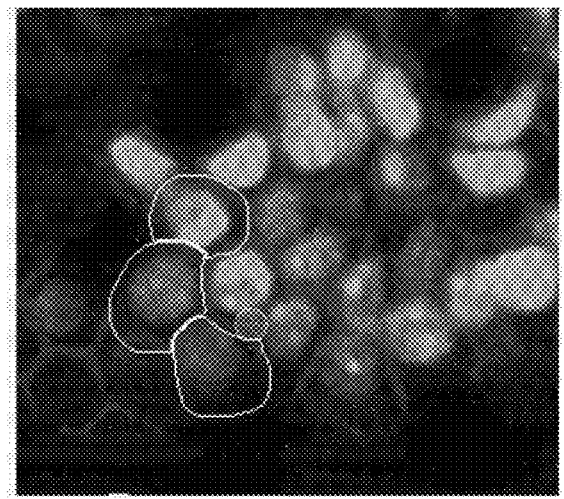
Figure 77R:
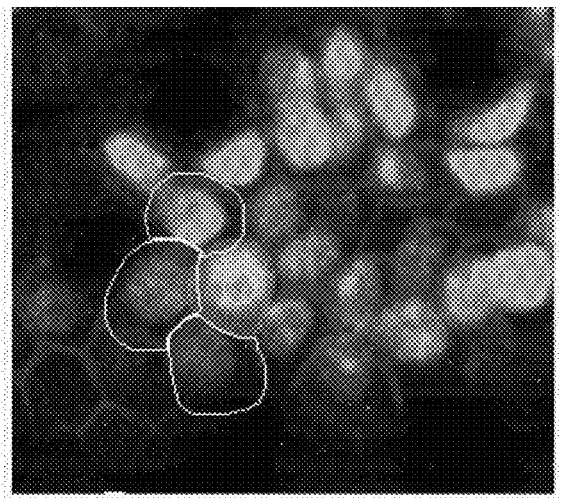
Figure 77T:
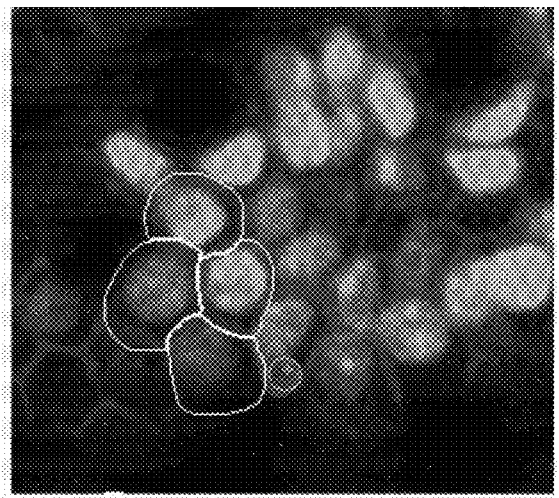
Figure 77Q:
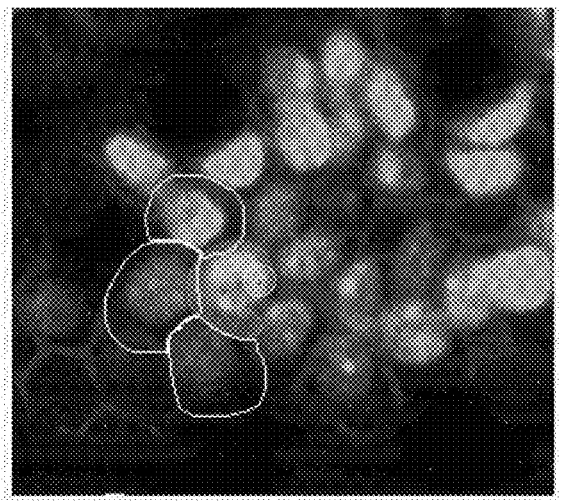
Figure 77S:
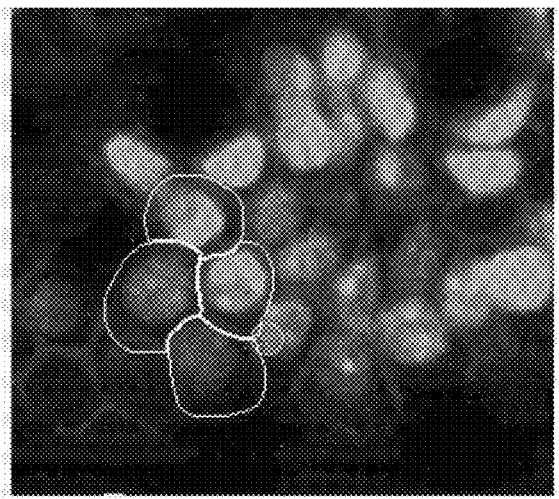
Figure 77U:
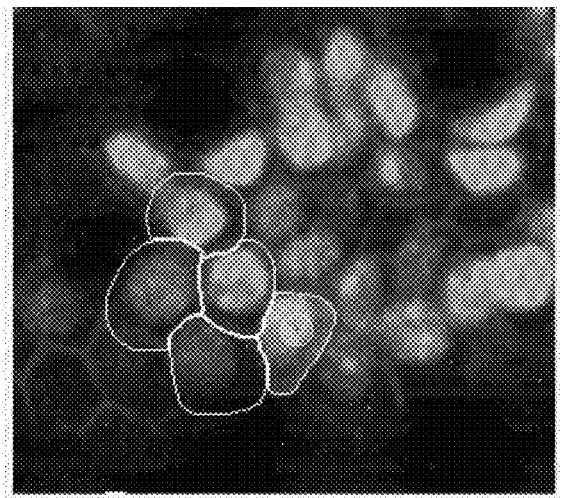
Figure 77X:
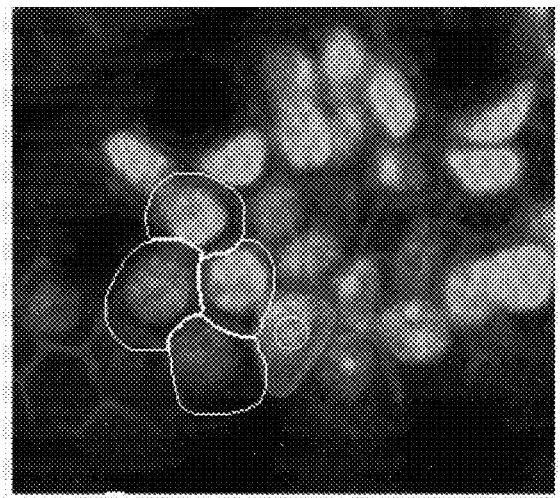
Figure 77U:
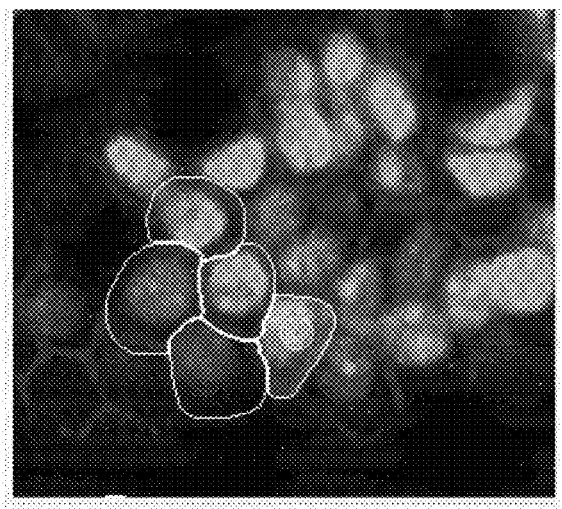
Figure 77W:
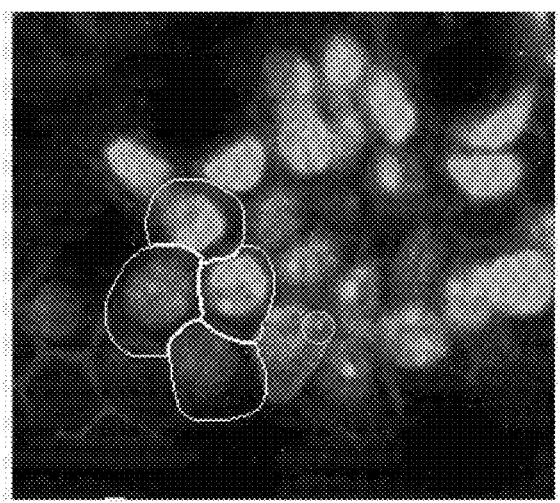

FIGS. 77A-77X. Removing multiple labels assigned to two cells and using the brush tool to draw the two cells.

FIGS. 76A-76D. Deleting a cell label (cell label 57 shown in the figures).

Examples of Common Tracking Errors and how to Fix them Using Desktop Caliban

Incorrect Segmentation of Two Cells—Some Frames

FIGS. 78A-78D show that cell 5 and cell 6 have been segmented in most frames. But there are a few frames (e.g., 7-15 and 17) where the cell mask (also referred to herein as the label mask) for "cell 5" covers both cells. This mask can be separated using watershed. First, click twice in the mask to pick seeds for the watershed transform.

Figure 78A:
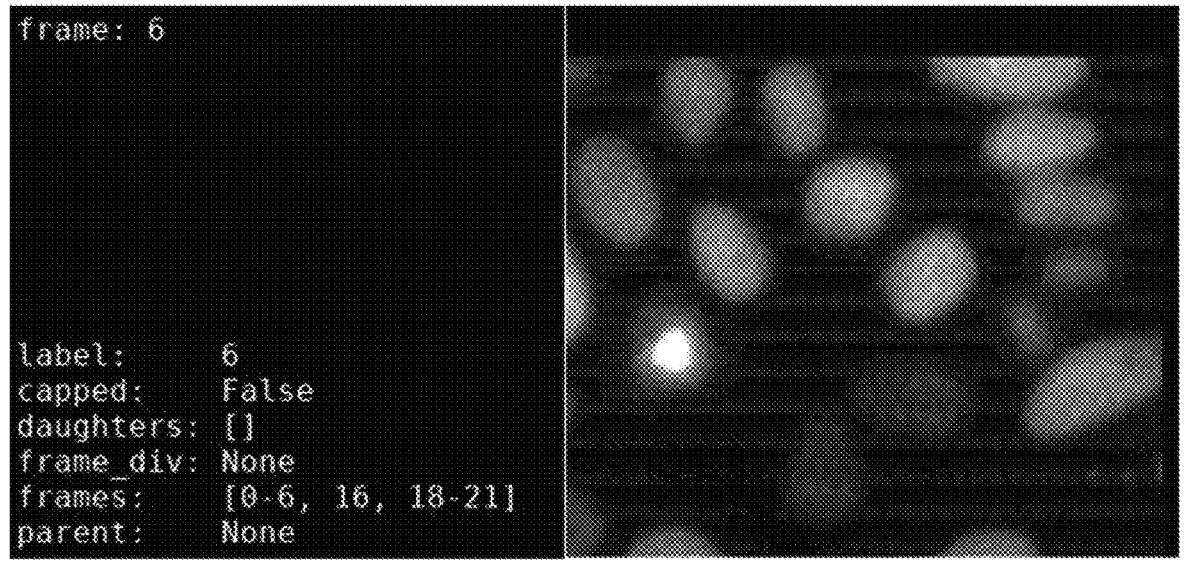
FIGS. 78A-78H. Incorrect segmentation of two cells—some frames.
Figure 78B:
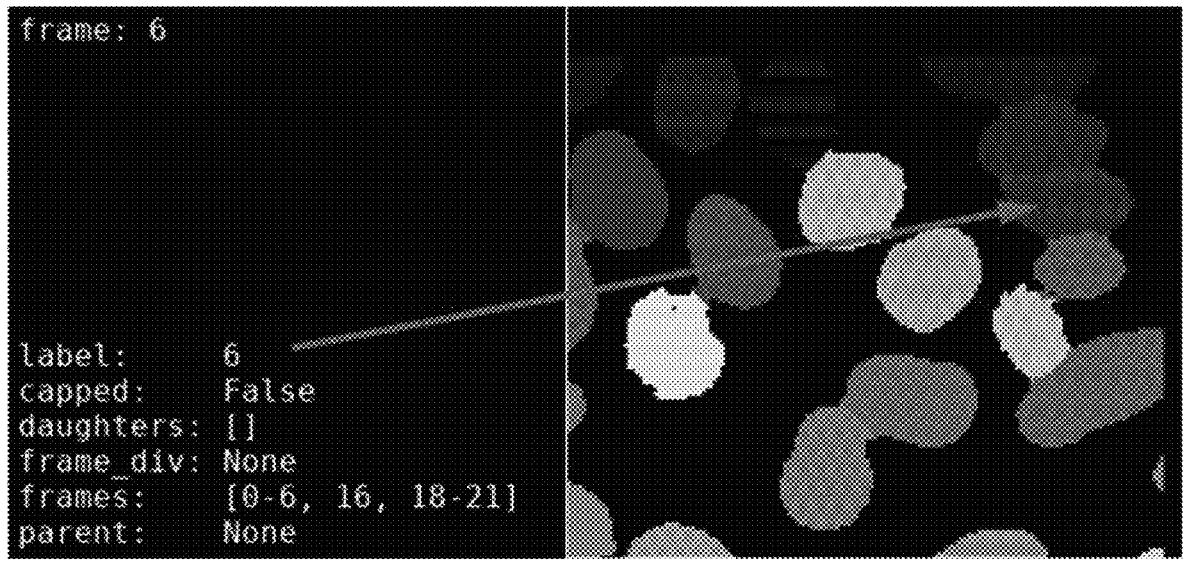
Figure 78C:
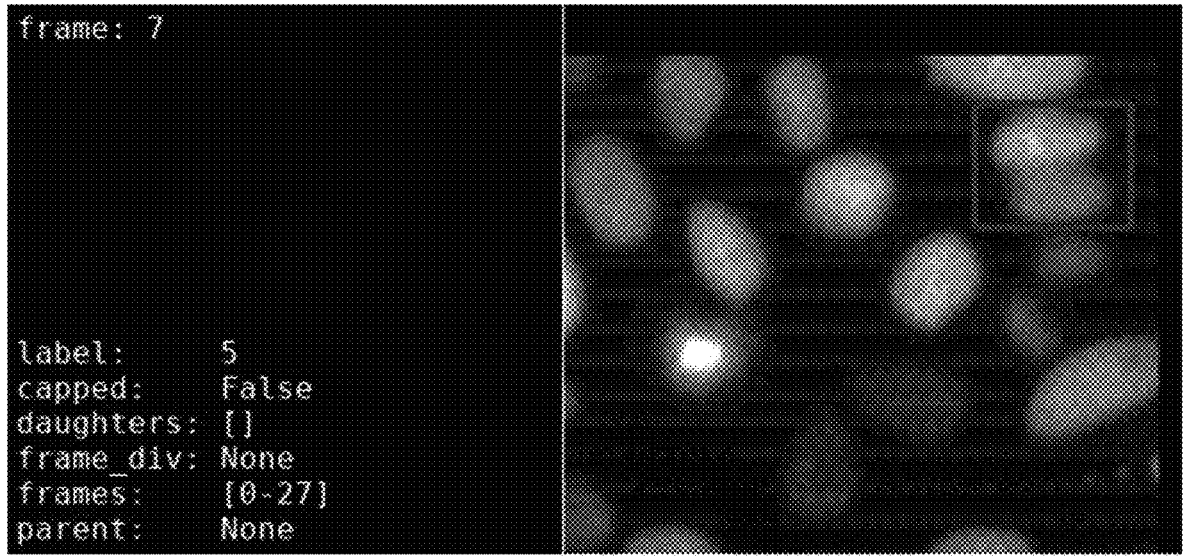
Figure 78D:
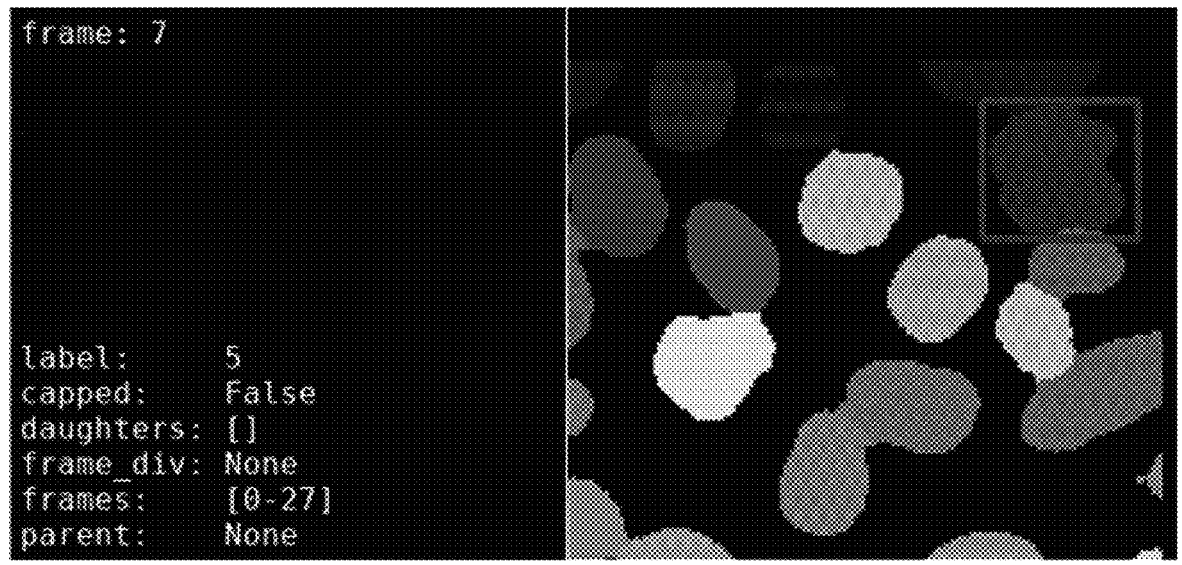
Figure 78E:
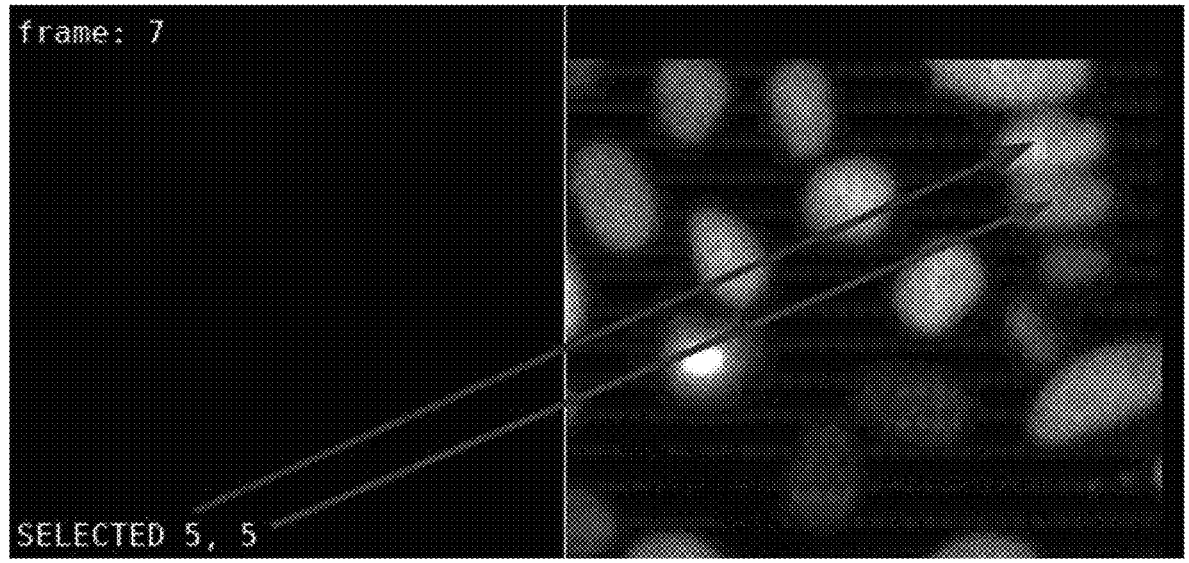

It matters where a user clicks to select each cell! Arrows in FIG. 78E point to the approximate locations clicked to separate these two. The red (top) arrow in FIG. 78E points to the first location, and the purple (bottom) arrow points to the second location. This order is important for the top cell to remain cell 5.

Figure 78F:
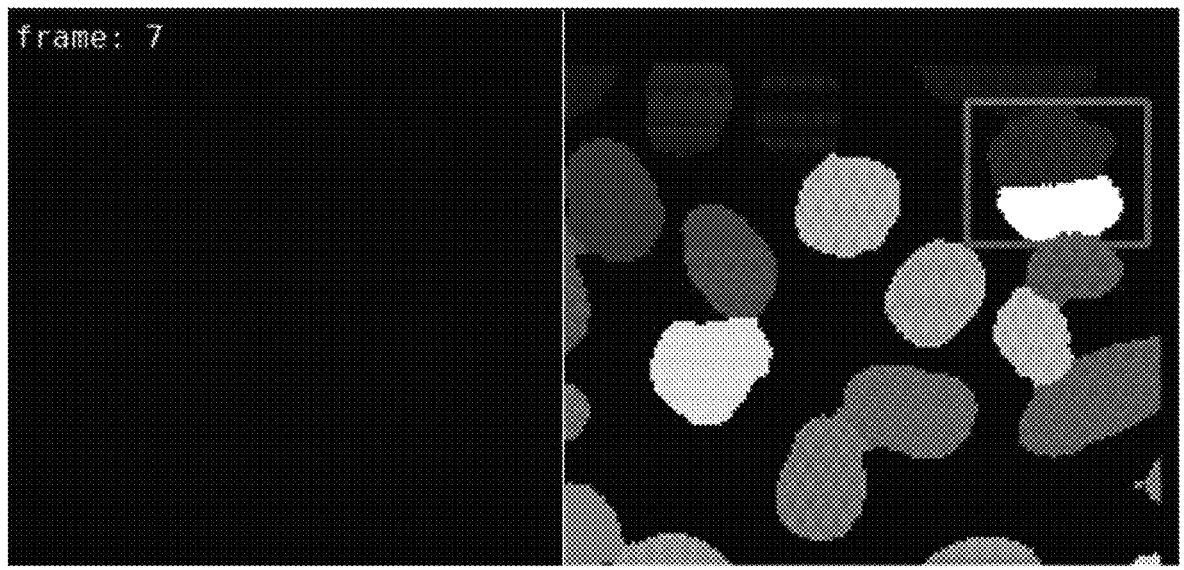

If the user picks good locations (and the contrast of the image is conducive to this operation), the user will get a watershed that looks like that shown in FIG. 78F. The dividing line between the old and new masks should be smooth and match what the user can see in the raw image. The new mask (white in FIG. 78F) will have a label but is not a proper new track. Replace the new mask with the cell label it should have.

Figure 78G:
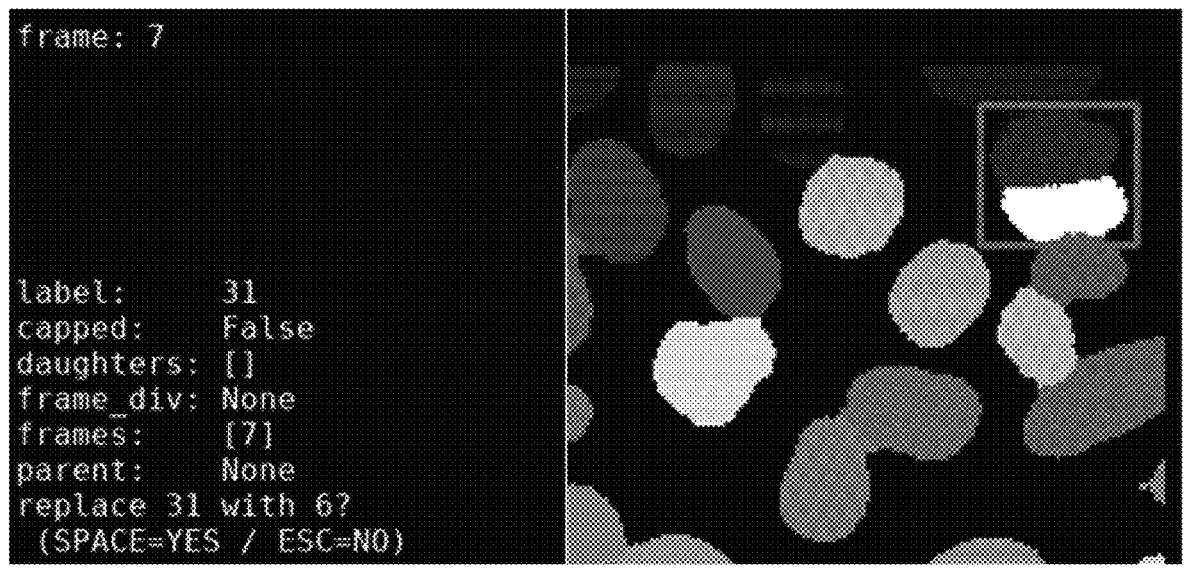
Figure 78H:
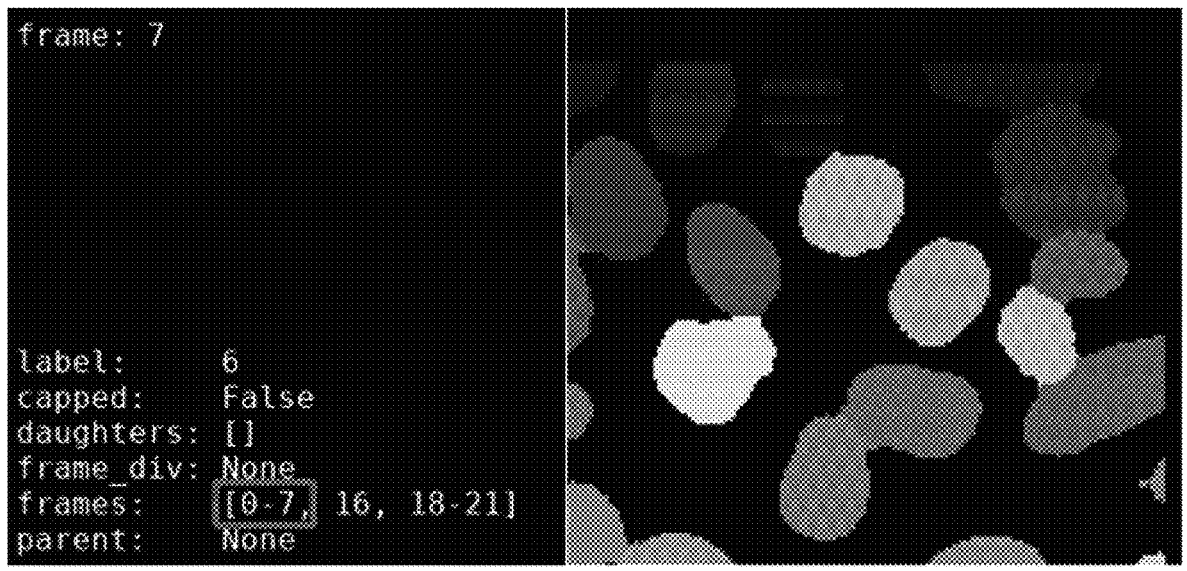

As shown in FIGS. 78G and 78H, now cell 6 has been added to frame 7 where it should be, alongside cell 5. This process will have to be repeated for the other frames where cell 5 and cell 6 share the same mask. In other cases, the cells may sometimes be labeled as both one cell (e.g., cell 5) in one frame and as both another cell (e.g., cell 6) in another frame.

Figure 79:
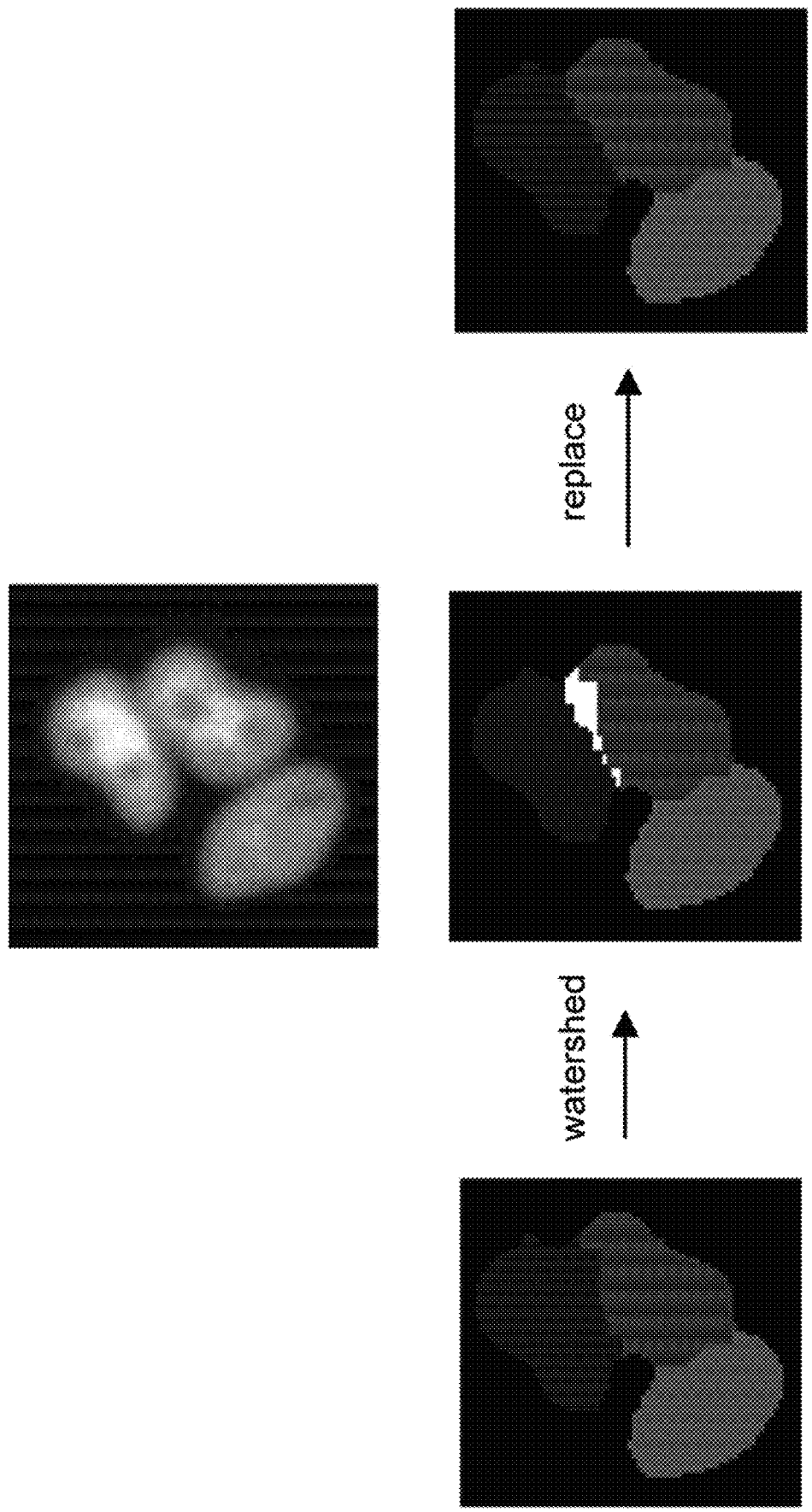
FIG. 79. Poor segmentation.

Watershed may also be used to fix poor segmentations of the type shown in FIG. 79 using the process shown in the figure.

Incorrect Segmentation of Two Cells—All Frames

Sometimes, two cells are segmented as one cell for the entire movie. This is a trickier case than the one before, because no second cell track exists that a user can use to replace the watershed-created new cell. In this situation, start by going to the last frame that the cell mask appears in. Create a new track on that cell. This new cell should have a white mask and only exist in one frame. Use watershed to split this cell; it may be tricky to see how well this works, because both masks will be very light colors. Without moving your cursor, go back one frame to click on the mask (this should be a darker color). Go forward and replace the watershed-created new cell. Now, in the last frame, the user should have two cells: one with the cell mask the user is trying to split, and one that the user has created. The user can now watershed and replace in the rest of the frames as you would in the above example.

Performing watershed and trying to create a new cell track on the watershed-created new cell does not work.

Single-Pixel Watershed

Some cells are more difficult to separate with watershed. With some patience and technique, many of these cases can still be fixed within Caliban. These cases occur, for example, when the contrast between the two cells is poor, common when both cells are very dim or very bright, and sometimes when one cell is much brighter than the other.

Figure 80:
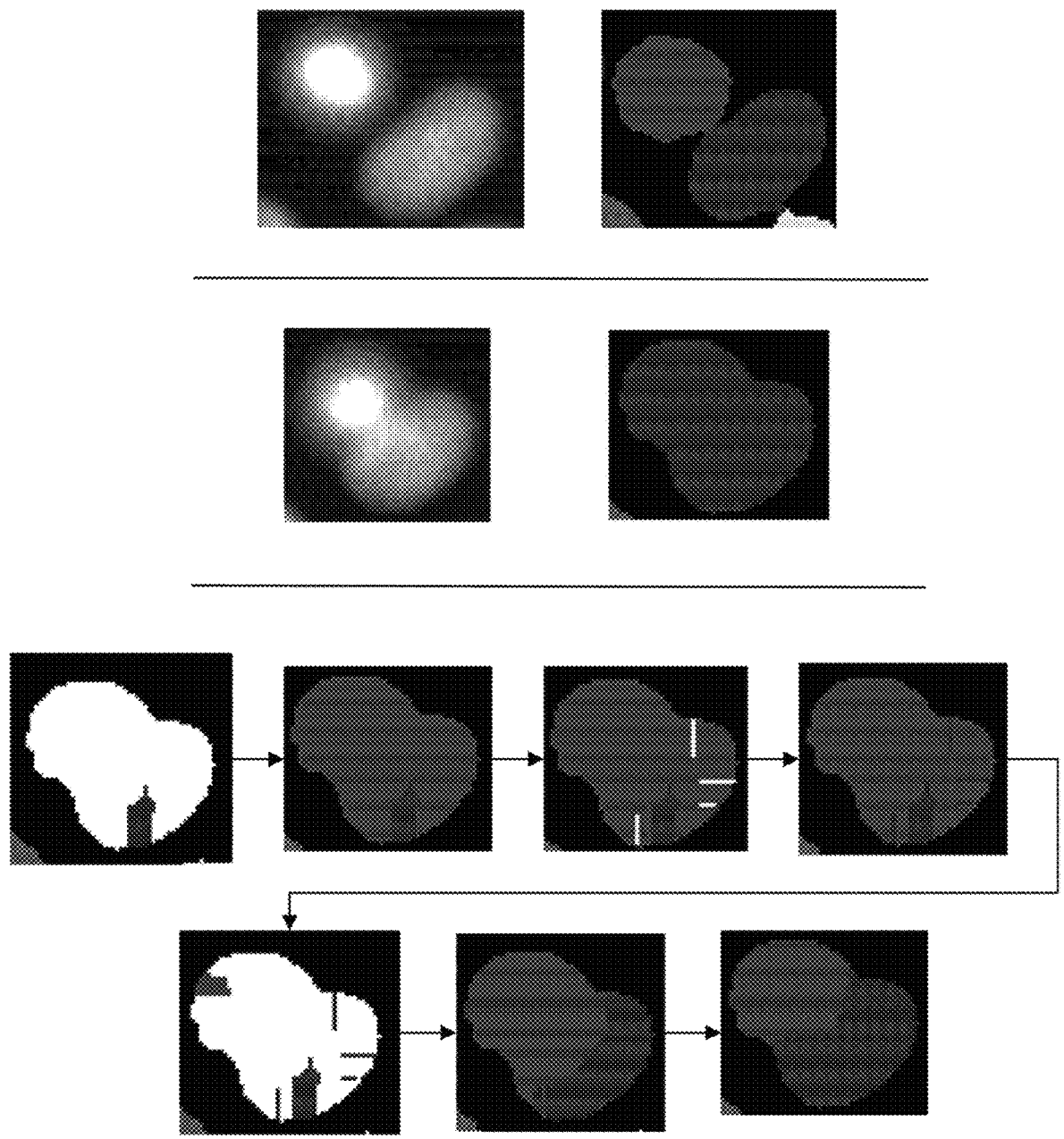
FIG. 80. Single-pixel watershed.

In this example, FIG. 80, shows a frame where the two cells are nearby and have well-defined segmentations (top row). In the next frame, the cells had moved closer together and share a segmentation mask (second row). However, using watershed to separate them is difficult. To approach this type of issue, start by using watershed to separate the cells, even though it may not work well. Replace the watershed-created new cell with the other cell from the previous frame. Next, using cell 1 as the watershed starting point, try a few watershed operations. Choosing conservative seed points for this is recommended (not points that are close to the border of the two cells).

Because of the way the watershed operation works, there is no need to replace the watershed-created new cell mask each time. A user can watershed a few times and then replace those regions all at once. Be sure to do this periodically, since watershed will sometimes overshoot. Keep trying to get small sections, working closer to the boundary between the two cells as you go. After several iterations of this process, the cells will be sufficiently segmented.

FIG. 81. Other examples of cells that are difficult to separate with the watershed tool.

For cells that are difficult to segment in only a few frames, this process of using watershed iteratively can be used. If the segmentations are particularly difficult to separate, or are difficult in more than a few frames, make a note of the separation difficulty and leave the file to be manually segmented. Try a few times before you give up; the user will start to get a feel for good seed locations for watershed.

Cells on Edges Tracked as Jumping Around

Figure 82A:
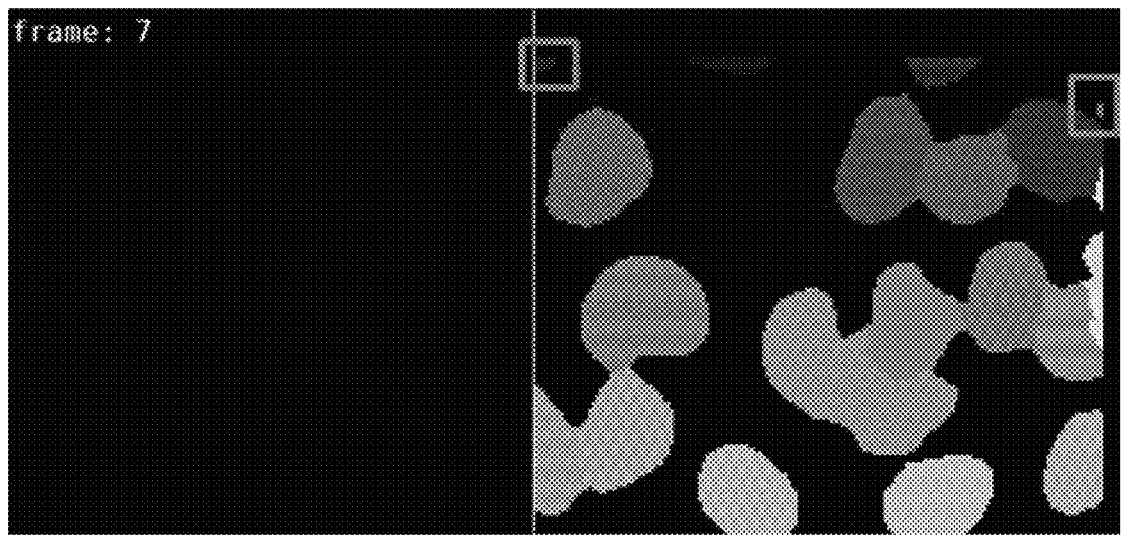
FIGS. 82A-82C. Cells on edges tracked as jumping around.
Figure 82B:
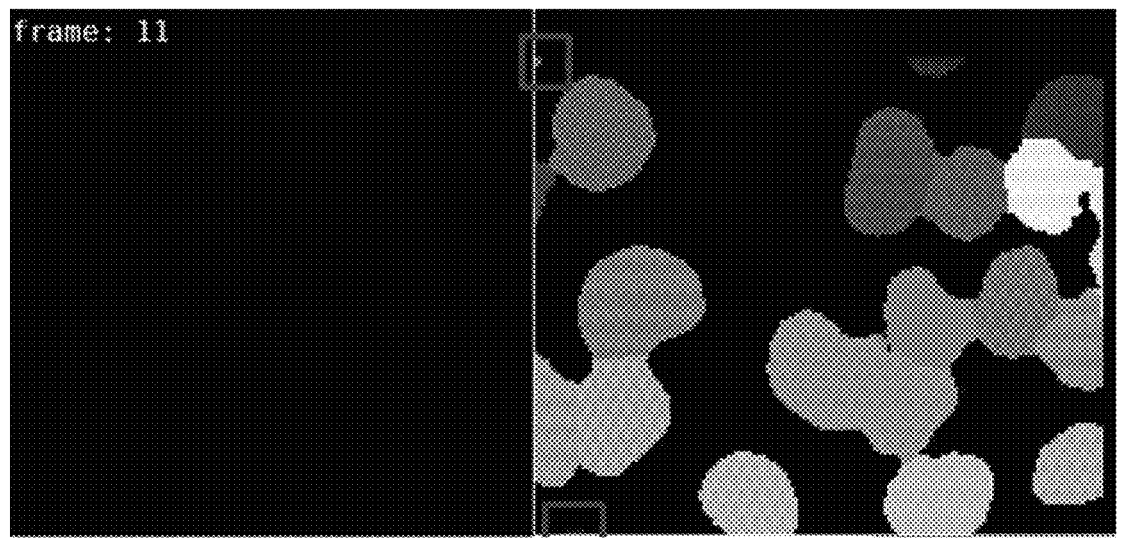
Figure 82C:
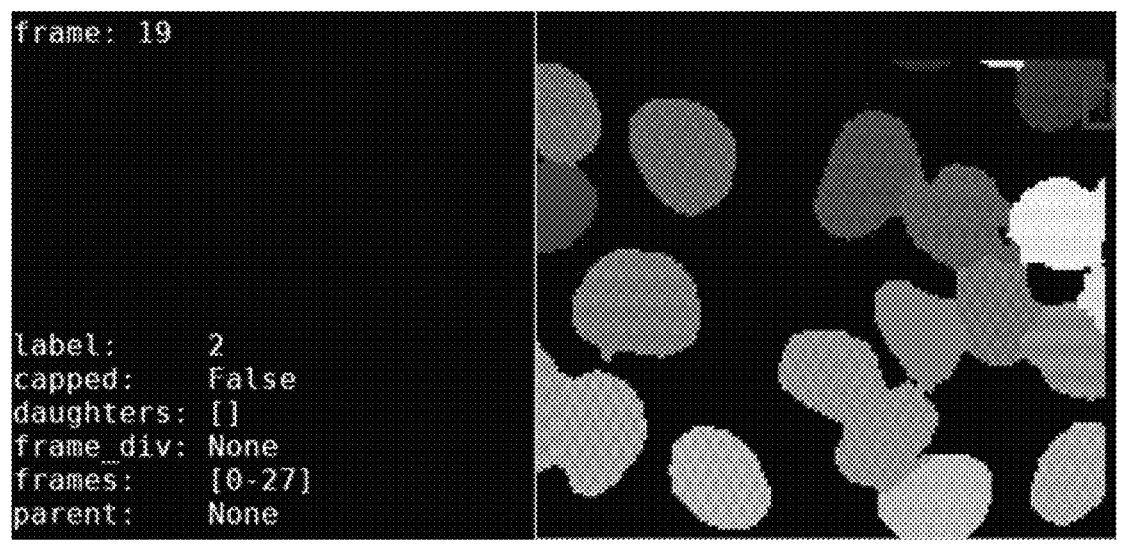

FIGS. 82A-82B show that the cells boxed in frame 7 are tracked very differently in frame 11. So although cell 2 (dark blue) does exist in both frames 7 and 11, and is tracked as existing in those frames, the tracking is still incorrect. To fix this, create a new track for both boxed cells in frame 11. Before replacing any cells, go forwards in the movie to make sure cells do not jump around further. In this example, cell 2 jumps one more time in frame 19 (FIG. 82C), but cell 9 (green) does not jump any more.

If the cells jump around further, create new tracks in each frame they appear in a different position. In this example, the two cells can appear as shown below.

| Cell # | Frames | Position |
| --- | --- | --- |
| 2 | 0-10 | Top left corner |
| 9 | 0-7 | Top right corner |
| New cell 1 | 11-18 | Bottom left corner |
| New cell 2 | 11-29 | Top left corner |
| New cell 3 | 19-27 | Top right corner |

Once the tracks have been disentangled from each other in this way, the user can start using replace to merge the tracks back together. In this example, the "new cell 2" (whatever that number happens to be) can be merged with cell 2. So the cell 2 stays in the top left corner and appears in frames 0-29. The "new cell 3" can be replaced with cell 9, giving a cell 9 that stays in the top right corner and appears in frames 0-7 and 19-27. New cell 1 will not necessarily get replaced.

Movies that have this type of error often have several. In this example, cell 9 is also mis-tracked as cell 24 in a single frame (not shown). The user would repeat the process above to fix this. The user is recommended to working on one cell value at a time, being careful to fully separate tracks before replacing. In this example, start by separating the cells that have been tracked as cell 2, then separate the cells that should have been tracked as cell 2. Once the appropriate masks have been replaced with cell 2, then the user can move onto the next cell.

Check the work on this type of error by looking at a single position when advancing through the full movie. The cell of interest should remain in roughly the same spot for all of the frames it is tracked in. Repeat this check for each edge cell.

Division not Detected

Division not detected is a common (and easy to fix) error. A cell will divide but will not be tracked as a division. Instead, a daughter cell is tracked as a second cell appearing next to the parent cell as shown in FIG. 83A.

First, check that the new cell does not appear in any previous frames. Sometimes, the cell (in this case, cell 31) is tracked as jumping over as shown in FIG. 83B. If this occurs, just create a new track in the frame where the daughter cells appear. (In this example, this step is not needed.) Next, create a new cell track for the daughter cell that has been tracked as the parent. FIG. 83B shows how the daughter cells should now look like.

Next, assign the daughter cells to the parent cell. Select the parent (in this case, cell 12), then one of the daughter cells, then press "p." FIGS. 83B-83C show how the cell information should look like after assigning the parent to both daughter cells.

Incorrect Division Detected

There are other cases where a division is detected, but assigned parent and daughters are not correct as shown in FIG. 84A.

The first step towards fixing this error is clearing the false parent/daughter relationship. A user can do this by replacing the false daughter with its parent as shown in FIG. 84B.

This will clear the parent information from the other "daughter" cell shown in FIG. 84C.

Once the false parent/daughter relationships have been cleared, the user can proceed to fix the division error as you would in a "division not detected" case.

Division Detected when there is No Division

Replace the falsely labeled "daughter" cell with the "parent" cell, as above. This will clear the parent information from any other cells mislabeled as daughters. This error usually happens when a new cell enters the edge of the movie.

Duplicate Label in Same Frame

Figure 85:
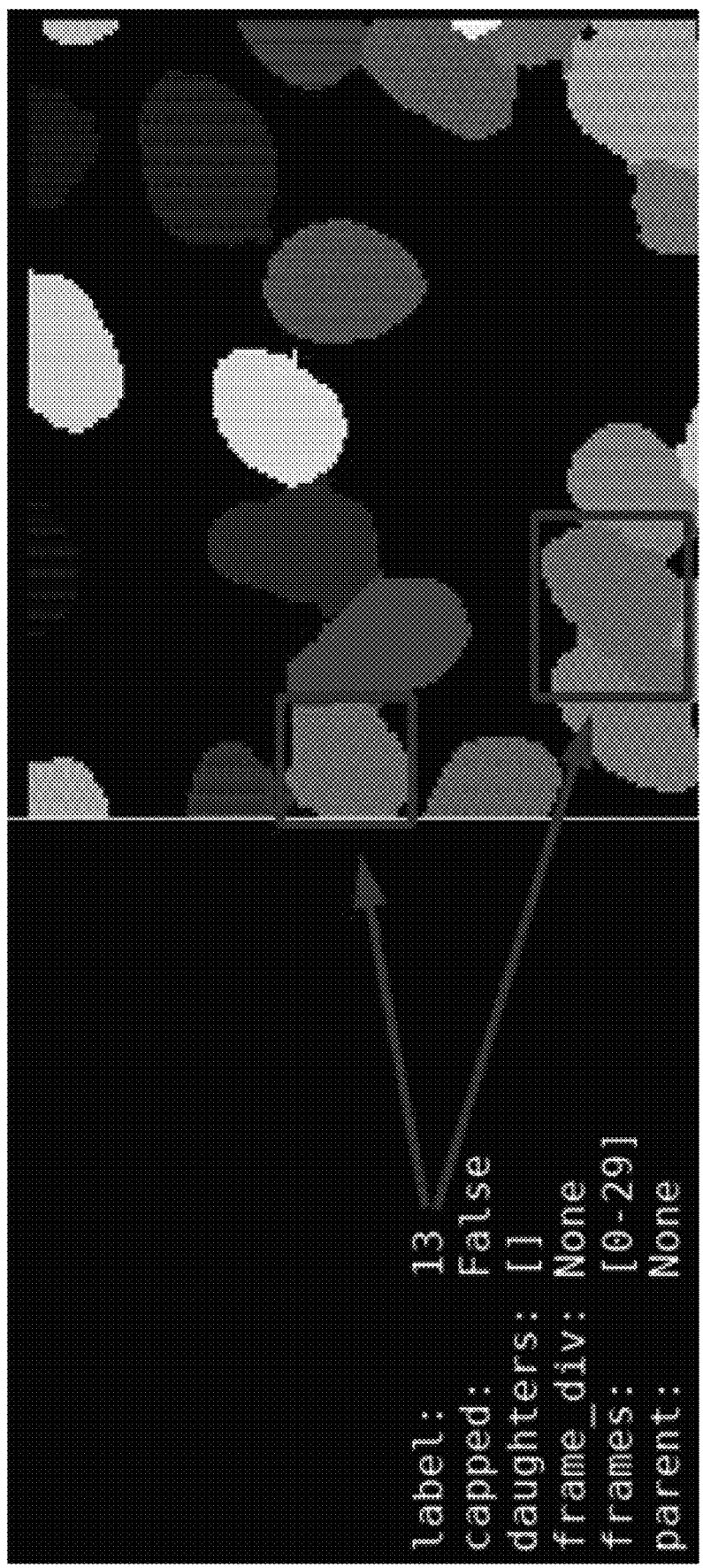
FIG. 85. Duplicate label in same frame.

FIG. 85 shows an example of the duplicate label in same frame error. The error is often a human-caused error in the .trk file where two distinct cells will share the same label, usually only for a frame. This can happen if a user has replaced one cell with another without properly disentangling the tracks first. This can also occur as an uncommon mistake during manual segmentation. The easiest way to look for this error is by paying attention to the colors of the labels. Carefully fixing the other errors will almost always prevent this error from occurring.

When this error is due to a mistake in manual segmentation, the error will usually occur only in one or two frames. If the user caused this error with "replace," the error will usually occur in many (or all) frames of the movie. It is usually more effective to start over with the backup version of the .trk file than trying to fix this error in every frame.

To fix this error, use watershed to separate the cells. If the error is in only one or two frames, the approach in "incorrect segmentation of two cells—some frames" ought to work smoothly. If the error is in all frames, the additional steps in "incorrect segmentation of two cells—all frames" is needed (or start over).

Approximate Order of Fixes

Before making any changes to the .trk file, look through all of the frames of the movie. A user can look through the raw frames first to get a sense of how messy the data is, and the types of tracking errors to look for in the annotations.

Next, see if there are any easy errors to fix. These are usually:

Division not detected

Incorrect segmentation (two cells share same label) in a few frames

Cell that is clearly one cell has been segmented into two cells

As the user works on these errors, keep an eye out for errors that are subtler, or take more effort to fix. Sometimes, what looks like an easy fix has other components the user might miss the first time through. This happens often when cell labels "jump around" in the movie. Once the user has implemented the quick fixes and are sure that doing so has not added errors to the movie, save the file before moving on to harder fixes.

Next, the user is recommended to work on difficult watershed cases. That way, if the user runs into a segmentation that the user can't fix with watershed, the user has not invested a lot of effort into finding and fixing more difficult errors, like disentangling tracks that jump around. For difficult watersheds, the user is recommended to save the file after a few frames.

After that, the user can work on any remaining errors, such as cells on the edges that have tracks that jump around the movie. Start with cells that have low numbers (especially cell 1): as the user create new cell tracks, the displayed colors will shift, and the first few cells will become harder to distinguish against the black background. Likewise, the cells with higher numbers will often become easier to distinguish from each other as they gain more colors. (This is another reason why this step can be saved for last.)

Finally, flip through the movie a few more times. Does everything look okay? Do cells jump around? Are there any duplicate labels? Mouse over edge cells and check to make sure edge cells are in all the frames listed, and only in the frames listed. Once the user has double-checked the file, save, and record the work. If a .trk file does not require any editing at all, the user should still save the file. This will help the user find the file later for uploading to the data server.

Code Availability

The source code for the Caliban software is available at github.com/vanvalenlab/Caliban, the content of which is incorporated herein by reference in its entirety.

Additional Considerations

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Accordingly, phrases such as "a device configured to" are intended to include one or more recited devices. Such one or more recited devices can also be collectively configured to carry out the stated recitations. For example, "a processor configured to carry out recitations A, B and C can include a first processor configured to carry out recitation A and working in conjunction with a second processor configured to carry out recitations B and C. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for determining biological object cell associations comprising:
    under control of a hardware processor:
        receiving raw images, frame numbers associated with the raw images, and associations each comprising a cell mask having pixels and an associated cell label assigned to one cell in the raw images;
        generating, or causing display, or both, a user interface comprising
            (i) a first panel for displaying a frame of at least one of (ia) at least one raw image of the raw images at a time, (ib) a mask image comprising one or more cell masks associated with one or more cells in the at least one raw image, and (ic) an outline corresponding to boundaries of the one or more cell masks associated with the one or more cells in the at least one raw image, and
            (ii) a second panel for displaying at least one of (iia) the frame number of the at least one raw image being displayed, (iib) tracking information associated with the one or more cells, and (iic) cell selection information of one or more cells selected;
        receiving a selection of one or more new cell mask pixels of the at least one raw image being displayed for a new cell mask;
        generating, or causing display, or both, an updated user interface comprising (i) the first panel displaying the frame of the at least one raw image of the raw images and the one or more new cell mask pixels highlighted;
        generating a new association of (iiia) the new cell mask having the one or more new cell mask pixels of the at least one raw image, and (iiib) a new cell label;
        receiving a user input of a mother-daughter relationship associated with three cell labels comprising two of the cell labels of the associations and the new cell label; and
        updating the associations comprising the three cell labels to comprise the mother-daughter relationship.

2. The method of claim 1, comprising:
    receiving a user input to modify at least one modified cell mask of the new association or one association of the associations;
    receiving a selection of modifying pixels of the at least one raw image being displayed; and
    updating the at least one modified cell mask to comprise one or more modifying pixels of the modifying pixels.

3. The method of claim 2, wherein updating the at least one modified cell mask comprises updating the at least one modified cell mask to comprise the modifying pixels.

4. The method of claim 2, wherein receiving a selection of the one or more modifying pixels comprises receiving the selection of the one or more modifying pixels selected using a brush tool.

5. The method of claim 4, wherein the brush tool is associated with a default brush size, the method comprising generating, or causing display, or both, an updated user interface comprising (i) the first panel displaying a visual representation of the brush tool with the default brush size overlaid on the frame.

6. The method of claim 4, wherein the brush tool is associated with a brush value of a cell label.

7. The method of claim 1, comprising:
    receiving a user input to modify at least one modified cell mask of the new association or one association of the associations;
    receiving a selection of one or more modifying pixels of the at least one raw image being displayed; and
    updating the at least one modified cell mask not to comprise the modifying pixels.

8. The method of claim 1, wherein receiving the selection of the one or more new cell mask pixels of the at least one raw image being displayed comprises:
    receiving a selection of pixels for determining the one or more new cell mask pixels; and
    determining the selection of the one or more new cell mask pixels of the at least one raw image from the selection the pixels for determining the one or more new cell mask pixels using a watershed function.

9. The method of claim 1, comprising:
    receiving a user display preference input; and
    generating, or causing display, or both, an updated user interface comprising (i) the first panel displaying, based on the user display preference input, the frame comprising (ia) the at least one raw image of the raw images, (ib) the mask image comprising the one or more cell masks associated with the one or more cells in the at least one raw image, or (ic) the outline corresponding to the boundaries of the one or more cell masks associated with the one or more cells objects in the at least one raw image.

10. The method of claim 1, comprising:
    receiving a user display preference input; and
    generating, or causing display, or both, an updated user interface comprising (i) the first panel displaying the frame of (ia) the at least one raw image with modified brightness or an inverse raw image of the at least one raw image.

11. The method of claim 1, wherein the mask image comprises the new cell mask in a light color, optionally wherein the light color is white.

12. The method of claim 1, wherein the mask image comprises one or more cell masks each in a different color, optionally wherein the mask image comprises one or more cell masks each in a different color that is invariant across mask images.

13. The method of claim 1, wherein the mask image comprises a dark background, optionally wherein the dark background comprises a black background.

14. The method of claim 1, comprising determining a color of a cell mask of the cell masks in the mask image based on a number of the cell masks, the cell label associated with the cell mask, or both.

15. The method of claim 1, comprising:
receiving a user input of a cell mask in the mask image; and
generating, or causing display, or both an updated user interface comprising the cell mask highlighted in the mask image of the updated user interface.

16. The method of claim 1, wherein the user interface comprises (i) the first panel on the right and (ii) the second panel on the left.

17. The method of claim 1, wherein (ii) the second panel comprises (iia) the frame number of the at least one raw image being displayed, (iib) tracking information associated with the one or more cells , and (iic) cell selection information of one or more cells selected, from top to bottom.

18. The method of claim 1, wherein the raw images comprise two-dimensional spatial images over time, a Z-stack of three-dimensional spatial images, multi-channel images, or a combination thereof.

19. The method of claim 1, comprising:
generating training data, or receiving training data generated, from the raw images, the frame numbers associated with the raw images, and the associations and the new association; and
training a deep learning model for cell tracking and lineage construction using the training data generated.

20. A system for analyzing images of cells biological objects comprising:
non-transitory memory configured to store executable instructions; and
a hardware processor in communication with the non-transitory memory, the hardware processor programmed by the executable instructions to: analyze images of cells using a deep learning model for cell tracking and lineage construction of claim 19.

21. The method of claim 1, comprising generating the associations from the raw images and the frame numbers using a deep learning model for cell tracking and lineage construction.

22. The method of claim 21, wherein generating the associations from the raw images and the frame numbers using the deep learning model for cell tracking and linage construction comprises generating the associations from the raw images and the frame numbers using a system that dynamically allocates computational resources for training the deep learning model based on GPU utilization and work demand.

23. The method of claim 22, wherein the system comprises pods, or wherein the system dynamically allocates the computational resources using horizontal pod scaling.

24. The method of claim 21, wherein the deep learning model comprises a hybrid convolutional/recurrent deep learning model.

25. The method of claim 24, wherein inputs of the deep learning model comprise an appearance of a cell, a neighborhood of the cell, a morphology of the cell, and a motion of the cell in a first raw image and an appearance of a cell, a neighborhood of the cell, a morphology of the cell, and a motion of the cell in a second raw image, optionally wherein the appearance of the cell, the neighborhood of the cell, the morphology of the cell, and the motion of the cell in the first raw image comprises appearance vectors, neighborhood vectors, morphology vectors, and motion vectors determined from a plurality of raw images comprising the first raw image, and optionally wherein the appearance of the cell, the neighborhood of the cell, the morphology of the cell, and optionally the motion of the cell in the second raw image is determined from the first raw image and the second raw image.

26. The method of claim 1, wherein receiving the selection of the one or more new cell mask pixels of the at least one raw image being displayed comprises receiving the selection of the one or more new cell mask pixels of the at least one raw image from a user input device.

27. The method of claim 1, wherein cell masks of the new association and the associations, other than the at least one modified cell mask, comprise none of the one or more modifying pixels.

28. The method of claim 1, comprising: storing the new association.

29. A system for determining biological object associations comprising:
non-transitory memory configured to store executable instructions; and
a hardware processor in communication with the non-transitory memory, the hardware processor programmed by the executable instructions to perform:
receiving raw images, frame numbers associated with the raw images, and associations each comprising a biological object mask having pixels and an associated biological object label assigned to one biological object in the raw images;
generating, or causing display, or both, a user interface comprising
(i) a first panel for displaying (ia) a raw image of the raw images, (ib) a mask image comprising one or more biological object masks associated with one or more biological objects in the raw image, and (ic) an outline corresponding to boundaries of the one or more biological object masks associated with the one or more biological objects in the raw image, and
(ii) a second panel for displaying (iia) the frame number of the raw image being displayed, (iib) tracking information associated with the one or more biological objects, (iic) biological object selection information of one or more biological objects selected, or a combination thereof;
receiving a user input to create a new biological object mask;
receiving a selection of one or more new biological object pixels of the at least one raw image being displayed;
generating, or causing display, or both, an updated user interface comprising (i) the first panel displaying the raw image of the raw images and the one or more new biological object mask pixels highlighted; and
generating a new association of (iiia) the new biological object mask having the one or more new biological object mask pixels of the raw image, and
(iiib) a new biological object label.

* * * * *